United States Patent [19]

Hillemann

[11] Patent Number: 4,981,509

[45] Date of Patent: * Jan. 1, 1991

[54] HERBICIDAL SULFONAMIDES

[75] Inventor: Craig L. Hillemann, Wilmington, Del.

[73] Assignee: E. I. Du Pont de Nemours and Company, Wilmington, Del.

[ * ] Notice: The portion of the term of this patent subsequent to Oct. 3, 2006 has been disclaimed.

[21] Appl. No.: 343,422

[22] Filed: Apr. 26, 1989

Related U.S. Application Data

[60] Division of Ser. No. 929,119, Nov. 10, 1986, which is a continuation-in-part of Ser. No. 867,351, May 8, 1986, Pat. No. 4,849,010, which is a continuation-in-part of Ser. No. 811,165, Nov. 22, 1985, Pat. No. 4,710,221, which is a continuation-in-part of Ser. No. 720,702, Apr. 10, 1985, abandoned, which is a continuation-in-part of Ser. No. 613,412, May 24, 1984, abandoned.

[51] Int. Cl.$^5$ .................. C07D 251/46; C07D 251/52; A01N 43/70; A01N 43/66
[52] U.S. Cl. ........................................... 71/93; 71/86; 71/87; 544/211; 544/206; 544/208; 544/195
[58] Field of Search ............... 71/93, 86, 87; 544/211, 544/206, 208, 195

[56] References Cited

U.S. PATENT DOCUMENTS

| | | | |
|---|---|---|---|
| 4,383,113 | 5/1983 | Levitt | 544/211 |
| 4,394,506 | 7/1983 | Levitt | 544/321 |
| 4,476,321 | 10/1984 | Meyer et al. | 564/86 |
| 4,510,325 | 4/1985 | Meyer et al. | 544/211 |
| 4,514,212 | 4/1985 | Meyer et al. | 544/211 |
| 4,537,619 | 8/1985 | Meyer et al. | 71/93 |
| 4,545,811 | 10/1985 | Meyer et al. | 544/211 |
| 4,780,125 | 10/1988 | Meyer et al. | 544/211 |
| 4,871,847 | 10/1989 | Hillemann | 71/93 |

FOREIGN PATENT DOCUMENTS

| | | |
|---|---|---|
| 81/4874 | 1/1982 | South Africa . |
| 82/5042 | 1/1983 | South Africa . |
| 82/5671 | 2/1983 | South Africa . |
| 82/7439 | 4/1983 | South Africa . |

*Primary Examiner*—John M. Ford

[57] ABSTRACT

This invention relates to certain sulfonylurea herbicidal compounds, agriculturally suitable compositions thereof and a method of their use.

43 Claims, No Drawings

4,981,509

HERBICIDAL SULFONAMIDES

This application is a divisional application of U.S. Ser. No. 06/929,119, filed Nov. 10, 1986, which is a continuation-in-part of application U.S. Ser. No. 867,351, filed May 8, 1986, now U.S. Pat. No. 4,849,010, issued July 18, 1989, which is a continuation-in-part of copending application U.S. Ser. No. 801,165, filed Nov. 22, 1985, now U.S. Pat. No. 4,710,221, issued Dec. 1, 1987, which is a continuation-in-part of U.S. Ser. No. 720,702, filed Apr. 10, 1985, now abandoned, which is a continuation-in-part of U.S. Ser. No. 613,412, filed May 24, 1984 now abandoned.

BACKGROUND OF THE INVENTION

This invention relates to novel sulfonylurea herbicidal compounds, agriculturally suitable compositions thereof and a method of using them to control the growth of undesired vegetation.

New compounds effective for controlling the growth of undesired vegetation are in constant demand. In the most common situation, such compounds are sought to selectively control the growth of weeds in useful crops such as cotton, rice, corn, wheat and soybeans, to name a few. Unchecked weed growth in such crops can cause significant losses, reducing profit to the farmer and increasing costs to the consumer. In other situations herbicides are desired which will control all plant growth. Examples of areas in which complete control of all vegetation is desired are areas around fuel storage tanks, ammunition depots and industrial storage areas. There are many products commercially available for these purposes, but the search continues for products which are more effective, less costly and environmentably safe.

The "sulfonylurea" herbicides are an extremely potent class of herbicides discovered within the last few years. A multitude of structural variations exist within this class of herbicides, but they generally consist of a sulfonylurea bridge, —SO$_2$NHCONH—, linking two aromatic or heteroaromatic rings.

U.S. Pat. No. 4,394,506 discloses herbicidal orthoalkoxycarbonylbenzenesulfonamides such as

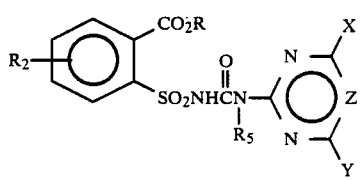

wherein
R$_2$ is H, F, Cl, Br, C$_1$–C$_3$ alkyl, NO$_2$, SO$_2$CH$_3$, OCH$_3$, SCH$_3$, CF$_3$, N(CH$_3$)$_2$, NH$_2$ or CN;
X is H, Cl, CH$_3$, OCH$_3$, OCH$_2$CH$_3$ or OCH$_2$CH$_2$OCH$_3$; and
Y is H, halogen, C$_1$–C$_4$ alkyl, C$_1$–C$_4$ substituted alkyl, C$_1$–C$_4$ alkoxy, alkylamino, dialkylamino, etc.

South African Patent Application No. 81/4874 discloses herbicidal sulfonamides of formula

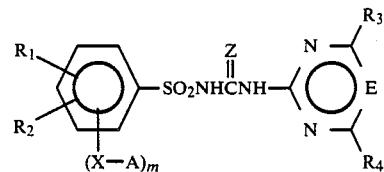

wherein
A is a C$_1$–C$_6$ alkyl radical which is substituted by halogen or various other organic substituents or a C$_2$–C$_6$ alkenyl radical which is substituted or unsubstituted.
X is O, S, SO or SO$_2$;
R$_1$ is H, halogen, C$_1$–C$_5$ alkyl, C$_2$–C$_5$ alkenyl or YR$_5$;
R$_2$ is H, halogen, C$_1$–C$_5$ alkyl, C$_2$–C$_5$ alkenyl, C$_1$–C$_4$ haloalkyl, CO$_2$R$_6$, YR$_5$, NO$_2$ or CONR$_7$R$_8$; and
R$_3$ and R$_4$, each independently of the other, are hydrogen, C$_1$–C$_4$ alkyl, C$_1$–C$_4$ alkoxy, C$_1$–C$_4$ alkylthio, C$_1$–C$_4$ haloalkyl, halogen or alkoxyalkyl of at most 4 carbon atoms.

South African Patent Application No. 82/5042 discloses herbicidal sulfonamides of formula

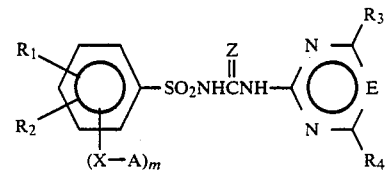

wherein
A is C$_3$–C$_6$ alkynyl;
X is O, S, SO or SO$_2$;
R$_1$ is H, halogen, C$_1$–C$_5$ alkyl, C$_2$–C$_5$ alkenyl or YR$_5$;
R$_2$ is H, halogen, C$_1$–C$_5$ alkyl, C$_1$–C$_5$ alkenyl, C$_1$–C$_4$ haloalkyl, CO$_2$R$_6$, YR$_5$, NO$_2$ or CONR$_7$R$_8$; and
R$_3$ and R$_4$, independently of one another, are hydrogen, C$_1$–C$_4$ alkyl, C$_1$–C$_{alkoxy}$, C$_1$–C$_4$ alkylthio, C$_1$–C$_4$ haloalkyl, C$_1$–C$_4$ haloalkoxy, halogen or alkoxyalkyl of at most 4 carbon atoms.

South African Patent Application No. 82/5671 discloses herbicidal sulfonamides of formula

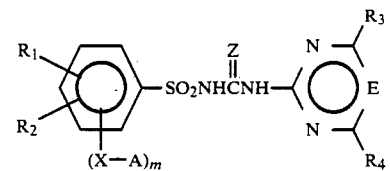

wherein
A is a C$_1$–C$_6$ alkyl radical or a C$_2$–C$_6$ alkenyl radical which is substituted by halogen or various other organic substituents;
X is O, S, SO or SO$_2$;
R$_1$ is H, halogen, C$_1$–C$_5$ alkyl, C$_2$–C$_5$ alkenyl or YR$_5$;
R$_2$ is H, halogen, C$_1$–C$_5$ alkyl, C$_2$–C$_5$ alkenyl, C$_1$–C$_{haloalkyl}$, CO$_2$R$_6$, YR$_5$, NO$_2$ or CONR$_7$R$_8$;
R$_3$ is hydrogen, C$_1$–C$_4$ alkyl, C$_1$–C$_4$ alkoxy, C$_1$–C$_4$ alkylthio, C$_1$–C$_4$ haloalkyl, C$_1$–C$_4$ haloalkoxy, halogen or alkoxyalkyl of at most 4 carbon atoms; and
R$_4$ is C$_1$–C$_4$ haloalkoxy or C$_1$–C$_4$ haloalkylthio.

South African Patent Application No. 82/7439 discloses herbicidal sulfonamides of formula

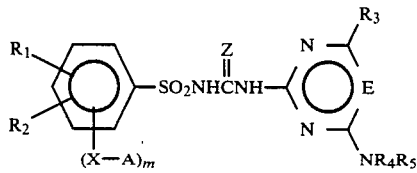

wherein

A is a $C_3-C_6$ alkynyl group, a $C_1-C_6$ alkyl group which is substituted by halogen, $C_1-C_4$ alkoxy, $C_1-C_4$ alkylthio, $C_1-C$ alkylsulfinyl, $C_1-C_4$ alkylsulfonyl, $C_1-C_4$ haloalkoxy, $C_1-C_4$ haloalkylthio, $C_1-C_4$ haloalkylsulfinyl or $C_1-C_4$ haloalkylsulfonyl, or it is a $C_2-C_6$ alkenyl group substituted by one of the above substituents;

X is O, S, SO or $SO_2$;

$R_1$ is hydrogen, halogen, $C_1-C_5$ alkyl, $C_2-C_5$ alkenyl or a $YR_6$ group;

$R_2$ is hydrogen, halogen, $C_1-C_5$ alkyl, $C_2-C_5$ alkenyl, $C_1-C_4$ haloalkyl, $YR_6$, $CO_2R_7$, $NO_2$ or $CONR_8R_9$;

$R_3$ is hydrogen, $C_1-C_4$ alkyl, $C_1-C_4$ alkoxy, $C_1-C_4$ alkylthio, $C_1-C_4$ haloalkyl, $C_1-C_4$ haloalkoxy, halogen or alkoxyalkyl having at most 4 carbon atoms;

$R_4$ is hydrogen, methyl or ethyl;

$R_5$ is hydrogen, $C_1-C_4$ alkyl, $C_1-C_3$ alkoxy, methoxymethyl, cyanomethyl or cyanoethyl;

$R_6$ and $R_7$ are each $C_1-C_5$ alkyl, $C_2-C_5$ alkenyl or $C_2-C_6$ alkynyl;

South African Patent Application No. 83/0441 (Swiss priority 1/25/82) discloses herbicidal benzenesulfonamides of formula

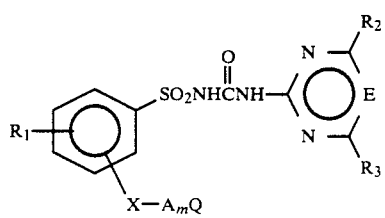

wherein $R_1$ is H, halogen, $NO_2$, $C_1-C_4$ haloalkyl, $C_1-C_4$ alkyl, $C_1-C_4$ alkoxy, $C_1-C_5$ alkenyl or $C_1-C_4$ alkoxycarbonyl;

$R_2$ is $C_1-C_3$ alkyl or $C_1-C_3$ alkoxy, each unsubstituted or substituted by 1 to 3 halogen atoms;

$R_3$ is halogen, H, $NR_4R_5$, $C_1-C_3$ alkyl, unsubstituted or substituted by 1 to 3 halogen atoms or $C_1-C_4$ alkoxy, or is $C_1-C_3$ alkoxy, unsubstituted or substituted by methoxy ethoxy or 1 to 3 halogen atoms;

A is $C_1-C_4$ alkylene or $C_2-C_4$ alkenylene each unsubstituted or substituted by $C_1-C_4$ alkyl;

m is 0 or 1;

E is N or CH;

X is oxygen, sulfur, SO or $SO_2$; and

Q is, in part, OH, CN, $NR_6R_7$, $SO_2R_8$, cycloalkyl or $COC_1-C_6$ alkyl.

South African Patent Application No. 83/3779 (Swiss priority 5/26/82) discloses herbicidal benzenesulfonamides of formula

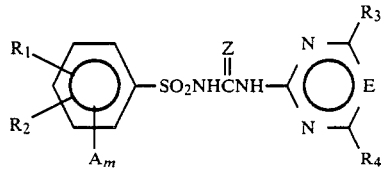

wherein

A is C≡CR;
m is 1 or 2;
E is CH or N;
Z is oxygen or sulfur,
R, is, in part, H, $C_1-C_9$ alkyl or $C_1-C_9$ haloalkyl;
$R_1$ is H, halogen, $C_1-C_5$ alkyl, $C_2-C_5$ alkenyl or $YR_5$;
$R_2$ is H, halogen, $C_1-C_5$ alkyl, $C_2-C_5$ alkenyl, $C_1-C_4$ haloalkyl, $YR_5$, $CO_2R_6$, $NO_2$ or $CONR_7R_8$; $R_3$ and $R_4$, each independently of the other, are H, $C_1-C_4$ alkyl, $C_1-C_4$ alkoxy, $C_1-C_4$ alkylthio, $C_1-C_4$ haloalkyl, $C_1-C_4$ haloalkoxy, $C_1-C_4$ haloalkylthio, halogen, $C_2-C_5$ alkoxyalkyl, $NR_9R_{10}$ or $OCH_2CH_2NR_9R_{10}$.

South African Patent Application No. 83/6449 (Swiss priority 9/1/82) discloses herbicidal benzenesulfonamides of formula

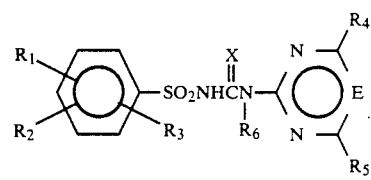

wherein $R_1$ is H, halogen, $NO_2$, amino, $C_1-C_5$ alkyl, $C_1-C_4$ haloalkyl or a $QR_7$, $CO_2R_8$ or $(CO)_nNR_9R_{10}$ radical;

$R_2$ is H, $C_1-C_4$ alkyl, $C_1-C_4$ alkoxy, $C_1-C_4$ alkylthio, $C_1-C_4$ haloalkyl, $C_1-C_4$ haloalkoxy, halogen or alkoxyalkyl containing not more than 4 carbon atoms;

$R_3$ is $C_2-C_{10}$ alkenyl which is substituted by one or more fluorine or bromine atoms or by one or more hydroxyl, cyano, nitro, $(Y)_mCO(Z)_nR_8$, $SO_2NR_{11}R_{12}$, $S(O)_pC_1-C_3$ haloalkyl or $S(O)_nC_1-C_3$ alkyl groups and which may additionally be substituted by one or more chlorine atoms;

$R_4$ is $C_1-C_3$ alkyl, $C_1-C_3$ haloalkyl, $C_1-C_3$ alkoxy or $C_1-C_3$ haloalkoxy;

$R_5$ is H, halogen, $NR_{13}R_{14}$, $C_1-C_3$ alkyl, $C_1-C_3$ haloalkyl, $C_1-C_3$ alkoxy or $C_1-C_2$ haloalkoxy; and E is CH or N.

South African Patent Application No. 84/2245 (Swiss priority 3/28/83) discloses herbicidal sulfonamides of

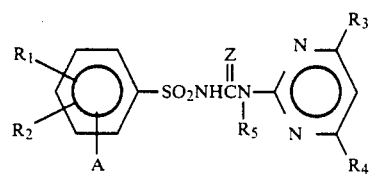

wherein

A is $C_1-C_6$ haloalkyl;

$R_1$ is hydrogen halogen, nitro, cyano, $C_1-C_4$ alkyl, $C_1-C_4$ haloalkyl, $C_1-C_4$ alkoxy, $C_1-C_4$ alkylthio, $C_1-C_4$ alkylsulfinyl, $C_1$–$C_4$ alkylsulfonyl, $COR_6$, $NR_7R_8$, $CONR_9R_{10}$ or $SO_2NR_{11}R_{12}$;

$R_2$ is hydrogen, halogen, $C_1$–$C_4$ alkyl, $C_1$–$C_4$ alkoxy, $C_1$–$C_4$ alkylthio, $C_1$–$C_4$ alkylsulfinyl or $C_1$–$C_4$ alkylsulfonyl; and $R_3$ and $R_4$, independently of one another, are each hydrogen, halogen, $C_1$–$C_4$ alkyl, $C_1$–$C_4$ haloalkyl, $C_1$–$C_4$ haloalkoxy, $C_1$–$C_4$ alkylthio, $C_1$–$C_4$ haloalkylthio, $C_2$–$C_4$ alkoxyalkyl, $C_1$–$C_4$ alkoxy or $NR_{12}R_{13}$.

South African Patent Application No. 84/2722 (Swiss priority 4/13/83) discloses herbicidal benzenesulfonamides of formula

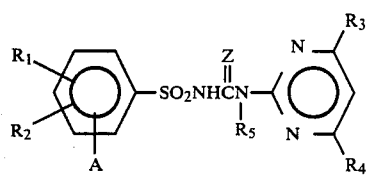

wherein

A is a radical of the formula $CR_6R_7XR_8$, $CR_9R_{10}R_{11}$ or $CHR_7SCQR_{21}$;

$R_1$ is hydrogen, halogen, nitro, cyano, $C_1$–$C_4$ alkyl, $C_1$–$C_4$ haloalkyl, $YR_{14}$, $CONR_{12}R_{13}$, $NR_{12}R_{13}$, $SONR_{15}R_{16}$, $OSO_2R_{17}$ or $COR_{18}$;

$R_2$ is hydrogen, halogen, $C_1$–$C_4$ alkyl, $C_1$–$C_4$ alkoxy, $C_1$–$C_4$ alkylthio, $C_1$–$C_4$ alkylsulfinyl or $C_1$–$C_4$ alkylsulfonyl;

$R_3$ and $R_4$, independently of one another, are each hydrogen, halogen, $C_1$–$C_4$ alkyl, $C_1$–$C_4$ haloalkyl, $C_1$–$C_4$ alkoxy, $C_1$–$C_4$ haloalkoxy, $C_1$–$C_4$ alkylthio, $C_1$–$C_4$ haloalkylthio, $C_1$–$C_5$ alkoxyalkyl or $NR_{19}R_{20}$;

$R_9$ is hydrogen, halogen, $C_1$–$C_4$ alkyl, $C_1$–$C_4$ alkoxy, $C_1$–$C_4$ alkylthio, $C_1$–$C_4$ alkylsulfinyl or $C_1$–$C_4$ alkylsulfonyl;

$R_{10}$ is hydrogen, halogen or methyl;

$R_{11}$ is a radical $COR_{24}$ or a $C_1$–$C_4$ alkyl group that is mono- or polysubstituted by substituents selected from the group: cyano, nitro, hydroxyl, $C_1$–$C_4$ alkoxy, $C_1$–$C_4$ alkylthio, etc.

$R_{18}$ is H, $C_1$–$C_4$ alkoxy and various other organic radicals.

There is a continuing need for new herbicidal compounds which have safety to selective crops and which control both grassy and broadleaf weeds.

SUMMARY OF THE INVENTION

This invention relates to certain compounds of the structural formula

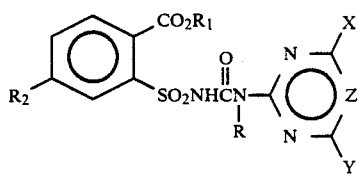

wherein

R is H or $CH_3$;

$R_1$ is $C_1$–$C_3$ alkyl, $C_3$–$C_4$ alkoxyalkyl, $C_2$–$C_4$ haloalkyl, $C_3$–$C_4$ alkenyl, $C_3$–$C_4$ alkynyl, $C_4$–$C_6$ cycloalkylalkyl or $C_4$–$C_5$ cycloalkyl;

$R_2$ is $C_2$–$C_6$ alkoxy, $C_3$–$C_6$ cycloalkoxy, $C_4$–$C_6$ cycloalkylalkoxy, $C_1$ haloalkoxy, $C_2$–$C_6$ haloalkoxy, $C_2$–$C_6$ alkenyloxy, $C_2$–$C_6$ haloalkenyloxy, $C_3$–$C_6$ alkynyloxy, $C_3$–$C_6$ haloalkenyloxy, $C_2$–$C_4$ alkoxyalkoxy, $C_2$–$C_4$ haloalkoxyalkoxy, $C_2$–$C_4$ alkylthioalkoxy, $C_2$–$C_4$ haloalkylthioalkoxy, $C_2$–$C_4$ alkylsulfonylalkoxy, $C_2$–$C_4$ haloalkylsulfinylalkoxy, $C_2$–$C_4$ alkylsulfonylalkoxy, $C_2$–$C_4$ haloalkylsulfonylalkoxy, $C_2$–$C_4$ cyanoalkoxy, $OCH_2C(O)CH_3$, $OCH_2CH_2C(O)CH_3$, $C_2$–$C_4$ aminoalkoxy, $C_1$–$C_8$ alkylthio, $C_3$–$C_6$ cycloalkylthio, $C_4$–$C_6$ cycloalkylalkylthio, $C_1$ haloalkylthio, $C_2$–$C_8$ haloalkylthio, $C_2$–$C_6$ alkenylthio, $C_2$–$C_6$ haloalkenylthio, $C_3$–$C_6$ alkynylthio, $C_3$–$C_6$ haloalkynylthio, $C_2$–$C_4$ alkoxyalkylthio, $C_2$–$C_4$ haloalkoxyalkylthio, $C_2$–$C_4$ alkylthioalkylthio, $C_2$–$C_4$ haloalkylthioalkylthio, $C_2$–$C_4$ cyanoalkylthio, $SCH_2C(O)CH_3$, $SCH_2CH_2CH_2C(O)CH_3$, $C_2$–$C_4$ aminoalkylthio, $SC_6H_5$, $SCH_2C_6H_5$, $C_1$–$C_8$ alkylsulfinyl, $C_3$–$C_6$ cycloalkylsulfinyl, $C_4$–$C_6$ cycloalkylalkylsulfinyl, $C_1$–$C_8$ haloalkylsulfinyl, $C_2$–$C_6$ alkenylsulfinyl, $C_2$–$C_6$ haloalkenylsulfinyl, $C_3$–$C_6$ alkynylsulfinyl, $C_3$–$C_6$ haloalkynylsulfinyl, $C_2$–$C_4$ alkoxyalkylsulfinyl, $C_2$–$C_4$ haloalkoxyalkylsulfinyl, $C_1$–$C_4$ cyanoalkylsulfinyl, $S(O)CH_2C(O)CH_3$, $S(O)CH_2CH_2C(O)CH_3$, $C_2$–$C_4$ aminoalkylsulfinyl, $C_2$–$C_8$ alkylsulfonyl, $C_3$–$C_6$ cycloalkylsulfonyl, $C_4$–$C_6$ cycloalkylalkylsulfonyl, $C_1$–$C_4$ haloalkylsulfonyl, $C_2$–$C_6$ alkenylsulfonyl, $C_1$–$C_8$ haloalkenylsulfonyl, $C_2$–$C_6$ alkynylsulfonyl, $C_3$–$C_6$ haloalkynylsulfonyl, $C_3$–$C_6$ alkoxyalkylsulfonyl, $C_2$–$C_4$ haloalkoxyalkylsulfonyl, $C_2$–$C_4$ cyanoalkylsulfonyl, $SO_2CH_2C(O)CH_2$, $SO_2CH_2CH_2C(O)CH_3$, $C_2$–$C_4$ aminoalkylsulfonyl, $CH_2F$, $CHF_2$, $CH_2Cl$, $CHCl_2$, $CH_2Br$, $CHBr_2$, $C_2$–$C_6$ alkyl substituted with 1–3 atoms of F, Cl or Br, $C_1$–$C_4$ alkenyl, $C_2$–$C_6$ haloalkenyl, $C\equiv CH$, $C_2$–$C_6$ haloalkynyl, $OC(O)C_1$–$C_4$ alkyl, $CH_2C(O)NR_aR_b$, $NHCH_3$, $NR_bR_c$ or $C_1$–$C_4$ alkyl substituted with $C_1$–$C_4$ alkoxy, $C_1$–$C_4$ cycloalkoxy, cyclopropylmethoxy, $C_1$–$C_4$ haloalkoxy, $C_1$–$C_4$ alkenyloxy, $C_2$–$C_4$ haloalkenyloxy, $C_1$–$C_4$ alkynyloxy, $C_1$–$C_4$ haloalkynyloxy, $C_1$–$C_4$ alkoxyalkoxy, $C_1$–$C_4$ aminoalkoxy, $C_1$–$C_4$ alkylcarbonyloxy, $C_1$–$C_4$ haloalkylcarbonyloxy, $C_1$–$C_4$ oarbamoyloxy, $C_1$–$C_4$ alkoxycarbonyloxy, OH, $OP(O)(OC_1$–$C_2$ alkyl)$_2$, $C_1$–$C_4$ alkylsulfonyloxy, $C_1$–$C_4$ haloalkylsulfonyloxy, $OSi(CH_3)_3$, $OSi(CH_3)_2C(CH_3)_3$, $C_1$–$C_4$ alkylthio, $C_1$–$C_4$ cycloalkylthio cyclopropylmethylthio, $C_1$–$C_4$ haloalkylthio, $C_1$–$C_4$ alkenylthio, $C_2$–$C_4$ haloalkenylthio, $C_1$–$C_4$ alkynylthio, $C_1$–$C_4$ haloalkynylthio, $C_1$–$C_4$ alkoxyalkylthio, $C_2$–$C_4$ aminoalkylthio, SH, $SP(O)(OC_1$–$C_2$ alkyl)$_2$, $C_1$–$C_4$ alkylsulfinyl, $C_3$–$C_4$ cycloalkylsulfonyl, cyclopropylmethylsulfinyl, $C_1$–$C_4$ haloalkylsulfinyl, $C_2$–$C_4$ alkenylsulfinyl, $C_2$–$C_4$ haloalkenylsulfinyl, $C_3$–$C_4$ alkynylsulfinyl, $C_1$–$C_4$ haloalkynylsulfinyl, $C_2$–$C_4$ alkoxyalkylsulfinyl, $C_2$–$C_4$ aminoalkylsulfinyl, $C_1$–$C_4$ alkylsulfonyl, $C_3$–$C_4$ cycloalkylsulfonyl, cyclopropylmethylsulfonyl, $C_1$–$C_4$ haloalkylsulfonyl, $C_1$–$C_4$ alkenylsulfonyl, $C_1$–$C_4$ haloalkenylsulfonyl, $C_3$–$C_4$ alkynylsulfonyl, $C_3$–$C_4$ haloalkynylsulfonyl, $C_2$–$C_4$ alkoxyalkylsulfonyl or $C_2$–$C_4$ aminoalkylsulfonyl;

$R_a$ and $R_b$ are independently H or $C_1$–$C_3$ alkyl;

$R_c$ is $C_2$–$C_4$ alkyl, cyclopropylmethyl, $C_1$–$C_4$ cyanoalkyl, $CH_2C(O)CH_3$, $CH_2CH_2C(O)CH_3$, $C_1$–$C_4$ haloalkyl, $C_3$–$C_4$ alkenyl, $C_3$–$C_4$ haloalkenyl, $C_3$–$C_4$ alkynyl, $C_3$–$C_4$ haloalkynyl, $C_1$–$C_4$ alkyl substituted with $C_1$–$C_4$ alkoxy, $C_1$–$C_4$ alkylthio, $C_1$–$C_4$ alkylsulfinyl, $C_1$–$C_4$ alkylsulfonyl, OH $NH_2$, $NHCH_3$ or $N(CH_3)_2$;

X is $CH_3$, $OCH_3$, $OC_2H_5$, Cl or Br;

Y is $C_1$–$C_2$ alkyl, $C_1$–$C_2$ alkoxy, $OCH_2CH_2F$, $OCH_2CHF_2$, $OCH_2CF_3$, $NHCH_3$ or $N(CH_3)_2$; and Z is CH or N; and their agriculturally suitable salts; provided that (1) when X is Cl or Br, then Z is CH and Y is $C_1$–$C_2$ alkoxy, $NHCH_3$ or $N(CH_3)_2$;

(2) when $R_2$ is $SCH_3$, then R is H, $R_1$ is $CH_3$, X is $OCH_3$, Y is $OCH_3$ and Z is CH;

(3) when $R_2$ is $OCF_2H$, $R_1$ is $CH_2CH_3$ and Z is CH, then X and Y cannot simultaneously be $OCH_3$; and (4) when $R_2$ is $OCH_2CF_3$, $R_1$ is $CH_3$ or $CH_2CH_3$ and Z is N, then X and Y cannot simultaneously be $OCH_3$.

In the above definitions, the rerm "alkyl", used either alone or in compound words such as "alkylthio" or "haloalkyl", denotes straight chain or branched alkyl, e.g., methyl, ethyl, n-propyl, isopropyl or the different butyl, pentyl, hexyl, heptyl and octyl isomers.

Alkoxy denotes methoxy, ethoxy, n-propoxy, isopropoxy and the different butoxy, pentoxy or hexoxy isomers.

Alkenyl denotes straight chain or branched alkenes, e.g., vinyl, 1-propenyl, 2-propenyl, 3-propenyl and the different butenyl, pentenyl and hexenyl isomers.

Alkynyl denotes straight chain or branched alkynes, e.g., ethynyl, 1-propynyl, 2-propynyl and the different butynyl, pentynyl and hexynyl isomers.

Cycloalkyl denotes cyclopropyl, cyclobutyl, cyclopentyl and cyclohexyl.

$C_4$–$C_6$ cycloalkylalkyl means cyclopropylmethyl through cyclopropylpropyl or cyclopentylmethyl.

The term "halogen", either alone or in compound words such as "haloalkyl", denotes fluorine chlorine, bromine or iodine. Further, when used in compound words such as "haloalkyl" said alkyl may be partially or fully substituted with halogen atoms which may be the same or different. Examples of haloalkyl include $CH_2CH_F$, $CF_2CF_3$ and $CH_2CHFCl$.

The total number of carbon atoms in a substituent group is indicated by the $C_i$–$C_j$ prefix where i and j are numbers from 1 to 8. For example, $C_1$–$C_3$ alkylsulfonyl would designate methylsulfonyl through propylsulfonyl, $C_2$ alkoxyalkoxy would designate $OCH_2OCH_3$; $C_4$ alkoxyalkoxy would designate the various isomers of an alkoxy group substituted with a second alkoxy group containing a total of 4 carbon atoms, examples including $OCH_2OCH_2CH_2CH_3$ and $OCH_2CH_2OCH_2CH_3$; $C_2$ cyanoalkyl would designate $CH_2CN$ and $C_3$ cyanoalkyl would designate $CH_2CH_2CN$ and $CH(CN)CH_3$; $C_4$ aminoalkoxy would designate the various isomers of an alkoxy group substituted by an amino, alkylamino or dialkylamino group containing a total of 4 carbon atoms, examples including $OCH_2CH_2CH_2CH_2NH_2$ and $OCH_2CH_2N(CH_3)_2$.

Other embodiments of the invention are the compounds of Formula I as defined above where $R_1$ is $C_1$–$C_3$ alkyl, $C_3$–$C_4$ alkoxyalkyl, $C_2$–$C_4$ haloalkyl, $C_3$–$C_4$ alkenyl or $C_3$–$C_4$ alkynyl, where $C_1$ haloalkoxy ($R_2$) is $OCF_2H$ and where $C_1$ haloalkylthio ($R_2$) is $SCF_2H$.

Compounds of the invention which are preferred for their higher herbicidal activity, greater plant growth regulant activity and/or more favorable ease of synthesis are:

(1) Compounds of Formula I wherein $R_2$ is $C_2$–$C_6$ alkoxy, $C_1$–$C_8$ alkylthio, $C_1$–$C_8$ alkylsulfinyl, $C_2$–$C_8$ alkylsulfonyl, $C_3$–$C_6$ alkenyloxy, $C_1$–$C_4$ alkynyloxy, $C_1$–$C_4$ alkenylthio, $C_3$–$C_6$ alkenylsulfinyl, $C_3$–$C_6$ alkenylsulfonyl, $C_3$–$C_6$ alkynylthio, $C_3$–$C_6$ alkynylsulfinyl, $C_3$–$C_6$ alkynylsulfonyl, $OCH_2CH_2OCH_3$, $OCH_2CH_2SCH_3$, $OCH_2CH_2S(O)CH_3$, $OCH_2CH_2SO_2CH_3$, $C_2$–$C_6$ alkyl substituted with 1-3 atoms of F, Cl or Br, $CH_2F$, $CHF_2$, $C_1$–$C_4$ alkyl substituted with $C_1$–$C_2$ alkoxy, $C_1$–$C_2$ alkylthio, $C_1$–$C_2$ alkylsulfinyl or $C_1$–$C_2$ alkylsulfonyl, $OCF_2H$, $OCH_2CH_2F$, $OCH_2CHF_2$, $OCH_2CF_3$, $OCH_2CH_2Cl$, S-cyclohexyl, $SC_6H_5$ $SCH_2C_6H_5$;

(2) Compounds of Preferred (1) where $R_2$ is $CH_3S$, $C_3$–$C_6$ alkenyloxy, $C_3$–$C_6$ alkynyloxy, $C_3$–$C_6$ alkenylthio, $C_1$–$C_6$ alkenylsulfinyl, $C_1$–$C_4$ alkenylsulfonyl, $C_3$–$C_6$ alkynylthio, $C_1$–$C_4$ alkynylsulfinyl, $C_1$–$C_4$ alkynylsulfonyl, $C_1$–$C_4$ alkyl substituted with 1-3 atoms of F, Cl or Br, $CH_2F$, $CHF_2$, $C_1$–$C_4$ alkyl substituted in a nonbenzylic position with $C_1$–$C_2$ alkoxy, $C_1$–$C_2$ alkylthio, $C_1$–$C_2$ alkylsulfinyl or $C_1$–$C_2$ alkylsulfonyl, $OCH_2CH_2OCH_3$, $OCH_2CH_2SCH_3$, $OCH_2CH_2S(O)CH_3$, $OCH_2CH_2SO_2CH_3$, $OCF_2H$, $OCH_2CH_F$, $OCH_2CHF_2$, $OCH_2CF_3$, $OCH_2CH_2Cl$, S-cyclohexyl $SC_6H_5$ or $SCH_2C_6H_5$.

(3) Compounds of Preferred (2) wherein R is H;

(4) Compounds of Preferred (3) wherein $R_2$ is $CH_3S$, $C_3$–$C_4$ alkenyloxy, $C_3$–$C_4$ alkenylthio, $C_3$–$C_4$ alkenylsulfinyl, $C_3$–$C_4$ alkenylsulfonyl, $C_2$–$C_3$ alkyl substituted with 1-3 atoms of F or Cl, $CH_2F$, $CHF_2$, $OCHF_2$, $OCH_2CH_2F$, $OCH_2CF_3$ or $OCH_2CH_2Cl$.

(5) Compounds of Preferred (4) wherein $R_1$ is $CH_3$, or $CH_2CH_3$;

X is $CH_3$, $OCH_3$ or Cl; and

Y is $CH_3$, $OCH_3$, $C_2H_5$ or $OC_2H_5$.

6) Compounds of Preferred (5) wherein $R_2$ is allyloxy, allylthio, propargyloxy, propargylthio, $CH_2F$, $OCHF_2$, $OCH_2CH_2F$ or $CH_3S$.

(7) Compounds of Preferred (1) wherein $R_2$ is $C_2$–$C_6$ alkoxy, $C_2$–$C_8$ alkylthio, $C_2$–$C_8$ alkylsulfonyl, $C_1$–$C_8$ alkylsulfinyl, $CH(H, C_1$–$C_3$ alkyl$)OC_1$–$C_2$ alkyl, $CH(H, C_1$–$C_3$ alkyl$)SC_1$–$C_2$ alkyl $CH(H, C_1$–$C_3$ alkyl$)S(O)C_1$–$C_2$ alkyl or $CH(H, C_1$–$C_3$ alkyl$)SO_2C_1$–$C_2$ alkyl.

(8) Compounds of Preferred (7) wherein R is H.

(9) Compounds of Preferred (8) wherein $R_2$ is $C_2$–$C_4$ alkoxy, $C_2$–$C_4$ alkylthio, $C_2$–$C_4$ alkylsulfonyl, $C_1$–$C_4$ alkylsulfinyl, $CH_2OC_1$–$C_2$ alkyl, $CH_2SC_1$–$C_2$ alkyl, $CH_2S(O)C_1$–$C_2$ alkyl or $CH_2SO_2C_1$–$C_2$ alkyl.

(10) Compounds of Preferred (9) wherein $R_1$ is $CH_3$ or $C_2H_5$;

X is $CH_3$, $OCH_3$ or Cl; and

Y is $CH_3$, $OCH_3$, $C_2H_5$ or $OC_2H_5$.

(11) Compounds of Preferred (10) wherein $R_2$ is $C_2$–$C_3$ alkoxy, $C_2$–$C_3$ alkylthio, $C_1$–$C_3$ alkylsulfinyl, $CH_2OCH_3$, $CH_2SCH_3$, $CH_2S(O)CH_3$ or $CH_2SO_2CH_3$.

(12) Compounds of Formula I wherein $R_2$ is $C_2$–$C_6$ alkoxy, $C_3$–$C_6$ haloalkynyloxy, $C_2$–$C_8$ alkylthio, $C_7$–$C_8$ haloalkylthio, $C_1$–$C_6$ haloalkynylthio, $C_1$–$C_8$ alkylsulfinyl, $C_7$–$C_8$ haloalkylsulfinyl, $C_3$–$C_6$ haloalkynylsulfinyl, $C_2$–$C_8$ alkylsulfonyl, $C_7$–$C_8$ haloalkylsulfonyl, $C_3$–$C_6$ haloalkynylsulfonyl, $C_2$–$C_6$ alkenyl, $CH_2C(O)NR_aR_b$, $NHCH_3$, $NR_bR_c$, $CH_2OC_1$–$C_4$ alkyl, $CH(CH_2CH_3)OC_1$–$C_4$ alkyl, $CH(CH_2CH_3)OC_1$–$C_4$ alkyl, $OC_1$–$C_4$ alkyl, $C(CH_3)(CH_2CH_3)CH(CH_2CH_2CH_3)OC_1$–$C_4$ alkyl, $CH[CH(CH_3)_2]OC_1$–$C_4$ alkyl, $CH_2OC_1$–$C_4$ haloalkyl, of at least 3 halogens, $CH(CH_3)OC_1$–$C_4$ haloalkyl of at least 3 halogens, $C(CH_3)_2OC_1$–$C_4$ haloalkyl of at least $C(CH_3)(CH_2CH_3)$ 3 halogens, $CH(CH_2CH_3)OC_1$–$C_4$ haloalkyl of at least 3 halogens, $C(CH_3)(CH_2CH_3)OC_1$–$C_4$ haloalkyl of at least 3 halogens, $CH(CH_2CH_2CH_3)OC_1$–$C_4$ haloalkyl of at least 3 halogens, CH[CH(CH$_3$)$_2$]OC$_1$–C$_4$ haloalkyl, of at least 3 halogens, CH$_2$CH$_2$OC$_2$–C$_4$ haloalkenyl, CH$_2$CH$_2$CH$_2$OC$_2$–C$_4$ haloalkenyl, CH$_2$CH$_2$CH$_2$CH$_2$OC$_2$–C$_4$ haloalkenyl, CH(CH$_3$)CH$_2$OC$_2$–C$_4$ haloalkenyl, C(CH$_3$)$_2$CH$_2$OC$_2$–C$_4$ haloalkenyl, CH(CH$_2$CH$_3$)CH$_2$OC$_2$–C$_4$ haloalkenyl, CH$_2$CH(CH$_3$)OC$_2$–C$_4$ haloalkenyl, CH$_2$C(CH$_3$)$_2$CH$_2$OC$_2$–C$_4$ haloalkenyl, CH$_2$CH(CH$_2$CH$_3$)CH$_2$OC$_2$–C$_4$ haloalkenyl, CH(CH$_3$)CH(CH$_3$)OC$_2$–C$_4$ haloalkenyl, CH$_2$C(CH$_3$)$_2$OC$_2$–C$_4$ haloalkenyl, CH(CH$_3$)CH(CH$_3$)OC$_2$–C$_4$ haloalkenyl, CH$_2$CH$_2$OC$_3$–C$_4$ alkynyl, CH$_2$CH$_2$CH$_2$OC$_3$–C$_4$ alkynyl, CH$_2$CH$_2$CH$_2$CH$_2$OC$_3$–C$_4$ alkynyl, CH(CH$_3$)CH$_2$OC$_3$–C$_4$ alkynyl, C(CH$_3$)$_2$CH$_2$OC$_3$–C$_4$ alkynyl, CH(CH$_2$CH$_3$)CH$_2$OC$_3$–C$_4$ alkynyl, CH$_2$CH(CH$_3$)OC$_3$–C$_4$ alkynyl, CH$_2$C(CH$_3$)$_2$OC$_3$–C$_4$ alkynyl, CH$_2$CH(CH$_2$CH$_3$)OC$_3$–C$_4$ alkynyl, CH(CH$_3$)CH(CH$_3$)OC$_3$–C$_4$ alkynyl, CH$_2$CH$_2$OC$_2$–C$_4$ alkoxyalkyl, CH$_2$CH$_2$CH$_2$OC$_2$–C$_4$ alkoxyalkyl, CH$_2$CH$_2$CH$_2$CH$_2$OC$_2$–C$_4$ alkoxyalkyl, CH(CH$_3$)CH$_2$OC$_2$–C$_4$ alkoxyalkyl C(CH$_3$)$_2$CH$_2$OC$_2$–C$_4$ alkoxyalkyl, CH(CH$_2$CH$_3$)CH$_2$OC$_2$–C$_4$ alkoxyalkyl, CH$_2$CH(CH$_3$)OC$_2$–C$_4$ alkoxyalkyl, CH$_2$C(CH$_3$)$_2$OC$_2$–C$_4$ alkoxyalkyl, CH$_2$CH(CH$_2$CH$_3$)OC$_2$–C$_4$ alkoxyalkyl, CH(CH$_3$)CH(CH$_3$)OC$_2$–C$_4$ alkoxyalkyl, CH$_2$OC$_1$–C$_4$ alkylcarbonyl CH(CH$_3$)OC$_1$–C$_4$ alkylcarbonyl, C(CH$_3$)$_2$OC$_1$–C$_4$ alkylcarbonyl, CH(CH$_2$CH$_3$)OC$_1$–C$_4$ alkylcarbonyl, C(CH$_3$)(CH$_2$CH$_3$)OC$_1$–C$_4$ alkylcarbonyl, CH(CH$_2$CH$_2$CH$_3$)OC$_1$–C$_4$ alkylcarbonyl, CH[CH(CH$_3$)$_2$]OC$_1$–C$_4$ alkylcarbonyl, CH$_2$OC$_1$–C$_4$ haloalkylcarbonyl, CH(CH$_3$)OC$_1$–C$_4$ haloalkylcarbonyl, C(CH$_3$)$_2$OC$_1$–C$_4$ haloalkylcarbonyl, CH(CH$_2$CH$_3$)OC$_1$–C$_4$ Haloalkylcarbonyl, C(CH$_3$)(CH$_2$CH$_3$)OC$_1$–C$_4$ haloalkylcarbonyl, CH(CH$_2$CH$_2$CH$_3$)OC$_1$–C$_4$ haloalkylcarbonyl, CH[CH(CH$_3$)$_2$]OC$_1$–C$_4$ haloalkylcarbonyl, CH$_2$OC$_1$–C$_4$alkoxycarbonyl, CH(CH$_3$)OC$_1$–C$_4$ alkoxycarbonyl, CH(CH$_2$CH$_3$)$_2$OC$_1$–C$_4$ alkoxycarbonyl, C(CH$_3$)(CH$_2$CH$_3$)OC$_1$–C$_4$alkoxycarbonyl CH(CH$_2$CH$_3$)OC$_1$–C$_4$ alkoxycarbonyl, CH(CH$_2$CH$_2$CH$_3$)OC$_1$–C$_4$ alkoxycarbonyl, CH[CH(CH$_3$)$_2$]OC$_1$–C$_4$ alkoxycarbonyl, CH$_2$OH, CH(CH$_3$)OH, C(CH$_3$)$_2$OH, CH(CH$_2$CH$_3$)OH, CH(CH$_3$)OH, C(CH$_3$)$_2$OH, CH(CH$_3$)OH, C(CH$_3$)(CH$_2$CH$_3$)OH, CH(CH$_2$CH$_2$CH$_3$)OH, CH[CH(CH$_3$)$_2$]OH, CH$_2$OC$_1$–C$_4$ alxylsulfonyl, CH(CH$_3$)OC$_1$–C$_4$ alkylsulfonyl, C(CH$_3$)$_2$OC$_1$–C$_4$ alkylsulfonyl, CH(CH$_2$CH$_3$)OC$_1$–C$_4$ alkylsulfonyl, C(CH$_3$)(CH$_2$CH$_3$)OC$_1$–C$_4$ alkylsulfonyl, CH$_2$CH$_2$CH[CH(CH$_3$)$_2$]OC$_1$–C$_4$ alkylsulfonyl, CH$_2$OC$_1$–C$_4$ haloalkylsulfonyl, CH(CH$_3$)OC$_1$–C$_4$ haloalkylsulfonyl, C(CH$_3$)$_2$OC$_1$–C$_4$ haloalkylsulfonyl, CH(CH$_2$CH$_3$)OC$_1$–C$_4$ haloalkylsulfonyl, CH(CH$_3$)(CH$_2$CH$_3$)OC$_1$–C$_4$ haloalkylsulfonyl, CH(CH$_2$CH$_2$CH$_3$)OC$_1$–C$_4$ haloalkylsulfonyl, CH[CH(CH$_3$)$_2$]OC$_1$–C$_4$ haloalkylsulfonyl, CH$_2$SC$_1$–C$_4$ alkyl, CH(CH$_3$)SC$_1$–C$_4$ alkyl, C(CH$_3$)$_2$SC$_1$–C$_4$ alkyl, CH(CH$_3$)SC$_1$–C$_4$ alkyl, C(CH$_3$)(CH$_2$CH$_3$)SC$_1$–C$_4$ alkyl, CH(CH$_2$CH$_2$CH$_3$)SC$_1$–C$_4$ alkyl, CH[CH(CH$_3$)$_2$]SC$_1$–C$_4$ alkyl, CH$_2$SC$_1$–C$_4$ haloalkyl of at least 3 halogens, CH(CH$_3$)SC$_1$–C$_4$ haloalkyl of at least 3 halogens, C(CH$_3$)$_2$SC$_1$–C$_4$ haloalkyl of at least 3 halogens, CH(CH$_2$CH$_3$)SC$_1$–C$_4$ haloalkyl of at least 3 halogens, C(CH$_3$)(CH$_2$CH$_3$)SC$_1$–C$_4$ haloalkyl of at least 3 halogens, CH(CH$_2$CH$_2$CH$_3$)SC$_1$–C$_4$ haloalkyl of at least 3 halogens, CH[CH(CH$_3$)$_2$]SC$_1$–C$_4$ haloalkyl of at least 3 halogens, CH$_2$CH$_2$SC$_2$–C$_4$ haloalkenyl, CH$_2$CH$_2$CH$_2$SC$_2$–C$_4$ haloalkenyl, CH$_2$CH$_2$CH$_2$CH$_2$SC$_2$–C$_4$ haloalkenyl, CH(CH$_3$)CH$_2$SC$_2$–C$_4$ haloalkenyl, C(CH$_3$)CH$_2$SC$_2$–C$_4$ haloalkenyl, CH(CH$_2$CH$_3$)CH$_2$SC$_2$–C$_4$ haloalkenyl, CH$_2$C(CH$_3$)SC$_2$–C$_4$ haloalkenyl, CH$_2$C(CH$_3$)$_2$SC$_2$–C$_4$ haloalkenyl, CH$_2$CH(CH$_2$CH$_3$)SC$_2$–C$_4$ haloalkenyl, CH(CH$_3$)CH(CH$_3$)SC$_2$–C$_4$ haloalkenyl, CH$_2$CH$_2$SC$_3$–C$_4$ alkynyl, CH$_2$CH$_2$CH$_2$SC$_3$–C$_4$ alkynyl, CH$_2$CH$_2$CH$_2$CH$_2$SC$_3$–C$_4$ alkynyl, CH(CH$_3$)CH$_2$SC$_3$–C$_4$ alkynyl, C(CH$_3$)$_2$CH$_2$SC$_3$–C$_4$ alkynyl, CH(CH$_2$CH(CH$_3$)CH$_2$SC$_3$–C$_4$ alkynyl, CH$_2$C(CH alkynyl, CH(CH alkynyl, alkynyl, CH$_2$CH(CH$_2$CH$_3$)SC$_3$–C$_4$ alkynyl. alkynyl, CH(CH$_3$)CH(CH$_3$) SC$_3$–C$_4$ alkynyl, C$_2$CH$_2$SC$_2$–C$_4$ alkoxyalkyl, CH$_2$CH$_2$CH$_2$SC$_2$–C$_4$ alkoxyalkyl, CH$_2$CH$_2$CH$_2$CH$_2$SC$_2$–C$_4$ alkoxyalkyl, CH(CH$_3$)CH$_2$SC$_2$–C$_4$ alkoxyalkyl, C(CH$_3$)$_2$CH$_2$SC$_2$–C$_4$ alkoxyalkyl, CH(CH$_2$CH$_3$)CH$_2$SC$_2$–C$_4$ alkoxyalkyl, CH$_2$CH(CH$_3$)SC$_2$–C$_4$ alkoxyalkyl, CH$_2$C(CH$_3$)$_2$SC$_2$–C$_4$ alkoxyalkyl, CH$_2$CH(CH$_2$CH$_3$)SC$_2$–C$_4$ alkoxyalkyl, CH$_2$CH(CH$_3$)SC$_2$–C$_4$ alkoxyalkyl, CH(CH$_3$)CH(CH$_3$)SC$_2$–C$_4$ alkoxyalkyl, CH$_2$S(O)C$_1$–C$_4$ alkyl, CH(CH$_3$)S(O)C$_1$–C$_4$ alkyl, C(CH$_3$)$_2$S(O)C$_1$–C$_4$ alkyl, CH(CH$_2$CH$_3$)S(O)C$_1$–C$_4$ alkyl, C(CH$_3$)(CH$_3$)S(O)C$_1$–C$_4$ alkyl, CH(CH$_2$CH$_{23}$)S(O)C$_1$–C$_4$ alkyl, CH[CH(CH(CH$_3$)$_2$]S(O)C$_1$–C$_4$ alkyl, CH$_2$S(O)C$_1$–C$_4$ alkyl of at least 3 halogens, CH(CH$_3$)S(O)C$_1$–C$_4$ alkyl of at least 3 halogens C(CH$_3$)$_2$S(O)C$_1$–C$_4$ alkyl of at least 3 halogens, CH(C$_2$CH$_3$)S(O)C$_1$–C$_4$ alkyl of at least 3 halogens. of at least 3 halogens. CH(CH$_3$)(CH$_2$CH$_3$)S(O)C$_1$–C$_4$ alkyl of at least 3 halogens. CH(CH$_2$CH$_2$CH$_3$)S(O)C$_1$–C$_4$ alkyl of at least 3 halogens, CH[CH(CH$_3$)$_2$]S(O)C$_1$–C$_4$ alkyl of at least 3 halogens, CH$_2$CH$_2$S(O)C$_1$–C$_4$ haloalkyl, CH$_2$CH$_2$CH$_2$S(O)C$_1$–C$_4$ haloalkyl, CH$_2$CH(CH$_3$)S(O)C$_1$–C$_4$ haloalkyl, CH$_2$C(CH$_3$)$_2$S(O)C$_1$–C$_4$ haloalkyl, CH$_2$CH$_2$CH$_2$CH$_2$S(O)C$_1$–C$_4$ haloalkyl, CH(CH$_3$)CH$_2$S(O)C$_1$–C$_4$ haloalkyl, C(CH$_3$)$_2$CH$_2$S(O)C$_1$–C$_4$ haloalkyl, CH(CH$_2$CH$_3$)CH$_2$S(O)C$_1$–C$_4$ haloalkyl, CH$_2$CH(CH$_2$CH$_3$)S(O)C$_1$–C$_4$ haloalkyl, CH(CH$_3$)CH(CH$_3$)S(O)C$_1$–C$_4$ haloalkenyl, CH$_2$CH$_2$S(O)C$_2$–C$_4$ haloalkyl, CH$_2$CH$_2$CH$_2$S(O)C$_2$–C$_4$ haloalkenyl, CH$_2$CH(CH$_3$)S(O)C$_2$–C$_4$ haloalkenyl, CH$_2$C(CH$_3$)$_2$S(O)C$_2$–C$_4$ haloalkenyl, CH$_2$CH$_2$CH$_2$CH$_2$S(O)C$_2$–C$_4$ haloalkenyl, CH(CH$_3$)CH$_2$S(O)C$_2$–C$_4$ haloalkenyl, C(CH$_3$)$_2$CH$_2$S(O)C$_2$–C$_4$ haloalkenyl, CH(CH$_2$CH$_3$)CH$_2$S(O)C$_2$–C$_4$ haloalkenyl, CH$_2$CH(CH$_2$CH$_3$)S(O)C$_2$–C$_4$ haloalkenyl, CH(CH$_3$)CH(CH$_3$)S(O)C$_2$–C$_4$ haloalkenyl, CH$_2$CH$_2$S(O)C$_2$–C$_4$ alkynyl, CH$_2$CH$_2$CH$_2$S(O)C$_2$–C$_4$ alkynyl, CH$_2$CH(CH$_3$)S(O)C$_2$–C$_4$ alkynyl, CH$_2$C(CH$_3$)$_2$S(O)C$_2$–C$_4$ alkynyl, CH$_2$CH$_2$CH$_2$S(O)C$_2$–C$_4$ alkynyl, CH(CH$_3$)CH$_2$S(O)C$_2$–C$_4$ alkynyl, C(CH$_3$)$_2$CH$_2$S(O)C$_2$–C$_4$ alkynyl, CH(CH$_2$CH$_3$)CH$_2$S(O)C$_2$–C$_4$ alkynyl, CH$_2$CH(CH$_2$CH$_3$S(O)C$_2$–C$_4$ alkynyl, CH(CH$_3$)CH(CH$_3$)S(O)C$_2$–C$_4$ alkynyl, CH$_2$CH$_2$S(O)C$_2$–C$_4$ alkoxyalkyl, CH$_2$CH$_2$CH$_2$S(O)C$_2$–C$_4$ alkoxyalkyl, CH$_2$CH(CH$_3$)S(O)C$_2$–C$_4$ alkoxyalkyl, CH$_2$C(CH$_3$)$_2$S(O)C$_2$–C$_4$ alkoxyalkyl, CH$_2$CH$_2$CH$_2$CH$_2$S(O)C$_2$–C$_4$ alkoxyalkyl, CH(CH$_3$)CH$_2$S(O)C$_2$–C$_4$ alkoxyalkyl, C(CH₃)₂CH₂S(O)C₂-C₄ alkoxyalkyl, CH(CH₂CH₃)CH₂S(O)C₂-C₄ alkoxyalkyl, CH₂CH(CH₂CH₃)S(O)C₂-C₄ alkoxyalkyl, CH(CH₃)CH(CH₃)S(O)C₂-C₄ alkoxyalkyl, CH₂SO₂C₁-C₄ alkyl, CH(CH₃)SO₂C₁-C₄ alkyl, C(CH₃)₂SO₂C₁-C₄ alkyl, CH(CH₂)SO₂C₂-C₄ alkyl, C(CH₃)(CH₂CH₃)SO₂C₁-C₄ alkyl, CH(CH₂CH₃)SO₂C₁-C₄ alkyl, CH[CH(CH₃)₂]SO₂C₁-C₄ alkyl, CH₂SO₂C₁-C₄ haloalkyl of at least 3 halogens, CH(CH₃)SO₂C₁-C₄ haloalkyl of at least 3 halogens, C(CH₃)₂SO₂C₁-C₄ haloalkyl of at least 3 halogens, CH(CH₂CH₃)SO₂C₁-C₄ haloalkyl of at least 3 halogens, C(CH₃)(CH₂CH₃)SO₂C₁C₄ haloalkyl of at least 3 halogens, CH(CH₂CH₂CH₃)SO₂C₁-C₄ haloalkyl of at least 3 halogens, CH[CH(CH₃)₂]SO₂C₁-C₄ haloalkyl of at least 3 halogens, CH₂CH₂SO₂C₁-C₄ haloalkyl, CH₂CH(CH₃)SO₂C₁-C₄ haloalkyl, CH₂C(CH₃)₂SO₂C₁-C₄ haloalkyl, CH₂CH₂CH₂SO₂C₁-C₄ haloalkyl, CH(CH₃)CH₂SO₂C₁-C₄ haloalkyl, C(CH₃)₂CH₂SO₂C₁-C₄ haloalkyl, CH(CH₂CH₃)CH₂SO₂C₁-C₄ haloalkyl, CH₂CH(CH₂CH₃)SO₂C₁-C₄ haloalkenyl CH(CH₃)CH(CH₃)SO₂C₁-C₄ haloalkenyl, CH₂CH₂SO₂C₂-C₄ haloalkenyl, CH₂CH₂CH₂SO₂C₂-C₄ haloalkenyl, CH₂CH(CH₃)SO₂C₂-C₄ haloalkenyl, CH₂C(CH₃)₂SO₂C₂-C₄ haloalkenyl, CH₂CH₂CH₂CH₂SO₂C₂-C₄ haloalkenyl, CH(CH₃)CH₂SO₂C₂-C₄ haloalkenyl, C(CH₃)₂CH₂SO₂C₂C₂-C₄ haloalkenyl, CH(CH₂CH₃)CH₂SO₂C₂-C₄ haloalkenyl, CH₂CH(CH₂CH₃)SO₂C₂-C₄ haloalkenyl, CH(CH₃)CH(CH₃)SO₂C₂-C₄ haloalkenyl, CH₂CH₂SO₂C₃-C₄ alkynyl, CH₂CH₂SO₂C₃-C₄ alkynyl, CH₂CH(CH₃)SO₂C₃-C₄ alkynyl, CH₂C(CH₃)₂SO₂C₃-C₄ alkynyl, CH₂CH₂CH₂CH₂SO₂C₃-C₄ alkynyl, CH(CH₃)CH₂SO₂C₃-C₄ alkynyl, C(CH₃)₂CH₂SO₂C₃-C₄ alkynyl, CH(CH₂CH₃)CH₂SO₂C₃-C₄ alkynyl, CH₂CH(CH₂CH₃)SO₂C₃-C₄ alkynyl, CH(CH₃)CH(CH₃)SO₂C₃-C₄ alkynyl, CH₂CH₂SO₂C₂-C₄ alkoxyalkyl, CH₂CH₂CH₂SO₂C₂-C₄ alkoxyalkyl, CH₂CH(CH₃)SO₂C₂-C₄ alkoxyalkyl, CH₂C(CH₃)₂SO₂C₂-C₄ alkoxyalkyl, CH₂CH₂CH₂CH₂SO₂C₂-C₄ alkoxyalkyl, CH(CH₃)CH₂SO₂C₂-C₄ alkoxyalkyl, CH(CH₂CH₃)CH₂SO₂C₂-C₄ alkoxyalkyl, CH₂CH(CH₂CH₃)SO₂C₂-C₄ alkoxyalkyl, CH(CH₃)CH(CH₃)SO₂C₂-C₄ alkoxyalkyl, C(CH₃)₂CH₂SO₂C₂-C₄ alkoxyalkyl, or C₁-C₄ substituted with C₃-C₄ cycloalkoxy, cyclopropylmethoxy, C₁-C₄ haloalkynyloxy C₁-C₄ aminoalkoxy, C₁-C₄ carbamoyloxy, OP(O)(OC₁-C₂ alkyl)₂, OSi(CH₃)₃, OSi(CH₃)₂C(CH₃)₃, C₃-C₄ cycloalkylthio, cyclopropylmethylthio C₂-C₄ alkenylthio, C₃-C₄ haloalkynylthio C₂-C₄ aminoalkylthio, SH, SP(O)(OC₁-C₂ alkyl)₂, C₃-C₄ cycloalkylsulfinyl, cyclopropylmethylsulfinyl, C₃-C₄ haloalkynylsulfinyl, C₂-C₄ aminoalkylsulfinyl, C₃-C₄ cycloalkylsulfonyl, cyclopropylmethylsulfonyl, C₂-C₄ alkenylsulfonyl C₃-C₄ haloalkynylsulfonyl or C₂-C₄ aminoalkylsulfonyl,

(13) Compounds of Preferred 12 wherein R₂ is C₂-C₄ alkoxy, C₃-haloalkynyloxy, C₂-C₄ alkylthio C₃-haloalkynylthio, C₁-C₃ alkylsulfinyl C₃-haloalkynylsulfinyl, C₂-C₃ alkylsulfonyl C₃-haloalkynylsulfonyl, C₂-C₃ alkenyl, CH₂C(O)NR$_a$R$_b$, NHCH₃ NR$_b$R$_c$, CH₂OC₁-C₂ alkyl, CH₂OC₁-C₂ haloalkyl of at least 3 halogens, CH₂CH₂OC₂-C₃ haloalkenyl, CH₂CH₂OC₃-C₄ alkynyl, CH₂CH₂OC₂-C₃ alkoxyalkyl, CH₂ OC-₁-C₂ alkylcarbonyl, CH₂OC₁-C₂ alkoxycarbonyl, CH₂OH, CH₂OC₁-C₂ alkylsulfonyl, CH₂OC₁-C₂-haloalkylsulfonyl, CH₂SC₁-C₂ alkyl, CH₂SC₁-C₂ haloalkyl of at least 3 halogens, CH₂CH₂SC₂-C₃ haloalkenyl, CH₂CH₂SC₃-C₄ alkynyl, CH₂CH₂SC₂-C₃ alkoxyalkyl, CH₂S(O)C₁-C₄ alkyl, CH₂S(O)C₁-C₂ alkyl of at least 3 halogens, CH₃CH₂S(O)C₁-C₂ haloalkyl, CH₂CH₂S(O)C₂-C₃ haloalkenyl, CH₂CH₂S(O)C₃-C₄ alkynyl, CH₂C₂S(O)C₂-C₃ alkoxyalkyl CH₂SO₂C₁-C₂ alkyl, CH₂SO₂C₁-C₂ haloalkyl of at least 3 halogens, CH₂CH₂SO₂C₁-C₂ haloalkyl, CH₂CH₂SO₂C₂-C₃ haloalkenyl CH₂CH₂SO₂C₃-C₄ alkynyl, CH₂CH₂SO₂C-₂-C₃ alkoxyalkyl or C₁-C₂ alkyl substituted with C₃-cycloalkoxy, cyclopropylmethoxy, C₃-C$_{haloalkynyloxy}$ C₂-C₃ aminoalkoxy, C₁-C₂ carbamoyloxy, OP(O)(OC-₁-C₂ alkyl)₂, OSi(CH₃)₃ OSi(CH₃)₂C(CH₃)₃ C₃-cycloalkylthio, cyclopropylmethylthio, C₂-C₃ alkenylthio, C₃-C₄ haloalkynylthio, C₂-C₃ aminoalkylthio, SH, SP(O)(OC₁-C₂ alkyl)₂, C₃-cycloalkylsulfinyl, cyclopropylmethylsulfinyl, C₃-C₄ haloalkynylsulfinyl, C₂-C₃ aminoalkylsulfinyl C -cycloalkylsulfonyl, cyclopropylmethylsulfonyl C₂-C₃ alkenylsulfonyl C₁-C₄ lkenylsulfonyl or C₂-C₃ aminoalkylsulfonyl,

(14) Compounds of Preferred 13 wherein
R₂ is OCH₂CH₃, OCH(CH₃)₂, C₃-haloalkynyloxy, SCH₂CH₃, SCH₂CH₃)₂, C₃-haloalkynylthio, S(O)CH₃, S(O)CH S(O)CH₂CH₃, S(O)CH(CH₃)₂, C₃-haloalkynylsulfinyl, SO₂CH₂CH₃, SO₂CH(CH₃)₂, C₃-haloalkynylsulfonyl, vinyl, allyl, CH₂C(O)N(CH₃)₂, NHCH₃, N(CH₃)₂, CH₂OCH₃, CH₂OCH₂CF₃, CH₂CH₂OC₂ Haloalkenyl, CH₂CH₂OCH₂C≡CH, CH₂CH₂OCH₂C-H₂OCH₃, CH₂OC(O)CH₃, CH₂OC(O)OCH₃, CH₂OH, CH₂OSO₂CH₃, CH₂OSO₂CF₃, CH₂OSO₂CH₂CF₃, CH₂SCH₃, CH₂SCH₂CF₃, CH₂CH₂SC₂ haloalkenyl, CH₂CH₂SCH₂C≡CH, CH₂CH₂SCH₂CH₂OCH₃, CH₂S(O)CH₃, CH₂S(O)CH₂CF₃, CH₂CH₂S(O)CH₂CF₃, CH₂CH₂S(O)C₂ haloalkenyl, CH₂CH₂S(O)CH₂C≡CH, CH₂CH₂S(O)CH₂C-H₂OCH₃, CH₂SO₂CH₃, CH₂SO₂CH₂CF₃, CH₂CH₂SO₂CH₂CF₃, CH₂CH₂SO₂C₂ haloalkenyl, CH₂CH₂SO₂CH₂C≡CH, CH₂CH₂SO₂CH₂CH₂OCH₃, or CH₂ substituted with cyclopropoxy, cyclopropylmethoxy, C₃-haloalkynyloxy, OCH₂CH₂NH₂, OC(O)NH₂, OP(O)(OCH₃)₂, OSi(CH₃)₃, OSi(CH₃)₂C(CH₃)₃, cyclopropylthio, cyclopropylmethylthio, allylthio C₃-haloalkenylthio, SCH₂CH₂NH₂, SH, SP(O)(OCH₃)₂, cyclopropylsulfinyl, cyclopropylmethylsulfinyl, C₃-haloalkynylsulfinyl, S(O)CH₂CH₂NH₂, cyclopropylsulfonyl, cyclopropylmethylsulfonyl, allylsulfonyl, C₃-haloalkenylsulfonyl or SO₂CH₂CH₂NH₂.

(15) Compounds of Formula I wherein
R₂ is OCF₂H, C₂-C₆ haloalkoxy, C₁-C₆ alkenyloxy, C₂-C₆ haloalkenyloxy, C₂-C₄ alkoxyalkoxy, C₂-C₄ haloalkoxyalkoxy, C₁-C₄ alkylthioalkoxy, C₂-C₄ haloalkylthioalkoxy, C₂-C₄ alkylsulfinylalkoxy, C₂-C₄ haloalkylsulfinylalkoxy, C₂-C₄ alkylsulfonylalkoxy, C₂-C₄ haloalkylsulfonylalkoxy, SCF₂H, C₂-C₆ haloalkylthio, C₂-C₆ alkenylthio, C₂-C₆ haloalkenylthio, C₂-C₄ alkoxyalkylthio, C₂-C₄ haloalkoxyalkylthio, C₂-C₄ alkylthioalkylthio, C₂-C₄ haloalkylthioalkylthio, C₁-C₆ haloalkylsulfinyl. C₂-C₆ alkenylsulfinyl, C₂-C₆ haloalkenylsulfinyl, C₂-C₄alkoxyalkylsulfinyl, C₂-C₄ haloalkoxyalkylsulfinyl, C₁-C₆ haloalkylsulfonyl, C₂-C₆ alkenylsulfonyl, C₂-C₆ haloalkenylsulfonyl, C₂-C₄ alkoxyalkylsulfonyl or C₂-C₄ haloalkoxyalkylsulfonyl,

(16) Compounds of Preferred 15 wherein

R$_2$ OCF$_2$H, C$_2$–C$_3$ haloalkoxy, C$_2$–C$_3$ alkenyloxy, C$_2$–C$_3$ haloalkenyloxy, C$_2$–C$_3$ alkoxyalkoxy, C$_2$–C$_3$ haloalkoxyalkoxy, C$_2$–C$_3$ alkylthioalkoxy, C$_2$–C$_3$ haloalkylthioalkoxy, C$_2$–C$_3$ alkylsulfinylalkoxy, C$_2$–C$_3$ haloalkylthioalkoxy, C$_2$–C$_3$ alkylsulfinylalkoxy, C$_2$–C$_3$ haloalkylsulfinylalkoxy, C$_2$–C$_3$ haloalkylsulfonylalkoxy, C$_2$–C$_3$ alkylsulfonylalkoxy, SCF$_2$H, C$_2$–C$_3$ haloalkylthio, C$_2$–C$_3$ alkenylthio, C$_2$–C$_3$ haloalkenylthio, C$_2$–C$_3$ alkoxyalkylthio, C$_2$–C$_3$ haloalkoxyalkylthio, C$_2$–C$_3$ alkylthioalkylthio, C$_2$–C$_3$ haloalkylthioalkylthio, C$_1$–C$_3$ haloalkylsulfinyl, C$_2$–C$_3$ alkenylsulfinyl, C$_1$–C$_3$ haloalkenylsulfinyl, C$_2$–C$_3$ alkoxyalkylsulfinyl, C$_2$–C$_3$ haloalkoxyalkylsulfinyl, C$_1$–C$_3$ haloalkylsulfonyl, C$_1$–C$_3$ alkenylsulfonyl, C$_2$–C$_3$ haloalkenylsulfonyl, C$_2$–C$_3$ alkoxysulfonyl, alkylsulfonyl or C$_2$–C$_3$ haloalkoxyalkyl

(17) Compounds of Preferred 16 wherein
R$_2$ is OCF$_2$H, OCH$_2$C$_3$, allyloxy, C$_3$-haloalkenyloxy,

(18) Compounds of Formula I wherein
R$_2$ is C$_3$–C$_6$ alkynyloxy, C$_3$–C$_6$ alkynylthio, C$_3$–C$_6$ alkynylsulfinyl or C$_3$–C$_6$ alkynylsulfonyl.

(19) Compounds of Preferred 18 wherein
R$_2$ is C$_3$–C$_2$ alkynyloxy, C$_3$–C$_4$ alkynylthio, C$_3$–C$_4$ alkynylsulfinyl or C$_3$–C$_4$ alkynylsulfonyl.

(20) Compounds of Preferred 19 wherein
R$_2$ is propargyloxy, propargylthio, propargylsulfinyl or propargylsulfonyl.

(21) Compounds of Formula I wherein
R$_2$ is OCF$_2$H, C$_2$–C$_6$ haloalkenyloxy, C$_2$–C$_4$ alkoxyalkoxy, C$_1$–C$_4$ haloalkoxy, C$_2$–C$_4$ alkylthioalkoxy, C$_2$–C$_4$ haloalkylthioalkoxy, C$_2$–C$_4$ alkylsulfinylalkoxy, C$_2$–C$_4$ haloalkylsulfinylalkoxy C$_2$–C$_4$ alkylsulfonylalkoxy, C$_1$–C$_4$ haloalkylsulfonylalkoxy, SCF$_2$ H, C$_2$–C$_6$ haloalkylthio, C$_1$214 C$_6$ haloalkenylthio, C$_2$–C$_4$ alkoxyalkylthio, C$_2$–C$_4$ haloalkoxyalkylthio, C$_2$–C$_4$ alkylthioalkylthio, C$_2$–C$_4$ haloalkylthioalkylthio, C$_1$–C$_6$ haloalkylsulfinyl, C$_2$–C$_6$ haloalkenylsulfinyl, C$_2$–C$_4$ alkoxyalkylsulfinyl, C$_1$–C$_4$ haloalkoxyalkylsulfinyl, C$_1$–C$_6$ haloalkylsulfonyl, C$_2$–C$_6$ haloalkenylsulfonyl, C$_2$–C$_4$ alkoxyalkylsulfonyl, or C$_2$–C$_4$ haloalkoxyalkylsulfonyl.

(22) Compounds of Preferred 21 wherein
R$_2$ is OCF$_2$H, C$_2$–C$_3$ haloalkoxy, C$_2$–C$_3$ haloalkenyloxy, C$_2$–C$_3$ alkoxyalkoxy, C$_2$–C$_3$ haloalkoxyalkoxy, C$_2$–C$_3$ alkylthioalkoxy, C$_2$–C$_3$ halo-alkylthioalkoxy, C$_2$–C$_3$ alkylsulfinylalkoxy, C$_2$–C$_3$ haloalkylsulfinylalkoxy, C$_2$–C$_3$ alkylsulfonylalkoxy, C$_2$–C$_3$ haloalkylsulfonylalkoxy, SCF$_2$H, C$_2$–C$_3$ haloalkylthio, C$_2$–C$_3$ alkenylthio, C$_2$–C$_3$ haloalkenylthio, C$_2$–C$_3$ alkoxyalkylthio, C$_2$–C$_3$ haloalkoxyalkylthio, C$_2$–C$_3$ alkylthioalkylthio, C$_2$–C$_3$ haloalkyl thioalkylthio, C$_1$–C$_3$ haloalkylsulfinyl, C$_2$–C$_3$ haloalkenylsulfinyl, C$_2$–C$_3$ alkoxyalkylsulfinyl, C$_2$–C$_4$ haloalkoxyalkylsulfinyl, C$_1$–C$_3$ haloalkylsulfonyl, C$_2$–C$_3$ haloalkenylsulfonyl, C$_2$–C$_3$ alkoxyalkylsulfonyl or C$_2$–C$_3$ haloalkoxyalkylsulfonyl.

(23) Compounds of Preferred 22 wherein
R$_2$ is OCF$_2$H, OCH$_2$CF$_3$, C$_3$-haloalkenyloxy,

(24) Compounds of Formula I wherein
R$_2$ is C$_2$–C$_6$ haloalkynyl,

(25) Compounds of Preferred 24 wherein
R$_2$ is C$_3$–C$_4$ haloalkynyl,

(26) Compounds of Preferred 25 wherein
R$_2$ is C$_3$-haloalkynyl.

(27) Compounds of Formula I wherein
R$_2$ is CH$_2$F, CHF$_2$, CH$_2$Cl, CHCl$_2$, CH$_2$Br, CHBr$_2$ or C$_2$–C$_6$ alkyl substituted with 1–3 atoms of F, Cl or Br.

(28) Compounds of Preferred 27 wherein
R$_2$ is CH$_2$F, CHF$_2$, CH$_2$Cl, CHCl$_2$, CH$_2$Br, CHBr$_2$ or C$_2$–C$_3$ alkyl substituted with 1–3 atoms of F, Cl or Br.

(29) Compounds of Preferred 28 wherein
R$_2$ is CH$_2$ F, CHF$_2$, CH$_2$Cl, CHCl$_2$, CH$_2$Br, CHBr$_2$, CH$_2$CHCl, CH$_2$CH$_2$F, CH$_2$CF$_3$, CF$_2$CF$_2$H or CF$_2$CF$_2$Cl.

(30) Compounds of Formula I wherein
R$_2$ is OCF$_2$H, C$_2$–C$_6$ haloalkoxy, C$_2$–C$_6$ haloalkenyloxy, C$_3$–C$_6$ alkynyloxy, C$_2$–C$_4$ alkoxyalkoxy, C$_2$–C$_4$ haloalkoxyalkoxy, C$_2$–C$_4$ alkylthioalkoxy, C$_2$–C$_4$ haloalkylthioalkoxy, C$_2$–C$_4$ alkylsulfinylalkoxy, C$_2$–C$_4$ haloalkylsulfinylalkoxy, C$_2$–C$_4$ alkylsulfonylalkoxy, C$_2$–C$_4$ haloalkylsulfonylalkoxy, SCF$_2$, H, C$_2$–C$_6$ haloalkylthio, C$_2$–C$_6$ haloalkenylthio, C$_3$–C$_6$ alkynylthio, C$_2$–C$_4$ alkoxyalkylthio, C$_2$–C$_4$ haloalkoxyalkylthio, C$_2$–C$_4$ alkylthioalkylthio, C$_2$–C$_4$ haloalkylthioalkylthio, C$_2$–C$_6$ haloalkylsulfinyl, C$_1$–C$_6$ haloalkenylsulfinyl, C$_3$–C$_6$ alkynylsulfinyl, C$_2$–C$_4$ alkoxyalkylsulfinyl, C$_2$–C$_4$ haloalkoxyalkylsulfinyl, C$_1$–C$_6$ haloalkylsulfonyl, C$_2$–C$_6$ haloalkenylsulfonyl, C$_3$–C$_6$ alkynylsulfonyl, C$_2$–C$_4$ alkoxyalkylsulfonyl or C$_2$–C$_4$ haloalkoxyalkylsulfonyl.

(31) Compounds of Preferred 30 wherein
R$_2$ is OCF$_2$H, C$_2$–C$_3$ haloalkoxy, C$_2$–C$_3$ haloalkenyloxy, C$_3$–C$_4$ alkynyloxy, C$_2$–C$_3$ alkoxyalkoxy, C$_2$–C$_3$ haloalkoxyalkoxy, C$_2$–C$_3$ alkylthioalkoxy, C$_2$–C$_3$ haloalkylthioalkoxy, C$_2$–C$_3$ alkylsulfinylalkoxy, C$_2$–C$_3$ haloalkylsulfinylalkoxy, C$_2$–C$_3$ alkylsulfonylalkoxy. C$_2$–C$_3$ haloalkylsulfonylalkoxy, SCF$_2$H, C$_2$–C$_3$ haloalkylthio, C$_2$–C$_3$ haloalkenylthio, C$_2$–C$_4$ alkynylthio, C$_2$–C$_3$ alkoxyalkylthio, C$_2$–C$_3$ haloalkoxyalkylthio, C$_2$–C$_3$ alkylthioalkylthio, C$_2$–C$_3$ haloalkylthioalkylthio, C$_1$–C$_3$ haloalkylsulfinyl, C$_2$–C$_3$ haloalkenylsulfinyl, C$_3$–C$_4$ alkynylsulfinyl, C$_2$–C$_3$ alkoxyalkylsulfinyl, C$_2$–C$_3$ haloalkoxyalkylsulfinyl, C$_1$–C$_3$ haloalkylsulfonyl, C$_2$–C$_3$ haloalkenylsulfonyl, C$_3$–C$_4$ alkynylsulfonyl, C$_2$–C$_3$ alkoxyalkylsulfonyl or C$_2$–C$_3$ haloalkoxyalkylsulfonyl.

(32) Compounds of Preferred 31 wherein
R$_2$ is OCF$_2$H, OCH$_2$CF$_3$-haloalkenyloxy, propargyloxy, OCH$_2$CH$_2$OCH$_3$, OCH$_2$OCH$_2$CF$_3$, OCH$_2$CH$_2$SCH$_3$, OCH$_2$SCH$_2$CF$_3$, OCH$_2$CH$_2$S(O)CH$_3$, OCH$_2$S(O)CH$_2$CF$_3$, OCH$_2$CH$_2$SO$_2$CH$_3$, OCH$_2$SO$_2$CH$_2$CF$_3$, SCF$_2$H, SCH$_2$CF$_3$, C$_2$-haloalkenylthio, propargylthio, SCH$_2$CH$_2$OCH$_3$, SCH$_2$OCH$_2$CF$_3$, SCH$_2$CH$_2$SCH$_3$, SCH$_2$SCH$_2$CF$_3$, S(O)CH$_2$CF$_3$, C$_2$-haloalkenylsulfinyl, propargylsulfinyl, S(O)CH$_2$CH$_2$OCH$_3$, S(O)CH$_2$OCH$_2$CF$_3$, SO$_2$CH$_2$CF$_3$, C$_2$-haloalkenylsulfonyl, propargylsulfonyl, SO$_2$CH$_2$CH$_2$PCH$_3$ or SO$_2$CH$_2$OCH$_2$CF$_3$.

(33) Compounds of Formula I wherein
R$_2$ is C$_2$–C$_6$ haloalkenyl.

(34) Compounds of Preferred 33 wherein
R$_2$ is C$_2$–C$_3$ haloalkenyl.

(35) Compounds of Preferred 34 wherein
R$_2$ is CF$_2$=CFCl or CF=CFCF$_3$.

(36) Compounds of Formula I wherein
R$_2$ is C$_3$–C$_6$ cycloalkoxy, C$_4$–C$_6$ cycloalkylalkoxy, C$_2$–C$_4$ cyanoalkoxy, OCH$_2$C(O)CH$_3$, OCH$_2$CH$_2$C(O)CH$_3$, C$_2$–C$_4$ aminoalkoxy, C$_3$–C$_6$ cycloalkylthio, C$_4$–C$_6$ cycloalkylalkylthio, C$_2$–C$_4$ cyanoalkylthio, SCH$_2$C(O)CH$_3$, SCH$_2$CH$_2$C(O)CH$_3$, C$_2$–C$_4$ aminoalkylthio, SC$_6$H$_5$, SCH$_2$C$_6$H$_5$, C$_3$–C$_6$ cycloalkylsulfinyl, C$_4$–C$_6$ cycloalkylalkylsulfinyl, C$_2$–C$_4$ cyanoalkylsulfinyl, S(O)CH$_2$C(O)CH$_3$, S(O)CH$_2$CH$_2$C(O)CH$_3$, C$_2$–C$_4$ aminoalkylsulfinyl, C$_3$–C$_6$ cycloalkylsulfonyl, C$_4$–C$_6$ cycloalkylalkylsulfonyl, C$_2$–C$_4$ cyanoalkylsulfonyl, $SO_2CH_2C(O)CH_3$, $SO_2CH_2CH_2C(O)CH_3$, $C_2$-$C_4$ aminoalkylsulfonyl or $OC(O)C_1$-$C_4$ alkyl.

(37) Compounds of Preferred 36 wherein $R_2$ is $C_3$-$C_4$ cycloalkoxy. $C_4$-$C_5$ cycloalkylalkoxy, $C_2$-$C_3$ cyanoalkoxy, $OCH_2C(O)CH_3$, $OCH_2CH_2C(O)CH_3$, $C_2$-$C_3$ aminoalkoxy, $C_3$-$C_4$ cycloalkylthio, $C_4$-$C_5$ cycloalkylalkylthio, $C_2$-$C_3$ cyanoalkylthio, $SCH_2C(O)CH_3$, $SCH_2CH_2C(O)CH_3$, $C_2$-$C_3$ aminoalkylthio, $SCH_6H_5$, $SCH_2C_6H_5$, $C_3$-$C_4$ cycloalkylsulfinyl, $C_4$-$C_5$ cycloalkylalkylsulfinyl, $C_2$-$C_3$ cyanoalkylsulfinyl, $S(O)CH_2C(O)CH_3$, $S(O)CH_2CH_2C(O)CH_3$, $C_2$-$C_3$ aminoalkylsulfinyl, $C_3$-$C_4$ cycloalkylsulfonyl, $C_4$-$C_5$ cycloalkylalkylsulfonyl, $C_2$-$C_3$ cyanoalkylsulfonyl, $SO_2CH_2C(O)CH_3$, $SO_2CH_2CH_2C(O)CH_3$, $C_2$-$C_3$ aminoalkylsulfonyl or $OC(O)C_1$-$C_2$ alkyl.

(38) Compounds of Preferred 37 wherein $R_2$ is cyclopropoxy, cyclopropylmethoxy, $OCHCH_2CN$, $OCH_2C(O)CH_3$, $OCH_2CH_2C(O)CH_3$, $OCH_2CH_2NH_2$, cyclopropylthio, cyclopropylmethylthio, $SCH_2CH_2CN$, $SCH_2(O)CH_3$, $SCH_2CH_2C(O)CH_3$, $SCH_2CH_2NH_2$, $SCH_2C_6H_5$, cyclopropylsulfinyl, cyclopropylmethylsulfinyl, $S(O)CH_2CH_2CH$, $S(O)CH_2C(O)CH_3$, $S(O)CH_2CH_2C(O)CH_3$, $S(O)CH_2CH_2NH_2$, cyclopropylsulfonyl, cyclopropylmethylsulfonyl, $SO_2CH_2CH_2CN$, $SO_2CH_2C(O)CH_3$, $SO_2CH_2CH_2C(O)CH_3$, $SO_2CH_2CH_2NH_2$ or $OC(O)CH_3$.

(39) Compounds of Formula I wherein $R_2$ is $CH_2OC_1$-$C_4$ haloalkyl of 1 or 2 halogens, $CH(CH_3)OC_1$-$C_4$ haloalkyl of 1 or 2 halogens, $C(CH_3)_2OC_1$-$C_4$ haloalkyl of 1 or 2 halogens, $CH(CH_2CH_3)OC_1$-$C_4$ haloalkyl of 1 or 2 halogens, $C(CH_3)(CH_2CH_3)OC_1$-$C_4$ haloalkyl of 1 or 2 halogens, $CH(CH_2CH_2CH_3)OC_1$-$C_4$ haloalkyl of 1 or 2 halogens, $CH[CH(CH_3)_2]OC_1$-$C_4$ haloalkyl of 1 or 2 halogens. $CH_2OC_2$-$C_4$ haloalkenyl, $CH(CH_3)OC_2$-$C_4$ haloalkenyl, $C(CH_3)_2OC_2$-$C_4$ haloalkenyl, $CH(CH_2CH_3)OC_2$-$C_4$ haloalkenyl, $C(CH_3)(CH_2CH_3)OC_2$-$C_4$ haloalkenyl, $CH(CH_2CH_2CH_3)OC_2$-$C_4$ haloalkenyl, $CH[CH(CH_3)_2]PC_2$-$C_4$ haloalkenyl, $CH_2OC_3$-$C_4$ alkynyl, $CH(CH_3)OC_3$-$C_4$ alkynyl, $C(CH_2CH_3)OC_3$-$C_4$ alkynyl, $C(CH_3)(CH_2CH_3)OC_3$-$C_4$ alkynyl, $CH(CH_2CH_2CH_3)OC_3$-$C_4$ alkynyl, $CH[CH(CH_3)_2]OC_3$-$C_4$ alkynyl, $C(CH_3)_2OC_3$-$C_4$ alkynyl, $CH_2OC_2$-$C_4$ alkoxyalkyl, $CH(CH_2)OC_2$-$C_4$ alkoxyalkyl, $C(CH_3)_2OC_2$-$C_4$ alkoxyalkyl, $CH(CH_2CH_3)OC_2$-$C_4$ alkoxyalkyl, $C(CH_3)(CH_2CH_3)OC_2$-$C_4$ alkoxyalkyl, $CH(CH_2CH_2CH_3)OC_2$-$C_4$ alkoxyalkyl, $CH[CH(CH_3)_2]OC_2$-$C_4$ alkoxyalkyl, $CH_2SC_1$-$C_4$ haloalkyl of 1 or 2 halogen, $CH(CH_3)SC_1$-$C_4$ haloalkyl of 1 or 2 halogens, $C(CH_3)_2SC_1$-$C_4$ haloalkyl of 1 or 2 halogens, $CH(CH_2)SC_1$-$C_4$ haloalkyl of 1 or 2 halogens, $C(CH_3)(CH_3)SC_1$-$C_4$ haloalkyl of 1 or 2 halogens, $CH(CH_3)(CH_2CH_3)SC_1$-$C_4$ haloalkyl of 1 or 2 halogens, $CH[CH(CH_3)_2]SC_1$-$C_4$ haloalkyl of 1 or 2 halogens, $CH_2SC_2$-$C_4$ haloalkenyl, $CH(CH_3)SC_2$-$C_4$ haloalkenyl. $C(CH_3)_2SC_2$-$C_4$ haloalkenyl, $CH(CH_2CH_3)SC_2$-$C_4$ haloalkenyl, $C(CH_3)(CH_2CH_3)SC_2$-$C_4$ haloalkenyl, $CH(CH_2CH_2CH_3)SC_2$-$C_4$ haloalkenyl, $CH[CH(CH_3)_2]SC_2$-$C_4$ haloalkenyl, $CH_2SC_3$-$C_4$ alkynyl, $CH(CH_3)SC_3$-$C_4$ alkynyl, $C(CH_3)_2SC_3$-$C_4$ alkynyl, $CH(CH_2CH_3)SC_3$-$C_4$ alkynyl, $C(CH_3)(CH_2CH_3)SC_3$-$C_4$ alkynyl, $CH(CH_2CH_2CH_3)SC_3$-$C_4$ alkynyl, $CH[CH(CH_3)_2]SC_3$-$C_4$ alkynyl, $CH_2SC_2$-$C_4$ alkoxyalkyl, $CH(CH_3)SC_2$-$C_4$ alkoxyalkyl, $C(CH_3)_2SC_2$-$C_4$ alkoxyalkyl, $CH(CH_2CH_3)SC_2$-$C_4$ alkoxyalkyl, $C(CH_3)(CH_2CH_3)SC_2$-$C_4$ alkoxyalkyl, $CH(CH_2CH_2CH_3)SC_2$-$C_4$ alkoxyalkyl, $CH[CH(CH_3)_2]SC_2$-$C_4$ alkoxyalkyl, $CH_2S(O)C_1$-$C_4$ haloalkyl of 1 or 2 halogens, $CH(CH_3)S(O)C_1$-$C_4$ haloalkyl of 1 or 2 halogens, $C(CH_3)_2S(O)C_1$-$C_4$ haloalkyl of 1 or 2 halogens, $CH(CH_2hd 3)S(O)C_1$-$C_4$ haloalkyl of 1 or 2 halogens, $C(CH_3)(CH_2CH_3)S(O)C_1$-$C_4$ haloalkyl of 1 or 2 halogens, $CH(CH_2CH_2CH_3)S(O)C_1$-$C_4$ haloalkyl of 1 or 2 halogens, $CH[CH(CH_3)_2]S(O)C_1$-$C_4$ haloalkyl of 1 or 2 halogens, $CH_2S(O)C_2$-$C_4$ haloalkenyl, $CH(CH_3)S(O)C_2$-$C_4$ haloalkenyl, $C(CH_3)_2S(O)C_2$-$C_4$ haloalkenyl, $CH(CH_2CH_3)S(O)C_2$-$C_4$ haloalkenyl, $C(CH_3)(CH_2CH_3)S(O)C_2$-$C_4$ haloalkenyl, $CH(CH_2CH_2CH_3)S(O)C_2$-$C_4$ haloalkenyl, $CH[CH(CH_3)_2]S(O)C_2$-$C_4$ haloalkenyl, $CH_2S(O)C_3$-$C_4$ alkynyl, $CH(CH_3)S(O)C_3$-$C_4$ alkynyl, $C(CH_3)_2S(O)C_3$-$C_4$ alkynyl, $CH(CH_2CH_3)S(O)C_3$-$C_4$ alkynyl, $C(CH_3)(CH_2CH_3)S(O)C_3$-$C_4$ alkynyl, $CH(CH_2CH_2CH_3)S(O)C_3$-$C_4$ alkynyl, $CH[CH(CH_3)_2]S(O)C_3$-$C_4$ alkynyl, $CH_2S(O)C_2$-$C_4$ alkoxyalkyl, $CH(CH_3)S(O)C_2$-$C_4$ alkoxyalkyl, $C(CH_3)_2S(O)C_2$-$C_4$ alkoxyalkyl, $CH(CH_2CH_3)S(O)C_2$-$C_4$ alkoxyalkyl, $C(CH_3)(CH_2CH_3)S(O)C_2$-$C_4$ alkoxyalkyl, $CH(CH_2CH_2CH_3)S(O)C_2$-$C_4$ alkoxyalkyl, $CH[CH(CH_3)_2]S(O)C_2$-$C_4$ alkoxyalkyl, $CH_2SO_2C_1$-$C_4$ haloalkyl of 1 or 2 halogens, $CH(CH_3)SO_2C_1$-$C_4$ haloalkyl of 1 or 2 halogens, $C(CH_3)_2SO_{C1}$-$C_4$ haloalkyl of 1 or 2 halogens, $CH(CH_2CH_3)SO_2C_1$-$C_4$ haloalkyl of 1 or 2 halogens, $C(CH_3)(CH_2CH_3)SO_2C_1$-$C_4$ haloalkyl of 1 or 2 halogens, $CH(CH_2CH_2CH_3)SO_2C_1$-$C_4$ haloalkyl of 1 or 2 halogens $CH[CH(CH_3)_2]SO_2C_1$-$C_4$ haloalkyl of 1 or 2 halogens. $H_2SO_2C_2$-$C_4$ haloalkenyl, $CH(CH_3)SO_2C_2$-$C_4$ haloalkenyl, $C(CH_3)_2SO_2C_2$-$C_4$ haloalkenyl, $CH(CH_2CH_3)SOC_2$-$C_4$ haloalkenyl, $C(CH_3)(CH_2CH_3)SO_2C_2$-$C_4$ haloalkenyl, $CH(CH_2CH_2CH_3)SO_2C_2$-$C_4$ haloalkenyl, $CH[CH(CH_3)_2]SO_2C_2$-$C_4$ haloalkenyl, $CH_2SO_2C_3$-$C_4$ alkynyl, $CH(CH_3)SO_2C_3$-$C_4$ alkynyl, $C(CH_3)_2SO_2C_3$-$C_4$ alkynyl, $CH(CH_2CH_3)SO_2C_3$-$C_4$ alkynyl, $C(CH_3)(CH_2CH_3)SO_2C_3$-$C_4$ alkynyl, $CH(CH_2CH_2CH_3)SO_2C_3$-$C_4$ alkynyl, $CH[CH(CH_3)_2]SO_2C_3$-$C_4$ alkynyl, $CH_2SO_2C_2$-$C_4$ alkoxyalkyl, $CH(CH_3)SO_2C_2$-$C_4$ alkoxyalkyl, $C(CH_3)_2SO_2C_2$-$C_4$ alkoxyalkyl, $CH(CH_2CH_3)SO_2C_2$-$C_4$ alkoxyalkyl, $C(CH_3)(CH_2CH_3)SO_2C_2$-$C_4$ alkoxyalkyl, $CH(CH_2CH_2CH_3)SO_2C_2$-$C_4$ alkoxyalkyl, $CH[CH(CH_3)_2]SO_2C_2$-$C_4$ alkoxyalkyl, $CH_2CH_2OC_1$-$C_4$ alkyl, $CH_2CH_2CH_2OC_1$-$C_4$ alkyl, $CH_2CH_2CH_2CH_2OC_1$-$C_4$ alkyl, $CH(CH_3)CH_2OC_1$-$C_4$ alkyl, $C(CH_3)_2CH_2OC_1$-$C_4$ alkyl, $CH(CH_2CH_3)CH_2OC_1$-$C_4$ alkyl, $CH_2CH(CH_3)OC_1$-$C_4$ alkyl, $CH_2C(CH_3)_2OC_1$-$C_4$ alkyl, $CH_2CH(CH_2CH_3)OC_1$-$C_4$ alkyl, $CH(CH_3)CH(CH_3)OC_1$-$C_4$ alkyl, $CH_2CH_2OC_1$-$C_4$ haloalkyl, $CH_2CH_2CH_2OC_1$-$C_4$ haloalkyl, $CH_2CH_2CH_2CH_2OC_1$-$C_4$ haloalkyl, $CH_2(CH_3)CH_2OC_1$-$C_4$ haloalkyl, $C(CH_2)_2CH_2OC_1$-$C_4$ haloalkyl, $CH(CH_2CH_3)CH_2OC_1$-$C_4$ haloalkyl, $CH_2CH(CH_3)OC_1$-$C_4$ haloalkyl, $CH_2C(CH_3)_2OC_1$-$C_4$ haloalkyl, $CH_2CH(CH_2CH_3)OC_1$-$C_4$ haloalkyl, $CH(CH_3)CH(CH_3)OC_1$-$C_4$ haloalkyl, $CH_2CH_2OC_1$-$C_4$ alkylcarbonyl, $CH_2CH_2CH_2OC_1$-$C_4$ alkylcarbonyl, $CH_2CH_2CH_2CH_2OC_1$-$C_4$ alkylcarbonyl, $CH(CH_3)CH_2OC_1$-$C_4$ alkylcarbonyl, $C(CH_3)_2CH_2OC_1$-$C_4$ alkylcarbonyl, $CH(CH_2CH_3)CH_2OC_1$-$C_4$ alkylcarbonyl, $CH_2CH(CH_3)OC_1$-$C_4$ alkylcarbonyl, $CH_2C(CH_3)_2OC_1$-$C_4$ alkylcarbonyl, CH₂CH(CH₂CH₃)OC₁-C₄ alkylcarbonyl, CH(CH₃)CH(CH₃)OC₁-C₄ alkylcarbonyl, CH₂CH₂OC₁-C₄ haloalkylcarbonyl, CH₂CH₂CH₂OC₁-C₄ haloalkylcarbonyl, CH₂CH₂CH₂CH₂OC₁-C₄ haloalkylcarbonyl, CH(CH₃)CH₂OC₁-C₄ haloalkylcarbonyl, C(CH₃)₂CH₂OC₁-C₄ haloalkylcarbonyl, CH(CH₂CH₃)CH₂OC₁-C₄ haloalkylcarbonyl, CH₂CH(CH₃)OC₁-C₄ haloalkylcarbonyl, CH₂C(CH₃)₂OC₁-C₄ haloalkylcarbonyl, CH₂CH(CH₂CH₃)OC₁-C₄ haloalkylcarbonyl, CH(CH₃)CH(CH₃)OC₁-C₄ haloalkylcarbonyl, CH₂CH₂OC₁-C₄ alkoxycarbonyl, CH₂CH₂CH₂OC₁-C₄ alkoxycarbonyl, CH₂CH₂CH₂CH₂OC₁-C₄ alkoxycarbonyl, CH(CH₃)CH₂OC₁-C₄ alkoxycarbonyl, C(CH₃)₂CH₂OC₁-C₄ alkoxycarbonyl, CH₂(CH₂CH₃)CH₂OC₁-C₄ alkoxycarbonyl, CH₂CH(CH₃)OC₁-C₄ alkoxycarbonyl, CH₂C(CH₃)₂OC₁-C₄ alkoxycarbonyl, CH₂CH(CH₂CH₃)OC₁-C₄ alkoxycarbonyl, CH(CH₃)CH(CH₃)OC₁-C₄ alkoxycarbonyl, CH₂CH₂OH, CH₂CH₂CH₂OH, CH₂CH₂CH₂CH₂OH, CH(CH₃)CH₂OH, C(CH₃)₂CH₂OH, CH(CH₂CH₃)CH₂OH, CH₂CH(CH₃)OH, CH₂C(CH₃)₂OH, CH₂CH(CH₂CH₃)OH, (CH₃)CH(CH₃)OH, CH₂CH₂OC₁-C₄ alkylsulfonyl, CH₂CH₂CH₂OC₁-C₄ alkylsulfonyl, CH₂CH₂CH₂CH₂OC₁-C₄ alkylsulfonyl, CH(CH₃)CH₂OC₁-C₄ alkylsulfonyl, C(CH₃)₂CH₂OC₁-C₄ alkylsulfonyl, CH(CH₂CH₃)CH₂OC₁-C₄ alkylsulfonyl, CH₂CH(CH₃)OC₁-C₄ alkylsulfonyl, CH₂C(CH₃)₂OC₁-C₄ alkylsulfonyl, CH₂CH(CH₂CH₃)OC₁-C₄ alkylsulfonyl, CH(CH₃)CH(CH₃)OC₁-C₄ alkylsulfonyl, CH₂CH₂OC₁-C₄ haloalkylsulfonyl, CH₂CH₂CH₂OC₁-C₄ haloalkylsulfonyl, CH₂CH₂CH₂CH₂OC₁-C₄ haloalkylsulfonyl, CH(CH₃)CH₂OC₁-C₄ haloalkylsulfonyl, C(CH₃)₂CH₂OC₁-C₄ haloalkylsulfonyl, CH(CH₂CH₃)CH₂OC₁-C₄ haloalkylsulfonyl, CH₂CH(CH₃)OC₁-C₄ haloalkylsulfonyl, CH₂C(CH₃)₂OC₁-C₄ haloalkylsulfonyl, CH₂CH(CH₂CH₃)OC₁-C₄ haloalkylsulfonyl, CH(CH₃)CH(CH₃)OC₁-C₄ haloalkylsulfonyl, CH₂CH₂SC₁-C₄ alkyl, CH₂CH₂CH₂SC₁-C₄ alkyl, CH₂CH₂CH₂CH₂SC₁-C₄ alkyl, CH(CH₃)CH₂SC₁-C₄ alkyl, CH(CH₃)CH₂SC₁-C₄ alkyl, C(CH₃)₂CH₂SC₁-C₄ alkyl, CH(CH₂CH₃)CH₂SC₁-C₄ alkyl, CH₂CH(CH₃)SC₁-C₄ alkyl, CH₂C(CH₃)₂SC₁-C₄ alkyl, CH₂CH(CH₂CH₃)SC₁-C₄ alkyl, CH(CH₃)CH(CH₃)SC₁-C₄ alkyl, CH₂CH₂SC₁-C₄ haloalkyl, CH₂CH₂CH₂SC₁-C₄ haloalkyl, CH₂CH₂CH₂CH₂SC₁-C₄ haloalkyl, CH(CH₃)CH₂SC₁-C₄ haloalkyl, C(CH₃)₂CH₂SC₁-C₄ haloalkyl, CH(CH₂CH₃)CH₂SC₁-C₄ haloalkyl, CH₂CH(CH₃)SC₁-C₄ haloalkyl, CH₂C(CH₃)₂SC₁-C₄ haloalkyl, CH₂CH(CH₂CH₃)SC₁-C₄ haloalkyl, CH(CH₃)CH(CH₃)SC₁-C₄ haloalkyl, CH₂CH₂S(O)C₁-C₄ alkyl, CH₂CH₂CH₂S(O)C₁-C₄ alkyl, CH₂CH₂CH₂CH₂S(O)C₁-C₄ alkyl, CH(CH₃)CH₂S(O)C₁-C₄ alkyl, C(CH₃)₂CH₂S(O)C₁-C₄ alkyl, CH(CH₂CH₃)CH₂S(O)C₁-C₄ alkyl, CH₂CH(CH₃)S(O)C₁-C₄ alkyl, CH₂C(CH₃)₂S(O)C₁-C₄ alkyl, CH₂CH(CH₂CH₃)S(O)C₁-C₄ alkyl, CH(CH₃)CH(CH₃)S(O)C₁-C₄ alkyl, CH₂CH₂SO₂C₁-C₄ alkyl, CH₂CH₂CH₂SO₂C₁-C₄ alkyl, CH₂CH₂CH₂CH₂SO₂C₁-C₄ alkyl, CH(CH₃)CH₂SO₂C₁-C₄ alkyl, C(CH₃)₂CH₂SO₂C₁-C₄ alkyl, CH(CH₂CH₃)CH₂SO₂C₁-C₄ alkyl, CH₂CH(CH₃)SO₂C₁-C₄ alkyl, CH₂C(C₃)₂SO₂C₁-C₄ alkyl, CH₂CH(CH₂CH₃)SO₂C₁-C₄ alkyl, or CH(CH₃)CH(CH₃)SO₂C₁-C₄ alkyl.

(40) Compounds of Preferred 39 wherein

R₂ is CH₂OC₁-C₂ haloalkyl of 1 or 2 halogens, CH₂OC₁-C₃ haloalkenyl, CH₂OC₃-C₄ alkynyl, CH₂OC₁-C₃ alkoxyalkyl, CH₂SC₁-C₂ haloalkyl of 1 or 2 halogens, CH₂SC₂-C₃ haloalkenyl, CH₂SC₃-C₄ alkynyl, CH₂SC₂-C₃ alkoxyalkyl, CH₂S(O)C₁-C₂ haloalkyl of 1 or 2 halogens, CH₂S(O)C₂-C₃ haloalkenyl, CH₂S(O)C₃-C₄ alkynyl, CH₂S(O)C₂-C₃ alkoxyalkyl, CH₂SO₂C₁-C₂ haloalkyl of 1 or 2 halogens, CH₂SO₂C₂-C₃ haloalkenyl, CH₂SO₂C₃-C₄ alkynyl, CH₂SO₂C₂-C₃ alkoxyalkyl, CH₂CH₂OC₁-C₂ alkyl, CH₂CH₂OC₁-C₂ haloalkyl, CH₂CH₂OC₁-C₂ alkylcarbonyl, CH₂CH₂OC₁-C₂ haloalkylcarbonyl, CH₂CH₂OC₁-C₂ alkoxycarbonyl, CH₂CH₂OH, CH₂Ch₂OC₁-C₂ alkylsulfonyl, CH₂CH₂OC₁-C₂ haloalkylsulfonyl, CH₂CH₂SC₁-C₂ alkyl, CH₂CH₂SC₁-C₂ haloalkyl, CH₂CH₂S(O)C₁-C₂ alkyl or CH₂CH₂SO₂C₁-C₂ alkyl.

(41) Compounds of Preferred 40 wherein

R₂ is CH₂ OCF₂H, CH₂OCH₂CH₂F, CH₂OC₃ haloalkenyl, CH₂OCH₂C≡CH, CH₂OCH₂CH₂OCH₃, CH₂SCF₂H, CH₂SCH₂CH₂F, CH₂SC₂ haloalkenyl, CH₂SCH₂C≡CH, CH₂SCH₂CH₂S(O)CF₂H, CH₂S(O)CH₂CH₂F, CH₂S(O)C₂-haloalkenyl, CH₂S(O)CH₂C≡CH, CH₂(O)CH₂CH₂OCH₃, CH₂SO₂CF₂H, CH₂SO₂CH₂F, CH₂SO₂C₂-haloalkenyl, CH₂SO₂CH₂C≡CH, CH₂SO₂CH₂CH₂OCH₃, CH₂CH₂OCH₃, CH₂CH₂OCF₂H, CH₂CH₂OCH₂CF₃, CH₂CH₂OC(O)CH₃, CH₂CH₃OC(O)CF₃, CH₂CH₂OH, CH₂CH₂OSO₂CH₃, CH₂CH₂OSO₂CF₃, CH₂CH₂OSO₂CH₂CF₃, CH₂CH₂SCH₃, CH₂CH₂SCF₂H, CH₂CH₂SCH₂CF₃, CH₂CH₂S(O)CH₃ or CH₂CH₂SO₂CH₃.

A compound of the invention which is specifically preferred for its highest herbicidal activity, greatest plant growth regulant activity and/or most favorable ease of synthesis is:

2-[[(4,6-dimethoxypyrimidin-2-yl)aminocarbonyl]aminoaminosulfonyl]-4-(methylthio)benzoic acid, methyl ester. m.p. 201°-202° C.

DETAILED DESCRIPTION OF THE INVENTION

Synthesis

The compounds of Formula I can be prepared by one or more of the following methods described in Equations 1 to 3 and 14.

As shown in Equation 1, compounds of Formula I can be prepared by reacting an appropriately substituted sulfonyl isocyanate of Formula (1) with an appropriate amino or methylamino heterocycle of Formula (2).

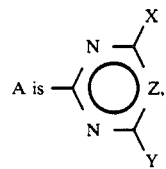

and R, R₁, R₂, X, Y and Z are as previously defined.

Equation 1

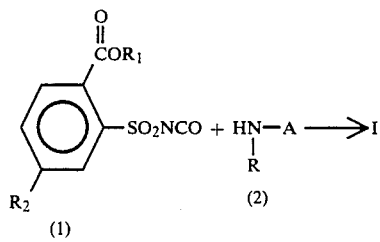

The reaction is best carried out in inert aprotic organic solvents such as dichloromethane, 1,2-dichloroethane, tetrahydrofuran, or acetonitrile, at a temperature between 20° and 85° C. The order of addition is not critical; however, it is often convenient to add the sulfonyl isocyanate or a solution of it in the reaction solvent to a stirred suspension of the amine.

In some cases, the desired product is insoluble in the reaction solvent at ambient temperature and crystallizes from it in pure form. Products soluble in the reaction solvent are isolated by evaporation of the solvent. Compounds of Formula I then may be purified by trituration of the evaporation residue with solvents such as 1-chlorobutane or ethyl ether and filtration, by recrystallization from mixtures of solvents such as 1,2-dichloroethane, 1-chlorobutane, and heptane, or by chromatography on silica gel.

Many of the compounds of Formula I can be prepared by the procedure shown in Equation 2, where A, R, $R_1$, and $R_2$ are as previously defined.

Equation 2

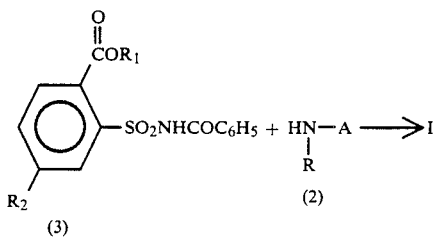

The reaction shown in Equation 2 is carried out by contacting phenyl carbamates of Formula (3) with aminoheterocycles of Formula (2) in an inert organic solvent such as dioxane or tetrahydrofuran at temperatures of about 20°–100° C. for a period of about one-half to twenty-four hours. The product can be isolated by evaporation of the reaction solvent and purified by methods previously described.

Phenyl carbamates of Formula (3) can be prepared by the methods described, or modifications thereof known to those skilled in the art, in European Patent Application No. 81810282.4 (Publication No. 44,808), published Jan. 27, 1982; or South African Patent Application No. 825042.

Alternatively, many of the compounds of Formula I can be prepared by the method described in Equation 3, where A, $R_1$, and $R_2$ are as previously defined and R is H.

Equation 3

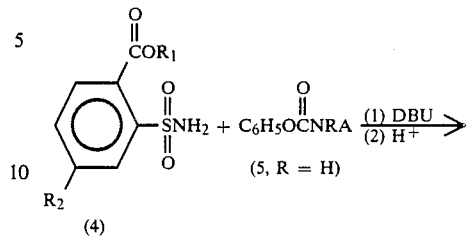

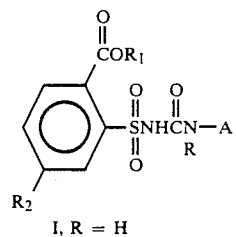

The reaction of Equation 3 can be carried out by contacting equimolar amounts of a sulfonamide of Formula (4) with a heterocyclic phenyl carbamate of Formula (5) in the presence of an equimolar amount of 1,8-diazabicyclo-[5,4,0]undec-7-ene (DBU), by methods analogous to those described in South African Patent Application No. 830441. The phenyl carbamate of Formula (5) can be prepared by methods or modifications thereof known to those skilled in the art, described in South African Patent Application No. 825671 and South African Patent Application No. 825045.

Some of the compounds of Formula I may be prepared from compounds of Formula 1 where $R_2$ is OH, $NR_bH$ or SH. See Equation 14 for a discussion of this method.

The unsubstituted and substituted alkoxy, alkenyloxy, and alkynyloxy benzenesulfonamide intermediates of Formula (4a) can be prepared by one or more of the following general methods.

As shown in Equation 4, one highly useful general route starts from the phenol (6).

Equation 4

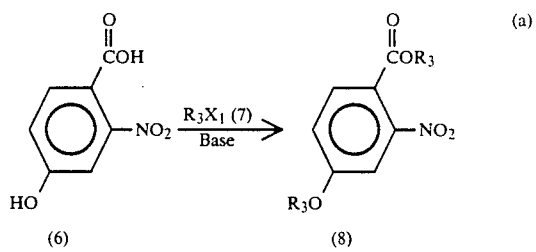

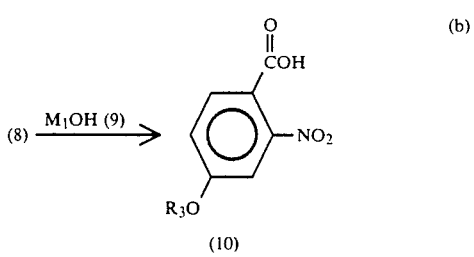

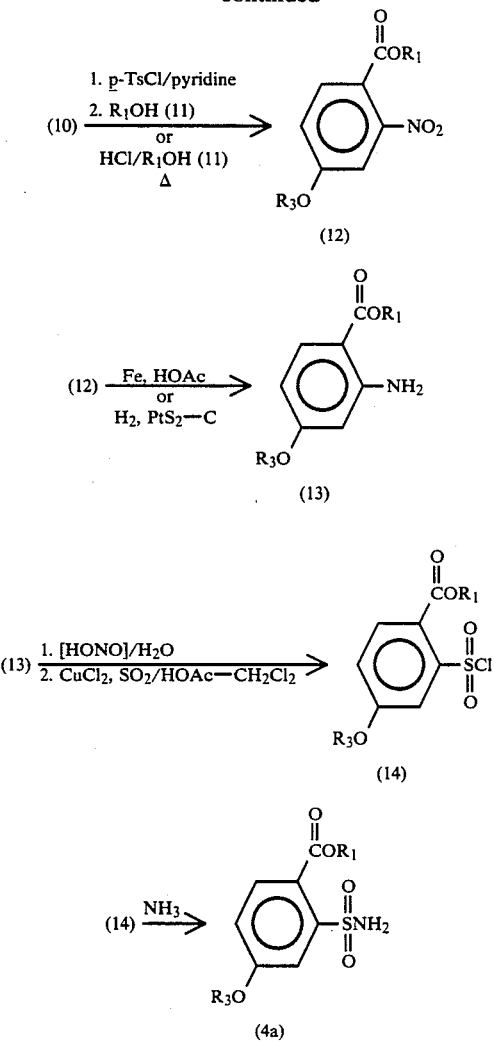

where $R_1$ is as previously defined, and $R_3$ is $C_2$–$C_6$ alkyl, $C_3$–$C_6$ cycloalkyl, $C_4$–$C_6$ cycloalkylalkyl, $C_1$–$C_6$ haloalkyl, $C_3$–$C_6$ alkenyl, $C_3$–$C_6$ haloalkenyl, $C_3$–$C_6$ haloalkynyl, $C_3$–$C_6$ alkynyl, $C_2$–$C_4$ alkoxyalkyl, $C_2$–$C_4$ haloalkoxyalkyl, $C_2$–$C_4$ alkylthioalkyl, $C_2$–$C_4$ haloalkythioalkyl, $CH_2C(O)CH_3$, $CH_2CH_2C(O)CH_3$, or benzyl, $M_1$ is Na or K. $X_1$ is Cl, Br, I,

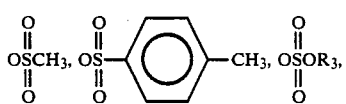

or $O(R_3)_2^\oplus \ BF_4^\ominus$, or

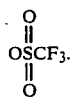

A solution or suspension of 4-hydroxy-2-nitrobenzoic acid (6) in a suitable polar aprotic solvent, such as dichloromethane or N,N-dimethylformamide (DMF). is treated with at least two equivalents of $R_3X_1$ (7) in the presence of at least two equivalents of a suitable base such as N,N-diisopropylethylamine or potassium carbonate and at a temperature between 20 and 155° C. for four to sixteen hours (Equation 4a). If the solvent is miscible with water, it is then evaporated, and the residue is taken up in dichloromethane. The product solution is washed with aqueous sodium or potassium carbonate solution and aqueous hydrochloric acid, and then is dried over a suitable desiccant such as magnesium sulfate. Filtration and evaporation of the solvent leaves (8) in semipurified form. It may be further purified through recrystallization or chromatography on a column of silica gel. The requisite alkylating, alkenylating, and alkynylating agents $R_3X_1$(7) are either known or may be made by a wide variety of methods known in the art.

In cases where $R_3$ is not the same as $R_1$, the ester (8) is treated with at least one equivalent of sodium or potassium hydroxide in a mixture of water and a suitable organic cosolvent such as ethanol or p-dioxane at a temperature between 20° and 100° C. for four to sixteen hours (Equation 4b). The reaction mixture is then acidified with concentrated hydrochloric acid. If the product separates out in crystalline form, it is collected. Otherwise the aqueous solution is extracted with ether. The ether solution is dried over sodium sulfate and filtered, and the solvent is evaporated to afford the carboxylic acid (10).

To convert carboxylic acid (10) to ester (12), a solution of it in pyridine is treated sequentially with p-toluenesulfonyl chloride and $R_1OH$ (11) according to the general procedure of J. H. Brewster and C. J. Ciotti, Jr., *J. Am. Chem. Soc.* 1955, 77, 6214.

Alternatively, the carboxylic acid (10) may be converted to ester (12) through the use of excess $R_1OH$ (11) and a strong acid catalyst such as hydrogen chloride as reviewed by C. A. Buehler and D. E. Pearson, *Survey of Organic Syntheses*, Wiley-Interscience, New York, 1970, pp 802–807 (Equation 4c).

The nitrobenzene (12) is reduced to the aniline (13) either by use of iron in acetic acid as reviewed by C. A. Buehler and D. E. Pearson (ibid, pp 413–414) or by hydrogenation using platinum sulfide as catalyst and the conditions of F. S. Dovel and H. Greenfield, *J Am. Chem. Soc.*, 87, 2767 (1965) (Equation 4d). When the other substituents present are not potentially susceptible to hydrogenation or hydrogenolysis, palladium may replace platinum sulfide as catalyst.

The aniline (13) is converted to the sulfonyl chloride (14) using the general procedures of H. Meerwein, G. Dittmar, R. Gollner, K. Hafner, F. Mensch, O. Steinfort, *Chem. Ber.* 90, 841 (1957) (Equation 4e). To limit the hydrolysis of the product during the coupling step, the use of dichloromethane as a cosolvent is advantageous.

Finally, the sulfonyl chloride (14) is aminated to give (4a) using two equivalents of ammonia in dichloromethane solution at a temperature between −30° and −10° C. (Equation 4f).

Alternatively, many of the sulfonamides of Formulae (4a) or (4c') can be prepared via the route shown in Equation 5.

Equation 5

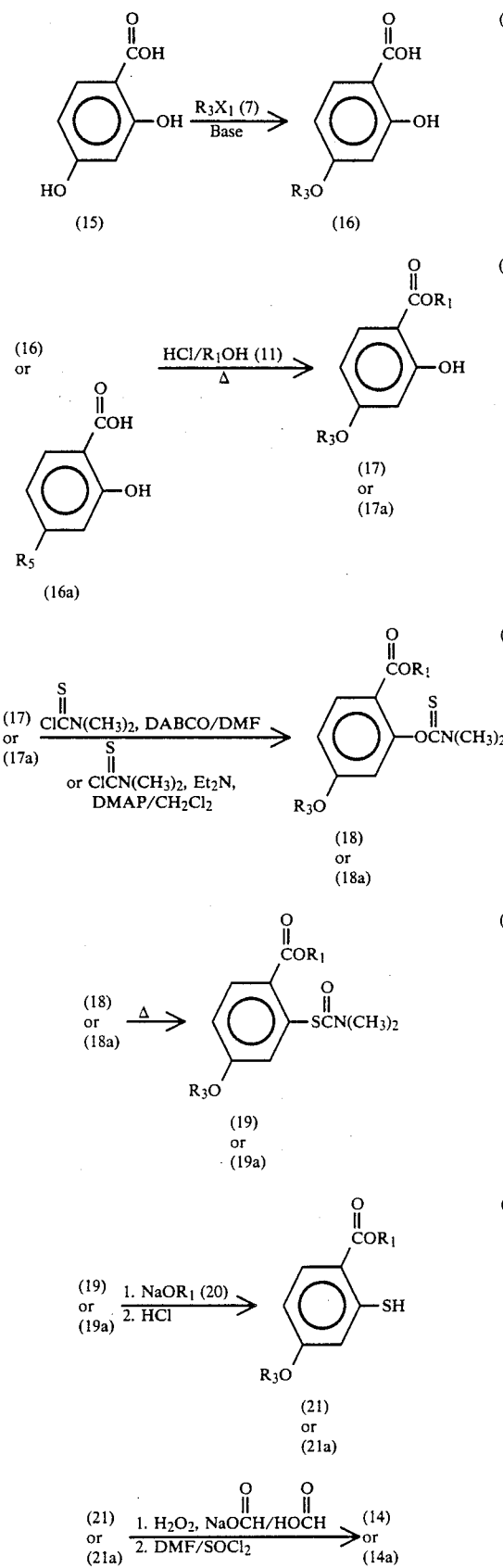

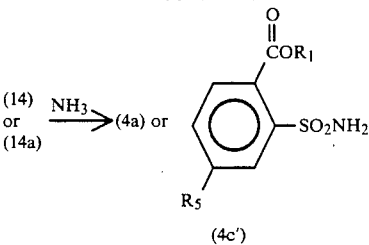

where $M_1$, $R_1$, $R_a$, $R_b$, and $X_1$ are as previously defined; $R_5$ is $C_1$-$C_6$ alkyl, $C_1$-$C_6$ haloalkyl or $CH_2C(O)NR_aR_b$; and $R_3$ is as previously defined or $C_2$-$C_4$ aminoalkyl but not $C_2$-$C_6$ alkenyl, $C_2$-$C_6$ haloalkenyl, $C_3$-$C_6$ alkynyl or $C_3$-$C_6$ haloalkynyl.

Phenol (15) is added to a solution of two equivalents of sodium in anhydrous methanol, ethanol, or amyl alcohol. A little more than one equivalent of $R_3X_1$ (7) is added and the mixture is heated at reflux for 4 to 24 hours. The solvent is removed in vacuo and the residue is partitioned between 1N hydrochloric acid and ether. The ether phase is dried over sodium sulfate, and filtered. Evaporation of the ether leaves the phenol (16) (Equation 5a).

In Equations 5b, c, d, e and f compounds 17a, 18a, 19a, 21a and 14a have the same structure as 17, 18, 19, 21, and 14 respectively except that the $OR_3$ substituent is replaced by $R_5$.

The carboxylic acid (16/16a) is converted to ester (17/17a) through the use of excess $R_1OH$ and a strong acid catalyst such as hydrogen chloride as reviewed by C. A. Buehler and D. E. Pearson (op.cit., pp 802-807) (Equation 5b).

The phenol (17/17a) is converted to the thiocarbamate (18/18a) through the use of dimethylthiocarbamoyl chloride and 1,4-diazabicyclo[2.2.2]octane (DABCO) in N,N-dimethylformamide according to the general procedure of M. S. Newman and H. A. Karnes, *J. Org. Chem.* 1966, 31, 3980 (Equation 5c). Alternatively a mixture of the phenol (17/17a), at least one equivalent of dimethylthiocarbamoyl chloride, at least one equivalent of triethylamine (Et$_3$N), and a catalytic amount of 4-dimethylaminopyridine (DMAP) in dichloromethane is heated at reflux for one to seven days. The reaction mixture is washed with 1N hydrochloric acid and 10% aqueous sodium hydroxide solution, then dried over magnesium sulfate and filtered. Evaporation of the solvent leaves crude (18/18a) which may be purified by chromatography on silica gel or by recrystallization if it is crystalline.

The thiocarbamate (18/18a) is converted to its isomer (19/19a) by heating according to the general procedure of M. S. Newman and H. A. Karnes (op.cit.) (Equation 5d).

To a solution of (19/19a) in anhydrous $R_1OH$ (11) is added little more than one equivalent of $NaOR_1$ (20). The mixture is heated at 60°-70° C. for 0.5-1 hour. The solvent is removed in vacuo, and the residue is partitioned between dichloromethane and water. The aqueous phase is washed with dichloromethane, acidified with 12N hydrochloric acid, and extracted with dichloromethane. The dichloromethane extracts are dried over sodium sulfate and filtered. Evaporation of the solvent leaves thiol (21/21a) (Equation 5e).

To a mixture of the thiol (21/21a) and at least one equivalent of sodium formate in formic acid is added at least three equivalents of hydrogen peroxide at such a rate as to keep the temperature between 40° and 50° C. The reaction mixture is then heated at 45°–55° C. for 1 to 5 hours. The excess peroxide is destroyed with sodium sulfite, and the solvent is evaporated. The residue is added to excess thionyl chloride, and a catalytic amount of N,N-dimethylformamide (DMF) is added. The mixture is heated at reflux for 8 to 24 hours, and then the solvent is evaporated. The residue is partitioned between water and ether. The ether solution is washed with aqueous sodium bicarbonate solution, dried over magnesium sulfate and filtered. Evaporation of the solvent leaves the sulfonyl chloride (14/14a) (Equation 5f).

Finally the sulfonyl chloride (14) is aminated giving the sulfonamide (4a) and likewise (14a) gives (4c') as already described for Equation 4f (Equation 5g).

Most of the sulfonamides (4a) can be prepared via the route shown in Equation 6 starting from 6-hydroxysaccharin (22).

Equation 6

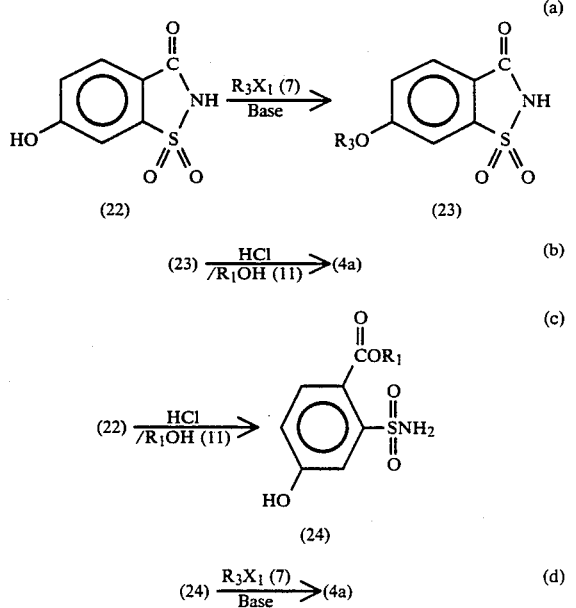

where $R_1$ and $X_1$ are as previously defined and $R_3$ is as defined for Equation 4 or $C_2$–$C_4$ cyanoalkyl, 6-Hydroxysaccharin (22) can be prepared as described by C. Finzi and M. Colonna, *Atti. accad. Lincei, Classe, sci. fis., mat. mat.*, 1937, 26, 19 (*Chem. Abst.* 1938, 32, 3762). Alternatively, (4a), where $R_1=CH_3$, $R_3=C_6H_5CH_2$ may be prepared via the route described by Equation 5. A solution of this sulfonamide in dichloromethane is treated with one equivalent of 1,8-diazabicyclo[5.4.0]undec-7-ene (DBU). The solvent is evaporated, and the residue is dissolved in minimal water and acidified with concentrated hydrochloric acid to precipitate 6-benzyloxysaccharin. This is dissolved in ethanol containing palladium catalyst. The mixture is hydrogenated at 20°–40° C. and 1–10 psi until hydrogen uptake ceases. Filtration and evaporation of the solvent affords 6-hydroxysaccharin (22).

In the method described by Equation 6a, 6-hydroxysaccharin (22) is added to a solution of two equivalents sodium in anhydrous methanol, ethanol, or amyl alcohol. A little more than one equivalent of $R_3X_1$ (7) is added and the mixture is heated at reflux for 4 to 24 hours. The solvent is removed in vacuo and the residue is dissolved in minimal water. It is acidified with concentrated hydrochloric acid. If the product crystallizes, it is collected, washed with dilute hydrochloric acid, and dried. If it does not crystallize, the aqueous mixture is extracted with dichloromethane. The dichloromethane phase is dried over sodium sulfate and filtered. Evaporation of the solvent leaves the saccharin (23) (Equation 6a).

A solution or suspension of the saccharin (23) in $R_1OH$ (11) is saturated with hydrogen chloride. The mixture is heated at 65°–80° C. for 1–6 hours. The solvent and hydrogen chloride are evaporated. The residue is dissolved in dichloromethane, washed with aqueous sodium bicarbonate solution, dried over sodium sulfate, and filtered. Evaporation of the solvent affords the sulfonamide (4a) (Equation 6b).

Alternatively, saccharin (22) may be opened to the sulfonamide (24) using the conditions already described for the conversion of (23) to (4a) in Equation 6b (Equation 6c). To a solution of the sulfonamide (24) in anhydrous methanol, ethanol, amyl alcohol, or a suitable aprotic solvent such as N,N-dimethylformamide is added one equivalent of sodium or potassium methoxide, ethoxide, or tert-butoxide followed by the alkylating agent $R_3X_1$ (7). The mixture is held at 20°–80° C. for 1–8 hours. The solvent is removed in vacuo, and the residue is dissolved in dichloromethane, washed with aqueous sodium bicarbonate solution, dried over $Na_2SO_4$, and filtered. Evaporation of the solvent affords the sulfonamide (4a) (Equation 6d).

Many sulfonamides of Formulae (4a), (4b) and (4e) can be prepared by the methods shown in Equation 7.

Equation 7

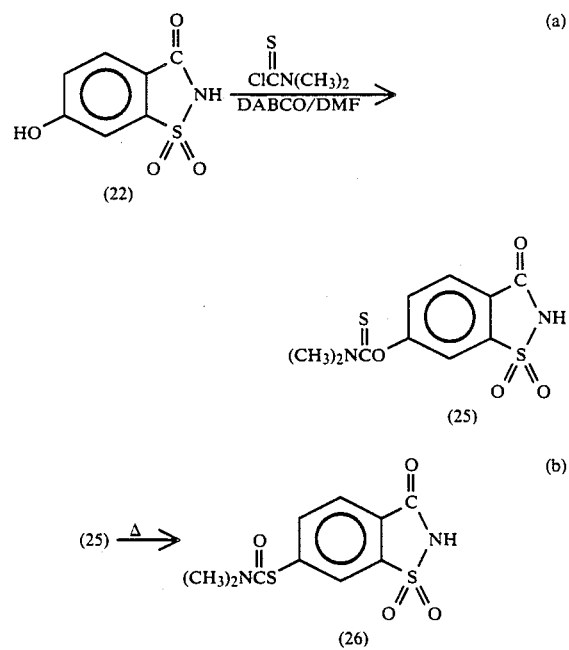

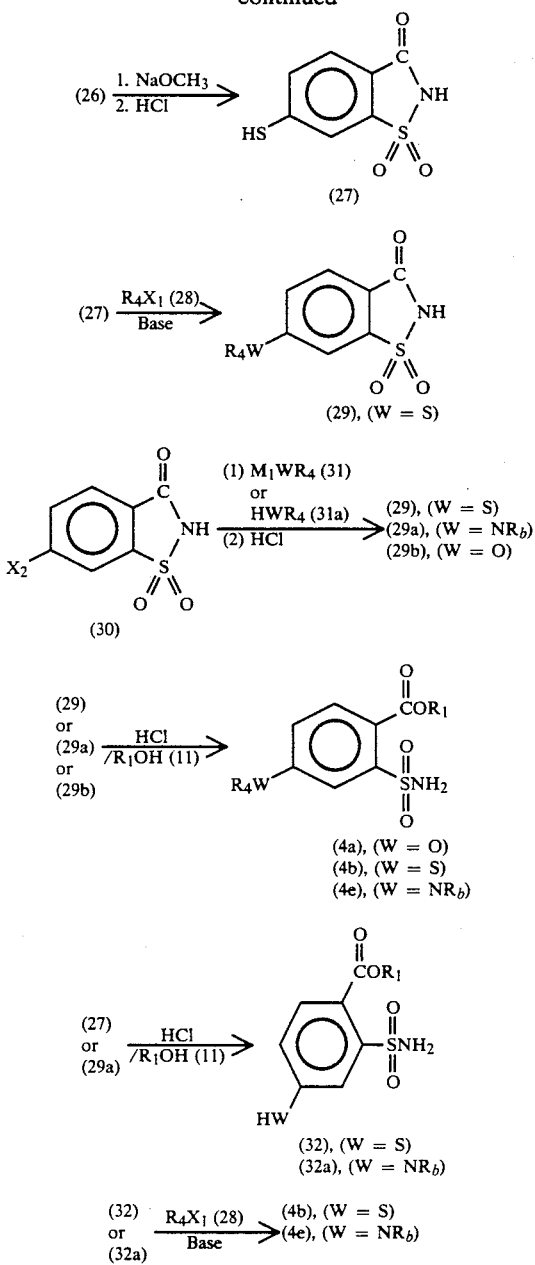

solvent is removed in vacuo, and the residue is partitioned between dichloromethane and water. The aqueous phase is washed with dichloromethane and acidified with concentrated hydrochloric acid. If the saccharin (27) crystallizes, it is collected, rinsed with dilute cold hydrochloric acid, and dried. If it does not crystallize, the aqueous phase is extracted with dichloromethane. The dichloromethane extracts are dried over sodium sulfate and filtered. Evaporation of the solvent leaves saccharin (27) (Equation 7c).

The mercaptan (27) is added to a solution of two equivalents sodium in anhydrous methanol, ethanol, or amyl alcohol. A little more than one equivalent of $R_4X_1$ (28) is added, and the mixture is heated at reflux for 1 to 8 hours. The requisite alkylating, alkenylating, and alkynylating agents $R_4X_1$ (28) are either known in the art or may be made by a wide variety of methods known in the art.

The solvent is removed in vacuo, and the residue is dissolved in minimal water. It is acidified with concentrated hydrochloric acid. If the saccharin (29) crystallizes, it is collected, washed with cold dilute hydrochloric acid, and dried. If it does not crystallize, the aqueous mixture is extracted with dichloromethane. The dichloromethane phase is dried over sodium sulfate and filtered. Evaporation of the solvent leaves the saccharin (29) (Equation 7d).

Alternatively, in many cases, the saccharins of Formula (29) or (29b) may be prepared by treating a halosaccharin (30) in a polar aprotic solvent such as N-N-dimethylformamide at 20°-100° C. with at least two equivalents of the corresponding thiolate or alkoxide of Formula (31) for 4-24 hours. The reaction is worked up by evaporation of the solvent. The residue is dissolved in minimal water and acidified with concentrated hydrochloric acid. If the saccharin (29/29b) crystallizes, it is filtered. Otherwise the aqueous solution is extracted with dichloromethane, and evaporation of the solvent leaves the saccharin (29/29b) (Equation 7e).

Many 5-aminosaccharins (29a) can be prepared by heating the halosaccharin (30) in N,N-dimethylformamide under pressure at 125°-190° C. in the presence of amines for 8-16 hours. The reaction is worked up as described in the preceeding paragraph.

In addition, aminosaccharins (29a) wherein $R_4$ is H can be alkylated in the same fashion as described previously for alkoxy and mercapto saccharins in Equations (6a) and (7d). The conversion of aminosaccharins (29a) into aminosulfonamides (4e) or (32a) can be effected using conditions described previously in Equations (6b and c) (Equation 7f).

The requisite precursor halosaccharins of Formula (30) may be prepared by conversion of the corresponding 4-halo-2-nitrobenzoic acids to esters of 2-(aminosulfonyl}-4-halobenzoic acids by use of methods analogous to those described for Equation 4. These esters are closed to the corresponding saccharins of Formula (30) by treatment with DBU according to the general method already described for the preparation of 6-benzyloxysaccharin.

Saccharins (29/29b) are similarly opened to the corresponding sulfonamides (4b/4a) using the conditions already described for the conversion of (23) to (4a) in Equation 6b (Equation 7f).

Alternatively, saccharin (27/29a) may be opened to the sulfonamide (32/32a) using the conditions already described for the conversion of (23) to (4a) in Equation where $M_1$, $R_1$ and $X_1$ are as previously defined, $X_2$ is F, Cl, Br or I, W is O, S, or $NR_b$:$R_b$ is as previously defined; and $R_4$ is $R_3$ as defined for Equation 6 or H, $CH_3$, cyclohexyl, or phenyl.

The hydroxysaccharin (22) is converted to the thiocarbamate (25) through the use of dimethylthiocarbamoyl chloride and 1,4-diazabicyclo[2.2.2]octane (DABCO) in N,N-dimethylformamide according to the general procedure, or modifications thereof known to those skilled in the art, of M. S. Newman and H. A. Karnes (op.cit.) (Equation 7a).

The thiocarbamate (25) is converted to its isomer (26) by heating according to the general procedure, or modifications thereof known to those skilled in the art, of M. S. Newman and H. A. Karnes (ibid.) (Equation 7b).

To a solution of (26) in anhydrous methanol is added a little more than two equivalents of sodium methoxide. The mixture is heated at 60°-70° C. for 0.5-1 hour. The 6b (Equation 7g). The thiol (32) or aniline (32a) is then converted to (4b/4e) using the method already described for the conversion of (24) to (4a) in Equation 6d (Equation 7h).

Most sulfonamides of Formula (4b) ($R_1$ and $R_4$ as previously defined) can also be prepared by synthetic routes analogous to that described for $R_1=R_4=CH_3$ in Examples 9 through 16.

Sulfonamides of Formula (4c) can be prepared by the method shown in Equation 8.

Equation 8

(a) 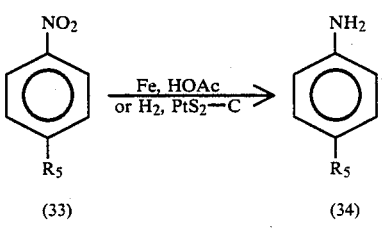
(33)    (34)

(b) 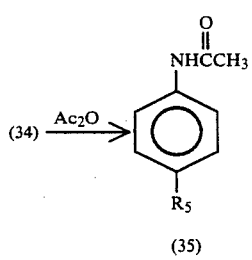
(35)

(c) 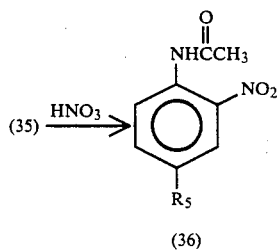
(36)

(d) 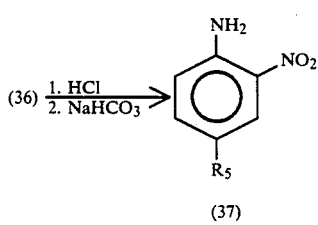
(37)

(e) 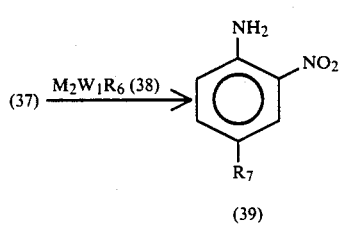
(39)

(f) 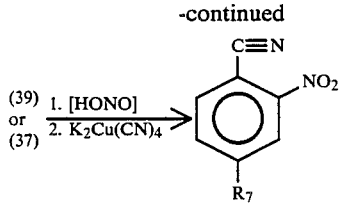
(40) or (40a, $R_7 = R_5$)

(g)

(41) or (41a, $R_7 = R_5$)

(h)

(4c) or (4c', $R_7 = R_5$)

(i)

(4c', $R_8 = H$)

(4c', $R_8 = SiMe_2\text{-}\underline{t}\text{-}Bu$)

(j) (4c', $R_8 = SiMe_2\text{-}\underline{t}\text{-}Bu$) $\xrightarrow{M_2W_1R_6 \text{ (38)}}$ (4c, $R_8 = SiMe_2\text{-}\underline{t}\text{-}Bu$)

where $R_1$ is as previously defined; $R_5$ is alkyl, haloalkyl, alkenyl, haloalkenyl, alkynyl, haloalkynyl or $CH_2C(O)NR_aR_b$; $R_a$ and $R_b$ are as previously defined; $W_1$ is O or S; $M_2$ is Na or K; $R_6$ is H, $C_1\text{-}C_4$ alkyl, $C_1\text{-}C_4$ haloalkyl, $C_3\text{-}C_4$ cycloalkyl, cyclopropylmethyl, $C_3\text{-}C_4$ alkenyl, $C_3\text{-}C_4$ haloalkenyl, $C_3\text{-}C_4$ alkynyl, $C_3\text{-}C_4$ haloalkynyl, $C_2\text{-}C_4$ alkoxyalkyl, or $C_2\text{-}C_4$ aminoalkyl; and $R_7$ is $C_1\text{-}C_4$ alkyl substituted with $W_1R_6$.

The starting nitrobenzenes (33) are either known in the art or may be made by a wide variety of methods known in the art. Some of these methods include the nitration (for a review, see G. Lehmann. H. Eichmann "Formation of Carbon-Nitrogen Bonds" in *Preparative*

*Organic Chemistry*, G. Hilgetag. A. Martini ed., Wiley-Interscience, New York. 1972) of the coupling product obtained from reaction of the appropriate halide with diphenylcuprate (for a review. see G. H. Posner "Substitution Reactions Using Organo-copper Reagents" in *Organic Reactions*, Vol. 22, W. G. Dauben ed., Wiley, New York, 1975).

Another method is the Friedel-Crafts acylation of benzene with the appropriate acid halide or anhydride (for a review, see G. A. Olah, *Friedel-Crafts* and Related Reactions, Volumes I-IV, Wiley-Interscience. New York, 1963-1965). followed by reductive removal of the carbonyl oxidation (for a review. see C. Bischoff, P.-G. Dietrich, E. Höft, D. Murowski, "Formation of Carbon-Hydrogen Bonds" in *Preparative Organic Chemistry*, G. Hilgetag, A. Martini ed., Wiley-Interscience, New York, 1972) and then nitration.

Still another method involves conversion of the appropriate 4-nitrobenzyl alcohols, aldehydes, or ketones to their mono or difluoro alkyl homologues using the conditions reviewed by G. A. Boswell, Jr., W. C. RiPka. R. M. Scribner. C. W. Tullock, "Fluorination by Sulfur Tetrafluoride" and C. M. Sharts, W. A. Sheppard "Modern Methods to prepare Monofluoroaliphatic Compounds" in *Organic Reactions*, Vol. 21. W. G. Dauben ed., Wiley. New York, 1974).

The nitrobenzene (33) is reduced to the aniline (34) using the conditions already described for the conversion of (12) to (13) in Equation 4d (Equation 8a).

The aniline (34) in a suitable solvent such as benzene is treated with at least one equivalent of acetic anhydride and heated at reflux for 8-24 hours. The reaction mixture is cooled, and if the acetanilide (35) crystallizes, it is collected and dried. If it does not crystallize, the benzene solution is washed with 1N hydrochloric acid and aqueous sodium bicarbonate solution, dried over magnesium sulfate, and filtered. Evaporation of the solvent leaves the acetanilide (35) (Equation 8b).

The acetanilide (35) is then nitrated using the general conditions reviewed by G. Lehmann and H. Teichmann (op.cit.) to give nitroacetanilide (36) (Equation 8c).

A slurry of acetanilide (36) in 1N hydrochloric acid is heated at reflux until all of the solid dissolves. The solution is then made slightly basic with sodium bicarbonate and is extracted with dichloromethane. The dichloromethane extracts are dried over sodium sulfate and filtered. Evaporation of the solvent leaves the aniline (37) (Equation 8d).

Many of the substituents described within R are prepared from aniline (37) having an $R_5$ substituent containing a displaceable halogen atom at the position where the substituent $W_1R_6$ is to be placed. Thus the halide (37) in a suitable solvent such as N,N-dimethylformamide is treated with a little more than one equivalent of the appropriate sodium or potassium salt (38).

The mixture is held at 20°-100° C. for 1-8 hours. The solvent is then evaporated, and the residue is partitioned between water and dichloromethane. The dichloromethane solution is dried over sodium sulfate and filtered. Evaporation leaves the desired compound (39) (Equation 8e).

The aniline (39/37) is then diazotized and subjected to the Sandmeyer reaction according to the general experimental procedure of G. T. Morgan and E. A. Coulson. *J. Chem. Soc.* 1929, 2551 to give nitrile (40/40a) (Equation 8f).

A suspension of the nitrile (40/40a) in 75-80% aqueous sulfuric acid is heated at 95°-100° C. for 2-5 hours. Then over 1-2 hours and at a temperature of 80°-100° C. 1.5-2.5 equivalents of sodium nitrile is added in small portions. The heating is continued 0.5-1 hour longer, then the mixture is cooled and poured onto excess ice. If the carboxylic acid (41/41a) crystallizes, it is collected, rinsed with ice water and dried. If it does not crystallize, the aqueous mixture is extracted with dichloromethane. The dichloromethane solution is extracted with aqueous 10% sodium carbonate solution. The aqueous extract is made acidic with concentrated hydrochloric acid. If the carboxylic acid (41/41a) then crystallizes, it is collected, rinsed with ice water and dried. If it does not crystallize, the aqueous solution is extracted with ether. The ether extracts are dried over magnesium sulfate and filtered. Evaporation of the solvent leaves carboxylic acid (41/41a) (Equation 8g).

By use of the methods previously described, carboxylic acid (41) can be converted to sulfonamide (4c) and likewise (41a) gives (4c') (Equation 8h).

In the case where $R_7$ substituents of sulfonamide (4c) are incompatible with the strongly acidic conditions described in Equation 8g. an alternative scheme is used.

Sulfonamide of Formula (4c') wherein $R_5$ is $C_1$-$C_4$ alkyl substituted with Cl, Br or I in a suitable solvent such as acetonitrile is treated with one equivalent of tert-butyldimethylsilyl chloride in the presence of a mild base such as pyridine at 15°-25° C. for 1-8 hours. When the reaction is judged complete by thin layer chromatography the mixture is poured onto ice water. If the silylsulfonamide crystallizes, it is collected, rinsed with water and dried. If not, the aqueous solution is extracted with ether. The ether extracts are dried and concentrated to furnish the silylsulfonamide of (4c') (Equation 8i).

A stirred solution of the silylsulfonamide of (4c') in a solvent such as DMF is treated at 0°-80° C. with at least one equivalent of (38) for 1-8 hours. When the reaction is judged complete by thin layer chromatography the mixture is poured onto ice water and the reaction is worked up as described in the previous paragraph (Equation 8j).

The silylsulfonamide of (4c) can then be converted directly into sulfonylurea (I) using the same conditions described in Equation 3. with the exception that tetra-n-butyl ammonium fluoride is used as base in lieu of 1,8-diazabicyclo[5.4.0]undec-7-ene (DBU).

Sulfonamides of Formula (4) where $R_2$ contains sulfinyl or sulfonyl groups can be prepared by peracid oxidation of the corresponding mercapto sulfonamides using methods analogous to those described for the preparation of sulfinyl sulfonamides of Formula (4d,n=1) and sulfonyl sulfonamides of Formula (4d,n=2) in Equation 9 (vide infra).

For example, the sulfinyl sulfonamides of Formula (4d,n=1) and sulfonyl sulfonamides of Formula (4d,n=2) can be be prepared from the corresponding thio sulfonamides of Formula (4b) as shown in Equation 9.

Equation 9

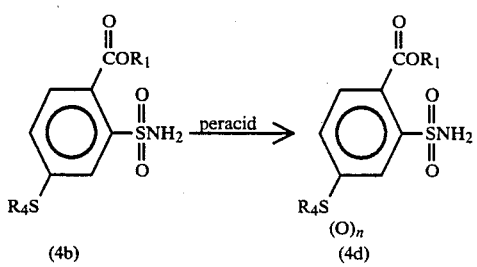

where $R_1$ and $R_4$ are as previously defined, except that $R_4$ cannot be alkylthioalkyl or haloalkylthioalkyl, and n is 1 or 2.

To prepare the sulfinyl sulfonamides of Formula (4d, n=1) a solution of one equivalent of a peracid, such as 3-chloroperoxybenzoic acid, in an inert solvent, such as dichloromethane, is added to a stirred solution of the appropriate thio sulfonamide (4b) in an inert solvent, such as a mixture of dichloromethane and tetrahydrofuran, at 0°–5° C. The mixture is then warmed to 20°–40° C. When thin layer chromatography has revealed the sulfonamide (4b) to have been oxidized, the mixture is washed in turn with 5% aqueous sodium sulfite solution, saturated aqueous sodium bicarbonate solution, water, and brine and then dried (MgSO$_4$). Evaporation of the solvent then leaves the sulfinyl sulfonamide of Formula (4d, n=1).

To prepare sulfonyl sulfonamides of Formula (4d, n=2) a solution of more than two equivalents (only two equivalents when $R_4$ is alkenyl or alkynyl) of a peracid, such as 3-chloroperoxybenzoic acid in an inert solvent, such as 1,2-dichloroethane, is added to a stirred mixture of the appropriate thio sulfonamide (4b) in an inert solvent, such as 1,2-dichloroethane, containing 1–5 mol % of a free radical inhibitor, such as 4,4-thiobis(6-tert-butyl-m-cresol). The mixture is heated to 50°–80° C. When thin layer chromatography shows the thio sulfonamide (4b) and intermediate sulfinyl sulfonamide (4d, n=1) to have been consumed, the mixture is cooled and diluted with tetrahydrofuran to maintain sulfonamide solubility. Using the same work up method as already described for the preparation of sulfinyl sulfonamides (4d, n=1), one obtains the sulfonyl sulfonamides of Formula (4d, n=2).

Sulfonamides of Formula (4d) where $R_4$ is alkylthioalkyl or haloalkylthioalkyl and n is 1 or 2 can be prepared from the homologous sulfonamides of Formula (4d) having a $R_4$ monohaloalkyl substituent with a displaceable halogen atom at the position where the alkylthioalkyl or haloalkylthioalkyl group is to be placed. These monohaloalkyl sulfonamides are first closed to the corresponding saccharins by use of DBU as previously described for the preparation of 6-benzyloxysaccharin. The halogen atom is then replaced with the appropriate alkylthio or haloalkylthio group using the displacement conditions previously described for the conversion of halide (37) to thioether (39) in Equation 8. When the appropriate haloalkylthiolate reagent is unstable to self-condensation, the corresponding hydroxy-, carbonyl-, and/or carboxy-containing alkylthiolate can be used. After formation of the thioether bridge, these oxygen-containing groups can be converted to the desired halogen substitution pattern by use of a wide variety of methods known in the art. Finally the saccharins are opened to the desired sulfonamides of Formula (4d) where $R_4$ is alkylthioalkyl or haloalkylthioalkyl and n is 1 or 2 by the method already described for the conversion of (23) to (4a) in Equation 6b.

Sulfonyl isocyanates (1) are prepared from the corresponding sulfonamides (4) with compatible $R_2$ substituents by one of the following two general methods.

Equation 10

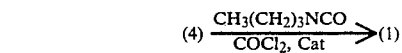

where $R_1$ and $R_2$ are as previously defined.

The sulfonamide (4) and an alkyl isocyanate (e.g., n-butyl isocyanate) in xylene or other solvent boiling above 135° C. are mixed in the presence or absence of a catalytic amount of 1,4-diaza[2.2.2]bicyclooctane (DABCO) and heated to 135°–140° C. After 5–60 minutes phosgene is slowly added to the heated mixture at such a rate that the temperature remains between 133°–135° C. When the consumption of phosgene has ceased, the mixture is cooled and filtered to remove insoluble material. Finally, the solvent, alkyl isocyanate, and excess Phosgene are evaporated, leaving the sulfonyl isocyanate (1).

If desired, the alkyl isocyanate-sulfonamide adduct can be made and isolated before reaction with the phosgene. In this case, the sulfonamide (4). alkyl isocyanate, and anhydrous base (e.g., K$_2$CO$_3$) in a polar, aprotic solvent (e.g. acetone, butanone, or acetonitrile) are mixed and heated under reflux for 1 to 6 hours. The reaction mixture is then diluted with water, and the pH is adjusted to about 3 with acid (e.g. HCl, H$_2$SO$_4$). The adduct is filtered out and dried, and then reacted with Phosgene as described above. This procedure modification is especially useful when sulfonamide (4) is high melting and has low solubility in the phosgenation solvent.

Sulfonyl isocyanates (1) can also be prepared by the following method.

Equation 11

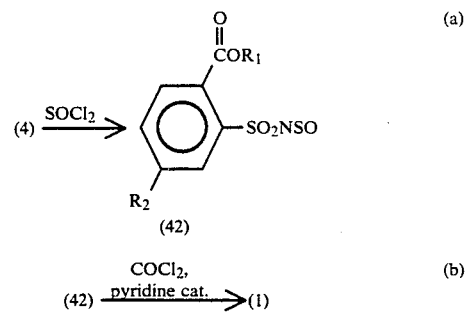

where $R_1$ and $R_2$ are as previously defined.

The sulfonamide (4) is heated at reflux in an excess of thinyl choride, the reaction is continued until the sulfonamide protons are no longer detectable in the proton magnetic resonance spectrum. From 16 hours to 5 days is typically sufficient for complete conversion to the thionylamide (42) (Equation 11a).

The thionyl chloride is evaporated and the residue is treated with an inert solvent (e.g. toluene) containing at least one equivalent (typically 2-3 equivalents) of phosgene. A catalytic amount of pyridine (typically 0.1 equivalent) is added, and the mixture is heated to about 60°-140° C. with 80°-100° preferred. Conversion to the isocyanate (1) is usually substantially complete within 15 minutes to 3 hours (Equation 11b). The mixture is than cooled and filtered, and the solvent is evaporated, leaving the sulfonyl isocyanate (1).

The heterocyclic amines of Formula (2) below are either known, disclosed in this application, or can be prepared by obvious methods by one skilled in the art.

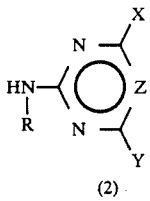

(2)

For a review of the synthesis and reactions of 2-amino and 2-methylaminopyrimidines (2, Z=CH) see *The chemistry of Heterocyclic Compounds*, Vol. 16, Wiley-Interscience, New York (1962). For a review of the synthesis and reactions 2-amino- and 2-methylaminostriazines (2, Z=N) see *The Chemistry of Heterocyclic Compounds*, Vol. 13, Wiley-Interscience, New York (1959), F. C. Schaefer, U.S. Pat. No. 3,154,537 and F. C. Schaefer and K. R. Huffman *J. Org. Chem.*, 28, 1812 (1963).

In some cases, heterocycles of Formula (2) may be more easily prepared with R being H than with R being $CH_3$. Many heterocycles (2, R=$CH_3$) can be prepared from the corresponding heterocycles (2, R=H) by one or more of the following two methods.

Equation 12

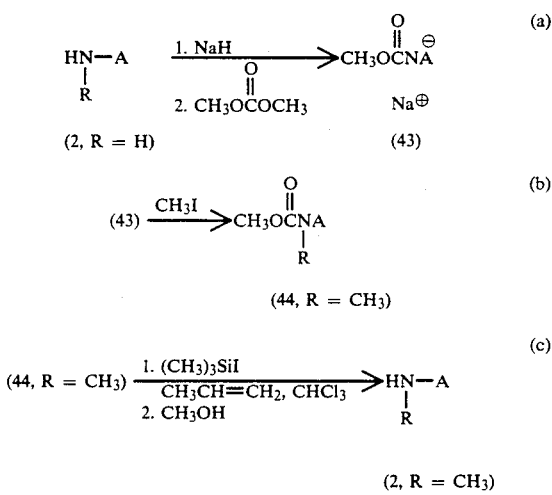

where A is as previously defined.

In this method, a solution or slurry of the appropriate heterocycle (2, R=H) in a suitable aprotic solvent (e.g., tetrahydrofuran, dioxane, glyme) at 0°-30° C. is treated with two equivalents of sodium hydride. After gas evolution ceases, the reaction mixture is treated with one equivalent of dimethyl carbonate and stirred at 20°-30° C. for 8 to 24 hours to provide a suspension of the sodium salt (43) (Equation 12a).

The reaction mixture containing (43) is treated with at least two equivalents of iodomethane and then heated at 60°-80° C. for 8 to 24 hours. The mixture is cooled and filtered, and the solvent is evaporated. The residue is taken up in dichloromethane, washed with water, and the solvent is evaporated, leaving the N-methyl carbamate (44. R=$CH_3$) (Equation 12b).

The carbamate (44, R=$CH_3$) is dissolved in anhydrous, alcohol-free chloroform saturated with propylene gas. Slightly more than one equivalent (typically 1.1-1.2 equivalents) of iodotrimethylsilane) is added and the stirred solution is heated at 50°-60° C. for 2 to 4 hours. The mixture is cooled and two equivalents of methanol is added. The solvent is evaporated and the residue is taken up in methanol. The mixture is carefully neutralized with 10% sodium methoxide in methanol, and then the solvent is evaporated. The residue is triturated with ice water. If a precipitate forms, it is filtered out, rinsed with ice water and dried to provide (2. R=$CH_3$). If no precipitate forms, the solution is saturated with sodium chloride and extracted with ethyl acetate. Evaporation of the solvent leaves heterocycle (2, R=$CH_3$)(Equation 12c).

Alternatively, the following two-step procedure is useful in many cases.

Equation 13

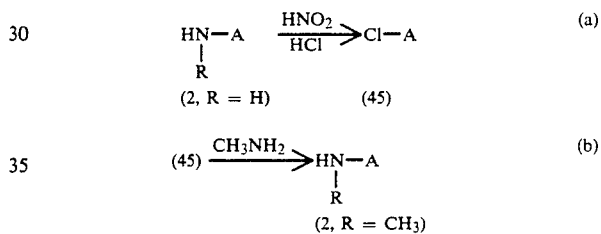

where A is as previously defined.

A solution of the amine (2. R=H) in concentrated hydrochloric acid is treated with sodium nitrite solution and the chloro compound (45) is isolated in the usual manner by filtration of the acidic solution (Equation 13a). A representative procedure is described by Bee and Rose in *J. Chem. Soc. C.* 1966, 2031 for the case in which Z=CH, and X=Y=$OCH_3$.

The heterocycle (45) is then treated with at least two equivalents of methylamine in a suitable inert solvent (e.g. tetrahydrofuran, glyme, or diglyme) at a temperature between 20° and 80° C. for 1-18 hours (Equation 13b). The reaction mixture is then cooled and filtered. Evaporation of the solvent leaves (2, R=$CH_3$) contaminated with a little $CH_3NH_3^+Cl^-$ salt. The product may be purified by trituration with ice water or by dissolution in dichloromethane, followed by washing with a small amount of water, drying, and evaporation of solvent. Further purification may be accomplished by recrystallization or column chromatography on silica gel.

As an alternative to the methods already described in which the sulfonamides of Formulae (4a), (4b). and (4e) are fully elaborated prior to construction of the urea bridge of compounds of Formula I, many compounds of Formula Ia may be prepared by the method described in Equation 14.

Equation 14

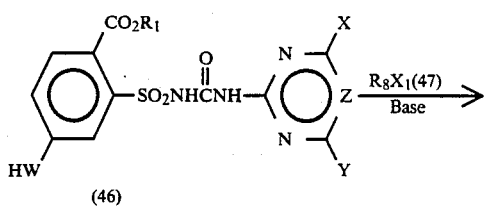

(46)

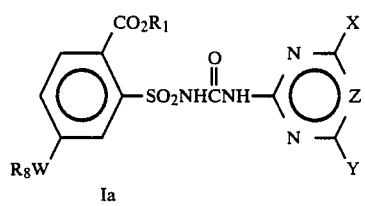

Ia where $R_1$, X, $X_1$, Y and Z are as previously defined; W is S, O or $NR_b$; $R_b$ is as previously defined; $R_8$ is $C_4$–$C_6$ cycloalkylalkyl, $C_2$–$C_6$ alkenyl, $C_2$–$C_6$ haloalkenyl, $C_3$–$C_6$ alkynyl, $C_3$–$C_6$ haloalkynyl, $C_2$–$C_8$ alkoxyalkyl, $C_2$–$C_4$ haloalkoxyalkyl, $C_2$–$C_8$ alkylthioalkyl, $C_2$–$C_4$ haloalkylthioalkyl, $C_2$–$C_4$ cyanoalkyl, $CH_2C(O)CH_3$, $CH_2CH_2C(O)CH_3$ or $C_1$–$C_6$ alkyl.

In this method a solution of the appropriate compound of Formula (46) in a polar solvent such as a mixture of acetonitrile and N,N-dimethylformamide is treated with two equivalents of a strong base such as sodium methoxide or sodium hydride with catalytic methanol followed by a little more than one equivalent of the appropriate alkylating alkenylating or alkynylating agent (47). The mixture is held at 20°–60° C. for 2–24 hours. Then the mixture is poured into excess hydrochloric acid. If the compound of Formula Ia crystallizes, it is filtered. Otherwise the aqueous mixture is extracted with dichloromethane, and evaporation of the solvent leaves the compound of Formula Ia. The compounds of Formula (46) are in turn prepared by coupling the appropriate sulfonamides of Formulae (4a, 4b or 4e) with the appropriate heterocyclic phenyl carbamates of Formula (5.R=H) according to the general method described for Equation 3.

Many of the compounds of Formula Ia where $R_8$ is alkyl, cycloalkyl, cycloalkylalkyl, haloalkyl, alkenyl, haloalkenyl, alkynyl, haloalkynyl, alkoxyalkyl haloalkoxyalkyl cyanoalkyl, —$CH_2C(O)CH_3$, or —$CH_2CH_2C(O)CH_3$ and W is S(O) or $S(O)_2$ can be made by oxidation of the corresponding compounds of Formula Ia where W is S using methods similar to those already described for the conversion of (4b) to (4d) in Equation 9.

Compounds of Formula I where $R_2$ contains a carbonyloxy, carbamoyloxy, phosphoryloxy, sulfonyloxy, silyloxy or phosphotylthio group are prepared from the corresponding compounds of Formula I where $R_2$ contains a hydroxyl or thiol group by use of a wide variety of methods known in the art.

The following examples further illustrate the synthesis of this invention.

EXAMPLE 1

Methyl 4-ethoxy-2-hydroxybenzoate

Hydrogen chloride was bubbled into a stirred solution of 4-ethoxy-2-hydroxybenzoic acid (10.10 g. 0.554 mol) in methanol (2000 mL) until the solution was saturated. The solution was heated under reflux for 3 days and then cooled to 15° C. This caused the product to crystallize out. The crystals were collected, rinsed with methanol and hexanes, and dried. Methyl 4-ethoxy-2-hydroxybenzoate was obtained as a pale amber solid (49.3 g) melting at 77°–78° C.

PMR (CDCl$_3$, 90 MHz): δ11.90 (slightly broadened s, 1H, OH); 7.76 (d, 1H, H ortho to $CO_2CH_3$); 6.35–6.55 (m. 2H. other aryl H's); 4.06 (q, 2H, $OCH_2CH_3$); 3.89 (s, 3H, $OCH_3$) 1.41 (t, 3H, $OCH_2CH_3$). IR (Nujol); 3130 (broad. w. OM): 1668 (s. C=O) cm$^{-1}$. More product was obtained by reworking the mother liquor.

EXAMPLE 2

Methyl 2-[(dimethylamino)thioxomethoxy]-4-ethoxybenzoate

Triethylamine (76.6 mL, 0.550 mol) was added via syringe to a stirred solution of methyl 4-ethoxy-2-hydroxybenzoate (49.3 g. 0.251 mol). 4-dimethylaminopyridine (3.06 g. 0.025 mol). and dimethylthiocarbamoyl chloride (54.4 g. 0.440 mol) in dry dichloromethane (411 mL). The reaction solution was heated at reflux three days and then allowed to stand at room temperature overnight. It was washed with hydrochloric acid (1N. 3×300 mL) and then dried (MgSO$_4$) and filtered. Rotary evaporation of the solvent left crude product (95.2 g) as a brown oil. This was applied to a column of silica gel and eluted with 2:1 followed by 1:1 hexanes-ether. Fractions containing product ($R_f$=0.43, 1:1 hexanes-ether UV) were rotary evaporated to give partially purified product (60.2 g) as a yellowish solid. Further purification was achieved by additional column chromatography employing a greater silica gel to sample ratio. Finally, the doubly chromatographed product (48.7 g including 7.4 g from another similar run) was recrystallized from boiling methanol (3 mL/g). After cooling in an ice bath, the crystals were collected rinsed with ice-cold methanol and dried. Methyl 2-[(dimethylamino)thioxomethoxy]-4-ethoxybenzoate was obtained as large white prisms (46.1 g) melting at 77°–79° C.

PMR (CDCl$_3$, 200 MHz): δ7.96 (d, 1H, H ortho to $CO_2CH_3$): 7.81 (dd. 1H, H para to OCSN); 6.62 (d, 1H, H ortho to OCSN): 4.08 (q, 2H, OCH ); 3.81 (s, 3H, $CO_2CH_3$); 3.47 (s. 3H, NCH$_3$); 3.40 (s, 3H, NCH$_3$); 1.42 (t, 3H, $OCH_2CH_3$). IR (Nujol): 1715 cm$^{-1}$ (vs, C=O).

EXAMPLE 3

Methyl 2-[(dimethylamino)carbonylthio]-4-ethoxybenzoate

Methyl 2-[(dimethylamino)thioxomethoxy]-4-ethoxybenzoate (28.3 g 0.100 mol) was heated under nitrogen at 220° C. for 1.5 hours. Thin layer chromatography (6:3:1 CH$_3$Cl$_2$-hexanes-ether, UV) showed a very faint spot at a $R_f$ of 0.63 (starting material) and a very intense spot at a $R_f$ of 0.35 (product). In this case the crude product was used in the next reaction step without further characterization or purification.

Crude product from a similar but smaller scale run was chromatographed on a column of silica gel using 4:1 ether-hexanes as eluant. Fractions containing product ($R_f$=0.40, same solvent, UV) were rotary evaporated to give an oil that slowly crystallized. This was dissolved in a little dichloromethane, diluted with 1-chlorobutane seeded and rotary evaporated. The residue was collected, rinsed with hexanes, and dried. Methyl 2-[(dimethylamino)carbonylthio]-4-ethoxybenzoate was obtained as white prisms melting at 65°-67° C. PMR (CDCl$_3$, 200 MHz): δ7.93 (d. 1H, H ortho to CO$_2$CH$_3$); 7.16 (d, 1H, H ortho to SCON); 6.89 (dd. 1H, H para to SCON); 4.08 (q, 2H, OCH$_2$CH$_3$); 3.84 (s, 3H, CO$_2$CH$_3$); 3.09 (broad s, 6H, N(CH$_3$)$_2$); 1.42 (t, 3H, OCH$_2$CH$_3$). IR (Nujol): 1730 (s. ester C=O); 1680 (s, carbonyl C=O)cm$^{-1}$.

EXAMPLE 4

Methyl 4-ethoxy-2-mercaptobenzoate

Methanolic sodium methoxide (4.9M. 22.4 mL, 0.11 mol) was added via syringe to a solution of methyl 2-[(dimethylamino)carbonylthio]-4-ethoxybenzoate (crude. ca. 28.3 g, 0.10 mol) in methanol (100 mL) under nitrogen. The reaction mixture was heated at reflux for 30 minutes, then cooled with the aid of a water bath. Rotary evaporation yielded a solid. This was partitioned between dichloromethane (100 mL) and water (100 mL). The aqueous layer was washed with dichloromethane (3×40 mL), acidified to PH <1 with concentrated hydrochloric acid, and then extracted with dichloromethane (3×40 mL). These dichloromethane extracts were combined dried (Na$_2$SO$_4$), and filtered. Rotary evaporation yielded methyl 4-ethoxy-2-mercaptobenzoate as an oil (18.4 g) that on standing formed a crystalline solid melting at 42°-44° C. PMR (CDCl$_3$, 200 MHz): δ7.97 (d, 1H. H ortho to CO$_2$CH$_3$); 6.78 (d, 1H. H ortho to SH); 6.64 (dd, 1H, H para to SH); 5.06 (s, 1H, SH); 4.05 (q. 2OCH$_2$CH$_3$); 3.88 (s. 3H, CO$_2$CH$_3$); 1.42 (t, 3H, OCH$_2$CH$_3$). TR (Nujol): 1686 (vs, C=O)cm$^{-1}$.

EXAMPLE 5

Methyl 2-(chlorosulfonyl)-4-ethoxybenzoate

Hydrogen Peroxide (30%, 9.79M, 30.7 mL, 300 mmol) was added dropwise to a stirred solution of methyl 4-ethoxy-2-mercaptobenzoate (18.2 g. 85.7 mmol) and sodium formate (11.7 g, 172 mmol) in formic acid (171.4 mL). Through the use of an ice bath, the internal temperature was held to 40°-50° C. during the first half of the hydrogen peroxide addition and 45°-50° C. during the second half of the addition. After completion of the addition and cessation of the exothermic reaction, the mixture was heated at 45°-55° C. for two hours. The excess hydrogen peroxide was destroyed with sodium sulfite, the solution was filtered, and the solvent was rotary evaporated. The residue was slurried in toluene and rotary evaporated. The process was repeated to give the sodium sulfonate salt as a moist white crystalline solid (21.7 g).

Without further purification or characterization, the sodium sulfonate salt was added portionwise to stirred thionyl chloride (150 mL. 2.1 mmol). Anhydrous N,N-dimethylformamide (1.0 mL, 13 mmol) was added slowly, and the reaction mixture was heated at reflux overnight. The reaction mixture was then rotary evaporated. Dichloromethane (150 mL) was added, and the solvent was again evaporated. The residue was partitioned between ether (100 mL) and ice water (100 mL). The aqueous layer was extracted with ether (2×50 mL). The combined ether solutions were washed with water (50 mL). saturated aqueous sodium bicarbonate solution (2×50 mL), dried (MgSO$_4$), and filtered. Rotary evaporation of the solvent left methyl 2-(chlorosulfonyl)-4-ethoxy-benzoate as pale orange oil (22.5g) that crystallized on scratching. The crystalline solid melted at 45°-48° C. PMR (CDCl$_3$, 200 MHz): δ7.76 (d, 1H, H ortho to CO$_2$CH$_3$); 7.65 (d, 1H. H ortho to SO$_2$Cl); 7.21 (dd, 1H, H para to SO$_2$Cl); 4.16 (q, 2H, OCH$_2$CH$_3$); 3.96 (s. 3H, CO$_2$CH$_3$); 1.48 (t, 3H, OCH$_2$CH$_3$). IR (Nujol): 1722 (vs. C=O) cm$^{-1}$.

EXAMPLE 6

Methyl 2-(aminosulfonyl)-4-ethoxybenzoate

Liquified ammonia (4.4 mL. 180 mmol) was added to a stirred solution of methyl 2-(chlorosulfonyl)-4-ethoxybenzoate (22.1 g. 79.3 mmol) in dichloromethane (221 mL) at −70° C. The reaction mixture was allowed to warm to −10° C. and was held at this temperature for 30 minutes. The mixture was then poured into water (221 mL). More water and dichloromethane were used for rinsing, and tetrahydrofuran (ca. 40 mL) was also added. The layers were shaken and separated and the aqueous layer was extracted with dichloromethane (2×221 mL). The combined dichloromethane solutions were washed with water (221 mL), and the aqueous wash was back-extracted with dichloromethane (ca. 120 mL). The combined dichloromethane solutions were dried (Na$_2$SO$_4$), and filtered. Rotary evaporation of the solvent left crude product as an off-white crystalline solid (18.1 g). This was dissolved in hot methanol (ca. 200 mL) and hot filtered. The solution was boiled down to a volume corresponding to 3 mL/g methanol. After seeding and cooling with the aid of an ice bath the crystals were collected, rinsed with ice-cold methanol and hexanes and dried. Methyl 2-(aminosulfonyl)-4-ethoxybenzoate (15.3 g) was obtained as white crystalline needles melting at 146°-148° C. PMR (CDCl$_3$, 200 mHz): δ7.91 (d, 1H, H ortho to CO$_2$CH$_3$); 7.68 (d, 1H, H ortho to SO$_2$NH$_2$); 7.04 (dd. 1H, M para to SO$_2$NH$_2$); 5.9I (broad s 2H, NH$_2$); 4.14 (q. 2H, OCH$_2$CH$_3$); 3.95 (s, 3H, CO$_2$CH$_3$); 1 45 (t, 3H, OCH$_2$CH$_3$). IR (Nujol): 3348 (m, NH); 3241 (m, NH); 1692 (s, C=O) cm$^{-1}$.

EXAMPLE 7

Methyl 4-ethoxy-2-(isocyanatosulfonyl)benzoate

A solution of methyl 2-(aminosulfonyl)-4-ethoxybenzoate (7.56 g. 29.2 mmol). n-butyl isocyanate (3.29 mL. 29.2 mmol). and 1.4-diaza[2.2.2]bicyclooctane (0.13 g 1.2 mmol) in mixed xylenes was heated at reflux for 10 minutes. Phosgene was then added at such a rate that the internal temperature stayed at 133° C. or above. When consumption of phosgene ceased, the solution was cooled to room temperature and then filtered under nitrogen. Rotary evaporation gave methyl 4-ethoxy-2-(isocyanatosulfonyl)benzoate as a cloudy yellow oil (8.2 g). This was used immediately without further purification or characterization.

EXAMPLE 8

Methyl 2-[[(4,6-dimethoxy-1,3,5-triazin-2-yl)aminocarbonyl]aminosulfonyl]-4-ethoxybenzoate To a slurry of 4,6-dimethoxy-1.3.5-triazin-2-amine (0.46 g, 2.9 mmol) in dry dichloromethane (5 mL) was added a solution of methyl 4-ethoxy-2-(isocyanatosulfonyl)benzoate (crude. ca. 1.2 g 4.2 mmol) in dichloromethane (5 mL). The reaction mixture was heated at reflux for 1.5 hours during which time the solid dissolved. On stirring at room temperature overnight a new solid formed. The solvent was rotary evaporated, leaving the crude product as a white solid (1.5 g). This was dissolved in warm 1.2-dichloroethane and chromatographed on a column of silica gel using as eluant 15:1, 10:1, and finally 7:1 dichloromethane-ether all containing 2 mL/L acetic acid. The appropriate fractions were diluted with toluene and rotary evaporated to give a solid. This was dissolved in minimal warm dichloromethane diluted with 1-chlorobutane and rotary evaporated to give a crystalline solid, this was slurried in hexanes, collected, rinsed with 1:1 1-chlorobutane-hexanes and hexanes, and dried. The product was obtained as a white crystalline powder (0.98 g) melting at 181°-183° C. PMR (CDCl$_3$, 200 MHz): δ12.15 (slightly broadened s, 1H, SO$_2$NHCO); 7.89 (d. 1H, H ortho to SO$_2$NH); 7.77 (d. 1H, H ortho to CO$_2$CH$_3$); 7.45 (slightly broadened s, 1H, CONH-Het); 7.11 (dd, 1H, H para to SO$_2$NH); 4.17 (q, 2H, OCH$_2$CH$_3$); 4.12 (s, 6H Het-OCH$_3$); 3.90 (s, 3H, CO$_2$CH$_3$); 1.46 (t, 3H, OCH$_2$CH$_3$). IR (Nujol): 1730 (vs, ester C=O); 1715 (s. urea C=O) cm$^{-1}$.

EXAMPLE 9

4-(Methylthio)-2-nitrobenzoic acid

4-Amino-2-nitrobenzoic acid (20.0 g, 110 mmol) was added to aqueous sulfuric acid (32.8 mL H$_2$O+24.0 mL conc. H$_2$SO$_4$). The stirred mixture was heated until all of the aniline dissolved and then was plunged into an ice bath to precipitate the anilinium salt as suspension of Very small crystals. Portions of aqueous sodium nitrite (8.8 g. 128 mmol in 18.4 mL H$_2$O) were then added over one hour to the stirred reaction mixture maintained at −5° to 0° C.

The diazotization mixture was then poured portionwise into a mixture of sodium hydroxide (24.4 g. 610 mmol) methanethiol (33.6 mL. 605 mmol); cupric sulfate (17.6 g, 110 mmol), and sodium acetate (55.2 g, 673 mmol) in 140 mL of water cooled with the aid of an ice bath. The addition was exothermic and accompanied by copious was evolution. A suspension of tan-yellow solid formed. The mixture was heated to 60° C., and then was allowed to cool to room temperature.

Dichloromethane (200 mL) and tetrahydrofuran (20 mL) were stirred in. Concentrated hydrochloric acid was added to brine the PH below 1. The mixture was suction filtered through Celite ®, with additional dichloromethane used for rinsing. The layers were separated, and the aqueous layer was extracted with dichloromethane (2×50 mL). The combined dichloromethane solutions were dried (Na$_2$SO$_4$) and suction filtered through Celite ®. The solvent was rotary evaporated. The residue was dissolved in minimal acetone, diluted with toluene, and evaporated. The residue was dissolved in minimal acetone, diluted with toluene, and evaporated. The process was repeated to leave crude 4-(methylthio)-2-nitrobenzoic acid as an orange solid (20.4 g) melting at 165°-168° C. This was used in the next step without further purification.

PMR (DMSO-d$_6$, 200 MHz): δ13.6 (very broad s. 1H. CO$_2$H); 7.83 (d, 1H. H ortho to CO$_2$H); 7.76 (d. 1H. H ortho to NO$_2$); 7.58 (dd. 1H, H para to NO$_2$); 2.58 (s. 3H, SCH$_3$). IR (Nujol): 2800 (very broad, m, OH); 1675 (s. C=O) cm$^{-1}$.

EXAMPLE 10

Methyl-4-(methylthio)-2-nitrobenzoate

To a stirred solution of 4-(methylthio)-2-nitrobenzoic acid (24.4 g, 114 mmol) in dry pyridine (265 mL) maintained at 5° C. under nitrogen was added p-toluenesulfonyl chloride (43.6 g, 229 mmol). After one hour and with continued cooling with the aid of an ice bath, dry methanol (6.2 mL. 153 mmol) was added. After the exothermicity subsided another portion of methanol (4.1 mL, 101 mmol) was added and the ice bath was removed.

The reaction solution was stirred at room temperature for one hour and then poured into ice water (1060 mL). Ether (530 mL) was stirred in, and the layers were separated. The aqueous layer was extracted with ether (2×530 mL). The combined ether solutions were washed with 10% aqueous sodium hydroxide solution (2×530 mL), dried (MgSO$_4$), and filtered. The solvent was rotary evaporated. The residue was taken up in toluene, which was subsequently rotary evaporated. This process was repeated once more to give a thick brown oil.

This oil was chromatographed on a column of silica gel using mixtures of hexanes and ether (first 2:1 then 3:2) as eluting solvents. Fractions containing product (R$_f$=0.38, UV, 2:1 hexanes-ether) were evaporated to leave a yellow solid. This was dissolved in minimal warm 1-chlorobutane, diluted with hexanes to saturation, and seeded. After crystallization was complete, the mixture was evaporated. The residue was slurried in hexanes, collected, rinsed with hexanes, and dried. Methyl 4-(methylthio)-2-nitrobenzoate was obtained as pale yellow needles (11.6 g) melting at 57°-59° C.

PMR(CDCl$_3$, 200 MHz): δ7.71 (d, 1H, H ortho to CO$_2$CH$_3$); 7.55 (d, 1H, H ortho to NO$_2$); 7.41 (dd, 1H, H para to NO$_2$); 3.90 (s, 3H, CO$_2$CH$_3$); 2.56 (s 3H, SCH$_3$). IR (Nujol): 1709 (vs, C=O) cm$^{-1}$.

EXAMPLE 11

Methyl 2-amino-4-(methylthio)benzoate

A mixture of methyl 4-(methylthio)-2-nitrobenzoate (11.3 g. 49.7 mmol) and 5% platinum sulfide on carbon catalyst (0.7 g) in methyl acetate (40 mL) was hydrogenated at 750 Psi and 75° C. until hydrogen uptake ceased. The mixture was filtered through Celite ®, and the filtrate solvent was rotary evaporated, leaving methyl 2-amino-4-(methylthio)benzoate as a slightly tan crystalline solid (8.7 g) melting at 57°-59° C.

PMR (CDCl$_3$, 200 MHz); δ7.74 (d, 1H, H ortho to CO$_2$CH$_3$); 6.50 (dd, 1H, H para to NH$_2$); 6.44 (dd, 1H, H ortho to NH$_2$); 5.75 (broad s, 2H, NH$_2$); 3.85 (s, 3H, CO$_2$CH$_3$); 2.46 (s, 3H, SCH$_3$). IR (Nujol); 3422 (m, NH); 3312 (m, NH); 1650 (s, C=O) cm$^{-1}$.

EXAMPLE 12

Methyl 2-(chlorosulfonyl)-4-(methylthio)benzoate

To a stirred aqueous sulfuric acid solution (7.2 mL concentrated H$_2$SO$_4$+51.6 mL H2O) maintained at −5° to 0° C. was added alternately portions of a solution of methyl 2-amino-4-(methylthio)benzoate (12.8 g, 64.9 mL) in glacial acetic acid (6.4 mL) and portions of aqueous sodium nitrite (4.9 g, 71 mmol in 7.8 mL H$_2$O).

The diazotization mixture was then poured portionwise into a mixture of cupric chloride dihydrate (5.5 g. 32 mmol). concentrated hydrochloric acid (13.0 mL) and liquified sulfur dioxide (5.5 mL, 129 mmol) in glacial acetic acid (51.6 mL) and dichloromethane (64.6 mL) at 0° C. Using dry ice-filled Dewar condensers the coupling mixture was heated at reflux for 45 minutes.

The reaction mixture was then poured into water (ca. 400 mL) with additional dichloromethane (ca 60 mL) used for rinsing. The layers were shaken and separated, and the aqueous layer was extracted with dichloromethane (3×50 mL). The combined dichloromethane solutions were washed with water (ca. 100 mL). Water (25 mL) was added to the dichloromethane solution and with vigorous stirring sodium bicarbonate was added until foaming ceased. The mixture was diluted with water (ca. 40 mL). and the layers were separated. The dichloromethane layer was washed with water (ca. 2×60 mL) and dried (MgSO4). Rotary evaporation of the solvent afforded crude methyl 2-(chlorosulfonyl)-4-(methylthio)benzoate as a yellow semisolid (10.0 g). This was immediately used in the next reaction step without further purification or characterization.

EXAMPLE 13

Methyl 2-(aminosulfonyl)-4-(methylthio)benzoate

Liquified ammonia (1.7 mL. 68 mmol) was added to a stirred solution of methyl 2-(chlorosulfonyl)-4-(methylthio)benzoate (10 g 36 mmol) in dichloromethane (100 mL) at −70° C. The reaction mixture was allowed to warm to −10° C. and was held at this temperature for 10 minutes. The mixture was then poured into water (100 mL). More water and dichloromethane were used for rinsing. The layers were shaken and separated, an the aqueous layer was extracted with dichloromethane (2×50 mL). The combined dichloromethane solutions were washed with water (100 mL), dried (Na2SO4). and filtered through Celite ®. Rotary evaporation of the solvent left crude product as a solid (9.0 g).

This was dissolved in dichloromethane and suspended on silica gel (27 g). The material was chromatographed on a column of silica gel using dichloromethane-hexanes-ether (6:3:1 then 6:2:2) as eluant. Rotary evaporation of the appropriate fractions left a solid. This was dissolved in dichloromethane diluted with hexanes, and rotary evaporated to give a crystalline solid. This was slurried in hexanes, collected, rinsed with 1:1 1-chlorobutane-hexanes and hexanes, and dried. Methyl 2-(aminosulfonyl)-4-(methylthio)benzoate was obtained as a white crystalline powder (6.7 g) melting at 123°–125° C.

PMR (CDCl3, 200 MHz): $\delta$7.97 (d. 1H. H ortho to SO2NH2): 7.82 (d, 1H, H ortho to CO2CH3); 7.39 (dd, 1 H para to SO2NH2); 5.86 (s, 2H, NH2); 3.97 (s, 3H, CO2CH3); 2.56 (s, 3H, SCH3). IR (Nujol): 3322 (m, NH2): 3245 (m, NH2); 1700 (s. C=O) cm−1.

EXAMPLE 14

Methyl 2-(isocyanatosulfonyl)-4-(methylthio)benzoate

A solution of methyl 2-(aminosulfonyl)-4-(methylthio)benzoate (5.23 g, 20.0 mmol), n-butyl isocyanate (2.25 mL, 20.0 mmol). and 1,4-diaza[2.2 2]bicyclooctane (0.09 g. 0.8 mmol) in mixed Xylenes (50 mL) was heated at reflux for 10 minutes. Phosgene was then added at such a rate that the internal temperature stayed at 133° C. or above. When consumption of phosgene ceased, the solution was cooled to room temperature and then filtered under nitrogen. Rotary evaporation gave methyl 2-(isocyanatosulfonyl)-4-(methylthio)benzoate as a yellow oil (6.4 g). This was used immediately without further purification or characterization.

EXAMPLE 15

Methyl 2-[[(4,6-dimethoxypyrimidin-2-yl)aminocarbonyl]-aminosulfonyl]-4-(methylthio)benzoate To a slurry of 4.6-dimethoxy-1 3-pyridimin-2-amine (0.36 g, 2.32 mmol) in dry dichloromethane (4 mL) was added a solution of methyl 2-(isocyanato- sulfonyl)-4-(methylthio)benzoate (crude, ca. 0.95 g. 3.3 mL) in dichloromethane (5 mL). The reaction mixture was heated at reflux for 2.5 hours, during which time a new solid formed.

On stirring at room temperature overnight a new solid formed. The mixture was diluted with a solution of 1:1 1-chlorobutane - hexanes (9 mL). and the solid was collected, rinsed with 1-chlorobutane and hexanes, and dried. The product was obtained as a white crystalline powder (0.92 g) melting at 201°–202° C.

PMR (CDCl3, 200 MHz): $\delta$12.57 (slightly broadened s. 1H. SO2NHCO); 8.20 (d. 1H. H ortho to SO2NH); 7.66 (d. 1H, H ortho to CO2CH3); 7.43 (dd, 1H, H para to SO2NH); 7.18 (slightly broadened s. 1H, CONH-Het); 5.79 (s. 1H. Het 5-H); 4.01 (s. 6H, Het-OCH3); 3.87 (s. 3H, CO2CH3); 2.58 (s, 3H, SCH3). IR (Nujol): 1721 (vs, ester C=O); 1698 (s. urea, C=O) cm−1.

EXAMPLE 16

1,2-Benzisothiazol-3(2H)-one-6-(methylthio)-1,1-dioxide

A solution of 1.2-benzoisothiazol-3(2H)-one-6-chloro-1,1-dioxide (10 g. 46 mmol) and potassium-tert-butoxide (13 g, 115 mmol) in N,N-dimethylformamide (100 mL) maintained at 0° C. was treated with excess of methyl mercaptan for 15 minutes. The mixture was then allowed to warm to 25° C. and after 2 hours at this temperature the reaction was heated to 110° C. for 1 hour. After this time the mixture was allowed to cool and then was poured onto ice water. The PH was adjusted to 2 and the solid was collected by filtration. The product was obtained as a white solid (10.2 g) melting at 232°–234° C.

PMR (D6-Acetone, 90 MHz): $\delta$8.2–8.0 (m, 3H, aryl-H) and 3.2 (s. 3H. SCH3).

Using the procedures and examples shown above, the compounds in Tables I and Ia can be prepared.

TABLE I

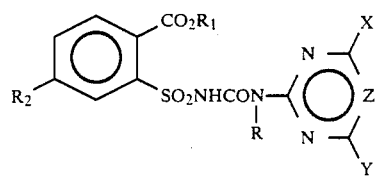

| R1 | R2 | R | X | Y | Z | m.p. (°C.) |
|---|---|---|---|---|---|---|
| CH3 | OC2H5 | H | CH3 | CH3 | CH | 192–194 (d) |
| CH3 | OC2H5 | H | OCH3 | CH3 | CH | 185–187 |
| CH3 | OC2H5 | H | OCH3 | OCH3 | CH | 192–195 |
| CH3 | OC2H5 | H | Cl | OCH3 | CH | 181–183 |
| CH3 | OC2H5 | H | OCH3 | N(CH3)2 | CH | 176–177 |

TABLE I-continued

| | | | | | | |
|---|---|---|---|---|---|---|
| CH₃ | OC₂H₅ | H | CH₃ | CH₃ | N | 118–120 |
| CH₃ | OC₂H₅ | H | OCH₃ | CH₃ | N | 162–164 |
| CH₃ | OC₂H₅ | H | OCH₃ | OCH₃ | N | 181–183 |
| CH₃ | OC₂H₅ | H | OCH₃ | N(CH₃)₂ | N | 164–165 |
| CH₃ | OC₂H₅ | H | OCH₃ | OCH₂CF₃ | N | 172–174 |
| CH₃ | OC₂H₅ | CH₃ | OCH₃ | CH₃ | N | 117–120 |
| CH₃ | OC₂H₅ | CH₃ | OCH₃ | OCH₃ | N | 130–131 |
| CH₃ | OC₂H₅ | CH₃ | CH₃ | OCH₃ | CH | |
| CH₃ | OC₂H₅ | CH₃ | OCH₃ | OCH₃ | CH | 147–148 |
| CH₃ | OC₂H₅ | H | Br | OCH₃ | CH | |
| CH₃ | OC₂H₅ | CH₃ | OCH₃ | N(CH₃)₂ | N | |
| CH₃ | OC₂H₅ | H | CH₃ | OCH₂CF₃ | N | 179–180 |
| CH₃ | OC₂H₅ | H | CH₃ | OCH₂CF₃ | CH | |
| CH₃ | OC₂H₅ | H | OCH₃ | OCH₂CF₃ | CH | |
| CH₃ | OC₂H₅ | H | OCH₃ | C₂H₅ | CH | |
| CH₃ | OC₂H₅ | H | OCH₃ | C₂H₅ | N | |
| CH₃ | OC₂H₅ | H | OCH₃ | NHCH₃ | CH | |
| CH₃ | OC₂H₅ | H | OCH₃ | NHCH₃ | N | |
| CH₃ | OC₂H₅ | H | CH₃ | OC₂H₅ | CH | |
| CH₃ | OC₂H₅ | H | OCH₃ | OC₂H₅ | CH | |
| CH₃ | OC₂H₅ | H | CH₃ | OC₂H₅ | N | |
| CH₃ | OC₂H₅ | H | OCH₃ | OC₂H₅ | N | |
| CH₃ | OC₂H₅ | H | CH₃ | OCH₂CHF₂ | CH | |
| CH₃ | OC₂H₅ | H | OCH₃ | OCH₂CHF₂ | CH | |
| CH₃ | OC₂H₅ | H | CH₃ | OCH₂CHF₂ | N | |
| CH₃ | OC₂H₅ | H | OCH₃ | OCH₂CHF₂ | N | |
| CH₃ | OC₂H₅ | H | CH₃ | OCH₂CH₂F | CH | |
| CH₃ | OC₂H₅ | H | OCH₃ | OCH₂CH₂F | CH | |
| CH₃ | OC₂H₅ | H | CH₃ | OCH₂CH₂F | N | |
| CH₃ | OC₂H₅ | CH₃ | OCH₃ | OCH₂CH₂F | N | |
| CH₃ | OC₂H₅ | CH₃ | Cl | OCH₃ | CH | |
| CH₃ | OC₂H₅ | H | Cl | N(CH₃)₂ | CH | |
| CH₃ | OC₂H₅ | H | Cl | OC₂H₅ | CH | |
| C₂H₅ | OC₂H₅ | H | CH₃ | CH₃ | CH | |
| C₂H₅ | OC₂H₅ | H | OCH₃ | CH₃ | CH | |
| C₂H₅ | OC₂H₅ | H | OCH₃ | OCH₃ | CH | |
| C₂H₅ | OC₂H₅ | H | Cl | OCH₃ | CH | |
| C₂H₅ | OC₂H₅ | H | CH₃ | CH₃ | N | |
| C₂H₅ | OC₂H₅ | H | OCH₃ | CH₃ | N | |
| C₂H₅ | OC₂H₅ | H | OCH₃ | OCH₃ | N | |
| C₂H₅ | OC₂H₅ | H | Br | OCH₃ | CH | |
| C₂H₅ | OC₂H₅ | H | OCH₃ | N(CH₃)₂ | CH | |
| C₂H₅ | OC₂H₅ | H | OCH₃ | N(CH₃)₂ | N | |
| C₂H₅ | OC₂H₅ | H | OCH₃ | NHCH₃ | N | |
| C₂H₅ | OC₂H₅ | H | OCH₃ | C₂H₅ | CH | |
| C₂H₅ | OC₂H₅ | H | OCH₃ | C₂H₅ | N | |
| C₂H₅ | OC₂H₅ | H | CH₃ | OC₂H₅ | CH | |
| C₂H₅ | OC₂H₅ | H | CH₃ | OC₂H₅ | N | |
| C₂H₅ | OC₂H₅ | H | OCH₃ | OC₂H₅ | CH | |
| C₂H₅ | OC₂H₅ | H | OCH₃ | OC₂H₅ | N | |
| C₂H₅ | OC₂H₅ | H | CH₃ | OCH₂CF₃ | CH | |
| C₂H₅ | OC₂H₅ | H | CH₃ | OCH₂CF₃ | N | |
| C₂H₅ | OC₂H₅ | H | OCH₃ | OCH₂CF₃ | CH | |
| C₂H₅ | OC₂H₅ | H | OCH₃ | OCH₂CF₃ | N | |
| C₂H₅ | OC₂H₅ | H | OCH₃ | OCH₂CHF₂ | CH | |
| C₂H₅ | OC₂H₅ | H | OCH₃ | OCH₂CHF₂ | N | |
| C₂H₅ | OC₂H₅ | H | CH₃ | OCH₂CHF₂ | N | |
| C₂H₅ | OC₂H₅ | H | OCH₃ | OCH₂CH₂F | CH | |
| C₂H₅ | OC₂H₅ | H | OCH₃ | OCH₂CH₂F | N | |
| C₂H₅ | OC₂H₅ | CH₃ | OCH₃ | OCH₃ | CH | |
| C₂H₅ | OC₂H₅ | CH₃ | CH₃ | OCH₃ | N | |
| C₂H₅ | OC₂H₅ | CH₃ | OCH₃ | OCH₃ | N | |
| n-C₃H₇ | OC₂H₅ | H | OCH₃ | OCH₃ | CH | |
| n-C₃H₇ | OC₂H₅ | H | CH₃ | OCH₃ | N | |
| CH(CH₃)₂ | OC₂H₅ | H | OCH₃ | CH₃ | CH | |
| CH(CH₃)₂ | OC₂H₅ | H | OCH₃ | OCH₃ | CH | |
| CH(CH₃)₂ | OC₂H₅ | H | Cl | OCH₃ | CH | |
| CH(CH₃)₂ | OC₂H₅ | H | OCH₃ | CH₃ | N | |
| CH(CH₃)₂ | OC₂H₅ | H | OCH₃ | OCH₃ | N | |
| CH(CH₃)₂ | OC₂H₅ | H | OCH₃ | N(CH₃)₂ | N | |
| CH₃ | O(CH₂)₂CH₃ | H | CH₃ | CH₃ | CH | |
| CH₃ | O(CH₂)₂CH₃ | H | OCH₃ | CH₃ | CH | 151–153 (d) |
| CH₃ | O(CH₂)₂CH₃ | H | OCH₃ | OCH₃ | CH | 169–172 (d) |
| CH₃ | O(CH₂)₂CH₃ | H | Cl | OCH₃ | CH | |
| CH₃ | O(CH₂)₂CH₃ | H | OCH₃ | N(CH₃)₂ | CH | |
| CH₃ | O(CH₂)₂CH₃ | H | CH₃ | CH₃ | N | |
| CH₃ | O(CH₂)₂CH₃ | H | OCH₃ | CH₃ | N | 144–147 (d) |
| CH₃ | O(CH₂)₂CH₃ | H | OCH₃ | OCH₃ | N | 176–179 (d) |
| CH₃ | O(CH₂)₂CH₃ | H | OCH₃ | N(CH₃)₂ | N | |
| CH₃ | O(CH₂)₂CH₃ | H | OCH₃ | OCH₂CF₃ | N | |
| CH₃ | O(CH₂)₂CH₃ | CH₃ | OCH₃ | CH₃ | N | |
| CH₃ | O(CH₂)₂CH₃ | CH₃ | OCH₃ | OCH₃ | N | |

TABLE I-continued

| | | | | | | |
|---|---|---|---|---|---|---|
| CH$_3$ | O(CH$_2$)$_2$CH$_3$ | CH$_3$ | CH$_3$ | OCH$_3$ | CH | |
| CH$_3$ | O(CH$_2$)$_2$CH$_3$ | CH$_3$ | OCH$_3$ | OCH$_3$ | CH | |
| CH$_3$ | O(CH$_2$)$_2$CH$_3$ | H | Br | OCH$_3$ | CH | |
| CH$_3$ | O(CH$_2$)$_2$CH$_3$ | CH$_3$ | OCH$_3$ | N(CH$_3$)$_2$ | N | |
| CH$_3$ | O(CH$_2$)$_2$CH$_3$ | H | CH$_3$ | OCH$_2$CF$_3$ | N | |
| CH$_3$ | O(CH$_2$)$_2$CH$_3$ | H | CH$_3$ | OCH$_2$CF$_3$ | CH | |
| CH$_3$ | O(CH$_2$)$_2$CH$_3$ | H | OCH$_3$ | OCH$_2$CF$_3$ | CH | |
| CH$_3$ | O(CH$_2$)$_2$CH$_3$ | H | OCH$_3$ | C$_2$H$_5$ | CH | |
| CH$_3$ | O(CH$_2$)$_2$CH$_3$ | H | OCH$_3$ | C$_2$H$_5$ | N | |
| CH$_3$ | O(CH$_2$)$_2$CH$_3$ | H | OCH$_3$ | NHCH$_3$ | CH | |
| CH$_3$ | O(CH$_2$)$_2$CH$_3$ | H | OCH$_3$ | NHCH$_3$ | N | |
| CH$_3$ | O(CH$_2$)$_2$CH$_3$ | H | CH$_3$ | OC$_2$H$_5$ | CH | |
| CH$_3$ | O(CH$_2$)$_2$CH$_3$ | H | OCH$_3$ | OC$_2$H$_5$ | CH | |
| CH$_3$ | O(CH$_2$)$_2$CH$_3$ | H | CH$_3$ | OC$_2$H$_5$ | N | |
| CH$_3$ | O(CH$_2$)$_2$CH$_3$ | H | OCH$_3$ | OC$_2$H$_5$ | N | |
| CH$_3$ | O(CH$_2$)$_2$CH$_3$ | H | CH$_3$ | OCH$_2$CHF$_2$ | CH | |
| CH$_3$ | O(CH$_2$)$_2$CH$_3$ | H | OCH$_3$ | OCH$_2$CHF$_2$ | CH | |
| CH$_3$ | O(CH$_2$)$_2$CH$_3$ | H | CH$_3$ | OCH$_2$CHF$_2$ | N | |
| CH$_3$ | O(CH$_2$)$_2$CH$_3$ | H | OCH$_3$ | OCH$_2$CHF$_2$ | N | |
| CH$_3$ | O(CH$_2$)$_2$CH$_3$ | H | CH$_3$ | OCH$_2$CH$_2$F | CH | |
| CH$_3$ | O(CH$_2$)$_2$CH$_3$ | H | OCH$_3$ | OCH$_2$CH$_2$F | CH | |
| CH$_3$ | O(CH$_2$)$_2$CH$_3$ | H | CH$_3$ | OCH$_2$CH$_2$F | N | |
| CH$_3$ | O(CH$_2$)$_2$CH$_3$ | CH$_3$ | OCH$_3$ | OCH$_2$CH$_2$F | N | |
| CH$_3$ | O(CH$_2$)$_2$CH$_3$ | CH$_3$ | Cl | OCH$_3$ | CH | |
| CH$_3$ | O(CH$_2$)$_2$CH$_3$ | H | Cl | N(CH$_3$)$_2$ | CH | |
| CH$_3$ | O(CH$_2$)$_2$CH$_3$ | H | Cl | OC$_2$H$_5$ | CH | |
| C$_2$H$_5$ | O(CH$_2$)$_2$CH$_3$ | H | CH$_3$ | CH$_3$ | CH | 154–159 (d) |
| C$_2$H$_5$ | O(CH$_2$)$_2$CH$_3$ | H | OCH$_3$ | CH$_3$ | CH | 173–176 (d) |
| C$_2$H$_5$ | O(CH$_2$)$_2$CH$_3$ | H | OCH$_3$ | OCH$_3$ | CH | |
| C$_2$H$_5$ | O(CH$_2$)$_2$CH$_3$ | H | Cl | OCH$_3$ | CH | 140–142 (d) |
| C$_2$H$_5$ | O(CH$_2$)$_2$CH$_3$ | H | CH$_3$ | CH$_3$ | N | |
| C$_2$H$_5$ | O(CH$_2$)$_2$CH$_3$ | H | OCH$_3$ | CH$_3$ | N | 131–135 (d) |
| C$_2$H$_5$ | O(CH$_2$)$_2$CH$_3$ | H | OCH$_3$ | OCH$_3$ | N | 145–150 (d) |
| C$_2$H$_5$ | O(CH$_2$)$_2$CH$_3$ | H | Br | OCH$_3$ | CH | |
| C$_2$H$_5$ | O(CH$_2$)$_2$CH$_3$ | H | OCH$_3$ | N(CH$_3$)$_2$ | CH | |
| C$_2$H$_5$ | O(CH$_2$)$_2$CH$_3$ | H | OCH$_3$ | N(CH$_3$)$_2$ | N | |
| C$_2$H$_5$ | O(CH$_2$)$_2$CH$_3$ | H | OCH$_3$ | NHCH$_3$ | N | |
| C$_2$H$_5$ | O(CH$_2$)$_2$CH$_3$ | H | OCH$_3$ | C$_2$H$_5$ | CH | |
| C$_2$H$_5$ | O(CH$_2$)$_2$CH$_3$ | H | OCH$_3$ | C$_2$H$_5$ | N | |
| C$_2$H$_5$ | O(CH$_2$)$_2$CH$_3$ | H | CH$_3$ | OC$_2$H$_5$ | CH | |
| C$_2$H$_5$ | O(CH$_2$)$_2$CH$_3$ | H | CH$_3$ | OC$_2$H$_5$ | N | |
| C$_2$H$_5$ | O(CH$_2$)$_2$CH$_3$ | H | OCH$_3$ | OC$_2$H$_5$ | CH | |
| C$_2$H$_5$ | O(CH$_2$)$_2$CH$_3$ | H | OCH$_3$ | OC$_2$H$_5$ | N | |
| C$_2$H$_5$ | O(CH$_2$)$_2$CH$_3$ | H | CH$_3$ | OCH$_2$CF$_3$ | CH | |
| C$_2$H$_5$ | O(CH$_2$)$_2$CH$_3$ | H | CH$_3$ | OCH$_2$CF$_3$ | N | |
| C$_2$H$_5$ | O(CH$_2$)$_2$CH$_3$ | H | OCH$_3$ | OCH$_2$CF$_3$ | CH | |
| C$_2$H$_5$ | O(CH$_2$)$_2$CH$_3$ | H | OCH$_3$ | OCH$_2$CF$_3$ | N | |
| C$_2$H$_5$ | O(CH$_2$)$_2$CH$_3$ | H | OCH$_3$ | OCH$_2$CHF$_2$ | CH | |
| C$_2$H$_5$ | O(CH$_2$)$_2$CH$_3$ | H | OCH$_3$ | OCH$_2$CHF$_2$ | N | |
| C$_2$H$_5$ | O(CH$_2$)$_2$CH$_3$ | H | CH$_3$ | OCH$_2$CHF$_2$ | N | |
| C$_2$H$_5$ | O(CH$_2$)$_2$CH$_3$ | H | OCH$_3$ | OCH$_2$CH$_2$F | CH | |
| C$_2$H$_5$ | O(CH$_2$)$_2$CH$_3$ | H | OCH$_3$ | OCH$_2$CH$_2$F | N | |
| C$_2$H$_5$ | O(CH$_2$)$_2$CH$_3$ | CH$_3$ | OCH$_3$ | OCH$_3$ | CH | |
| C$_2$H$_5$ | O(CH$_2$)$_2$CH$_3$ | CH$_3$ | CH$_3$ | OCH$_3$ | N | |
| C$_2$H$_5$ | O(CH$_2$)$_2$CH$_3$ | CH$_3$ | OCH$_3$ | OCH$_3$ | N | |
| n-C$_3$H$_7$ | O(CH$_2$)$_2$CH$_3$ | H | OCH$_3$ | OCH$_3$ | CH | |
| n-C$_3$H$_7$ | O(CH$_2$)$_2$CH$_3$ | H | CH$_3$ | OCH$_3$ | N | |
| CH(CH$_3$)$_2$ | O(CH$_2$)$_2$CH$_3$ | H | OCH$_3$ | CH$_3$ | CH | |
| CH(CH$_3$)$_2$ | O(CH$_2$)$_2$CH$_3$ | H | OCH$_3$ | OCH$_3$ | CH | |
| CH(CH$_3$)$_2$ | O(CH$_2$)$_2$CH$_3$ | H | Cl | OCH$_3$ | CH | |
| CH(CH$_3$)$_2$ | O(CH$_2$)$_2$CH$_3$ | H | OCH$_3$ | CH$_3$ | N | |
| CH(CH$_3$)$_2$ | O(CH$_2$)$_2$CH$_3$ | H | OCH$_3$ | OCH$_3$ | N | |
| CH(CH$_3$)$_2$ | O(CH$_2$)$_2$CH$_3$ | H | OCH$_3$ | N(CH$_3$)$_2$ | N | |
| CH$_3$ | OCH(CH$_3$)$_2$ | H | CH$_3$ | CH$_3$ | CH | 165–168 (d) |
| CH$_3$ | OCH(CH$_3$)$_2$ | H | OCH$_3$ | CH$_3$ | CH | 143–146 (d) |
| CH$_3$ | OCH(CH$_3$)$_2$ | H | OCH$_3$ | OCH$_3$ | CH | 170–172 (d) |
| CH$_3$ | OCH(CH$_3$)$_2$ | H | Cl | OCH$_3$ | CH | 148–152 (d) |
| CH$_3$ | OCH(CH$_3$)$_2$ | H | OCH$_3$ | CH$_3$ | N | 132–134 (d) |
| CH$_3$ | OCH(CH$_3$)$_2$ | H | OCH$_3$ | OCH$_3$ | N | 156–159 (d) |
| CH$_3$ | OCH(CH$_3$)$_2$ | H | OCH$_3$ | N(CH$_3$)$_2$ | N | |
| CH$_3$ | OCH(CH$_3$)$_2$ | H | OCH$_3$ | Br | CH | 127–129 |
| C$_2$H$_5$ | OCH(CH$_3$)$_2$ | H | Cl | OCH$_3$ | CH | 83–89 |
| C$_2$H$_5$ | OCH(CH$_3$)$_2$ | H | OCH$_3$ | CH$_3$ | N | 129–135 |
| C$_2$H$_5$ | OCH(CH$_3$)$_2$ | H | OCH$_3$ | OCH$_3$ | CH | 150–155 |
| C$_2$H$_5$ | OCH(CH$_3$)$_2$ | H | OCH$_3$ | CH$_3$ | CH | 127–133 |
| C$_2$H$_5$ | OCH(CH$_3$)$_2$ | H | CH$_3$ | CH$_3$ | CH | 165–168 |
| C$_2$H$_5$ | OCH(CH$_3$)$_2$ | H | OCH$_3$ | OCH$_3$ | N | 168–194 |
| C$_2$H$_5$ | OCH(CH$_3$)$_2$ | H | OCH$_3$ | Br | CH | 105–110 |
| CH$_3$ | O(CH$_2$)$_3$CH$_3$ | H | CH$_3$ | CH$_3$ | CH | |
| CH$_3$ | O(CH$_2$)$_3$CH$_3$ | H | OCH$_3$ | CH$_3$ | CH | |
| CH$_3$ | O(CH$_2$)$_3$CH$_3$ | H | OCH$_3$ | OCH$_3$ | CH | |
| CH$_3$ | O(CH$_2$)$_3$CH$_3$ | H | Cl | OCH$_3$ | CH | |

TABLE I-continued

| | | | | | |
|---|---|---|---|---|---|
| CH₃ | O(CH₂)₃CH₃ | H | CH₃ | CH₃ | N |
| CH₃ | O(CH₂)₃CH₃ | H | OCH₃ | CH₃ | N |
| CH₃ | O(CH₂)₃CH₃ | H | OCH₃ | OCH₃ | N |
| CH₃ | O(CH₂)₃CH₃ | H | OCH₃ | N(CH₃)₂ | CH |
| CH₃ | O(CH₂)₃CH₃ | H | OCH₃ | N(CH₃)₂ | N |
| CH₃ | O(CH₂)₃CH₃ | H | OCH₃ | OCH₂CF₃ | N |
| CH₃ | O(CH₂)₃CH₃ | CH₃ | OCH₃ | CH₃ | N |
| CH₃ | O(CH₂)₃CH₃ | CH₃ | OCH₃ | OCH₃ | N |
| CH₃ | O(CH₂)₃CH₃ | CH₃ | CH₃ | OCH₃ | CH |
| CH₃ | O(CH₂)₃CH₃ | CH₃ | OCH₃ | OCH₃ | CH |
| CH₃ | O(CH₂)₃CH₃ | H | Br | OCH₃ | CH |
| CH₃ | O(CH₂)₃CH₃ | H | CH₃ | OCH₂CF₃ | N |
| CH₃ | O(CH₂)₃CH₃ | H | CH₃ | OCH₂CF₃ | CH |
| CH₃ | O(CH₂)₃CH₃ | H | OCH₃ | OCH₂CF₃ | CH |
| CH₃ | O(CH₂)₃CH₃ | H | OCH₃ | NHCH₃ | N |
| C₂H₅ | O(CH₂)₃CH₃ | H | CH₃ | CH₃ | CH |
| C₂H₅ | O(CH₂)₃CH₃ | H | OCH₃ | CH₃ | CH |
| C₂H₅ | O(CH₂)₃CH₃ | H | OCH₃ | OCH₃ | OCH₃ CH |
| C₂H₅ | O(CH₂)₃CH₃ | H | Cl | OCH₃ | CH |
| C₂H₅ | O(CH₂)₃CH₃ | H | OCH₃ | CH₃ | N |
| C₂H₅ | O(CH₂)₃CH₃ | H | OCH₃ | N(CH₃)₂ | CH |
| CH(CH₃)₂ | O(CH₂)₃CH₃ | H | OCH₃ | CH₃ | CH |
| CH(CH₃)₂ | O(CH₂)₃CH₃ | H | OCH₃ | OCH₃ | CH |
| CH(CH₃)₂ | O(CH₂)₃CH₃ | H | Cl | OCH₃ | CH |
| CH(CH₃)₂ | O(CH₂)₃CH₃ | H | OCH₃ | CH₃ | N |
| CH(CH₃)₂ | O(CH₂)₃CH₃ | H | OCH₃ | OCH₃ | N |
| CH₃ | O(CH₂)₄CH₃ | H | CH₃ | CH₃ | CH |
| CH₃ | O(CH₂)₄CH₃ | H | OCH₃ | CH₃ | CH |
| CH₃ | O(CH₂)₄CH₃ | H | OCH₃ | OCH₃ | CH |
| CH₃ | O(CH₂)₄CH₃ | H | Cl | OCH₃ | CH |
| CH₃ | O(CH₂)₄CH₃ | H | CH₃ | CH₃ | N |
| CH₃ | O(CH₂)₄CH₃ | H | OCH₃ | CH₃ | N |
| CH₃ | O(CH₂)₄CH₃ | H | OCH₃ | OCH₃ | N |
| CH₃ | O(CH₂)₄CH₃ | H | OCH₃ | N(CH₃)₂ | CH |
| CH₃ | O(CH₂)₄CH₃ | H | OCH₃ | N(CH₃)₂ | N |
| CH₃ | O(CH₂)₄CH₃ | H | OCH₃ | OCH₂CF₃ | N |
| CH₃ | O(CH₂)₄CH₃ | CH₃ | OCH₃ | CH₃ | N |
| CH₃ | O(CH₂)₄CH₃ | CH₃ | OCH₃ | OCH₃ | N |
| CH₃ | O(CH₂)₄CH₃ | CH₃ | CH₃ | OCH₃ | CH |
| CH₃ | O(CH₂)₄CH₃ | CH₃ | OCH₃ | OCH₃ | CH |
| CH₃ | O(CH₂)₄CH₃ | H | Br | OCH₃ | CH |
| CH₃ | O(CH₂)₄CH₃ | H | CH₃ | OCH₂CF₃ | N |
| CH₃ | O(CH₂)₄CH₃ | H | CH₃ | OCH₂CF₃ | CH |
| CH₃ | O(CH₂)₄CH₃ | H | OCH₃ | OCH₂CF₃ | CH |
| CH₃ | O(CH₂)₄CH₃ | H | OCH₃ | NHCH₃ | N |
| C₂H₅ | O(CH₂)₄CH₃ | H | CH₃ | CH₃ | CH |
| C₂H₅ | O(CH₂)₄CH₃ | H | OCH₃ | OCH₃ | CH |
| C₂H₅ | O(CH₂)₄CH₃ | H | OCH₃ | OCH₃ | CH |
| C₂H₅ | O(CH₂)₄CH₃ | H | Cl | OCH₃ | CH |
| C₂H₅ | O(CH₂)₄CH₃ | H | OCH₃ | CH₃ | N |
| C₂H₅ | O(CH₂)₄CH₃ | H | OCH₃ | N(CH₃)₂ | CH |
| CH(CH₃)₂ | O(CH₂)₄CH₃ | H | OCH₃ | CH₃ | CH |
| CH(CH₃)₂ | O(CH₂)₄CH₃ | H | OCH₃ | OCH₃ | CH |
| CH(CH₃)₂ | O(CH₂)₄CH₃ | H | Cl | OCH₃ | CH |
| CH(CH₃)₂ | O(CH₂)₄CH₃ | H | OCH₃ | CH₃ | N |
| CH(CH₃)₂ | O(CH₂)₄CH₃ | H | OCH₃ | OCH₃ | N |
| CH₃ | O(CH₂)₅CH₃ | H | CH₃ | CH₃ | CH |
| CH₃ | O(CH₂)₅CH₃ | H | OCH₃ | CH₃ | CH |
| CH₃ | O(CH₂)₅CH₃ | H | OCH₃ | OCH₃ | CH |
| CH₃ | O(CH₂)₅CH₃ | H | Cl | OCH₃ | CH |
| CH₃ | O(CH₂)₅CH₃ | H | CH₃ | CH₃ | N |
| CH₃ | O(CH₂)₅CH₃ | H | OCH₃ | CH₃ | N |
| CH₃ | O(CH₂)₅CH₃ | H | OCH₃ | OCH₃ | N |
| CH₃ | O(CH₂)₅CH₃ | H | OCH₃ | N(CH₃)₂ | CH |
| CH₃ | O(CH₂)₅CH₃ | H | OCH₃ | N(CH₃)₂ | N |
| CH₃ | O(CH₂)₅CH₃ | H | OCH₃ | OCH₂CF₃ | N |
| CH₃ | O(CH₂)₅CH₃ | CH₃ | OCH₃ | CH₃ | N |
| CH₃ | O(CH₂)₅CH₃ | CH₃ | OCH₃ | OCH₃ | N |
| CH₃ | O(CH₂)₅CH₃ | CH₃ | CH₃ | OCH₃ | CH |
| CH₃ | O(CH₂)₅CH₃ | CH₃ | OCH₃ | OCH₃ | CH |
| CH₃ | O(CH₂)₅CH₃ | H | Br | OCH₃ | CH |
| CH₃ | O(CH₂)₅CH₃ | H | CH₃ | OCH₂CF₃ | N |
| CH₃ | O(CH₂)₅CH₃ | H | CH₃ | OCH₂CF₃ | CH |
| CH₃ | O(CH₂)₅CH₃ | H | OCH₃ | OCH₂CF₃ | CH |
| CH₃ | O(CH₂)₅CH₃ | H | OCH₃ | NHCH₃ | N |
| C₂H₅ | O(CH₂)₅CH₃ | H | CH₃ | CH₃ | CH |
| C₂H₅ | O(CH₂)₅CH₃ | H | OCH₃ | CH₃ | CH |
| C₂H₅ | O(CH₂)₅CH₃ | H | OCH₃ | OCH₃ | CH |
| C₂H₅ | O(CH₂)₅CH₃ | H | Cl | OCH₃ | CH |
| C₂H₅ | O(CH₂)₅CH₃ | H | OCH₃ | CH₃ | N |
| C₂H₅ | O(CH₂)₅CH₃ | H | OCH₃ | N(CH₃)₂ | CH |
| CH(CH₃)₂ | O(CH₂)₅CH₃ | H | OCH₃ | CH₃ | CH |

TABLE I-continued

| | | | | | | |
|---|---|---|---|---|---|---|
| CH(CH₃)₂ | O(CH₂)₅CH₃ | H | OCH₃ | OCH₃ | CH | |
| CH(CH₃)₂ | O(CH₂)₅CH₃ | H | Cl | OCH₃ | CH | |
| CH(CH₃)₂ | O(CH₂)₅CH₃ | H | OCH₃ | CH₃ | N | |
| CH(CH₃)₂ | O(CH₂)₅CH₃ | H | OCH₃ | OCH₃ | N | |
| CH₃ | OCH₂CH(CH₃)₂ | H | CH₃ | OCH₃ | CH | |
| CH₃ | O(CH₂)CH(CH₃)₂ | H | OCH₃ | OCH₃ | N | |
| CH₃ | O(CH₂)₃CH(CH₃)₂ | H | CH₃ | OCH₃ | N | |
| CH₃ | OCH(CH₃)(C₂H₅) | H | OCH₃ | OCH₃ | CH | |
| CH₃ | OCH₂CH(CH₃)(C₂H₅) | H | CH₃ | OCH₃ | CH | |
| CH₃ | O(CH₂)₂CH(CH₃)(C₂H₅) | H | OCH₃ | OCH₃ | N | |
| CH₃ | SCH₃ | H | OCH₃ | OCH₃ | CH | 201–202 |
| CH₃ | SC₂H₅ | H | CH₃ | CH₃ | CH | 193–196 (d) |
| CH₃ | SC₂H₅ | H | OCH₃ | CH₃ | CH | 198–200 (d) |
| CH₃ | SC₂H₅ | H | OCH₃ | OCH₃ | CH | 193–195 (d) |
| CH₃ | SC₂H₅ | H | Cl | OCH₃ | CH | 205–208 (d) |
| CH₃ | SC₂H₅ | H | OCH₃ | N(CH₃)₂ | CH | |
| CH₃ | SC₂H₅ | H | CH₃ | CH₃ | N | |
| CH₃ | SC₂H₅ | H | OCH₃ | CH₃ | N | 185–187 (d) |
| CH₃ | SC₂H₅ | H | OCH₃ | OCH₃ | N | 201–204 (d) |
| CH₃ | SC₂H₅ | H | OCH₃ | N(CH₃)₂ | N | |
| CH₃ | SC₂H₅ | H | OCH₃ | OCH₂CF₃ | N | |
| CH₃ | SC₂H₅ | CH₃ | OCH₃ | CH₃ | N | |
| CH₃ | SC₂H₅ | CH₃ | OCH₃ | OCH₃ | N | |
| CH₃ | SC₂H₅ | CH₃ | CH₃ | OCH₃ | CH | |
| CH₃ | SC₂H₅ | CH₃ | OCH₃ | OCH₃ | CH | |
| CH₃ | SC₂H₅ | H | Br | OCH₃ | CH | 134–137 |
| CH₃ | SC₂H₅ | CH₃ | OCH₃ | N(CH₃)₂ | N | |
| CH₃ | SC₂H₅ | H | CH₃ | OCH₂CF₃ | N | |
| CH₃ | SC₂H₅ | H | CH₃ | OCH₂CF₃ | CH | |
| CH₃ | SC₂H₅ | H | OCH₃ | OCH₂CF₃ | CH | |
| CH₃ | SC₂H₅ | H | OCH₃ | C₂H₅ | CH | |
| CH₃ | SC₂H₅ | H | OCH₃ | C₂H₅ | N | |
| CH₃ | SC₂H₅ | H | OCH₃ | NHCH₃ | CH | |
| CH₃ | SC₂H₅ | H | OCH₃ | NHCH₃ | N | |
| CH₃ | SC₂H₅ | H | CH₃ | OC₂H₅ | CH | |
| CH₃ | SC₂H₅ | H | OCH₃ | OC₂H₅ | CH | |
| CH₃ | SC₂H₅ | H | CH₃ | OC₂H₅ | N | |
| CH₃ | SC₂H₅ | H | OCH₃ | OC₂H₅ | N | |
| CH₃ | SC₂H₅ | H | CH₃ | OCH₂CHF₂ | CH | |
| CH₃ | SC₂H₅ | H | OCH₃ | OCH₂CHF₂ | CH | |
| CH₃ | SC₂H₅ | H | CH₃ | OCH₂CHF₂ | N | |
| CH₃ | SC₂H₅ | H | OCH₃ | OCH₂CHF₂ | N | |
| CH₃ | SC₂H₅ | H | CH₃ | OCH₂CH₂F | CH | |
| CH₃ | SC₂H₅ | H | OCH₃ | OCH₂CH₂F | CH | |
| CH₃ | SC₂H₅ | H | CH₃ | OCH₂CH₂F | N | |
| CH₃ | SC₂H₅ | CH₃ | OCH₃ | OCH₂CH₂F | N | |
| CH₃ | SC₂H₅ | CH₃ | Cl | OCH₃ | CH | |
| CH₃ | SC₂H₅ | H | Cl | N(CH₃)₂ | CH | |
| CH₃ | SC₂H₅ | H | Cl | OC₂H₅ | CH | |
| C₂H₅ | SC₂H₅ | H | CH₃ | CH₃ | CH | 158–160 (d) |
| C₂H₅ | SC₂H₅ | H | OCH₃ | CH₃ | CH | 105–107 (d) |
| C₂H₅ | SC₂H₅ | H | OCH₃ | OCH₃ | CH | 198–200 (d) |
| C₂H₅ | SC₂H₅ | H | Cl | OCH₃ | CH | 97–103 (d) |
| C₂H₅ | SC₂H₅ | H | CH₃ | CH₃ | N | |
| C₂H₅ | SC₂H₅ | H | OCH₃ | CH₃ | N | 170–172 (d) |
| C₂H₅ | SC₂H₅ | H | OCH₃ | OCH₃ | N | 155–157 (d) |
| C₂H₅ | SC₂H₅ | H | Br | OCH₃ | CH | 75–80 |
| C₂H₅ | SC₂H₅ | H | OCH₃ | N(CH₃)₂ | CH | |
| C₂H₅ | SC₂H₅ | H | OCH₃ | N(CH₃)₂ | N | |
| C₂H₅ | SC₂H₅ | H | OCH₃ | MHCH₃ | N | |
| C₂H₅ | SC₂H₅ | H | OCH₃ | C₂H₅ | CH | |
| C₂H₅ | SC₂H₅ | H | OCH₃ | C₂H₅ | N | |
| C₂H₅ | SC₂H₅ | H | CH₃ | OC₂H₅ | CH | |
| C₂H₅ | SC₂H₅ | H | CH₃ | OC₂H₅ | N | |
| C₂H₅ | SC₂H₅ | H | OCH₃ | OC₂H₅ | CH | |
| C₂H₅ | SC₂H₅ | H | OCH₃ | OC₂H₅ | N | |
| C₂H₅ | SC₂H₅ | H | CH₃ | OCH₂CF₃ | CH | |
| C₂H₅ | SC₂H₅ | H | CH₃ | OCH₂CF₃ | N | |
| C₂H₅ | SC₂H₅ | H | OCH₃ | OCH₂CF₃ | CH | |
| C₂H₅ | SC₂H₅ | H | OCH₃ | OCH₂CF₃ | N | |
| C₂H₅ | SC₂H₅ | H | OCH₃ | OCH₂CHF₂ | CH | |
| C₂H₅ | SC₂H₅ | H | OCH₃ | OCH₂CHF₂ | N | |
| C₂H₅ | SC₂H₅ | H | CH₃ | OCH₂CHF₂ | N | |
| C₂H₅ | SC₂H₅ | H | OCH₃ | OCH₂CH₂F | CH | |
| C₂H₅ | SC₂H₅ | H | OCH₃ | OCH₂CH₂F | N | |
| C₂H₅ | SC₂H₅ | CH₃ | OCH₃ | OCH₃ | CH | |
| C₂H₅ | SC₂H₅ | CH₃ | CH₃ | OCH₃ | N | |
| C₂H₅ | SC₂H₅ | CH₃ | OCH₃ | OCH₃ | N | |
| n-C₃H₇ | SC₂H₅ | H | OCH₃ | OCH₃ | CH | |
| n-C₃H₇ | SC₂H₅ | H | CH₃ | OCH₃ | N | |
| CH(CH₃)₂ | SC₂H₅ | H | OCH₃ | CH₃ | CH | |
| CH(CH₃)₂ | SC₂H₅ | H | OCH₃ | OCH₃ | CH | |

TABLE I-continued

| | | | | | | |
|---|---|---|---|---|---|---|
| CH(CH₃)₂ | SC₂H₅ | H | Cl | OCH₃ | CH | |
| CH(CH₃)₂ | SC₂H₅ | H | OCH₃ | CH₃ | N | |
| CH(CH₃)₂ | SC₂H₅ | H | OCH₃ | OCH₃ | N | |
| CH(CH₃)₂ | SC₂H₅ | H | OCH₃ | N(CH₃)₂ | N | |
| CH₃ | S(CH₂)₂CH₃ | H | CH₃ | CH₃ | CH | 122–125 (d) |
| CH₃ | S(CH₂)₂CH₃ | H | OCH₃ | CH₃ | CH | 128–130 (d) |
| CH₃ | S(CH₂)₂CH₃ | H | OCH₃ | OCH₃ | CH | 101–104 (d) |
| CH₃ | S(CH₂)₂CH₃ | H | Cl | OCH₃ | CH | 137–139 (d) |
| CH₃ | S(CH₂)₂CH₃ | H | OCH₃ | N(CH₃)₂ | CH | |
| CH₃ | S(CH₂)₂CH₃ | H | CH₃ | CH₃ | N | |
| CH₃ | S(CH₂)₂CH₃ | H | OCH₃ | CH₃ | N | 138–140 (d) |
| CH₃ | S(CH₂)₂CH₃ | H | OCH₃ | OCH₃ | N | 111–114 (d) |
| CH₃ | S(CH₂)₂CH₃ | H | OCH₃ | N(CH₃)₂ | N | |
| CH₃ | S(CH₂)₂CH₃ | H | OCH₃ | OCH₂CF₃ | N | |
| CH₃ | S(CH₂)₂CH₃ | CH₃ | OCH₃ | CH₃ | N | |
| CH₃ | S(CH₂)₂CH₃ | CH₃ | OCH₃ | OCH₃ | N | |
| CH₃ | S(CH₂)₂CH₃ | CH₃ | CH₃ | OCH₃ | CH | |
| CH₃ | S(CH₂)₂CH₃ | CH₃ | OCH₃ | OCH₃ | CH | |
| CH₃ | S(CH₂)₂CH₃ | H | Br | OCH₃ | CH | 132–134 |
| CH₃ | S(CH₂)₂CH₃ | CH₃ | OCH₃ | N(CH₃)₂ | N | |
| CH₃ | S(CH₂)₂CH₃ | H | CH₃ | OCH₂CF₃ | N | |
| CH₃ | S(CH₂)₂CH₃ | H | CH₃ | OCH₂CF₃ | CH | |
| CH₃ | S(CH₂)₂CH₃ | H | OCH₃ | OCH₂CF₃ | CH | |
| CH₃ | S(CH₂)₂CH₃ | H | OCH₃ | C₂H₅ | CH | |
| CH₃ | S(CH₂)₂CH₃ | H | OCH₃ | C₂H₅ | N | |
| CH₃ | S(CH₂)₂CH₃ | H | OCH₃ | NHCH₃ | CH | |
| CH₃ | S(CH₂)₂CH₃ | H | OCH₃ | NHCH₃ | N | |
| CH₃ | S(CH₂)₂CH₃ | H | CH₃ | OC₂H₅ | CH | |
| CH₃ | S(CH₂)₂CH₃ | H | OCH₃ | OC₂H₅ | CH | |
| CH₃ | S(CH₂)₂CH₃ | H | CH₃ | OC₂H₅ | N | |
| CH₃ | S(CH₂)₂CH₃ | H | OCH₃ | OC₂H₅ | N | |
| CH₃ | S(CH₂)₂CH₃ | H | CH₃ | OCH₂CHF₂ | CH | |
| CH₃ | S(CH₂)₂CH₃ | H | OCH₃ | OCH₂CHF₂ | CH | |
| CH₃ | S(CH₂)₂CH₃ | H | CH₃ | OCH₂CHF₂ | N | |
| CH₃ | S(CH₂)₂CH₃ | H | OCH₃ | OCH₂CHF₂ | N | |
| CH₃ | S(CH₂)₂CH₃ | H | CH₃ | OCH₂CH₂F | CH | |
| CH₃ | S(CH₂)₂CH₃ | H | OCH₃ | OCH₂CH₂F | CH | |
| CH₃ | S(CH₂)₂CH₃ | H | CH₃ | OCH₂CH₂F | N | |
| CH₃ | S(CH₂)₂CH₃ | CH₃ | OCH₃ | OCH₂CH₂F | N | |
| CH₃ | S(CH₂)₂CH₃ | CH₃ | Cl | OCH₃ | CH | |
| CH₃ | S(CH₂)₂CH₃ | H | Cl | N(CH₃)₂ | CH | |
| CH₃ | S(CH₂)₂CH₃ | H | Cl | OC₂H₅ | CH | |
| C₂H₅ | S(CH₂)₂CH₃ | H | CH₃ | CH₃ | CH | 142–143 (d) |
| C₂H₅ | S(CH₂)₂CH₃ | H | OCH₃ | CH₃ | CH | 109–114 (d) |
| C₂H₅ | S(CH₂)₂CH₃ | H | OCH₃ | OCH₃ | CH | 130–133 (d) |
| C₂H₅ | S(CH₂)₂CH₃ | H | Cl | OCH₃ | CH | 98–100 (d) |
| C₂H₅ | S(CH₂)₂CH₃ | H | CH₃ | CH₃ | N | |
| C₂H₅ | S(CH₂)₂CH₃ | H | OCH₃ | CH₃ | N | 100–103 (d) |
| C₂H₅ | S(CH₂)₂CH₃ | H | OCH₃ | OCH₃ | N | 108–110 (d) |
| C₂H₅ | S(CH₂)₂CH₃ | H | Br | OCH₃ | CH | 104–107 |
| C₂H₅ | S(CH₂)₂CH₃ | H | OCH₃ | N(CH₃)₂ | CH | |
| C₂H₅ | S(CH₂)₂CH₃ | H | OCH₃ | N(CH₃)₂ | N | |
| C₂H₅ | S(CH₂)₂CH₃ | H | OCH₃ | NHCH₃ | N | |
| C₂H₅ | S(CH₂)₂CH₃ | H | OCH₃ | C₂H₅ | CH | |
| C₂H₅ | S(CH₂)₂CH₃ | H | OCH₃ | C₂H₅ | N | |
| C₂H₅ | S(CH₂)₂CH₃ | H | CH₃ | OC₂H₅ | CH | |
| C₂H₅ | S(CH₂)₂CH₃ | H | CH₃ | OC₂H₅ | CH | |
| C₂H₅ | S(CH₂)₂CH₃ | H | OCH₃ | OC₂H₅ | N | |
| C₂H₅ | S(CH₂)₂CH₃ | H | CH₃ | OCH₂CF₃ | CH | |
| C₂H₅ | S(CH₂)₂CH₃ | H | CH₃ | OCH₂CF₃ | N | |
| C₂H₅ | S(CH₂)₂CH₃ | H | OCH₃ | OCH₂CF₃ | CH | |
| C₂H₅ | S(CH₂)₂CH₃ | H | OCH₃ | OCH₂CF₃ | N | |
| C₂H₅ | S(CH₂)₂CH₃ | H | OCH₃ | OCH₂CHF₂ | CH | |
| C₂H₅ | S(CH₂)₂CH₃ | H | OCH₃ | OCH₂CHF₂ | N | |
| C₂H₅ | S(CH₂)₂CH₃ | H | CH₃ | OCH₂CHF₂ | N | |
| C₂H₅ | S(CH₂)₂CH₃ | H | OCH₃ | OCH₂CH₂F | CH | |
| C₂H₅ | S(CH₂)₂CH₃ | H | OCH₃ | OCH₂CH₂F | N | |
| C₂H₅ | S(CH₂)₂CH₃ | CH₃ | OCH₃ | OCH₃ | CH | |
| C₂H₅ | S(CH₂)₂CH₃ | CH₃ | CH₃ | OCH₃ | N | |
| C₂H₅ | S(CH₂)₂CH₃ | CH₃ | OCH₃ | OCH₃ | N | |
| n-C₃H₇ | S(CH₂)₂CH₃ | H | OCH₃ | OCH₃ | CH | |
| n-C₃H₇ | S(CH₂)₂CH₃ | H | CH₃ | OCH₃ | N | |
| CH(CH₃)₂ | S(CH₂)₂CH₃ | H | OCH₃ | CH₃ | CH | |
| CH(CH₃)₂ | S(CH₂)₂CH₃ | H | OCH₃ | OCH₃ | CH | |
| CH(CH₃)₂ | S(CH₂)₂CH₃ | H | Cl | OCH₃ | CH | |
| CH(CH₃)₂ | S(CH₂)₂CH₃ | H | OCH₃ | CH₃ | N | |
| CH(CH₃)₂ | S(CH₂)₂CH₃ | H | OCH₃ | OCH₃ | N | |
| CH(CH₃)₂ | S(CH₂)₂CH₃ | H | OCH₃ | N(CH₃)₂ | N | |
| CH₃ | SCH(CH₃)₂ | H | CH₃ | CH₃ | CH | 147–149 (d) |
| CH₃ | SCH(CH₃)₂ | H | OCH₃ | CH₃ | CH | 107–109 (d) |
| CH₃ | SCH(CH₃)₂ | H | OCH₃ | OCH₃ | CH | 114–117 (d) |

TABLE I-continued

| | | | | | | |
|---|---|---|---|---|---|---|
| CH₃ | SCH(CH₃)₂ | H | Cl | OCH₃ | CH | 144–145 (d) |
| CH₃ | SCH(CH₃)₂ | H | OCH₃ | CH₃ | N | 124–126 (d) |
| CH₃ | SCH(CH₃)₂ | H | OCH₃ | OCH₃ | N | 134–136 (d) |
| C₂H₅ | SCH(CH₃)₂ | H | OCH₃ | CH₃ | CH | 162–163 (d) |
| C₂H₅ | SCH(CH₃)₂ | H | OCH₃ | OCH₃ | CH | 87–90 (d) |
| C₂H₅ | SCH(CH₃)₂ | H | OCH₃ | Cl | CH | 152–154 (d) |
| C₂H₅ | SCH(CH₃)₂ | H | OCH₃ | CH₃ | N | |
| C₂H₅ | SCH(CH₃)₂ | H | OCH₃ | OCH₃ | N | 110–113 (d) |
| C₂H₅ | SCH(CH₃)₂ | H | OCH₃ | Br | CH | 141–144 |
| CH₃ | S(CH₂)₃CH₃ | H | CH₃ | CH₃ | CH | |
| CH₃ | S(CH₂)₃CH₃ | H | OCH₃ | CH₃ | CH | |
| CH₃ | S(CH₂)₃CH₃ | H | OCH₃ | OCH₃ | CH | |
| CH₃ | S(CH₂)₃CH₃ | H | Cl | OCH₃ | CH | |
| CH₃ | S(CH₂)₃CH₃ | H | CH₃ | CH₃ | N | |
| CH₃ | S(CH₂)₃CH₃ | H | OCH₃ | CH₃ | N | |
| CH₃ | S(CH₂)₃CH₃ | H | OCH₃ | OCH₃ | N | |
| CH₃ | S(CH₂)₃CH₃ | H | OCH₃ | N(CH₃)₂ | CH | |
| CH₃ | S(CH₂)₃CH₃ | H | OCH₃ | N(CH₃)₂ | N | |
| CH₃ | S(CH₂)₃CH₃ | H | OCH₃ | OCH₂CF₃ | N | |
| CH₃ | S(CH₂)₃CH₃ | CH₃ | OCH₃ | CH₃ | N | |
| CH₃ | S(CH₂)₃CH₃ | CH₃ | OCH₃ | OCH₃ | N | |
| CH₃ | S(CH₂)₃CH₃ | CH₃ | CH₃ | OCH₃ | CH | |
| CH₃ | S(CH₂)₃CH₃ | CH₃ | OCH₃ | OCH₃ | CH | |
| CH₃ | S(CH₂)₃CH₃ | H | Br | OCH₃ | CH | |
| CH₃ | S(CH₂)₃CH₃ | H | CH₃ | OCH₂CF₃ | N | |
| CH₃ | S(CH₂)₃CH₃ | H | CH₃ | OCH₂CF₃ | CH | |
| CH₃ | S(CH₂)₃CH₃ | H | OCH₃ | OCH₂CF₃ | CH | |
| CH₃ | S(CH₂)₃CH₃ | H | OCH₃ | NHCH₃ | N | |
| C₂H₅ | S(CH₂)₃CH₃ | H | CH₃ | CH₃ | CH | |
| C₂H₅ | S(CH₂)₃CH₃ | H | OCH₃ | CH₃ | CH | |
| C₂H₅ | S(CH₂)₃CH₃ | H | OCH₃ | OCH₃ | CH | |
| C₂H₅ | S(CH₂)₃CH₃ | H | Cl | OCH₃ | CH | |
| C₂H₅ | S(CH₂)₃CH₃ | H | OCH₃ | CH₃ | N | |
| C₂H₅ | S(CH₂)₃CH₃ | H | OCH₃ | N(CH₃)₂ | CH | |
| CH(CH₃)₂ | S(CH₂)₃CH₃ | H | OCH₃ | CH₃ | CH | |
| CH(CH₃)₂ | S(CH₂)₃CH₃ | H | OCH₃ | OCH₃ | CH | |
| CH(CH₃)₂ | S(CH₂)₃CH₃ | H | Cl | OCH₃ | CH | |
| CH(CH₃)₂ | S(CH₂)₃CH₃ | H | OCH₃ | CH₃ | N | |
| CH(CH₃)₂ | S(CH₂)₃CH₃ | H | OCH₃ | OCH₃ | N | |
| CH₃ | SC(CH₃)₃ | H | OCH₃ | OCH₃ | N | 160–162 (d) |
| CH₃ | SC(CH₃)₃ | H | OCH₃ | CH₃ | N | 158–159 (d) |
| CH₃ | SC(CH₃)₃ | H | OCH₃ | OCH₃ | CH | 157–158 (d) |
| CH₃ | SC(CH₃)₃ | H | OCH₃ | CH₃ | CH | 113–115 |
| CH₃ | SC(CH₃)₃ | H | Cl | OCH₃ | CH | 105–107 (d) |
| CH₃ | SC(CH₃)₃ | H | CH₃ | CH₃ | CH | 170–173 (d) |
| C₂H₅ | SC(CH₃)₃ | H | OCH₃ | OCH₃ | N | |
| C₂H₅ | SC(CH₃)₃ | H | OCH₃ | CH₃ | N | |
| C₂H₅ | SC(CH₃)₃ | H | OCH₃ | OCH₃ | CH | |
| C₂H₅ | SC(CH₃)₃ | H | OCH₃ | CH₃ | CH | |
| C₂H₅ | SC(CH₃)₃ | H | Cl | OCH₃ | CH | |
| C₂H₅ | SC(CH₃)₃ | H | CH₃ | CH₃ | CH | |
| CH₃ | S(CH₂)₄CH₃ | H | CH₃ | CH₃ | CH | |
| CH₃ | S(CH₂)₄CH₃ | H | OCH₃ | CH₃ | CH | |
| CH₃ | S(CH₂)₄CH₃ | H | OCH₃ | OCH₃ | CH | |
| CH₃ | S(CH₂)₄CH₃ | H | Cl | OCH₃ | CH | |
| CH₃ | S(CH₂)₄CH₃ | H | CH₃ | CH₃ | N | |
| CH₃ | S(CH₂)₄CH₃ | H | OCH₃ | CH₃ | N | |
| CH₃ | S(CH₂)₄CH₃ | H | OCH₃ | OCH₃ | N | |
| CH₃ | S(CH₂)₄CH₃ | H | OCH₃ | N(CH₃)₂ | CH | |
| CH₃ | S(CH₂)₄CH₃ | H | OCH₃ | N(CH₃)₂ | N | |
| CH₃ | S(CH₂)₄CH₃ | H | OCH₃ | OCH₂CF₃ | N | |
| CH₃ | S(CH₂)₄CH₃ | CH₃ | OCH₃ | CH₃ | N | |
| CH₃ | S(CH₂)₄CH₃ | CH₃ | OCH₃ | OCH₃ | N | |
| CH₃ | S(CH₂)₄CH₃ | CH₃ | CH₃ | OCH₃ | CH | |
| CH₃ | S(CH₂)₄CH₃ | CH₃ | OCH₃ | OCH₃ | CH | |
| CH₃ | S(CH₂)₄CH₃ | H | Br | OCH₃ | CH | |
| CH₃ | S(CH₂)₄CH₃ | H | CH₃ | OCH₂CF₃ | N | |
| CH₃ | S(CH₂)₄CH₃ | H | CH₃ | OCH₂CF₃ | CH | |
| CH₃ | S(CH₂)₄CH₃ | H | OCH₃ | OCH₂CF₃ | CH | |
| CH₃ | S(CH₂)₄CH₃ | H | OCH₃ | NHCH₃ | N | |
| C₂H₅ | S(CH₂)₄CH₃ | H | CH₃ | CH₃ | CH | |
| C₂H₅ | S(CH₂)₄CH₃ | H | OCH₃ | CH₃ | CH | |
| C₂H₅ | S(CH₂)₄CH₃ | H | OCH₃ | OCH₃ | CH | |
| C₂H₅ | S(CH₂)₄CH₃ | H | Cl | OCH₃ | CH | |
| C₂H₅ | S(CH₂)₄CH₃ | H | OCH₃ | CH₃ | N | |
| C₂H₅ | S(CH₂)₄CH₃ | H | OCH₃ | N(CH₃)₂ | CH | |
| CH(CH₃)₂ | S(CH₂)₄CH₃ | H | OCH₃ | CH₃ | CH | |
| CH(CH₃)₂ | S(CH₂)₄CH₃ | H | OCH₃ | OCH₃ | CH | |
| CH(CH₃)₂ | S(CH₂)₄CH₃ | H | Cl | OCH₃ | CH | |
| CH(CH₃)₂ | S(CH₂)₄CH₃ | H | OCH₃ | CH₃ | N | |
| CH(CH₃)₂ | S(CH₂)₄CH₃ | H | OCH₃ | OCH₃ | N | |
| CH₃ | S(CH₂)₅CH₃ | H | CH₃ | CH₃ | CH | 160–167 |

TABLE I-continued

| | | | | | | |
|---|---|---|---|---|---|---|
| CH₃ | S(CH₂)₅CH₃ | H | OCH₃ | CH₃ | CH | 190-195 (d) |
| CH₃ | S(CH₂)₅CH₃ | H | OCH₃ | OCH₃ | CH | 185-191 (d) |
| CH₃ | S(CH₂)₅CH₃ | H | Cl | OCH₃ | CH | 108-113 (d) |
| CH₃ | S(CH₂)₅CH₃ | H | CH₃ | CH₃ | N | |
| CH₃ | S(CH₂)₅CH₃ | H | OCH₃ | CH₃ | N | 89-95 (d) |
| CH₃ | S(CH₂)₅CH₃ | H | OCH₃ | OCH₃ | N | 90-95 (d) |
| CH₃ | S(CH₂)₅CH₃ | H | OCH₃ | N(CH₃)₂ | CH | |
| CH₃ | S(CH₂)₅CH₃ | H | OCH₃ | N(CH₃)₂ | N | |
| CH₃ | S(CH₂)₅CH₃ | H | OCH₃ | OCH₂CF₃ | N | |
| CH₃ | S(CH₂)₅CH₃ | CH₃ | OCH₃ | CH₃ | N | |
| CH₃ | S(CH₂)₅CH₃ | CH₃ | OCH₃ | OCH₃ | N | |
| CH₃ | S(CH₂)₅CH₃ | CH₃ | CH₃ | OCH₃ | CH | |
| CH₃ | S(CH₂)₅CH₃ | CH₃ | OCH₃ | OCH₃ | CH | |
| CH₃ | S(CH₂)₅CH₃ | H | Br | OCH₃ | CH | |
| CH₃ | S(CH₂)₅CH₃ | H | CH₃ | OCH₂CF₃ | N | |
| CH₃ | S(CH₂)₅CH₃ | H | CH₃ | OCH₂CF₃ | CH | |
| CH₃ | S(CH₂)₅CH₃ | H | OCH₃ | OCH₂CF₃ | CH | |
| CH₃ | S(CH₂)₅CH₃ | H | OCH₃ | NHCH₃ | N | |
| C₂H₅ | S(CH₂)₅CH₃ | H | CH₃ | CH₃ | CH | 150-157 |
| C₂H₅ | S(CH₂)₅CH₃ | H | OCH₃ | CH₃ | CH | 115-123 |
| C₂H₅ | S(CH₂)₅CH₃ | H | OCH₃ | OCH₃ | CH | 86-89 |
| C₂H₅ | S(CH₂)₅CH₃ | H | Cl | OCH₃ | CH | 90-92 |
| C₂H₅ | S(CH₂)₅CH₃ | H | OCH₃ | OCH₃ | N | 74-76 |
| C₂H₅ | S(CH₂)₅CH₃ | H | OCH₃ | CH₃ | N | 77-80 |
| C₂H₅ | S(CH₂)₅CH₃ | H | OCH₃ | N(CH₃)₂ | CH | |
| CH(CH₃)₂ | S(CH₂)₅CH₃ | H | OCH₃ | CH₃ | CH | |
| CH(CH₃)₂ | S(CH₂)₅CH₃ | H | OCH₃ | OCH₃ | CH | |
| CH(CH₃)₂ | S(CH₂)₅CH₃ | H | Cl | OCH₃ | CH | |
| CH(CH₃)₂ | S(CH₂)₅CH₃ | H | OCH₃ | CH₃ | N | |
| CH(CH₃)₂ | S(CH₂)₅CH₃ | H | OCH₃ | OCH₃ | N | |
| CH₃ | SCH₂CH(CH₃)₂ | H | CH₃ | OCH₃ | CH | |
| CH₃ | S(CH₂)₂CH(CH₃)₂ | H | OCH₃ | OCH₃ | N | |
| CH₃ | S(CH₂)₃CH(CH₃)₂ | H | CH₃ | OCH₃ | N | |
| CH₃ | SCH(CH₃)(C₂H₅) | H | OCH₃ | OCH₃ | CH | |
| CH₃ | SCH₂CH(CH₃)(C₂H₅) | H | CH₃ | OCH₃ | CH | |
| CH₃ | S(CH₂)₂CH(CH₃)(C₂H₅) | H | OCH₃ | OCH₃ | CH | |
| CH₃ | S(CH₂)₇CH₃ | H | OCH₃ | OCH₃ | CH | |
| CH₃ | S(CH₂)₇CH₃ | H | OCH₃ | CH₃ | N | |
| CH₃ | SCH(CH₃)(n-C₆H₁₃) | H | OCH₃ | CH₃ | CH | |
| CH₃ | S-cyclohexyl | H | CH₃ | CH₃ | CH | |
| CH₃ | S-cyclohexyl | H | CH₃ | OCH₃ | CH | |
| CH₃ | S-cyclohexyl | H | OCH₃ | OCH₃ | CH | |
| CH₃ | S-cyclohexyl | H | Cl | OCH₃ | CH | |
| CH₃ | S-cyclohexyl | H | CH₃ | CH₃ | N | |
| CH₃ | S-cyclohexyl | H | OCH₃ | OCH₃ | N | |
| CH₃ | SC₆H₅ | H | CH₃ | OCH₃ | CH | |
| CH₃ | SC₆H₅ | H | OCH₃ | OCH₃ | CH | |
| CH₃ | SC₆H₅ | H | Cl | OCH₃ | CH | |
| CH₃ | SC₆H₅ | H | CH₃ | OCH₃ | N | |
| CH₃ | SC₆H₅ | H | OCH₃ | OCH₃ | N | |
| CH₃ | SCH₂C₆H₅ | H | CH₃ | OCH₃ | CH | 187-189 |
| CH₃ | SCH₂C₆H₅ | H | OCH₃ | OCH₃ | CH | 186-188 |
| CH₃ | SCH₂C₆H₅ | H | Cl | OCH₃ | CH | 183-185 |
| CH₃ | SCH₂C₆H₅ | H | CH₃ | OCH₃ | N | 157-159 |
| CH₃ | SCH₂C₆H₅ | H | OCH₃ | OCH₃ | N | 145-147 |
| CH₃ | SCH₂C₆H₅ | H | CH₃ | CH₃ | CH | 196-198 |
| CH₂CH₃ | SCH₂C₆H₅ | H | OCH₃ | OCH₃ | N | 145-147 |
| CH₂CH₃ | SCH₂C₆H₅ | H | CH₃ | OCH₃ | N | 174-176 |
| CH₂CH₃ | SCH₂C₆H₅ | H | OCH₃ | OCH₃ | CH | 163-165 |
| CH₂CH₃ | SCH₂C₆H₅ | H | CH₃ | OCH₃ | CH | 151-154 |
| CH₂CH₃ | SCH₂C₆H₅ | H | Cl | OCH₃ | CH | 154-156 |
| CH₂CH₃ | SCH₂C₆H₅ | H | CH₃ | CH₃ | CH | 172-175 |
| CH₃ | S(O)(CH₃) | H | CH₃ | CH₃ | CH | 119-120 (d) |
| CH₃ | S(O)(CH₃) | H | OCH₃ | CH₃ | CH | 160-161 (d) |
| CH₃ | S(O)(CH₃) | H | OCH₃ | OCH₃ | CH | 190-191 (d) |
| CH₃ | S(O)(CH₃) | H | Cl | OCH₃ | CH | 206-209 (d) |
| CH₃ | S(O)(CH₃) | H | OCH₃ | N(CH₃)₂ | CH | |
| CH₃ | S(O)(CH₃) | H | CH₃ | CH₃ | N | |
| CH₃ | S(O)(CH₃) | H | OCH₃ | CH₃ | N | 198-200 (d) |
| CH₃ | S(O)(CH₃) | H | OCH₃ | OCH₃ | N | 194-196 (d) |
| CH₃ | S(O)(CH₃) | H | OCH₃ | N(CH₃)₂ | N | |
| CH₃ | S(O)(CH₃) | H | OCH₃ | OCH₂CF₃ | N | |
| CH₃ | S(O)(CH₃) | CH₃ | OCH₃ | CH₃ | N | |
| CH₃ | S(O)(CH₃) | CH₃ | OCH₃ | OCH₃ | N | |
| CH₃ | S(O)(CH₃) | CH₃ | CH₃ | OCH₃ | CH | |
| CH₃ | S(O)(CH₃) | CH₃ | OCH₃ | OCH₃ | CH | |
| CH₃ | S(O)(CH₃) | H | Br | OCH₃ | CH | |
| CH₃ | S(O)(CH₃) | H | OCH₃ | N(CH₃)₂ | CH | |
| CH₃ | S(O)(CH₃) | CH₃ | OCH₃ | N(CH₃)₂ | N | |
| CH₃ | S(O)(CH₃) | H | CH₃ | OCH₂CF₃ | N | |
| CH₃ | S(O)(CH₃) | H | CH₃ | OCH₂CF₃ | CH | |
| CH₃ | S(O)(CH₃) | H | OCH₃ | OCH₂CF₃ | CH | |

TABLE I-continued

| | | | | | | |
|---|---|---|---|---|---|---|
| CH$_3$ | S(O)(CH$_3$) | H | OCH$_3$ | C$_2$H$_5$ | CH | |
| CH$_3$ | S(O)(CH$_3$) | H | OCH$_3$ | C$_2$H$_5$ | N | |
| CH$_3$ | S(O)(CH$_3$) | H | OCH$_3$ | NHCH$_3$ | CH | |
| CH$_3$ | S(O)(CH$_3$) | H | OCH$_3$ | NHCH$_3$ | N | |
| CH$_3$ | S(O)(CH$_3$) | H | CH$_3$ | OC$_2$H$_5$ | CH | |
| CH$_3$ | S(O)(CH$_3$) | H | OCH$_3$ | OC$_2$H$_5$ | CH | |
| CH$_3$ | S(O)(CH$_3$) | H | CH$_3$ | OC$_2$H$_5$ | N | |
| CH$_3$ | S(O)(CH$_3$) | H | OCH$_3$ | OC$_2$H$_5$ | N | |
| CH$_3$ | S(O)(CH$_3$) | H | CH$_3$ | OCH$_2$CHF$_2$ | CH | |
| CH$_3$ | S(O)(CH$_3$) | H | OCH$_3$ | OCH$_2$CHF$_2$ | CH | |
| CH$_3$ | S(O)(CH$_3$) | H | CH$_3$ | OCH$_2$CHF$_2$ | N | |
| CH$_3$ | S(O)(CH$_3$) | H | OCH$_3$ | OCH$_2$CHF$_2$ | N | |
| CH$_3$ | S(O)(CH$_3$) | H | CH$_3$ | OCH$_2$CHF$_2$ | CH | |
| CH$_3$ | S(O)(CH$_3$) | H | OCH$_3$ | OCH$_2$CHF$_2$ | CH | |
| CH$_3$ | S(O)(CH$_3$) | H | CH$_3$ | OCH$_2$CHF$_2$ | N | |
| CH$_3$ | S(O)(CH$_3$) | H | OCH$_3$ | OCH$_2$CHF$_2$ | N | |
| CH$_3$ | S(O)(CH$_3$) | CH$_3$ | Cl | OCH$_3$ | CH | |
| CH$_3$ | S(O)(CH$_3$) | H | Cl | N(CH$_3$)$_2$ | CH | |
| CH$_3$ | S(O)(CH$_3$) | H | Cl | OC$_2$H$_5$ | CH | |
| C$_2$H$_5$ | S(O)(CH$_3$) | H | CH$_3$ | CH$_3$ | CH | 100–103 |
| C$_2$H$_5$ | S(O)(CH$_3$) | H | OCH$_3$ | CH$_3$ | CH | 141–144 |
| C$_2$H$_5$ | S(O)(CH$_3$) | H | OCH$_3$ | OCH$_3$ | CH | 132–134 |
| C$_2$H$_5$ | S(O)(CH$_3$) | H | Cl | OCH$_3$ | CH | 151–154 |
| C$_2$H$_5$ | S(O)(CH$_3$) | H | CH$_3$ | CH$_3$ | N | |
| C$_2$H$_5$ | S(O)(CH$_3$) | H | OCH$_3$ | CH$_3$ | N | 148–150 |
| C$_2$H$_5$ | S(O)(CH$_3$) | H | OCH$_3$ | OCH$_3$ | N | 145–146 |
| C$_2$H$_5$ | S(O)(CH$_3$) | H | Br | OCH$_3$ | CH | |
| C$_2$H$_5$ | S(O)(CH$_3$) | H | OCH$_3$ | N(CH$_3$)$_2$ | CH | |
| C$_2$H$_5$ | S(O)(CH$_3$) | H | OCH$_3$ | N(CH$_3$)$_2$ | N | |
| C$_2$H$_5$ | S(O)(CH$_3$) | H | OCH$_3$ | NHCH$_3$ | N | |
| C$_2$H$_5$ | S(O)(CH$_3$) | H | OCH$_3$ | C$_2$H$_5$ | CH | |
| C$_2$H$_5$ | S(O)(CH$_3$) | H | OCH$_3$ | C$_2$H$_5$ | N | |
| C$_2$H$_5$ | S(O)(CH$_3$) | H | CH$_3$ | OC$_2$H$_5$ | CH | |
| C$_2$H$_5$ | S(O)(CH$_3$) | H | CH$_3$ | OC$_2$H$_5$ | N | |
| C$_2$H$_5$ | S(O)(CH$_3$) | H | OCH$_3$ | OC$_2$H$_5$ | CH | |
| C$_2$H$_5$ | S(O)(CH$_3$) | H | OCH$_3$ | OC$_2$H$_5$ | N | |
| C$_2$H$_5$ | S(O)(CH$_3$) | H | CH$_3$ | OCH$_2$CF$_3$ | CH | |
| C$_2$H$_5$ | S(O)(CH$_3$) | H | CH$_3$ | OCH$_2$CF$_3$ | N | |
| C$_2$H$_5$ | S(O)(CH$_3$) | H | OCH$_3$ | OCH$_2$CF$_3$ | CH | |
| C$_2$H$_5$ | S(O)(CH$_3$) | H | OCH$_3$ | OCH$_2$CF$_3$ | N | |
| C$_2$H$_5$ | S(O)(CH$_3$) | H | OCH$_3$ | OCH$_2$CHF$_2$ | CH | |
| C$_2$H$_5$ | S(O)(CH$_3$) | H | OCH$_3$ | OCH$_2$CHF$_2$ | N | |
| C$_2$H$_5$ | S(O)(CH$_3$) | H | CH$_3$ | OCH$_2$CHF$_2$ | N | |
| C$_2$H$_5$ | S(O)(CH$_3$) | H | OCH$_3$ | OCH$_2$CHF$_2$ | CH | |
| C$_2$H$_5$ | S(O)(CH$_3$) | H | OCH$_3$ | OCH$_2$CH$_2$F | N | |
| C$_2$H$_5$ | S(O)(CH$_3$) | CH$_3$ | OCH$_3$ | OCH$_3$ | CH | |
| C$_2$H$_5$ | S(O)(CH$_3$) | CH$_3$ | CH$_3$ | OCH$_3$ | N | |
| C$_2$H$_5$ | S(O)(CH$_3$) | CH$_3$ | OCH$_3$ | OCH$_3$ | N | |
| n-C$_3$H$_7$ | S(O)(CH$_3$) | H | OCH$_3$ | OCH$_3$ | CH | |
| n-C$_3$H$_7$ | S(O)(CH$_3$) | H | CH$_3$ | OCH$_3$ | N | |
| CH(CH$_3$)$_2$ | S(O)(CH$_3$) | H | OCH$_3$ | CH$_3$ | CH | |
| CH(CH$_3$)$_2$ | S(O)(CH$_3$) | H | OCH$_3$ | OCH$_3$ | CH | |
| CH(CH$_3$)$_2$ | S(O)(CH$_3$) | H | Cl | OCH$_3$ | CH | |
| CH(CH$_3$)$_2$ | S(O)(CH$_3$) | H | OCH$_3$ | CH$_3$ | N | |
| CH(CH$_3$)$_2$ | S(O)(CH$_3$) | H | OCH$_3$ | OCH$_3$ | N | |
| CH(CH$_3$)$_2$ | S(O)(CH$_3$) | H | OCH$_3$ | N(CH$_3$)$_2$ | N | |
| CH$_3$ | S(O)(CH$_2$CH$_3$) | H | CH$_3$ | CH$_3$ | CH | 105–110 |
| CH$_3$ | S(O)(CH$_2$CH$_3$) | H | OCH$_3$ | CH$_3$ | CH | 95–102 |
| CH$_3$ | S(O)(CH$_2$CH$_3$) | H | OCH$_3$ | OCH$_3$ | CH | 105–106 (d) |
| CH$_3$ | S(O)(CH$_2$CH$_3$) | H | Cl | OCH$_3$ | CH | 150–155 (d) |
| CH$_3$ | S(O)(CH$_2$CH$_3$) | H | CH$_3$ | CH$_3$ | N | |
| CH$_3$ | S(O)(CH$_2$CH$_3$) | H | OCH$_3$ | CH$_3$ | N | 146–148 |
| CH$_3$ | S(O)(CH$_2$CH$_3$) | H | OCH$_3$ | OCH$_3$ | N | |
| CH$_3$ | S(O)(CH$_2$CH$_3$) | H | OCH$_3$ | N(CH$_3$)$_2$ | CH | |
| CH$_3$ | S(O)(CH$_2$CH$_3$) | H | OCH$_3$ | N(CH$_3$)$_2$ | N | |
| CH$_3$ | S(O)(CH$_2$CH$_3$) | H | OCH$_3$ | OCH$_2$CF$_3$ | N | |
| CH$_3$ | S(O)(CH$_2$CH$_3$) | CH$_3$ | OCH$_3$ | CH$_3$ | N | |
| CH$_3$ | S(O)(CH$_2$CH$_3$) | CH$_3$ | OCH$_3$ | OCH$_3$ | N | |
| CH$_3$ | S(O)(CH$_2$CH$_3$) | CH$_3$ | CH$_3$ | OCH$_3$ | CH | |
| CH$_3$ | S(O)(CH$_2$CH$_3$) | CH$_3$ | OCH$_3$ | OCH$_3$ | CH | |
| CH$_3$ | S(O)(CH$_2$CH$_3$) | H | Br | OCH$_3$ | CH | |
| CH$_3$ | S(O)(CH$_2$CH$_3$) | H | CH$_3$ | OCH$_2$CF$_3$ | N | |
| CH$_3$ | S(O)(CH$_2$CH$_3$) | H | CH$_3$ | OCH$_2$CF$_3$ | CH | |
| CH$_3$ | S(O)(CH$_2$CH$_3$) | H | OCH$_3$ | OCH$_2$CF$_3$ | CH | |
| CH$_3$ | S(O)(CH$_2$CH$_3$) | H | OCH$_3$ | NHCH$_3$ | N | |
| C$_2$H$_5$ | S(O)(CH$_2$CH$_3$) | H | CH$_3$ | CH$_3$ | CH | |
| C$_2$H$_5$ | S(O)(CH$_2$CH$_3$) | H | OCH$_3$ | CH$_3$ | CH | |
| C$_2$H$_5$ | S(O)(CH$_2$CH$_3$) | H | OCH$_3$ | OCH$_3$ | CH | |
| C$_2$H$_5$ | S(O)(CH$_2$CH$_3$) | H | Cl | OCH$_3$ | CH | |
| C$_2$H$_5$ | S(O)(CH$_2$CH$_3$) | H | OCH$_3$ | CH$_3$ | N | |
| C$_2$H$_5$ | S(O)(CH$_2$CH$_3$) | H | OCH$_3$ | N(CH$_3$)$_2$ | N | |
| CH(CH$_3$)$_2$ | S(O)(CH$_2$CH$_3$) | H | OCH$_3$ | CH$_3$ | CH | |

TABLE I-continued

| | | | | | | |
|---|---|---|---|---|---|---|
| CH(CH₃)₂ | S(O)(CH₂CH₃) | H | OCH₃ | OCH₃ | CH | |
| CH(CH₃)₂ | S(O)(CH₂CH₃) | H | Cl | OCH₃ | CH | |
| CH(CH₃)₂ | S(O)(CH₂CH₃) | H | OCH₃ | CH₃ | N | |
| CH(CH₃)₂ | S(O)(CH₂CH₃) | H | OCH₃ | OCH₃ | N | |
| CH₃ | S(O)((CH₂)₂CH₃) | H | CH₃ | CH₃ | CH | 123–124 |
| CH₃ | S(O)((CH₂)₂CH₃) | H | OCH₃ | CH₃ | CH | 106–107 |
| CH₃ | S(O)((CH₂)₂CH₃) | H | OCH₃ | OCH₃ | CH | 163–167 |
| CH₃ | S(O)((CH₂)₂CH₃) | H | Cl | OCH₃ | CH | 138–140 |
| CH₃ | S(O)((CH₂)₂CH₃) | H | CH₃ | CH₃ | N | 136–138 |
| CH₃ | S(O)((CH₂)₂CH₃) | H | OCH₃ | CH₃ | N | 154–155 |
| CH₃ | S(O)((CH₂)₂CH₃) | H | OCH₃ | OCH₃ | N | 118–119 |
| CH₂CH₃ | S(O)((CH₂)₂CH₃) | H | CH₃ | CH₃ | CH | 168–169 |
| CH₂CH₃ | S(O)((CH₂)₂CH₃) | H | OCH₃ | CH₃ | CH | 175–177 |
| CH₂CH₃ | S(O)((CH₂)₂CH₃) | H | OCH₃ | OCH₃ | CH | 174–175 |
| CH₂CH₃ | S(O)((CH₂)₂CH₃) | H | Cl | OCH₃ | CH | 187–189 |
| CH₂CH₃ | S(O)((CH₂)₂CH₃) | H | CH₃ | CH₃ | N | 156–158 |
| CH₂CH₃ | S(O)((CH₂)₂CH₃) | H | OCH₃ | CH₃ | N | 139–145 |
| CH₂CH₃ | S(O)((CH₂)₂CH₃) | H | OCH₃ | OCH₃ | N | 147–149 |
| CH₃ | S(O)(CH(CH₃)₂) | H | CH₃ | CH₃ | CH | 105–107 |
| CH₃ | S(O)(CH(CH₃)₂) | H | OCH₃ | CH₃ | CH | 127–128 |
| CH₃ | S(O)(CH(CH₃)₂) | H | OCH₃ | OCH₃ | CH | 153–154 |
| CH₃ | S(O)(CH(CH₃)₂) | H | Cl | OCH₃ | CH | 108–111 |
| CH₃ | S(O)(CH(CH₃)₂) | H | CH₃ | CH₃ | N | |
| CH₃ | S(O)(CH(CH₃)₂) | H | OCH₃ | CH₃ | N | 118–120 |
| CH₃ | S(O)(CH(CH₃)₂) | H | OCH₃ | OCH₃ | N | 120–122 |
| CH₃ | S(O)((CH₂)₃CH₃) | H | OCH₃ | CH₃ | CH | |
| CH₃ | S(O)((CH₂)₃CH₃) | H | OCH₃ | OCH₃ | CH | |
| CH₃ | S(O)((CH₂)₃CH₃) | H | Cl | OCH₃ | CH | |
| CH₃ | S(O)((CH₂)₃CH₃) | H | OCH₃ | CH₃ | N | |
| CH₃ | S(O)((CH₂)₃CH₃) | H | OCH₃ | OCH₃ | N | |
| CH₃ | S(O)((CH₂)₄CH₃) | H | OCH₃ | CH₃ | CH | |
| CH₃ | S(O)((CH₂)₄CH₃) | H | OCH₃ | OCH₃ | CH | |
| CH₃ | S(O)((CH₂)₄CH₃) | H | Cl | OCH₃ | CH | |
| CH₃ | S(O)((CH₂)₄CH₃) | H | OCH₃ | CH₃ | N | |
| CH₃ | S(O)((CH₂)₄CH₃) | H | OCH₃ | OCH₃ | N | |
| CH₃ | S(O)((CH₂)₅CH₃) | H | CH₃ | CH₃ | CH | |
| CH₃ | S(O)((CH₂)₆CH₃) | H | OCH₃ | OCH₃ | N | |
| CH₃ | S(O)((CH₂)₇CH₃) | H | OCH₃ | CH₃ | CH | |
| CH₃ | S(O)((CH₂)₂CH(CH₃)₂) | H | OCH₃ | CH₃ | N | |
| CH₃ | S(O)((CH₂)₅CH(CH₃)₂) | H | OCH₃ | OCH₃ | CH | |
| CH₃ | S(O)((CH₂CH(CH₃)(CH₂CH₃)) | H | OCH₃ | CH₃ | CH | |
| CH₃ | S(O)₂(CH₃) | H | CH₃ | CH₃ | CH | 138–140 |
| CH₃ | S(O)₂(CH₃) | H | OCH₃ | CH₃ | CH | 180–183 |
| CH₃ | S(O)₂(CH₃) | H | OCH₃ | OCH₃ | CH | 177–180 |
| CH₃ | S(O)₂(CH₃) | H | Cl | OCH₃ | CH | 178–180 |
| CH₃ | S(O)₂(CH₃) | H | CH₃ | CH₃ | N | |
| CH₃ | S(O)₂(CH₃) | H | OCH₃ | CH₃ | N | 149–152 |
| CH₃ | S(O)₂(CH₃) | H | OCH₃ | OCH₃ | N | 140–142 |
| CH₃ | S(O)₂(CH₃) | H | OCH₃ | N(CH₃)₂ | CH | |
| CH₃ | S(O)₂(CH₃) | H | OCH₃ | N(CH₃)₂ | N | |
| CH₃ | S(O)₂(CH₃) | H | OCH₃ | OCH₂CF₃ | N | |
| CH₃ | S(O)₂(CH₃) | CH₃ | OCH₃ | CH₃ | N | |
| CH₃ | S(O)₂(CH₃) | CH₃ | OCH₃ | OCH₃ | N | |
| CH₃ | S(O)₂(CH₃) | CH₃ | CH₃ | OCH₃ | CH | |
| CH₃ | S(O)₂(CH₃) | CH₃ | OCH₃ | OCH₃ | CH | |
| CH₃ | S(O)₂(CH₃) | H | Br | OCH₃ | CH | |
| CH₃ | S(O)₂(CH₃) | H | CH₃ | OCH₂CF₃ | N | |
| CH₃ | S(O)₂(CH₃) | H | OCH₃ | OCH₂CF₃ | CH | |
| CH₃ | S(O)₂(CH₃) | H | OCH₃ | NHCH₃ | N | |
| C₂H₅ | S(O)₂(CH₃) | H | CH₃ | CH₃ | CH | |
| C₂H₅ | S(O)₂(CH₃) | H | OCH₃ | CH₃ | CH | |
| C₂H₅ | S(O)₂(CH₃) | H | OCH₃ | OCH₃ | CH | |
| C₂H₅ | S(O)₂(CH₃) | H | Cl | OCH₃ | CH | |
| C₂H₅ | S(O)₂(CH₃) | H | OCH₃ | CH₃ | N | |
| C₂H₅ | S(O)₂(CH₃) | H | OCH₃ | N(CH₃)₂ | N | |
| CH(CH₃)₂ | S(O)₂(CH₃) | H | OCH₃ | CH₃ | CH | |
| CH(CH₃)₂ | S(O)₂(CH₃) | H | OCH₃ | OCH₃ | CH | |
| CH(CH₃)₂ | S(O)₂(CH₃) | H | Cl | OCH₃ | CH | |
| CH(CH₃)₂ | S(O)₂(CH₃) | H | OCH₃ | CH₃ | N | |
| CH(CH₃)₂ | S(O)₂(CH₃) | H | OCH₃ | OCH₃ | N | |
| CH₃ | S(O)₂(CH₂CH₃) | H | CH₃ | CH₃ | CH | |
| CH₃ | S(O)₂(CH₂CH₃) | H | OCH₃ | CH₃ | CH | |
| CH₃ | S(O)₂(CH₂CH₃) | H | OCH₃ | OCH₃ | CH | |
| CH₃ | S(O)₂(CH₂CH₃) | H | Cl | OCH₃ | CH | |
| CH₃ | S(O)₂(CH₂CH₃) | H | CH₃ | CH₃ | N | |
| CH₃ | S(O)₂(CH₂CH₃) | H | OCH₃ | CH₃ | N | |
| CH₃ | S(O)₂(CH₂CH₃) | H | OCH₃ | OCH₃ | N | |
| CH₃ | S(O)₂((CH₂)₂CH₃) | H | OCH₃ | CH₃ | CH | |
| CH₃ | S(O)₂((CH₂)₂CH₃) | H | OCH₃ | OCH₃ | CH | |
| CH₃ | S(O)₂((CH₂)₂CH₃) | H | Cl | OCH₃ | CH | |
| CH₃ | S(O)₂((CH₂)₂CH₃) | H | OCH₃ | CH₃ | N | |

TABLE I-continued

| | | | | | | |
|---|---|---|---|---|---|---|
| CH₃ | S(O)₂((CH₂)₂CH₃) | H | OCH₃ | OCH₃ | N | |
| CH₃ | S(O)₂(CH(₃)₂) | H | OCH₃ | CH₃ | CH | |
| CH₃ | S(O)₂(CH(CH₃)₂) | H | OCH₃ | OCH₃ | CH | |
| CH₃ | S(O)₂(CH(CH₃)₂) | H | Cl | OCH₃ | CH | |
| CH₃ | S(O)₂(CH(CH₃)₂) | H | OCH₃ | CH₃ | N | |
| CH₃ | S(O)₂(CH(CH₃)₂) | H | OCH₃ | OCH₃ | N | |
| CH₃ | S(O)₂((CH₂)₃CH₃) | H | OCH₃ | CH₃ | CH | |
| CH₃ | S(O)₂((CH₂)₃CH₃) | H | OCH₃ | OCH₃ | CH | |
| CH₃ | S(O)₂((CH₂)₃CH₃) | H | Cl | OCH₃ | CH | |
| CH₃ | S(O)₂((CH₂)₃CH₃) | H | OCH₃ | CH₃ | N | |
| CH₃ | S(O)₂((CH₂)₃CH₃) | H | OCH₃ | OCH₃ | N | |
| CH₃ | S(O)₂((CH₂)₄CH₃) | H | OCH₃ | CH₃ | CH | |
| CH₃ | S(O)₂((CH₂)₅CH₃) | H | OCH₃ | OCH₃ | CH | |
| CH₃ | S(O)₂((CH₂)₆CH₃) | H | )CH₃ | CH₃ | N | |
| CH₃ | S(O)₂((CH₂)₇CH₃) | H | OCH₃ | OCH₃ | N | |
| CH₃ | S(O)₂((CH₂)₂CH(CH₃)₂) | H | CH₃ | OCH₃ | CH | |
| CH₃ | OCH₂CH=CH₂ | H | CH₃ | CH₃ | CH | |
| CH₃ | OCH₂CH=CH₂ | H | OCH₃ | CH₃ | CH | 167–169 (d) |
| CH₃ | OCH₂CH=CH₂ | H | OCH₃ | OCH₃ | CH | 190–192 (d) |
| CH₃ | OCH₂CH=CH₂ | H | Cl | OCH₃ | CH | |
| CH₃ | OCH₂CH=CH₂ | H | OCH₃ | N(CH₃)₂ | CH | |
| CH₃ | OCH₂CH=CH₂ | H | CH₃ | CH₃ | N | |
| CH₃ | OCH₂CH=CH₂ | H | OCH₃ | CH₃ | N | 133–135 (d) |
| CH₃ | OCH₂CH=CH₂ | H | OCH₃ | OCH₃ | N | 174–177 |
| CH₃ | OCH₂CH=CH₂ | H | OCH₃ | N(CH₃)₂ | N | |
| CH₃ | OCH₂CH=CH₂ | H | OCH₃ | OCH₂CF₃ | N | |
| CH₃ | OCH₂CH=CH₂ | CH₃ | OCH₃ | CH₃ | N | |
| CH₃ | OCH₂CH=CH₂ | CH₃ | OCH₃ | OCH₃ | N | |
| CH₃ | OCH₂CH=CH₂ | CH₃ | CH₃ | OCH₃ | CH | |
| CH₃ | OCH₂CH=CH₂ | CH₃ | OCH₃ | OCH₃ | CH | |
| CH₃ | OCH₂CH=CH₂ | H | Br | OCH₃ | CH | |
| CH₃ | OCH₂CH=CH₂ | CH₃ | OCH₃ | N(CH₃)₂ | N | |
| CH₃ | OCH₂CH=CH₂ | H | CH₃ | OCH₂CF₃ | N | |
| CH₃ | OCH₂CH=CH₂ | H | CH₃ | OCH₂CF₃ | CH | |
| CH₃ | OCH₂CH=CH₂ | H | OCH₃ | OCH₂CF₃ | CH | |
| CH₃ | OCH₂CH=CH₂ | H | OCH₃ | C₂H₅ | CH | |
| CH₃ | OCH₂CH=CH₂ | H | OCH₃ | C₂H₅ | N | |
| CH₃ | OCH₂CH=CH₂ | H | OCH₃ | NHCH₃ | CH | |
| CH₃ | OCH₂CH=CH₂ | H | OCH₃ | NHCH₃ | N | |
| CH₃ | OCH₂CH=CH₂ | H | CH₃ | OC₂H₅ | CH | |
| CH₃ | OCH₂CH=CH₂ | H | OCH₃ | OC₂H₅ | CH | |
| CH₃ | OCH₂CH=CH₂ | H | CH₃ | OC₂H₅ | N | |
| CH₃ | OCH₂CH=CH₂ | H | OCH₃ | OC₂H₅ | N | |
| CH₃ | OCH₂CH=CH₂ | H | CH₃ | OCH₂CHF₂ | CH | |
| CH₃ | OCH₂CH=CH₂ | H | OCH₃ | OCH₂CHF₂ | CH | |
| CH₃ | OCH₂CH=CH₂ | H | CH₃ | OCH₂CHF₂ | N | |
| CH₃ | OCH₂CH=CH₂ | H | OCH₃ | OCH₂CHF₂ | N | |
| CH₃ | OCH₂CH=CH₂ | H | CH₃ | OCH₂CH₂F | CH | |
| CH₃ | OCH₂CH=CH₂ | H | OCH₃ | OCH₂CH₂F | CH | |
| CH₃ | OCH₂CH=CH₂ | H | CH₃ | OCH₂CH₂F | N | |
| CH₃ | OCH₂CH=CH₂ | CH₃ | OCH₃ | OCH₂CH₂F | N | |
| CH₃ | OCH₂CH=CH₂ | CH₃ | Cl | OCH₃ | CH | |
| CH₃ | OCH₂CH=CH₂ | H | Cl | N(CH₃)₂ | CH | |
| CH₃ | OCH₂CH=CH₂ | H | Cl | OC₂H₅ | CH | |
| C₂H₅ | OCH₂CH=CH₂ | H | CH₃ | CH₃ | CH | |
| C₂H₅ | OCH₂CH=CH₂ | H | OCH₃ | CH₃ | CH | |
| C₂H₅ | OCH₂CH=CH₂ | H | OCH₃ | OCH₃ | CH | |
| C₂H₅ | OCH₂CH=CH₂ | H | Cl | OCH₃ | CH | |
| C₂H₅ | OCH₂CH=CH₂ | H | CH₃ | CH₃ | N | |
| C₂H₅ | OCH₂CH=CH₂ | H | OCH₃ | CH₃ | N | |
| C₂H₅ | OCH₂CH=CH₂ | H | OCH₃ | OCH₃ | N | |
| C₂H₅ | OCH₂CH=CH₂ | H | Br | OCH₃ | CH | |
| C₂H₅ | OCH₂CH=CH₂ | H | OCH₃ | N(CH₃)₂ | CH | |
| C₂H₅ | OCH₂CH=CH₂ | H | OCH₃ | N(CH₃)₂ | N | |
| C₂H₅ | OCH₂CH=CH₂ | H | OCH₃ | NHCH₃ | N | |
| C₂H₅ | OCH₂CH=CH₂ | H | OCH₃ | C₂H₅ | CH | |
| C₂H₅ | OCH₂CH=CH₂ | H | OCH₃ | C₂H₅ | N | |
| C₂H₅ | OCH₂CH=CH₂ | H | CH₃ | OC₂H₅ | CH | |
| C₂H₅ | OCH₂CH=CH₂ | H | CH₃ | OC₂H₅ | N | |
| C₂H₅ | OCH₂CH=CH₂ | H | OCH₃ | OC₂H₅ | CH | |
| C₂H₅ | OCH₂CH=CH₂ | H | OCH₃ | OC₂H₅ | N | |
| C₂H₅ | OCH₂CH=CH₂ | H | CH₃ | OCH₂CF₃ | CH | |
| C₂H₅ | OCH₂CH=CH₂ | H | CH₃ | OCH₂CF₃ | N | |
| C₂H₅ | OCH₂CH=CH₂ | H | OCH₃ | OCH₂CF₃ | CH | |
| C₂H₅ | OCH₂CH=CH₂ | H | OCH₃ | OCH₂CF₃ | N | |
| C₂H₅ | OCH₂CH=CH₂ | H | OCH₃ | OCH₂CHF₂ | CH | |
| C₂H₅ | OCH₂CH=CH₂ | H | OCH₃ | OCH₂CHF₂ | N | |
| C₂H₅ | OCH₂CH=CH₂ | H | CH₃ | OCH₂CHF₂ | N | |
| C₂H₅ | OCH₂CH=CH₂ | H | OCH₃ | OCH₂CF₂F | CH | |
| C₂H₅ | OCH₂CH=CH₂ | H | OCH₃ | OCH₂CH₂F | N | |
| C₂H₅ | OCH₂CH=CH₂ | CH₃ | OCH₃ | OCH₃ | CH | |
| C₂H₅ | OCH₂CH=CH₂ | CH₃ | CH₃ | OCH₃ | N | |

TABLE I-continued

| | | | | | |
|---|---|---|---|---|---|
| C₂H₅ | OCH₂CH=CH₂ | CH₃ | OCH₃ | OCH₃ | N |
| n-C₃H₇ | OCH₂CH=CH₂ | H | OCH₃ | OCH₃ | CH |
| n-C₃H₇ | OCH₂CH=CH₂ | H | CH₃ | OCH₃ | N |
| CH(CH₃)₂ | OCH₂CH=CH₂ | H | OCH₃ | CH₃ | CH |
| CH(CH₃)₂ | OCH₂CH=CH₂ | H | OCH₃ | OCH₃ | CH |
| CH(CH₃)₂ | OCH₂CH=CH₂ | H | Cl | OCH₃ | CH |
| CH(CH₃)₂ | OCH₂CH=CH₂ | H | OCH₃ | CH₃ | N |
| CH(CH₃)₂ | OCH₂CH=CH₂ | H | OCH₃ | OCH₃ | N |
| CH(CH₃)₂ | OCH₂CH=CH₂ | H | OCH₃ | N(CH₃)₂ | N |
| CH₃ | OCH₂CH=CHCH₃ | H | CH₃ | CH₃ | CH |
| CH₃ | OCH₂CH=CHCH₃ | H | OCH₃ | CH₃ | CH |
| CH₃ | OCH₂CH=CHCH₃ | H | OCH₃ | OCH₃ | CH |
| CH₃ | OCH₂CH=CHCH₃ | H | Cl | OCH₃ | CH |
| CH₃ | OCH₂CH=CHCH₃ | H | CH₃ | CH₃ | N |
| CH₃ | OCH₂CH=CHCH₃ | H | OCH₃ | CH₃ | N |
| CH₃ | OCH₂CH=CHCH₃ | H | OCH₃ | OCH₃ | N |
| CH₃ | OCH₂CH=CHCH₃ | H | OCH₃ | N(CH₃)₂ | CH |
| CH₃ | OCH₂CH=CHCH₃ | H | OCH₃ | N(CH₃)₂ | N |
| CH₃ | OCH₂CH=CHCH₃ | H | OCH₃ | OCH₂CF₃ | N |
| CH₃ | OCH₂CH=CHCH₃ | CH₃ | OCH₃ | CH₃ | N |
| CH₃ | OCH₂CH=CHCH₃ | CH₃ | OCH₃ | OCH₃ | N |
| CH₃ | OCH₂CH=CHCH₃ | CH₃ | CH₃ | OCH₃ | CH |
| CH₃ | OCH₂CH=CHCH₃ | CH₃ | OCH₃ | OCH₃ | CH |
| CH₃ | OCH₂CH=CHCH₃ | H | Br | OCH₃ | CH |
| CH₃ | OCH₂CH=CHCH₃ | H | CH₃ | OCH₂CF₃ | N |
| CH₃ | OCH₂CH=CHCH₃ | H | CH₃ | OCH₂CF₃ | CH |
| CH₃ | OCH₂CH=CHCH₃ | H | OCH₃ | OCH₂CF₃ | CH |
| CH₃ | OCH₂CH=CHCH₃ | H | OCH₃ | NHCH₃ | N |
| C₂H₅ | OCH₂CH=CHCH₃ | H | CH₃ | CH₃ | CH |
| C₂H₅ | OCH₂CH=CHCH₃ | H | OCH₃ | CH₃ | CH |
| C₂H₅ | OCH₂CH=CHCH₃ | H | OCH₃ | OCH₃ | CH |
| C₂H₅ | OCH₂CH=CHCH₃ | H | Cl | OCH₃ | CH |
| C₂H₅ | OCH₂CH=CHCH₃ | H | OCH₃ | CH₃ | N |
| C₂H₅ | OCH₂CH=CHCH₃ | H | OCH₃ | N(CH₃)₂ | CH |
| CH(CH₃)₂ | OCH₂CH=CHCH₃ | H | OCH₃ | CH₃ | CH |
| CH(CH₃)₂ | OCH₂CH=CHCH₃ | H | OCH₃ | OCH₃ | CH |
| CH(CH₃)₂ | OCH₂CH=CHCH₃ | H | Cl | OCH₃ | CH |
| CH(CH₃)₂ | OCH₂CH=CHCH₃ | H | OCH₃ | CH₃ | N |
| CH(CH₃)₂ | OCH₂CH=CHCH₃ | H | OCH₃ | OCH₃ | N |
| CH₃ | OCH₂CH=CHC₂H₅ | H | CH₃ | CH₃ | CH |
| CH₃ | OCH₂CH=CHC₂H₅ | H | OCH₃ | CH₃ | CH |
| CH₃ | OCH₂CH=CHC₂H₅ | H | OCH₃ | OCH₃ | CH |
| CH₃ | OCH₂CH=CHC₂H₅ | H | Cl | OCH₃ | CH |
| CH₃ | OCH₂CH=CHC₂H₅ | H | CH₃ | CH₃ | N |
| CH₃ | OCH₂CH=CHC₂H₅ | H | OCH₃ | CH₃ | N |
| CH₃ | OCH₂CH=CHC₂H₅ | H | OCH₃ | OCH₃ | N |
| CH₃ | OCH₂CH=CHC₂H₅ | H | OCH₃ | N(CH₃)₂ | CH |
| CH₃ | OCH₂CH=CHC₂H₅ | H | OCH₃ | N(CH₃)₂ | N |
| CH₃ | OCH₂CH=CHC₂H₅ | H | OCH₃ | OCH₂CF₃ | N |
| CH₃ | OCH₂CH=CHC₂H₅ | CH₃ | OCH₃ | CH₃ | N |
| CH₃ | OCH₂CH=CHC₂H₅ | CH₃ | OCH₃ | OCH₃ | N |
| CH₃ | OCH₂CH=CHC₂H₅ | CH₃ | CH₃ | OCH₃ | CH |
| CH₃ | OCH₂CH=CHC₂H₅ | CH₃ | OCH₃ | OCH₃ | CH |
| CH₃ | OCH₂CH=CHC₂H₅ | H | Br | OCH₃ | CH |
| CH₃ | OCH₂CH=CHC₂H₅ | H | CH₃ | OCH₂CF₃ | N |
| CH₃ | OCH₂CH=CHC₂H₅ | H | CH₃ | OCH₂CF₃ | CH |
| CH₃ | OCH₂CH=CHC₂H₅ | H | OCH₃ | OCH₂CF₃ | CH |
| CH₃ | OCH₂CH=CHC₂H₅ | H | OCH₃ | NHCH₃ | N |
| C₂H₅ | OCH₂CH=CHC₂H₅ | H | CH₃ | CH₃ | CH |
| C₂H₅ | OCH₂CH=CHC₂H₅ | H | OCH₃ | CH₃ | CH |
| C₂H₅ | OCH₂CH=CHC₂H₅ | H | OCH₃ | OCH₃ | CH |
| C₂H₅ | OCH₂CH=CHC₂H₅ | H | Cl | OCH₃ | CH |
| C₂H₅ | OCH₂CH=CHC₂H₅ | H | OCH₃ | CH₃ | N |
| C₂H₅ | OCH₂CH=CHC₂H₅ | H | OCH₃ | N(CH₃)₂ | CH |
| CH(CH₃)₂ | OCH₂CH=CHC₂H₅ | H | OCH₃ | CH₃ | CH |
| CH(CH₃)₂ | OCH₂CH=CHC₂H₅ | H | OCH₃ | OCH₃ | CH |
| CH(CH₃)₂ | OCH₂CH=CHC₂H₅ | H | Cl | OCH₃ | CH |
| CH(CH₃)₂ | OCH₂CH=CHC₂H₅ | H | OCH₃ | CH₃ | N |
| CH(CH₃)₂ | OCH₂CH=CHC₂H₅ | H | OCH₃ | OCH₃ | N |
| CH₃ | O(CH₂)₂CH=CH₂ | H | CH₃ | OCH₃ | CH |
| CH₃ | O(CH₂)₃CH=CH₂ | H | OCH₃ | OCH₃ | CH |
| CH₃ | O(CH₂)₂C(CH₃)=CH₂ | H | CH₃ | OCH₃ | N |
| CH₃ | O(CH₂)₂CH=CHCH₃ | H | OCH₃ | OCH₃ | N |
| CH₃ | OCH₂C≡CH | H | CH₃ | CH₃ | CH |
| CH₃ | OCH₂C≡CH | H | OCH₃ | CH₃ | CH |
| CH₃ | OCH₂C≡CH | H | OCH₃ | OCH₃ | CH |
| CH₃ | OCH₂C≡CH | H | Cl | OCH₃ | CH |
| CH₃ | OCH₂C≡CH | H | OCH₃ | N(CH₃)₂ | CH |
| CH₃ | OCH₂C≡CH | H | CH₃ | CH₃ | N |
| CH₃ | OCH₂C≡CH | H | OCH₃ | CH₃ | N |
| CH₃ | OCH₂C≡CH | H | OCH₃ | OCH₃ | N |
| CH₃ | OCH₂C≡CH | H | OCH₃ | N(CH₃)₂ | N |

TABLE I-continued

| | | | | | | |
|---|---|---|---|---|---|---|
| CH₃ | OCH₂C≡CH | H | OCH₃ | OCH₂CF₃ | N | |
| CH₃ | OCH₂C≡CH | CH₃ | OCH₃ | CH₃ | N | |
| CH₃ | OCH₂C≡CH | CH₃ | OCH₃ | OCH₃ | N | |
| CH₃ | OCH₂C≡CH | CH₃ | CH₃ | OCH₃ | CH | |
| CH₃ | OCH₂C≡CH | CH₃ | OCH₃ | OCH₃ | CH | |
| CH₃ | OCH₂C≡CH | H | Br | OCH₃ | CH | |
| CH₃ | OCH₂C≡CH | CH₃ | OCH₃ | N(CH₃)₂ | N | |
| CH₃ | OCH₂C≡CH | H | CH₃ | OCH₂CF₃ | N | |
| CH₃ | OCH₂C≡CH | H | CH₃ | OCH₂CF₃ | CH | |
| CH₃ | OCH₂C≡CH | H | OCH₃ | OCH₂CF₃ | CH | |
| CH₃ | OCH₂C≡CH | H | OCH₃ | C₂H₅ | CH | |
| CH₃ | OCH₂C≡CH | H | OCH₃ | C₂H₅ | N | |
| CH₃ | OCH₂C≡CH | H | OCH₃ | NHCH₃ | CH | |
| CH₃ | OCH₂C≡CH | H | OCH₃ | NHCH₃ | N | |
| CH₃ | OCH₂C≡CH | H | CH₃ | OC₂H₅ | CH | |
| CH₃ | OCH₂C≡CH | H | OCH₃ | OC₂H₅ | CH | |
| CH₃ | OCH₂C≡CH | H | CH₃ | OC₂H₅ | N | |
| CH₃ | OCH₂C≡CH | H | OCH₃ | OC₂H₅ | N | |
| CH₃ | OCH₂C≡CH | H | CH₃ | OCH₂CHF₂ | CH | |
| CH₃ | OCH₂C≡CH | H | OCH₃ | OCH₂CHF₂ | CH | |
| CH₃ | OCH₂C≡CH | H | CH₃ | OCH₂CHF₂ | N | |
| CH₃ | OCH₂C≡CH | H | OCH₃ | OCH₂CHF₂ | N | |
| CH₃ | OCH₂C≡CH | H | CH₃ | OCH₂CH₂F | CH | |
| CH₃ | OCH₂C≡CH | H | OCH₃ | OCH₂CH₂F | CH | |
| CH₃ | OCH₂C≡CH | H | CH₃ | OCH₂CF₃ | N | |
| CH₃ | OCH₂C≡CH | CH₃ | OCH₃ | OCH₂CF₃ | N | |
| CH₃ | OCH₂C≡CH | CH₃ | Cl | OCH₃ | CH | |
| CH₃ | OCH₂C≡CH | H | Cl | N(CH₃)₂ | CH | |
| CH₃ | OCH₂C≡CH | H | Cl | OC₂H₅ | CH | |
| C₂H₅ | OCH₂C≡CH | H | CH₃ | CH₃ | CH | |
| C₂H₅ | OCH₂C≡CH | H | OCH₃ | CH₃ | CH | |
| C₂H₅ | OCH₂C≡CH | H | OCH₃ | OCH₃ | CH | 171-176 |
| C₂H₅ | OCH₂C≡CH | H | Cl | OCH₃ | CH | 171-181 (d) |
| C₂H₅ | OCH₂C≡CH | H | CH₃ | CH₃ | N | |
| C₂H₅ | OCH₂C≡CH | H | OCH₃ | CH₃ | N | |
| C₂H₅ | OCH₂C≡CH | H | OCH₃ | OCH₃ | N | |
| C₂H₅ | OCH₂C≡CH | H | Br | OCH₃ | CH | |
| C₂H₅ | OCH₂C≡CH | H | OCH₃ | N(CH₃)₂ | CH | |
| C₂H₅ | OCH₂C≡CH | H | OCH₃ | N(CH₃)₂ | N | |
| C₂H₅ | OCH₂C≡CH | H | OCH₃ | NHCH₃ | N | |
| C₂H₅ | OCH₂C≡CH | H | OCH₃ | C₂H₅ | CH | |
| C₂H₅ | OCH₂C≡CH | H | OCH₃ | C₂H₅ | N | |
| C₂H₅ | OCH₂C≡CH | H | CH₃ | OC₂H₅ | CH | |
| C₂H₅ | OCH₂C≡CH | H | CH₃ | OC₂H₅ | N | |
| C₂H₅ | OCH₂C≡CH | H | OCH₃ | OC₂H₅ | CH | |
| C₂H₅ | OCH₂C≡CH | H | OCH₃ | OC₂H₅ | N | |
| C₂H₅ | OCH₂C≡CH | H | CH₃ | OCH₂CF₃ | CH | |
| C₂H₅ | OCH₂C≡CH | H | CH₃ | OCH₂CF₃ | N | |
| C₂H₅ | OCH₂C≡CH | H | OCH₃ | OCH₂CF₃ | CH | |
| C₂H₅ | OCH₂C≡CH | H | OCH₃ | OCH₂CF₃ | N | |
| C₂H₅ | OCH₂C≡CH | H | OCH₃ | OCH₂CHF₂ | CH | |
| C₂H₅ | OCH₂C≡CH | H | OCH₃ | OCH₂CHF₂ | N | |
| C₂H₅ | OCH₂C≡CH | H | CH₃ | OCH₂CHF₂ | N | |
| C₂H₅ | OCH₂C≡CH | H | OCH₃ | OCH₂CH₂F | CH | |
| C₂H₅ | OCH₂C≡CH | H | OCH₃ | OCH₂CH₂F | N | |
| C₂H₅ | OCH₂C≡CH | CH₃ | OCH₃ | OCH₃ | CH | |
| C₂H₅ | OCH₂C≡CH | CH₃ | CH₃ | OCH₃ | N | |
| C₂H₅ | OCH₂C≡CH | CH₃ | OCH₃ | OCH₃ | N | |
| n-C₃H₇ | OCH₂C≡CH | H | OCH₃ | OCH₃ | CH | |
| n-C₃H₇ | OCH₂C≡CH | H | CH₃ | OCH₃ | N | |
| CH(CH₃)₂ | OCH₂C≡CH | H | OCH₃ | CH₃ | CH | |
| CH(CH₃)₂ | OCH₂C≡CH | H | OCH₃ | OCH₃ | CH | |
| CH(CH₃)₂ | OCH₂C≡CH | H | Cl | OCH₃ | CH | |
| CH(CH₃)₂ | OCH₂C≡CH | H | OCH₃ | CH₃ | N | |
| CH(CH₃)₂ | OCH₂C≡CH | H | OCH₃ | OCH₃ | N | |
| CH(CH₃)₂ | OCH₂C≡CH | H | OCH₃ | N(CH₃)₂ | N | |
| CH₃ | OCH₂C≡CCH₃ | H | CH₃ | CH₃ | CH | |
| CH₃ | OCH₂C≡CCH₃ | H | OCH₃ | CH₃ | CH | |
| CH₃ | OCH₂C≡CCH₃ | H | OCH₃ | OCH₃ | CH | |
| CH₃ | OCH₂C≡CCH₃ | H | Cl | OCH₃ | CH | |
| CH₃ | OCH₂C≡CCH₃ | H | CH₃ | CH₃ | N | |
| CH₃ | OCH₂C≡CCH₃ | H | OCH₃ | CH₃ | N | |
| CH₃ | OCH₂C≡CCH₃ | H | OCH₃ | OCH₃ | N | |
| CH₃ | OCH₂C≡CCH₃ | H | OCH₃ | N(CH₃)₂ | CH | |
| CH₃ | OCH₂C≡CCH₃ | H | OCH₃ | N(CH₃)₂ | N | |
| CH₃ | OCH₂C≡CCH₃ | H | OCH₃ | OCH₂CF₃ | N | |
| CH₃ | OCH₂C≡CCH₃ | CH₃ | OCH₃ | CH₃ | N | |
| CH₃ | OCH₂C≡CCH₃ | CH₃ | OCH₃ | OCH₃ | N | |
| CH₃ | OCH₂C≡CCH₃ | CH₃ | CH₃ | OCH₃ | CH | |
| CH₃ | OCH₂C≡CCH₃ | CH₃ | OCH₃ | OCH₃ | CH | |
| CH₃ | OCH₂C≡CCH₃ | H | Br | OCH₃ | CH | |
| CH₃ | OCH₂C≡CCH₃ | H | CH₃ | OCH₂CF₃ | N | |

TABLE I-continued

| R₁ | | R | X | Y | Z |
|---|---|---|---|---|---|
| CH₃ | OCH₂C≡CCH₃ | H | CH₃ | OCH₂CF₃ | CH |
| CH₃ | OCH₂C≡CCH₃ | H | OCH₃ | OCH₂CF₃ | CH |
| CH₃ | OCH₂C≡CCH₃ | H | OCH₃ | NHCH₃ | N |
| C₂H₅ | OCH₂C≡CCH₃ | H | CH₃ | CH₃ | CH |
| C₂H₅ | OCH₂C≡CCH₃ | H | OCH₃ | CH₃ | CH |
| C₂H₅ | OCH₂C≡CCH₃ | H | OCH₃ | OCH₃ | CH |
| C₂H₅ | OCH₂C≡CCH₃ | H | Cl | OCH₃ | CH |
| C₂H₅ | OCH₂C≡CCH₃ | H | OCH₃ | CH₃ | N |
| C₂H₅ | OCH₂C≡CCH₃ | H | OCH₃ | N(CH₃)₂ | CH |
| CH(CH₃)₂ | OCH₂C≡CCH₃ | H | OCH₃ | CH₃ | CH |
| CH(CH₃)₂ | OCH₂C≡CCH₃ | H | OCH₃ | OCH₃ | CH |
| CH(CH₃)₂ | OCH₂C≡CCH₃ | H | Cl | OCH₃ | CH |
| CH(CH₃)₂ | OCH₂C≡CCH₃ | H | OCH₃ | CH₃ | N |
| CH(CH₃)₂ | OCH₂C≡CCH₃ | H | OCH₃ | OCH₃ | N |
| CH₃ | OCH₂C≡CC₂H₅ | H | CH₃ | CH₃ | CH |
| CH₃ | OCH₂C≡CC₂H₅ | H | OCH₃ | CH₃ | CH |
| CH₃ | OCH₂C≡CC₂H₅ | H | OCH₃ | OCH₃ | CH |
| CH₃ | OCH₂C≡CC₂H₅ | H | Cl | OCH₃ | CH |
| CH₃ | OCH₂C≡CC₂H₅ | H | CH₃ | CH₃ | N |
| CH₃ | OCH₂C≡CC₂H₅ | H | OCH₃ | CH₃ | N |
| CH₃ | OCH₂C≡CC₂H₅ | H | OCH₃ | OCH₃ | N |
| CH₃ | OCH₂C≡CC₂H₅ | H | OCH₃ | N(CH₃)₂ | CH |
| CH₃ | OCH₂C≡CC₂H₅ | H | OCH₃ | N(CH₃)₂ | N |
| CH₃ | OCH₂C≡CC₂H₅ | H | OCH₃ | OCH₂CF₃ | N |
| CH₃ | OCH₂C≡CC₂H₅ | CH₃ | OCH₃ | CH₃ | N |
| CH₃ | OCH₂C≡CC₂H₅ | CH₃ | OCH₃ | OCH₃ | N |

TABLE I

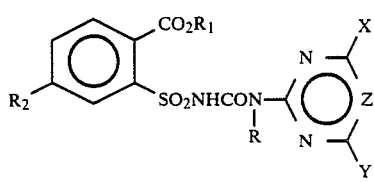

| R₁ | R₂ | R | X | Y | Z | m.p. (°C.) |
|---|---|---|---|---|---|---|
| CH₃ | OCH₂C≡CC₂H₅ | CH₃ | CH₃ | OCH₃ | CH | |
| CH₃ | OCH₂C≡CC₂H₅ | CH₃ | OCH₃ | OCH₃ | CH | |
| CH₃ | OCH₂C≡CC₂H₅ | H | Br | OCH₃ | CH | |
| CH₃ | OCH₂C≡CC₂H₅ | H | CH₃ | OCH₂CF₃ | N | |
| CH₃ | OCH₂C≡CC₂H₅ | H | CH₃ | OCH₂CF₃ | CH | |
| CH₃ | OCH₂C≡CC₂H₅ | H | OCH₃ | OCH₂CF₃ | CH | |
| CH₃ | OCH₂C≡CC₂H₅ | H | OCH₃ | NHCH₃ | N | |
| C₂H₅ | OCH₂C≡CC₂H₅ | H | CH₃ | CH₃ | CH | |
| C₂H₅ | OCH₂C≡CC₂H₅ | H | OCH₃ | CH₃ | CH | |
| C₂H₅ | OCH₂C≡CC₂H₅ | H | OCH₃ | OCH₃ | CH | |
| C₂H₅ | OCH₂C≡CC₂H₅ | H | Cl | OCH₃ | CH | |
| C₂H₅ | OCH₂C≡CC₂H₅ | H | OCH₃ | CH₃ | N | |
| C₂H₅ | OCH₂C≡CC₂H₅ | H | OCH₃ | N(CH₃)₂ | CH | |
| CH(CH₃)₂ | OCH₂C≡CC₂H₅ | H | OCH₃ | CH₃ | CH | |
| CH(CH₃)₂ | OCH₂C≡CC₂H₅ | H | OCH₃ | OCH₃ | CH | |
| CH(CH₃)₂ | OCH₂C≡CC₂H₅ | H | Cl | OCH₃ | CH | |
| CH(CH₃)₂ | OCH₂C≡CC₂H₅ | H | OCH₃ | CH₃ | N | |
| CH(CH₃)₂ | OCH₂C≡CC₂H₅ | H | OCH₃ | OCH₃ | N | |
| CH₃ | O(CH₂)₂C≡CH | H | CH₃ | OCH₃ | CH | |
| CH₃ | O(CH₂)₃C≡CH | H | OCH₃ | OCH₃ | CH | |
| CH₃ | O(CH₂)₂C≡CCH₃ | H | CH₃ | OCH₃ | N | |
| CH₃ | SCH₂CH=CH₂ | H | CH₃ | CH₃ | CH | |
| CH₃ | SCH₂CH=CH₂ | H | OCH₃ | CH₃ | CH | |
| CH₃ | SCH₂CH=CH₂ | H | OCH₃ | OCH₃ | CH | |
| CH₃ | SCH₂CH=CH₂ | H | Cl | OCH₃ | CH | |
| CH₃ | SCH₂CH=CH₂ | H | OCH₃ | N(CH₃)₂ | N | |
| CH₃ | SCH₂CH=CH₂ | H | CH₃ | CH₃ | N | |
| CH₃ | SCH₂CH=CH₂ | H | OCH₃ | CH₃ | N | |
| CH₃ | SCH₂CH=CH₂ | H | OCH₃ | OCH₃ | N | |
| CH₃ | SCH₂CH=CH₂ | H | OCH₃ | N(CH₃)₂ | N | |
| CH₃ | SCH₂CH=CH₂ | H | OCH₃ | OCH₂CF₃ | N | |
| CH₃ | SCH₂CH=CH₂ | CH₃ | OCH₃ | CH₃ | N | |
| CH₃ | SCH₂CH=CH₂ | CH₃ | OCH₃ | OCH₃ | N | |
| CH₃ | SCH₂CH=CH₂ | CH₃ | CH₃ | OCH₃ | CH | |
| CH₃ | SCH₂CH=CH₂ | CH₃ | OCH₃ | OCH₃ | CH | |
| CH₃ | SCH₂CH=CH₂ | H | Br | OCH₃ | CH | |
| CH₃ | SCH₂CH=CH₂ | CH₃ | OCH₃ | N(CH₃)₂ | N | |
| CH₃ | SCH₂CH=CH₂ | H | CH₃ | OCH₂CF₃ | N | |
| CH₃ | SCH₂CH=CH₂ | H | CH₃ | OCH₂CF₃ | CH | |
| CH₃ | SCH₂CH=CH₂ | H | OCH₃ | OCH₂CF₃ | CH | |
| CH₃ | SCH₂CH=CH₂ | H | OCH₃ | C₂H₅ | CH | |

TABLE I-continued

| | | | | | | |
|---|---|---|---|---|---|---|
| CH₃ | SCH₂CH=CH₂ | H | OCH₃ | C₂H₅ | CH |
| CH₃ | SCH₂CH=CH₂ | H | OCH₃ | NHCH₃ | CH |
| CH₃ | SCH₂CH=CH₂ | H | OCH₃ | NHCH₃ | N |
| CH₃ | SCH₂CH=CH₂ | H | CH₃ | OC₂H₅ | CH |
| CH₃ | SCH₂CH=CH₂ | H | OCH₃ | OC₂H₅ | CH |
| CH₃ | SCH₂CH=CH₂ | H | CH₃ | OC₂H₅ | N |
| CH₃ | SCH₂CH=CH₂ | H | OCH₃ | OC₂H₅ | N |
| CH₃ | SCH₂CH=CH₂ | H | CH₃ | OCH₂CHF₂ | CH |
| CH₃ | SCH₂CH=CH₂ | H | OCH₃ | OCH₂CHF₂ | CH |
| CH₃ | SCH₂CH=CH₂ | H | CH₃ | OCH₂CHF₂ | N |
| CH₃ | SCH₂CH=CH₂ | H | OCH₃ | OCH₂CHF₂ | N |
| CH₃ | SCH₂CH=CH₂ | H | CH₃ | OCH₂CH₂F | CH |
| CH₃ | SCH₂CH=CH₂ | H | OCH₃ | OCH₂CH₂F | CH |
| CH₃ | SCH₂CH=CH₂ | H | CH₃ | OCH₂CH₂F | N |
| CH₃ | SCH₂CH=CH₂ | H | OCH₃ | OCH₂CH₂F | N |
| CH₃ | SCH₂CH=CH₂ | CH₃ | Cl | OCH₃ | CH |
| CH₃ | SCH₂CH=CH₂ | H | Cl | N(CH₃)₂ | CH |
| CH₃ | SCH₂CH=CH₂ | H | Cl | OC₂H₅ | CH |
| C₂H₅ | SCH₂CH=CH₂ | H | CH₃ | CH₃ | CH |
| C₂H₅ | SCH₂CH=CH₂ | H | OCH₃ | CH₃ | CH |
| C₂H₅ | SCH₂CH=CH₂ | H | OCH₃ | OCH₃ | CH |
| C₂H₅ | SCH₂CH=CH₂ | H | Cl | OCH₃ | CH |
| C₂H₅ | SCH₂CH=CH₂ | H | CH₃ | CH₃ | N |
| C₂H₅ | SCH₂CH=CH₂ | H | OCH₃ | CH₃ | N |
| C₂H₅ | SCH₂CH=CH₂ | H | OCH₃ | OCH₃ | N |
| C₂H₅ | SCH₂CH=CH₂ | H | Br | OCH₃ | CH |
| C₂H₅ | SCH₂CH=CH₂ | H | OCH₃ | N(CH₃)₂ | CH |
| C₂H₅ | SCH₂CH=CH₂ | H | OCH₃ | N(CH₃)₂ | N |
| C₂H₅ | SCH₂CH=CH₂ | H | OCH₃ | NHCH₃ | N |
| C₂H₅ | SCH₂CH=CH₂ | H | OCH₃ | C₂H₅ | CH |
| C₂H₅ | SCH₂CH=CH₂ | H | OCH₃ | C₂H₅ | N |
| C₂H₅ | SCH₂CH=CH₂ | H | CH₃ | OC₂H₅ | CH |
| C₂H₅ | SCH₂CH=CH₂ | H | CH₃ | OC₂H₅ | N |
| C₂H₅ | SCH₂CH=CH₂ | H | OCH₃ | OC₂H₅ | CH |
| C₂H₅ | SCH₂CH=CH₂ | H | OCH₃ | OC₂H₅ | N |
| C₂H₅ | SCH₂CH=CH₂ | H | CH₃ | OCH₂CF₃ | CH |
| C₂H₅ | SCH₂CH=CH₂ | H | CH₃ | OCH₂CF₃ | N |
| C₂H₅ | SCH₂CH=CH₂ | H | OCH₃ | OCH₂CF₃ | CH |
| C₂H₅ | SCH₂CH=CH₂ | H | OCH₃ | OCH₂CF₃ | N |
| C₂H₅ | SCH₂CH=CH₂ | H | OCH₃ | OCH₂CF₂ | CH |
| C₂H₅ | SCH₂CH=CH₂ | H | OCH₃ | OCH₂CHF₂ | N |
| C₂H₅ | SCH₂CH=CH₂ | H | CH₃ | OCH₂CHF₂ | N |
| C₂H₅ | SCH₂CH=CH₂ | H | OCH₃ | OCH₂CH₂F | CH |
| C₂H₅ | SCH₂CH=CH₂ | H | OCH₃ | OCH₂CH₂F | N |
| C₂H₅ | SCH₂CH=CH₂ | CH₃ | OCH₃ | OCH₃ | CH |
| C₂H₅ | SCH₂CH=CH₂ | CH₃ | CH₃ | OCH₃ | N |
| C₂H₅ | SCH₂CH=CH₂ | CH₃ | OCH₃ | OCH₃ | N |
| n-C₃H₇ | SCH₂CH=CH₂ | H | OCH₃ | OCH₃ | CH |
| n-C₃H₇ | SCH₂CH=CH₂ | H | CH₃ | OCH₃ | N |
| CH(CH₃)₂ | SCH₂CH=CH₂ | H | OCH₃ | CH₃ | CH |
| CH(CH₃)₂ | SCH₂CH=CH₂ | H | OCH₃ | OCH₃ | CH |
| CH(CH₃)₂ | SCH₂CH=CH₂ | H | Cl | OCH₃ | CH |
| CH(CH₃)₂ | SCH₂CH=CH₂ | H | OCH₃ | CH₃ | N |
| CH(CH₃)₂ | SCH₂CH=CH₂ | H | OCH₃ | OCH₃ | N |
| CH(CH₃)₂ | SCH₂CH=CH₂ | H | OCH₃ | N(CH₃)₂ | N |
| CH₃ | SCH₂CH=CHCH₃ | H | CH₃ | CH₃ | CH |
| CH₃ | SCH₂CH=CHCH₃ | H | OCH₃ | CH₃ | CH |
| CH₃ | SCH₂CH=CHCH₃ | H | OCH₃ | OCH₃ | CH |
| CH₃ | SCH₂CH=CHCH₃ | H | Cl | OCH₃ | CH |
| CH₃ | SCH₂CH=CHCH₃ | H | CH₃ | CH₃ | N |
| CH₃ | SCH₂CH=CHCH₃ | H | OCH₃ | CH₃ | N |
| CH₃ | SCH₂CH=CHCH₃ | H | OCH₃ | OCH₃ | N |
| CH₃ | SCH₂CH=CHCH₃ | H | OCH₃ | N(CH₃)₂ | CH |
| CH₃ | SCH₂CH=CHCH₃ | H | OCH₃ | N(CH₃)₂ | N |
| CH₃ | SCH₂CH=CHCH₃ | H | OCH₃ | OCH₂CF₃ | N |
| CH₃ | SCH₂CH=CHCH₃ | CH₃ | OCH₃ | CH₃ | N |
| CH₃ | SCH₂CH=CHCH₃ | CH₃ | OCH₃ | OCH₃ | N |
| CH₃ | SCH₂CH=CHCH₃ | CH₃ | CH₃ | OCH₃ | CH |
| CH₃ | SCH₂CH=CHCH₃ | CH₃ | OCH₃ | OCH₃ | CH |
| CH₃ | SCH₂CH=CHCH₃ | H | Br | OCH₃ | CH |
| CH₃ | SCH₂CH=CHCH₃ | H | CH₃ | OCH₂CF₃ | N |
| CH₃ | SCH₂CH=CHCH₃ | H | CH₃ | OCH₂CF₃ | CH |
| CH₃ | SCH₂CH=CHCH₃ | H | OCH₃ | OCH₂CF₃ | CH |
| CH₃ | SCH₂CH=CHCH₃ | H | OCH₃ | NHCH₃ | N |
| C₂H₅ | SCH₂CH=CHCH₃ | H | CH₃ | CH₃ | CH |
| C₂H₅ | SCH₂CH=CHCH₃ | H | OCH₃ | CH₃ | CH |
| C₂H₅ | SCH₂CH=CHCH₃ | H | OCH₃ | OCH₃ | CH |
| C₂H₅ | SCH₂CH=CHCH₃ | H | Cl | OCH₃ | CH |
| C₂H₅ | SCH₂CH=CHCH₃ | H | OCH₃ | CH₃ | N |
| C₂H₅ | SCH₂CH=CHCH₃ | H | OCH₃ | N(CH₃)₂ | CH |
| CH(CH₃)₂ | SCH₂CH=CHCH₃ | H | OCH₃ | CH₃ | CH |
| CH(CH₃)₂ | SCH₂CH=CHCH₃ | H | OCH₃ | OCH₃ | CH |

TABLE I-continued

| | | | | | |
|---|---|---|---|---|---|
| CH(CH₃)₂ | SCH₂CH=CHCH₃ | H | Cl | OCH₃ | CH |
| CH(CH₃)₂ | SCH₂CH=CHCH₃ | H | OCH₃ | CH₃ | N |
| CH(CH₃)₂ | SCH₂CH=CHCH₃ | H | OCH₃ | OCH₃ | N |
| CH₃ | SCH₂CH=CHC₂H₅ | H | CH₃ | CH₃ | CH |
| CH₃ | SCH₂CH=CHC₂H₅ | H | OCH₃ | CH₃ | CH |
| CH₃ | SCH₂CH=CHC₂H₅ | H | OCH₃ | OCH₃ | CH |
| CH₃ | SCH₂CH=CHC₂H₅ | H | Cl | OCH₃ | CH |
| CH₃ | SCH₂CH=CHC₂H₅ | H | CH₃ | CH₃ | N |
| CH₃ | SCH₂CH=CHC₂H₅ | H | OCH₃ | CH₃ | N |
| CH₃ | SCH₂CH=CHC₂H₅ | H | OCH₃ | OCH₃ | N |
| CH₃ | SCH₂CH=CHC₂H₅ | H | OCH₃ | N(CH₃)₂ | CH |
| CH₃ | SCH₂CH=CHC₂H₅ | H | OCH₃ | N(CH₃)₂ | N |
| CH₃ | SCH₂CH=CHC₂H₅ | H | OCH₃ | OCH₂CF₃ | N |
| CH₃ | SCH₂CH=CHC₂H₅ | CH₃ | OCH₃ | CH₃ | N |
| CH₃ | SCH₂CH=CHC₂H₅ | CH₃ | OCH₃ | OCH₃ | N |
| CH₃ | SCH₂CH=CHC₂H₅ | CH₃ | CH₃ | OCH₃ | CH |
| CH₃ | SCH₂CH=CHC₂H₅ | CH₃ | OCH₃ | OCH₃ | CH |
| CH₃ | SCH₂CH=CHC₂H₅ | H | Br | OCH₃ | CH |
| CH₃ | SCH₂CH=CHC₂H₅ | H | CH₃ | OCH₂CF₃ | N |
| CH₃ | SCH₂CH=CHC₂H₅ | H | CH₃ | OCH₂CF₃ | CH |
| CH₃ | SCH₂CH=CHC₂H₅ | H | OCH₃ | OCH₂CF₃ | CH |
| CH₃ | SCH₂CH=CHC₂H₅ | H | OCH₃ | NHCH₃ | N |
| C₂H₅ | SCH₂CH=CHC₂H₅ | H | CH₃ | CH₃ | CH |
| C₂H₅ | SCH₂CH=CHC₂H₅ | H | OCH₃ | CH₃ | CH |
| C₂H₅ | SCH₂CH=CHC₂H₅ | H | OCH₃ | OCH₃ | CH |
| C₂H₅ | SCH₂CH=CHC₂H₅ | H | Cl | OCH₃ | CH |
| C₂H₅ | SCH₂CH=CHC₂H₅ | H | OCH₃ | CH₃ | N |
| C₂H₅ | SCH₂CH=CHC₂H₅ | H | OCH₃ | N(CH₃)₂ | CH |
| CH(CH₃)₂ | SCH₂CH=CHC₂H₅ | H | OCH₃ | CH₃ | CH |
| CH(CH₃)₂ | SCH₂CH=CHC₂H₅ | H | OCH₃ | OCH₃ | CH |
| CH(CH₃)₂ | SCH₂CH=CHC₂H₅ | H | Cl | OCH₃ | CH |
| CH(CH₃)₂ | SCH₂CH=CHC₂H₅ | H | OCH₃ | CH₃ | N |
| CH(CH₃)₂ | SCH₂CH=CHC₂H₅ | H | OCH₃ | OCH₃ | N |
| CH₃ | S(CH₂)₂CH=CH₂ | H | CH₃ | OCH₃ | CH |
| CH₃ | S(CH₂)₂CH=CH₂ | H | OCH₃ | OCH₃ | CH |
| CH₃ | S(CH₂)₂CH=CH₂ | H | CH₃ | OCH₃ | N |
| CH₃ | S(CH₂)₂CH=CH₂ | H | OCH₃ | OCH₃ | N |
| CH₃ | S(O)(CH₂CH=CH₂) | H | CH₃ | CH₃ | CH |
| CH₃ | S(O)(CH₂CH=CH₂) | H | OCH₃ | CH₃ | CH |
| CH₃ | S(O)(CH₂CH=CH₂) | H | OCH₃ | OCH₃ | CH |
| CH₃ | S(O)(CH₂CH=CH₂) | H | Cl | OCH₃ | CH |
| CH₃ | S(O)(CH₂CH=CH₂) | H | CH₃ | CH₃ | N |
| CH₃ | S(O)(CH₂CH=CH₂) | H | OCH₃ | CH₃ | N |
| CH₃ | S(O)(CH₂CH=CH₂) | H | OCH₃ | OCH₃ | N |
| CH₃ | S(O)(CH₂CH=CH₂) | H | OCH₃ | N(CH₃)₂ | CH |
| CH₃ | S(O)(CH₂CH=CH₂) | H | OCH₃ | N(CH₃)₂ | N |
| CH₃ | S(O)(CH₂CH=CH₂) | H | OCH₃ | OCH₂CF₃ | N |
| CH₃ | S(O)(CH₂CH=CH₂) | CH₃ | OCH₃ | CH₃ | N |
| CH₃ | S(O)(CH₂CH=CH₂) | CH₃ | OCH₃ | OCH₃ | N |
| CH₃ | S(O)(CH₂CH=CH₂) | CH₃ | CH₃ | OCH₃ | CH |
| CH₃ | S(O)(CH₂CH=CH₂) | CH₃ | OCH₃ | OCH₃ | CH |
| CH₃ | S(O)(CH₂CH=CH₂) | H | Br | OCH₃ | CH |
| CH₃ | S(O)(CH₂CH=CH₂) | H | CH₃ | OCH₂CF₃ | N |
| CH₃ | S(O)(CH₂CH=CH₂) | H | CH₃ | OCH₂CF₃ | CH |
| CH₃ | S(O)(CH₂CH=CH₂) | H | OCH₃ | OCH₂CF₃ | CH |
| CH₃ | S(O)(CH₂CH=CH₂) | H | OCH₃ | NHCH₃ | N |
| C₂H₅ | S(O)(CH₂CH=CH₂) | H | CH₃ | CH₃ | CH |
| C₂H₅ | S(O)(CH₂CH=CH₂) | H | OCH₃ | CH₃ | CH |
| C₂H₅ | S(O)(CH₂CH=CH₂) | H | OCH₃ | OCH₃ | CH |
| C₂H₅ | S(O)(CH₂CH=CH₂) | H | Cl | OCH₃ | CH |
| C₂H₅ | S(O)(CH₂CH=CH₂) | H | OCH₃ | CH₃ | N |
| C₂H₅ | S(O)(CH₂CH=CH₂) | H | OCH₃ | N(CH₃)₂ | N |
| CH(CH₃)₂ | S(O)(CH₂CH=CH₂) | H | OCH₃ | CH₃ | CH |
| CH(CH₃)₂ | S(O)(CH₂CH=CH₂) | H | OCH₃ | OCH₃ | CH |
| CH(CH₃)₂ | S(O)(CH₂CH=CH₂) | H | Cl | OCH₃ | CH |
| CH(CH₃)₂ | S(O)(CH₂CH=CH₂) | H | OCH₃ | CH₃ | N |
| CH(CH₃)₂ | S(O)(CH₂CH=CH₂) | H | OCH₃ | OCH₃ | N |
| CH₃ | S(O)(CH₂CH=CHCH₃) | H | OCH₃ | CH₃ | CH |
| CH₃ | S(O)(CH₂CH=CHCH₃) | H | OCH₃ | OCH₃ | CH |
| CH₃ | S(O)(CH₂CH=CHCH₃) | H | Cl | OCH₃ | CH |
| CH₃ | S(O)(CH₂CH=CHCH₃) | H | OCH₃ | CH₃ | N |
| CH₃ | S(O)(CH₂CH=CHCH₃) | H | OCH₃ | OCH₃ | N |
| CH₃ | S(O)((CH₂)₂CH=CH₂) | H | OCH₃ | CH₃ | CH |
| CH₃ | S(O)(CH₂CH=CHCH₂CH₃) | H | OCH₃ | OCH₃ | CH |
| CH₃ | S(O)(CH₂CH=CH(CH₂)₂CH₃) | H | OCH₃ | CH₃ | N |
| CH₃ | S(O)((CH₂)₂CH=CHCH₂CH₃) | H | OCH₃ | OCH₃ | N |
| CH₃ | S(O)(CH₂CH=C(CH₃)₂) | H | OCH₃ | CH₃ | CH |
| CH₃ | SCH₂C≡CH | H | CH₃ | CH₃ | CH |
| CH₃ | SCH₂C≡CH | H | OCH₃ | CH₃ | CH |
| CH₃ | SCH₂C≡CH | H | OCH₃ | OCH₃ | CH |
| CH₃ | SCH₂C≡CH | H | Cl | OCH₃ | CH |
| CH₃ | SCH₂C≡CH | H | OCH₃ | N(CH₃)₂ | N |

TABLE I-continued

| | | | | | |
|---|---|---|---|---|---|
| CH₃ | SCH₂C≡CH | H | CH₃ | CH₃ | N |
| CH₃ | SCH₂C≡CH | H | OCH₃ | CH₃ | N |
| CH₃ | SCH₂C≡CH | H | OCH₃ | OCH₃ | N |
| CH₃ | SCH₂C≡CH | H | OCH₃ | N(CH₃)₂ | N |
| CH₃ | SCH₂C≡CH | H | OCH₃ | OCH₂CF₃ | N |
| CH₃ | SCH₂C≡CH | CH₃ | OCH₃ | CH₃ | N |
| CH₃ | SCH₂C≡CH | CH₃ | OCH₃ | OCH₃ | N |
| CH₃ | SCH₂C≡CH | CH₃ | CH₃ | OCH₃ | CH |
| CH₃ | SCH₂C≡CH | CH₃ | OCH₃ | OCH₃ | CH |
| CH₃ | SCH₂C≡CH | H | Br | OCH₃ | CH |
| CH₃ | SCH₂C≡CH | CH₃ | OCH₃ | N(CH₃)₂ | N |
| CH₃ | SCH₂C≡CH | H | CH₃ | OCH₂CF₃ | N |
| CH₃ | SCH₂C≡CH | H | CH₃ | OCH₂CF₃ | CH |
| CH₃ | SCH₂C≡CH | H | OCH₃ | OCH₂CF₃ | CH |
| CH₃ | SCH₂C≡CH | H | OCH₃ | C₂H₅ | CH |
| CH₃ | SCH₂C≡CH | H | OCH₃ | C₂H₅ | CH |
| CH₃ | SCH₂C≡CH | H | OCH₃ | NHCH₃ | CH |
| CH₃ | SCH₂C≡CH | H | OCH₃ | NHCH₃ | N |
| CH₃ | SCH₂C≡CH | H | CH₃ | OC₂H₅ | CH |
| CH₃ | SCH₂C≡CH | H | OCH₃ | OC₂H₅ | CH |
| CH₃ | SCH₂C≡CH | H | CH₃ | OC₂H₅ | N |
| CH₃ | SCH₂C≡CH | H | OCH₃ | OC₂H₅ | N |
| CH₃ | SCH₂C≡CH | H | CH₃ | OCH₂CHF₂ | CH |
| CH₃ | SCH₂C≡CH | H | OCH₃ | OCH₂CHF₂ | CH |
| CH₃ | SCH₂C≡CH | H | CH₃ | OCH₂CHF₂ | N |
| CH₃ | SCH₂C≡CH | H | OCH₃ | OCH₂CHF₂ | N |
| CH₃ | SCH₂C≡CH | H | CH₃ | OCH₂CH₂F | CH |
| CH₃ | SCH₂C≡CH | H | OCH₃ | OCH₂CH₂F | CH |
| CH₃ | SCH₂C≡CH | H | CH₃ | OCH₂CH₂F | N |
| CH₃ | SCH₂C≡CH | H | OCH₃ | OCH₂CH₂F | N |
| CH₃ | SCH₂C≡CH | CH₃ | Cl | OCH₃ | CH |
| CH₃ | SCH₂C≡CH | H | Cl | N(CH₃)₂ | CH |
| CH₃ | SCH₂C≡CH | H | Cl | OC₂H₅ | CH |
| C₂H₅ | SCH₂C≡CH | H | CH₃ | CH₃ | CH |
| C₂H₅ | SCH₂C≡CH | H | OCH₃ | CH₃ | CH |
| C₂H₅ | SCH₂C≡CH | H | OCH₃ | OCH₃ | CH |
| C₂H₅ | SCH₂C≡CH | H | Cl | OCH₃ | CH |
| C₂H₅ | SCH₂C≡CH | H | CH₃ | CH₃ | N |
| C₂H₅ | SCH₂C≡CH | H | OCH₃ | CH₃ | N |
| C₂H₅ | SCH₂C≡CH | H | OCH₃ | OCH₃ | N |
| C₂H₅ | SCH₂C≡CH | H | Br | OCH₃ | CH |
| C₂H₅ | SCH₂C≡CH | H | OCH₃ | N(CH₃)₂ | CH |
| C₂H₅ | SCH₂C≡CH | H | OCH₃ | N(CH₃)₂ | N |
| C₂H₅ | SCH₂C≡CH | H | OCH₃ | NHCH₃ | N |
| C₂H₅ | SCH₂C≡CH | H | OCH₃ | C₂H₅ | CH |
| C₂H₅ | SCH₂C≡CH | H | OCH₃ | C₂H₅ | N |
| C₂H₅ | SCH₂C≡CH | H | CH₃ | OC₂H₅ | CH |
| C₂H₅ | SCH₂C≡CH | H | CH₃ | OC₂H₅ | N |
| C₂H₅ | SCH₂C≡CH | H | OCH₃ | OC₂H₅ | CH |
| C₂H₅ | SCH₂C≡CH | H | OCH₃ | OC₂H₅ | N |
| C₂H₅ | SCH₂C≡CH | H | CH₃ | OCH₂CF₃ | CH |
| C₂H₅ | SCH₂C≡CH | H | CH₃ | OCH₂CF₃ | N |
| C₂H₅ | SCH₂C≡CH | H | OCH₃ | OCH₂CF₃ | CH |
| C₂H₅ | SCH₂C≡CH | H | OCH₃ | OCH₂CF₃ | N |
| C₂H₅ | SCH₂C≡CH | H | OCH₃ | OCH₂CF₂ | CH |
| C₂H₅ | SCH₂C≡CH | H | OCH₃ | OCH₂CHF₂ | N |
| C₂H₅ | SCH₂C≡CH | H | CH₃ | OCH₂CHF₂ | N |
| C₂H₅ | SCH₂C≡CH | H | OCH₃ | OCH₂CH₂F | CH |
| C₂H₅ | SCH₂C≡CH | H | OCH₃ | OCH₂CH₂F | N |
| C₂H₅ | SCH₂C≡CH | CH₃ | OCH₃ | OCH₃ | CH |
| C₂H₅ | SCH₂C≡CH | CH₃ | CH₃ | OCH₃ | N |
| C₂H₅ | SCH₂C≡CH | CH₃ | OCH₃ | OCH₃ | N |
| n-C₃H₇ | SCH₂C≡CH | H | OCH₃ | OCH₃ | CH |
| n-C₃H₇ | SCH₂C≡CH | H | CH₃ | OCH₃ | N |
| CH(CH₃)₂ | SCH₂C≡CH | H | OCH₃ | CH₃ | CH |
| CH(CH₃)₂ | SCH₂C≡CH | H | OCH₃ | OCH₃ | CH |
| CH(CH₃)₂ | SCH₂C≡CH | H | Cl | OCH₃ | CH |
| CH(CH₃)₂ | SCH₂C≡CH | H | OCH₃ | CH₃ | N |
| CH(CH₃)₂ | SCH₂C≡CH | H | OCH₃ | OCH₃ | N |
| CH(CH₃)₂ | SCH₂C≡CH | H | OCH₃ | N(CH₃)₂ | N |
| CH₃ | SCH₂C≡CCH₃ | H | CH₃ | CH₃ | CH |
| CH₃ | SCH₂C≡CCH₃ | H | OCH₃ | CH₃ | CH |
| CH₃ | SCH₂C≡CCH₃ | H | OCH₃ | OCH₃ | CH |
| CH₃ | SCH₂C≡CCH₃ | H | Cl | OCH₃ | CH |
| CH₃ | SCH₂C≡CCH₃ | H | CH₃ | CH₃ | N |
| CH₃ | SCH₂C≡CCH₃ | H | OCH₃ | CH₃ | N |
| CH₃ | SCH₂C≡CCH₃ | H | OCH₃ | OCH₃ | N |
| CH₃ | SCH₂C≡CCH₃ | H | OCH₃ | N(CH₃)₂ | CH |
| CH₃ | SCH₂C≡CCH₃ | H | OCH₃ | N(CH₃)₂ | N |
| CH₃ | SCH₂C≡CCH₃ | H | OCH₃ | OCH₂CF₃ | N |
| CH₃ | SCH₂C≡CCH₃ | CH₃ | OCH₃ | CH₃ | N |
| CH₃ | SCH₂C≡CCH₃ | CH₃ | OCH₃ | OCH₃ | N |

TABLE I-continued

| | | | | | |
|---|---|---|---|---|---|
| CH$_3$ | SCH$_2$C≡CCH$_3$ | CH$_3$ | CH$_3$ | OCH$_3$ | CH |
| CH$_3$ | SCH$_2$C≡CCH$_3$ | CH$_3$ | OCH$_3$ | OCH$_3$ | CH |
| CH$_3$ | SCH$_2$C≡CCH$_3$ | H | Br | OCH$_3$ | CH |
| CH$_3$ | SCH$_2$C≡CCH$_3$ | H | CH$_3$ | OCH$_2$CF$_3$ | N |
| CH$_3$ | SCH$_2$C≡CCH$_3$ | H | CH$_3$ | OCH$_2$CF$_3$ | CH |
| CH$_3$ | SCH$_2$C≡CCH$_3$ | H | OCH$_3$ | OCH$_2$CF$_3$ | CH |
| CH$_3$ | SCH$_2$C≡CCH$_3$ | H | OCH$_3$ | NHCH$_3$ | N |
| C$_2$H$_5$ | SCH$_2$C≡CCH$_3$ | H | CH$_3$ | CH$_3$ | CH |
| C$_2$H$_5$ | SCH$_2$C≡CCH$_3$ | H | OCH$_3$ | CH$_3$ | CH |
| C$_2$H$_5$ | SCH$_2$C≡CCH$_3$ | H | OCH$_3$ | OCH$_3$ | CH |
| C$_2$H$_5$ | SCH$_2$C≡CCH$_3$ | H | Cl | OCH$_3$ | CH |
| C$_2$H$_5$ | SCH$_2$C≡CCH$_3$ | H | OCH$_3$ | CH$_3$ | N |
| C$_2$H$_5$ | SCH$_2$C≡CCH$_3$ | H | OCH$_3$ | N(CH$_3$)$_2$ | CH |
| CH(CH$_3$)$_2$ | SCH$_2$C≡CCH$_3$ | H | OCH$_3$ | CH$_3$ | CH |
| CH(CH$_3$)$_2$ | SCH$_2$C≡CCH$_3$ | H | OCH$_3$ | OCH$_3$ | CH |
| CH(CH$_3$)$_2$ | SCH$_2$C≡CCH$_3$ | H | Cl | OCH$_3$ | CH |
| CH(CH$_3$)$_2$ | SCH$_2$C≡CCH$_3$ | H | OCH$_3$ | CH$_3$ | N |
| CH(CH$_3$)$_2$ | SCH$_2$C≡CCH$_3$ | H | OCH$_3$ | OCH$_3$ | N |
| CH$_3$ | SCH$_2$C≡CC$_2$H$_5$ | H | CH$_3$ | CH$_3$ | CH |
| CH$_3$ | SCH$_2$C≡CC$_2$H$_5$ | H | OCH$_3$ | CH$_3$ | CH |
| CH$_3$ | SCH$_2$C≡CC$_2$H$_5$ | H | OCH$_3$ | OCH$_3$ | CH |
| CH$_3$ | SCH$_2$C≡CC$_2$H$_5$ | H | Cl | OCH$_3$ | CH |
| CH$_3$ | SCH$_2$C≡CC$_2$H$_5$ | H | CH$_3$ | CH$_3$ | N |
| CH$_3$ | SCH$_2$C≡CC$_2$H$_5$ | H | OCH$_3$ | CH$_3$ | N |
| CH$_3$ | SCH$_2$C≡CC$_2$H$_5$ | H | OCH$_3$ | OCH$_3$ | N |
| CH$_3$ | SCH$_2$C≡CC$_2$H$_5$ | H | OCH$_3$ | N(CH$_3$)$_2$ | CH |
| CH$_3$ | SCH$_2$C≡CC$_2$H$_5$ | H | OCH$_3$ | N(CH$_3$)$_2$ | N |
| CH$_3$ | SCH$_2$C≡CC$_2$H$_5$ | H | OCH$_3$ | OCH$_2$CF$_3$ | N |
| CH$_3$ | SCH$_2$C≡CC$_2$H$_5$ | CH$_3$ | OCH$_3$ | CH$_3$ | N |
| CH$_3$ | SCH$_2$C≡CC$_2$H$_5$ | CH$_3$ | OCH$_3$ | OCH$_3$ | N |
| CH$_3$ | SCH$_2$C≡CC$_2$H$_5$ | CH$_3$ | CH$_3$ | OCH$_3$ | CH |
| CH$_3$ | SCH$_2$C≡CC$_2$H$_5$ | CH$_3$ | OCH$_3$ | OCH$_3$ | CH |
| CH$_3$ | SCH$_2$C≡CC$_2$H$_5$ | H | Br | OCH$_3$ | CH |
| CH$_3$ | SCH$_2$C≡CC$_2$H$_5$ | H | CH$_3$ | OCH$_2$CF$_3$ | N |
| CH$_3$ | SCH$_2$C≡CC$_2$H$_5$ | H | CH$_3$ | OCH$_2$CF$_3$ | CH |
| CH$_3$ | SCH$_2$C≡CC$_2$H$_5$ | H | OCH$_3$ | OCH$_2$CF$_3$ | CH |
| CH$_3$ | SCH$_2$C≡CC$_2$H$_5$ | H | OCH$_3$ | NHCH$_3$ | N |
| C$_2$H$_5$ | SCH$_2$C≡CC$_2$H$_5$ | H | CH$_3$ | CH$_3$ | CH |
| C$_2$H$_5$ | SCH$_2$C≡CC$_2$H$_5$ | H | OCH$_3$ | CH$_3$ | CH |
| C$_2$H$_5$ | SCH$_2$C≡CC$_2$H$_5$ | H | OCH$_3$ | OCH$_3$ | CH |
| C$_2$H$_5$ | SCH$_2$C≡CC$_2$H$_5$ | H | Cl | OCH$_3$ | CH |
| C$_2$H$_5$ | SCH$_2$C≡CC$_2$H$_5$ | H | OCH$_3$ | CH$_3$ | N |
| C$_2$H$_5$ | SCH$_2$C≡CC$_2$H$_5$ | H | OCH$_3$ | N(CH$_3$)$_2$ | CH |
| CH(CH$_3$)$_2$ | SCH$_2$C≡CC$_2$H$_5$ | H | OCH$_3$ | CH$_3$ | CH |
| CH(CH$_3$)$_2$ | SCH$_2$C≡CC$_2$H$_5$ | H | OCH$_3$ | OCH$_3$ | CH |
| CH(CH$_3$)$_2$ | SCH$_2$C≡CC$_2$H$_5$ | H | Cl | OCH$_3$ | CH |
| CH(CH$_3$)$_2$ | SCH$_2$C≡CC$_2$H$_5$ | H | OCH$_3$ | CH$_3$ | N |
| CH(CH$_3$)$_2$ | SCH$_2$C≡CC$_2$H$_5$ | H | OCH$_3$ | OCH$_3$ | N |
| CH$_3$ | S(CH$_2$)$_2$C≡CH | H | CH$_3$ | OCH$_3$ | CH |
| CH$_3$ | S(CH$_2$)$_2$C≡CH | H | OCH$_3$ | OCH$_3$ | CH |
| CH$_3$ | S(CH$_2$)$_2$C≡CH | H | CH$_3$ | OCH$_3$ | N |
| CH$_3$ | S(O)(CH$_2$C≡CH) | H | CH$_3$ | CH$_3$ | CH |
| CH$_3$ | S(O)(CH$_2$C≡CH) | H | OCH$_3$ | CH$_3$ | CH |
| CH$_3$ | S(O)(CH$_2$C≡CH) | H | OCH$_3$ | OCH$_3$ | CH |
| CH$_3$ | S(O)(CH$_2$C≡CH) | H | Cl | OCH$_3$ | CH |
| CH$_3$ | S(O)(CH$_2$C≡CH) | H | CH$_3$ | CH$_3$ | N |
| CH$_3$ | S(O)(CH$_2$C≡CH) | H | OCH$_3$ | CH$_3$ | N |
| CH$_3$ | S(O)(CH$_2$C≡CH) | H | OCH$_3$ | OCH$_3$ | N |
| CH$_3$ | S(O)(CH$_2$C≡CH) | H | OCH$_3$ | N(CH$_3$)$_2$ | CH |
| CH$_3$ | S(O)(CH$_2$C≡CH) | H | OCH$_3$ | N(CH$_3$)$_2$ | N |
| CH$_3$ | S(O)(CH$_2$C≡CH) | H | OCH$_3$ | OCH$_2$CF$_3$ | N |
| CH$_3$ | S(O)(CH$_2$C≡CH) | CH$_3$ | OCH$_3$ | CH$_3$ | N |
| CH$_3$ | S(O)(CH$_2$C≡CH) | CH$_3$ | OCH$_3$ | OCH$_3$ | N |
| CH$_3$ | S(O)(CH$_2$C≡CH) | CH$_3$ | CH$_3$ | OCH$_3$ | CH |
| CH$_3$ | S(O)(CH$_2$C≡CH) | CH$_3$ | OCH$_3$ | OCH$_3$ | CH |
| CH$_3$ | S(O)(CH$_2$C≡CH) | H | Br | OCH$_3$ | CH |
| CH$_3$ | S(O)(CH$_2$C≡CH) | H | CH$_3$ | OCH$_2$CF$_3$ | N |
| CH$_3$ | S(O)(CH$_2$C≡CH) | H | CH$_3$ | OCH$_2$CF$_3$ | CH |
| CH$_3$ | S(O)(CH$_2$C≡CH) | H | OCH$_3$ | OCH$_2$CF$_3$ | CH |
| CH$_3$ | S(O)(CH$_2$C≡CH) | H | OCH$_3$ | NHCH$_3$ | N |
| C$_2$H$_5$ | S(O)(CH$_2$C≡CH) | H | CH$_3$ | CH$_3$ | CH |
| C$_2$H$_5$ | S(O)(CH$_2$C≡CH) | H | OCH$_3$ | CH$_3$ | CH |
| C$_2$H$_5$ | S(O)(CH$_2$C≡CH) | H | OCH$_3$ | OCH$_3$ | CH |
| C$_2$H$_5$ | S(O)(CH$_2$C≡CH) | H | Cl | OCH$_3$ | CH |
| C$_2$H$_5$ | S(O)(CH$_2$C≡CH) | H | OCH$_3$ | CH$_3$ | N |
| C$_2$H$_5$ | S(O)(CH$_2$C≡CH) | H | OCH$_3$ | N(CH$_3$)$_2$ | N |
| CH(CH$_3$)$_2$ | S(O)(CH$_2$C≡CH) | H | OCH$_3$ | CH$_3$ | CH |
| CH(CH$_3$)$_2$ | S(O)(CH$_2$C≡CH) | H | OCH$_3$ | OCH$_3$ | CH |
| CH(CH$_3$)$_2$ | S(O)(CH$_2$C≡CH) | H | Cl | OCH$_3$ | CH |
| CH(CH$_3$)$_2$ | S(O)(CH$_2$C≡CH) | H | OCH$_3$ | CH$_3$ | N |
| CH(CH$_3$)$_2$ | S(O)(CH$_2$C≡CH) | H | OCH$_3$ | OCH$_3$ | N |
| CH$_3$ | S(O)(CH$_2$C≡CCH$_3$) | H | OCH$_3$ | CH$_3$ | CH |

TABLE I-continued

| | | | | | |
|---|---|---|---|---|---|
| CH$_3$ | S(O)(CH$_2$C≡CCH$_3$) | H | OCH$_3$ | OCH$_3$ | CH |
| CH$_3$ | S(O)(CH$_2$C≡CCH$_3$) | H | Cl | OCH$_3$ | CH |
| CH$_3$ | S(O)(CH$_2$C≡CCH$_3$) | H | OCH$_3$ | CH$_3$ | N |
| CH$_3$ | S(O)(CH$_2$C≡CCH$_3$) | H | OCH$_3$ | OCH$_3$ | N |
| CH$_3$ | S(O)((CH$_2$)$_2$C≡CH) | H | OCH$_3$ | CH$_3$ | CH |
| CH$_3$ | S(O)(CH$_2$C≡CCH$_2$CH$_3$) | H | OCH$_3$ | OCH$_3$ | CH |
| CH$_3$ | S(O)((CH$_2$)$_2$C≡CCH$_3$) | H | OCH$_3$ | CH$_3$ | CH |
| CH$_3$ | S(O)((CH$_2$)$_2$C≡CCH$_2$CH$_3$) | H | OCH$_3$ | OCH$_3$ | CH |
| CH$_3$ | S(O)((CH$_2$)$_4$C≡CH) | H | OCH$_3$ | CH$_3$ | N |
| CH$_3$ | S(O)$_2$(CH$_2$CH=CH$_2$) | H | CH$_3$ | CH$_3$ | CH |
| CH$_3$ | S(O)$_2$(CH$_2$CH=CH$_2$) | H | OCH$_3$ | CH$_3$ | CH |
| CH$_3$ | S(O)$_2$(CH$_2$CH=CH$_2$) | H | OCH$_3$ | OCH$_3$ | CH |
| CH$_3$ | S(O)$_2$(CH$_2$CH=CH$_2$) | H | Cl | OCH$_3$ | CH |
| CH$_3$ | S(O)$_2$(CH$_2$CH=CH$_2$) | H | CH$_3$ | CH$_3$ | N |
| CH$_3$ | S(O)$_2$(CH$_2$CH=CH$_2$) | H | OCH$_3$ | CH$_3$ | N |
| CH$_3$ | S(O)$_2$(CH$_2$CH=CH$_2$) | H | OCH$_3$ | OCH$_3$ | N |
| CH$_3$ | S(O)$_2$(CH$_2$CH=CHCH$_3$) | H | OCH$_3$ | CH$_3$ | CH |
| CH$_3$ | S(O)$_2$(CH$_2$CH=CHCH$_3$) | H | OCH$_3$ | OCH$_3$ | CH |
| CH$_3$ | S(O)$_2$(CH$_2$CH=CHCH$_3$) | H | Cl | OCH$_3$ | CH |
| CH$_3$ | S(O)$_2$(CH$_2$CH=CHCH$_3$) | H | OCH$_3$ | CH$_3$ | N |
| CH$_3$ | S(O)$_2$(CH$_2$CH=CHCH$_3$) | H | OCH$_3$ | OCH$_3$ | N |
| CH$_3$ | S(O)$_2$((CH$_2$)$_2$CH=CH$_2$) | H | OCH$_3$ | CH$_3$ | CH |
| CH$_3$ | S(O)$_2$(CH$_2$CH=CHCH$_2$CH$_3$) | H | OCH$_3$ | OCH$_3$ | N |
| CH$_3$ | S(O)$_2$(CH$_2$CH=CH(CH$_2$)$_2$CH$_3$) | H | OCH$_3$ | CH$_3$ | N |
| CH$_3$ | S(O)$_2$((CH$_2$)$_2$CH=CH(CH$_2$)$_2$CH$_3$) | H | OCH$_3$ | OCH$_3$ | CH |
| CH$_3$ | S(O)$_2$(CH$_2$CH=C(CH$_3$)$_2$) | H | OCH$_3$ | CH$_3$ | CH |
| CH$_3$ | S(O)$_2$(CH$_2$C≡CH) | H | CH$_3$ | CH$_3$ | CH |
| CH$_3$ | S(O)$_2$(CH$_2$C≡CH) | H | OCH$_3$ | CH$_3$ | CH |
| CH$_3$ | S(O)$_2$(CH$_2$C≡CH) | H | OCH$_3$ | OCH$_3$ | CH |
| CH$_3$ | S(O)$_2$(CH$_2$C≡CH) | H | Cl | OCH$_3$ | CH |
| CH$_3$ | S(O)$_2$(CH$_2$C≡CH) | H | CH$_3$ | CH$_3$ | N |
| CH$_3$ | S(O)$_2$(CH$_2$C≡CH) | H | OCH$_3$ | CH$_3$ | N |
| CH$_3$ | S(O)$_2$(CH$_2$C≡CH) | H | OCH$_3$ | OCH$_3$ | N |
| CH$_3$ | S(O)$_2$(CH$_2$C≡CCH$_3$) | H | OCH$_3$ | CH$_3$ | CH |
| CH$_3$ | S(O)$_2$(CH$_2$C≡CCH$_3$) | H | OCH$_3$ | OCH$_3$ | CH |
| CH$_3$ | S(O)$_2$(CH$_2$C≡CCH$_3$) | H | Cl | OCH$_3$ | CH |
| CH$_3$ | S(O)$_2$(CH$_2$C≡CCH$_3$) | H | OCH$_3$ | CH$_3$ | N |
| CH$_3$ | S(O)$_2$(CH$_2$C≡CCH$_3$) | H | OCH$_3$ | OCH$_3$ | N |
| CH$_3$ | S(O)$_2$((CH$_2$)$_2$C≡CH) | H | OCH$_3$ | OCH$_3$ | N |
| CH$_3$ | S(O)$_2$((CH$_2$)$_2$C≡CCH$_2$CH$_3$) | H | CH$_3$ | OCH$_3$ | CH |
| CH$_3$ | S(O)$_2$((CH$_2$)$_2$C≡CCH$_3$) | H | OCH$_3$ | OCH$_3$ | CH |
| CH$_3$ | S(O)$_2$((CH$_2$)$_2$C≡CCH$_2$CH$_3$) | H | CH$_3$ | OCH$_3$ | CH |
| CH$_3$ | S(O)$_2$((CH$_2$)$_4$C≡CH) | H | OCH$_3$ | CH$_3$ | CH |
| CH$_3$ | CH$_2$CH$_2$F | H | CH$_3$ | CH$_3$ | CH |
| CH$_3$ | CH$_2$CH$_2$F | H | OCH$_3$ | CH$_3$ | CH |
| CH$_3$ | CH$_2$CH$_2$F | H | OCH$_3$ | OCH$_3$ | CH |
| CH$_3$ | CH$_2$CH$_2$F | H | Cl | OCH$_3$ | CH |
| CH$_3$ | CH$_2$CH$_2$F | H | OCH$_3$ | N(CH$_3$)$_2$ | CH |
| CH$_3$ | CH$_2$CH$_2$F | H | CH$_3$ | CH$_3$ | N |
| CH$_3$ | CH$_2$CH$_2$F | H | OCH$_3$ | CH$_3$ | N |
| CH$_3$ | CH$_2$CH$_2$F | H | OCH$_3$ | OCH$_3$ | N |
| CH$_3$ | CH$_2$CH$_2$F | H | OCH$_3$ | N(CH$_3$)$_2$ | N |
| CH$_3$ | CH$_2$CH$_2$F | H | OCH$_3$ | OCH$_2$CF$_3$ | N |
| CH$_3$ | CH$_2$CH$_2$F | CH$_3$ | OCH$_3$ | CH$_3$ | N |
| CH$_3$ | CH$_2$CH$_2$F | CH$_3$ | OCH$_3$ | OCH$_3$ | N |
| CH$_3$ | CH$_2$CH$_2$F | CH$_3$ | CH$_3$ | OCH$_3$ | CH |
| CH$_3$ | CH$_2$CH$_2$F | CH$_3$ | OCH$_3$ | OCH$_3$ | CH |
| CH$_3$ | CH$_2$CH$_2$F | H | Br | OCH$_3$ | CH |
| CH$_3$ | CH$_2$CH$_2$F | CH$_3$ | OCH$_3$ | N(CH$_3$)$_2$ | N |
| CH$_3$ | CH$_2$CH$_2$F | H | CH$_3$ | OCH$_2$CF$_3$ | N |
| CH$_3$ | CH$_2$CH$_2$F | H | CH$_3$ | OCH$_2$CF$_3$ | CH |
| CH$_3$ | CH$_2$CH$_2$F | H | OCH$_3$ | OCH$_2$CF$_3$ | CH |
| CH$_3$ | CH$_2$CH$_2$F | H | OCH$_3$ | C$_2$H$_5$ | CH |
| CH$_3$ | CH$_2$CH$_2$F | H | OCH$_3$ | C$_2$H$_5$ | N |
| CH$_3$ | CH$_2$CH$_2$F | H | OCH$_3$ | NHCH$_3$ | CH |
| CH$_3$ | CH$_2$CH$_2$F | H | OCH$_3$ | NHCH$_3$ | N |
| CH$_3$ | CH$_2$CH$_2$F | H | CH$_3$ | OC$_2$H$_5$ | CH |
| CH$_3$ | CH$_2$CH$_2$F | H | OCH$_3$ | OC$_2$H$_5$ | CH |
| CH$_3$ | CH$_2$CH$_2$F | H | CH$_3$ | OC$_2$H$_5$ | N |
| CH$_3$ | CH$_2$CH$_2$F | H | OCH$_3$ | OC$_2$H$_5$ | N |
| CH$_3$ | CH$_2$CH$_2$F | H | CH$_3$ | OCH$_2$CHF$_2$ | CH |
| CH$_3$ | CH$_2$CH$_2$F | H | OCH$_3$ | OCH$_2$CHF$_2$ | CH |
| CH$_3$ | CH$_2$CH$_2$F | H | CH$_3$ | OCH$_2$CHF$_2$ | N |
| CH$_3$ | CH$_2$CH$_2$F | H | OCH$_3$ | OCH$_2$CHF$_2$ | N |
| CH$_3$ | CH$_2$CH$_2$F | H | CH$_3$ | OCH$_2$CH$_2$F | CH |
| CH$_3$ | CH$_2$CH$_2$F | H | OCH$_3$ | OCH$_2$CH$_2$F | CH |
| CH$_3$ | CH$_2$CH$_2$F | H | CH$_3$ | OCH$_2$CF$_3$ | N |
| CH$_3$ | CH$_2$CH$_2$F | CH$_3$ | OCH$_3$ | OCH$_2$CF$_3$ | N |
| CH$_3$ | CH$_2$CH$_2$F | CH$_3$ | Cl | OCH$_3$ | CH |
| CH$_3$ | CH$_2$CH$_2$F | H | Cl | N(CH$_3$)$_2$ | CH |
| CH$_3$ | CH$_2$CH$_2$F | H | Cl | OC$_2$H$_5$ | CH |
| C$_2$H$_5$ | CH$_2$CH$_2$F | H | CH$_3$ | CH$_3$ | CH |

TABLE I-continued

| | | | | | |
|---|---|---|---|---|---|
| $C_2H_5$ | $CH_2CH_2F$ | H | $OCH_3$ | $CH_3$ | CH |
| $C_2H_5$ | $CH_2CH_2F$ | H | $OCH_3$ | $OCH_3$ | CH |
| $C_2H_5$ | $CH_2CH_2F$ | H | Cl | $OCH_3$ | CH |
| $C_2H_5$ | $CH_2CH_2F$ | H | $CH_3$ | $CH_3$ | N |
| $C_2H_5$ | $CH_2CH_2F$ | H | $OCH_3$ | $CH_3$ | N |
| $C_2H_5$ | $CH_2CH_2F$ | H | $OCH_3$ | $OCH_3$ | N |
| $C_2H_5$ | $CH_2CH_2F$ | H | Br | $OCH_3$ | CH |
| $C_2H_5$ | $CH_2CH_2F$ | H | $OCH_3$ | $N(CH_3)_2$ | CH |
| $C_2H_5$ | $CH_2CH_2F$ | H | $OCH_3$ | $N(CH_3)_2$ | N |
| $C_2H_5$ | $CH_2CH_2F$ | H | $OCH_3$ | $NHCH_3$ | N |
| $C_2H_5$ | $CH_2CH_2F$ | H | $OCH_3$ | $C_2H_5$ | CH |
| $C_2H_5$ | $CH_2CH_2F$ | H | $OCH_3$ | $C_2H_5$ | N |
| $C_2H_5$ | $CH_2CH_2F$ | H | $CH_3$ | $OC_2H_5$ | CH |
| $C_2H_5$ | $CH_2CH_2F$ | H | $CH_3$ | $OC_2H_5$ | N |
| $C_2H_5$ | $CH_2CH_2F$ | H | $OCH_3$ | $OC_2H_5$ | CH |
| $C_2H_5$ | $CH_2CH_2F$ | H | $OCH_3$ | $OC_2H_5$ | N |
| $C_2H_5$ | $CH_2CH_2F$ | H | $CH_3$ | $OCH_2CF_3$ | CH |
| $C_2H_5$ | $CH_2CH_2F$ | H | $CH_3$ | $OCH_2CF_3$ | N |
| $C_2H_5$ | $CH_2CH_2F$ | H | $OCH_3$ | $OCH_2CF_3$ | CH |
| $C_2H_5$ | $CH_2CH_2F$ | H | $OCH_3$ | $OCH_2CF_3$ | N |
| $C_2H_5$ | $CH_2CH_2F$ | H | $OCH_3$ | $OCH_2CHF_2$ | CH |
| $C_2H_5$ | $CH_2CH_2F$ | H | $OCH_3$ | $OCH_2CHF_2$ | N |
| $C_2H_5$ | $CH_2CH_2F$ | H | $CH_3$ | $OCH_2CHF_2$ | N |
| $C_2H_5$ | $CH_2CH_2F$ | H | $OCH_3$ | $OCH_2CH_2F$ | CH |
| $C_2H_5$ | $CH_2CH_2F$ | H | $OCH_3$ | $OCH_2CH_2F$ | N |
| $C_2H_5$ | $CH_2CH_2F$ | $CH_3$ | $OCH_3$ | $OCH_3$ | CH |
| $C_2H_5$ | $CH_2CH_2F$ | $CH_3$ | $CH_3$ | $OCH_3$ | N |
| $C_2H_5$ | $CH_2CH_2F$ | $CH_3$ | $OCH_3$ | $OCH_3$ | N |
| n-$C_3H_7$ | $CH_2CH_2F$ | H | $OCH_3$ | $OCH_3$ | CH |
| n-$C_3H_7$ | $CH_2CH_2F$ | H | $CH_3$ | $OCH_3$ | N |
| $CH(CH_3)_2$ | $CH_2CH_2F$ | H | $OCH_3$ | $CH_3$ | CH |
| $CH(CH_3)_2$ | $CH_2CH_2F$ | H | $OCH_3$ | $OCH_3$ | CH |
| $CH(CH_3)_2$ | $CH_2CH_2F$ | H | Cl | $OCH_3$ | CH |
| $CH(CH_3)_2$ | $CH_2CH_2F$ | H | $OCH_3$ | $CH_3$ | N |
| $CH(CH_3)_2$ | $CH_2CH_2F$ | H | $OCH_3$ | $OCH_3$ | N |
| $CH(CH_3)_2$ | $CH_2CH_2F$ | H | $OCH_3$ | $N(CH_3)_2$ | N |
| $CH_3$ | $CH_2CHF_2$ | H | $CH_3$ | $CH_3$ | CH |
| $CH_3$ | $CH_2CHF_2$ | H | $OCH_3$ | $CH_3$ | CH |
| $CH_3$ | $CH_2CHF_2$ | H | $OCH_3$ | $OCH_3$ | CH |
| $CH_3$ | $CH_2CHF_2$ | H | Cl | $OCH_3$ | CH |
| $CH_3$ | $CH_2CHF_2$ | H | $OCH_3$ | $N(CH_3)_2$ | CH |
| $CH_3$ | $CH_2CHF_2$ | H | $CH_3$ | $CH_3$ | N |
| $CH_3$ | $CH_2CHF_2$ | H | $OCH_3$ | $CH_3$ | N |
| $CH_3$ | $CH_2CHF_2$ | H | $OCH_3$ | $OCH_3$ | N |
| $CH_3$ | $CH_2CHF_2$ | H | $OCH_3$ | $N(CH_3)_2$ | N |
| $CH_3$ | $CH_2CHF_2$ | H | $OCH_3$ | $OCH_2CF_3$ | N |
| $CH_3$ | $CH_2CHF_2$ | $CH_3$ | $OCH_3$ | $CH_3$ | N |
| $CH_3$ | $CH_2CHF_2$ | $CH_3$ | $OCH_3$ | $OCH_3$ | N |
| $CH_3$ | $CH_2CHF_2$ | $CH_3$ | $CH_3$ | $OCH_3$ | CH |
| $CH_3$ | $CH_2CHF_2$ | $CH_3$ | $OCH_3$ | $OCH_3$ | CH |
| $CH_3$ | $CH_2CHF_2$ | H | Br | $OCH_3$ | CH |
| $CH_3$ | $CH_2CHF_2$ | $CH_3$ | $OCH_3$ | $N(CH_3)_2$ | N |
| $CH_3$ | $CH_2CHF_2$ | H | $CH_3$ | $OCH_2CF_3$ | N |
| $CH_3$ | $CH_2CHF_2$ | H | $CH_3$ | $OCH_2CF_3$ | CH |
| $CH_3$ | $CH_2CHF_2$ | H | $OCH_3$ | $OCH_2CF_3$ | CH |
| $CH_3$ | $CH_2CHF_2$ | H | $OCH_3$ | $C_2H_5$ | CH |
| $CH_3$ | $CH_2CHF_2$ | H | $OCH_3$ | $C_2H_5$ | N |
| $CH_3$ | $CH_2CHF_2$ | H | $OCH_3$ | $NHCH_3$ | CH |
| $CH_3$ | $CH_2CHF_2$ | H | $OCH_3$ | $NHCH_3$ | N |
| $CH_3$ | $CH_2CHF_2$ | H | $CH_3$ | $OC_2H_5$ | CH |
| $CH_3$ | $CH_2CHF_2$ | H | $OCH_3$ | $OC_2H_5$ | CH |
| $CH_3$ | $CH_2CHF_2$ | H | $CH_3$ | $OC_2H_5$ | N |
| $CH_3$ | $CH_2CHF_2$ | H | $OCH_3$ | $OC_2H_5$ | N |
| $CH_3$ | $CH_2CHF_2$ | H | $CH_3$ | $OCH_2CHF_2$ | CH |
| $CH_3$ | $CH_2CHF_2$ | H | $OCH_3$ | $OCH_2CHF_2$ | CH |
| $CH_3$ | $CH_2CHF_2$ | H | $CH_3$ | $OCH_2CHF_2$ | N |
| $CH_3$ | $CH_2CHF_2$ | H | $OCH_3$ | $OCH_2CHF_2$ | N |
| $CH_3$ | $CH_2CHF_2$ | H | $CH_3$ | $OCH_2CH_2F$ | CH |
| $CH_3$ | $CH_2CHF_2$ | H | $OCH_3$ | $OCH_2CH_2F$ | CH |
| $CH_3$ | $CH_2CHF_2$ | H | $CH_3$ | $OCH_2CF_3$ | N |
| $CH_3$ | $CH_2CHF_2$ | $CH_3$ | $OCH_3$ | $OCH_2CF_3$ | N |
| $CH_3$ | $CH_2CHF_2$ | $CH_3$ | Cl | $OCH_3$ | CH |
| $CH_3$ | $CH_2CHF_2$ | H | Cl | $N(CH_3)_2$ | CH |
| $C_2H_5$ | $CH_2CHF_2$ | H | $CH_3$ | $CH_3$ | CH |
| $C_2H_5$ | $CH_2CHF_2$ | H | $OCH_3$ | $CH_3$ | CH |
| $C_2H_5$ | $CH_2CHF_2$ | H | $OCH_3$ | $OCH_3$ | CH |
| $C_2H_5$ | $CH_2CHF_2$ | H | Cl | $OCH_3$ | CH |
| $C_2H_5$ | $CH_2CHF_2$ | H | $CH_3$ | $CH_3$ | N |
| $C_2H_5$ | $CH_2CHF_2$ | H | $OCH_3$ | $CH_3$ | N |
| $C_2H_5$ | $CH_2CHF_2$ | H | $OCH_3$ | $OCH_3$ | N |
| $C_2H_5$ | $CH_2CHF_2$ | H | Br | $OCH_3$ | CH |
| $C_2H_5$ | $CH_2CHF_2$ | H | $OCH_3$ | $N(CH_3)_2$ | CH |

TABLE I-continued

| | | | | | | |
|---|---|---|---|---|---|---|
| C₂H₅ | CH₂CHF₂ | | H | OCH₃ | N(CH₃)₂ | N |
| C₂H₅ | CH₂CHF₂ | | H | OCH₃ | NHCH₃ | N |
| C₂H₅ | CH₂CHF₂ | | H | OCH₃ | C₂H₅ | CH |
| C₂H₅ | CH₂CHF₂ | | H | OCH₃ | C₂H₅ | N |
| C₂H₅ | CH₂CHF₂ | | H | CH₃ | OC₂H₅ | CH |
| C₂H₅ | CH₂CHF₂ | | H | CH₃ | OC₂H₅ | N |
| C₂H₅ | CH₂CHF₂ | | H | OCH₃ | OC₂H₅ | CH |
| C₂H₅ | CH₂CHF₂ | | H | OCH₃ | OC₂H₅ | N |
| C₂H₅ | CH₂CHF₂ | | H | CH₃ | OCH₂CF₃ | CH |
| C₂H₅ | CH₂CHF₂ | | H | CH₃ | OCH₂CF₃ | N |
| C₂H₅ | CH₂CHF₂ | | H | OCH₃ | OCH₂CF₃ | CH |
| C₂H₅ | CH₂CHF₂ | | H | OCH₃ | OCH₂CF₃ | N |
| C₂H₅ | CH₂CHF₂ | | H | OCH₃ | OCH₂CHF₂ | CH |
| C₂H₅ | CH₂CHF₂ | | H | OCH₃ | OCH₂CHF₂ | N |
| C₂H₅ | CH₂CHF₂ | | H | CH₃ | OCH₂CHF₂ | N |
| C₂H₅ | CH₂CHF₂ | | H | OCH₃ | OCH₂CH₂F | CH |
| C₂H₅ | CH₂CHF₂ | | H | OCH₃ | OCH₂CH₂F | N |
| C₂H₅ | CH₂CHF₂ | | CH₃ | OCH₃ | OCH₃ | CH |
| C₂H₅ | CH₂CHF₂ | | CH₃ | CH₃ | OCH₃ | N |
| C₂H₅ | CH₂CHF₂ | | CH₃ | OCH₃ | OCH₃ | N |
| n-C₃H₇ | CH₂CHF₂ | | H | OCH₃ | OCH₃ | CH |
| n-C₃H₇ | CH₂CHF₂ | | H | CH₃ | OCH₃ | N |
| CH(CH₃)₂ | CH₂CHF₂ | | H | OCH₃ | CH₃ | CH |
| CH(CH₃)₂ | CH₂CHF₂ | | H | OCH₃ | OCH₃ | CH |
| CH(CH₃)₂ | CH₂CHF₂ | | H | Cl | OCH₃ | CH |
| CH(CH₃)₂ | CH₂CHF₂ | | H | OCH₃ | CH₃ | N |
| CH(CH₃)₂ | CH₂CHF₂ | | H | OCH₃ | OCH₃ | N |
| CH(CH₃)₂ | CH₂CHF₂ | | H | OCH₃ | N(CH₃)₂ | N |
| CH₃ | CH₂CF₃ | | H | CH₃ | CH₃ | CH |
| CH₃ | CH₂CF₃ | | H | OCH₃ | CH₃ | CH |
| CH₃ | CH₂CF₃ | | H | OCH₃ | OCH₃ | CH |
| CH₃ | CH₂CF₃ | | H | Cl | OCH₃ | CH |
| CH₃ | CH₂CF₃ | | H | OCH₃ | N(CH₃)₂ | CH |
| CH₃ | CH₂CF₃ | | H | CH₃ | CH₃ | N |
| CH₃ | CH₂CF₃ | | H | OCH₃ | CH₃ | N |
| CH₃ | CH₂CF₃ | | H | OCH₃ | OCH₃ | N |
| CH₃ | CH₂CF₃ | | H | OCH₃ | N(CH₃)₂ | N |
| CH₃ | CH₂CF₃ | | H | OCH₃ | OCH₂CF₃ | N |
| CH₃ | CH₂CF₃ | | CH₃ | OCH₃ | CH₃ | N |
| CH₃ | CH₂CF₃ | | CH₃ | OCH₃ | OCH₃ | N |
| CH₃ | CH₂CF₃ | | CH₃ | CH₃ | OCH₃ | CH |
| CH₃ | CH₂CF₃ | | CH₃ | OCH₃ | OCH₃ | CH |
| CH₃ | CH₂CF₃ | | H | Br | OCH₃ | CH |
| CH₃ | CH₂CF₃ | | CH₃ | OCH₃ | N(CH₃)₂ | N |
| CH₃ | CH₂CF₃ | | H | CH₃ | OCH₂CF₃ | N |
| CH₃ | CH₂CF₃ | | H | CH₃ | OCH₂CF₃ | CH |
| CH₃ | CH₂CF₃ | | H | OCH₃ | OCH₂CF₃ | CH |
| CH₃ | CH₂CF₃ | | H | OCH₃ | C₂H₅ | CH |
| CH₃ | CH₂CF₃ | | H | OCH₃ | C₂H₅ | N |
| CH₃ | CH₂CF₃ | | H | OCH₃ | NHCH₃ | CH |
| CH₃ | CH₂CF₃ | | H | OCH₃ | NHCH₃ | N |
| CH₃ | CH₂CF₃ | | H | CH₃ | OC₂H₅ | CH |
| CH₃ | CH₂CF₃ | | H | OCH₃ | OC₂H₅ | CH |
| CH₃ | CH₂CF₃ | | H | CH₃ | OC₂H₅ | N |
| CH₃ | CH₂CF₃ | | H | OCH₃ | OC₂H₅ | N |
| CH₃ | CH₂CF₃ | | H | CH₃ | OCH₂CHF₂ | CH |
| CH₃ | CH₂CF₃ | | H | OCH₃ | OCH₂CHF₂ | CH |
| CH₃ | CH₂CF₃ | | H | CH₃ | OCH₂CHF₂ | N |
| CH₃ | CH₂CF₃ | | H | OCH₃ | OCH₂CHF₂ | N |
| CH₃ | CH₂CF₃ | | H | CH₃ | OCH₂CH₂F | CH |
| CH₃ | CH₂CF₃ | | H | OCH₃ | OCH₂CH₂F | CH |
| CH₃ | CH₂CF₃ | | H | CH₃ | OCH₂CH₂F | N |
| CH₃ | CH₂CF₃ | | CH₃ | OCH₃ | OCH₂CH₂F | N |
| CH₃ | CH₂CF₃ | | CH₃ | Cl | OCH₃ | CH |
| CH₃ | CH₂CF₃ | | H | Cl | N(CH₃)₂ | CH |
| CH₃ | CH₂CF₃ | | H | Cl | OC₂H₅ | CH |
| C₂H₅ | CH₂CF₃ | | H | CH₃ | CH₃ | CH |
| C₂H₅ | CH₂CF₃ | | H | OCH₃ | CH₃ | CH |
| C₂H₅ | CH₂CF₃ | | H | OCH₃ | OCH₃ | CH |
| C₂H₅ | CH₂CF₃ | | H | Cl | OCH₃ | CH |
| C₂H₅ | CH₂CF₃ | | H | CH₃ | CH₃ | N |
| C₂H₅ | CH₂CF₃ | | H | OCH₃ | CH₃ | N |
| C₂H₅ | CH₂CF₃ | | H | OCH₃ | OCH₃ | N |
| C₂H₅ | CH₂CF₃ | | H | Br | OCH₃ | CH |
| C₂H₅ | CH₂CF₃ | | H | OCH₃ | N(CH₃)₂ | CH |
| C₂H₅ | CH₂CF₃ | | H | OCH₃ | N(CH₃)₂ | N |
| C₂H₅ | CH₂CF₃ | | H | OCH₃ | NHCH₃ | N |
| C₂H₅ | CH₂CF₃ | | H | OCH₃ | C₂H₅ | CH |
| C₂H₅ | CH₂CF₃ | | H | OCH₃ | C₂H₅ | N |
| C₂H₅ | CH₂CF₃ | | H | CH₃ | OC₂H₅ | CH |
| C₂H₅ | CH₂CF₃ | | H | CH₃ | OC₂H₅ | N |
| C₂H₅ | CH₂CF₃ | | H | OCH₃ | OC₂H₅ | CH |

TABLE I-continued

| | | | | | |
|---|---|---|---|---|---|
| C₂H₅ | CH₂CF₃ | H | OCH₃ | OC₂H₅ | N |
| C₂H₅ | CH₂CF₃ | H | CH₃ | OCH₂CF₃ | CH |
| C₂H₅ | CH₂CF₃ | H | CH₃ | OCH₂CF₃ | N |
| C₂H₅ | CH₂CF₃ | H | OCH₃ | OCH₂CF₃ | CH |
| C₂H₅ | CH₂CF₃ | H | OCH₃ | OCH₂CF₃ | N |
| C₂H₅ | CH₂CF₃ | H | OCH₃ | OCH₂CHF₂ | CH |
| C₂H₅ | CH₂CF₃ | H | OCH₃ | )CH₂CHF₂ | N |
| C₂H₅ | CH₂CF₃ | H | CH₃ | OCH₂CHF₂ | N |
| C₂H₅ | CH₂CF₃ | H | OCH₃ | OCH₂CH₂F | CH |
| C₂H₅ | CH₂CF₃ | H | OCH₃ | OCH₂CH₂F | N |
| C₂H₅ | CH₂CF₃ | CH₃ | OCH₃ | OCH₃ | CH |
| C₂H₅ | CH₂CF₃ | CH₃ | CH₃ | OCH₃ | N |
| C₂H₅ | CH₂CF₃ | CH₃ | OCH₃ | OCH₃ | N |
| n-C₃H₇ | CH₂CF₃ | H | OCH₃ | OCH₃ | CH |
| n-C₃H₇ | CH₂CF₃ | H | CH₃ | OCH₃ | N |
| CH(CH₃)₂ | CH₂CF₃ | H | OCH₃ | CH₃ | CH |
| CH(CH₃)₂ | CH₂CF₃ | H | OCH₃ | OCH₃ | CH |
| CH(CH₃)₂ | CH₂CF₃ | H | Cl | OCH₃ | CH |
| CH(CH₃)₂ | CH₂CF₃ | H | OCH₃ | CH₃ | N |
| CH(CH₃)₂ | CH₂CF₃ | H | OCH₃ | OCH₃ | N |
| CH(CH₃)₂ | CH₂CF₃ | H | OCH₃ | N(CH₃)₂ | N |
| CH₃ | CHFCH₃ | H | CH₃ | CH₃ | CH |
| CH₃ | CHFCH₃ | H | OCH₃ | CH₃ | CH |
| CH₃ | CHFCH₃ | H | OCH₃ | OCH₃ | CH |
| CH₃ | CHFCH₃ | H | Cl | OCH₃ | CH |
| CH₃ | CHFCH₃ | H | OCH₃ | N(CH₃)₂ | CH |
| CH₃ | CHFCH₃ | H | CH₃ | CH₃ | N |
| CH₃ | CHFCH₃ | H | OCH₃ | CH₃ | N |
| CH₃ | CHFCH₃ | H | OCH₃ | OCH₃ | N |
| CH₃ | CHFCH₃ | H | OCH₃ | N(CH₃)₂ | N |
| CH₃ | CHFCH₃ | H | OCH₃ | OCH₂CF₃ | N |
| CH₃ | CHFCH₃ | CH₃ | OCH₃ | CH₃ | N |
| CH₃ | CHFCH₃ | CH₃ | OCH₃ | OCH₃ | N |
| CH₃ | CHFCH₃ | CH₃ | CH₃ | OCH₃ | CH |
| CH₃ | CHFCH₃ | CH₃ | OCH₃ | OCH₃ | CH |
| CH₃ | CHFCH₃ | H | Br | OCH₃ | CH |
| CH₃ | CHFCH₃ | CH₃ | OCH₃ | N(CH₃)₂ | N |
| CH₃ | CHFCH₃ | H | CH₃ | OCH₂CF₃ | N |
| CH₃ | CHFCH₃ | H | CH₃ | OCH₂CF₃ | CH |
| CH₃ | CHFCH₃ | H | OCH₃ | OCH₂CF₃ | CH |
| CH₃ | CHFCH₃ | H | OCH₃ | C₂H₅ | CH |
| CH₃ | CHFCH₃ | H | OCH₃ | C₂H₅ | N |
| CH₃ | CHFCH₃ | H | OCH₃ | NHCH₃ | CH |
| CH₃ | CHFCH₃ | H | OCH₃ | NHCH₃ | N |
| CH₃ | CHFCH₃ | H | CH₃ | OC₂H₅ | CH |
| CH₃ | CHFCH₃ | H | OCH₃ | OC₂H₅ | CH |
| CH₃ | CHFCH₃ | H | CH₃ | OC₂H₅ | N |
| CH₃ | CHFCH₃ | H | OCH₃ | OC₂H₅ | N |
| CH₃ | CHFCH₃ | H | CH₃ | OCH₂CHF₂ | CH |
| CH₃ | CHFCH₃ | H | OCH₃ | OCH₂CHF₂ | CH |
| CH₃ | CHFCH₃ | H | CH₃ | OCH₂CHF₂ | N |
| CH₃ | CHFCH₃ | H | OCH₃ | OCH₂CHF₂ | N |
| CH₃ | CHFCH₃ | H | CH₃ | OCH₂CH₂F | CH |
| CH₃ | CHFCH₃ | H | OCH₃ | OCH₂CH₂F | CH |
| CH₃ | CHFCH₃ | H | CH₃ | OCH₂CF₃ | N |
| CH₃ | CHFCH₃ | CH₃ | OCH₃ | OCH₂CF₃ | N |
| CH₃ | CHFCH₃ | CH₃ | Cl | OCH₃ | CH |
| CH₃ | CHFCH₃ | H | Cl | N(CH₃)₂ | CH |
| CH₃ | CHFCH₃ | H | Cl | OC₂H₅ | CH |
| C₂H₅ | CHFCH₃ | H | CH₃ | CH₃ | CH |
| C₂H₅ | CHFCH₃ | H | OCH₃ | CH₃ | CH |
| C₂H₅ | CHFCH₃ | H | OCH₃ | OCH₃ | CH |
| C₂H₅ | CHFCH₃ | H | Cl | OCH₃ | CH |
| C₂H₅ | CHFCH₃ | H | CH₃ | CH₃ | N |
| C₂H₅ | CHFCH₃ | H | OCH₃ | CH₃ | N |
| C₂H₅ | CHFCH₃ | H | OCH₃ | OCH₃ | N |
| C₂H₅ | CHFCH₃ | H | Br | OCH₃ | CH |
| C₂H₅ | CHFCH₃ | H | OCH₃ | N(CH₃)₂ | CH |
| C₂H₅ | CHFCH₃ | H | OCH₃ | N(CH₃)₂ | N |
| C₂H₅ | CHFCH₃ | H | OCH₃ | NHCH₃ | N |
| C₂H₅ | CHFCH₃ | H | OCH₃ | C₂H₅ | CH |
| C₂H₅ | CHFCH₃ | H | OCH₃ | C₂H₅ | N |
| C₂H₅ | CHFCH₃ | H | CH₃ | OC₂H₅ | CH |
| C₂H₅ | CHFCH₃ | H | CH₃ | OC₂H₅ | N |
| C₂H₅ | CHFCH₃ | H | OCH₃ | OC₂H₅ | CH |
| C₂H₅ | CHFCH₃ | H | OCH₃ | OC₂H₅ | N |
| C₂H₅ | CHFCH₃ | H | CH₃ | OCH₂CF₃ | CH |
| C₂H₅ | CHFCH₃ | H | CH₃ | OCH₂CF₃ | N |
| C₂H₅ | CHFCH₃ | H | OCH₃ | OCH₂CF₃ | CH |
| C₂H₅ | CHFCH₃ | H | OCH₃ | OCH₂CF₃ | N |
| C₂H₅ | CHFCH₃ | H | OCH₃ | OCH₂CHF₂ | CH |
| C₂H₅ | CHFCH₃ | H | OCH₃ | OCH₂CHF₂ | N |

TABLE I-continued

| | | | | | |
|---|---|---|---|---|---|
| C₂H₅ | CHFCH₃ | H | CH₃ | OCH₂CHF₂ | N |
| C₂H₅ | CHFCH₃ | H | OCH₃ | OCH₂CH₂F | CH |
| C₂H₅ | CHFCH₃ | H | OCH₃ | OCH₂CH₂F | N |
| C₂H₅ | CHFCH₃ | CH₃ | OCH₃ | OCH₃ | CH |
| C₂H₅ | CHFCH₃ | CH₃ | CH₃ | OCH₃ | N |
| C₂H₅ | CHFCH₃ | CH₃ | OCH₃ | OCH₃ | N |
| n-C₃H₇ | CHFCH₃ | H | OCH₃ | OCH₃ | CH |
| n-C₃H₇ | CHFCH₃ | H | CH₃ | OCH₃ | N |
| CH(CH₃)₂ | CHFCH₃ | H | OCH₃ | CH₃ | CH |
| CH(CH₃)₂ | CHFCH₃ | H | OCH₃ | OCH₃ | CH |
| CH(CH₃)₂ | CHFCH₃ | H | Cl | OCH₃ | CH |
| CH(CH₃)₂ | CHFCH₃ | H | OCH₃ | CH₃ | N |
| CH(CH₃)₂ | CHFCH₃ | H | OCH₃ | OCH₃ | N |
| CH(CH₃)₂ | CHFCH₃ | H | OCH₃ | N(CH₃)₂ | N |
| CH₃ | CF₂CH₃ | H | CH₃ | CH₃ | CH |
| CH₃ | CF₂CH₃ | H | OCH₃ | CH₃ | CH |
| CH₃ | CF₂CH₃ | H | OCH₃ | OCH₃ | CH |
| CH₃ | CF₂CH₃ | H | Cl | OCH₃ | CH |
| CH₃ | CF₂CH₃ | H | OCH₃ | N(CH₃)₂ | CH |
| CH₃ | CF₂CH₃ | H | CH₃ | CH₃ | N |
| CH₃ | CF₂CH₃ | H | OCH₃ | CH₃ | N |
| CH₃ | CF₂CH₃ | H | OCH₃ | OCH₃ | N |
| CH₃ | CF₂CH₃ | H | OCH₃ | N(CH₃)₂ | N |
| CH₃ | CF₂CH₃ | H | OCH₃ | OCH₂CF₃ | N |
| CH₃ | CF₂CH₃ | CH₃ | OCH₃ | CH₃ | N |
| CH₃ | CF₂CH₃ | CH₃ | OCH₃ | OCH₃ | N |
| CH₃ | CF₂CH₃ | CH₃ | CH₃ | OCH₃ | CH |
| CH₃ | CF₂CH₃ | CH₃ | OCH₃ | OCH₃ | CH |
| CH₃ | CF₂CH₃ | H | Br | OCH₃ | CH |
| CH₃ | CF₂CH₃ | CH₃ | OCH₃ | N(CH₃)₂ | N |
| CH₃ | CF₂CH₃ | H | CH₃ | OCH₂CF₃ | N |
| CH₃ | CF₂CH₃ | H | CH₃ | OCH₂CF₃ | CH |
| CH₃ | CF₂CH₃ | H | OCH₃ | OCH₂CF₃ | CH |
| CH₃ | CF₂CH₃ | H | OCH₃ | C₂H₅ | CH |
| CH₃ | CF₂CH₃ | H | OCH₃ | C₂H₅ | N |
| CH₃ | CF₂CH₃ | H | OCH₃ | NHCH₃ | CH |
| CH₃ | CF₂CH₃ | H | OCH₃ | NHCH₃ | N |
| CH₃ | CF₂CH₃ | H | CH₃ | OC₂H₅ | CH |
| CH₃ | CF₂CH₃ | H | OCH₃ | OC₂H₅ | CH |
| CH₃ | CF₂CH₃ | H | CH₃ | OC₂H₅ | N |
| CH₃ | CF₂CH₃ | H | OCH₃ | OC₂H₅ | N |
| CH₃ | CF₂CH₃ | H | CH₃ | OCH₂CHF₂ | CH |
| CH₃ | CF₂CH₃ | H | OCH₃ | OCH₂CHF₂ | CH |
| CH₃ | CF₂CH₃ | H | CH₃ | OCH₂CHF₂ | N |
| CH₃ | CF₂CH₃ | H | OCH₃ | OCH₂CHF₂ | N |
| CH₃ | CF₂CH₃ | H | CH₃ | OCH₂CH₂F | CH |
| CH₃ | CF₂CH₃ | H | OCH₃ | OCH₂CH₂F | CH |
| CH₃ | CF₂CH₃ | H | CH₃ | OCH₂CF₃ | N |
| CH₃ | CF₂CH₃ | CH₃ | OCH₃ | OCH₂CF₃ | N |
| CH₃ | CF₂CH₃ | CH₃ | Cl | OCH₃ | CH |
| CH₃ | CF₂CH₃ | H | Cl | N(CH₃)₂ | CH |
| CH₃ | CF₂CH₃ | H | Cl | OC₂H₅ | CH |
| C₂H₅ | CF₂CH₃ | H | CH₃ | CH₃ | CH |
| C₂H₅ | CF₂CH₃ | H | OCH₃ | CH₃ | CH |
| C₂H₅ | CF₂CH₃ | H | OCH₃ | OCH₃ | CH |
| C₂H₅ | CF₂CH₃ | H | Cl | OCH₃ | CH |
| C₂H₅ | CF₂CH₃ | H | CH₃ | CH₃ | N |
| C₂H₅ | CF₂CH₃ | H | OCH₃ | CH₃ | N |
| C₂H₅ | CF₂CH₃ | H | OCH₃ | OCH₃ | N |
| C₂H₅ | CF₂CH₃ | H | Br | OCH₃ | CH |
| C₂H₅ | CF₂CH₃ | H | OCH₃ | N(CH₃)₂ | CH |
| C₂H₅ | CF₂CH₃ | H | OCH₃ | N(CH₃)₂ | N |
| C₂H₅ | CF₂CH₃ | H | OCH₃ | NHCH₃ | N |
| C₂H₅ | CF₂CH₃ | H | OCH₃ | C₂H₅ | CH |
| C₂H₅ | CF₂CH₃ | H | OCH₃ | C₂H₅ | N |
| C₂H₅ | CF₂CH₃ | H | CH₃ | OC₂H₅ | CH |
| C₂H₅ | CF₂CH₃ | H | CH₃ | OC₂H₅ | N |
| C₂H₅ | CF₂CH₃ | H | OCH₃ | OC₂H₅ | CH |
| C₂H₅ | CF₂CH₃ | H | OCH₃ | OC₂H₅ | N |
| C₂H₅ | CF₂CH₃ | H | CH₃ | OCH₂CF₃ | CH |
| C₂H₅ | CF₂CH₃ | H | CH₃ | OCH₂CF₃ | N |
| C₂H₅ | CF₂CH₃ | H | OCH₃ | OCH₂CF₃ | CH |
| C₂H₅ | CF₂CH₃ | H | OCH₃ | OCH₂CF₃ | N |
| C₂H₅ | CF₂CH₃ | H | OCH₃ | OCH₂CHF₂ | CH |
| C₂H₅ | CF₂CH₃ | H | OCH₃ | OCH₂CHF₂ | N |
| C₂H₅ | CF₂CH₃ | H | CH₃ | OCH₂CHF₂ | N |
| C₂H₅ | CF₂CH₃ | H | OCH₃ | OCH₂CH₂F | CH |
| C₂H₅ | CF₂CH₃ | H | OCH₃ | OCH₂CH₂F | N |
| C₂H₅ | CF₂CH₃ | CH₃ | OCH₃ | OCH₃ | CH |
| C₂H₅ | CF₂CH₃ | CH₃ | CH₃ | OCH₃ | N |
| C₂H₅ | CF₂CH₃ | CH₃ | OCH₃ | OCH₃ | N |
| n-C₃H₇ | CF₂CH₃ | H | OCH₃ | OCH₃ | CH |

TABLE I-continued

| | | | | | |
|---|---|---|---|---|---|
| n-C₃H₇ | CF₂CH₃ | H | CH₃ | OCH₃ | N |
| CH(CH₃)₂ | CF₂CH₃ | H | OCH₃ | CH₃ | CH |
| CH(CH₃)₂ | CF₂CH₃ | H | OCH₃ | OCH₃ | CH |
| CH(CH₃)₂ | CF₂CH₃ | H | Cl | OCH₃ | CH |
| CH(CH₃)₂ | CF₂CH₃ | H | OCH₃ | CH₃ | N |
| CH(CH₃)₂ | CF₂CH₃ | H | OCH₃ | OCH₃ | N |
| CH(CH₃)₂ | CF₂CH₃ | H | OCH₃ | N(CH₃)₂ | N |
| CH₃ | CH₂CH₂Cl | H | CH₃ | CH₃ | CH |
| CH₃ | CH₂CH₂Cl | H | OCH₃ | CH₃ | CH |
| CH₃ | CH₂CH₂Cl | H | OCH₃ | OCH₃ | CH |
| CH₃ | CH₂CH₂Cl | H | Cl | OCH₃ | CH |
| CH₃ | CH₂CH₂Cl | H | OCH₃ | N(CH₃)₂ | CH |
| CH₃ | CH₂CH₂Cl | H | CH₃ | CH₃ | N |
| CH₃ | CH₂CH₂Cl | H | OCH₃ | CH₃ | N |
| CH₃ | CH₂CH₂Cl | H | OCH₃ | OCH₃ | N |
| CH₃ | CH₂CH₂Cl | H | OCH₃ | N(CH₃)₂ | N |
| CH₃ | CH₂CH₂Cl | H | OCH₃ | OCH₂CF₃ | N |
| CH₃ | CH₂CH₂Cl | CH₃ | OCH₃ | CH₃ | N |
| CH₃ | CH₂CH₂Cl | CH₃ | OCH₃ | OCH₃ | N |
| CH₃ | CH₂CH₂Cl | CH₃ | CH₃ | OCH₃ | CH |
| CH₃ | CH₂CH₂Cl | CH₃ | OCH₃ | OCH₃ | CH |
| CH₃ | CH₂CH₂Cl | H | Br | OCH₃ | CH |
| CH₃ | CH₂CH₂Cl | CH₃ | OCH₃ | N(CH₃)₂ | N |
| CH₃ | CH₂CH₂Cl | H | CH₃ | OCH₂CF₃ | N |
| CH₃ | CH₂CH₂Cl | H | CH₃ | OCH₂CF₃ | CH |
| CH₃ | CH₂CH₂Cl | H | OCH₃ | OCH₂CF₃ | CH |
| CH₃ | CH₂CH₂Cl | H | OCH₃ | C₂H₅ | CH |
| CH₃ | CH₂CH₂Cl | H | OCH₃ | C₂H₅ | N |
| CH₃ | CH₂CH₂Cl | H | OCH₃ | NHCH₃ | CH |
| CH₃ | CH₂CH₂Cl | H | OCH₃ | NHCH₃ | N |
| CH₃ | CH₂CH₂Cl | H | CH₃ | OC₂H₅ | CH |
| CH₃ | CH₂CH₂Cl | H | OCH₃ | OC₂H₅ | CH |
| CH₃ | CH₂CH₂Cl | H | CH₃ | OC₂H₅ | N |
| CH₃ | CH₂CH₂Cl | H | OCH₃ | OC₂H₅ | N |
| CH₃ | CH₂CH₂Cl | H | CH₃ | OCH₂CHF₂ | CH |
| CH₃ | CH₂CH₂Cl | H | OCH₃ | OCH₂CHF₂ | CH |
| CH₃ | CH₂CH₂Cl | H | CH₃ | OCH₂CHF₂ | N |
| CH₃ | CH₂CH₂Cl | H | OCH₃ | OCH₂CHF₂ | N |
| CH₃ | CH₂CH₂Cl | H | CH₃ | OCH₂CH₂F | CH |
| CH₃ | CH₂CH₂Cl | H | OCH₃ | OCH₂CH₂F | CH |
| CH₃ | CH₂CH₂Cl | H | CH₃ | OCH₂CF₃ | N |
| CH₃ | CH₂CH₂Cl | CH₃ | OCH₃ | OCH₂CF₃ | N |
| CH₃ | CH₂CH₂Cl | CH₃ | Cl | OCH₃ | CH |
| CH₃ | CH₂CH₂Cl | H | Cl | N(CH₃)₂ | CH |
| CH₃ | CH₂CH₂Cl | H | Cl | OC₂H₅ | CH |
| C₂H₅ | CH₂CH₂Cl | H | CH₃ | CH₃ | CH |
| C₂H₅ | CH₂CH₂Cl | H | OCH₃ | CH₃ | CH |
| C₂H₅ | CH₂CH₂Cl | H | OCH₃ | OCH₃ | CH |
| C₂H₅ | CH₂CH₂Cl | H | Cl | OCH₃ | CH |
| C₂H₅ | CH₂CH₂Cl | H | CH₃ | CH₃ | N |
| C₂H₅ | CH₂CH₂Cl | H | OCH₃ | CH₃ | N |
| C₂H₅ | CH₂CH₂Cl | H | OCH₃ | OCH₃ | N |
| C₂H₅ | CH₂CH₂Cl | H | Br | OCH₃ | CH |
| C₂H₅ | CH₂CH₂Cl | H | OCH₃ | N(CH₃)₂ | CH |
| C₂H₅ | CH₂CH₂Cl | H | OCH₃ | N(CH₃)₂ | N |
| C₂H₅ | CH₂CH₂Cl | H | OCH₃ | NHCH₃ | N |
| C₂H₅ | CH₂CH₂Cl | H | OCH₃ | C₂H₅ | CH |
| C₂H₅ | CH₂CH₂Cl | H | OCH₃ | C₂H₅ | N |
| C₂H₅ | CH₂CH₂Cl | H | CH₃ | OC₂H₅ | CH |
| C₂H₅ | CH₂CH₂Cl | H | CH₃ | OC₂H₅ | N |
| C₂H₅ | CH₂CH₂Cl | H | OCH₃ | OC₂H₅ | CH |
| C₂H₅ | CH₂CH₂Cl | H | OCH₃ | OC₂H₅ | N |
| C₂H₅ | CH₂CH₂Cl | H | CH₃ | OCH₂CF₃ | CH |
| C₂H₅ | CH₂CH₂Cl | H | CH₃ | OCH₂CF₃ | N |
| C₂H₅ | CH₂CH₂Cl | H | OCH₃ | OCH₂CF₃ | CH |
| C₂H₅ | CH₂CH₂Cl | H | OCH₃ | OCH₂CF₃ | N |
| C₂H₅ | CH₂CH₂Cl | H | OCH₃ | OCH₂CHF₂ | CH |
| C₂H₅ | CH₂CH₂Cl | H | OCH₃ | OCH₂CHF₂ | N |
| C₂H₅ | CH₂CH₂Cl | H | CH₃ | OCH₂CHF₂ | N |
| C₂H₅ | CH₂CH₂Cl | H | OCH₃ | OCH₂CH₂F | CH |
| C₂H₅ | CH₂CH₂Cl | H | OCH₃ | OCH₂CH₂F | N |
| C₂H₅ | CH₂CH₂Cl | CH₃ | OCH₃ | OCH₃ | CH |
| C₂H₅ | CH₂CH₂Cl | CH₃ | CH₃ | OCH₃ | N |
| C₂H₅ | CH₂CH₂Cl | CH₃ | OCH₃ | OCH₃ | N |
| n-C₃H₇ | CH₂CH₂Cl | H | OCH₃ | OCH₃ | CH |
| n-C₃H₇ | CH₂CH₂Cl | H | CH₃ | OCH₃ | N |
| CH(CH₃)₂ | CH₂CH₂Cl | H | OCH₃ | CH₃ | CH |
| CH(CH₃)₂ | CH₂CH₂Cl | H | OCH₃ | OCH₃ | CH |
| CH(CH₃)₂ | CH₂CH₂Cl | H | Cl | OCH₃ | CH |
| CH(CH₃)₂ | CH₂CH₂Cl | H | OCH₃ | CH₃ | N |
| CH(CH₃)₂ | CH₂CH₂Cl | H | OCH₃ | OCH₃ | N |
| CH(CH₃)₂ | CH₂CH₂Cl | H | OCH₃ | N(CH₃)₂ | N |

TABLE I-continued

| | | | | | |
|---|---|---|---|---|---|
| CH$_3$ | CH$_2$CHCl$_2$ | H | CH$_3$ | CH$_3$ | CH |
| CH$_3$ | CH$_2$CHCl$_2$ | H | OCH$_3$ | CH$_3$ | CH |
| CH$_3$ | CH$_2$CHCl$_2$ | H | OCH$_3$ | OCH$_3$ | CH |
| CH$_3$ | CH$_2$CHCl$_2$ | H | Cl | OCH$_3$ | CH |
| CH$_3$ | CH$_2$CHCl$_2$ | H | OCH$_3$ | N(CH$_3$)$_2$ | CH |
| CH$_3$ | CH$_2$CHCl$_2$ | H | CH$_3$ | CH$_3$ | N |
| CH$_3$ | CH$_2$CHCl$_2$ | H | OCH$_3$ | CH$_3$ | N |
| CH$_3$ | CH$_2$CHCl$_2$ | H | OCH$_3$ | OCH$_3$ | N |
| CH$_3$ | CH$_2$CHCl$_2$ | H | OCH$_3$ | N(CH$_3$)$_2$ | N |
| CH$_3$ | CH$_2$CHCl$_2$ | H | OCH$_3$ | OCH$_2$CF$_3$ | N |
| CH$_3$ | CH$_2$CHCl$_2$ | CH$_3$ | OCH$_3$ | CH$_3$ | N |
| CH$_3$ | CH$_2$CHCl$_2$ | CH$_3$ | OCH$_3$ | OCH$_3$ | N |
| CH$_3$ | CH$_2$CHCl$_2$ | CH$_3$ | CH$_3$ | OCH$_3$ | CH |
| CH$_3$ | CH$_2$CHCl$_2$ | CH$_3$ | OCH$_3$ | OCH$_3$ | CH |
| CH$_3$ | CH$_2$CHCl$_2$ | H | Br | OCH$_3$ | CH |
| CH$_3$ | CH$_2$CHCl$_2$ | CH$_3$ | OCH$_3$ | N(CH$_3$)$_2$ | N |
| CH$_3$ | CH$_2$CHCl$_2$ | H | CH$_3$ | OCH$_2$CF$_3$ | N |
| CH$_3$ | CH$_2$CHCl$_2$ | H | CH$_3$ | OCH$_2$CF$_3$ | CH |
| CH$_3$ | CH$_2$CHCl$_2$ | H | OCH$_3$ | OCH$_2$CF$_3$ | CH |
| CH$_3$ | CH$_2$CHCl$_2$ | H | OCH$_3$ | C$_2$H$_5$ | CH |
| CH$_3$ | CH$_2$CHCl$_2$ | H | OCH$_3$ | C$_2$H$_5$ | N |
| CH$_3$ | CH$_2$CHCl$_2$ | H | OCH$_3$ | NHCH$_3$ | CH |
| CH$_3$ | CH$_2$CHCl$_2$ | H | OCH$_3$ | NHCH$_3$ | N |
| CH$_3$ | CH$_2$CHCl$_2$ | H | CH$_3$ | OC$_2$H$_5$ | CH |
| CH$_3$ | CH$_2$CHCl$_2$ | H | OCH$_3$ | OC$_2$H$_5$ | CH |
| CH$_3$ | CH$_2$CHCl$_2$ | H | CH$_3$ | OC$_2$H$_5$ | N |
| CH$_3$ | CH$_2$CHCl$_2$ | H | OCH$_3$ | OC$_2$H$_5$ | N |
| CH$_3$ | CH$_2$CHCl$_2$ | H | CH$_3$ | OCH$_2$CHF$_2$ | CH |
| CH$_3$ | CH$_2$CHCl$_2$ | H | OCH$_3$ | OCH$_2$CHF$_2$ | CH |
| CH$_3$ | CH$_2$CHCl$_2$ | H | CH$_3$ | OCH$_2$CHF$_2$ | N |
| CH$_3$ | CH$_2$CHCl$_2$ | H | OCH$_3$ | OCH$_2$CHF$_2$ | N |
| CH$_3$ | CH$_2$CHCl$_2$ | H | CH$_3$ | OCH$_2$CH$_2$F | CH |
| CH$_3$ | CH$_2$CHCl$_2$ | H | OCH$_3$ | OCH$_2$CH$_2$F | CH |
| CH$_3$ | CH$_2$CHCl$_2$ | H | CH$_3$ | OCH$_2$CF$_3$ | N |
| CH$_3$ | CH$_2$CHCl$_2$ | CH$_3$ | OCH$_3$ | OCH$_2$CF$_3$ | N |
| CH$_3$ | CH$_2$CHCl$_2$ | CH$_3$ | Cl | OCH$_3$ | CH |
| CH$_3$ | CH$_2$CHCl$_2$ | H | Cl | N(CH$_3$)$_2$ | CH |
| CH$_3$ | CH$_2$CHCl$_2$ | H | Cl | OC$_2$H$_5$ | CH |
| C$_2$H$_5$ | CH$_2$CHCl$_2$ | H | CH$_3$ | CH$_3$ | CH |
| C$_2$H$_5$ | CH$_2$CHCl$_2$ | H | OCH$_3$ | CH$_3$ | CH |
| C$_2$H$_5$ | CH$_2$CHCl$_2$ | H | OCH$_3$ | OCH$_3$ | CH |
| C$_2$H$_5$ | CH$_2$CHCl$_2$ | H | Cl | OCH$_3$ | CH |
| C$_2$H$_5$ | CH$_2$CHCl$_2$ | H | CH$_3$ | CH$_3$ | N |
| C$_2$H$_5$ | CH$_2$CHCl$_2$ | H | OCH$_3$ | CH$_3$ | N |
| C$_2$H$_5$ | CH$_2$CHCl$_2$ | H | OCH$_3$ | OCH$_3$ | N |
| C$_2$H$_5$ | CH$_2$CHCl$_2$ | H | Br | OCH$_3$ | CH |
| C$_2$H$_5$ | CH$_2$CHCl$_2$ | H | OCH$_3$ | N(CH$_3$)$_2$ | CH |
| C$_2$H$_5$ | CH$_2$CHCl$_2$ | H | OCH$_3$ | N(CH$_3$)$_2$ | N |
| C$_2$H$_5$ | CH$_2$CHCl$_2$ | H | OCH$_3$ | NHCH$_3$ | N |
| C$_2$H$_5$ | CH$_2$CHCl$_2$ | H | OCH$_3$ | C$_2$H$_5$ | CH |
| C$_2$H$_5$ | CH$_2$CHCl$_2$ | H | OCH$_3$ | C$_2$H$_5$ | N |
| C$_2$H$_5$ | CH$_2$CHCl$_2$ | H | CH$_3$ | OC$_2$H$_5$ | CH |
| C$_2$H$_5$ | CH$_2$CHCl$_2$ | H | CH$_3$ | OC$_2$H$_5$ | N |
| C$_2$H$_5$ | CH$_2$CHCl$_2$ | H | OCH$_3$ | OC$_2$H$_5$ | CH |
| C$_2$H$_5$ | CH$_2$CHCl$_2$ | H | OCH$_3$ | OC$_2$H$_5$ | N |
| C$_2$H$_5$ | CH$_2$CHCl$_2$ | H | CH$_3$ | OCH$_2$CF$_3$ | CH |
| C$_2$H$_5$ | CH$_2$CHCl$_2$ | H | CH$_3$ | OCH$_2$CF$_3$ | N |
| C$_2$H$_5$ | CH$_2$CHCl$_2$ | H | OCH$_3$ | OCH$_2$CF$_3$ | CH |
| C$_2$H$_5$ | CH$_2$CHCl$_2$ | H | OCH$_3$ | OCH$_2$CHF$_2$ | CH |
| C$_2$H$_5$ | CH$_2$CHCl$_2$ | H | OCH$_3$ | OCH$_2$CHF$_2$ | N |
| C$_2$H$_5$ | CH$_2$CHCl$_2$ | H | CH$_3$ | OCH$_2$CHF$_2$ | N |
| C$_2$H$_5$ | CH$_2$CHCl$_2$ | H | OCH$_3$ | OCH$_2$CH$_2$F | CH |
| C$_2$H$_5$ | CH$_2$CHCl$_2$ | H | OCH$_3$ | OCH$_2$CH$_2$F | N |
| C$_2$H$_5$ | CH$_2$CHCl$_2$ | CH$_3$ | OCH$_3$ | OCH$_3$ | CH |
| C$_2$H$_5$ | CH$_2$CHCl$_2$ | CH$_3$ | CH$_3$ | OCH$_3$ | N |
| C$_2$H$_5$ | CH$_2$CHCl$_2$ | CH$_3$ | OCH$_3$ | OCH$_3$ | N |
| n-C$_3$H$_7$ | CH$_2$CHCl$_2$ | H | OCH$_3$ | OCH$_3$ | CH |
| n-C$_3$H$_7$ | CH$_2$CHCl$_2$ | H | CH$_3$ | OCH$_3$ | N |
| CH(CH$_3$)$_2$ | CH$_2$CHCl$_2$ | H | OCH$_3$ | CH$_3$ | CH |
| CH(CH$_3$)$_2$ | CH$_2$CHCl$_2$ | H | OCH$_3$ | OCH$_3$ | CH |
| CH(CH$_3$)$_2$ | CH$_2$CHCl$_2$ | H | Cl | OCH$_3$ | CH |
| CH(CH$_3$)$_2$ | CH$_2$CHCl$_2$ | H | OCH$_3$ | CH$_3$ | N |
| CH(CH$_3$)$_2$ | CH$_2$CHCl$_2$ | H | OCH$_3$ | OCH$_3$ | N |
| CH(CH$_3$)$_2$ | CH$_2$CHCl$_2$ | H | OCH$_3$ | N(CH$_3$)$_2$ | N |
| CH$_3$ | CH$_2$CCl$_3$ | H | CH$_3$ | CH$_3$ | CH |
| CH$_3$ | CH$_2$CCl$_3$ | H | OCH$_3$ | CH$_3$ | CH |
| CH$_3$ | CH$_2$CCl$_3$ | H | OCH$_3$ | OCH$_3$ | CH |
| CH$_3$ | CH$_2$CCl$_3$ | H | Cl | OCH$_3$ | CH |
| CH$_3$ | CH$_2$CCl$_3$ | H | OCH$_3$ | N(CH$_3$)$_2$ | CH |
| CH$_3$ | CH$_2$CCl$_3$ | H | CH$_3$ | CH$_3$ | N |
| CH$_3$ | CH$_2$CCl$_3$ | H | OCH$_3$ | CH$_3$ | N |

TABLE I-continued

| | | | | | |
|---|---|---|---|---|---|
| CH$_3$ | CH$_2$CCl$_3$ | H | OCH$_3$ | OCH$_3$ | N |
| CH$_3$ | CH$_2$CCl$_3$ | H | OCH$_3$ | N(CH$_3$)$_2$ | N |
| CH$_3$ | CH$_2$CCl$_3$ | H | OCH$_3$ | OCH$_2$CF$_3$ | N |
| CH$_3$ | CH$_2$CCl$_3$ | CH$_3$ | OCH$_3$ | CH$_3$ | N |
| CH$_3$ | CH$_2$CCl$_3$ | CH$_3$ | OCH$_3$ | OCH$_3$ | N |
| CH$_3$ | CH$_2$CCl$_3$ | CH$_3$ | CH$_3$ | OCH$_3$ | CH |
| CH$_3$ | CH$_2$CCl$_3$ | CH$_3$ | OCH$_3$ | OCH$_3$ | CH |
| CH$_3$ | CH$_2$CCl$_3$ | H | Br | OCH$_3$ | CH |
| CH$_3$ | CH$_2$CCl$_3$ | CH$_3$ | OCH$_3$ | N(CH$_3$)$_2$ | N |
| CH$_3$ | CH$_2$CCl$_3$ | H | CH$_3$ | OCH$_2$CF$_3$ | N |
| CH$_3$ | CH$_2$CCl$_3$ | H | CH$_3$ | OCH$_2$CF$_3$ | CH |
| CH$_3$ | CH$_2$CCl$_3$ | H | OCH$_3$ | OCH$_2$CF$_3$ | CH |
| CH$_3$ | CH$_2$CCl$_3$ | H | OCH$_3$ | C$_2$H$_5$ | CH |
| CH$_3$ | CH$_2$CCl$_3$ | H | OCH$_3$ | C$_2$H$_5$ | N |
| CH$_3$ | CH$_2$CCl$_3$ | H | OCH$_3$ | NHCH$_3$ | CH |
| CH$_3$ | CH$_2$CCl$_3$ | H | OCH$_3$ | NHCH$_3$ | N |
| CH$_3$ | CH$_2$CCl$_3$ | H | CH$_3$ | OC$_2$H$_5$ | CH |
| CH$_3$ | CH$_2$CCl$_3$ | H | OCH$_3$ | OC$_2$H$_5$ | CH |
| CH$_3$ | CH$_2$CCl$_3$ | H | CH$_3$ | OC$_2$H$_5$ | N |
| CH$_3$ | CH$_2$CCl$_3$ | H | OCH$_3$ | OC$_2$H$_5$ | N |
| CH$_3$ | CH$_2$CCl$_3$ | H | CH$_3$ | OCH$_2$CHF$_2$ | CH |
| CH$_3$ | CH$_2$CCl$_3$ | H | OCH$_3$ | OCH$_2$CHF$_2$ | CH |
| CH$_3$ | CH$_2$CCl$_3$ | H | CH$_3$ | OCH$_2$CHF$_2$ | N |
| CH$_3$ | CH$_2$CCl$_3$ | H | OCH$_3$ | OCH$_2$CHF$_2$ | N |
| CH$_3$ | CH$_2$CCl$_3$ | H | CH$_3$ | OCH$_2$CH$_2$F | CH |
| CH$_3$ | CH$_2$CCl$_3$ | H | OCH$_3$ | OCH$_2$CH$_2$F | CH |
| CH$_3$ | CH$_2$CCl$_3$ | H | CH$_3$ | OCH$_2$CH$_2$F | N |
| CH$_3$ | CH$_2$CCl$_3$ | CH$_3$ | OCH$_3$ | OCH$_2$CH$_2$F | N |
| CH$_3$ | CH$_2$CCl$_3$ | CH$_3$ | Cl | OCH$_3$ | CH |
| CH$_3$ | CH$_2$CCl$_3$ | H | Cl | N(CH$_3$)$_2$ | CH |
| CH$_3$ | CH$_2$CCl$_3$ | H | Cl | OC$_2$H$_5$ | CH |
| C$_2$H$_5$ | CH$_2$CCl$_3$ | H | CH$_3$ | CH$_3$ | CH |
| C$_2$H$_5$ | CH$_2$CCl$_3$ | H | OCH$_3$ | CH$_3$ | CH |
| C$_2$H$_5$ | CH$_2$CCl$_3$ | H | OCH$_3$ | OCH$_3$ | CH |
| C$_2$H$_5$ | CH$_2$CCl$_3$ | H | Cl | OCH$_3$ | CH |
| C$_2$H$_5$ | CH$_2$CCl$_3$ | H | CH$_3$ | CH$_3$ | N |
| C$_2$H$_5$ | CH$_2$CCl$_3$ | H | OCH$_3$ | CH$_3$ | N |
| C$_2$H$_5$ | CH$_2$CCl$_3$ | H | OCH$_3$ | OCH$_3$ | N |
| C$_2$H$_5$ | CH$_2$CCl$_3$ | H | Br | OCH$_3$ | CH |
| C$_2$H$_5$ | CH$_2$CCl$_3$ | H | OCH$_3$ | N(CH$_3$)$_2$ | CH |
| C$_2$H$_5$ | CH$_2$CCl$_3$ | H | OCH$_3$ | N(CH$_3$)$_2$ | N |
| C$_2$H$_5$ | CH$_2$CCl$_3$ | H | OCH$_3$ | NHCH$_3$ | N |
| C$_2$H$_5$ | CH$_2$CCl$_3$ | H | OCH$_3$ | C$_2$H$_5$ | CH |
| C$_2$H$_5$ | CH$_2$CCl$_3$ | H | OCH$_3$ | C$_2$H$_5$ | N |
| C$_2$H$_5$ | CH$_2$CCl$_3$ | H | CH$_3$ | OC$_2$H$_5$ | CH |
| C$_2$H$_5$ | CH$_2$CCl$_3$ | H | CH$_3$ | OC$_2$H$_5$ | N |
| C$_2$H$_5$ | CH$_2$CCl$_3$ | H | OCH$_3$ | OC$_2$H$_5$ | CH |
| C$_2$H$_5$ | CH$_2$CCl$_3$ | H | OCH$_3$ | OC$_2$H$_5$ | N |
| C$_2$H$_5$ | CH$_2$CCl$_3$ | H | CH$_3$ | OCH$_2$CF$_3$ | CH |
| C$_2$H$_5$ | CH$_2$CCl$_3$ | H | CH$_3$ | OCH$_2$CF$_3$ | N |
| C$_2$H$_5$ | CH$_2$CCl$_3$ | H | OCH$_3$ | OCH$_2$CF$_3$ | CH |
| C$_2$H$_5$ | CH$_2$CCl$_3$ | H | OCH$_3$ | OCH$_2$CF$_3$ | N |
| C$_2$H$_5$ | CH$_2$CCl$_3$ | H | OCH$_3$ | OCH$_2$CHF$_2$ | CH |
| C$_2$H$_5$ | CH$_2$CCl$_3$ | H | OCH$_3$ | OCH$_2$CHF$_2$ | N |
| C$_2$H$_5$ | CH$_2$CCl$_3$ | H | CH$_3$ | OCH$_2$CHF$_2$ | N |
| C$_2$H$_5$ | CH$_2$CCl$_3$ | H | OCH$_3$ | OCH$_2$CH$_2$F | CH |
| C$_2$H$_5$ | CH$_2$CCl$_3$ | H | OCH$_3$ | OCH$_2$CH$_2$F | N |
| C$_2$H$_5$ | CH$_2$CCl$_3$ | CH$_3$ | OCH$_3$ | OCH$_3$ | CH |
| C$_2$H$_5$ | CH$_2$CCl$_3$ | CH$_3$ | CH$_3$ | OCH$_3$ | N |
| C$_2$H$_5$ | CH$_2$CCl$_3$ | CH$_3$ | OCH$_3$ | OCH$_3$ | N |
| n-C$_3$H$_7$ | CH$_2$CCl$_3$ | H | OCH$_3$ | OCH$_3$ | CH |
| n-C$_3$H$_7$ | CH$_2$CCl$_3$ | H | CH$_3$ | OCH$_3$ | N |
| CH(CH$_3$)$_2$ | CH$_2$CCl$_3$ | H | OCH$_3$ | CH$_3$ | CH |
| CH(CH$_3$)$_2$ | CH$_2$CCl$_3$ | H | OCH$_3$ | OCH$_3$ | CH |
| CH(CH$_3$)$_2$ | CH$_2$CCl$_3$ | H | Cl | OCH$_3$ | CH |
| CH(CH$_3$)$_2$ | CH$_2$CCl$_3$ | H | OCH$_3$ | CH$_3$ | N |
| CH(CH$_3$)$_2$ | CH$_2$CCl$_3$ | H | OCH$_3$ | OCH$_3$ | N |
| CH(CH$_3$)$_2$ | CH$_2$CCl$_3$ | H | OCH$_3$ | N(CH$_3$)$_2$ | N |
| CH$_3$ | CF$_2$CH$_2$F | H | CH$_3$ | OCH$_3$ | CH |
| CH$_3$ | CHFCH$_2$F | H | OCH$_3$ | OCH$_3$ | N |
| CH$_3$ | CHFCHF$_2$ | H | OCH$_3$ | CH$_3$ | N |
| CH$_3$ | CH$_2$CH$_2$CH$_2$F | H | OCH$_3$ | OCH$_3$ | CH |
| CH$_3$ | CH$_2$CH$_2$CHF$_2$ | H | CH$_3$ | OCH$_3$ | CH |
| CH$_3$ | CH$_2$CH$_2$CF$_3$ | H | OCH$_3$ | OCH$_3$ | N |
| CH$_3$ | CHFCH$_2$CH$_3$ | H | OCH$_3$ | CH$_3$ | N |
| CH$_3$ | CF$_2$CH$_2$CH$_3$ | H | OCH$_3$ | OCH$_3$ | CH |
| CH$_3$ | CF$_2$CH$_2$CH$_2$F | H | CH$_3$ | OCH$_3$ | CH |
| CH$_3$ | CF$_2$CHFCH$_3$ | H | OCH$_3$ | OCH$_3$ | N |
| CH$_3$ | CHFCHFCH$_2$F | H | OCH$_3$ | CH$_3$ | N |
| CH$_3$ | CF(CH$_3$)$_2$ | H | OCH$_3$ | OCH$_3$ | CH |
| CH$_3$ | CH(CH$_3$)CF$_3$ | H | CH$_3$ | OCH$_3$ | CH |
| CH$_3$ | CHClCH$_3$ | H | OCH$_3$ | OCH$_3$ | N |

TABLE I-continued

| R1 | R2 | R | X | Y | Z |
|---|---|---|---|---|---|
| CH3 | CCl2CH3 | H | OCH3 | CH3 | N |
| CH3 | CCl2CH2Cl | H | OCH3 | OCH3 | CH |
| CH3 | CHClCH2Cl | H | CH3 | OCH3 | CH |
| CH3 | CHClCHCl2 | H | OCH3 | OCH3 | N |
| CH3 | CH2CH2CH2Cl | H | OCH3 | CH3 | N |
| CH3 | CH2CH2CHCl2 | H | OCH3 | OCH3 | CH |
| CH3 | CH2CH2CCl3 | H | CH3 | OCH3 | CH |
| CH3 | CHClCH2CH3 | H | OCH3 | OCH3 | N |
| CH3 | CCl2CH2CH3 | H | OCH3 | CH3 | N |
| CH3 | CCl2CH2CH2Cl | H | OCH3 | OCH3 | CH |
| CH3 | CCl2CHClCH3 | H | CH3 | OCH3 | CH |
| CH3 | CHClCHClCH2Cl | H | OCH3 | OCH3 | N |
| CH3 | CCl(CH3)2 | H | OCH3 | CH3 | N |
| CH3 | CH(CH3)(CCl3) | H | OCH3 | OCH3 | CH |
| CH3 | (CH2)3CF3 | H | CH3 | OCH3 | CH |
| CH3 | (CH2)4CF3 | H | OCH3 | OCH3 | N |
| CH3 | (CH2)5CF3 | H | CH3 | OCH3 | N |
| CH3 | CHF(CH2)2CH3 | H | OCH3 | OCH3 | CH |
| CH3 | CHF(CH2)3CH3 | H | CH3 | OCH3 | CH |
| CH3 | CHF(CH2)4CH3 | H | OCH3 | OCH3 | N |
| CH3 | CF2(CH2)2CH3 | H | CH3 | OCH3 | N |
| CH3 | CF2(CH2)3CH3 | H | OCH3 | OCH3 | CH |
| CH3 | CF2(CH2)4CH3 | H | CH3 | OCH3 | CH |
| CH3 | CH2CHF(CH2)3CH3 | H | OCH3 | OCH3 | N |
| CH3 | (CH2)2CHF(CH2)2CH3 | H | CH3 | OCH3 | N |
| CH3 | (CH2)3CHFCH2CH3 | H | OCH3 | OCH3 | CH |
| CH3 | (CH2)4CHFCH3 | H | CH3 | OCH3 | CH |
| CH3 | (CH2)3CH(CH3)(CF3) | H | OCH3 | OCH3 | N |
| CH3 | (CH2)3CH2Cl | H | CH3 | OCH3 | N |
| CH3 | (CH2)4CH2Cl | H | OCH3 | OCH3 | CH |
| CH3 | (CH2)5CH2Cl | H | CH3 | OCH3 | CH |

TABLE I

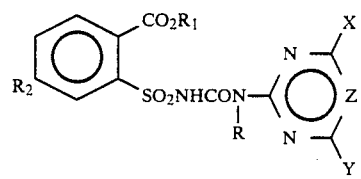

| R1 | R2 | R | X | Y | Z | m.p. (°C.) |
|---|---|---|---|---|---|---|
| CH3 | (CH2)3CHCl2 | H | OCH3 | OCH3 | N | |
| CH3 | (CH2)4CHCl2 | H | CH3 | OCH3 | N | |
| CH3 | (CH2)5CHCl2 | H | OCH3 | OCH3 | CH | |
| CH3 | (CH2)3CCl3 | H | CH3 | OCH3 | CH | |
| CH3 | (CH2)4CCl3 | H | OCH3 | OCH3 | N | |
| CH3 | (CH2)5CCl3 | H | CH3 | OCH3 | N | |
| CH3 | CH2(CHCl)2CH3 | H | OCH3 | OCH3 | CH | |
| CH3 | CH2CHClCH2CHClCH3 | H | CH3 | OCH3 | CH | |
| CH3 | CH2F | H | CH3 | CH3 | CH | |
| CH3 | CH2F | H | OCH3 | CH3 | CH | |
| CH3 | CH2F | H | OCH3 | OCH3 | CH | |
| CH3 | CH2F | H | Cl | OCH3 | CH | |
| CH3 | CH2F | H | OCH3 | N(CH3)2 | CH | |
| CH3 | CH2F | H | CH3 | CH3 | N | |
| CH3 | CH2F | H | OCH3 | CH3 | N | |
| CH3 | CH2F | H | OCH3 | OCH3 | N | |
| CH3 | CH2F | H | OCH3 | N(CH3)2 | N | |
| CH3 | CH2F | H | OCH3 | OCH2CF3 | N | |
| CH3 | CH2F | CH3 | OCH3 | CH3 | N | |
| CH3 | CH2F | CH3 | OCH3 | OCH3 | N | |
| CH3 | CH2F | CH3 | CH3 | OCH3 | CH | |
| CH3 | CH2F | CH3 | OCH3 | OCH3 | CH | |
| CH3 | CH2F | H | Br | OCH3 | CH | |
| CH3 | CH2F | CH3 | OCH3 | N(CH3)2 | N | |
| CH3 | CH2F | H | CH3 | OCH2CF3 | N | |
| CH3 | CH2F | H | CH3 | OCH2CF3 | CH | |
| CH3 | CH2F | H | OCH3 | OCH2CF3 | CH | |
| CH3 | CH2F | H | OCH3 | C2H5 | CH | |
| CH3 | CH2F | H | OCH3 | C2H5 | N | |
| CH3 | CH2F | H | OCH3 | NHCH3 | CH | |
| CH3 | CH2F | H | OCH3 | NHCH3 | N | |
| CH3 | CH2F | H | CH3 | OC2H5 | CH | |
| CH3 | CH2F | H | OCH3 | OC2H5 | CH | |
| CH3 | CH2F | H | CH3 | OC2H5 | N | |
| CH3 | CH2F | H | OCH3 | OC2H5 | N | |
| CH3 | CH2F | H | CH3 | OCH2CHF2 | CH | |

TABLE I-continued

| | | | | | |
|---|---|---|---|---|---|
| CH₃ | CH₂F | H | OCH₃ | OCH₂CHF₂ | CH |
| CH₃ | CH₂F | H | CH₃ | OCH₂CHF₂ | N |
| CH₃ | CH₂F | H | OCH₃ | OCH₂CHF₂ | N |
| CH₃ | CH₂F | H | CH₃ | OCH₂CH₂F | CH |
| CH₃ | CH₂F | H | OCH₃ | OCH₂CH₂F | CH |
| CH₃ | CH₂F | H | CH₃ | OCH₂CH₂F | N |
| CH₃ | CH₂F | CH₃ | OCH₃ | OCH₂CH₂F | N |
| CH₃ | CH₂F | CH₃ | Cl | OCH₃ | CH |
| CH₃ | CH₂F | H | Cl | N(CH₃)₂ | CH |
| CH₃ | CH₂F | H | Cl | OC₂H₅ | CH |
| C₂H₅ | CH₂F | H | CH₃ | CH₃ | CH |
| C₂H₅ | CH₂F | H | OCH₃ | CH₃ | CH |
| C₂H₅ | CH₂F | H | OCH₃ | OCH₃ | CH |
| C₂H₅ | CH₂F | H | Cl | OCH₃ | CH |
| C₂H₅ | CH₂F | H | CH₃ | CH₃ | N |
| C₂H₅ | CH₂F | H | OCH₃ | CH₃ | N |
| C₂H₅ | CH₂F | H | OCH₃ | OCH₃ | N |
| C₂H₅ | CH₂F | H | Br | OCH₃ | CH |
| C₂H₅ | CH₂F | H | OCH₃ | N(CH₃)₂ | CH |
| C₂H₅ | CH₂F | H | OCH₃ | N(CH₃)₂ | N |
| C₂H₅ | CH₂F | H | OCH₃ | NHCH₃ | N |
| C₂H₅ | CH₂F | H | OCH₃ | C₂H₅ | CH |
| C₂H₅ | CH₂F | H | OCH₃ | C₂H₅ | N |
| C₂H₅ | CH₂F | H | CH₃ | OC₂H₅ | CH |
| C₂H₅ | CH₂F | H | CH₃ | OC₂H₅ | N |
| C₂H₅ | CH₂F | H | OCH₃ | OC₂H₅ | CH |
| C₂H₅ | CH₂F | H | OCH₃ | OC₂H₅ | N |
| C₂H₅ | CH₂F | H | CH₃ | OCH₂CF₃ | CH |
| C₂H₅ | CH₂F | H | CH₃ | OCH₂CF₃ | N |
| C₂H₅ | CH₂F | H | OCH₃ | OCH₂CF₃ | CH |
| C₂H₅ | CH₂F | H | OCH₃ | OCH₂CF₃ | N |
| C₂H₅ | CH₂F | H | OCH₃ | OCH₂CHF₂ | CH |
| C₂H₅ | CH₂F | H | OCH₃ | OCH₂CHF₂ | N |
| C₂H₅ | CH₂F | H | CH₃ | OCH₂CHF₂ | N |
| C₂H₅ | CH₂F | H | OCH₃ | OCH₂CH₂F | CH |
| C₂H₅ | CH₂F | H | OCH₃ | OCH₂CH₂F | N |
| C₂H₅ | CH₂F | CH₃ | OCH₃ | OCH₃ | CH |
| C₂H₅ | CH₂F | CH₃ | CH₃ | OCH₃ | N |
| C₂H₅ | CH₂F | CH₃ | OCH₃ | OCH₃ | N |
| n-C₃H₇ | CH₂F | H | OCH₃ | OCH₃ | CH |
| n-C₃H₇ | CH₂F | H | CH₃ | OCH₃ | N |
| CH(CH₃)₂ | CH₂F | H | OCH₃ | CH₃ | CH |
| CH(CH₃)₂ | CH₂F | H | OCH₃ | OCH₃ | CH |
| CH(CH₃)₂ | CH₂F | H | Cl | OCH₃ | CH |
| CH(CH₃)₂ | CH₂F | H | OCH₃ | CH₃ | N |
| CH(CH₃)₂ | CH₂F | H | OCH₃ | OCH₃ | N |
| CH(CH₃)₂ | CH₂F | H | OCH₃ | N(CH₃)₂ | N |
| CH₃ | CHF₂ | H | CH₃ | CH₃ | CH |
| CH₃ | CHF₂ | H | OCH₃ | CH₃ | CH |
| CH₃ | CHF₂ | H | OCH₃ | OCH₃ | CH |
| CH₃ | CHF₂ | H | Cl | OCH₃ | CH |
| CH₃ | CHF₂ | H | OCH₃ | N(CH₃)₂ | CH |
| CH₃ | CHF₂ | H | CH₃ | CH₃ | N |
| CH₃ | CHF₂ | H | OCH₃ | CH₃ | N |
| CH₃ | CHF₂ | H | OCH₃ | OCH₃ | N |
| CH₃ | CHF₂ | H | OCH₃ | N(CH₃)₂ | N |
| CH₃ | CHF₂ | H | OCH₃ | OCH₂CF₃ | N |
| CH₃ | CHF₂ | CH₃ | OCH₃ | CH₃ | N |
| CH₃ | CHF₂ | CH₃ | OCH₃ | OCH₃ | N |
| CH₃ | CHF₂ | CH₃ | CH₃ | OCH₃ | CH |
| CH₃ | CHF₂ | CH₃ | OCH₃ | OCH₃ | CH |
| CH₃ | CHF₂ | H | Br | OCH₃ | CH |
| CH₃ | CHF₂ | CH₃ | OCH₃ | N(CH₃)₂ | N |
| CH₃ | CHF₂ | H | CH₃ | OCH₂CF₃ | N |
| CH₃ | CHF₂ | H | CH₃ | OCH₂CF₃ | CH |
| CH₃ | CHF₂ | H | OCH₃ | OCH₂CF₃ | CH |
| CH₃ | CHF₂ | H | OCH₃ | C₂H₅ | CH |
| CH₃ | CHF₂ | H | OCH₃ | C₂H₅ | N |
| CH₃ | CHF₂ | H | OCH₃ | NHCH₃ | CH |
| CH₃ | CHF₂ | H | OCH₃ | NHCH₃ | N |
| CH₃ | CHF₂ | H | CH₃ | OC₂H₅ | CH |
| CH₃ | CHF₂ | H | OCH₃ | OC₂H₅ | CH |
| CH₃ | CHF₂ | H | CH₃ | OC₂H₅ | N |
| CH₃ | CHF₂ | H | OCH₃ | OC₂H₅ | N |
| CH₃ | CHF₂ | H | CH₃ | OCH₂CHF₂ | CH |
| CH₃ | CHF₂ | H | OCH₃ | OCH₂CHF₂ | CH |
| CH₃ | CHF₂ | H | CH₃ | OCH₂CHF₂ | N |
| CH₃ | CHF₂ | H | OCH₃ | OCH₂CHF₂ | N |
| CH₃ | CHF₂ | H | CH₃ | OCH₂CH₂F | CH |
| CH₃ | CHF₂ | H | OCH₃ | OCH₂CH₂F | CH |
| CH₃ | CHF₂ | H | CH₃ | OCH₂CH₂F | N |
| CH₃ | CHF₂ | CH₃ | OCH₃ | OCH₂CH₂F | N |

TABLE I-continued

| | | | | | | |
|---|---|---|---|---|---|---|
| CH₃ | CHF₂ | CH₃ | Cl | OCH₃ | CH | |
| CH₃ | CHF₂ | H | Cl | N(CH₃)₂ | CH | |
| CH₃ | CHF₂ | H | Cl | OC₂H₅ | CH | |
| C₂H₅ | CHF₂ | H | CH₃ | CH₃ | CH | |
| C₂H₅ | CHF₂ | H | OCH₃ | CH₃ | CH | |
| C₂H₅ | CHF₂ | H | OCH₃ | OCH₃ | CH | |
| C₂H₅ | CHF₂ | H | Cl | OCH₃ | CH | |
| C₂H₅ | CHF₂ | H | CH₃ | CH₃ | N | |
| C₂H₅ | CHF₂ | H | OCH₃ | CH₃ | N | |
| C₂H₅ | CHF₂ | H | OCH₃ | OCH₃ | N | |
| C₂H₅ | CHF₂ | H | Br | OCH₃ | CH | |
| C₂H₅ | CHF₂ | H | OCH₃ | N(CH₃)₂ | CH | |
| C₂H₅ | CHF₂ | H | OCH₃ | N(CH₃)₂ | N | |
| C₂H₅ | CHF₂ | H | OCH₃ | NHCH₃ | N | |
| C₂H₅ | CHF₂ | H | OCH₃ | C₂H₅ | CH | |
| C₂H₅ | CHF₂ | H | OCH₃ | C₂H₅ | N | |
| C₂H₅ | CHF₂ | H | CH₃ | OC₂H₅ | CH | |
| C₂H₅ | CHF₂ | H | CH₃ | OC₂H₅ | N | |
| C₂H₅ | CHF₂ | H | OCH₃ | OC₂H₅ | CH | |
| C₂H₅ | CHF₂ | H | OCH₃ | OC₂H₅ | N | |
| C₂H₅ | CHF₂ | H | CH₃ | OCH₂CF₃ | CH | |
| C₂H₅ | CHF₂ | H | CH₃ | OCH₂CF₃ | N | |
| C₂H₅ | CHF₂ | H | OCH₃ | OCH₂CF₃ | CH | |
| C₂H₅ | CHF₂ | H | OCH₃ | OCH₂CF₃ | N | |
| C₂H₅ | CHF₂ | H | OCH₃ | OCH₂CHF₂ | CH | |
| C₂H₅ | CHF₂ | H | OCH₃ | OCH₂CHF₂ | N | |
| C₂H₅ | CHF₂ | H | CH₃ | OCH₂CHF₂ | N | |
| C₂H₅ | CHF₂ | H | OCH₃ | OCH₂CH₂F | CH | |
| C₂H₅ | CHF₂ | H | OCH₃ | OCH₂CH₂F | N | |
| C₂H₅ | CHF₂ | CH₃ | OCH₃ | OCH₃ | CH | |
| C₂H₅ | CHF₂ | CH₃ | CH₃ | OCH₃ | N | |
| C₂H₅ | CHF₂ | CH₃ | OCH₃ | OCH₃ | N | |
| n-C₃H₇ | CHF₂ | H | OCH₃ | OCH₃ | CH | |
| n-C₃H₇ | CHF₂ | H | CH₃ | OCH₃ | N | |
| CH(CH₃)₂ | CHF₂ | H | OCH₃ | CH₃ | CH | |
| CH(CH₃)₂ | CHF₂ | H | OCH₃ | OCH₃ | CH | |
| CH(CH₃)₂ | CHF₂ | H | Cl | OCH₃ | CH | |
| CH(CH₃)₂ | CHF₂ | H | OCH₃ | CH₃ | N | |
| CH(CH₃)₂ | CHF₂ | H | OCH₃ | OCH₃ | N | |
| CH(CH₃)₂ | CHF₂ | H | OCH₃ | N(CH₃)₂ | N | |
| CH₃ | CH₂OCH₃ | H | CH₃ | CH₃ | CH | 168–170 |
| CH₃ | CH₂OCH₃ | H | OCH₃ | CH₃ | CH | 147–148 (d) |
| CH₃ | CH₂OCH₃ | H | OCH₃ | OCH₃ | CH | 151–153 (d) |
| CH₃ | CH₂OCH₃ | H | Cl | OCH₃ | CH | 157–159 |
| CH₃ | CH₂OCH₃ | H | CH₃ | CH₃ | N | |
| CH₃ | CH₂OCH₃ | H | OCH₃ | CH₃ | N | 110–112 (d) |
| CH₃ | CH₂OCH₃ | H | OCH₃ | OCH₃ | N | 105–106 (d) |
| CH₃ | CH₂OCH₃ | H | OCH₃ | N(CH₃)₂ | N | |
| CH₃ | CH₂OCH₃ | H | OCH₃ | OCH₂CF₃ | N | |
| CH₃ | CH₂OCH₃ | CH₃ | OCH₃ | CH₃ | N | |
| CH₃ | CH₂OCH₃ | CH₃ | OCH₃ | OCH₃ | N | |
| CH₃ | CH₂OCH₃ | CH₃ | CH₃ | OCH₃ | CH | |
| CH₃ | CH₂OCH₃ | CH₃ | OCH₃ | OCH₃ | CH | |
| CH₃ | CH₂OCH₃ | H | Br | OCH₃ | CH | 145–146 |
| CH₃ | CH₂OCH₃ | H | OCH₃ | N(CH₃)₂ | CH | |
| CH₃ | CH₂OCH₃ | CH₃ | OCH₃ | N(CH₃)₂ | N | |
| CH₃ | CH₂OCH₃ | H | CH₃ | OCH₂CF₃ | CH | |
| CH₃ | CH₂OCH₃ | H | CH₃ | OCH₂CF₃ | CH | |
| CH₃ | CH₂OCH₃ | H | OCH₃ | OCH₂CF₃ | CH | |
| CH₃ | CH₂OCH₃ | H | OCH₃ | C₂H₅ | CH | |
| CH₃ | CH₂OCH₃ | H | OCH₃ | C₂H₅ | CH | |
| CH₃ | CH₂OCH₃ | H | OCH₃ | NHCH₃ | CH | |
| CH₃ | CH₂OCH₃ | H | OCH₃ | NHCH₃ | N | |
| CH₃ | CH₂OCH₃ | H | CH₃ | OC₂H₅ | CH | |
| CH₃ | CH₂OCH₃ | H | OCH₃ | OC₂H₅ | CH | |
| CH₃ | CH₂OCH₃ | H | CH₃ | OC₂H₅ | N | |
| CH₃ | CH₂OCH₃ | H | OCH₃ | OC₂H₅ | N | |
| CH₃ | CH₂OCH₃ | H | CH₃ | OCH₂CHF₂ | CH | |
| CH₃ | CH₂OCH₃ | H | OCH₃ | OCH₂CHF₂ | CH | |
| CH₃ | CH₂OCH₃ | H | CH₃ | OCH₂CHF₂ | N | |
| CH₃ | CH₂OCH₃ | H | OCH₃ | OCH₂CHF₂ | N | |
| CH₃ | CH₂OCH₃ | H | CH₃ | OCH₂CH₂F | CH | |
| CH₃ | CH₂OCH₃ | H | OCH₃ | OCH₂CH₂F | CH | |
| CH₃ | CH₂OCH₃ | H | CH₃ | OCH₂CH₂F | N | |
| CH₃ | CH₂OCH₃ | CH₃ | OCH₃ | OCH₂CH₂F | N | |
| CH₃ | CH₂OCH₃ | CH₃ | Cl | OCH₃ | CH | |
| CH₃ | CH₂OCH₃ | H | Cl | N(CH₃)₂ | CH | |
| CH₃ | CH₂OCH₃ | H | Cl | OC₂H₅ | CH | |
| C₂H₅ | CH₂OCH₃ | H | CH₃ | CH₃ | CH | 174–175 |
| C₂H₅ | CH₂OCH₃ | H | OCH₃ | CH₃ | CH | 146–147 |
| C₂H₅ | CH₂OCH₃ | H | OCH₃ | OCH₃ | CH | 77–79 |

TABLE I-continued

| | | | | | | |
|---|---|---|---|---|---|---|
| $C_2H_5$ | $CH_2OCH_3$ | H | Cl | $OCH_3$ | CH | |
| $C_2H_5$ | $CH_2OCH_3$ | H | $CH_3$ | $CH_3$ | N | |
| $C_2H_5$ | $CH_2OCH_3$ | H | $OCH_3$ | $CH_3$ | N | 134–136 |
| $C_2H_5$ | $CH_2OCH_3$ | H | $OCH_3$ | $OCH_3$ | N | 76–78 |
| $C_2H_5$ | $CH_2OCH_3$ | H | Br | $OCH_3$ | CH | |
| $C_2H_5$ | $CH_2OCH_3$ | H | $OCH_3$ | $N(CH_3)_2$ | CH | |
| $C_2H_5$ | $CH_2OCH_3$ | H | $OCH_3$ | $N(CH_3)_2$ | N | |
| $C_2H_5$ | $CH_2OCH_3$ | H | $OCH_3$ | $NHCH_3$ | N | |
| $C_2H_5$ | $CH_2OCH_3$ | H | $OCH_3$ | $C_2H_5$ | CH | |
| $C_2H_5$ | $CH_2OCH_3$ | H | $OCH_3$ | $C_2H_5$ | N | |
| $C_2H_5$ | $CH_2OCH_3$ | H | $CH_3$ | $OC_2H_5$ | CH | |
| $C_2H_5$ | $CH_2OCH_3$ | H | $CH_3$ | $OC_2H_5$ | N | |
| $C_2H_5$ | $CH_2OCH_3$ | H | $OCH_3$ | $OC_2H_5$ | CH | |
| $C_2H_5$ | $CH_2OCH_3$ | H | $OCH_3$ | $OC_2H_5$ | N | |
| $C_2H_5$ | $CH_2OCH_3$ | H | $CH_3$ | $OCH_2CF_3$ | CH | |
| $C_2H_5$ | $CH_2OCH_3$ | H | $CH_3$ | $OCH_2CF_3$ | N | |
| $C_2H_5$ | $CH_2OCH_3$ | H | $OCH_3$ | $OCH_2CF_3$ | CH | |
| $C_2H_5$ | $CH_2OCH_3$ | H | $OCH_3$ | $OCH_2CF_3$ | N | |
| $C_2H_5$ | $CH_2OCH_3$ | H | $OCH_3$ | $OCH_2CHF_2$ | CH | |
| $C_2H_5$ | $CH_2OCH_3$ | H | $OCH_3$ | $OCH_2CHF_2$ | N | |
| $C_2H_5$ | $CH_2OCH_3$ | H | $CH_3$ | $OCH_2CHF_2$ | N | |
| $C_2H_5$ | $CH_2OCH_3$ | H | $OCH_3$ | $OCH_2CH_2F$ | CH | |
| $C_2H_5$ | $CH_2OCH_3$ | H | $OCH_3$ | $OCH_2CH_2F$ | N | |
| $C_2H_5$ | $CH_2OCH_3$ | $CH_3$ | $OCH_3$ | $OCH_3$ | CH | |
| $C_2H_5$ | $CH_2OCH_3$ | $CH_3$ | $CH_3$ | $OCH_3$ | N | |
| $C_2H_5$ | $CH_2OCH_3$ | $CH_3$ | $OCH_3$ | $OCH_3$ | N | |
| n-$C_3H_7$ | $CH_2OCH_3$ | H | $OCH_3$ | $OCH_3$ | CH | |
| n-$C_3H_7$ | $CH_2OCH_3$ | H | $CH_3$ | $OCH_3$ | N | |
| $CH(CH_3)_2$ | $CH_2OCH_3$ | H | $OCH_3$ | $CH_3$ | CH | |
| $CH(CH_3)_2$ | $CH_2OCH_3$ | H | Cl | $OCH_3$ | CH | |
| $CH(CH_3)_2$ | $CH_2OCH_3$ | H | $OCH_3$ | $CH_3$ | N | |
| $CH(CH_3)_2$ | $CH_2OCH_3$ | H | $OCH_3$ | $OCH_3$ | N | |
| $CH(CH_3)_2$ | $CH_2OCH_3$ | H | $OCH_3$ | $N(CH_3)_2$ | N | |
| $CH_3$ | $CH_2CH_2OCH_3$ | H | $CH_3$ | $CH_3$ | CH | |
| $CH_3$ | $CH_2CH_2OCH_3$ | H | $OCH_3$ | $CH_3$ | CH | |
| $CH_3$ | $CH_2CH_2OCH_3$ | H | $OCH_3$ | $OCH_3$ | CH | |
| $CH_3$ | $CH_2CH_2OCH_3$ | H | Cl | $OCH_3$ | CH | |
| $CH_3$ | $CH_2CH_2OCH_3$ | H | $OCH_3$ | $N(CH_3)_2$ | CH | |
| $CH_3$ | $CH_2CH_2OCH_3$ | H | $CH_3$ | $CH_3$ | N | |
| $CH_3$ | $CH_2CH_2OCH_3$ | H | $OCH_3$ | $CH_3$ | N | 136 (d) |
| $CH_3$ | $CH_2CH_2OCH_3$ | H | $OCH_3$ | $OCH_3$ | N | |
| $CH_3$ | $CH_2CH_2OCH_3$ | H | $OCH_3$ | $N(CH_3)_2$ | N | |
| $CH_3$ | $CH_2CH_2OCH_3$ | H | $OCH_3$ | $OCH_2CF_3$ | N | |
| $CH_3$ | $CH_2CH_2OCH_3$ | $CH_3$ | $OCH_3$ | $CH_3$ | N | |
| $CH_3$ | $CH_2CH_2OCH_3$ | $CH_3$ | $OCH_3$ | $OCH_3$ | N | |
| $CH_3$ | $CH_2CH_2OCH_3$ | $CH_3$ | $CH_3$ | $OCH_3$ | CH | |
| $CH_3$ | $CH_2CH_2OCH_3$ | $CH_3$ | $OCH_3$ | $OCH_3$ | CH | |
| $CH_3$ | $CH_2CH_2OCH_3$ | H | Br | $OCH_3$ | CH | |
| $CH_3$ | $CH_2CH_2OCH_3$ | $CH_3$ | $OCH_3$ | $N(CH_3)_2$ | N | |
| $CH_3$ | $CH_2CH_2OCH_3$ | H | $CH_3$ | $OCH_2CF_3$ | N | |
| $CH_3$ | $CH_2CH_2OCH_3$ | H | $CH_3$ | $OCH_2CF_3$ | CH | |
| $CH_3$ | $CH_2CH_2OCH_3$ | H | $OCH_3$ | $OCH_2CF_3$ | CH | |
| $CH_3$ | $CH_2CH_2OCH_3$ | H | $OCH_3$ | $C_2H_5$ | CH | |
| $CH_3$ | $CH_2CH_2OCH_3$ | H | $OCH_3$ | $C_2H_5$ | N | |
| $CH_3$ | $CH_2CH_2OCH_3$ | H | $OCH_3$ | $NHCH_3$ | CH | |
| $CH_3$ | $CH_2CH_2OCH_3$ | H | $OCH_3$ | $NHCH_3$ | N | |
| $CH_3$ | $CH_2CH_2OCH_3$ | H | $CH_3$ | $OC_2H_5$ | CH | |
| $CH_3$ | $CH_2CH_2OCH_3$ | H | $OCH_3$ | $OC_2H_5$ | CH | |
| $CH_3$ | $CH_2CH_2OCH_3$ | H | $CH_3$ | $OC_2H_5$ | N | |
| $CH_3$ | $CH_2CH_2OCH_3$ | H | $OCH_3$ | $OC_2H_5$ | N | |
| $CH_3$ | $CH_2CH_2OCH_3$ | H | $CH_3$ | $OCH_2CHF_2$ | CH | |
| $CH_3$ | $CH_2CH_2OCH_3$ | H | $OCH_3$ | $OCH_2CHF_2$ | CH | |
| $CH_3$ | $CH_2CH_2OCH_3$ | H | $CH_3$ | $OCH_2CHF_2$ | N | |
| $CH_3$ | $CH_2CH_2OCH_3$ | H | $OCH_3$ | $OCH_2CHF_2$ | N | |
| $CH_3$ | $CH_2CH_2OCH_3$ | H | $CH_3$ | $OCH_2CH_2F$ | CH | |
| $CH_3$ | $CH_2CH_2OCH_3$ | H | $OCH_3$ | $OCH_2CH_2F$ | CH | |
| $CH_3$ | $CH_2CH_2OCH_3$ | H | $CH_3$ | $OCH_2CF_N$ | | |
| $CH_3$ | $CH_2CH_2OCH_3$ | $CH_3$ | $OCH_3$ | $OCH_2CF_3$ | N | |
| $CH_3$ | $CH_2CH_2OCH_3$ | $CH_3$ | Cl | $OCH_3$ | CH | |
| $CH_3$ | $CH_2CH_2OCH_3$ | H | Cl | $N(CH_3)_2$ | CH | |
| $C_2H_5$ | $CH_2CH_2OCH_3$ | H | Cl | $OC_2H_5$ | CH | |
| $C_2H_5$ | $CH_2CH_2OCH_3$ | H | $CH_3$ | $CH_3$ | CH | |
| $C_2H_5$ | $CH_2CH_2OCH_3$ | H | $OCH_3$ | $CH_3$ | CH | |
| $C_2H_5$ | $CH_2CH_2OCH_3$ | H | $OCH_3$ | $OCH_3$ | CH | |
| $C_2H_5$ | $CH_2CH_2OCH_3$ | H | Cl | $OCH_3$ | CH | |
| $C_2H_5$ | $CH_2CH_2OCH_3$ | H | $CH_3$ | $CH_3$ | N | |
| $C_2H_5$ | $CH_2CH_2OCH_3$ | H | $OCH_3$ | $CH_3$ | N | |
| $C_2H_5$ | $CH_2CH_2OCH_3$ | H | $OCH_3$ | $OCH_3$ | N | |
| $C_2H_5$ | $CH_2CH_2OCH_3$ | H | Br | $OCH_3$ | CH | |
| $C_2H_5$ | $CH_2CH_2OCH_3$ | H | $OCH_3$ | $N(CH_3)_2$ | CH | |
| $C_2H_5$ | $CH_2CH_2OCH_3$ | H | $OCH_3$ | $N(CH_3)_2$ | N | |

TABLE I-continued

| | | | | | |
|---|---|---|---|---|---|
| $C_2H_5$ | $CH_2CH_2OCH_3$ | H | $OCH_3$ | $NHCH_3$ | N |
| $C_2H_5$ | $CH_2CH_2OCH_3$ | H | $OCH_3$ | $C_2H_5$ | CH |
| $C_2H_5$ | $CH_2CH_2OCH_3$ | H | $OCH_3$ | $C_2H_5$ | N |
| $C_2H_5$ | $CH_2CH_2OCH_3$ | H | $CH_3$ | $OC_2H_5$ | CH |
| $C_2H_5$ | $CH_2CH_2OCH_3$ | H | $CH_3$ | $OC_2H_5$ | N |
| $C_2H_5$ | $CH_2CH_2OCH_3$ | H | $OCH_3$ | $OC_2H_5$ | CH |
| $C_2H_5$ | $CH_2CH_2OCH_3$ | H | $OCH_3$ | $OC_2H_5$ | N |
| $C_2H_5$ | $CH_2CH_2OCH_3$ | H | $CH_3$ | $OCH_2CF_3$ | CH |
| $C_2H_5$ | $CH_2CH_2OCH_3$ | H | $CH_3$ | $OCH_2CF_3$ | N |
| $C_2H_5$ | $CH_2CH_2OCH_3$ | H | $OCH_3$ | $OCH_2CF_3$ | CH |
| $C_2H_5$ | $CH_2CH_2OCH_3$ | H | $OCH_3$ | $OCH_2CF_3$ | N |
| $C_2H_5$ | $CH_2CH_2OCH_3$ | H | $OCH_3$ | $OCH_2CHF_2$ | CH |
| $C_2H_5$ | $CH_2CH_2OCH_3$ | H | $OCH_3$ | $OCH_2CHF_2$ | N |
| $C_2H_5$ | $CH_2CH_2OCH_3$ | H | $CH_3$ | $OCH_2CHF_2$ | N |
| $C_2H_5$ | $CH_2CH_2OCH_3$ | H | $OCH_3$ | $OCH_2CH_2F$ | CH |
| $C_2H_5$ | $CH_2CH_2OCH_3$ | H | $OCH_3$ | $OCH_2CH_2F$ | N |
| $C_2H_5$ | $CH_2CH_2OCH_3$ | $CH_3$ | $OCH_3$ | $OCH_3$ | CH |
| $C_2H_5$ | $CH_2CH_2OCH_3$ | $CH_3$ | $CH_3$ | $OCH_3$ | N |
| $C_2H_5$ | $CH_2CH_2OCH_3$ | $CH_3$ | $OCH_3$ | $OCH_3$ | N |
| n-$C_3H_7$ | $CH_2CH_2OCH_3$ | H | $OCH_3$ | $OCH_3$ | CH |
| n-$C_3H_7$ | $CH_2CH_2OCH_3$ | H | $CH_3$ | $OCH_3$ | N |
| $CH(CH_3)_2$ | $CH_2CH_2OCH_3$ | H | $OCH_3$ | $CH_3$ | CH |
| $CH(CH_3)_2$ | $CH_2CH_2OCH_3$ | H | $OCH_3$ | $OCH_3$ | CH |
| $CH(CH_3)_2$ | $CH_2CH_2OCH_3$ | H | Cl | $OCH_3$ | CH |
| $CH(CH_3)_2$ | $CH_2CH_2OCH_3$ | H | $OCH_3$ | $CH_3$ | N |
| $CH(CH_3)_2$ | $CH_2CH_2OCH_3$ | H | $OCH_3$ | $OCH_3$ | N |
| $CH(CH_3)_2$ | $CH_2CH_2OCH_3$ | H | $OCH_3$ | $N(CH_3)_2$ | N |
| $CH_3$ | $CH(CH_3)(OCH_3)$ | H | $OCH_3$ | $CH_3$ | CH |
| $CH_3$ | $CH(CH_3)(OCH_3)$ | H | $OCH_3$ | $OCH_3$ | CH |
| $CH_3$ | $CH(CH_3)(OCH_3)$ | H | $OCH_3$ | Cl | CH |
| $CH_3$ | $CH(CH_3)(OCH_3)$ | H | $OCH_3$ | $CH_3$ | N |
| $CH_3$ | $CH(CH_3)(OCH_3)$ | H | $OCH_3$ | $OCH_3$ | N |
| $C_2H_5$ | $CH(CH_3)(OCH_3)$ | H | $OCH_3$ | $CH_3$ | CH |
| $C_2H_5$ | $CH(CH_3)(OCH_3)$ | H | $OCH_3$ | $OCH_3$ | CH |
| $C_2H_5$ | $CH(CH_3)(OCH_3)$ | H | $OCH_3$ | Cl | CH |
| $C_2H_5$ | $CH(CH_3)(OCH_3)$ | H | $OCH_3$ | $CH_3$ | N |
| $C_2H_5$ | $CH(CH_3)(OCH_3)$ | H | $OCH_3$ | $OCH_3$ | N |
| $CH_3$ | $(CH_2)_3OCH_3$ | H | $CH_3$ | $CH_3$ | CH |
| $CH_3$ | $(CH_2)_3OCH_3$ | H | $OCH_3$ | $CH_3$ | CH |
| $CH_3$ | $(CH_2)_3OCH_3$ | H | $OCH_3$ | $OCH_3$ | CH |
| $CH_3$ | $(CH_2)_3OCH_3$ | H | Cl | $OCH_3$ | CH |
| $CH_3$ | $(CH_2)_3OCH_3$ | H | | | |
| $CH_3$ | $(CH_3$ | $CH_3$ | N | | |
| $CH_3$ | $(CH_2)_3OCH_3$ | H | $OCH_3$ | $OCH_3$ | N |
| $CH_3$ | $(CH_2)_3OCH_3$ | H | $OCH_3$ | $N(CH_3)_2$ | CH |
| $CH_3$ | $(CH_2)_3OCH_3$ | H | $OCH_3$ | $N(CH_3)_2$ | N |
| $CH_3$ | $(CH_2)_3OCH_3$ | H | $OCH_3$ | $OCH_2CF_3$ | N |
| $CH_3$ | $(CH_2)_3OCH_3$ | $CH_3$ | $OCH_3$ | $CH_3$ | N |
| $CH_3$ | $(CH_2)_3OCH_3$ | $CH_3$ | $OCH_3$ | $OCH_3$ | N |
| $CH_3$ | $(CH_2)_3OCH_3$ | $CH_3$ | $CH_3$ | $OCH_3$ | CH |
| $CH_3$ | $(CH_2)_3OCH_3$ | $CH_3$ | $OCH_3$ | $OCH_3$ | CH |
| $CH_3$ | $(CH_2)_3OCH_3$ | H | Br | $OCH_3$ | CH |
| $CH_3$ | $(CH_2)_3OCH_3$ | H | $CH_3$ | $OCH_2CF_3$ | N |
| $CH_3$ | $(CH_2)_3OCH_3$ | H | $CH_3$ | $OCH_2CF_3$ | CH |
| $CH_3$ | $(CH_2)_3OCH_3$ | H | $OCH_3$ | $OCH_2CF_3$ | CH |
| $CH_3$ | $(CH_2)_3OCH_3$ | H | $OCH_3$ | $NHCH_3$ | N |
| $C_2H_5$ | $(CH_2)_3OCH_3$ | H | $CH_3$ | $CH_3$ | CH |
| $C_2H_5$ | $(CH_2)_3OCH_3$ | H | $OCH_3$ | $CH_3$ | CH |
| $C_2H_5$ | $(CH_2)_3OCH_3$ | H | $OCH_3$ | $OCH_3$ | CH |
| $C_2H_5$ | $(CH_2)_3OCH_3$ | H | Cl | $OCH_3$ | CH |
| $C_2H_5$ | $(CH_2)_3OCH_3$ | H | $OCH_3$ | $CH_3$ | N |
| $C_2H_5$ | $(CH_2)_3OCH_3$ | H | $OCH_3$ | $N(CH_3)_2$ | CH |
| $CH(CH_3)_2$ | $(CH_2)_3OCH_3$ | H | $OCH_3$ | $CH_3$ | CH |
| $CH(CH_3)_2$ | $(CH_2)_3OCH_3$ | H | $OCH_3$ | $OCH_3$ | CH |
| $CH(CH_3)_2$ | $(CH_2)_3OCH_3$ | H | Cl | $OCH_3$ | CH |
| $CH(CH_3)_2$ | $(CH_2)_3OCH_3$ | H | $OCH_3$ | $CH_3$ | N |
| $CH(CH_3)_2$ | $(CH_2)_3OCH_3$ | H | $OCH_3$ | $OCH_3$ | N |
| $CH_3$ | $(CH_2)_4OCH_3$ | H | $CH_3$ | $CH_3$ | CH |
| $CH_3$ | $(CH_2)_4OCH_3$ | H | $OCH_3$ | $OCH_3$ | CH |
| $CH_3$ | $(CH_2)_4OCH_3$ | H | Cl | $OCH_3$ | CH |
| $CH_3$ | $(CH_2)_4OCH_3$ | H | $CH_3$ | $CH_3$ | N |
| $CH_3$ | $(CH_2)_4OCH_3$ | H | $OCH_3$ | $CH_3$ | N |
| $CH_3$ | $(CH_2)_4OCH_3$ | H | $OCH_3$ | $OCH_3$ | N |
| $CH_3$ | $(CH_2)_4OCH_3$ | H | $OCH_3$ | $N(CH_3)_2$ | CH |
| $CH_3$ | $(CH_2)_4OCH_3$ | H | $OCH_3$ | $N(CH_3)_2$ | N |
| $CH_3$ | $(CH_2)_4OCH_3$ | H | $OCH_3$ | $OCH_2CF_3$ | N |
| $CH_3$ | $(CH_2)_4OCH_3$ | $CH_3$ | $OCH_3$ | $CH_3$ | N |
| $CH_3$ | $(CH_2)_4OCH_3$ | $CH_3$ | $OCH_3$ | $OCH_3$ | N |
| $CH_3$ | $(CH_2)_4OCH_3$ | $CH_3$ | $CH_3$ | $OCH_3$ | CH |
| $CH_3$ | $(CH_2)_4OCH_3$ | $CH_3$ | $OCH_3$ | $OCH_3$ | CH |

TABLE I-continued

| | | | | | |
|---|---|---|---|---|---|
| CH₃ | (CH₂)₄OCH₃ | H | Br | OCH₃ | CH |
| CH₃ | (CH₂)₄OCH₃ | H | CH₃ | OCH₂CF₃ | N |
| CH₃ | (CH₂)₄OCH₃ | H | CH₃ | OCH₂CF₃ | CH |
| CH₃ | (CH₂)₄OCH₃ | H | OCH₃ | NHCH₃ | N |
| C₂H₅ | (CH₂)₄OCH₃ | H | CH₃ | CH₃ | CH |
| C₂H₅ | (CH₂)₄OCH₃ | H | OCH₃ | CH₃ | CH |
| C₂H₅ | (CH₂)₄OCH₃ | H | OCH₃ | OCH₃ | CH |
| C₂H₅ | (CH₂)₄OCH₃ | H | Cl | OCH₃ | CH |
| C₂H₅ | (CH₂)₄OCH₃ | H | OCH₃ | CH₃ | N |
| C₂H₅ | (CH₂)₄OCH₃ | H | OCH₃ | N(CH₃)₂ | CH |
| CH(CH₃)₂ | (CH₂)₄OCH₃ | H | OCH₃ | CH₃ | CH |
| CH(CH₃)₂ | (CH₂)₄OCH₃ | H | OCH₃ | OCH₃ | CH |
| CH(CH₃)₂ | (CH₂)₄OCH₃ | H | Cl | OCH₃ | CH |
| CH(CH₃)₂ | (CH₂)₄OCH₃ | H | OCH₃ | CH₃ | N |
| CH(CH₃)₂ | (CH₂)₄OCH₃ | H | OCH₃ | OCH₃ | N |
| CH₃ | CH₂OC₂H₅ | H | CH₃ | CH₃ | CH |
| CH₃ | CH₂OC₂H₅ | H | OCH₃ | CH₃ | CH |
| CH₃ | CH₂OC₂H₅ | H | OCH₃ | OCH₃ | CH |
| CH₃ | CH₂OC₂H₅ | H | Cl | OCH₃ | CH |
| CH₃ | CH₂OC₂H₅ | H | CH₃ | CH₃ | N |
| CH₃ | CH₂OC₂H₅ | H | OCH₃ | CH₃ | N |
| CH₃ | CH₂OC₂H₅ | H | OCH₃ | OCH₃ | N |
| CH₃ | CH₂OC₂H₅ | H | OCH₃ | N(CH₃)₂ | CH |
| CH₃ | CH₂OC₂H₅ | H | OCH₃ | N(CH₃)₂ | N |
| CH₃ | CH₂OC₂H₅ | H | OCH₃ | OCH₂CF₃ | N |
| CH₃ | CH₂OC₂H₅ | CH₃ | OCH₃ | CH₃ | N |
| CH₃ | CH₂OC₂H₅ | CH₃ | OCH₃ | OCH₃ | N |
| CH₃ | CH₂OC₂H₅ | CH₃ | CH₃ | OCH₃ | CH |
| CH₃ | CH₂OC₂H₅ | CH₃ | OCH₃ | OCH₃ | CH |
| CH₃ | CH₂OC₂H₅ | H | Br | OCH₃ | CH |
| CH₃ | CH₂OC₂H₅ | H | CH₃ | OCH₂CF₃ | N |
| CH₃ | CH₂OC₂H₅ | H | CH₃ | OCH₂CF₃ | CH |
| CH₃ | CH₂OC₂H₅ | H | OCH₃ | OCH₂CF₃ | CH |
| CH₃ | CH₂OC₂H₅ | H | OCH₃ | NHCH₃ | N |
| C₂H₅ | CH₂OC₂H₅ | H | CH₃ | CH₃ | CH |
| C₂H₅ | CH₂OC₂H₅ | H | OCH₃ | CH₃ | CH |
| C₂H₅ | CH₂OC₂H₅ | H | OCH₃ | OCH₃ | CH |
| C₂H₅ | CH₂OC₂H₅ | H | Cl | OCH₃ | CH |
| C₂H₅ | CH₂OC₂H₅ | H | OCH₃ | CH₃ | N |
| C₂H₅ | CH₂OC₂H₅ | H | OCH₃ | N(CH₃)₂ | CH |
| CH(CH₃)₂ | CH₂OC₂H₅ | H | OCH₃ | CH₃ | CH |
| CH(CH₃)₂ | CH₂OC₂H₅ | H | OCH₃ | OCH₃ | CH |
| CH(CH₃)₂ | CH₂OC₂H₅ | H | Cl | OCH₃ | CH |
| CH(CH₃)₂ | CH₂OC₂H₅ | H | OCH₃ | CH₃ | N |
| CH(CH₃)₂ | CH₂OC₂H₅ | H | OCH₃ | OCH₃ | N |
| CH₃ | (CH₂)₂OC₂H₅ | H | CH₃ | CH₃ | CH |
| CH₃ | (CH₂)₂OC₂H₅ | H | OCH₃ | CH₃ | CH |
| CH₃ | (CH₂)₂OC₂H₅ | H | OCH₃ | OCH₃ | CH |
| CH₃ | (CH₂)₂OC₂H₅ | H | Cl | OCH₃ | CH |
| CH₃ | (CH₂)₂OC₂H₅ | H | CH₃ | CH₃ | N |
| CH₃ | (CH₂)₂OC₂H₅ | H | OCH₃ | CH₃ | N |
| CH₃ | (CH₂)₂OC₂H₅ | H | OCH₃ | OCH₃ | N |
| CH₃ | (CH₂)₂OC₂H₅ | H | OCH₃ | N(CH₃)₂ | CH |
| CH₃ | (CH₂)₂OC₂H₅ | H | OCH₃ | N(CH₃)₂ | N |
| CH₃ | (CH₂)₂OC₂H₅ | H | OCH₃ | OCH₂CF₃ | N |
| CH₃ | (CH₂)₂OC₂H₅ | CH₃ | OCH₃ | CH₃ | N |
| CH₃ | (CH₂)₂OC₂H₅ | CH₃ | OCH₃ | OCH₃ | N |
| CH₃ | (CH₂)₂OC₂H₅ | CH₃ | CH₃ | OCH₃ | CH |
| CH₃ | (CH₂)₂OC₂H₅ | CH₃ | OCH₃ | OCH₃ | CH |
| CH₃ | (CH₂)₂OC₂H₅ | H | Br | OCH₃ | CH |
| CH₃ | (CH₂)₂OC₂H₅ | H | CH₃ | OCH₂CF₃ | N |
| CH₃ | (CH₂)₂OC₂H₅ | H | CH₃ | OCH₂CF₃ | CH |
| CH₃ | (CH₂)₂OC₂H₅ | H | OCH₃ | OCH₂CF₃ | CH |
| CH₃ | (CH₂)₂OC₂H₅ | H | OCH₃ | NHCH₃ | N |
| C₂H₅ | (CH₂)₂OC₂H₅ | H | CH₃ | CH₃ | CH |
| C₂H₅ | (CH₂)₂OC₂H₅ | H | OCH₃ | CH₃ | CH |
| C₂H₅ | (CH₂)₂OC₂H₅ | H | OCH₃ | OCH₃ | CH |
| C₂H₅ | (CH₂)₂OC₂H₅ | H | Cl | OCH₃ | CH |
| C₂H₅ | (CH₂)₂OC₂H₅ | H | OCH₃ | CH₃ | N |
| C₂H₅ | (CH₂)₂OC₂H₅ | H | OCH₃ | N(CH₃)₂ | CH |
| CH(CH₃)₂ | (CH₂)₂OC₂H₅ | H | OCH₃ | CH₃ | CH |
| CH(CH₃)₂ | (CH₂)₂OC₂H₅ | H | OCH₃ | OCH₃ | CH |
| CH(CH₃)₂ | (CH₂)₂OC₂H₅ | H | Cl | OCH₃ | CH |
| CH(CH₃)₂ | (CH₂)₂OC₂H₅ | H | OCH₃ | CH₃ | N |
| CH(CH₃)₂ | (CH₂)₂OC₂H₅ | H | OCH₃ | OCH₃ | N |
| CH₃ | (CH₂)₃OC₂H₅ | H | CH₃ | CH₃ | CH |
| CH₃ | (CH₂)₃OC₂H₅ | H | OCH₃ | CH₃ | CH |
| CH₃ | (CH₂)₃OC₂H₅ | H | OCH₃ | OCH₃ | CH |
| CH₃ | (CH₂)₃OC₂H₅ | H | Cl | OCH₃ | CH |
| CH₃ | (CH₂)₃OC₂H₅ | H | CH₃ | CH₃ | N |
| CH₃ | (CH₂)₃OC₂H₅ | H | OCH₃ | CH₃ | N |
| CH₃ | (CH₂)₃OC₂H₅ | H | OCH₃ | OCH₃ | N |

TABLE I-continued

| | | | | | | |
|---|---|---|---|---|---|---|
| CH₃ | (CH₂)₃OC₂H₅ | H | OCH₃ | N(CH₃)₂ | CH | |
| CH₃ | (CH₂)₃OC₂H₅ | H | OCH₃ | N(CH₃)₂ | N | |
| CH₃ | (CH₂)₃OC₂H₅ | H | OCH₃ | OCH₂CF₃ | N | |
| CH₃ | (CH₂)₃OC₂H₅ | CH₃ | OCH₃ | CH₃ | N | |
| CH₃ | (CH₂)₃OC₂H₅ | CH₃ | OCH₃ | OCH₃ | N | |
| CH₃ | (CH₂)₃OC₂H₅ | CH₃ | CH₃ | OCH₃ | CH | |
| CH₃ | (CH₂)₃OC₂H₅ | CH₃ | OCH₃ | OCH₃ | CH | |
| CH₃ | (CH₂)₃OC₂H₅ | H | Br | OCH₃ | CH | |
| CH₃ | (CH₂)₃OC₂H₅ | H | CH₃ | OCH₂CF₃ | N | |
| CH₃ | (CH₂)₃OC₂H₅ | H | CH₃ | OCH₂CF₃ | CH | |
| CH₃ | (CH₂)₃OC₂H₅ | H | OCH₃ | OCH₂CF₃ | CH | |
| CH₃ | (CH₂)₃OC₂H₅ | H | OCH₃ | NHCH₃ | N | |
| C₂H₅ | (CH₂)₃OC₂H₅ | H | CH₃ | CH₃ | CH | |
| C₂H₅ | (CH₂)₃OC₂H₅ | H | OCH₃ | CH₃ | CH | |
| C₂H₅ | (CH₂)₃OC₂H₅ | H | OCH₃ | OCH₃ | CH | |
| C₂H₅ | (CH₂)₃OC₂H₅ | H | Cl | OCH₃ | CH | |
| C₂H₅ | (CH₂)₃OC₂H₅ | H | OCH₃ | CH₃ | N | |
| C₂H₅ | (CH₂)₃OC₂H₅ | H | OCH₃ | N(CH₃)₂ | CH | |
| CH(CH₃)₂ | (CH₂)₃OC₂H₅ | H | OCH₃ | CH₃ | CH | |
| CH(CH₃)₂ | (CH₂)₃OC₂H₅ | H | OCH₃ | OCH₃ | CH | |
| CH(CH₃)₂ | (CH₂)₃OC₂H₅ | H | Cl | OCH₃ | CH | |
| CH(CH₃)₂ | (CH₂)₃OC₂H₅ | H | OCH₃ | CH₃ | N | |
| CH(CH₃)₂ | (CH₂)₃OC₂H₅ | H | OCH₃ | OCH₃ | N | |
| CH₃ | (CH₂)₄OC₂H₅ | H | OCH₃ | CH₃ | CH | |
| CH₃ | (CH₂)₄OC₂H₅ | H | OCH₃ | OCH₃ | CH | |
| CH₃ | (CH₂)₄OC₂H₅ | H | Cl | OCH₃ | CH | |
| CH₃ | (CH₂)₄OC₂H₅ | H | OCH₃ | CH₃ | N | |
| CH₃ | (CH₂)₄OC₂H₅ | H | OCH₃ | OCH₃ | N | |
| CH₃ | CH₂CH(CH₃)(OCH₃) | H | CH₃ | OCH₃ | CH | |
| CH₃ | (CH₂)₂CH(CH₃)(OCH₃) | H | OCH₃ | OCH₃ | N | |
| CH₃ | CH₂CH(CH₃)(OC₂H₅) | H | CH₃ | OCH₃ | N | |
| CH₃ | (CH₂)₂CH(CH₃)(OC₂H₅) | H | OCH₃ | OCH₃ | CH | |
| CH₃ | CH(C₂H₅)(OCH₃) | H | CH₃ | OCH₃ | CH | |
| CH₃ | CH(C₂H₅)(OC₂H₅) | H | OCH₃ | OCH₃ | N | |
| CH₃ | CH₂CH(C₂H₅)(OCH₃) | H | CH₃ | OCH₃ | N | |
| CH₃ | CH₂CH(C₂H₅)(OC₂H₅) | H | OCH₃ | OCH₃ | CH | |
| CH₃ | CH(CH₃)(CH₂OCH₃) | H | CH₃ | OCH₃ | CH | |
| CH₃ | CH₂CH(CH₃)(CH₂OCH₃) | H | OCH₃ | OCH₃ | N | |
| CH₃ | CH₂SCH₃ | H | CH₃ | CH₃ | CH | 163-165 |
| CH₃ | CH₂SCH₃ | H | OCH₃ | CH₃ | CH | 152-154 |
| CH₃ | CH₂SCH₃ | H | OCH₃ | OCH₃ | CH | 146-148 |
| CH₃ | CH₂SCH₃ | H | Cl | OCH₃ | CH | 140-142 |
| CH₃ | CH₂SCH₃ | H | OCH₃ | N(CH₃)₂ | CH | |
| CH₃ | CH₂SCH₃ | H | CH₃ | CH₃ | N | |
| CH₃ | CH₂SCH₃ | H | OCH₃ | CH₃ | N | 131-135 |
| CH₃ | CH₂SCH₃ | H | OCH₃ | OCH₃ | N | 123-125 |
| CH₃ | CH₂SCH₃ | H | OCH₃ | N(CH₃)₂ | N | |
| CH₃ | CH₂SCH₃ | H | OCH₃ | OCH₂CF₃ | N | |
| CH₃ | CH₂SCH₃ | H | OCH₃ | CH₃ | N | |
| CH₃ | CH₂SCH₃ | CH₃ | OCH₃ | OCH₃ | N | |
| CH₃ | CH₂SCH₃ | CH₃ | CH₃ | OCH₃ | CH | |
| CH₃ | CH₂SCH₃ | CH₃ | OCH₃ | OCH₃ | CH | |
| CH₃ | CH₂SCH₃ | H | Br | OCH₃ | CH | |
| CH₃ | CH₂SCH₃ | CH₃ | OCH₃ | N(CH₃)₂ | N | |
| CH₃ | CH₂SCH₃ | H | CH₃ | OCH₂CF₃ | N | |
| CH₃ | CH₂SCH₃ | H | CH₃ | OCH₂CF₃ | CH | |
| CH₃ | CH₂SCH₃ | H | OCH₃ | OCH₂CF₃ | CH | |
| CH₃ | CH₂SCH₃ | H | OCH₃ | C₂H₅ | CH | |
| CH₃ | CH₂SCH₃ | H | OCH₃ | C₂H₅ | N | |
| CH₃ | CH₂SCH₃ | H | OCH₃ | NHCH₃ | CH | |
| CH₃ | CH₂SCH₃ | H | OCH₃ | NHCH₃ | N | |
| CH₃ | CH₂SCH₃ | H | CH₃ | OC₂H₅ | CH | |
| CH₃ | CH₂SCH₃ | H | OCH₃ | OC₂H₅ | CH | |
| CH₃ | CH₂SCH₃ | H | CH₃ | OC₂H₅ | N | |
| CH₃ | CH₂SCH₃ | H | OCH₃ | OC₂H₅ | N | |
| CH₃ | CH₂SCH₃ | H | CH₃ | OCH₂CHF₂ | CH | |
| CH₃ | CH₂SCH₃ | H | OCH₃ | OCH₂CHF₂ | CH | |
| CH₃ | CH₂SCH₃ | H | CH₃ | OCH₂CHF₂ | N | |
| CH₃ | CH₂SCH₃ | H | OCH₃ | OCH₂CHF₂ | N | |
| CH₃ | CH₂SCH₃ | H | CH₃ | OCH₂CH₂F | CH | |
| CH₃ | CH₂SCH₃ | H | OCH₃ | OCH₂CH₂F | CH | |
| CH₃ | CH₂SCH₃ | H | CH₃ | OCH₂CH₂F | N | |
| CH₃ | CH₂SCH₃ | CH₃ | OCH₃ | OCH₂CH₂F | N | |
| CH₃ | CH₂SCH₃ | CH₃ | Cl | OCH₃ | CH | |
| CH₃ | CH₂SCH₃ | H | Cl | N(CH₃)₂ | CH | |
| CH₃ | CH₂SCH₃ | H | Cl | OC₂H₅ | CH | |
| C₂H₅ | CH₂SCH₃ | H | CH₃ | CH₃ | CH | 165-167 |
| C₂H₅ | CH₂SCH₃ | H | OCH₃ | CH₃ | CH | 148-150 |
| C₂H₅ | CH₂SCH₃ | H | OCH₃ | OCH₃ | CH | 154-156 |
| C₂H₅ | CH₂SCH₃ | H | Cl | OCH₃ | CH | 124-126 |
| C₂H₅ | CH₂SCH₃ | H | CH₃ | CH₃ | N | |
| C₂H₅ | CH₂SCH₃ | H | OCH₃ | CH₃ | N | 135-137 |

TABLE I-continued

| | | | | | | |
|---|---|---|---|---|---|---|
| C$_2$H$_5$ | CH$_2$SCH$_3$ | H | OCH$_3$ | OCH$_3$ | N | |
| C$_2$H$_5$ | CH$_2$SCH$_3$ | H | Br | OCH$_3$ | CH | 111-114 |
| C$_2$H$_5$ | CH$_2$SCH$_3$ | H | OCH$_3$ | N(CH$_3$)$_2$ | CH | |
| C$_2$H$_5$ | CH$_2$SCH$_3$ | H | OCH$_3$ | N(CH$_3$)$_2$ | N | |
| C$_2$H$_5$ | CH$_2$SCH$_3$ | H | OCH$_3$ | NHCH$_3$ | N | |
| C$_2$H$_5$ | CH$_2$SCH$_3$ | H | OCH$_3$ | C$_2$H$_5$ | CH | |
| C$_2$H$_5$ | CH$_2$SCH$_3$ | H | OCH$_3$ | C$_2$H$_5$ | N | |
| C$_2$H$_5$ | CH$_2$SCH$_3$ | H | CH$_3$ | OC$_2$H$_5$ | CH | |
| C$_2$H$_5$ | CH$_2$SCH$_3$ | H | CH$_3$ | OC$_2$H$_5$ | N | |
| C$_2$H$_5$ | CH$_2$SCH$_3$ | H | OCH$_3$ | OC$_2$H$_5$ | CH | |
| C$_2$H$_5$ | CH$_2$SCH$_3$ | H | OCH$_3$ | OC$_2$H$_5$ | N | |
| C$_2$H$_5$ | CH$_2$SCH$_3$ | H | CH$_3$ | OCH$_2$CF$_3$ | CH | |
| C$_2$H$_5$ | CH$_2$SCH$_3$ | H | CH$_3$ | OCH$_2$CF$_3$ | N | |
| C$_2$H$_5$ | CH$_2$SCH$_3$ | H | OCH$_3$ | OCH$_2$CF$_3$ | CH | |
| C$_2$H$_5$ | CH$_2$SCH$_3$ | H | OCH$_3$ | OCH$_2$CF$_3$ | N | |
| C$_2$H$_5$ | CH$_2$SCH$_3$ | H | OCH$_3$ | OCH$_2$CHF$_2$ | CH | |
| C$_2$H$_5$ | CH$_2$SCH$_3$ | H | OCH$_3$ | OCH$_2$CHF$_2$ | N | |
| C$_2$H$_5$ | CH$_2$SCH$_3$ | H | CH$_3$ | OCH$_2$CHF$_2$ | N | |
| C$_2$H$_5$ | CH$_2$SCH$_3$ | H | OCH$_3$ | OCH$_2$CH$_2$F | CH | |
| C$_2$H$_5$ | CH$_2$SCH$_3$ | H | OCH$_3$ | OCH$_2$CH$_2$F | N | |
| C$_2$H$_5$ | CH$_2$SCH$_3$ | CH$_3$ | OCH$_3$ | OCH$_3$ | CH | |
| C$_2$H$_5$ | CH$_2$SCH$_3$ | CH$_3$ | CH$_3$ | OCH$_3$ | N | |
| C$_2$H$_5$ | CH$_2$SCH$_3$ | CH$_3$ | OCH$_3$ | OCH$_3$ | N | |
| n-C$_3$H$_7$ | CH$_2$SCH$_3$ | H | OCH$_3$ | OCH$_3$ | CH | |
| n-C$_3$H$_7$ | CH$_2$SCH$_3$ | H | CH$_3$ | OCH$_3$ | N | |
| CH(CH$_3$)$_2$ | CH$_2$SCH$_3$ | H | OCH$_3$ | CH$_3$ | CH | |
| CH(CH$_3$)$_2$ | CH$_2$SCH$_3$ | H | OCH$_3$ | OCH$_3$ | CH | |
| CH(CH$_3$)$_2$ | CH$_2$SCH$_3$ | H | Cl | OCH$_3$ | CH | |
| CH(CH$_3$)$_2$ | CH$_2$SCH$_3$ | H | OCH$_3$ | CH$_3$ | N | |
| CH(CH$_3$)$_2$ | CH$_2$SCH$_3$ | H | OCH$_3$ | OCH$_3$ | N | |
| CH(CH$_3$)$_2$ | CH$_2$SCH$_3$ | H | OCH$_3$ | N(CH$_3$)$_2$ | N | |
| CH$_3$ | CH$_2$CH$_2$SCH$_3$ | H | CH$_3$ | CH$_3$ | CH | |
| CH$_3$ | CH$_2$CH$_2$SCH$_3$ | H | OCH$_3$ | OCH$_3$ | CH | |
| CH$_3$ | CH$_2$CH$_2$SCH$_3$ | H | Cl | OCH$_3$ | CH | |
| CH$_3$ | CH$_2$CH$_2$SCH$_3$ | H | OCH$_3$ | N(CH$_3$)$_2$ | CH | |
| CH$_3$ | CH$_2$CH$_2$SCH$_3$ | H | CH$_3$ | CH$_3$ | N | |
| CH$_3$ | CH$_2$CH$_2$SCH$_3$ | H | OCH$_3$ | CH$_3$ | N | |
| CH$_3$ | CH$_2$CH$_2$SCH$_3$ | H | OCH$_3$ | OCH$_3$ | N | |
| CH$_3$ | CH$_2$CH$_2$SCH$_3$ | H | OCH$_3$ | N(CH$_3$)$_2$ | N | |
| CH$_3$ | CH$_2$CH$_2$SCH$_3$ | H | OCH$_3$ | OCH$_2$CF$_3$ | N | |
| CH$_3$ | CH$_2$CH$_2$SCH$_3$ | CH$_3$ | OCH$_3$ | CH$_3$ | N | |
| CH$_3$ | CH$_2$CH$_2$SCH$_3$ | CH$_3$ | OCH$_3$ | OCH$_3$ | N | |
| CH$_3$ | CH$_2$CH$_2$SCH$_3$ | CH$_3$ | CH$_3$ | OCH$_3$ | CH | |
| CH$_3$ | CH$_2$CH$_2$SCH$_3$ | CH$_3$ | OCH$_3$ | OCH$_3$ | CH | |
| CH$_3$ | CH$_2$CH$_2$SCH$_3$ | H | Br | OCH$_3$ | CH | |
| CH$_3$ | CH$_2$CH$_2$SCH$_3$ | CH$_3$ | OCH$_3$ | N(CH$_3$)$_2$ | N | |
| CH$_3$ | CH$_2$CH$_2$SCH$_3$ | H | CH$_3$ | OCH$_2$CF$_3$ | N | |
| CH$_3$ | CH$_2$CH$_2$SCH$_3$ | H | CH$_3$ | OCH$_2$CF$_3$ | CH | |
| CH$_3$ | CH$_2$CH$_2$SCH$_3$ | H | OCH$_3$ | OCH$_2$CF$_3$ | CH | |
| CH$_3$ | CH$_2$CH$_2$SCH$_3$ | H | OCH$_3$ | C$_2$H$_5$ | CH | |
| CH$_3$ | CH$_2$CH$_2$SCH$_3$ | H | OCH$_3$ | C$_2$H$_5$ | N | |
| CH$_3$ | CH$_2$CH$_2$SCH$_3$ | H | OCH$_3$ | NHCH$_3$ | CH | |
| CH$_3$ | CH$_2$CH$_2$SCH$_3$ | H | OCH$_3$ | NHCH$_3$ | N | |
| CH$_3$ | CH$_2$CH$_2$SCH$_3$ | H | CH$_3$ | OC$_2$H$_5$ | CH | |
| CH$_3$ | CH$_2$CH$_2$SCH$_3$ | H | OCH$_3$ | OC$_2$H$_5$ | CH | |
| CH$_3$ | CH$_2$CH$_2$SCH$_3$ | H | CH$_3$ | OC$_2$H$_5$ | N | |
| CH$_3$ | CH$_2$CH$_2$SCH$_3$ | H | OCH$_3$ | OC$_2$H$_5$ | N | |
| CH$_3$ | CH$_2$CH$_2$SCH$_3$ | H | CH$_3$ | OCH$_2$CHF$_2$ | CH | |
| CH$_3$ | CH$_2$CH$_2$SCH$_3$ | H | OCH$_3$ | OCH$_2$CHF$_2$ | CH | |
| CH$_3$ | CH$_2$CH$_2$SCH$_3$ | H | CH$_3$ | OCH$_2$CHF$_2$ | N | |
| CH$_3$ | CH$_2$CH$_2$SCH$_3$ | H | OCH$_3$ | OCH$_2$CHF$_2$ | N | |
| CH$_3$ | CH$_2$CH$_2$SCH$_3$ | H | CH$_3$ | OCH$_2$CH$_2$F | CH | |
| CH$_3$ | CH$_2$CH$_2$SCH$_3$ | H | OCH$_3$ | OCH$_2$CH$_2$F | CH | |
| CH$_3$ | CH$_2$CH$_2$SCH$_3$ | H | CH$_3$ | OCH$_2$CH$_2$F | N | |
| CH$_3$ | CH$_2$CH$_2$SCH$_3$ | CH$_3$ | OCH$_3$ | OCH$_2$CH$_2$F | N | |
| CH$_3$ | CH$_2$CH$_2$SCH$_3$ | CH$_3$ | Cl | OCH$_3$ | CH | |
| CH$_3$ | CH$_2$CH$_2$SCH$_3$ | H | Cl | N(CH$_3$)$_2$ | CH | |
| CH$_3$ | CH$_2$CH$_2$SCH$_3$ | H | Cl | OC$_2$H$_5$ | CH | |
| C$_2$H$_5$ | CH$_2$CH$_2$SCH$_3$ | H | CH$_3$ | CH$_3$ | CH | |
| C$_2$H$_5$ | CH$_2$CH$_2$SCH$_3$ | H | OCH$_3$ | CH$_3$ | CH | |
| C$_2$H$_5$ | CH$_2$CH$_2$SCH$_3$ | H | OCH$_3$ | OCH$_3$ | CH | |
| C$_2$H$_5$ | CH$_2$CH$_2$SCH$_3$ | H | Cl | OCH$_3$ | CH | |
| C$_2$H$_5$ | CH$_2$CH$_2$SCH$_3$ | H | CH$_3$ | CH$_3$ | N | |
| C$_2$H$_5$ | CH$_2$CH$_2$SCH$_3$ | H | OCH$_3$ | CH$_3$ | N | |
| C$_2$H$_5$ | CH$_2$CH$_2$SCH$_3$ | H | OCH$_3$ | OCH$_3$ | N | |
| C$_2$H$_5$ | CH$_2$CH$_2$SCH$_3$ | H | Br | OCH$_3$ | CH | |
| C$_2$H$_5$ | CH$_2$CH$_2$SCH$_3$ | H | OCH$_3$ | N(CH$_3$)$_2$ | CH | |
| C$_2$H$_5$ | CH$_2$CH$_2$SCH$_3$ | H | OCH$_3$ | N(CH$_3$)$_2$ | N | |
| C$_2$H$_5$ | CH$_2$CH$_2$SCH$_3$ | H | OCH$_3$ | NHCH$_3$ | N | |
| C$_2$H$_5$ | CH$_2$CH$_2$SCH$_3$ | H | OCH$_3$ | C$_2$H$_5$ | CH | |
| C$_2$H$_5$ | CH$_2$CH$_2$SCH$_3$ | H | OCH$_3$ | C$_2$H$_5$ | N | |

TABLE I-continued

| | | | | | |
|---|---|---|---|---|---|
| C₂H₅ | CH₂CH₂SCH₃ | H | CH₃ | OC₂H₅ | CH |
| C₂H₅ | CH₂CH₂SCH₃ | H | CH₃ | OC₂H₅ | N |
| C₂H₅ | CH₂CH₂SCH₃ | H | OCH₃ | OC₂H₅ | CH |
| C₂H₅ | CH₂CH₂SCH₃ | H | OCH₃ | OC₂H₅ | N |
| C₂H₅ | CH₂CH₂SCH₃ | H | CH₃ | OCH₂CF₃ | CH |
| C₂H₅ | CH₂CH₂SCH₃ | H | CH₃ | OCH₂CF₃ | N |
| C₂H₅ | CH₂CH₂SCH₃ | H | OCH₃ | OCH₂CF₃ | CH |
| C₂H₅ | CH₂CH₂SCH₃ | H | OCH₃ | OCH₂CF₃ | N |
| C₂H₅ | CH₂CH₂SCH₃ | H | OCH₃ | OCH₂CHF₂ | CH |
| C₂H₅ | CH₂CH₂SCH₃ | H | OCH₃ | OCH₂CHF₂ | N |
| C₂H₅ | CH₂CH₂SCH₃ | H | CH₃ | OCH₂CHF₂ | N |
| C₂H₅ | CH₂CH₂SCH₃ | H | OCH₃ | OCH₂CH₂F | CH |
| C₂H₅ | CH₂CH₂SCH₃ | H | OCH₃ | OCH₂F | N |
| C₂H₅ | CH₂CH₂SCH₃ | CH₃ | OCH₃ | OCH₃ | CH |
| C₂H₅ | CH₂CH₂SCH₃ | CH₃ | CH₃ | OCH₃ | N |
| C₂H₅ | CH₂CH₂SCH₃ | CH₃ | OCH₃ | OCH₃ | N |
| n-C₃H₇ | CH₂CH₂SCH₃ | H | OCH₃ | OCH₃ | CH |
| n-C₃H₇ | CH₂CH₂SCH₃ | H | CH₃ | OCH₃ | N |
| CH(CH₃)₂ | CH₂CH₂SCH₃ | H | OCH₃ | CH₃ | CH |
| CH(CH₃)₂ | CH₂CH₂SCH₃ | H | OCH₃ | OCH₃ | CH |
| CH(CH₃)₂ | CH₂CH₂SCH₃ | H | Cl | OCH₃ | CH |
| CH(CH₃)₂ | CH₂CH₂SCH₃ | H | OCH₃ | CH₃ | N |
| CH(CH₃)₂ | CH₂CH₂SCH₃ | H | OCH₃ | OCH₃ | N |
| CH(CH₃)₂ | CH₂CH₂SCH₃ | H | OCH₃ | N(CH₃)₂ | N |
| CH₃ | CH(CH₃)(SCH₃) | H | OCH₃ | CH₃ | CH |
| CH₃ | CH(CH₃)(SCH₃) | H | OCH₃ | OCH₃ | CH |
| CH₃ | CH(CH₃)(SCH₃) | H | OCH₃ | CH₃ | N |
| CH₃ | CH(CH₃)(SCH₃) | H | OCH₃ | OCH₃ | N |
| CH₃ | CH(CH₃)(SCH₃) | H | OCH₃ | Cl | CH |
| CH₃ | (CH₂)₃SCH₃ | H | CH₃ | CH₃ | CH |
| CH₃ | (CH₂)₃SCH₃ | H | OCH₃ | CH₃ | CH |
| CH₃ | (CH₂)₃SCH₃ | H | OCH₃ | OCH₃ | CH |
| CH₃ | (CH₂)₃SCH₃ | H | Cl | OCH₃ | CH |
| CH₃ | (CH₂)₃SCH₃ | H | CH₃ | CH₃ | N |
| CH₃ | (CH₂)₃SCH₃ | H | OCH₃ | CH₃ | N |
| CH₃ | (CH₂)₃SCH₃ | H | OCH₃ | OCH₃ | N |
| CH₃ | (CH₂)₃SCH₃ | H | OCH₃ | N(CH₃)₂ | CH |
| CH₃ | (CH₂)₃SCH₃ | H | OCH₃ | N(CH₃)₂ | N |
| CH₃ | (CH₂)₃SCH₃ | H | OCH₃ | OCH₂CF₃ | N |
| CH₃ | (CH₂)₃SCH₃ | CH₃ | OCH₃ | CH₃ | N |
| CH₃ | (CH₂)₃SCH₃ | CH₃ | OCH₃ | OCH₃ | N |
| CH₃ | (CH₂)₃SCH₃ | CH₃ | CH₃ | OCH₃ | CH |
| CH₃ | (CH₂)₃SCH₃ | CH₃ | OCH₃ | OCH₃ | CH |
| CH₃ | (CH₂)₃SCH₃ | H | Br | OCH₃ | CH |
| CH₃ | (CH₂)₃SCH₃ | H | CH₃ | OCH₂CF₃ | N |
| CH₃ | (CH₂)₃SCH₃ | H | CH₃ | OCH₂CF₃ | CH |
| CH₃ | (CH₂)₃SCH₃ | H | OCH₃ | OCH₂CF₃ | CH |
| CH₃ | (CH₂)₃SCH₃ | H | OCH₃ | NHCH₃ | N |
| C₂H₅ | (CH₂)₃SCH₃ | H | CH₃ | CH₃ | CH |
| C₂H₅ | (CH₂)₃SCH₃ | H | OCH₃ | CH₃ | CH |
| C₂H₅ | (CH₂)₃SCH₃ | H | OCH₃ | OCH₃ | CH |
| C₂H₅ | (CH₂)₃SCH₃ | H | Cl | OCH₃ | CH |
| C₂H₅ | (CH₂)₃SCH₃ | H | OCH₃ | CH₃ | N |
| C₂H₅ | (CH₂)₃SCH₃ | H | OCH₃ | N(CH₃)₂ | CH |
| CH(CH₃)₂ | (CH₂)₃SCH₃ | H | OCH₃ | CH₃ | CH |
| CH(CH₃)₂ | (CH₂)₃SCH₃ | H | OCH₃ | OCH₃ | CH |
| CH(CH₃)₂ | (CH₂)₃SCH₃ | H | Cl | OCH₃ | CH |
| CH(CH₃)₂ | (CH₂)₃SCH₃ | H | OCH₃ | CH₃ | N |
| CH(CH₃)₂ | (CH₂)₃SCH₃ | H | OCH₃ | OCH₃ | N |
| CH₃ | (CH₂)₄SCH₃ | H | CH₃ | CH₃ | CH |
| CH₃ | (CH₂)₄SCH₃ | H | OCH₃ | CH₃ | CH |
| CH₃ | (CH₂)₄SCH₃ | H | OCH₃ | OCH₃ | CH |
| CH₃ | (CH₂)₄SCH₃ | H | Cl | OCH₃ | CH |
| CH₃ | (CH₂)₄SCH₃ | H | CH₃ | CH₃ | N |
| CH₃ | (CH₂)₄SCH₃ | H | OCH₃ | CH₃ | N |
| CH₃ | (CH₂)₄SCH₃ | H | OCH₃ | OCH₃ | N |
| CH₃ | (CH₂)₄SCH₃ | H | OCH₃ | N(CH₃)₂ | CH |
| CH₃ | (CH₂)₄SCH₃ | H | OCH₃ | N(CH₃)₂ | N |
| CH₃ | (CH₂)₄SCH₃ | H | OCH₃ | OCH₂CF₃ | N |
| CH₃ | (CH₂)₄SCH₃ | CH₃ | OCH₃ | CH₃ | N |
| CH₃ | (CH₂)₄SCH₃ | CH₃ | OCH₃ | OCH₃ | N |
| CH₃ | (CH₂)₄SCH₃ | CH₃ | CH₃ | OCH₃ | CH |
| CH₃ | (CH₂)₄SCH₃ | CH₃ | OCH₃ | OCH₃ | CH |
| CH₃ | (CH₂)₄SCH₃ | H | Br | OCH₃ | CH |
| CH₃ | (CH₂)₄SCH₃ | H | CH₃ | OCH₂CF₃ | N |
| CH₃ | (CH₂)₄SCH₃ | H | CH₃ | OCH₂CF₃ | CH |
| CH₃ | (CH₂)₄SCH₃ | H | OCH₃ | OCH₂CF₃ | CH |
| CH₃ | (CH₂)₄SCH₃ | H | OCH₃ | NHCH₃ | N |
| C₂H₅ | (CH₂)₄SCH₃ | H | CH₃ | CH₃ | CH |
| C₂H₅ | (CH₂)₄SCH₃ | H | OCH₃ | CH₃ | CH |
| C₂H₅ | (CH₂)₄SCH₃ | H | OCH₃ | OCH₃ | CH |
| C₂H₅ | (CH₂)₄SCH₃ | H | Cl | OCH₃ | CH |

TABLE I-continued

| | | | | | |
|---|---|---|---|---|---|
| C₂H₅ | (CH₂)₄SCH₃ | H | OCH₃ | CH₃ | N |
| C₂H₅ | (CH₂)₄SCH₃ | H | OCH₃ | N(CH₃)₂ | CH |
| CH(CH₃)₂ | (CH₂)₄SCH₃ | H | OCH₃ | CH₃ | CH |
| CH(CH₃)₂ | (CH₂)₄SCH₃ | H | OCH₃ | OCH₃ | CH |
| CH(CH₃)₂ | (CH₂)₄SCH₃ | H | Cl | OCH₃ | CH |
| CH(CH₃)₂ | (CH₂)₄SCH₃ | H | OCH₃ | CH₃ | N |
| CH(CH₃)₂ | (CH₂)₄SCH₃ | H | OCH₃ | OCH₃ | N |
| CH₃ | CH₂SC₂H₅ | H | CH₃ | CH₃ | CH |
| CH₃ | CH₂SC₂H₅ | H | OCH₃ | CH₃ | CH |
| CH₃ | CH₂SC₂H₅ | H | OCH₃ | OCH₃ | CH |
| CH₃ | CH₂SC₂H₅ | H | Cl | OCH₃ | CH |
| CH₃ | CH₂SC₂H₅ | H | CH₃ | CH₃ | N |
| CH₃ | CH₂SC₂H₅ | H | OCH₃ | CH₃ | N |
| CH₃ | CH₂SC₂H₅ | H | OCH₃ | OCH₃ | N |
| CH₃ | CH₂SC₂H₅ | H | OCH₃ | N(CH₃)₂ | CH |
| CH₃ | CH₂SC₂H₅ | H | OCH₃ | N(CH₃)₂ | N |
| CH₃ | CH₂SC₂H₅ | H | OCH₃ | OCH₂CF₃ | N |
| CH₃ | CH₂SC₂H₅ | CH₃ | OCH₃ | CH₃ | N |
| CH₃ | CH₂SC₂H₅ | CH₃ | OCH₃ | OCH₃ | N |
| CH₃ | CH₂SC₂H₅ | CH₃ | CH₃ | OCH₃ | CH |
| CH₃ | CH₂SC₂H₅ | CH₃ | OCH₃ | OCH₃ | CH |
| CH₃ | CH₂SC₂H₅ | H | Br | OCH₃ | CH |
| CH₃ | CH₂SC₂H₅ | H | CH₃ | OCH₂CF₃ | N |
| CH₃ | CH₂SC₂H₅ | H | CH₃ | OCH₂CF₃ | CH |
| CH₃ | CH₂SC₂H₅ | H | OCH₃ | OCH₂CF₃ | CH |
| CH₃ | CH₂SC₂H₅ | H | OCH₃ | NHCH₃ | N |
| C₂H₅ | CH₂SC₂H₅ | H | CH₃ | CH₃ | CH |
| C₂H₅ | CH₂SC₂H₅ | H | OCH₃ | CH₃ | CH |
| C₂H₅ | CH₂SC₂H₅ | H | OCH₃ | OCH₃ | CH |
| C₂H₅ | CH₂SC₂H₅ | H | Cl | OCH₃ | CH |
| C₂H₅ | CH₂SC₂H₅ | H | OCH₃ | CH₃ | N |
| C₂H₅ | CH₂SC₂H₅ | H | OCH₃ | N(CH₃)₂ | CH |
| CH(CH₃)₂ | CH₂SC₂H₅ | H | OCH₃ | CH₃ | CH |
| CH(CH₃)₂ | CH₂SC₂H₅ | H | OCH₃ | OCH₃ | CH |
| CH(CH₃)₂ | CH₂SC₂H₅ | H | Cl | OCH₃ | CH |
| CH(CH₃)₂ | CH₂SC₂H₅ | H | OCH₃ | CH₃ | N |
| CH(CH₃)₂ | CH₂SC₂H₅ | H | OCH₃ | OCH₃ | N |
| CH₃ | (CH₂)₂SC₂H₅ | H | CH₃ | CH₃ | CH |
| CH₃ | (CH₂)₂SC₂H₅ | H | OCH₃ | CH₃ | CH |
| CH₃ | (CH₂)₂SC₂H₅ | H | OCH₃ | OCH₃ | CH |
| CH₃ | (CH₂)₂SC₂H₅ | H | Cl | OCH₃ | CH |
| CH₃ | (CH₂)₂SC₂H₅ | H | CH₃ | CH₃ | N |
| CH₃ | (CH₂)₂SC₂H₅ | H | OCH₃ | CH₃ | N |
| CH₃ | (CH₂)₂SC₂H₅ | H | OCH₃ | OCH₃ | N |
| CH₃ | (CH₂)₂SC₂H₅ | H | OCH₃ | N(CH₃)₂ | CH |
| CH₃ | (CH₂)₂SC₂H₅ | H | OCH₃ | N(CH₃)₂ | N |
| CH₃ | (CH₂)₂SC₂H₅ | H | OCH₃ | OCH₂CF₃ | N |
| CH₃ | (CH₂)₂SC₂H₅ | CH₃ | OCH₃ | CH₃ | N |
| CH₃ | (CH₂)₂SC₂H₅ | CH₃ | OCH₃ | OCH₃ | N |
| CH₃ | (CH₂)₂SC₂H₅ | CH₃ | CH₃ | OCH₃ | CH |
| CH₃ | (CH₂)₂SC₂H₅ | CH₃ | OCH₃ | OCH₃ | CH |
| CH₃ | (CH₂)₂SC₂H₅ | H | Br | OCH₃ | CH |
| CH₃ | (CH₂)₂SC₂H₅ | H | CH₃ | OCH₂CF₃ | N |
| CH₃ | (CH₂)₂SC₂H₅ | H | CH₃ | OCH₂CF₃ | CH |
| CH₃ | (CH₂)₂SC₂H₅ | H | OCH₃ | OCH₂CF₃ | CH |
| CH₃ | (CH₂)₂SC₂H₅ | H | OCH₃ | NHCH₃ | N |
| C₂H₅ | (CH₂)₂SC₂H₅ | H | CH₃ | CH₃ | CH |
| C₂H₅ | (CH₂)₂SC₂H₅ | H | OCH₃ | CH₃ | CH |
| C₂H₅ | (CH₂)₂SC₂H₅ | H | OCH₃ | OCH₃ | CH |
| C₂H₅ | (CH₂)₂SC₂H₅ | H | Cl | OCH₃ | CH |
| C₂H₅ | (CH₂)₂SC₂H₅ | H | OCH₃ | CH₃ | N |
| C₂H₅ | (CH₂)₂SC₂H₅ | H | OCH₃ | N(CH₃)₂ | CH |
| CH(CH₃)₂ | (CH₂)₂SC₂H₅ | H | OCH₃ | CH₃ | CH |
| CH(CH₃)₂ | (CH₂)₂SC₂H₅ | H | OCH₃ | OCH₃ | CH |
| CH(CH₃)₂ | (CH₂)₂SC₂H₅ | H | Cl | OCH₃ | CH |
| CH(CH₃)₂ | (CH₂)₂SC₂H₅ | H | OCH₃ | CH₃ | N |
| CH(CH₃)₂ | (CH₂)₂SC₂H₅ | H | OCH₃ | OCH₃ | N |
| CH₃ | (CH₂)₃SC₂H₅ | H | CH₃ | CH₃ | CH |
| CH₃ | (CH₂)₃SC₂H₅ | H | OCH₃ | CH₃ | CH |
| CH₃ | (CH₂)₃SC₂H₅ | H | OCH₃ | OCH₃ | CH |
| CH₃ | (CH₂)₃SC₂H₅ | H | Cl | OCH₃ | CH |
| CH₃ | (CH₂)₃SC₂H₅ | H | CH₃ | CH₃ | N |
| CH₃ | (CH₂)₃SC₂H₅ | H | OCH₃ | CH₃ | N |
| CH₃ | (CH₂)₃SC₂H₅ | H | OCH₃ | OCH₃ | N |
| CH₃ | (CH₂)₃SC₂H₅ | H | OCH₃ | N(CH₃)₂ | CH |
| CH₃ | (CH₂)₃SC₂H₅ | H | OCH₃ | N(CH₃)₂ | N |
| CH₃ | (CH₂)₃SC₂H₅ | H | OCH₃ | OCH₂CF₃ | N |
| CH₃ | (CH₂)₃SC₂H₅ | CH₃ | OCH₃ | CH₃ | N |
| CH₃ | (CH₂)₃SC₂H₅ | CH₃ | OCH₃ | OCH₃ | N |
| CH₃ | (CH₂)₃SC₂H₅ | CH₃ | CH₃ | OCH₃ | CH |
| CH₃ | (CH₂)₃SC₂H₅ | CH₃ | OCH₃ | OCH₃ | CH |
| CH₃ | (CH₂)₃SC₂H₅ | H | Br | OCH₃ | CH |

TABLE I-continued

| | | | | | |
|---|---|---|---|---|---|
| CH$_3$ | (CH$_2$)$_3$SC$_2$H$_5$ | H | CH$_3$ | OCH$_2$CF$_3$ | N |
| CH$_3$ | (CH$_2$)$_3$SC$_2$H$_5$ | H | CH$_3$ | OCH$_2$CF$_3$ | CH |
| CH$_3$ | (CH$_2$)$_3$SC$_2$H$_5$ | H | OCH$_3$ | OCH$_2$CF$_3$ | CH |
| CH$_3$ | (CH$_2$)$_3$SC$_2$H$_5$ | H | OCH$_3$ | NHCH$_3$ | N |
| C$_2$H$_5$ | (CH$_2$)$_3$SC$_2$H$_5$ | H | CH$_3$ | CH$_3$ | CH |
| C$_2$H$_5$ | (CH$_2$)$_3$SC$_2$H$_5$ | H | OCH$_3$ | CH$_3$ | CH |
| C$_2$H$_5$ | (CH$_2$)$_3$SC$_2$H$_5$ | H | OCH$_3$ | OCH$_3$ | CH |
| C$_2$H$_5$ | (CH$_2$)$_3$SC$_2$H$_5$ | H | Cl | OCH$_3$ | CH |
| C$_2$H$_5$ | (CH$_2$)$_3$SC$_2$H$_5$ | H | OCH$_3$ | CH$_3$ | N |
| C$_2$H$_5$ | (CH$_2$)$_3$SC$_2$H$_5$ | H | OCH$_3$ | N(CH$_3$)$_2$ | CH |
| CH(CH$_3$)$_2$ | (CH$_2$)$_3$SC$_2$H$_5$ | H | OCH$_3$ | CH$_3$ | CH |
| CH(CH$_3$)$_2$ | (CH$_2$)$_3$SC$_2$H$_5$ | H | OCH$_3$ | OCH$_3$ | CH |
| CH(CH$_3$)$_2$ | (CH$_2$)$_3$SC$_2$H$_5$ | H | Cl | OCH$_3$ | CH |
| CH(CH$_3$)$_2$ | (CH$_2$)$_3$SC$_2$H$_5$ | H | OCH$_3$ | CH$_3$ | N |
| CH(CH$_3$)$_2$ | (CH$_2$)$_3$SC$_2$H$_5$ | H | OCH$_3$ | OCH$_3$ | N |
| CH$_3$ | (CH$_2$)$_4$SC$_2$H$_5$ | H | OCH$_3$ | CH$_3$ | CH |
| CH$_3$ | (CH$_2$)$_4$SC$_2$H$_5$ | H | OCH$_3$ | OCH$_3$ | CH |
| CH$_3$ | (CH$_2$)$_4$SC$_2$H$_5$ | H | Cl | OCH$_3$ | CH |
| CH$_3$ | (CH$_2$)$_4$SC$_2$H$_5$ | H | OCH$_3$ | CH$_3$ | N |
| CH$_3$ | (CH$_2$)$_4$SC$_2$H$_5$ | H | OCH$_3$ | OCH$_3$ | N |
| CH$_3$ | CH$_2$CH(CH$_3$)(SCH$_3$) | H | CH$_3$ | OCH$_3$ | CH |
| CH$_3$ | (CH$_2$)$_2$CH(CH$_3$)(SCH$_3$) | H | OCH$_3$ | OCH$_3$ | N |
| CH$_3$ | CH$_2$CH(CH$_3$)(SC$_2$H$_5$) | H | CH$_3$ | OCH$_3$ | N |
| CH$_3$ | (CH$_2$)$_2$CH(CH$_3$)(SC$_2$H$_5$) | H | OCH$_3$ | OCH$_3$ | CH |
| CH$_3$ | CH(C$_2$H$_5$)(SCH$_3$) | H | CH$_3$ | OCH$_3$ | CH |
| CH$_3$ | CH(C$_2$H$_5$)(SC$_2$H$_5$) | H | OCH$_3$ | OCH$_3$ | N |
| CH$_3$ | CH$_2$CH(C$_2$H$_5$)(SCH$_3$) | H | CH$_3$ | OCH$_3$ | N |
| CH$_3$ | CH$_2$CH(C$_2$H$_5$)(SC$_2$H$_5$) | H | OCH$_3$ | OCH$_3$ | CH |
| CH$_3$ | CH(CH$_3$)(SC$_2$SCH$_3$) | H | CH$_3$ | OCH$_3$ | CH |
| CH$_3$ | CH$_2$CH(CH$_3$)(CH$_2$SCH$_3$) | H | OCH$_3$ | OCH$_3$ | N |
| CH$_3$ | CH$_2$S(O)(CH$_3$) | H | CH$_3$ | CH$_3$ | CH |
| CH$_3$ | CH$_2$S(O)(CH$_3$) | H | OCH$_3$ | CH$_3$ | CH |
| CH$_3$ | CH$_2$S(O)(CH$_3$) | H | OCH$_3$ | OCH$_3$ | CH |
| CH$_3$ | CH$_2$S(O)(CH$_3$) | H | Cl | OCH$_3$ | CH |
| CH$_3$ | CH$_2$S(O)(CH$_3$) | H | OCH$_3$ | N(CH$_3$)$_2$ | CH |
| CH$_3$ | CH$_2$S(O)(CH$_3$) | H | CH$_3$ | CH$_3$ | N |
| CH$_3$ | CH$_2$S(O)(CH$_3$) | H | OCH$_3$ | CH$_3$ | N |
| CH$_3$ | CH$_2$S(O)(CH$_3$) | H | OCH$_3$ | OCH$_3$ | N |
| CH$_3$ | CH$_2$S(O)(CH$_3$) | H | OCH$_3$ | N(CH$_3$)$_2$ | N |
| CH$_3$ | CH$_2$S(O)(CH$_3$) | H | OCH$_3$ | OCH$_2$CF$_3$ | N |
| CH$_3$ | CH$_2$S(O)(CH$_3$) | CH$_3$ | OCH$_3$ | CH$_3$ | N |
| CH$_3$ | CH$_2$S(O)(CH$_3$) | CH$_3$ | OCH$_3$ | OCH$_3$ | N |
| CH$_3$ | CH$_2$S(O)(CH$_3$) | CH$_3$ | CH$_3$ | OCH$_3$ | CH |
| CH$_3$ | CH$_2$S(O)(CH$_3$) | CH$_3$ | OCH$_3$ | OCH$_3$ | CH |
| CH$_3$ | CH$_2$S(O)(CH$_3$) | H | Br | OCH$_3$ | CH |
| CH$_3$ | CH$_2$S(O)(CH$_3$) | H | OCH$_3$ | N(CH$_3$)$_2$ | CH |
| CH$_3$ | CH$_2$S(O)(CH$_3$) | CH$_3$ | OCH$_3$ | N(CH$_3$)$_2$ | N |
| CH$_3$ | CH$_2$S(O)(CH$_3$) | H | CH$_3$ | OCH$_2$CF$_3$ | N |
| CH$_3$ | CH$_2$S(O)(CH$_3$) | H | OCH$_3$ | OCH$_2$CF$_3$ | CH |
| CH$_3$ | CH$_2$S(O)(CH$_3$) | H | OCH$_3$ | C$_2$H$_5$ | CH |
| CH$_3$ | CH$_2$S(O)(CH$_3$) | H | OCH$_3$ | C$_2$H$_5$ | N |
| CH$_3$ | CH$_2$S(O)(CH$_3$) | H | OCH$_3$ | NHCH$_3$ | CH |
| CH$_3$ | CH$_2$S(O)(CH$_3$) | H | OCH$_3$ | NHCH$_3$ | N |
| CH$_3$ | CH$_2$S(O)(CH$_3$) | H | CH$_3$ | OC$_2$H$_5$ | CH |
| CH$_3$ | CH$_2$S(O)(CH$_3$) | H | CH$_3$ | OC$_2$H$_5$ | N |
| CH$_3$ | CH$_2$S(O)(CH$_3$) | H | OCH$_3$ | OC$_2$H$_5$ | N |
| CH$_3$ | CH$_2$S(O)(CH$_3$) | H | CH$_3$ | OCH$_2$CHF$_2$ | CH |
| CH$_3$ | CH$_2$S(O)(CH$_3$) | H | OCH$_3$ | OCH$_2$CHF$_2$ | CH |
| CH$_3$ | CH$_2$S(O)(CH$_3$) | H | CH$_3$ | OCH$_2$CHF$_2$ | N |
| CH$_3$ | CH$_2$S(O)(CH$_3$) | H | CH$_3$ | OCH$_2$CHF$_2$ | N |
| CH$_3$ | CH$_2$S(O)(CH$_3$) | H | CH$_3$ | OCH$_2$CH$_2$F | CH |
| CH$_3$ | CH$_2$S(O)(CH$_3$) | H | OCH$_3$ | OCH$_2$CH$_2$F | CH |
| CH$_3$ | CH$_2$S(O)(CH$_3$) | H | CH$_3$ | OCH$_2$CH$_2$F | N |
| CH$_3$ | CH$_2$S(O)(CH$_3$) | H | OCH$_3$ | OCH$_2$CH$_2$F | N |
| CH$_3$ | CH$_2$S(O)(CH$_3$) | CH$_3$ | Cl | OCH$_3$ | CH |
| CH$_3$ | CH$_2$S(O)(CH$_3$) | H | Cl | N(CH$_3$)$_2$ | CH |
| CH$_3$ | CH$_2$S(O)(CH$_3$) | H | Cl | OC$_2$H$_5$ | CH |
| C$_2$H$_5$ | CH$_2$S(O)(CH$_3$) | H | CH$_3$ | CH$_3$ | CH |
| C$_2$H$_5$ | CH$_2$S(O)(CH$_3$) | H | OCH$_3$ | CH$_3$ | CH |
| C$_2$H$_5$ | CH$_2$S(O)(CH$_3$) | H | OCH$_3$ | OCH$_3$ | CH |
| C$_2$H$_5$ | CH$_2$S(O)(CH$_3$) | H | Cl | OCH$_3$ | CH |
| C$_2$H$_5$ | CH$_2$S(O)(CH$_3$) | H | CH$_3$ | CH$_3$ | N |
| C$_2$H$_5$ | CH$_2$S(O)(CH$_3$) | H | OCH$_3$ | CH$_3$ | N |
| C$_2$H$_5$ | CH$_2$S(O)(CH$_3$) | H | OCH$_3$ | OCH$_3$ | N |
| C$_2$H$_5$ | CH$_2$S(O)(CH$_3$) | H | Br | OCH$_3$ | CH |
| C$_2$H$_5$ | CH$_2$S(O)(CH$_3$) | H | OCH$_3$ | N(CH$_3$)$_2$ | CH |
| C$_2$H$_5$ | CH$_2$S(O)(CH$_3$) | H | OCH$_3$ | N(CH$_3$)$_2$ | N |
| C$_2$H$_5$ | CH$_2$S(O)(CH$_3$) | H | OCH$_3$ | NHCH$_3$ | N |
| CH$_3$ | (CH$_2$S(O)(CH$_2$CH$_3$) | H | CH$_3$ | CH$_3$ | CH |
| CH$_3$ | (CH$_2$S(O)(CH$_2$CH$_3$) | H | OCH$_3$ | CH$_3$ | CH |
| CH$_3$ | (CH$_2$S(O)(CH$_2$CH$_3$) | H | OCH$_3$ | OCH$_3$ | CH |

TABLE I-continued

| | | | | | |
|---|---|---|---|---|---|
| CH₃ | (CH₂S(O)(CH₂CH₃) | H | Cl | OCH₃ | CH |
| CH₃ | (CH₂S(O)(CH₂CH₃) | H | CH₃ | CH₃ | N |
| CH₃ | (CH₂S(O)(CH₂CH₃) | H | OCH₃ | CH₃ | N |
| CH₃ | (CH₂S(O)(CH₂CH₃) | H | OCH₃ | OCH₃ | N |
| CH₃ | (CH₂S(O)(CH₂CH₃) | H | OCH₃ | N(CH₃)₂ | CH |
| CH₃ | (CH₂S(O)(CH₂CH₃) | H | OCH₃ | N(CH₃)₂ | N |
| CH₃ | (CH₂S(O)(CH₂CH₃) | H | OCH₃ | OCH₂CF₃ | N |
| CH₃ | (CH₂S(O)(CH₂CH₃) | CH₃ | OCH₃ | CH₃ | N |
| CH₃ | (CH₂S(O)(CH₂CH₃) | CH₃ | OCH₃ | OCH₃ | N |
| CH₃ | (CH₂S(O)(CH₂CH₃) | CH₃ | CH₃ | OCH₃ | CH |
| CH₃ | (CH₂S(O)(CH₂CH₃) | CH₃ | OCH₃ | OCH₃ | CH |
| CH₃ | (CH₂S(O)(CH₂CH₃) | H | Br | OCH₃ | CH |
| CH₃ | (CH₂S(O)(CH₂CH₃) | H | CH₃ | OCH₂CF₃ | N |
| CH₃ | (CH₂S(O)(CH₂CH₃) | H | CH₃ | OCH₂CF₃ | CH |
| CH₃ | (CH₂S(O)(CH₂CH₃) | H | OCH₃ | OCH₂CF₃ | CH |
| CH₃ | (CH₂S(O)(CH₂CH₃) | H | OCH₃ | NHCH₃ | N |
| C₂H₅ | (CH₂S(O)(CH₂CH₃) | H | CH₃ | CH₃ | CH |
| C₂H₅ | (CH₂S(O)(CH₂CH₃) | H | OCH₃ | CH₃ | CH |
| C₂H₅ | (CH₂S(O)(CH₂CH₃) | H | OCH₃ | OCH₃ | CH |
| C₂H₅ | (CH₂S(O)(CH₂CH₃) | H | Cl | OCH₃ | CH |
| C₂H₅ | (CH₂S(O)(CH₂CH₃) | H | OCH₃ | CH₃ | N |
| C₂H₅ | (CH₂S(O)(CH₂CH₃) | H | OCH₃ | N(CH₃)₂ | N |
| CH(CH₃)₂ | (CH₂S(O)(CH₂CH₃) | H | OCH₃ | CH₃ | CH |
| CH(CH₃)₂ | (CH₂S(O)(CH₂CH₃) | H | OCH₃ | OCH₃ | CH |
| CH(CH₃)₂ | (CH₂S(O)(CH₂CH₃) | H | CL | OCH₃ | CH |
| CH(CH₃)₂ | (CH₂S(O)(CH₂CH₃) | H | OCH₃ | CH₃ | N |
| CH(CH₃)₂ | (CH₂S(O)(CH₂CH₃) | H | OCH₃ | OCH₃ | N |
| CH₃ | (CH₂)₂S(O)(CH₃) | H | OCH₃ | CH₃ | CH |
| CH₃ | (CH₂)₂S(O)(CH₃) | H | OCH₃ | OCH₃ | CH |
| CH₃ | (CH₂)₂(CH₂)₂S(O)(CH₃) | H | Cl | OCH₃ | CH |
| CH₃ | (CH₂)₂(CH₂)₂S(O)(CH₃) | H | OCH₃ | CH₃ | N |
| CH₃ | (CH₂)₂(CH₂)₂S(O)(CH₃) | H | OCH₃ | OCH₃ | N |
| CH₃ | (CH₂)₂S(O)(CH₂CH₃) | H | OCH₃ | CH₃ | CH |
| CH₃ | (CH₂)₂S(O)(CH₂CH₃) | H | OCH₃ | OCH₃ | CH |
| CH₃ | (CH₂)₂S(O)(CH₂CH₃) | H | Cl | OCH₃ | CH |
| CH₃ | (CH₂)₂S(O)(CH₂CH₃) | H | OCH₃ | CH₃ | N |
| CH₃ | (CH₂)₂S(O)(CH₂CH₃) | H | OCH₃ | OCH₃ | N |
| CH₃ | (CH₂)₃S(O)(CH₃) | H | CH₃ | OCH₃ | CH |
| CH₃ | (CH₂)₄S(O)(CH₃) | H | OCH₃ | OCH₃ | N |
| CH₃ | (CH₂)₃S(O)(CH₂CH₃) | H | CH₃ | OCH₃ | CH |
| CH₃ | (CH₂)₄S(O)(CH₂CH₃) | H | OCH₃ | OCH₃ | CH |
| CH₃ | (CH(CH₃)(S(O)(CH₃)) | H | CH₃ | OCH₃ | N |
| CH₃ | CH₂S(O)₂(CH₃) | H | CH₃ | CH₃ | CH |
| CH₃ | CH₂S(O)₂(CH₃) | H | OCH₃ | CH₃ | CH |
| CH₃ | CH₂S(O)₂(CH₃) | H | OCH₃ | CH₃ | CH |
| CH₃ | CH₂S(O)₂(CH₃) | H | OCH₃ | OCH₃ | CH |
| CH₃ | CH₂S(O)₂(CH₃) | H | Cl | OCH₃ | CH |
| CH₃ | CH₂S(O)₂(CH₃) | H | OCH₃ | N(CH₃)₂ | CH |
| CH₃ | CH₂S(O)₂(CH₃) | H | CH₃ | CH₃ | N |
| CH₃ | CH₂S(O)₂(CH₃) | H | OCH₃ | CH₃ | N |
| CH₃ | CH₂S(O)₂(CH₃) | H | OCH₃ | OCH₃ | N |
| CH₃ | CH₂S(O)₂(CH₃) | H | OCH₃ | N(CH₃)₂ | N |
| CH₃ | CH₂S(O)₂(CH₃) | H | OCH₃ | OCH₂CF₃ | N |
| CH₃ | CH₂S(O)₂(CH₃) | CH₃ | OCH₃ | CH₃ | N |
| CH₃ | CH₂S(O)₂(CH₃) | CH₃ | OCH₃ | OCH₃ | N |
| CH₃ | CH₂S(O)₂(CH₃) | CH₃ | CH₃ | OCH₃ | CH |
| CH₃ | CH₂S(O)₂(CH₃) | CH₃ | OCH₃ | OCH₃ | CH |
| CH₃ | CH₂S(O)₂(CH₃) | H | Br | OCH₃ | CH |
| CH₃ | CH₂S(O)₂(CH₃) | H | OCH₃ | N(CH₃)₂ | CH |
| CH₃ | CH₂S(O)₂(CH₃) | CH₃ | OCH₃ | N(CH₃)₂ | N |
| CH₃ | CH₂S(O)₂(CH₃) | H | CH₃ | OCH₂CF₃ | N |
| CH₃ | CH₂S(O)₂(CH₃) | H | CH₃ | OCH₂CF₃ | CH |
| CH₃ | CH₂S(O)₂(CH₃) | H | OCH₃ | OCH₂CF₃ | CH |
| CH₃ | CH₂S(O)₂(CH₃) | H | OCH₃ | C₂H₅ | CH |
| CH₃ | CH₂S(O)₂(CH₃) | H | OCH₃ | C₂H₅ | N |
| CH₃ | CH₂S(O)₂(CH₃) | H | OCH₃ | NHCH₃ | CH |
| CH₃ | CH₂S(O)₂(CH₃) | H | OCH₃ | NHCH₃ | N |
| CH₃ | CH₂S(O)₂(CH₃) | H | CH₃ | OC₂H₅ | CH |
| CH₃ | CH₂S(O)₂(CH₃) | H | OCH₃ | OC₂H₅ | CH |
| CH₃ | CH₂S(O)₂(CH₃) | H | CH₃ | OC₂H₅ | N |
| CH₃ | CH₂S(O)₂(CH₃) | H | OCH₃ | OC₂H₅ | N |
| CH₃ | CH₂S(O)₂(CH₃) | H | CH₃ | OCH₂CHF₂ | CH |
| CH₃ | CH₂S(O)₂(CH₃) | H | OCH₃ | OCH₂CHF₂ | CH |
| CH₃ | CH₂S(O)₂(CH₃) | H | CH₃ | OCH₂CHF₂ | N |
| CH₃ | CH₂S(O)₂(CH₃) | H | OCH₃ | OCH₂CHF₂ | N |
| CH₃ | CH₂S(O)₂(CH₃) | H | CH₃ | OCH₂CH₂F | CH |
| CH₃ | CH₂S(O)₂(CH₃) | H | OCH₃ | OCH₂CH₂F | CH |
| CH₃ | CH₂S(O)₂(CH₃) | H | CH₃ | OCH₂CH₂F | N |
| CH₃ | CH₂S(O)₂(CH₃) | H | OCH₃ | OCH₂CH₂F | N |
| CH₃ | CH₂S(O)₂(CH₃) | CH₃ | Cl | OCH₃ | CH |
| CH₃ | CH₂S(O)₂(CH₃) | H | Cl | N(CH₃)₂ | CH |
| CH₃ | CH₂S(O)₂(CH₃) | H | Cl | OC₂H₅ | CH |

TABLE I-continued

| | | | | | |
|---|---|---|---|---|---|
| $C_2H_5$ | $CH_2S(O)_2(CH_3)$ | H | $CH_3$ | $CH_3$ | CH |
| $C_2H_5$ | $CH_2S(O)_2(CH_3)$ | H | $OCH_3$ | $CH_3$ | CH |
| $C_2H_5$ | $CH_2S(O)_2(CH_3)$ | H | $OCH_3$ | $OCH_3$ | CH |
| $C_2H_5$ | $CH_2S(O)_2(CH_3)$ | H | Cl | $OCH_3$ | CH |
| $C_2H_5$ | $CH_2S(O)_2(CH_3)$ | H | $CH_3$ | $CH_3$ | N |
| $C_2H_5$ | $CH_2S(O)_2(CH_3)$ | H | $OCH_3$ | $CH_3$ | N |
| $C_2H_5$ | $CH_2S(O)_2(CH_3)$ | H | $OCH_3$ | $OCH_3$ | N |
| $C_2H_5$ | $CH_2S(O)_2(CH_3)$ | H | Br | $OCH_3$ | CH |
| $C_2H_5$ | $CH_2S(O)_2(CH_3)$ | H | $OCH_3$ | $N(CH_3)_2$ | CH |
| $C_2H_5$ | $CH_2S(O)_2(CH_3)$ | H | $OCH_3$ | $N(CH_3)_2$ | N |
| $C_2H_5$ | $CH_2S(O)_2(CH_3)$ | H | $OCH_3$ | $NHCH_3$ | N |
| $C_2H_5$ | $CH_2S(O)_2(CH_3)$ | H | $OCH_3$ | $C_2H_5$ | CH |
| $C_2H_5$ | $CH_2S(O)_2(CH_3)$ | H | $OCH_3$ | $C_2H_5$ | N |
| $C_2H_5$ | $CH_2S(O)_2(CH_3)$ | H | $CH_3$ | $OC_2H_5$ | CH |
| $C_2H_5$ | $CH_2S(O)_2(CH_3)$ | H | $CH_3$ | $OC_2H_5$ | CH |
| $C_2H_5$ | $CH_2S(O)_2(CH_3)$ | H | $CH_3$ | $OC_2H_5$ | N |
| $C_2H_5$ | $CH_2S(O)_2(CH_3)$ | H | $OCH_3$ | $OC_2H_5$ | CH |
| $C_2H_5$ | $CH_2S(O)_2(CH_3)$ | H | $OCH_3$ | $OC_2H_5$ | N |
| $C_2H_5$ | $CH_2S(O)_2(CH_3)$ | H | $CH_3$ | $OCH_2CF_3$ | CH |
| $C_2H_5$ | $CH_2S(O)_2(CH_3)$ | H | $CH_3$ | $OCH_2CF_3$ | N |
| $C_2H_5$ | $CH_2S(O)_2(CH_3)$ | H | $OCH_3$ | $OCH_2CF_3$ | CH |
| $C_2H_5$ | $CH_2S(O)_2(CH_3)$ | H | $OCH_3$ | $OCH_2CF_3$ | N |
| $C_2H_5$ | $CH_2S(O)_2(CH_3)$ | H | $OCH_3$ | $OCH_2CHF_2$ | CH |
| $C_2H_5$ | $CH_2S(O)_2(CH_3)$ | H | $OCH_3$ | $OCH_2CHF_2$ | N |
| $C_2H_5$ | $CH_2S(O)_2(CH_3)$ | H | $CH_3$ | $OCH_2CHF_2$ | N |
| $C_2H_5$ | $CH_2S(O)_2(CH_3)$ | H | $OCH_3$ | $OCH_2CH_2F$ | CH |
| $C_2H_5$ | $CH_2S(O)_2(CH_3)$ | H | $OCH_3$ | $OCH_2CH_2F$ | N |
| $C_2H_5$ | $CH_2S(O)_2(CH_3)$ | $CH_3$ | $OCH_3$ | $OCH_3$ | CH |
| $C_2H_5$ | $CH_2S(O)_2(CH_3)$ | $CH_3$ | $CH_3$ | $OCH_3$ | N |
| $C_2H_5$ | $CH_2S(O)_2(CH_3)$ | $CH_3$ | $OCH_3$ | $OCH_3$ | N |
| n-$C_3H_7$ | $CH_2S(O)_2(CH_3)$ | H | $OCH_3$ | $OCH_3$ | CH |
| n-$C_3H_7$ | $CH_2S(O)_2(CH_3)$ | H | $CH_3$ | $OCH_3$ | N |
| $CH(CH_3)_2$ | $CH_2S(O)_2(CH_3)$ | H | $OCH_3$ | $CH_3$ | CH |
| $CH(CH_3)_2$ | $CH_2S(O)_2(CH_3)$ | H | $OCH_3$ | $OCH_3$ | CH |
| $CH(CH_3)_2$ | $CH_2S(O)_2(CH_3)$ | H | Cl | $OCH_3$ | CH |
| $CH(CH_3)_2$ | $CH_2S(O)_2(CH_3)$ | H | $OCH_3$ | $CH_3$ | N |
| $CH(CH_3)_2$ | $CH_2S(O)_2(CH_3)$ | H | $OCH_3$ | $OCH_3$ | N |
| $CH(CH_3)_2$ | $CH_2S(O)_2(CH_3)$ | H | $OCH_3$ | $N(CH_3)_2$ | N |
| $CH_3$ | $CH_2S(O)_2(CH_2CH_3)$ | H | $CH_3$ | $CH_3$ | CH |
| $CH_3$ | $CH_2S(O)_2(CH_2CH_3)$ | H | $OCH_3$ | $CH_3$ | CH |
| $CH_3$ | $CH_2S(O)_2(CH_2CH_3)$ | H | $OCH_3$ | $OCH_3$ | CH |
| $CH_3$ | $CH_2S(O)_2(CH_2CH_3)$ | H | Cl | $OCH_3$ | CH |
| $CH_3$ | $CH_2S(O)_2(CH_2CH_3)$ | H | $CH_3$ | $CH_3$ | N |
| $CH_3$ | $CH_2S(O)_2(CH_2CH_3)$ | H | $OCH_3$ | $CH_3$ | N |
| $CH_3$ | $CH_2S(O)_2(CH_2CH_3)$ | H | $OCH_3$ | $OCH_3$ | N |
| $CH_3$ | $CH_2S(O)_2(CH_2CH_3)$ | H | $OCH_3$ | $N(CH_3)_2$ | CH |
| $CH_3$ | $CH_2S(O)_2(CH_2CH_3)$ | H | $OCH_3$ | $N(CH_3)_2$ | N |
| $CH_3$ | $CH_2S(O)_2(CH_2CH_3)$ | H | $OCH_3$ | $OCH_2CF_3$ | N |
| $CH_3$ | $CH_2S(O)_2(CH_2CH_3)$ | $CH_3$ | $OCH_3$ | $CH_3$ | N |
| $CH_3$ | $CH_2S(O)_2(CH_2CH_3)$ | $CH_3$ | $OCH_3$ | $OCH_3$ | N |
| $CH_3$ | $CH_2S(O)_2(CH_2CH_3)$ | $CH_3$ | $CH_3$ | $OCH_3$ | CH |
| $CH_3$ | $CH_2S(O)_2(CH_2CH_3)$ | $CH_3$ | $OCH_3$ | $OCH_3$ | CH |
| $CH_3$ | $CH_2S(O)_2(CH_2CH_3)$ | H | Br | $OCH_3$ | CH |
| $CH_3$ | $CH_2S(O)_2(CH_2CH_3)$ | H | $CH_3$ | $OCH_2CF_3$ | N |
| $CH_3$ | $CH_2S(O)_2(CH_2CH_3)$ | H | $CH_3$ | $OCH_2CF_3$ | CH |
| $CH_3$ | $CH_2S(O)_2(CH_2CH_3)$ | H | $OCH_3$ | $OCH_2CF_3$ | CH |
| $CH_3$ | $CH_2S(O)_2(CH_2CH_3)$ | H | $OCH_3$ | $NHCH_3$ | N |
| $C_2H_5$ | $CH_2S(O)_2(CH_2CH_3)$ | H | $CH_3$ | $CH_3$ | CH |
| $C_2H_5$ | $CH_2S(O)_2(CH_2CH_3)$ | H | $OCH_3$ | $CH_3$ | CH |
| $C_2H_5$ | $CH_2S(O)_2(CH_2CH_3)$ | H | $OCH_3$ | $OCH_3$ | CH |
| $C_2H_5$ | $CH_2S(O)_2(CH_2CH_3)$ | H | Cl | $OCH_3$ | CH |
| $C_2H_5$ | $CH_2S(O)_2(CH_2CH_3)$ | H | $OCH_3$ | $CH_3$ | N |
| $C_2H_5$ | $CH_2S(O)_2(CH_2CH_3)$ | H | $OCH_3$ | $N(CH_3)_2$ | N |
| $CH(CH_3)_2$ | $CH_2S(O)_2(CH_2CH_3)$ | H | $OCH_3$ | $CH_3$ | CH |
| $CH(CH_3)_2$ | $CH_2S(O)_2(CH_2CH_3)$ | H | $OCH_3$ | $OCH_3$ | CH |
| $CH(CH_3)_2$ | $CH_2S(O)_2(CH_2CH_3)$ | H | Cl | $OCH_3$ | CH |
| $CH(CH_3)_2$ | $CH_2S(O)_2(CH_2CH_3)$ | H | $OCH_3$ | $CH_3$ | N |
| $CH(CH_3)_2$ | $CH_2S(O)_2(CH_2CH_3)$ | H | $OCH_3$ | $OCH_3$ | N |
| $CH_3$ | $(CH_2)_2S(O)_2(CH_3)$ | H | $OCH_3$ | $CH_3$ | CH |
| $CH_3$ | $(CH_2)_2S(O)_2(CH_3)$ | H | $OCH_3$ | $OCH_3$ | CH |
| $CH_3$ | $(CH_2)_2S(O)_2(CH_3)$ | H | Cl | $OCH_3$ | CH |
| $CH_3$ | $(CH_2)_2S(O)_2(CH_3)$ | H | $OCH_3$ | $CH_3$ | N |
| $CH_3$ | $(CH_2)_2S(O)_2(CH_3)$ | H | $OCH_3$ | $OCH_3$ | N |
| $CH_3$ | $(CH_2)_2S(O)_2(CH_2CH_3)$ | H | $OCH_3$ | $CH_3$ | CH |
| $CH_3$ | $(CH_2)_2S(O)_2(CH_2CH_3)$ | H | $OCH_3$ | $OCH_3$ | CH |
| $CH_3$ | $(CH_2)_2S(O)_2(CH_2CH_3)$ | H | Cl | $OCH_3$ | CH |
| $CH_3$ | $(CH_2)_2S(O)_2(CH_2CH_3)$ | H | $OCH_3$ | $CH_3$ | N |
| $CH_3$ | $(CH_2)_2S(O)_2(CH_2CH_3)$ | H | $OCH_3$ | $OCH_3$ | N |
| $CH_3$ | $(CH_2)_4S(O)_2(CH_3)$ | H | $CH_3$ | $OCH_3$ | CH |
| $CH_3$ | $(CH_2)_4S(O)_2(CH_3)$ | H | $OCH_3$ | $OCH_3$ | N |
| $CH_3$ | $(CH_2)_4S(O)_2(CH_2CH_3)$ | H | $OCH_3$ | $OCH_3$ | CH |
| $CH_3$ | $(CH_2)_4S(O)_2(CH_2CH_3)$ | H | $OCH_3$ | $CH_3$ | N |

TABLE I-continued

| R₁ | R₂ | R | X | Y | Z | m.p. (°C.) |
|---|---|---|---|---|---|---|
| CH₃ | CH(CH₃)(S(O)₂(CH₃)) | H | OCH₃ | OCH₃ | CH | |
| CH₃ | OCF₂H | H | CH₃ | CH₃ | CH | |
| CH₃ | OCF₂H | H | OCH₃ | CH₃ | CH | 164–165 |
| CH₃ | OCF₂H | H | OCH₃ | OCH₃ | CH | 188–190 |
| CH₃ | OCF₂H | H | Cl | OCH₃ | CH | 165–166 |
| CH₃ | OCF₂H | H | OCH₃ | N(CH₃)₂ | CH | |
| CH₃ | OCF₂H | H | CH₃ | CH₃ | N | |
| CH₃ | OCF₂H | H | OCH₃ | CH₃ | N | 162–165 |
| CH₃ | OCF₂H | H | OCH₃ | OCH₃ | N | |
| CH₃ | OCF₂H | H | OCH₃ | N(CH₃)₂ | N | |
| CH₃ | OCF₂H | H | OCH₃ | OCH₂CF₃ | N | |
| CH₃ | OCF₂H | CH₃ | OCH₃ | CH₃ | N | |
| CH₃ | OCF₂H | CH₃ | OCH₃ | OCH₃ | N | |
| CH₃ | OCF₂H | CH₃ | CH₃ | OCH₃ | CH | |
| CH₃ | OCF₂H | CH₃ | OCH₃ | OCH₃ | CH | |
| CH₃ | OCF₂H | H | Br | OCH₃ | CH | |
| CH₃ | OCF₂H | CH₃ | OCH₃ | N(CH₃)₂ | N | |
| CH₃ | OCF₂H | H | CH₃ | OCH₂CF₃ | N | |
| CH₃ | OCF₂H | H | CH₃ | OCH₂CF₃ | CH | |
| CH₃ | OCF₂H | H | OCH₃ | OCH₂CF₃ | CH | |
| CH₃ | OCF₂H | H | OCH₃ | C₂H₅ | CH | |
| CH₃ | OCF₂H | H | OCH₃ | C₂H₅ | N | |
| CH₃ | OCF₂H | H | OCH₃ | NHCH₃ | CH | |
| CH₃ | OCF₂H | H | OCH₃ | NHCH₃ | N | |
| CH₃ | OCF₂H | H | CH₃ | OC₂H₅ | CH | |
| CH₃ | OCF₂H | H | OCH₃ | OC₂H₅ | CH | |
| CH₃ | OCF₂H | H | CH₃ | OC₂H₅ | N | |
| CH₃ | OCF₂H | H | OCH₃ | OC₂H₅ | N | |
| CH₃ | OCF₂H | H | CH₃ | OCH₂CHF₂ | CH | |
| CH₃ | OCF₂H | H | OCH₃ | OCH₂CHF₂ | CH | |
| CH₃ | OCF₂H | H | CH₃ | OCH₂CHF₂ | N | |
| CH₃ | OCF₂H | H | OCH₃ | OCH₂CHF₂ | N | |
| CH₃ | OCF₂H | H | CH₃ | OCH₂CH₂F | CH | |
| CH₃ | OCF₂H | H | OCH₃ | OCH₂CH₂F | CH | |
| CH₃ | OCF₂H | H | CH₃ | OCH₂CH₂F | N | |
| CH₃ | OCF₂H | H | OCH₃ | OCH₂CH₂F | N | |

TABLE I

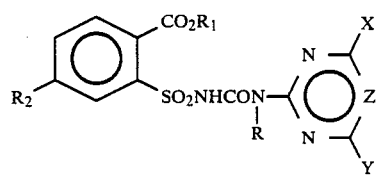

| R₁ | R₂ | R | X | Y | Z | m.p. (°C.) |
|---|---|---|---|---|---|---|
| CH₃ | OCF₂H | CH₃ | Cl | OCH₃ | CH | |
| CH₃ | OCF₂H | H | Cl | N(CH₃)₂ | CH | |
| CH₃ | OCF₂H | H | Cl | OC₂H₅ | CH | |
| C₂H₅ | OCF₂H | H | CH₃ | CH₃ | CH | |
| C₂H₅ | OCF₂H | H | OCH₃ | CH₃ | CH | 160–162 |
| C₂H₅ | OCF₂H | H | OCH₃ | OCH₃ | CH | 146–149 |
| C₂H₅ | OCF₂H | H | Cl | OCH₃ | CH | |
| C₂H₅ | OCF₂H | H | CH₃ | CH₃ | N | |
| C₂H₅ | OCF₂H | H | OCH₃ | CH₃ | N | 168–169 |
| C₂H₅ | OCF₂H | H | OCH₃ | OCH₃ | N | |
| C₂H₅ | OCF₂H | H | Br | OCH₃ | CH | |
| C₂H₅ | OCF₂H | H | OCH₃ | N(CH₃)₂ | CH | |
| C₂H₅ | OCF₂H | H | OCH₃ | N(CH₃)₂ | N | |
| C₂H₅ | OCF₂H | H | OCH₃ | NHCH₃ | N | |
| C₂H₅ | OCF₂H | H | OCH₃ | C₂H₅ | CH | |
| C₂H₅ | OCF₂H | H | OCH₃ | C₂H₅ | N | |
| C₂H₅ | OCF₂H | H | CH₃ | OC₂H₅ | CH | |
| C₂H₅ | OCF₂H | H | CH₃ | OC₂H₅ | N | |
| C₂H₅ | OCF₂H | H | OCH₃ | OC₂H₅ | CH | |
| C₂H₅ | OCF₂H | H | OCH₃ | OC₂H₅ | N | |
| C₂H₅ | OCF₂H | H | CH₃ | OCH₂CF₃ | CH | |
| C₂H₅ | OCF₂H | H | CH₃ | OCH₂CF₃ | N | |
| C₂H₅ | OCF₂H | H | OCH₃ | OCH₂CF₃ | CH | |
| C₂H₅ | OCF₂H | H | OCH₃ | OCH₂CF₃ | N | |
| C₂H₅ | OCF₂H | H | OCH₃ | OCH₂CHF₂ | CH | |
| C₂H₅ | OCF₂H | H | OCH₃ | OCH₂CHF₂ | N | |
| C₂H₅ | OCF₂H | H | CH₃ | OCH₂CHF₂ | CH | |
| C₂H₅ | OCF₂H | H | OCH₃ | OCH₂CH₂F | CH | |
| C₂H₅ | OCF₂H | H | OCH₃ | OCH₂CH₂F | N | |
| C₂H₅ | OCF₂H | CH₃ | OCH₃ | OCH₃ | CH | |
| C₂H₅ | OCF₂H | CH₃ | CH₃ | OCH₃ | N | |

TABLE I-continued

| | | | | | | |
|---|---|---|---|---|---|---|
| C$_2$H$_5$ | OCF$_2$H | CH$_3$ | OCH$_3$ | OCH$_3$ | N | |
| n-C$_3$H$_7$ | OCF$_2$H | H | OCH$_3$ | OCH$_3$ | CH | |
| n-C$_3$H$_7$ | OCF$_2$H | H | CH$_3$ | OCH$_3$ | N | |
| CH(CH$_3$)$_2$ | OCF$_2$H | H | OCH$_3$ | CH$_3$ | CH | |
| CH(CH$_3$)$_2$ | OCF$_2$H | H | OCH$_3$ | OCH$_3$ | CH | |
| CH(CH$_3$)$_2$ | OCF$_2$H | H | Cl | OCH$_3$ | CH | |
| CH(CH$_3$)$_2$ | OCF$_2$H | H | OCH$_3$ | CH$_3$ | N | |
| CH(CH$_3$)$_2$ | OCF$_2$H | H | OCH$_3$ | OCH$_3$ | N | |
| CH(CH$_3$)$_2$ | OCF$_2$H | H | OCH$_3$ | N(CH$_3$)$_2$ | N | |
| CH$_3$ | OCH$_2$CH$_2$F | H | CH$_3$ | CH$_3$ | CH | |
| CH$_3$ | OCH$_2$CH$_2$F | H | OCH$_3$ | CH$_3$ | CH | 168–170 |
| CH$_3$ | OCH$_2$CH$_2$F | H | OCH$_3$ | OCH$_3$ | CH | 205–206 |
| CH$_3$ | OCH$_2$CH$_2$F | H | Cl | OCH$_3$ | CH | 158–162 (d) |
| CH$_3$ | OCH$_2$CH$_2$F | H | OCH$_3$ | N(CH$_3$)$_2$ | CH | |
| CH$_3$ | OCH$_2$CH$_2$F | H | CH$_3$ | CH$_3$ | N | |
| CH$_3$ | OCH$_2$CH$_2$F | H | OCH$_3$ | CH$_3$ | N | 138–140 (d) |
| CH$_3$ | OCH$_2$CH$_2$F | H | OCH$_3$ | OCH$_3$ | N | |
| CH$_3$ | OCH$_2$CH$_2$F | H | OCH$_3$ | N(CH$_3$)$_2$ | N | |
| CH$_3$ | OCH$_2$CH$_2$F | H | OCH$_3$ | OCH$_2$CF$_3$ | N | |
| CH$_3$ | OCH$_2$CH$_2$F | CH$_3$ | OCH$_3$ | CH$_3$ | N | |
| CH$_3$ | OCH$_2$CH$_2$F | CH$_3$ | OCH$_3$ | OCH$_3$ | N | |
| CH$_3$ | OCH$_2$CH$_2$F | CH$_3$ | CH$_3$ | OCH$_3$ | CH | |
| CH$_3$ | OCH$_2$CH$_2$F | CH$_3$ | OCH$_3$ | OCH$_3$ | CH | |
| CH$_3$ | OCH$_2$CH$_2$F | H | Br | OCH$_3$ | CH | |
| CH$_3$ | OCH$_2$CH$_2$F | CH$_3$ | OCH$_3$ | N(CH$_3$)$_2$ | N | |
| CH$_3$ | OCH$_2$CH$_2$F | N | CH$_3$ | OCH$_2$CF$_3$ | N | |
| CH$_3$ | OCH$_2$CH$_2$F | H | CH$_3$ | OCH$_2$CF$_3$ | CH | |
| CH$_3$ | OCH$_2$CH$_2$F | H | OCH$_3$ | OCH$_2$CF$_3$ | CH | |
| CH$_3$ | OCH$_2$CH$_2$F | H | OCH$_3$ | C$_2$H$_5$ | CH | |
| CH$_3$ | OCH$_2$CH$_2$F | H | OCH$_3$ | C$_2$H$_5$ | N | |
| CH$_3$ | OCH$_2$CH$_2$F | H | OCH$_3$ | NHCH$_3$ | CH | |
| CH$_3$ | OCH$_2$CH$_2$F | H | OCH$_3$ | NHCH$_3$ | N | |
| CH$_3$ | OCH$_2$CH$_2$F | H | CH$_3$ | OC$_2$H$_5$ | CH | |
| CH$_3$ | OCH$_2$CH$_2$F | H | OCH$_3$ | OC$_5$H$_5$ | CH | |
| CH$_3$ | OCH$_2$CH$_2$F | H | CH$_3$ | OC$_2$H$_5$ | N | |
| CH$_3$ | OCH$_2$CH$_2$F | H | OCH$_3$ | OC$_2$H$_5$ | N | |
| CH$_3$ | OCH$_2$CH$_2$F | H | CH$_3$ | OCH$_2$CHF$_2$ | CH | |
| CH$_3$ | OCH$_2$CH$_2$F | H | OCH$_3$ | OCH$_2$CHF$_2$ | CH | |
| CH$_3$ | OCH$_2$CH$_2$F | H | CH$_3$ | OCH$_2$CHF$_2$ | N | |
| CH$_3$ | OCH$_2$CH$_2$F | H | OCH$_3$ | OCH$_2$CHF$_2$ | N | |
| CH$_3$ | OCH$_2$CH$_2$F | H | CH$_3$ | OCH$_2$CH$_2$F | CH | |
| CH$_3$ | OCH$_2$CH$_2$F | H | OCH$_3$ | OCH$_2$CH$_2$F | CH | |
| CH$_3$ | OCH$_2$CH$_2$F | H | CH$_3$ | OCH$_2$CH$_2$F | N | |
| CH$_3$ | OCH$_2$CH$_2$F | CH$_3$ | OCH$_3$ | OCH$_2$CH$_2$F | N | |
| CH$_3$ | OCH$_2$CH$_2$F | CH$_3$ | Cl | OCH$_3$ | CH | |
| CH$_3$ | OCH$_2$CH$_2$F | H | Cl | N(CH$_3$)$_2$ | CH | |
| CH$_3$ | OCH$_2$CH$_2$F | H | Cl | OC$_2$H$_5$ | CH | |
| C$_2$H$_5$ | OCH$_2$CH$_2$F | H | CH$_3$ | CH$_3$ | CH | |
| C$_2$H$_5$ | OCH$_2$CH$_2$F | H | OCH$_3$ | CH$_3$ | CH | |
| C$_2$H$_5$ | OCH$_2$CH$_2$F | H | OCH$_3$ | OCH$_3$ | CH | |
| C$_2$H$_5$ | OCH$_2$CH$_2$F | H | Cl | OCH$_3$ | CH | |
| C$_2$H$_5$ | OCH$_2$CH$_2$F | H | CH$_3$ | CH$_3$ | N | |
| C$_2$H$_5$ | OCH$_2$CH$_2$F | H | OCH$_3$ | CH$_3$ | N | |
| C$_2$H$_5$ | OCH$_2$CH$_2$F | H | OCH$_3$ | OCH$_3$ | N | |
| C$_2$H$_5$ | OCH$_2$CH$_2$F | H | Br | OCH$_3$ | CH | |
| C$_2$H$_5$ | OCH$_2$CH$_2$F | H | OCH$_3$ | N(CH$_3$)$_2$ | CH | |
| C$_2$H$_5$ | OCH$_2$CH$_2$F | H | OCH$_3$ | N(CH$_3$)$_2$ | N | |
| C$_2$H$_5$ | OCH$_2$CH$_2$F | H | OCH$_3$ | NHCH$_3$ | N | |
| C$_2$H$_5$ | OCH$_2$CH$_2$F | H | OCH$_3$ | C$_2$H$_5$ | CH | |
| C$_2$H$_5$ | OCH$_2$CH$_2$F | H | OCH$_3$ | C$_2$H$_5$ | N | |
| C$_2$H$_5$ | OCH$_2$CH$_2$F | H | CH$_3$ | OC$_2$H$_5$ | CH | |
| C$_2$H$_5$ | OCH$_2$CH$_2$F | H | CH$_3$ | OC$_2$H$_5$ | N | |
| C$_2$H$_5$ | OCH$_2$CH$_2$F | H | OCH$_3$ | OC$_2$H$_5$ | CH | |
| C$_2$H$_5$ | OCH$_2$CH$_2$F | H | OCH$_3$ | OC$_2$H$_5$ | N | |
| C$_2$H$_5$ | OCH$_2$CH$_2$F | H | CH$_3$ | OCH$_2$CF$_3$ | CH | |
| C$_2$H$_5$ | OCH$_2$CH$_2$F | H | CH$_3$ | OCH$_2$CF$_3$ | N | |
| C$_2$H$_5$ | OCH$_2$CH$_2$F | H | OCH$_3$ | OCH$_2$CF$_3$ | CH | |
| C$_2$H$_5$ | OCH$_2$CH$_2$F | H | OCH$_3$ | OCH$_2$CF$_3$ | N | |
| C$_2$H$_5$ | OCH$_2$CH$_2$F | H | OCH$_3$ | OCH$_2$CHF$_2$ | CH | |
| C$_2$H$_5$ | OCH$_2$CH$_2$F | H | OCH$_3$ | OCH$_2$CHF$_2$ | N | |
| C$_2$H$_5$ | OCH$_2$CH$_2$F | H | CH$_3$ | OCH$_2$CHF$_2$ | N | |
| C$_2$H$_5$ | OCH$_2$CH$_2$F | H | OCH$_3$ | OCH$_2$CH$_2$F | CH | |
| C$_2$H$_5$ | OCH$_2$CH$_2$F | H | OCH$_3$ | OCH$_2$CH$_2$F | N | |
| C$_2$H$_5$ | OCH$_2$CH$_2$F | CH$_3$ | OCH$_3$ | OCH$_3$ | CH | |
| C$_2$H$_5$ | OCH$_2$CH$_2$F | CH$_3$ | CH$_3$ | OCH$_3$ | N | |
| C$_2$H$_5$ | OCH$_2$CH$_2$F | CH$_3$ | OCH$_3$ | OCH$_3$ | N | |
| n-C$_3$H$_7$ | OCH$_2$CH$_2$F | H | OCH$_3$ | OCH$_3$ | CH | |
| n-C$_3$H$_7$ | OCH$_2$CH$_2$F | H | CH$_3$ | OCH$_3$ | N | |
| CH(CH$_3$)$_2$ | OCH$_2$CH$_2$F | H | OCH$_3$ | CH$_3$ | CH | |
| CH(CH$_3$)$_2$ | OCH$_2$CH$_2$F | H | OCH$_3$ | OCH$_3$ | CH | |
| CH(CH$_3$)$_2$ | OCH$_2$CH$_2$F | H | Cl | OCH$_3$ | CH | |
| CH(CH$_3$)$_2$ | OCH$_2$CH$_2$F | H | OCH$_3$ | CH$_3$ | N | |

TABLE I-continued

| | | | | | | |
|---|---|---|---|---|---|---|
| CH(CH₃)₂ | OCH₂CH₂F | H | OCH₃ | OCH₃ | N | |
| CH(CH₃)₂ | OCH₂CH₂F | H | OCH₃ | N(CH₃)₂ | N | |
| CH₃ | OCH₂CHF₂ | H | CH₃ | CH₃ | CH | |
| CH₃ | OCH₂CHF₂ | H | OCH₃ | CH₃ | CH | |
| CH₃ | OCH₂CHF₂ | H | OCH₃ | OCH₃ | CH | |
| CH₃ | OCH₂CHF₂ | H | Cl | OCH₃ | CH | |
| CH₃ | OCH₂CHF₂ | H | OCH₃ | N(CH₃)₂ | CH | |
| CH₃ | OCH₂CHF₂ | H | CH₃ | CH₃ | N | |
| CH₃ | OCH₂CHF₂ | H | OCH₃ | CH₃ | N | |
| CH₃ | OCH₂CHF₂ | H | OCH₃ | OCH₃ | N | |
| CH₃ | OCH₂CHF₂ | H | OCH₃ | N(CH₃)₂ | N | |
| CH₃ | OCH₂CHF₂ | H | OCH₃ | OCH₂CF₃ | N | |
| CH₃ | OCH₂CHF₂ | CH₃ | OCH₃ | CH₃ | N | |
| CH₃ | OCH₂CHF₂ | CH₃ | OCH₃ | OCH₃ | N | |
| CH₃ | OCH₂CHF₂ | CH₃ | CH₃ | OCH₃ | CH | |
| CH₃ | OCH₂CHF₂ | CH₃ | OCH₃ | OCH₃ | CH | |
| CH₃ | OCH₂CHF₂ | H | Br | OCH₃ | CH | |
| CH₃ | OCH₂CHF₂ | CH₃ | OCH₃ | N(CH₃)₂ | N | |
| CH₃ | OCH₂CHF₂ | H | CH₃ | OCH₂CF₃ | N | |
| CH₃ | OCH₂CHF₂ | H | CH₃ | OCH₂CF₃ | CH | |
| CH₃ | OCH₂CHF₂ | H | OCH₃ | OCH₂CF₃ | CH | |
| CH₃ | OCH₂CHF₂ | H | OCH₃ | C₂H₅ | CH | |
| CH₃ | OCH₂CHF₂ | H | OCH₃ | C₂H₅ | N | |
| CH₃ | OCH₂CHF₂ | H | OCH₃ | NHCH₃ | CH | |
| CH₃ | OCH₂CHF₂ | H | OCH₃ | NHCH₃ | N | |
| CH₃ | OCH₂CHF₂ | H | CH₃ | OC₂H₅ | CH | |
| CH₃ | OCH₂CHF₂ | H | OCH₃ | OC₂H₅ | CH | |
| CH₃ | OCH₂CHF₂ | H | CH₃ | OC₂H₅ | N | |
| CH₃ | OCH₂CHF₂ | H | OCH₃ | OC₂H₅ | N | |
| CH₃ | OCH₂CHF₂ | H | CH₃ | OCH₂CHF₂ | CH | |
| CH₃ | OCH₂CHF₂ | H | OCH₃ | OCH₂CHF₂ | CH | |
| CH₃ | OCH₂CHF₂ | H | CH₃ | OCH₂CHF₂ | N | |
| CH₃ | OCH₂CHF₂ | H | OCH₃ | OCH₂CHF₂ | N | |
| CH₃ | OCH₂CHF₂ | H | CH₃ | OCH₂CH₂F | CH | |
| CH₃ | OCH₂CHF₂ | H | OCH₃ | OCH₂CH₂F | CH | |
| CH₃ | OCH₂CHF₂ | H | CH₃ | OCH₂CH₂F | N | |
| CH₃ | OCH₂CHF₂ | CH₃ | OCH₃ | OCH₂CH₂F | N | |
| CH₃ | OCH₂CHF₂ | CH₃ | Cl | OCH₃ | CH | |
| CH₃ | OCH₂CHF₂ | H | Cl | N(CH₃)₂ | CH | |
| CH₃ | OCH₂CHF₂ | H | Cl | OC₂H₅ | CH | |
| C₂H₅ | OCH₂CHF₂ | H | CH₃ | CH₃ | CH | |
| C₂H₅ | OCH₂CHF₂ | H | OCH₃ | CH₃ | CH | |
| C₂H₅ | OCH₂CHF₂ | H | OCH₃ | OCH₃ | CH | |
| C₂H₅ | OCH₂CHF₂ | H | Cl | OCH₃ | CH | |
| C₂H₅ | OCH₂CHF₂ | H | CH₃ | CH₃ | N | |
| C₂H₅ | OCH₂CHF₂ | H | OCH₃ | CH₃ | N | |
| C₂H₅ | OCH₂CHF₂ | H | OCH₃ | OCH₃ | N | |
| C₂H₅ | OCH₂CHF₂ | H | Br | OCH₃ | CH | |
| C₂H₅ | OCH₂CHF₂ | H | OCH₃ | N(CH₃)₂ | CH | |
| C₂H₅ | OCH₂CHF₂ | H | OCH₃ | N(CH₃)₂ | N | |
| C₂H₅ | OCH₂CHF₂ | H | OCH₃ | NHCH₃ | N | |
| C₂H₅ | OCH₂CHF₂ | H | OCH₃ | C₂H₅ | CH | |
| C₂H₅ | OCH₂CHF₂ | H | OCH₃ | C₂H₅ | N | |
| C₂H₅ | OCH₂CHF₂ | H | CH₃ | OC₂H₅ | CH | |
| C₂H₅ | OCH₂CHF₂ | H | CH₃ | OC₂H₅ | CH | |
| C₂H₅ | OCH₂CHF₂ | H | OCH₃ | OC₂H₅ | N | |
| C₂H₅ | OCH₂CHF₂ | H | CH₃ | OCH₂CF₃ | N | |
| C₂H₅ | OCH₂CHF₂ | H | OCH₃ | OCH₂CF₃ | CH | |
| C₂H₅ | OCH₂CHF₂ | H | OCH₃ | OCH₂CF₃ | N | |
| C₂H₅ | OCH₂CHF₂ | H | OCH₃ | OCH₂CHF₂ | CH | |
| C₂H₅ | OCH₂CHF₂ | H | OCH₃ | OCH₂CHF₂ | N | |
| C₂H₅ | OCH₂CHF₂ | H | CH₃ | OCH₂CHF₂ | N | |
| C₂H₅ | OCH₂CHF₂ | H | OCH₃ | OCH₂CHF₂ | CH | |
| C₂H₅ | OCH₂CHF₂ | H | OCH₃ | OCH₂CHF₂ | N | |
| C₂H₅ | OCH₂CHF₂ | CH₃ | OCH₃ | OCH₃ | CH | |
| C₂H₅ | OCH₂CHF₂ | CH₃ | CH₃ | OCH₃ | N | |
| C₂H₅ | OCH₂CHF₂ | CH₃ | OCH₃ | OCH₃ | N | |
| n-C₃H₇ | OCH₂CHF₂ | H | OCH₃ | OCH₃ | CH | |
| n-C₃H₇ | OCH₂CHF₂ | H | CH₃ | OCH₃ | N | |
| CH(CH₃)₂ | OCH₂CHF₂ | H | OCH₃ | CH₃ | CH | |
| CH(CH₃)₂ | OCH₂CHF₂ | H | OCH₃ | OCH₃ | CH | |
| CH(CH₃)₂ | OCH₂CHF₂ | H | Cl | OCH₃ | CH | |
| CH(CH₃)₂ | OCH₂CHF₂ | H | OCH₃ | CH₃ | N | |
| CH(CH₃)₂ | OCH₂CHF₂ | H | OCH₃ | OCH₃ | N | |
| CH(CH₃)₂ | OCH₂CHF₂ | H | OCH₃ | N(CH₃)₂ | N | |
| CH₃ | OCH₂CF₃ | H | CH₃ | CH₃ | CH | 178–181(d) |
| CH₃ | OCH₂CF₃ | H | OCH₃ | CH₃ | CH | 177–178(d) |
| CH₃ | OCH₂CF₃ | H | OCH₃ | OCH₃ | CH | 215–216(d) |
| CH₃ | OCH₂CF₃ | H | Cl | OCH₃ | CH | 185–187(d) |
| CH₃ | OCH₂CF₃ | H | OCH₃ | N(CH₃)₂ | CH | |

TABLE I-continued

| | | | | | | |
|---|---|---|---|---|---|---|
| CH$_3$ | OCH$_2$CF$_3$ | H | CH$_3$ | CH$_3$ | N | |
| CH$_3$ | OCH$_2$CF$_3$ | H | OCH$_3$ | CH$_3$ | N | 168–160(d) |
| CH$_3$ | OCH$_2$CF$_3$ | H | OCH$_3$ | OCH$_3$ | N | 178–180(d) |
| CH$_3$ | OCH$_2$CF$_3$ | H | OCH$_3$ | N(CH$_3$)$_2$ | N | |
| CH$_3$ | OCH$_2$CF$_3$ | H | OCH$_3$ | OCH$_2$CF$_3$ | N | |
| CH$_3$ | OCH$_2$CF$_3$ | H | OC$_2$H$_5$ | NHCH$_3$ | N | |
| CH$_3$ | OCH$_2$CF$_3$ | CH$_3$ | OCH$_3$ | CH$_3$ | N | |
| CH$_3$ | OCH$_2$CF$_3$ | CH$_3$ | OCH$_3$ | OCH$_3$ | N | |
| CH$_3$ | OCH$_2$CF$_3$ | CH$_3$ | CH$_3$ | OCH$_3$ | CH | |
| CH$_3$ | OCH$_2$CF$_3$ | CH$_3$ | OCH$_3$ | OCH$_3$ | CH | |
| CH$_3$ | OCH$_2$CF$_3$ | H | Br | OCH$_3$ | CH | 169–172 |
| CH$_3$ | OCH$_2$CF$_3$ | CH$_3$ | OCH$_3$ | N(CH$_3$)$_2$ | N | |
| CH$_3$ | OCH$_2$CF$_3$ | H | CH$_3$ | OCH$_2$CF$_3$ | N | |
| CH$_3$ | OCH$_2$CF$_3$ | H | CH$_3$ | OCH$_2$CF$_3$ | CH | |
| CH$_3$ | OCH$_2$CF$_3$ | H | OCH$_3$ | OCH$_2$CF$_3$ | CH | |
| CH$_3$ | OCH$_2$CF$_3$ | H | OCH$_3$ | C$_2$H$_5$ | CH | |
| CH$_3$ | OCH$_2$CF$_3$ | H | OCH$_3$ | C$_2$H$_5$ | N | |
| CH$_3$ | OCH$_2$CF$_3$ | H | OCH$_3$ | NHCH$_3$ | CH | |
| CH$_3$ | OCH$_2$CF$_3$ | H | OCH$_3$ | NHCH$_3$ | N | |
| CH$_3$ | OCH$_2$CF$_3$ | H | CH$_3$ | OC$_2$H$_5$ | CH | |
| CH$_3$ | OCH$_2$CF$_3$ | H | OCH$_3$ | OC$_2$H$_5$ | CH | |
| CH$_3$ | OCH$_2$CF$_3$ | H | CH$_3$ | OC$_2$H$_5$ | N | |
| CH$_3$ | OCH$_2$CF$_3$ | H | OCH$_3$ | OC$_2$H$_5$ | N | |
| CH$_3$ | OCH$_2$CF$_3$ | H | CH$_3$ | OCH$_2$CHF$_2$ | CH | |
| CH$_3$ | OCH$_2$CF$_3$ | H | OCH$_3$ | OCH$_2$CHF$_2$ | CH | |
| CH$_3$ | OCH$_2$CF$_3$ | H | CH$_3$ | OCH$_2$CHF$_2$ | N | |
| CH$_3$ | OCH$_2$CF$_3$ | H | OCH$_3$ | OCH$_2$CHF$_2$ | N | |
| CH$_3$ | OCH$_2$CF$_3$ | H | CH$_3$ | OCH$_2$CH$_2$F | CH | |
| CH$_3$ | OCH$_2$CF$_3$ | H | OCH$_3$ | OCH$_2$CH$_2$F | CH | |
| CH$_3$ | OCH$_2$CF$_3$ | H | CH$_3$ | OCH$_2$CH$_2$F | N | |
| CH$_3$ | OCH$_2$CF$_3$ | CH$_3$ | OCH$_3$ | OCH$_2$CH$_2$F | N | |
| CH$_3$ | OCH$_2$CF$_3$ | CH$_3$ | Cl | OCH$_3$ | CH | |
| CH$_3$ | OCH$_2$CF$_3$ | H | Cl | N(CH$_3$)$_2$ | CH | |
| CH$_3$ | OCH$_2$CF$_3$ | H | Cl | OC$_2$H$_5$ | CH | |
| C$_2$H$_5$ | OCH$_2$CF$_3$ | H | CH$_3$ | CH$_3$ | CH | 196–198 |
| C$_2$H$_5$ | OCH$_2$CF$_3$ | H | OCH$_3$ | CH$_3$ | CH | 179–180 |
| C$_2$H$_5$ | OCH$_2$CF$_3$ | H | OCH$_3$ | OCH$_3$ | CH | 200–202 |
| C$_2$H$_5$ | OCH$_2$CF$_3$ | H | Cl | OCH$_3$ | CH | 170–172 |
| C$_2$H$_5$ | OCH$_2$CF$_3$ | H | CH$_3$ | CH$_3$ | N | |
| C$_2$H$_5$ | OCH$_2$CF$_3$ | H | OCH$_3$ | CH$_3$ | N | 159–163 |
| C$_2$H$_5$ | OCH$_2$CF$_3$ | H | OCH$_3$ | OCH$_3$ | N | 141–143 |
| C$_2$H$_5$ | OCH$_2$CF$_3$ | H | Br | OCH$_3$ | CH | 177–179 |
| C$_2$H$_5$ | OCH$_2$CF$_3$ | H | OCH$_3$ | N(CH$_3$)$_2$ | CH | |
| C$_2$H$_5$ | OCH$_2$CF$_3$ | H | OCH$_3$ | N(CH$_3$)$_2$ | N | |
| C$_2$H$_5$ | OCH$_2$CF$_3$ | H | OCH$_3$ | NHCH$_3$ | N | |
| C$_2$H$_5$ | OCH$_2$CF$_3$ | H | OCH$_3$ | C$_2$H$_5$ | CH | |
| C$_2$H$_5$ | OCH$_2$CF$_3$ | H | OCH$_3$ | C$_2$H$_5$ | N | |
| C$_2$H$_5$ | OCH$_2$CF$_3$ | H | CH$_3$ | OC$_2$H$_5$ | CH | |
| C$_2$H$_5$ | OCH$_2$CF$_3$ | H | CH$_3$ | OC$_2$H$_5$ | N | |
| C$_2$H$_5$ | OCH$_2$CF$_3$ | H | OCH$_3$ | OC$_2$H$_5$ | CH | |
| C$_2$H$_5$ | OCH$_2$CF$_3$ | H | OCH$_3$ | OC$_2$H$_5$ | N | |
| C$_2$H$_5$ | OCH$_2$CF$_3$ | H | CH$_3$ | OCH$_2$CF$_3$ | CH | |
| C$_2$H$_5$ | OCH$_2$CF$_3$ | H | CH$_3$ | OCH$_2$CF$_3$ | N | |
| C$_2$H$_5$ | OCH$_2$CF$_3$ | H | OCH$_3$ | OCH$_2$CF$_3$ | CH | |
| C$_2$H$_5$ | OCH$_2$CF$_3$ | H | OCH$_3$ | OCH$_2$CF$_3$ | N | |
| C$_2$H$_5$ | OCH$_2$CF$_3$ | H | OCH$_3$ | OCH$_2$CHF$_2$ | CH | |
| C$_2$H$_5$ | OCH$_2$CF$_3$ | H | OCH$_3$ | OCH$_2$CHF$_2$ | N | |
| C$_2$H$_5$ | OCH$_2$CF$_3$ | H | CH$_3$ | OCH$_2$CHF$_2$ | N | |
| C$_2$H$_5$ | OCH$_2$CF$_3$ | H | OCH$_3$ | OCH$_2$CH$_2$F | CH | |
| C$_2$H$_5$ | OCH$_2$CF$_3$ | H | OCH$_3$ | OCH$_2$CH$_2$F | N | |
| C$_2$H$_5$ | OCH$_2$CF$_3$ | CH$_3$ | OCH$_3$ | OCH$_3$ | CH | |
| C$_2$H$_5$ | OCH$_2$CF$_3$ | CH$_3$ | CH$_3$ | OCH$_3$ | N | |
| C$_2$H$_5$ | OCH$_2$CF$_3$ | CH$_3$ | OCH$_3$ | OCH$_3$ | N | |
| n-C$_3$H$_7$ | OCH$_2$CF$_3$ | H | OCH$_3$ | OCH$_3$ | CH | |
| n-C$_3$H$_7$ | OCH$_2$CF$_3$ | H | CH$_3$ | OCH$_3$ | N | |
| CH(CH$_3$)$_2$ | OCH$_2$CF$_3$ | H | OCH$_3$ | CH$_3$ | CH | |
| CH(CH$_3$)$_2$ | OCH$_2$CF$_3$ | H | OCH$_3$ | OCH$_3$ | CH | |
| CH(CH$_3$)$_2$ | OCH$_2$CF$_3$ | H | Cl | OCH$_3$ | CH | |
| CH(CH$_3$)$_2$ | OCH$_2$CF$_3$ | H | OCH$_3$ | CH$_3$ | N | |
| CH(CH$_3$)$_2$ | OCH$_2$CF$_3$ | H | OCH$_3$ | OCH$_3$ | N | |
| CH(CH$_3$)$_2$ | OCH$_2$CF$_3$ | H | OCH$_3$ | N(CH$_3$)$_2$ | N | |
| CH$_3$ | OCH$_2$CH$_2$Cl | H | CH$_3$ | CH$_3$ | CH | |
| CH$_3$ | OCH$_2$CH$_2$Cl | H | OCH$_3$ | CH$_3$ | CH | |
| CH$_3$ | OCH$_2$CH$_2$Cl | H | OCH$_3$ | OCH$_3$ | CH | |
| CH$_3$ | OCH$_2$CH$_2$Cl | H | Cl | OCH$_3$ | CH | |
| CH$_3$ | OCH$_2$CH$_2$Cl | H | OCH$_3$ | N(CH$_3$)$_2$ | CH | |
| CH$_3$ | OCH$_2$CH$_2$Cl | H | CH$_3$ | CH$_3$ | N | |
| CH$_3$ | OCH$_2$CH$_2$Cl | H | OCH$_3$ | CH$_3$ | N | |
| CH$_3$ | OCH$_2$CH$_2$Cl | H | OCH$_3$ | OCH$_3$ | N | |
| CH$_3$ | OCH$_2$CH$_2$Cl | H | OCH$_3$ | N(CH$_3$)$_2$ | N | |
| CH$_3$ | OCH$_2$CH$_2$Cl | H | OCH$_3$ | OCH$_2$CF$_3$ | N | |
| CH$_3$ | OCH$_2$CH$_2$Cl | CH$_3$ | OCH$_3$ | CH$_3$ | N | |

TABLE I-continued

| | | | | | | |
|---|---|---|---|---|---|---|
| CH₃ | OCH₂CH₂Cl | CH₃ | OCH₃ | OCH₃ | N | |
| CH₃ | OCH₂CH₂Cl | CH₃ | CH₃ | OCH₃ | CH | |
| CH₃ | OCH₂CH₂Cl | CH₃ | OCH₃ | OCH₃ | CH | |
| CH₃ | OCH₂CH₂Cl | H | Br | OCH₃ | CH | |
| CH₃ | OCH₂CH₂Cl | CH₃ | OCH₃ | N(CH₃)₂ | N | |
| CH₃ | OCH₂CH₂Cl | H | CH₃ | OCH₂CF₃ | N | |
| CH₃ | OCH₂CH₂Cl | H | CH₃ | OCH₂CF₃ | CH | |
| CH₃ | OCH₂CH₂Cl | H | OCH₃ | OCH₂CF₃ | CH | |
| CH₃ | OCH₂CH₂Cl | H | OCH₃ | C₂H₅ | CH | |
| CH₃ | OCH₂CH₂Cl | H | OCH₃ | C₂H₅ | N | |
| CH₃ | OCH₂CH₂Cl | H | OCH₃ | NHCH₃ | CH | |
| CH₃ | OCH₂CH₂Cl | H | OCH₃ | NHCH₃ | N | |
| CH₃ | OCH₂CH₂Cl | H | CH₃ | OC₂H₅ | CH | |
| CH₃ | OCH₂CH₂Cl | H | OCH₃ | OC₂H₅ | CH | |
| CH₃ | OCH₂CH₂Cl | H | CH₃ | OC₂H₅ | N | |
| CH₃ | OCH₂CH₂Cl | H | OCH₃ | OC₂H₅ | N | |
| CH₃ | OCH₂CH₂Cl | H | CH₃ | OCH₂CHF₂ | CH | |
| CH₃ | OCH₂CH₂Cl | H | OCH₃ | OCH₂CHF₂ | CH | |
| CH₃ | OCH₂CH₂Cl | H | CH₃ | OCH₂CHF₂ | N | |
| CH₃ | OCH₂CH₂Cl | H | OCH₃ | OCH₂CHF₂ | N | |
| CH₃ | OCH₂CH₂Cl | H | CH₃ | OCH₂CH₂F | CH | |
| CH₃ | OCH₂CH₂Cl | H | OCH₃ | OCH₂CH₂F | CH | |
| CH₃ | OCH₂CH₂Cl | H | CH₃ | OCH₂CH₂F | N | |
| CH₃ | OCH₂CH₂Cl | CH₃ | OCH₃ | OCH₂CH₂F | N | |
| CH₃ | OCH₂CH₂Cl | CH₃ | Cl | OCH₃ | CH | |
| CH₃ | OCH₂CH₂Cl | H | Cl | N(CH₃)₂ | CH | |
| CH₃ | OCH₂CH₂Cl | H | Cl | OC₂H₅ | CH | |
| C₂H₅ | OCH₂CH₂Cl | H | CH₃ | CH₃ | CH | |
| C₂H₅ | OCH₂CH₂Cl | H | OCH₃ | CH₃ | CH | |
| C₂H₅ | OCH₂CH₂Cl | H | OCH₃ | OCH₃ | CH | |
| C₂H₅ | OCH₂CH₂Cl | H | Cl | OCH₃ | CH | |
| C₂H₅ | OCH₂CH₂Cl | H | CH₃ | CH₃ | N | |
| C₂H₅ | OCH₂CH₂Cl | H | OCH₃ | CH₃ | N | |
| C₂H₅ | OCH₂CH₂Cl | H | OCH₃ | OCH₃ | N | |
| C₂H₅ | OCH₂CH₂Cl | H | Br | OCH₃ | CH | |
| C₂H₅ | OCH₂CH₂Cl | H | OCH₃ | N(CH₃)₂ | CH | |
| C₂H₅ | OCH₂CH₂Cl | H | OCH₃ | N(CH₃)₂ | N | |
| C₂H₅ | OCH₂CH₂Cl | H | OCH₃ | NHCH₃ | N | |
| C₂H₅ | OCH₂CH₂Cl | H | OCH₃ | C₂H₅ | CH | |
| C₂H₅ | OCH₂CH₂Cl | H | OCH₃ | C₂H₅ | N | |
| C₂H₅ | OCH₂CH₂Cl | H | CH₃ | OC₂H₅ | CH | |
| C₂H₅ | OCH₂CH₂Cl | H | CH₃ | OC₂H₅ | N | |
| C₂H₅ | OCH₂CH₂Cl | H | OCH₃ | OC₂H₅ | CH | |
| C₂H₅ | OCH₂CH₂Cl | H | OCH₃ | OC₂H₅ | N | |
| C₂H₅ | OCH₂CH₂Cl | H | CH₃ | OCH₂CF₃ | CH | |
| C₂H₅ | OCH₂CH₂Cl | H | CH₃ | OCH₂CF₃ | N | |
| C₂H₅ | OCH₂CH₂Cl | H | OCH₃ | OCH₂CF₃ | CH | |
| C₂H₅ | OCH₂CH₂Cl | H | OCH₃ | OCH₂CF₃ | N | |
| C₂H₅ | OCH₂CH₂Cl | H | OCH₃ | OCH₂CHF₂ | CH | |
| C₂H₅ | OCH₂CH₂Cl | H | OCH₃ | OCH₂CHF₂ | N | |
| C₂H₅ | OCH₂CH₂Cl | H | CH₃ | OCH₂CHF₂ | N | |
| C₂H₅ | OCH₂CH₂Cl | H | OCH₃ | OCH₂CH₂F | CH | |
| C₂H₅ | OCH₂CH₂Cl | H | OCH₃ | OCH₂CH₂F | N | |
| C₂H₅ | OCH₂CH₂Cl | CH₃ | OCH₃ | OCH₃ | CH | |
| C₂H₅ | OCH₂CH₂Cl | CH₃ | CH₃ | OCH₃ | N | |
| C₂H₅ | OCH₂CH₂Cl | CH₃ | OCH₃ | OCH₃ | N | |
| n-C₃H₇ | OCH₂CH₂Cl | H | OCH₃ | OCH₃ | CH | |
| n-C₃H₇ | OCH₂CH₂Cl | H | CH₃ | OCH₃ | N | |
| CH(CH₃)₂ | OCH₂CH₂Cl | H | OCH₃ | CH₃ | CH | |
| CH(CH₃)₂ | OCH₂CH₂Cl | H | OCH₃ | OCH₃ | CH | |
| CH(CH₃)₂ | OCH₂CH₂Cl | H | Cl | OCH₃ | CH | |
| CH(CH₃)₂ | OCH₂CH₂Cl | H | OCH₃ | CH₃ | N | |
| CH(CH₃)₂ | OCH₂CH₂Cl | H | OCH₃ | OCH₃ | N | |
| CH(CH₃)₂ | OCH₂CH₂Cl | H | OCH₃ | N(CH₃)₂ | N | |
| CH₃ | OCH₂CH₂OCH₃ | H | CH₃ | CH₃ | CH | 167–169 (d) |
| CH₃ | OCH₂CH₂OCH₃ | H | OCH₃ | CH₃ | CH | oil |
| CH₃ | OCH₂CH₂OCH₃ | H | OCH₃ | OCH₃ | CH | 175–177 (d) |
| CH₃ | OCH₂CH₂OCH₃ | H | Cl | OCH₃ | CH | 98–100 (d) |
| CH₃ | OCH₂CH₂OCH₃ | H | OCH₃ | N(CH₃)₂ | CH | |
| CH₃ | OCH₂CH₂OCH₃ | H | CH₃ | CH₃ | N | 117–120 (d) |
| CH₃ | OCH₂CH₂OCH₃ | H | OCH₃ | CH₃ | N | 75–80 (d) |
| CH₃ | OCH₂CH₂OCH₃ | H | OCH₃ | OCH₃ | N | 154–156 (d) |
| CH₃ | OCH₂CH₂OCH₃ | H | OCH₃ | N(CH₃)₂ | N | |
| CH₃ | OCH₂CH₂OCH₃ | H | OCH₃ | OCH₂CF₃ | N | |
| CH₃ | OCH₂CH₂OCH₃ | CH₃ | OCH₃ | CH₃ | N | |
| CH₃ | OCH₂CH₂OCH₃ | CH₃ | OCH₃ | OCH₃ | N | |
| CH₃ | OCH₂CH₂OCH₃ | CH₃ | CH₃ | OCH₃ | CH | |
| CH₃ | OCH₂CH₂OCH₃ | CH₃ | OCH₃ | OCH₃ | CH | |
| CH₃ | OCH₂CH₂OCH₃ | H | Br | OCH₃ | CH | |
| CH₃ | OCH₂CH₂OCH₃ | H | CH₃ | OCH₂CF₃ | N | |
| CH₃ | OCH₂CH₂OCH₃ | H | CH₃ | OCH₂CF₃ | CH | |
| CH₃ | OCH₂CH₂OCH₃ | H | OCH₃ | OCH₂CF₃ | CH | |

TABLE I-continued

| | | | | | |
|---|---|---|---|---|---|
| CH₃ | OCH₂CH₂OCH₃ | H | OCH₃ | C₂H₅ | CH |
| CH₃ | OCH₂CH₂OCH₃ | H | OCH₃ | C₂H₅ | N |
| CH₃ | OCH₂CH₂OCH₃ | H | OCH₃ | NHCH₃ | CH |
| CH₃ | OCH₂CH₂OCH₃ | H | OCH₃ | NHCH₃ | N |
| CH₃ | OCH₂CH₂OCH₃ | H | CH₃ | OC₂H₅ | CH |
| CH₃ | OCH₂CH₂OCH₃ | H | OCH₃ | OC₂H₅ | CH |
| CH₃ | OCH₂CH₂OCH₃ | H | CH₃ | OC₂H₅ | N |
| CH₃ | OCH₂CH₂OCH₃ | H | OCH₃ | OC₂H₅ | N |
| CH₃ | OCH₂CH₂OCH₃ | H | CH₃ | OCH₂CHF₂ | CH |
| CH₃ | OCH₂CH₂OCH₃ | H | OCH₃ | OCH₂CHF₂ | CH |
| CH₃ | OCH₂CH₂OCH₃ | H | CH₃ | OCH₂CHF₂ | N |
| CH₃ | OCH₂CH₂OCH₃ | H | OCH₃ | OCH₂CHF₂ | N |
| CH₃ | OCH₂CH₂OCH₃ | H | CH₃ | OCH₂CH₂F | CH |
| CH₃ | OCH₂CH₂OCH₃ | H | OCH₃ | OCH₂CH₂F | CH |
| CH₃ | OCH₂CH₂OCH₃ | H | CH₃ | OCH₂CF₃ | N |
| CH₃ | OCH₂CH₂OCH₃ | CH₃ | OCH₃ | OCH₂CF₃ | N |
| CH₃ | OCH₂CH₂OCH₃ | CH₃ | Cl | OCH₃ | CH |
| CH₃ | OCH₂CH₂OCH₃ | H | Cl | N(CH₃)₂ | CH |
| CH₃ | OCH₂CH₂OCH₃ | H | Cl | OC₂H₅ | CH |
| C₂H₅ | OCH₂CH₂OCH₃ | H | Cl | OC₂H₅ | CH |
| C₂H₅ | OCH₂CH₂OCH₃ | H | CH₃ | CH₃ | CH |
| C₂H₅ | OCH₂CH₂OCH₃ | H | OCH₃ | CH₃ | CH |
| C₂H₅ | OCH₂CH₂OCH₃ | H | OCH₃ | OCH₃ | CH |
| C₂H₅ | OCH₂CH₂OCH₃ | H | Cl | OCH₃ | CH |
| C₂H₅ | OCH₂CH₂OCH₃ | H | CH₃ | CH₃ | N |
| C₂H₅ | OCH₂CH₂OCH₃ | H | OCH₃ | CH₃ | N |
| C₂H₅ | OCH₂CH₂OCH₃ | H | OCH₃ | OCH₃ | N |
| C₂H₅ | OCH₂CH₂OCH₃ | H | Br | OCH₃ | CH |
| C₂H₅ | OCH₂CH₂OCH₃ | H | OCH₃ | N(CH₃)₂ | CH |
| C₂H₅ | OCH₂CH₂OCH₃ | H | OCH₃ | N(CH₃)₂ | N |
| C₂H₅ | OCH₂CH₂OCH₃ | H | OCH₃ | NHCH₃ | N |
| C₂H₅ | OCH₂CH₂OCH₃ | H | OCH₃ | C₂H₅ | CH |
| C₂H₅ | OCH₂CH₂OCH₃ | H | OCH₃ | C₂H₅ | N |
| C₂H₅ | OCH₂CH₂OCH₃ | H | CH₃ | OC₂H₅ | CH |
| C₂H₅ | OCH₂CH₂OCH₃ | H | CH₃ | OC₂H₅ | N |
| C₂H₅ | OCH₂CH₂OCH₃ | H | OCH₃ | OC₂H₅ | CH |
| C₂H₅ | OCH₂CH₂OCH₃ | H | OCH₃ | OC₂H₅ | N |
| C₂H₅ | OCH₂CH₂OCH₃ | H | CH₃ | OCH₂CF₃ | CH |
| C₂H₅ | OCH₂CH₂OCH₃ | H | CH₃ | OCH₂CF₃ | N |
| C₂H₅ | OCH₂CH₂OCH₃ | H | OCH₃ | OCH₂CF₃ | CH |
| C₂H₅ | OCH₂CH₂OCH₃ | H | OCH₃ | OCH₂CF₃ | N |
| C₂H₅ | OCH₂CH₂OCH₃ | H | OCH₃ | OCH₂CHF₂ | CH |
| C₂H₅ | OCH₂CH₂OCH₃ | H | OCH₃ | OCH₂CHF₂ | N |
| C₂H₅ | OCH₂CH₂OCH₃ | H | CH₃ | OCH₂CHF₂ | N |
| C₂H₅ | OCH₂CH₂OCH₃ | H | OCH₃ | OCH₂CH₂F | CH |
| C₂H₅ | OCH₂CH₂OCH₃ | H | OCH₃ | OCH₂CH₂F | N |
| C₂H₅ | OCH₂CH₂OCH₃ | CH₃ | OCH₃ | OCH₃ | CH |
| C₂H₅ | OCH₂CH₂OCH₃ | CH₃ | CH₃ | OCH₃ | N |
| C₂H₅ | OCH₂CH₂OCH₃ | CH₃ | OCH₃ | OCH₃ | N |
| n-C₃H₇ | OCH₂CH₂OCH₃ | H | OCH₃ | OCH₃ | CH |
| n-C₃H₇ | OCH₂CH₂OCH₃ | H | CH₃ | OCH₃ | N |
| CH(CH₃)₂ | OCH₂CH₂OCH₃ | H | OCH₃ | CH₃ | CH |
| CH(CH₃)₂ | OCH₂CH₂OCH₃ | H | OCH₃ | OCH₃ | CH |
| CH(CH₃)₂ | OCH₂CH₂OCH₃ | H | Cl | OCH₃ | CH |
| CH(CH₃)₂ | OCH₂CH₂OCH₃ | H | OCH₃ | CH₃ | N |
| CH(CH₃)₂ | OCH₂CH₂OCH₃ | H | OCH₃ | OCH₃ | N |
| CH(CH₃)₂ | OCH₂CH₂OCH₃ | H | OCH₃ | N(CH₃)₂ | N |
| CH₃ | OCH₂CH₂S(O)CH₃ | H | OCH₃ | CH₃ | CH |
| CH₃ | OCH₂CH₂S(O)CH₃ | H | OCH₃ | OCH₃ | CH |
| CH₃ | OCH₂CH₂S(O)CH₃ | H | OCH₃ | OCH₃ | N |
| CH₃ | OCH₂CH₂S(O)CH₃ | H | OCH₃ | CH₃ | N |
| CH₃ | OCH₂CH₂SO₂CH₃ | H | OCH₃ | OCH₃ | N |
| CH₃ | OCH₂CH₂SO₂CH₃ | H | OCH₃ | CH₃ | N |
| CH₃ | OCH₂CH₂SO₂CH₃ | H | OCH₃ | OCH₃ | CH |
| CH₃ | OCH₂CH₂SO₂CH₃ | H | OCH₃ | CH₃ | CH |
| CH₃ | OCH₂CH₂SCH₃ | H | CH₃ | CH₃ | CH |
| CH₃ | OCH₂CH₂SCH₃ | H | OCH₃ | CH₃ | CH |
| CH₃ | OCH₂CH₂SCH₃ | H | OCH₃ | OCH₃ | CH |
| CH₃ | OCH₂CH₂SCH₃ | H | Cl | OCH₃ | CH |
| CH₃ | OCH₂CH₂SCH₃ | H | OCH₃ | N(CH₃)₂ | CH |
| CH₃ | OCH₂CH₂SCH₃ | H | CH₃ | CH₃ | N |
| CH₃ | OCH₂CH₂SCH₃ | H | OCH₃ | CH₃ | N |
| CH₃ | OCH₂CH₂SCH₃ | H | OCH₃ | OCH₃ | N |
| CH₃ | OCH₂CH₂SCH₃ | H | OCH₃ | N(CH₃)₂ | N |
| CH₃ | OCH₂CH₂SCH₃ | H | OCH₃ | OCH₂CF₃ | N |
| CH₃ | OCH₂CH₂SCH₃ | CH₃ | OCH₃ | CH₃ | N |
| CH₃ | OCH₂CH₂SCH₃ | CH₃ | OCH₃ | OCH₃ | N |
| CH₃ | OCH₂CH₂SCH₃ | CH₃ | CH₃ | OCH₃ | CH |
| CH₃ | OCH₂CH₂SCH₃ | CH₃ | OCH₃ | OCH₃ | CH |
| CH₃ | OCH₂CH₂SCH₃ | H | Br | OCH₃ | CH |
| CH₃ | OCH₂CH₂SCH₃ | CH₃ | OCH₃ | N(CH₃)₂ | N |
| CH₃ | OCH₂CH₂SCH₃ | H | CH₃ | OCH₂CF₃ | N |

TABLE I-continued

| | | | | | | |
|---|---|---|---|---|---|---|
| CH₃ | OCH₂CH₂SCH₃ | H | CH₃ | OCH₂CF₃ | CH | |
| CH₃ | OCH₂CH₂SCH₃ | H | OCH₃ | OCH₂CF₃ | CH | |
| CH₃ | OCH₂CH₂SCH₃ | H | OCH₃ | C₂H₅ | CH | |
| CH₃ | OCH₂CH₂SCH₃ | H | OCH₃ | C₂H₅ | N | |
| CH₃ | OCH₂CH₂SCH₃ | H | OCH₃ | NHCH₃ | CH | |
| CH₃ | OCH₂CH₂SCH₃ | H | OCH₃ | NHCH₃ | N | |
| CH₃ | OCH₂CH₂SCH₃ | H | CH₃ | OC₂H₅ | CH | |
| CH₃ | OCH₂CH₂SCH₃ | H | OCH₃ | OC₂H₅ | CH | |
| CH₃ | OCH₂CH₂SCH₃ | H | CH₃ | OC₂H₅ | N | |
| CH₃ | OCH₂CH₂SCH₃ | H | OCH₃ | OC₂H₅ | N | |
| CH₃ | OCH₂CH₂SCH₃ | H | CH₃ | OCH₂CHF₂ | CH | |
| CH₃ | OCH₂CH₂SCH₃ | H | OCH₃ | OCH₂CHF₂ | CH | |
| CH₃ | OCH₂CH₂SCH₃ | H | CH₃ | OCH₂CHF₂ | N | |
| CH₃ | OCH₂CH₂SCH₃ | H | OCH₃ | OCH₂CHF₂ | N | |
| CH₃ | OCH₂CH₂SCH₃ | H | CH₃ | OCH₂CH₂F | CH | |
| CH₃ | OCH₂CH₂SCH₃ | H | OCH₃ | OCH₂CH₂F | CH | |
| CH₃ | OCH₂CH₂SCH₃ | H | CH₃ | OCH₂CH₂F | N | |
| CH₃ | OCH₂CH₂SCH₃ | CH₃ | OCH₃ | OCH₂CH₂F | N | |
| CH₃ | OCH₂CH₂SCH₃ | CH₃ | Cl | OCH₃ | CH | |
| CH₃ | OCH₂CH₂SCH₃ | H | Cl | N(CH₃)₂ | CH | |
| CH₃ | OCH₂CH₂SCH₃ | H | Cl | OC₂H₅ | CH | |
| C₂H₅ | OCH₂CH₂SCH₃ | H | CH₃ | CH₃ | CH | |
| C₂H₅ | OCH₂CH₂SCH₃ | H | OCH₃ | CH₃ | CH | |
| C₂H₅ | OCH₂CH₂SCH₃ | H | OCH₃ | OCH₃ | CH | |
| C₂H₅ | OCH₂CH₂SCH₃ | H | Cl | OCH₃ | CH | |
| C₂H₅ | OCH₂CH₂SCH₃ | H | CH₃ | CH₃ | N | |
| C₂H₅ | OCH₂CH₂SCH₃ | H | OCH₃ | CH₃ | N | |
| C₂H₅ | OCH₂CH₂SCH₃ | H | OCH₃ | OCH₃ | N | |
| C₂H₅ | OCH₂CH₂SCH₃ | H | Br | OCH₃ | CH | |
| C₂H₅ | OCH₂CH₂SCH₃ | H | OCH₃ | N(CH₃)₂ | CH | |
| C₂H₅ | OCH₂CH₂SCH₃ | H | OCH₃ | N(CH₃)₂ | N | |
| C₂H₅ | OCH₂CH₂SCH₃ | H | OCH₃ | NHCH₃ | N | |
| C₂H₅ | OCH₂CH₂SCH₃ | H | OCH₃ | C₂H₅ | CH | |
| C₂H₅ | OCH₂CH₂SCH₃ | H | OCH₃ | C₂H₅ | N | |
| C₂H₅ | OCH₂CH₂SCH₃ | H | CH₃ | OC₂H₅ | CH | |
| C₂H₅ | OCH₂CH₂SCH₃ | H | CH₃ | OC₂H₅ | N | |
| C₂H₅ | OCH₂CH₂SCH₃ | H | OCH₃ | OC₂H₅ | CH | |
| C₂H₅ | OCH₂CH₂SCH₃ | H | OCH₃ | OC₂H₅ | N | |
| C₂H₅ | OCH₂CH₂SCH₃ | H | CH₃ | OCH₂CF₃ | CH | |
| C₂H₅ | OCH₂CH₂SCH₃ | H | CH₃ | OCH₂CF₃ | N | |
| C₂H₅ | OCH₂CH₂SCH₃ | H | OCH₃ | OCH₂CF₃ | CH | |
| C₂H₅ | OCH₂CH₂SCH₃ | H | OCH₃ | OCH₂CF₃ | N | |
| C₂H₅ | OCH₂CH₂SCH₃ | H | OCH₃ | OCH₂CHF₂ | CH | |
| C₂H₅ | OCH₂CH₂SCH₃ | H | OCH₃ | OCH₂CHF₂ | N | |
| C₂H₅ | OCH₂CH₂SCH₃ | H | CH₃ | OCH₂CHF₂ | N | |
| C₂H₅ | OCH₂CH₂SCH₃ | H | OCH₃ | OCH₂CH₂F | CH | |
| C₂H₅ | OCH₂CH₂SCH₃ | H | OCH₃ | OCH₂CH₂F | N | |
| C₂H₅ | OCH₂CH₂SCH₃ | CH₃ | OCH₃ | OCH₃ | CH | |
| C₂H₅ | OCH₂CH₂SCH₃ | CH₃ | CH₃ | OCH₃ | N | |
| C₂H₅ | OCH₂CH₂SCH₃ | CH₃ | OCH₃ | OCH₃ | N | |
| n-C₃H₇ | OCH₂CH₂SCH₃ | H | OCH₃ | OCH₃ | CH | |
| n-C₃H₇ | OCH₂CH₂SCH₃ | H | CH₃ | OCH₃ | N | |
| CH(CH₃)₂ | OCH₂CH₂SCH₃ | H | OCH₃ | CH₃ | CH | |
| CH(CH₃)₂ | OCH₂CH₂SCH₃ | H | OCH₃ | OCH₃ | CH | |
| CH(CH₃)₂ | OCH₂CH₂SCH₃ | H | Cl | OCH₃ | CH | |
| CH(CH₃)₂ | OCH₂CH₂SCH₃ | H | OCH₃ | CH₃ | N | |
| CH(CH₃)₂ | OCH₂CH₂SCH₃ | H | OCH₃ | OCH₃ | N | |
| CH(CH₃)₂ | OCH₂CH₂SCH₃ | H | OCH₃ | N(CH₃)₂ | N | |
| CH₃ | OCH₂CH₃ | H | OCH₂CH₃ | NHCH₃ | N | 205–207 |
| CH₃ | CH₂CH₃ | H | OCH₂CH₃ | NHCH₃ | N | 184–190 |
| CH₃ | SC(CH₃)₃ | H | OCH₂CH₃ | NHCH₃ | N | 145–147 |
| CH₃ | S(O)CH₂CH₃ | H | OCH₂CH₃ | NHCH₃ | N | 125–130 |
| CH₃ | S(O)CH₂CH₂CH₃ | H | OCH₂CH₃ | NHCH₃ | N | 123–124 |
| CH₃ | S(O)₂CH₃ | H | OCH₂CH₃ | NHCH₃ | N | 160–166 |

TABLE Ia

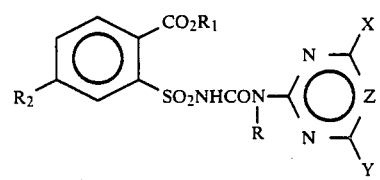

TABLE Ia-continued

| R₁ | R₂ | R | X | Y | Z | m.p. (°C.) |
|---|---|---|---|---|---|---|
| CH₃ | O-cyclopropyl | H | CH₃ | CH₃ | CH | |
| CH₃ | O-cyclopropyl | H | OCH₃ | CH₃ | CH | |
| CH₃ | O-cyclopropyl | H | OCH₃ | OCH₃ | CH | |
| CH₃ | O-cyclopropyl | H | Cl | OCH₃ | CH | |
| CH₃ | O-cyclopropyl | H | OCH₃ | N(CH₃)₂ | CH | |
| CH₃ | O-cyclopropyl | H | CH₃ | CH₃ | N | |
| CH₃ | O-cyclopropyl | H | OCH₃ | CH₃ | N | |
| CH₃ | O-cyclopropyl | H | OCH₃ | OCH₃ | N | |
| CH₃ | O-cyclopropyl | H | OCH₃ | N(CH₃)₂ | N | |
| CH₃ | O-cyclopropyl | H | OCH₃ | OCH₂CF₃ | N | |
| CH₃ | O-cyclopropyl | CH₃ | OCH₃ | CH₃ | N | |
| CH₃ | O-cyclopropyl | CH₃ | OCH₃ | OCH₃ | N | |
| CH₃ | O-cyclopropyl | CH₃ | CH₃ | OCH₃ | CH | |
| CH₃ | O-cyclopropyl | CH₃ | OCH₃ | OCH₃ | CH | |
| CH₃ | O-cyclopropyl | H | Br | OCH₃ | CH | |
| CH₃ | O-cyclopropyl | CH₃ | OCH₃ | N(CH₃)₂ | N | |
| CH₃ | O-cyclopropyl | H | CH₃ | OCH₂CF₃ | N | |
| CH₃ | O-cyclopropyl | H | CH₃ | OCH₂CF₃ | CH | |
| CH₃ | O-cyclopropyl | H | OCH₃ | OCH₂CF₃ | CH | |
| CH₃ | O-cyclopropyl | H | OCH₃ | C₂H₅ | CH | |
| CH₃ | O-cyclopropyl | H | OCH₃ | C₂H₅ | N | |
| CH₃ | O-cyclopropyl | H | OCH₃ | NHCH₃ | CH | |
| CH₃ | O-cyclopropyl | H | OCH₃ | NHCH₃ | N | |
| CH₃ | O-cyclopropyl | H | CH₃ | OC₂H₅ | CH | |
| CH₃ | O-cyclopropyl | H | OCH₃ | OC₂H₅ | CH | |
| CH₃ | O-cyclopropyl | H | CH₃ | OC₂H₅ | N | |
| CH₃ | O-cyclopropyl | H | OCH₃ | OC₂H₅ | N | |
| CH₃ | O-cyclopropyl | H | CH₃ | OCH₂CHF₂ | CH | |
| CH₃ | O-cyclopropyl | H | OCH₃ | OCH₂CHF₂ | CH | |
| CH₃ | O-cyclopropyl | H | CH₃ | OCH₂CHF₂ | N | |
| CH₃ | O-cyclopropyl | H | OCH₃ | OCH₂CHF₂ | N | |
| CH₃ | O-cyclopropyl | H | CH₃ | OCH₂CH₂F | CH | |
| CH₃ | O-cyclopropyl | H | OCH₃ | OCH₂CH₂F | CH | |
| CH₃ | O-cyclopropyl | H | CH₃ | OCH₂CH₂F | N | |
| CH₃ | O-cyclopropyl | CH₃ | OCH₃ | OCH₂CH₂F | N | |
| CH₃ | O-cyclopropyl | CH₃ | Cl | OCH₃ | CH | |
| CH₃ | O-cyclopropyl | H | Cl | N(CH₃)₂ | CH | |
| CH₃ | O-cyclopropyl | H | Cl | OC₂H₅ | CH | |
| C₂H₅ | O-cyclopropyl | H | CH₃ | CH₃ | CH | |
| C₂H₅ | O-cyclopropyl | H | OCH₃ | CH₃ | CH | |
| C₂H₅ | O-cyclopropyl | H | OCH₃ | OCH₃ | CH | |
| C₂H₅ | O-cyclopropyl | H | Cl | OCH₃ | CH | |
| C₂H₅ | O-cyclopropyl | H | CH₃ | CH₃ | N | |
| C₂H₅ | O-cyclopropyl | H | OCH₃ | CH₃ | N | |
| C₂H₅ | O-cyclopropyl | H | OCH₃ | OCH₃ | N | |
| C₂H₅ | O-cyclopropyl | H | Br | OCH₃ | CH | |
| C₂H₅ | O-cyclopropyl | H | OCH₃ | N(CH₃)₂ | CH | |
| C₂H₅ | O-cyclopropyl | H | OCH₃ | N(CH₃)₂ | N | |
| C₂H₅ | O-cyclopropyl | H | OCH₃ | NHCH₃ | N | |
| C₂H₅ | O-cyclopropyl | H | OCH₃ | C₂H₅ | CH | |
| C₂H₅ | O-cyclopropyl | H | OCH₃ | C₂H₅ | N | |
| C₂H₅ | O-cyclopropyl | H | CH₃ | OC₂H₅ | CH | |
| C₂H₅ | O-cyclopropyl | H | CH₃ | OC₂H₅ | N | |
| C₂H₅ | O-cyclopropyl | H | OCH₃ | OC₂H₅ | CH | |
| C₂H₅ | O-cyclopropyl | H | OCH₃ | OC₂H₅ | N | |
| C₂H₅ | O-cyclopropyl | H | CH₃ | OCH₂CF₃ | CH | |
| C₂H₅ | O-cyclopropyl | H | CH₃ | OCH₂CF₃ | N | |
| C₂H₅ | O-cyclopropyl | H | OCH₃ | OCH₂CF₃ | CH | |
| C₂H₅ | O-cyclopropyl | H | OCH₃ | OCH₂CF₃ | N | |
| C₂H₅ | O-cyclopropyl | H | OCH₃ | OCH₂CHF₂ | CH | |
| C₂H₅ | O-cyclopropyl | H | OCH₃ | OCH₂CHF₂ | N | |
| C₂H₅ | O-cyclopropyl | H | CH₃ | OCH₂CHF₂ | N | |
| C₂H₅ | O-cyclopropyl | H | OCH₃ | OCH₂CH₂F | CH | |
| C₂H₅ | O-cyclopropyl | H | OCH₃ | OCH₂CH₂F | N | |
| C₂H₅ | O-cyclopropyl | CH₃ | OCH₃ | OCH₃ | CH | |
| C₂H₅ | O-cyclopropyl | CH₃ | CH₃ | OCH₃ | N | |
| C₂H₅ | O-cyclopropyl | CH₃ | OCH₃ | OCH₃ | N | |
| n-C₃H₇ | O-cyclopropyl | H | OCH₃ | OCH₃ | CH | |
| n-C₃H₇ | O-cyclopropyl | H | CH₃ | OCH₃ | N | |
| CH(CH₃)₂ | O-cyclopropyl | H | OCH₃ | CH₃ | CH | |
| CH(CH₃)₂ | O-cyclopropyl | H | OCH₃ | OCH₃ | CH | |
| CH(CH₃)₂ | O-cyclopropyl | H | Cl | OCH₃ | CH | |
| CH(CH₃)₂ | O-cyclopropyl | H | OCH₃ | CH₃ | N | |
| CH(CH₃)₂ | O-cyclopropyl | H | OCH₃ | OCH₃ | N | |
| CH(CH₃)₂ | O-cyclopropyl | H | OCH₃ | N(CH₃)₂ | N | |
| CH₃ | OCH₂-cyclopropyl | H | OCH₃ | OCH₃ | CH | 183–185 |
| CH₃ | OCH₂-cyclopropyl | H | OCH₃ | CH₃ | CH | |
| CH₃ | OCH₂-cyclopropyl | H | OCH₃ | Cl | CH | 146–149 |
| CH₃ | OCH₂-cyclopropyl | H | CH₃ | CH₃ | CH | |
| CH₃ | OCH₂-cyclopropyl | H | OCH₃ | OCH₃ | N | |
| CH₃ | OCH₂-cyclopropyl | H | OCH₃ | CH₃ | N | 153–156 |

TABLE Ia-continued

| | | | | | |
|---|---|---|---|---|---|
| CH₃ | O-cyclobutyl | H | OCH₃ | OCH₃ | CH |
| CH₃ | O-cyclobutyl | H | OCH₃ | CH₃ | CH |
| CH₃ | O-cyclobutyl | H | OCH₃ | Cl | CH |
| CH₃ | O-cyclobutyl | H | CH₃ | CH₃ | CH |
| CH₃ | O-cyclobutyl | H | OCH₃ | OCH₃ | N |
| CH₂CH₃ | O-cyclobutyl | H | OCH₃ | CH₃ | N |
| CH₃ | OCH₂CF₂CF₃ | H | OCH₃ | OCH₃ | CH |
| CH₃ | OCH₂CF₂CF₃ | H | OCH₃ | CH₃ | CH |
| CH₃ | OCH₂CF₂CF₃ | H | OCH₃ | Cl | CH |
| CH₃ | OCH₂CF₂CF₃ | H | CH₃ | CH₃ | CH |
| CH₃ | OCH₂CF₂CF₃ | H | OCH₃ | OCH₃ | N |
| CH₃ | OCH₂CF₂CF₃ | H | OCH₃ | CH₃ | N |
| CH₃ | OCH(CF₃)CH₃ | H | OCH₃ | OCH₃ | CH |
| CH₃ | OCH(CF₃)CH₃ | H | OCH₃ | CH₃ | CH |
| CH₃ | OCH(CF₃)CH₃ | H | OCH₃ | Cl | CH |
| CH₃ | OCH(CF₃)CH₃ | H | CH₃ | CH₃ | CH |
| CH₃ | OCH(CF₃)CH₃ | H | OCH₃ | OCH₃ | N |
| CH₃ | OCH(CF₃)CH₃ | H | OCH₃ | CH₃ | N |
| CH₃ | OCH₂CF₂CF₂H | H | OCH₃ | OCH₃ | CH |
| CH₃ | OCH₂CF₂CF₂H | H | OCH₃ | CH₃ | CH |
| CH₃ | OCH₂CF₂CF₂H | H | OCH₃ | Cl | CH |
| CH₃ | OCH₂CF₂CF₂H | H | CH₃ | CH₃ | CH |
| CH₃ | OCH₂CF₂CF₂H | H | OCH₃ | OCH₃ | N |
| CH₂CH₃ | OCH₂CF₂CF₂H | H | OCH₃ | CH₃ | N |
| CH₃ | OCH(CH₂F)₂ | H | OCH₃ | OCH₃ | CH |
| CH₃ | OCH(CH₂F)₂ | H | OCH₃ | CH₃ | CH |
| CH₃ | OCH(CH₂F)₂ | H | OCH₃ | Cl | CH |
| CH₃ | OCH(CH₂F)₂ | H | CH₃ | CH₃ | CH |
| CH₃ | OCH(CH₂F)₂ | H | OCH₃ | OCH₃ | N |
| CH₃ | OCH(CH₂F)₂ | H | OCH₃ | CH₃ | N |
| CH₃ | OCH(CH₂F)CH₃ | H | OCH₃ | OCH₃ | CH |
| CH₃ | OCH(CH₂F)CH₃ | H | OCH₃ | CH₃ | CH |
| CH₃ | OCH(CH₂F)CH₃ | H | OCH₃ | Cl | CH |
| CH₃ | OCH(CH₂F)CH₃ | H | CH₃ | CH₃ | CH |
| CH₃ | OCH(CH₂F)CH₃ | H | OCH₃ | OCH₃ | N |
| CH₃ | OCH(CH₂F)CH₃ | H | OCH₃ | CH₃ | N |
| CH₃ | O(CH₂)₅CH₂Cl | H | OCH₃ | OCH₃ | CH |
| CH₃ | O(CH₂)₅CH₂Cl | H | OCH₃ | CH₃ | CH |
| CH₃ | O(CH₂)₅CH₂Cl | H | OCH₃ | Cl | CH |
| CH₃ | O(CH₂)₅CH₂Cl | H | CH₃ | CH₃ | CH |
| CH₃ | O(CH₂)₅CH₂Cl | H | OCH₃ | OCH₃ | N |
| CH₂CH₃ | O(CH₂)₅CH₂Cl | H | OCH₃ | CH₃ | N |
| CH₃ | OC(Cl)CHCl | H | OCH₃ | OCH₃ | CH |
| CH₃ | OC(Cl)CHCl | H | OCH₃ | CH₃ | CH |
| CH₃ | OC(Cl)CHCl | H | OCH₃ | Cl | CH |
| CH₃ | OC(Cl)CHCl | H | CH₃ | CH₃ | CH |
| CH₃ | OC(Cl)CHCl | H | OCH₃ | OCH₃ | N |
| CH₃ | OC(Cl)CHCl | H | OCH₃ | CH₃ | N |
| CH₃ | OCH₂C(Cl)CH₂ | H | OCH₃ | OCH₃ | CH |
| CH₃ | OCH₂C(Cl)CH₂ | H | OCH₃ | CH₃ | CH |
| CH₃ | OCH₂C(Cl)CH₂ | H | OCH₃ | Cl | CH |
| CH₃ | OCH₂C(Cl)CH₂ | H | CH₃ | CH₃ | CH |
| CH₃ | OCH₂C(Cl)CH₂ | H | OCH₃ | OCH₃ | N |
| CH₃ | OCH₂C(Cl)CH₂ | H | OCH₃ | CH₃ | N |
| CH₃ | OCH₂CCCH₂Cl | H | OCH₃ | OCH₃ | CH |
| CH₃ | OCH₂CCCH₂Cl | H | OCH₃ | CH₃ | CH |
| CH₃ | OCH₂CCCH₂Cl | H | OCH₃ | Cl | CH |
| CH₃ | OCH₂CCCH₂Cl | H | CH₃ | CH₃ | CH |
| CH₃ | OCH₂CCCH₂Cl | H | OCH₃ | OCH₃ | N |
| CH₂CH₃ | OCH₂CCCH₂Cl | H | OCH₃ | CH₃ | N |
| CH₃ | OCH₂OCH₃ | H | OCH₃ | OCH₃ | CH |
| CH₃ | OCH₂OCH₃ | H | OCH₃ | CH₃ | CH |
| CH₃ | OCH₂OCH₃ | H | OCH₃ | Cl | CH |
| CH₃ | OCH₂OCH₃ | H | CH₃ | CH₃ | CH |
| CH₃ | OCH₂OCH₃ | H | OCH₃ | OCH₃ | N |
| CH₃ | OCH₂OCH₃ | H | OCH₃ | CH₃ | N |
| CH₃ | OCH₂OCH₂CF₃ | H | OCH₃ | OCH₃ | CH |
| CH₃ | OCH₂OCH₂CF₃ | H | OCH₃ | CH₃ | CH |
| CH₃ | OCH₂OCH₂CF₃ | H | OCH₃ | Cl | CH |
| CH₃ | OCH₂OCH₂CF₃ | H | CH₃ | CH₃ | CH |
| CH₃ | OCH₂OCH₂CF₃ | H | OCH₃ | OCH₃ | N |
| CH₃ | OCH₂OCH₂CF₃ | H | OCH₃ | CH₃ | N |
| CH₃ | OCH₂SCH₃ | H | OCH₃ | OCH₃ | CH |
| CH₃ | OCH₂SCH₃ | H | OCH₃ | CH₃ | CH |
| CH₃ | OCH₂SCH₃ | H | OCH₃ | Cl | CH |
| CH₃ | OCH₂SCH₃ | H | CH₃ | CH₃ | CH |
| CH₃ | OCH₂SCH₃ | H | OCH₃ | OCH₃ | N |
| CH₂CH₃ | OCH₂SCH₃ | H | OCH₃ | CH₃ | N |
| CH₃ | OCH₂CN | H | OCH₃ | OCH₃ | CH |
| CH₃ | OCH₂CN | H | OCH₃ | CH₃ | CH |
| CH₃ | OCH₂CN | H | OCH₃ | Cl | CH |
| CH₃ | OCH₂CN | H | CH₃ | CH₃ | CH |

TABLE Ia-continued

| | | | | | |
|---|---|---|---|---|---|
| CH$_3$ | OCH$_2$CN | H | OCH$_3$ | OCH$_3$ | N |
| CH$_3$ | OCH$_2$CN | H | OCH$_3$ | CH$_3$ | N |
| CH$_3$ | OCH$_2$C(O)CH$_3$ | H | OCH$_3$ | OCH$_3$ | CH |
| CH$_3$ | OCH$_2$C(O)CH$_3$ | H | OCH$_3$ | CH$_3$ | CH |
| CH$_3$ | OCH$_2$C(O)CH$_3$ | H | OCH$_3$ | Cl | CH |
| CH$_3$ | OCH$_2$C(O)CH$_3$ | H | CH$_3$ | CH$_3$ | CH |
| CH$_3$ | OCH$_2$C(O)CH$_3$ | H | OCH$_3$ | OCH$_3$ | N |
| CH$_3$ | OCH$_2$C(O)CH$_3$ | H | OCH$_3$ | CH$_3$ | N |
| CH$_3$ | OCH$_2$CH$_2$N(CH$_3$)$_2$ | H | OCH$_3$ | OCH$_3$ | CH |
| CH$_3$ | OCH$_2$CH$_2$N(CH$_3$)$_2$ | H | OCH$_3$ | CH$_3$ | CH |
| CH$_3$ | OCH$_2$CH$_2$N(CH$_3$)$_2$ | H | OCH$_3$ | Cl | CH |
| CH$_3$ | OCH$_2$CH$_2$N(CH$_3$)$_2$ | H | CH$_3$ | CH$_3$ | CH |
| CH$_3$ | OCH$_2$CH$_2$N(CH$_3$)$_2$ | H | OCH$_3$ | OCH$_3$ | N |
| CH$_2$CH$_3$ | OCH$_2$CH$_2$N(CH$_3$)$_2$ | H | OCH$_3$ | CH$_3$ | N |
| CH$_3$ | OCH$_2$CH$_2$OCH$_2$CF$_3$ | H | OCH$_3$ | OCH$_3$ | CH |
| CH$_3$ | OCH$_2$CH$_2$OCH$_2$CF$_3$ | H | OCH$_3$ | CH$_3$ | CH |
| CH$_3$ | OCH$_2$CH$_2$OCH$_2$CF$_3$ | H | OCH$_3$ | Cl | CH |
| CH$_3$ | OCH$_2$CH$_2$OCH$_2$CF$_3$ | H | CH$_3$ | CH$_3$ | CH |
| CH$_3$ | OCH$_2$CH$_2$OCH$_2$CF$_3$ | H | OCH$_3$ | OCH$_3$ | N |
| CH$_3$ | OCH$_2$CH$_2$OCH$_2$CF$_3$ | H | OCH$_3$ | CH$_3$ | N |
| CH$_3$ | OCH$_2$CH$_2$SCH$_2$CF$_3$ | H | OCH$_3$ | OCH$_3$ | CH |
| CH$_3$ | OCH$_2$CH$_2$SCH$_2$CF$_3$ | H | OCH$_3$ | CH$_3$ | CH |
| CH$_3$ | OCH$_2$CH$_2$SCH$_2$CF$_3$ | H | OCH$_3$ | Cl | CH |
| CH$_3$ | OCH$_2$CH$_2$SCH$_2$CF$_3$ | H | CH$_3$ | CH$_3$ | CH |
| CH$_3$ | OCH$_2$CH$_2$SCH$_2$CF$_3$ | H | OCH$_3$ | OCH$_3$ | N |
| CH$_3$ | OCH$_2$CH$_2$SCH$_2$CF$_3$ | H | OCH$_3$ | CH$_3$ | N |
| CH$_3$ | OCF$_2$CF$_2$H | H | OCH$_3$ | OCH$_3$ | CH |
| CH$_3$ | OCF$_2$CF$_2$H | H | OCH$_3$ | CH$_3$ | CH |
| CH$_3$ | OCF$_2$CF$_2$H | H | OCH$_3$ | Cl | CH |
| CH$_3$ | OCF$_2$CF$_2$H | H | CH$_3$ | CH$_3$ | CH |
| CH$_3$ | OCF$_2$CF$_2$H | H | OCH$_3$ | OCH$_3$ | N |
| CH$_2$CH$_3$ | OCF$_2$CF$_2$H | H | OCH$_3$ | CH$_3$ | N |
| CH$_3$ | OCH$_2$CH$_2$S(O)CH$_2$CF$_3$ | H | OCH$_3$ | OCH$_3$ | CH |
| CH$_3$ | OCH$_2$CH$_2$S(O)CH$_2$CF$_3$ | H | OCH$_3$ | CH$_3$ | CH |
| CH$_3$ | OCH$_2$CH$_2$S(O)CH$_2$CF$_3$ | H | OCH$_3$ | Cl | CH |
| CH$_3$ | OCH$_2$CH$_2$S(O)CH$_2$CF$_3$ | H | CH$_3$ | CH$_3$ | CH |
| CH$_3$ | OCH$_2$CH$_2$S(O)CH$_2$CF$_3$ | H | OCH$_3$ | OCH$_3$ | N |
| CH$_3$ | OCH$_2$CH$_2$S(O)CH$_2$CF$_3$ | H | OCH$_3$ | CH$_3$ | N |
| CH$_3$ | OCH$_2$CH$_2$S(O)$_2$CH$_2$CF$_3$ | H | OCH$_3$ | OCH$_3$ | CH |
| CH$_3$ | OCH$_2$CH$_2$S(O)$_2$CH$_2$CF$_3$ | H | OCH$_3$ | CH$_3$ | CH |
| CH$_3$ | OCH$_2$CH$_2$S(O)$_2$CH$_2$CF$_3$ | H | OCH$_3$ | Cl | CH |
| CH$_3$ | OCH$_2$CH$_2$S(O)$_2$CH$_2$CF$_3$ | H | CH$_3$ | CH$_3$ | CH |
| CH$_3$ | OCH$_2$CH$_2$S(O)$_2$CH$_2$CF$_3$ | H | OCH$_3$ | OCH$_3$ | N |
| CH$_3$ | OCH$_2$CH$_2$S(O)$_2$CH$_2$CF$_3$ | H | OCH$_3$ | CH$_3$ | N |
| CH$_3$ | OCH$_2$CH$_2$CN | H | OCH$_3$ | OCH$_3$ | CH |
| CH$_3$ | OCH$_2$CH$_2$CN | H | OCH$_3$ | CH$_3$ | CH |
| CH$_3$ | OCH$_2$CH$_2$CN | H | OCH$_3$ | Cl | CH |
| CH$_3$ | OCH$_2$CH$_2$CN | H | CH$_3$ | CH$_3$ | CH |
| CH$_3$ | OCH$_2$CH$_2$CN | H | OCH$_3$ | OCH$_3$ | N |
| CH$_2$CH$_3$ | OCH$_2$CH$_2$CN | H | OCH$_3$ | CH$_3$ | N |
| CH$_3$ | S-cyclopropyl | H | OCH$_3$ | OCH$_3$ | CH |
| CH$_3$ | S-cyclopropyl | H | OCH$_3$ | CH$_3$ | CH |
| CH$_3$ | S-cyclopropyl | H | OCH$_3$ | Cl | CH |
| CH$_3$ | S-cyclopropyl | H | CH$_3$ | CH$_3$ | CH |
| CH$_3$ | S-cyclopropyl | H | OCH$_3$ | OCH$_3$ | N |
| CH$_3$ | S-cyclopropyl | H | OCH$_3$ | CH$_3$ | N |
| CH$_3$ | SCH$_2$-cyclopropyl | H | OCH$_3$ | OCH$_3$ | CH |
| CH$_3$ | SCH$_2$-cyclopropyl | H | OCH$_3$ | CH$_3$ | CH |
| CH$_3$ | SCH$_2$-cyclopropyl | H | OCH$_3$ | Cl | CH |
| CH$_3$ | SCH$_2$-cyclopropyl | H | CH$_3$ | CH$_3$ | CH |
| CH$_3$ | SCH$_2$-cyclopropyl | H | OCH$_3$ | OCH$_3$ | N |
| CH$_3$ | SCH$_2$-cyclopropyl | H | OCH$_3$ | CH$_3$ | N |
| CH$_3$ | S-cyclobutyl | H | OCH$_3$ | OCH$_3$ | CH |
| CH$_3$ | S-cyclobutyl | H | OCH$_3$ | CH$_3$ | CH |
| CH$_3$ | S-cyclobutyl | H | OCH$_3$ | Cl | CH |
| CH$_3$ | S-cyclobutyl | H | CH$_3$ | CH$_3$ | CH |
| CH$_3$ | S-cyclobutyl | H | OCH$_3$ | OCH$_3$ | N |
| CH$_2$CH$_3$ | S-cyclobutyl | H | OCH$_3$ | CH$_3$ | N |
| CH$_3$ | SCH$_2$CF$_2$CF$_3$ | H | OCH$_3$ | OCH$_3$ | CH |
| CH$_3$ | SCH$_2$CF$_2$CF$_3$ | H | OCH$_3$ | CH$_3$ | CH |
| CH$_3$ | SCH$_2$CF$_2$CF$_3$ | H | OCH$_3$ | Cl | CH |
| CH$_3$ | SCH$_2$CF$_2$CF$_3$ | H | CH$_3$ | CH$_3$ | CH |
| CH$_3$ | SCH$_2$CF$_2$CF$_3$ | H | OCH$_3$ | OCH$_3$ | N |
| CH$_3$ | SCH$_2$CF$_2$CF$_3$ | H | OCH$_3$ | CH$_3$ | N |
| CH$_3$ | SCH(CF$_3$)CH$_3$ | H | OCH$_3$ | OCH$_3$ | CH |
| CH$_3$ | SCH(CF$_3$)CH$_3$ | H | OCH$_3$ | CH$_3$ | CH |
| CH$_3$ | SCH(CF$_3$)CH$_3$ | H | OCH$_3$ | Cl | CH |
| CH$_3$ | SCH(CF$_3$)CH$_3$ | H | CH$_3$ | CH$_3$ | CH |
| CH$_3$ | SCH(CF$_3$)CH$_3$ | H | OCH$_3$ | OCH$_3$ | N |
| CH$_3$ | SCH(CF$_3$)CH$_3$ | H | OCH$_3$ | CH$_3$ | N |
| CH$_3$ | SCH$_2$CF$_2$CF$_2$H | H | OCH$_3$ | OCH$_3$ | CH |
| CH$_3$ | SCH$_2$CF$_2$CF$_2$H | H | OCH$_3$ | CH$_3$ | CH |

TABLE Ia-continued

| | | | | | |
|---|---|---|---|---|---|
| CH$_3$ | SCH$_2$CF$_2$CF$_2$H | H | OCH$_3$ | Cl | CH |
| CH$_3$ | SCH$_2$CF$_2$CF$_2$H | H | CH$_3$ | CH$_3$ | CH |
| CH$_3$ | SCH$_2$CF$_2$CF$_2$H | H | OCH$_3$ | OCH$_3$ | N |
| CH$_2$CH$_3$ | SCH$_2$CF$_2$CF$_2$H | H | OCH$_3$ | CH$_3$ | N |
| CH$_3$ | SCH(CH$_2$F)$_2$ | H | OCH$_3$ | OCH$_3$ | CH |
| CH$_3$ | SCH(CH$_2$F)$_2$ | H | OCH$_3$ | CH$_3$ | CH |
| CH$_3$ | SCH(CH$_2$F)$_2$ | H | OCH$_3$ | Cl | CH |
| CH$_3$ | SCH(CH$_2$F)$_2$ | H | CH$_3$ | CH$_3$ | CH |
| CH$_3$ | SCH(CH$_2$F)$_2$ | H | OCH$_3$ | OCH$_3$ | N |
| CH$_3$ | SCH(CH$_2$F)$_2$ | H | OCH$_3$ | CH$_3$ | N |
| CH$_3$ | SCH(CH$_2$F)CH$_3$ | H | OCH$_3$ | OCH$_3$ | CH |
| CH$_3$ | SCH(CH$_2$F)CH$_3$ | H | OCH$_3$ | CH$_3$ | CH |
| CH$_3$ | SCH(CH$_2$F)CH$_3$ | H | OCH$_3$ | Cl | CH |
| CH$_3$ | SCH(CH$_2$F)CH$_3$ | H | CH$_3$ | CH$_3$ | CH |
| CH$_3$ | SCH(CH$_2$F)CH$_3$ | H | OCH$_3$ | OCH$_3$ | N |
| CH$_3$ | SCH(CH$_2$F)CH$_3$ | H | OCH$_3$ | CH$_3$ | N |
| CH$_3$ | S(CH$_2$)$_5$CH$_2$Cl | H | OCH$_3$ | OCH$_3$ | CH |
| CH$_3$ | S(CH$_2$)$_5$CH$_2$Cl | H | OCH$_3$ | CH$_3$ | CH |
| CH$_3$ | S(CH$_2$)$_5$CH$_2$Cl | H | OCH$_3$ | Cl | CH |
| CH$_3$ | S(CH$_2$)$_5$CH$_2$Cl | H | CH$_3$ | CH$_3$ | CH |
| CH$_3$ | S(CH$_2$)$_5$CH$_2$Cl | H | OCH$_3$ | OCH$_3$ | N |
| CH$_2$CH$_3$ | S(CH$_2$)$_5$CH$_2$Cl | H | OCH$_3$ | CH$_3$ | N |
| CH$_3$ | SC(Cl)CHCl | H | OCH$_3$ | OCH$_3$ | CH |
| CH$_3$ | SC(Cl)CHCl | H | OCH$_3$ | CH$_3$ | CH |
| CH$_3$ | SC(Cl)CHCl | H | OCH$_3$ | Cl | CH |
| CH$_3$ | SC(Cl)CHCl | H | CH$_3$ | CH$_3$ | CH |
| CH$_3$ | SC(Cl)CHCl | H | OCH$_3$ | OCH$_3$ | N |
| CH$_3$ | SC(Cl)CHCl | H | OCH$_3$ | CH$_3$ | N |
| CH$_3$ | SCH$_2$C(Cl)CH$_2$ | H | OCH$_3$ | OCH$_3$ | CH |
| CH$_3$ | SCH$_2$C(Cl)CH$_2$ | H | OCH$_3$ | CH$_3$ | CH |
| CH$_3$ | SCH$_2$C(Cl)CH$_2$ | H | OCH$_3$ | Cl | CH |
| CH$_3$ | SCH$_2$C(Cl)CH$_2$ | H | CH$_3$ | CH$_3$ | CH |
| CH$_3$ | SCH$_2$C(Cl)CH$_2$ | H | OCH$_3$ | OCH$_3$ | N |
| CH$_3$ | SCH$_2$C(Cl)CH$_2$ | H | OCH$_3$ | CH$_3$ | N |
| CH$_3$ | SCH$_2$CCCH$_2$Cl | H | OCH$_3$ | OCH$_3$ | CH |
| CH$_3$ | SCH$_2$CCCH$_2$Cl | H | OCH$_3$ | CH$_3$ | CH |
| CH$_3$ | SCH$_2$CCCH$_2$Cl | H | OCH$_3$ | Cl | CH |
| CH$_3$ | SCH$_2$CCCH$_2$Cl | H | CH$_3$ | CH$_3$ | CH |
| CH$_3$ | SCH$_2$CCCH$_2$Cl | H | OCH$_3$ | OCH$_3$ | N |
| CH$_2$CH$_3$ | SCH$_2$CCCH$_2$Cl | H | OCH$_3$ | CH$_3$ | N |
| CH$_3$ | SCH$_2$OCH$_3$ | H | OCH$_3$ | OCH$_3$ | CH |
| CH$_3$ | SCH$_2$OCH$_3$ | H | OCH$_3$ | CH$_3$ | CH |
| CH$_3$ | SCH$_2$OCH$_3$ | H | OCH$_3$ | Cl | CH |
| CH$_3$ | SCH$_2$OCH$_3$ | H | CH$_3$ | CH$_3$ | CH |
| CH$_3$ | SCH$_2$OCH$_3$ | H | OCH$_3$ | OCH$_3$ | N |
| CH$_3$ | SCH$_2$OCH$_3$ | H | OCH$_3$ | CH$_3$ | N |
| CH$_3$ | SCH$_2$OCH$_2$CF$_3$ | H | OCH$_3$ | OCH$_3$ | CH |
| CH$_3$ | SCH$_2$OCH$_2$CF$_3$ | H | OCH$_3$ | CH$_3$ | CH |
| CH$_3$ | SCH$_2$OCH$_2$CF$_3$ | H | OCH$_3$ | Cl | CH |
| CH$_3$ | SCH$_2$OCH$_2$CF$_3$ | H | CH$_3$ | CH$_3$ | CH |
| CH$_3$ | SCH$_2$OCH$_2$CF$_3$ | H | OCH$_3$ | OCH$_3$ | N |
| CH$_3$ | SCH$_2$OCH$_2$CF$_3$ | H | OCH$_3$ | CH$_3$ | N |
| CH$_3$ | SCH$_2$SCH$_3$ | H | OCH$_3$ | OCH$_3$ | CH |
| CH$_3$ | SCH$_2$SCH$_3$ | H | OCH$_3$ | CH$_3$ | CH |
| CH$_3$ | SCH$_2$SCH$_3$ | H | OCH$_3$ | Cl | CH |
| CH$_3$ | SCH$_2$SCH$_3$ | H | CH$_3$ | CH$_3$ | CH |
| CH$_3$ | SCH$_2$SCH$_3$ | H | OCH$_3$ | OCH$_3$ | N |
| CH$_2$CH$_3$ | SCH$_2$SCH$_3$ | H | OCH$_3$ | CH$_3$ | N |
| CH$_3$ | SCH$_2$CN | H | OCH$_3$ | OCH$_3$ | CH |
| CH$_3$ | SCH$_2$CN | H | OCH$_3$ | CH$_3$ | CH |
| CH$_3$ | SCH$_2$CN | H | OCH$_3$ | Cl | CH |
| CH$_3$ | SCH$_2$CN | H | CH$_3$ | CH$_3$ | CH |
| CH$_3$ | SCH$_2$CN | H | OCH$_3$ | OCH$_3$ | N |
| CH$_3$ | SCH$_2$CN | H | OCH$_3$ | CH$_3$ | N |
| CH$_3$ | SCH$_2$C(O)CH$_3$ | H | OCH$_3$ | OCH$_3$ | CH |
| CH$_3$ | SCH$_2$C(O)CH$_3$ | H | OCH$_3$ | CH$_3$ | CH |
| CH$_3$ | SCH$_2$C(O)CH$_3$ | H | OCH$_3$ | Cl | CH |
| CH$_3$ | SCH$_2$C(O)CH$_3$ | H | CH$_3$ | CH$_3$ | CH |
| CH$_3$ | SCH$_2$C(O)CH$_3$ | H | OCH$_3$ | OCH$_3$ | N |
| CH$_3$ | SCH$_2$C(O)CH$_3$ | H | OCH$_3$ | CH$_3$ | N |
| CH$_3$ | SCH$_2$CH$_2$N(CH$_3$)$_2$ | H | OCH$_3$ | OCH$_3$ | CH |
| CH$_3$ | SCH$_2$CH$_2$N(CH$_3$)$_2$ | H | OCH$_3$ | CH$_3$ | CH |
| CH$_3$ | SCH$_2$CH$_2$N(CH$_3$)$_2$ | H | OCH$_3$ | Cl | CH |
| CH$_3$ | SCH$_2$CH$_2$N(CH$_3$)$_2$ | H | CH$_3$ | CH$_3$ | CH |
| CH$_3$ | SCH$_2$CH$_2$N(CH$_3$)$_2$ | H | OCH$_3$ | OCH$_3$ | N |
| CH$_2$CH$_3$ | SCH$_2$CH$_2$N(CH$_3$)$_2$ | H | OCH$_3$ | CH$_3$ | N |
| CH$_3$ | SCH$_2$CH$_2$OCH$_2$CF$_3$ | H | OCH$_3$ | OCH$_3$ | CH |
| CH$_3$ | SCH$_2$CH$_2$OCH$_2$CF$_3$ | H | OCH$_3$ | CH$_3$ | CH |
| CH$_3$ | SCH$_2$CH$_2$OCH$_2$CF$_3$ | H | OCH$_3$ | Cl | CH |
| CH$_3$ | SCH$_2$CH$_2$OCH$_2$CF$_3$ | H | CH$_3$ | CH$_3$ | CH |
| CH$_3$ | SCH$_2$CH$_2$OCH$_2$CF$_3$ | H | OCH$_3$ | OCH$_3$ | N |
| CH$_3$ | SCH$_2$CH$_2$OCH$_2$CF$_3$ | H | OCH$_3$ | CH$_3$ | N |

TABLE Ia-continued

| | | | | | | |
|---|---|---|---|---|---|---|
| CH$_3$ | SCH$_2$CH$_2$SCH$_2$CF$_3$ | H | OCH$_3$ | OCH$_3$ | CH | |
| CH$_3$ | SCH$_2$CH$_2$SCH$_2$CF$_3$ | H | OCH$_3$ | CH$_3$ | CH | |
| CH$_3$ | SCH$_2$CH$_2$SCH$_2$CF$_3$ | H | OCH$_3$ | Cl | CH | |
| CH$_3$ | SCH$_2$CH$_2$SCH$_2$CF$_3$ | H | CH$_3$ | CH$_3$ | CH | |
| CH$_3$ | SCH$_2$CH$_2$SCH$_2$CF$_3$ | H | OCH$_3$ | OCH$_3$ | N | |
| CH$_3$ | SCH$_2$CH$_2$SCH$_2$CF$_3$ | H | OCH$_3$ | CH$_3$ | N | |
| CH$_3$ | SCF$_2$CF$_2$H | H | OCH$_3$ | OCH$_3$ | CH | |
| CH$_3$ | SCF$_2$CF$_2$H | H | OCH$_3$ | CH$_3$ | CH | |
| CH$_3$ | SCF$_2$CF$_2$H | H | OCH$_3$ | Cl | CH | |
| CH$_3$ | SCF$_2$CF$_2$H | H | CH$_3$ | CH$_3$ | CH | |
| CH$_3$ | SCF$_2$CF$_2$H | H | OCH$_3$ | OCH$_3$ | N | |
| CH$_2$CH$_3$ | SCF$_2$CF$_3$H | H | OCH$_3$ | CH$_3$ | N | |
| CH$_3$ | SCH$_2$CH$_2$CN | H | OCH$_3$ | OCH$_3$ | CH | |
| CH$_3$ | SCH$_2$CH$_2$CN | H | OCH$_3$ | CH$_3$ | CH | |
| CH$_3$ | SCH$_2$CH$_2$CN | H | OCH$_3$ | Cl | CH | |
| CH$_3$ | SCH$_2$CH$_2$CN | H | CH$_3$ | CH$_3$ | CH | |
| CH$_3$ | SCH$_2$CH$_2$CN | H | OCH$_3$ | OCH$_3$ | N | |
| CH$_2$CH$_3$ | SCH$_2$CH$_2$CN | H | OCH$_3$ | CH$_3$ | N | |
| CH$_3$ | SCH$_2$CH$_2$F | H | OCH$_3$ | OCH$_3$ | CH | |
| CH$_3$ | SCH$_2$CH$_2$F | H | OCH$_3$ | CH$_3$ | CH | |
| CH$_3$ | SCH$_2$CH$_2$F | H | OCH$_3$ | Cl | CH | |
| CH$_3$ | SCH$_2$CH$_2$F | H | CH$_3$ | CH$_3$ | CH | |
| CH$_3$ | SCH$_2$CH$_2$F | H | OCH$_3$ | OCH$_3$ | N | |
| CH$_3$ | SCH$_2$CH$_2$F | H | OCH$_3$ | CH$_3$ | N | |
| CH$_3$ | SCH$_2$CHF$_2$ | H | OCH$_2$ | OCH$_3$ | CH | |
| CH$_3$ | SCH$_2$CHF$_2$ | H | OCH$_3$ | CH$_3$ | CH | |
| CH$_3$ | SCH$_2$CHF$_2$ | H | OCH$_3$ | Cl | CH | |
| CH$_3$ | SCH$_2$CHF$_2$ | H | CH$_3$ | CH$_3$ | CH | |
| CH$_3$ | SCH$_2$CHF$_2$ | H | OCH$_3$ | OCH$_3$ | N | |
| CH$_3$ | SCH$_2$CHF$_2$ | H | OCH$_3$ | CH$_3$ | N | |
| CH$_3$ | SCH$_2$CF$_3$ | H | OCH$_3$ | OCH$_3$ | CH | 171–173 |
| CH$_3$ | SCH$_2$CF$_3$ | H | OCH$_3$ | CH$_3$ | CH | 143–147 |
| CH$_3$ | SCH$_2$CF$_3$ | H | OCH$_3$ | Cl | CH | 139–147 |
| CH$_3$ | SCH$_2$CF$_3$ | H | CH$_3$ | CH$_3$ | CH | 172–174 |
| CH$_3$ | SCH$_2$CF$_3$ | H | OCH$_3$ | OCH$_3$ | N | 150–152 |
| CH$_3$ | SCH$_2$CF$_3$ | H | OCH$_3$ | CH$_3$ | N | 142–162 |
| CH$_3$ | SCH$_2$CF$_3$ | H | OCH$_2$CH$_3$ | NHCH$_3$ | N | 189–190 |
| C$_2$H$_5$ | SCH$_2$CF$_3$ | H | CH$_3$ | CH$_3$ | CH | 166–170 |
| C$_2$H$_5$ | SCH$_2$CF$_3$ | H | OCH$_3$ | CH$_3$ | CH | 139–142 |
| C$_2$H$_5$ | SCH$_2$CF$_3$ | H | OCH$_3$ | OCH$_3$ | CH | 127–130 |
| C$_2$H$_5$ | SCH$_2$CF$_3$ | H | Cl | OCH$_3$ | CH | 98–106 |
| C$_2$H$_5$ | SCH$_2$CF$_3$ | H | CH$_3$ | OCH$_3$ | N | 136–142 |
| C$_2$H$_5$ | SCH$_2$CF$_3$ | H | OCH$_3$ | OCH$_3$ | N | 147–151 |
| C$_2$H$_5$ | SCH$_2$CF$_3$ | H | OCH$_2$CH$_3$ | NHCH$_3$ | N | 147–168 |
| CH$_3$ | S(O)-cyclopropyl | H | OCH$_3$ | OCH$_3$ | CH | |
| CH$_3$ | S(O)-cyclopropyl | H | OCH$_3$ | CH$_3$ | CH | |
| CH$_3$ | S(O)-cyclopropyl | H | OCH$_3$ | Cl | CH | |
| CH$_3$ | S(O)-cyclopropyl | H | CH$_3$ | CH$_3$ | CH | |
| CH$_3$ | S(O)-cyclopropyl | H | OCH$_3$ | OCH$_3$ | N | |
| CH$_3$ | S(O)-cyclopropyl | H | OCH$_3$ | CH$_3$ | N | |
| CH$_3$ | S(O)-cyclopropyl | H | OCH$_3$ | OCH$_3$ | CH | |
| CH$_3$ | S(O)-cyclopropyl | H | OCH$_3$ | CH$_3$ | CH | |
| CH$_3$ | S(O)-cyclopropyl | H | OCH$_3$ | Cl | CH | |
| CH$_3$ | S(O)-cyclopropyl | H | CH$_3$ | CH$_3$ | CH | |
| CH$_3$ | S(O)-cyclopropyl | H | OCH$_3$ | OCH$_3$ | N | |
| CH$_3$ | S(O)-cyclopropyl | H | OCH$_3$ | CH$_3$ | N | |
| CH$_3$ | S(O)-cyclobutyl | H | OCH$_3$ | OCH$_3$ | CH | |
| CH$_3$ | S(O)-cyclobutyl | H | OCH$_3$ | CH$_3$ | CH | |
| CH$_3$ | S(O)-cyclobutyl | H | OCH$_3$ | Cl | CH | |
| CH$_3$ | S(O)-cyclobutyl | H | CH$_3$ | CH$_3$ | CH | |
| CH$_3$ | S(O)-cyclobutyl | H | OCH$_3$ | OCH$_3$ | N | |
| CH$_2$CH$_3$ | S(O)-cyclobutyl | H | OCH$_3$ | CH$_3$ | N | |
| CH$_3$ | S(O)CH$_2$CF$_2$CF$_3$ | H | OCH$_3$ | OCH$_3$ | CH | |
| CH$_3$ | S(O)CH$_2$CF$_2$CF$_3$ | H | OCH$_3$ | CH$_3$ | CH | |
| CH$_3$ | S(O)CH$_2$CF$_2$CF$_3$ | H | OCH$_3$ | Cl | CH | |
| CH$_3$ | S(O)CH$_2$CF$_2$CF$_3$ | H | CH$_3$ | CH$_3$ | CH | |
| CH$_3$ | S(O)CH$_2$CF$_2$CF$_3$ | H | OCH$_3$ | OCH$_3$ | N | |
| CH$_3$ | S(O)CH$_2$CF$_2$CF$_3$ | H | OCH$_3$ | CH$_3$ | N | |
| CH$_3$ | S(O)CH(CF$_3$)CH$_3$ | H | OCH$_3$ | OCH$_3$ | CH | |
| CH$_3$ | S(O)CH(CF$_3$)CH$_3$ | H | OCH$_3$ | CH$_3$ | CH | |
| CH$_3$ | S(O)CH(CF$_3$)CH$_3$ | H | OCH$_3$ | Cl | CH | |
| CH$_3$ | S(O)CH(CF$_3$)CH$_3$ | H | CH$_3$ | CH$_3$ | CH | |
| CH$_3$ | S(O)CH(CF$_3$)CH$_3$ | H | OCH$_3$ | OCH$_3$ | N | |
| CH$_3$ | S(O)CH(CF$_3$)CH$_3$ | H | OCH$_3$ | CH$_3$ | N | |
| CH$_3$ | S(O)CH$_2$CF$_2$CF$_2$H | H | OCH$_3$ | OCH$_3$ | CH | |
| CH$_3$ | S(O)CH$_2$CF$_2$CF$_2$H | H | OCH$_3$ | CH$_3$ | CH | |
| CH$_3$ | S(O)CH$_2$CF$_2$CF$_2$H | H | OCH$_3$ | Cl | CH | |
| CH$_3$ | S(O)CH$_2$CF$_2$CF$_2$H | H | CH$_3$ | CH$_3$ | CH | |
| CH$_3$ | S(O)CH$_2$CF$_2$CF$_2$H | H | OCH$_3$ | OCH$_3$ | N | |
| CH$_2$CH$_3$ | S(O)CH$_2$CF$_2$CF$_2$H | H | OCH$_3$ | CH$_3$ | N | |
| CH$_3$ | S(O)CH(CH$_2$F)$_2$ | H | OCH$_3$ | OCH$_3$ | CH | |
| CH$_3$ | S(O)CH(CH$_2$F)$_2$ | H | OCH$_3$ | CH$_3$ | CH | |

TABLE Ia-continued

| | | | | | |
|---|---|---|---|---|---|
| CH$_3$ | S(O)CH(CH$_2$F)$_2$ | H | OCH$_3$ | Cl | CH |
| CH$_3$ | S(O)CH(CH$_2$F)$_2$ | H | CH$_3$ | CH$_3$ | CH |
| CH$_3$ | S(O)CH(CH$_2$F)$_2$ | H | OCH$_3$ | OCH$_3$ | N |
| CH$_3$ | S(O)CH(CH$_2$F)$_2$ | H | OCH$_3$ | CH$_3$ | N |
| CH$_3$ | S(O)CH(CH$_2$F)CH$_3$ | H | OCH$_3$ | OCH$_3$ | CH |
| CH$_3$ | S(O)CH(CH$_2$F)CH$_3$ | H | OCH$_3$ | CH$_3$ | CH |
| CH$_3$ | S(O)CH(CH$_2$F)CH$_3$ | H | OCH$_3$ | Cl | CH |
| CH$_3$ | S(O)CH(CH$_2$F)CH$_3$ | H | CH$_3$ | CH$_3$ | CH |
| CH$_3$ | S(O)CH(CH$_2$F)CH$_3$ | H | OCH$_3$ | OCH$_3$ | N |
| CH$_3$ | S(O)CH(CH$_2$F)CH$_3$ | H | OCH$_3$ | CH$_3$ | N |
| CH$_3$ | S(O)(CH$_2$)$_5$CH$_2$Cl | H | OCH$_3$ | OCH$_3$ | CH |
| CH$_3$ | S(O)(CH$_2$)$_5$CH$_2$Cl | H | OCH$_3$ | CH$_3$ | CH |
| CH$_3$ | S(O)(CH$_2$)$_5$CH$_2$Cl | H | OCH$_3$ | Cl | CH |
| CH$_3$ | S(O)(CH$_2$)$_5$CH$_2$Cl | H | CH$_3$ | CH$_3$ | CH |
| CH$_3$ | S(O)(CH$_2$)$_5$CH$_2$Cl | H | OCH$_3$ | OCH$_3$ | N |
| CH$_2$CH$_3$ | S(O)(CH$_2$)$_5$CH$_2$Cl | H | OCH$_3$ | CH$_3$ | N |
| CH$_3$ | S(O)C(Cl)CHCl | H | OCH$_3$ | OCH$_3$ | CH |
| CH$_3$ | S(O)C(Cl)CHCl | H | OCH$_3$ | CH$_3$ | CH |
| CH$_3$ | S(O)C(Cl)CHCl | H | OCH$_3$ | Cl | CH |
| CH$_3$ | S(O)C(Cl)CHCl | H | CH$_3$ | CH$_3$ | CH |
| CH$_3$ | S(O)C(Cl)CHCl | H | OCH$_3$ | OCH$_3$ | N |
| CH$_3$ | S(O)C(Cl)CHCl | H | OCH$_3$ | CH$_3$ | N |
| CH$_3$ | S(O)CH$_2$C(Cl)CH$_2$ | H | OCH$_3$ | OCH$_3$ | CH |
| CH$_3$ | S(O)CH$_2$C(Cl)CH$_2$ | H | OCH$_3$ | CH$_3$ | CH |
| CH$_3$ | S(O)CH$_2$C(Cl)CH$_2$ | H | OCH$_3$ | Cl | CH |
| CH$_3$ | S(O)CH$_2$C(Cl)CH$_2$ | H | CH$_3$ | CH$_3$ | CH |
| CH$_3$ | S(O)CH$_2$C(Cl)CH$_2$ | H | OCH$_3$ | OCH$_3$ | N |
| CH$_3$ | S(O)CH$_2$C(Cl)CH$_2$ | H | OCH$_3$ | CH$_3$ | N |
| CH$_3$ | S(O)CH$_2$CCCH$_2$Cl | H | OCH$_3$ | OCH$_3$ | CH |
| CH$_3$ | S(O)CH$_2$CCCH$_2$Cl | H | OCH$_3$ | CH$_3$ | CH |
| CH$_3$ | S(O)CH$_2$CCCH$_2$Cl | H | OCH$_3$ | Cl | CH |
| CH$_3$ | S(O)CH$_2$CCCH$_2$Cl | H | CH$_3$ | CH$_3$ | CH |
| CH$_3$ | S(O)CH$_2$CCCH$_2$Cl | H | OCH$_3$ | OCH$_3$ | N |
| CH$_2$CH$_3$ | S(O)CH$_2$CCCH$_2$Cl | H | OCH$_3$ | CH$_3$ | N |
| CH$_3$ | S(O)CH$_2$OCH$_3$ | H | OCH$_3$ | OCH$_3$ | CH |
| CH$_3$ | S(O)CH$_2$OCH$_3$ | H | OCH$_3$ | CH$_3$ | CH |
| CH$_3$ | S(O)CH$_2$OCH$_3$ | H | OCH$_3$ | Cl | CH |
| CH$_3$ | S(O)CH$_2$OCH$_3$ | H | CH$_3$ | CH$_3$ | CH |
| CH$_3$ | S(O)CH$_2$OCH$_3$ | H | OCH$_3$ | OCH$_3$ | N |
| CH$_3$ | S(O)CH$_2$OCH$_3$ | H | OCH$_3$ | CH$_3$ | N |
| CH$_3$ | S(O)CH$_2$OCH$_2$CF$_3$ | H | OCH$_3$ | OCH$_3$ | CH |
| CH$_3$ | S(O)CH$_2$OCH$_2$CF$_3$ | H | OCH$_3$ | CH$_3$ | CH |
| CH$_3$ | S(O)CH$_2$OCH$_2$CF$_3$ | H | OCH$_3$ | Cl | CH |
| CH$_3$ | S(O)CH$_2$OCH$_2$CF$_3$ | H | CH$_3$ | CH$_3$ | CH |
| CH$_3$ | S(O)CH$_2$OCH$_2$CF$_3$ | H | OCH$_3$ | OCH$_3$ | N |
| CH$_3$ | S(O)CH$_2$OCH$_2$CF$_3$ | H | OCH$_3$ | CH$_3$ | N |
| CH$_3$ | S(O)CH$_2$CN | H | OCH$_3$ | OCH$_3$ | CH |
| CH$_3$ | S(O)CH$_2$CN | H | OCH$_3$ | CH$_3$ | CH |
| CH$_3$ | S(O)CH$_2$CN | H | OCH$_3$ | Cl | CH |
| CH$_3$ | S(O)CH$_2$CN | H | CH$_3$ | CH$_3$ | CH |
| CH$_3$ | S(O)CH$_2$CN | H | OCH$_3$ | OCH$_3$ | N |
| CH$_3$ | S(O)CH$_2$CN | H | OCH$_3$ | CH$_3$ | N |
| CH$_3$ | S(O)CH$_2$C(O)CH$_3$ | H | OCH$_3$ | OCH$_3$ | CH |
| CH$_3$ | S(O)CH$_2$C(O)CH$_3$ | H | OCH$_3$ | CH$_3$ | CH |
| CH$_3$ | S(O)CH$_2$C(O)CH$_3$ | H | OCH$_3$ | Cl | CH |
| CH$_3$ | S(O)CH$_2$C(O)CH$_3$ | H | CH$_3$ | CH$_3$ | CH |
| CH$_3$ | S(O)CH$_2$C(O)CH$_3$ | H | OCH$_3$ | OCH$_3$ | N |
| CH$_3$ | S(O)CH$_2$C(O)CH$_3$ | H | OCH$_3$ | CH$_3$ | N |
| CH$_3$ | S(O)CH$_2$CH$_2$N(CH$_3$)$_2$ | H | OCH$_3$ | OCH$_3$ | CH |
| CH$_3$ | S(O)CH$_2$CH$_2$N(CH$_3$)$_2$ | H | OCH$_3$ | CH$_3$ | CH |
| CH$_3$ | S(O)CH$_2$CH$_2$N(CH$_3$)$_2$ | H | OCH$_3$ | Cl | CH |
| CH$_3$ | S(O)CH$_2$CH$_2$N(CH$_3$)$_2$ | H | CH$_3$ | CH$_3$ | CH |
| CH$_3$ | S(O)CH$_2$CH$_2$N(CH$_3$)$_2$ | H | OCH$_3$ | OCH$_3$ | N |
| CH$_2$CH$_3$ | S(O)CH$_2$CH$_2$N(CH$_3$)$_2$ | H | OCH$_3$ | CH$_3$ | N |
| CH$_3$ | S(O)CH$_2$CH$_2$OCH$_2$CF$_3$ | H | OCH$_3$ | OCH$_3$ | CH |
| CH$_3$ | S(O)CH$_2$CH$_2$OCH$_2$CF$_3$ | H | OCH$_3$ | CH$_3$ | CH |
| CH$_3$ | S(O)CH$_2$CH$_2$OCH$_2$CF$_3$ | H | OCH$_3$ | Cl | CH |
| CH$_3$ | S(O)CH$_2$CH$_2$OCH$_2$CF$_3$ | H | CH$_3$ | CH$_3$ | CH |
| CH$_3$ | S(O)CH$_2$CH$_2$OCH$_2$CF$_3$ | H | OCH$_3$ | OCH$_3$ | N |
| CH$_3$ | S(O)CH$_2$CH$_2$OCH$_2$CF$_3$ | H | OCH$_3$ | CH$_3$ | N |
| CH$_3$ | S(O)CF$_2$CF$_2$H | H | OCH$_3$ | OCH$_3$ | CH |
| CH$_3$ | S(O)CF$_2$CF$_2$H | H | OCH$_3$ | CH$_3$ | CH |
| CH$_3$ | S(O)CF$_2$CF$_2$H | H | OCH$_3$ | Cl | CH |
| CH$_3$ | S(O)CF$_2$CF$_2$H | H | CH$_3$ | CH$_3$ | CH |
| CH$_3$ | S(O)CF$_2$CF$_2$H | H | OCH$_3$ | OCH$_3$ | N |
| CH$_2$CH$_3$ | S(O)CF$_2$CF$_2$H | H | OCH$_3$ | CH$_3$ | N |
| CH$_3$ | S(O)CH$_2$CH$_2$CN | H | OCH$_3$ | OCH$_3$ | CH |
| CH$_3$ | S(O)CH$_2$CH$_2$CN | H | OCH$_3$ | CH$_3$ | CH |
| CH$_3$ | S(O)CH$_2$CH$_2$CN | H | OCH$_3$ | Cl | CH |
| CH$_3$ | S(O)CH$_2$CH$_2$CN | H | CH$_3$ | CH$_3$ | CH |
| CH$_3$ | S(O)CH$_2$CH$_2$CN | H | OCH$_3$ | OCH$_3$ | N |
| CH$_2$CH$_3$ | S(O)CH$_2$CH$_2$CN | H | OCH$_3$ | CH$_3$ | N |

TABLE Ia-continued

| | | | | | |
|---|---|---|---|---|---|
| CH$_3$ | S(O)CH$_2$CH$_2$F | H | OCH$_3$ | OCH$_3$ | CH |
| CH$_3$ | S(O)CH$_2$CH$_2$F | H | OCH$_3$ | CH$_3$ | CH |
| CH$_3$ | S(O)CH$_2$CH$_2$F | H | OCH$_3$ | Cl | CH |
| CH$_3$ | S(O)CH$_2$CH$_2$F | H | CH$_3$ | CH$_3$ | CH |
| CH$_3$ | S(O)CH$_2$CH$_2$F | H | OCH$_3$ | OCH$_3$ | N |
| CH$_3$ | S(O)CH$_2$cH$_2$F | H | OCH$_3$ | CH$_3$ | N |
| CH$_3$ | S(O)CH$_2$CHF$_2$ | H | OCH$_3$ | OCH$_3$ | CH |
| CH$_3$ | S(O)CH$_2$CHF$_2$ | H | OCH$_3$ | CH$_3$ | CH |
| CH$_3$ | S(O)CH$_2$CHF$_2$ | H | OCH$_3$ | Cl | CH |
| CH$_3$ | S(O)CH$_2$CHF$_2$ | H | CH$_3$ | CH$_3$ | CH |
| CH$_3$ | S(O)CH$_2$CHF$_2$ | H | OCH$_3$ | OCH$_3$ | N |
| CH$_3$ | S(O)CH$_2$CHF$_2$ | H | OCH$_3$ | CH$_3$ | N |
| CH$_3$ | S(O)CH$_2$CF$_3$ | H | OCH$_3$ | OCH$_3$ | CH |
| CH$_3$ | S(O)CH$_2$CF$_3$ | H | OCH$_3$ | CH$_3$ | CH |
| CH$_3$ | S(O)CH$_2$CF$_3$ | H | OCH$_3$ | Cl | CH |
| CH$_3$ | S(O)CH$_2$CF$_3$ | H | CH$_3$ | CH$_3$ | CH |
| CH$_3$ | S(O)CH$_2$CF$_3$ | H | OCH$_3$ | OCH$_3$ | N |
| CH$_2$CH$_3$ | S(O)CH$_2$CF$_3$ | H | OCH$_3$ | CH$_3$ | N |
| CH$_3$ | S(O)$_2$-cyclopropyl | H | OCH$_3$ | OCH$_3$ | CH |
| CH$_3$ | S(O)$_2$-cyclopropyl | H | OCH$_3$ | CH$_3$ | CH |
| CH$_3$ | S(O)$_2$-cyclopropyl | H | OCH$_3$ | Cl | CH |
| CH$_3$ | S(O)$_2$-cyclopropyl | H | CH$_3$ | CH$_3$ | CH |
| CH$_3$ | S(O)$_2$-cyclopropyl | H | OCH$_3$ | OCH$_3$ | N |
| CH$_3$ | S(O)$_2$-cyclopropyl | H | OCH$_3$ | CH$_3$ | N |
| CH$_3$ | S(O)$_2$CH$_2$-cyclopropyl | H | OCH$_3$ | OCH$_3$ | CH |
| CH$_3$ | S(O)$_2$CH$_2$-cyclopropyl | H | OCH$_3$ | CH$_3$ | CH |
| CH$_3$ | S(O)$_2$CH$_2$-cyclopropyl | H | OCH$_3$ | Cl | CH |
| CH$_3$ | S(O)$_2$CH$_2$-cyclopropyl | H | CH$_3$ | CH$_3$ | CH |
| CH$_3$ | S(O)$_2$CH$_2$-cyclopropyl | H | OCH$_3$ | OCH$_3$ | N |
| CH$_3$ | S(O)$_2$CH$_2$-cyclopropyl | H | OCH$_3$ | CH$_3$ | N |
| CH$_3$ | S(O)$_2$-cyclobutyl | H | OCH$_3$ | OCH$_3$ | CH |
| CH$_3$ | S(O)$_2$-cyclobutyl | H | OCH$_3$ | CH$_3$ | CH |
| CH$_3$ | S(O)$_2$-cyclobutyl | H | OCH$_3$ | Cl | CH |
| CH$_3$ | S(O)$_2$-cyclobutyl | H | CH$_3$ | CH$_3$ | CH |
| CH$_3$ | S(O)$_2$-cyclobutyl | H | OCH$_3$ | OCH$_3$ | N |
| CH$_2$CH$_3$ | S(O)$_2$-cyclobutyl | H | OCH$_3$ | CH$_3$ | N |
| CH$_3$ | S(O)$_2$CH$_2$CF$_2$CF$_3$ | H | OCH$_3$ | OCH$_3$ | CH |
| CH$_3$ | S(O)$_2$CH$_2$CF$_2$CF$_3$ | H | OCH$_3$ | CH$_3$ | CH |
| CH$_3$ | S(O)$_2$CH$_2$CF$_2$CF$_3$ | H | OCH$_3$ | Cl | CH |
| CH$_3$ | S(O)$_2$CH$_2$CF$_2$CF$_3$ | H | CH$_3$ | CH$_3$ | CH |
| CH$_3$ | S(O)$_2$CH$_2$CF$_2$CF$_3$ | H | OCH$_3$ | OCH$_3$ | N |
| CH$_3$ | S(O)$_2$CH$_2$CF$_2$CF$_3$ | H | OCH$_3$ | CH$_3$ | N |
| CH$_3$ | S(O)$_2$CH(CF$_3$)CH$_3$ | H | OCH$_3$ | OCH$_3$ | CH |
| CH$_3$ | S(O)$_2$CH(CF$_3$)CH$_3$ | H | OCH$_3$ | CH$_3$ | CH |
| CH$_3$ | S(O)$_2$CH(CF$_3$)CH$_3$ | H | OCH$_3$ | Cl | CH |
| CH$_3$ | S(O)$_2$CH(CF$_3$)CH$_3$ | H | CH$_3$ | CH$_3$ | CH |
| CH$_3$ | S(O)$_2$CH(CF$_3$)CH$_3$ | H | OCH$_3$ | OCH$_3$ | N |
| CH$_3$ | S(O)$_2$CH(CF$_3$)CH$_3$ | H | OCH$_3$ | CH$_3$ | N |
| CH$_3$ | S(O)$_2$CH$_2$CF$_2$CF$_2$H | H | OCH$_3$ | OCH$_3$ | CH |
| CH$_3$ | S(O)$_2$CH$_2$CF$_2$CF$_2$H | H | OCH$_3$ | CH$_3$ | CH |
| CH$_3$ | S(O)$_2$CH$_2$CF$_2$CF$_2$H | H | OCH$_3$ | Cl | CH |
| CH$_3$ | S(O)$_2$CH$_2$CF$_2$CF$_2$H | H | CH$_3$ | CH$_3$ | CH |
| CH$_3$ | S(O)$_2$CH$_2$CF$_2$CF$_2$H | H | OCH$_3$ | OCH$_3$ | N |
| CH$_2$CH$_3$ | S(O)$_2$CH$_2$CF$_2$CF$_2$H | H | OCH$_3$ | CH$_3$ | N |
| CH$_3$ | S(O)$_2$CH(CH$_2$F)$_2$ | H | OCH$_3$ | OCH$_3$ | CH |
| CH$_3$ | S(O)$_2$CH(CH$_2$F)$_2$ | H | OCH$_3$ | CH$_3$ | CH |
| CH$_3$ | S(O)$_2$CH(CH$_2$F)$_2$ | H | OCH$_3$ | Cl | CH |
| CH$_3$ | S(O)$_2$CH(CH$_2$F)$_2$ | H | CH$_3$ | CH$_3$ | CH |
| CH$_3$ | S(O)$_2$CH(CH$_2$F)$_2$ | H | OCH$_3$ | OCH$_3$ | N |
| CH$_3$ | S(O)$_2$CH(CH$_2$F)$_2$ | H | OCH$_3$ | CH$_3$ | N |
| CH$_3$ | S(O)$_2$CH(CH$_2$F)CH$_3$ | H | OCH$_3$ | OCH$_3$ | CH |
| CH$_3$ | S(O)$_2$CH(CH$_2$F)CH$_3$ | H | OCH$_3$ | CH$_3$ | CH |
| CH$_3$ | S(O)$_2$CH(CH$_2$F)CH$_3$ | H | OCH$_3$ | Cl | CH |
| CH$_3$ | S(O)$_2$CH(CH$_2$F)CH$_3$ | H | CH$_3$ | CH$_3$ | CH |
| CH$_3$ | S(O)$_2$CH(CH$_2$F)CH$_3$ | H | OCH$_3$ | OCH$_3$ | N |
| CH$_3$ | S(O)$_2$CH(CH$_2$F)CH$_3$ | H | OCH$_3$ | CH$_3$ | N |
| CH$_3$ | S(O)$_2$(CH$_2$)$_5$CH$_2$Cl | H | OCH$_3$ | OCH$_3$ | CH |
| CH$_3$ | S(O)$_2$(CH$_2$)$_5$CH$_2$Cl | H | OCH$_3$ | CH$_3$ | CH |
| CH$_3$ | S(O)$_2$(CH$_2$)$_5$CH$_2$Cl | H | OCH$_3$ | Cl | CH |
| CH$_3$ | S(O)$_2$(CH$_2$)$_5$CH$_2$Cl | H | CH$_3$ | CH$_3$ | CH |
| CH$_3$ | S(O)$_2$(CH$_2$)$_5$CH$_2$Cl | H | OCH$_3$ | OCH$_3$ | N |
| CH$_2$CH$_3$ | S(O)$_2$(CH$_2$)$_5$CH$_2$Cl | H | OCH$_3$ | CH$_3$ | N |
| CH$_3$ | S(O)$_2$C(Cl)CHCl | H | OCH$_3$ | OCH$_3$ | CH |
| CH$_3$ | S(O)$_2$C(Cl)CHCl | H | OCH$_3$ | CH$_3$ | CH |
| CH$_3$ | S(O)$_2$C(Cl)CHCl | H | OCH$_3$ | Cl | CH |
| CH$_3$ | S(O)$_2$C(Cl)CHCl | H | CH$_3$ | CH$_3$ | CH |
| CH$_3$ | S(O)$_2$C(Cl)CHCl | H | OCH$_3$ | OCH$_3$ | N |
| CH$_3$ | S(O)$_2$C(Cl)CHCl | H | OCH$_3$ | CH$_3$ | N |
| CH$_3$ | S(O)$_2$CH$_2$C(Cl)CH$_2$ | H | OCH$_3$ | OCH$_3$ | CH |
| CH$_3$ | S(O)$_2$CH$_2$C(Cl)CH$_2$ | H | OCH$_3$ | CH$_3$ | CH |
| CH$_3$ | S(O)$_2$CH$_2$C(Cl)CH$_2$ | H | OCH$_3$ | Cl | CH |
| CH$_3$ | S(O)$_2$CH$_2$C(Cl)CH$_2$ | H | CH$_3$ | CH$_3$ | CH |

TABLE Ia-continued

| | | | | | |
|---|---|---|---|---|---|
| CH$_3$ | S(O)$_2$CH$_2$C(Cl)CH$_2$ | H | OCH$_3$ | OCH$_3$ | N |
| CH$_3$ | S(O)$_2$CH$_2$C(Cl)CH$_2$ | H | OCH$_3$ | CH$_3$ | N |
| CH$_3$ | S(O)$_2$CH$_2$CCCH$_2$Cl | H | OCH$_3$ | OCH$_3$ | CH |
| CH$_3$ | S(O)$_2$CH$_2$CCCH$_2$Cl | H | OCH$_3$ | CH$_3$ | CH |
| CH$_3$ | S(O)$_2$CH$_2$CCCH$_2$Cl | H | OCH$_3$ | Cl | CH |
| CH$_3$ | S(O)$_2$CH$_2$CCCH$_2$Cl | H | CH$_3$ | CH$_3$ | CH |
| CH$_3$ | S(O)$_2$CH$_2$CCCH$_2$Cl | H | OCH$_3$ | OCH$_3$ | N |
| CH$_2$CH$_3$ | S(O)$_2$CH$_2$CCH$_2$Cl | H | OCH$_3$ | CH$_3$ | N |
| CH$_3$ | S(O)$_2$CH$_2$OCH$_3$ | H | OCH$_3$ | OCH$_3$ | CH |
| CH$_3$ | S(O)$_2$CH$_2$OCH$_3$ | H | OCH$_3$ | CH$_3$ | CH |
| CH$_3$ | S(O)$_2$CH$_2$OCH$_3$ | H | OCH$_3$ | Cl | CH |
| CH$_3$ | S(O)$_2$CH$_2$OCH$_3$ | H | CH$_3$ | CH$_3$ | CH |
| CH$_3$ | S(O)$_2$CH$_2$OCH$_3$ | H | OCH$_3$ | OCH$_3$ | N |
| CH$_3$ | S(O)$_2$CH$_2$OCH$_3$ | H | OCH$_3$ | CH$_3$ | N |
| CH$_3$ | S(O)$_2$CH$_2$OCH$_2$CF$_3$ | H | OCH$_3$ | OCH$_3$ | CH |
| CH$_3$ | S(O)$_2$CH$_2$OCH$_2$CF$_3$ | H | OCH$_3$ | CH$_3$ | CH |
| CH$_3$ | S(O)$_2$CH$_2$OCH$_2$CF$_3$ | H | OCH$_3$ | Cl | CH |
| CH$_3$ | S(O)$_2$CH$_2$OCH$_2$CF$_3$ | H | CH$_3$ | CH$_3$ | CH |
| CH$_3$ | S(O)$_2$CH$_2$OCH$_2$CF$_3$ | H | OCH$_3$ | OCH$_3$ | N |
| CH$_3$ | S(O)$_2$CH$_2$OCH$_2$CF$_3$ | H | OCH$_3$ | CH$_3$ | N |
| CH$_3$ | S(O)$_2$CH$_2$CN | H | OCH$_3$ | OCH$_3$ | CH |
| CH$_3$ | S(O)$_2$CH$_2$CN | H | OCH$_3$ | CH$_3$ | CH |
| CH$_3$ | S(O)$_2$CH$_2$CN | H | OCH$_3$ | Cl | CH |
| CH$_3$ | S(O)$_2$CH$_2$CN | H | CH$_3$ | CH$_3$ | CH |
| CH$_3$ | S(O)$_2$CH$_2$CN | H | OCH$_3$ | OCH$_3$ | N |
| CH$_3$ | S(O)$_2$CH$_2$CN | H | OCH$_3$ | CH$_3$ | N |
| CH$_3$ | S(O)$_2$CH$_2$C(O)CH$_3$ | H | OCH$_3$ | OCH$_3$ | CH |
| CH$_3$ | S(O)$_2$CH$_2$C(O)CH$_3$ | H | OCH$_3$ | CH$_3$ | CH |
| CH$_3$ | S(O)$_2$CH$_2$C(O)CH$_3$ | H | OCH$_3$ | Cl | CH |
| CH$_3$ | S(O)$_2$CH$_2$C(O)CH$_3$ | H | CH$_3$ | CH$_3$ | CH |
| CH$_3$ | S(O)$_2$CH$_2$C(O)CH$_3$ | H | OCH$_3$ | OCH$_3$ | N |
| CH$_3$ | S(O)$_2$CH$_2$C(O)CH$_3$ | H | OCH$_3$ | CH$_3$ | N |
| CH$_3$ | S(O)$_2$CH$_2$CH$_2$N(CH$_3$)$_2$ | H | OCH$_3$ | OCH$_3$ | CH |
| CH$_3$ | S(O)$_2$CH$_2$CH$_2$N(CH$_3$)$_2$ | H | OCH$_3$ | CH$_3$ | CH |
| CH$_3$ | S(O)$_2$CH$_2$CH$_2$N(CH$_3$)$_2$ | H | OCH$_3$ | Cl | CH |
| CH$_3$ | S(O)$_2$CH$_2$CH$_2$N(CH$_3$)$_2$ | H | CH$_3$ | CH$_3$ | CH |
| CH$_3$ | S(O)$_2$CH$_2$CH$_2$N(CH$_3$)$_2$ | H | OCH$_3$ | OCH$_3$ | N |
| CH$_2$CH$_3$ | S(O)$_2$CH$_2$CH$_2$N(CH$_3$)$_2$ | H | OCH$_3$ | CH$_3$ | N |
| CH$_3$ | S(O)$_2$CH$_2$CH$_2$OCH$_2$CF$_3$ | H | OCH$_3$ | OCH$_3$ | CH |
| CH$_3$ | S(O)$_2$CH$_2$CH$_2$OCH$_2$CF$_3$ | H | OCH$_3$ | CH$_3$ | CH |
| CH$_3$ | S(O)$_2$CH$_2$CH$_2$OCH$_2$CF$_3$ | H | OCH$_3$ | Cl | H |
| CH$_3$ | S(O)$_2$CH$_2$CH$_2$OCH$_2$CF$_3$ | H | CH$_3$ | CH$_3$ | CH |
| CH$_3$ | S(O)$_2$CH$_2$CH$_2$OCH$_2$CF$_3$ | H | OCH$_3$ | OCH$_3$ | N |
| CH$_3$ | S(O)$_2$CH$_2$CH$_2$OCH$_2$CF$_3$ | H | OCH$_3$ | CH$_3$ | N |
| CH$_3$ | S(O)$_2$CF$_2$CF$_2$H | H | OCH$_3$ | OCH$_3$ | CH |
| CH$_3$ | S(O)$_2$CF$_2$CF$_2$H | H | OCH$_3$ | CH$_3$ | CH |
| CH$_3$ | S(O)$_2$CF$_2$CF$_2$H | H | OCH$_3$ | Cl | CH |
| CH$_3$ | S(O)$_2$CF$_2$CF$_2$H | H | CH$_3$ | CH$_3$ | CH |
| CH$_3$ | S(O)$_2$CF$_2$CF$_2$H | H | OCH$_3$ | OCH$_3$ | N |
| CH$_2$CH$_3$ | S(O)$_2$CF$_2$CF$_2$H | H | OCH$_3$ | CH$_3$ | N |
| CH$_3$ | S(O)$_2$CH$_2$CH$_2$CN | H | OCH$_3$ | OCH$_3$ | CH |
| CH$_3$ | S(O)$_2$CH$_2$CH$_2$CN | H | OCH$_3$ | CH$_3$ | CH |
| CH$_3$ | S(O)$_2$CH$_2$CH$_2$CN | H | OCH$_3$ | Cl | CH |
| CH$_3$ | S(O)$_2$CH$_2$CH$_2$CN | H | CH$_3$ | CH$_3$ | CH |
| CH$_3$ | S(O)$_2$CH$_2$CH$_2$CN | H | OCH$_3$ | OCH$_3$ | N |
| CH$_2$CH$_3$ | S(O)$_2$CH$_2$CH$_2$CN | H | OCH$_3$ | CH$_3$ | N |
| CH$_3$ | S(O)$_2$CH$_2$CH$_2$F | H | OCH$_3$ | OCH$_3$ | CH |
| CH$_3$ | S(O)$_2$CH$_2$CH$_2$F | H | OCH$_3$ | CH$_3$ | CH |
| CH$_3$ | S(O)$_2$CH$_2$CH$_2$F | H | OCH$_3$ | Cl | CH |
| CH$_3$ | S(O)$_2$CH$_2$CH$_2$F | H | CH$_3$ | CH$_3$ | CH |
| CH$_3$ | S(O)$_2$CH$_2$CH$_2$F | H | OCH$_3$ | OCH$_3$ | N |
| CH$_3$ | S(O)$_2$CH$_2$CH$_2$F | H | OCH$_3$ | CH$_3$ | N |
| CH$_3$ | S(O)$_2$CH$_2$CHF$_2$ | H | OCH$_3$ | OCH$_3$ | CH |
| CH$_3$ | S(O)$_2$CH$_2$CHF$_2$ | H | OCH$_3$ | CH$_3$ | CH |
| CH$_3$ | S(O)$_2$CH$_2$CHF$_2$ | H | OCH$_3$ | Cl | CH |
| CH$_3$ | S(O)$_2$CH$_2$CHF$_2$ | H | CH$_3$ | CH$_3$ | CH |
| CH$_3$ | S(O)$_2$CH$_2$CHF$_2$ | H | OCH$_3$ | OCH$_3$ | N |
| CH$_3$ | S(O)$_2$CH$_2$CHF$_2$ | H | OCH$_3$ | CH$_3$ | N |
| CH$_3$ | S(O)$_2$CH$_2$CF$_3$ | H | OCH$_3$ | OCH$_3$ | CH |
| CH$_3$ | S(O)$_2$CH$_2$CF$_3$ | H | OCH$_3$ | CH$_3$ | CH |
| CH$_3$ | S(O)$_2$CH$_2$CF$_3$ | H | OCH$_3$ | Cl | CH |
| CH$_3$ | S(O)$_2$CH$_2$CF$_3$ | H | CH$_3$ | CH$_3$ | CH |
| CH$_3$ | S(O)$_2$CH$_2$CF$_3$ | H | OCH$_3$ | OCH$_3$ | N |
| CH$_2$CH$_3$ | S(O)$_2$CH$_2$CF$_3$ | H | OCH$_3$ | CH$_3$ | N |
| CH$_3$ | NHCH$_2$-cyclopropyl | H | OCH$_3$ | OCH$_3$ | CH |
| CH$_3$ | NHCH$_2$-cyclopropyl | H | OCH$_3$ | CH$_3$ | CH |
| CH$_3$ | NHCH$_2$-cyclopropyl | H | OCH$_3$ | Cl | CH |
| CH$_3$ | NHCH$_2$-cyclopropyl | H | CH$_3$ | CH$_3$ | CH |
| CH$_3$ | NHCH$_2$-cyclopropyl | H | OCH$_3$ | OCH$_3$ | N |
| CH$_3$ | NHCH$_2$-cyclopropyl | H | OCH$_3$ | CH$_3$ | N |
| CH$_3$ | NHCH$_2$CF$_2$CF$_3$ | H | OCH$_3$ | OCH$_3$ | CH |
| CH$_3$ | NHCH$_2$CF$_2$CF$_3$ | H | OCH$_3$ | CH$_3$ | CH |

TABLE Ia-continued

| | | | | | |
|---|---|---|---|---|---|
| CH₃ | NHCH₂CF₂CF₃ | H | OCH₃ | Cl | CH |
| CH₃ | NHCH₂CF₂CF₃ | H | CH₃ | CH₃ | CH |
| CH₃ | NHCH₂CF₂CF₃ | H | OCH₃ | OCH₃ | N |
| CH₃ | NHCH₂CF₂CF₃ | H | OCH₃ | CH₃ | N |
| CH₃ | NHCH(CF₃)CH₃ | H | OCH₃ | OCH₃ | CH |
| CH₃ | NHCH(CF₃)CH₃ | H | OCH₃ | CH₃ | CH |
| CH₃ | NHCH(CF₃)CH₃ | H | OCH₃ | Cl | CH |
| CH₃ | NHCH(CF₃)CH₃ | H | CH₃ | CH₃ | CH |
| CH₃ | NHCH(CF₃)CH₃ | H | OCH₃ | OCH₃ | N |
| CH₃ | NHCH(CF₃)CH₃ | H | OCH₃ | CH₃ | N |
| CH₃ | NHCH₂CF₂CF₂H | H | OCH₃ | OCH₃ | CH |
| CH₃ | NHCH₂CF₂CF₂H | H | OCH₃ | CH₃ | CH |
| CH₃ | NHCH₂CF₂CF₂H | H | OCH₃ | Cl | CH |
| CH₃ | NHCH₂CF₂CF₂H | H | CH₃ | CH₃ | CH |
| CH₃ | NHCH₂CF₂CF₂H | H | OCH₃ | OCH₃ | N |
| CH₂CH₃ | NHCH₂CF₂CF₂H | H | OCH₃ | CH₃ | N |
| CH₃ | NHCH(CH₂F)₂ | H | OCH₃ | OCH₃ | CH |
| CH₃ | NHCH(CH₂F)₂ | H | OCH₃ | CH₃ | CH |
| CH₃ | NHCH(CH₂F)₂ | H | OCH₃ | Cl | CH |
| CH₃ | NHCH(CH₂F)₂ | H | CH₃ | CH₃ | CH |
| CH₃ | NHCH(CH₂F)₂ | H | OCH₃ | OCH₃ | N |
| CH₃ | NHCH(CH₂F)₂ | H | OCH₃ | CH₃ | N |
| CH₃ | NHCH(CH₂F)CH₃ | H | OCH₃ | OCH₃ | CH |
| CH₃ | NHCH(CH₂F)CH₃ | H | OCH₃ | CH₃ | CH |
| CH₃ | NHCH(CH₂F)CH₃ | H | OCH₃ | Cl | CH |
| CH₃ | NHCH(CH₂F)CH₃ | H | CH₃ | CH₃ | CH |
| CH₃ | NHCH(CH₂F)CH₃ | H | OCH₃ | OCH₃ | N |
| CH₃ | NHCH(CH₂F)CH₃ | H | OCH₃ | CH₃ | N |
| CH₃ | NH(CH₂)₃CH₂Cl | H | OCH₃ | OCH₃ | CH |
| CH₃ | NH(CH₂)₃CH₂Cl | H | OCH₃ | CH₃ | CH |
| CH₃ | NH(CH₂)₃CH₂Cl | H | OCH₃ | Cl | CH |
| CH₃ | NH(CH₂)₃CH₂Cl | H | CH₃ | CH₃ | CH |
| CH₃ | NH(CH₂)₃CH₂Cl | H | OCH₃ | OCH₃ | N |
| CH₂CH₃ | NH(CH₂)₃CH₂Cl | H | OCH₃ | CH₃ | N |
| CH₃ | NHC(Cl)CHCl | H | OCH₃ | OCH₃ | CH |
| CH₃ | NHC(Cl)CHCl | H | OCH₃ | CH₃ | CH |
| CH₃ | NHC(Cl)CHCl | H | OCH₃ | Cl | CH |
| CH₃ | NHC(Cl)CHCl | H | CH₃ | CH₃ | CH |
| CH₃ | NHC(Cl)CHCl | H | OCH₃ | OCH₃ | N |
| CH₃ | NHC(Cl)CHCl | H | OCH₃ | CH₃ | N |
| CH₃ | NHCH₂C(Cl)CH₂ | H | OCH₃ | OCH₃ | CH |
| CH₃ | NHCH₂C(Cl)CH₂ | H | OCH₃ | CH₃ | CH |
| CH₃ | NHCH₂C(Cl)CH₂ | H | OCH₃ | Cl | CH |
| CH₃ | NHCH₂C(Cl)CH₂ | H | CH₃ | CH₃ | CH |
| CH₃ | NHCH₂C(Cl)CH₂ | H | OCH₃ | OCH₃ | N |
| CH₃ | NHCH₂C(Cl)CH₂ | H | OCH₃ | CH₃ | N |
| CH₃ | NHCH₂CCCH₂Cl | H | OCH₃ | OCH₃ | CH |
| CH₃ | NHCH₂CCCH₂Cl | H | OCH₃ | CH₃ | CH |
| CH₃ | NHCH₂CCCH₂Cl | H | OCH₃ | Cl | CH |
| CH₃ | NHCH₂CCCH₂Cl | H | CH₃ | CH₃ | CH |
| CH₃ | NHCH₂CCCH₂Cl | H | OCH₃ | OCH₃ | N |
| CH₂CH₃ | NHCH₂CCCH₂Cl | H | OCH₃ | CH₃ | N |
| CH₃ | NHCH₂OCH₃ | H | OCH₃ | OCH₃ | CH |
| CH₃ | NHCH₂OCH₃ | H | OCH₃ | CH₃ | CH |
| CH₃ | NHCH₂OCH₃ | H | OCH₃ | Cl | CH |
| CH₃ | NHCH₂OCH₃ | H | CH₃ | CH₃ | CH |
| CH₃ | NHCH₂OCH₃ | H | OCH₃ | OCH₃ | N |
| CH₃ | NHCH₂OCH₃ | H | OCH₃ | CH₃ | N |
| CH₃ | NHCH₂SCH₃ | H | OCH₃ | OCH₃ | CH |
| CH₃ | NHCH₂SCH₃ | H | OCH₃ | CH₃ | CH |
| CH₃ | NHCH₂SCH₃ | H | OCH₃ | Cl | CH |
| CH₃ | NHCH₂SCH₃ | H | CH₃ | CH₃ | CH |
| CH₃ | NHCH₂SCH₃ | H | OCH₃ | OCH₃ | N |
| CH₂CH₃ | NHCH₂SCH₃ | H | OCH₃ | CH₃ | N |
| CH₃ | NHCH₂CN | H | OCH₃ | OCH₃ | CH |
| CH₃ | NHCH₂CN | H | OCH₃ | CH₃ | CH |
| CH₃ | NHCH₂CN | H | OCH₃ | Cl | CH |
| CH₃ | NHCH₂CN | H | CH₃ | CH₃ | CH |
| CH₃ | NHCH₂CN | H | OCH₃ | OCH₃ | N |
| CH₃ | NHCH₂CN | H | OCH₃ | CH₃ | N |
| CH₃ | NHCH₂C(O)CH₃ | H | OCH₃ | OCH₃ | CH |
| CH₃ | NHCH₂C(O)CH₃ | H | OCH₃ | CH₃ | CH |
| CH₃ | NHCH₂C(O)CH₃ | H | OCH₃ | Cl | CH |
| CH₃ | NHCH₂C(O)CH₃ | H | CH₃ | CH₃ | CH |
| CH₃ | NHCH₂C(O)CH₃ | H | OCH₃ | OCH₃ | N |
| CH₃ | NHCH₂C(O)CH₃ | H | OCH₃ | CH₃ | N |
| CH₃ | NHCH₂CH₂N(CH₃)₂ | H | OCH₃ | OCH₃ | CH |
| CH₃ | NHCH₂CH₂N(CH₃)₂ | H | OCH₃ | CH₃ | CH |
| CH₃ | NHCH₂CH₂N(CH₃)₂ | H | OCH₃ | Cl | CH |
| CH₃ | NHCH₂CH₂N(CH₃)₂ | H | CH₃ | CH₃ | CH |
| CH₃ | NHCH₂CH₂N(CH₃)₂ | H | OCH₃ | OCH₃ | N |
| CH₂CH₃ | NHCH₂CH₂N(CH₃)₂ | H | OCH₃ | CH₃ | N |

TABLE Ia-continued

| | | | | | | |
|---|---|---|---|---|---|---|
| CH₃ | NHCH₂CH₂OCH₃ | H | OCH₃ | OCH₃ | CH | |
| CH₃ | NHCH₂CH₂OCH₃ | H | OCH₃ | CH₃ | CH | |
| CH₃ | NHCH₂CH₂OCH₃ | H | OCH₃ | Cl | CH | |
| CH₃ | NHCH₂CH₂OCH₃ | H | CH₃ | CH₃ | CH | |
| CH₃ | NHCH₂CH₂OCH₃ | H | OCH₃ | OCH₃ | N | |
| CH₃ | NHCH₂CH₂OCH₃ | H | OCH₃ | CH₃ | N | |
| CH₃ | NHCH₂CH₂CN | H | OCH₃ | OCH₃ | CH | |
| CH₃ | NHCH₂CH₂CN | H | OCH₃ | CH₃ | CH | |
| CH₃ | NHCH₂CH₂CN | H | OCH₃ | Cl | CH | |
| CH₃ | NHCH₂CH₂CN | H | CH₃ | CH₃ | CH | |
| CH₃ | NHCH₂CH₂CN | H | OCH₃ | OCH₃ | N | |
| CH₂CH₃ | NHCH₂CH₂CN | H | OCH₃ | CH₃ | N | |
| CH₃ | NHCH₂CH₂F | H | OCH₃ | OCH₃ | CH | |
| CH₃ | NHCH₂CH₂F | H | OCH₃ | CH₃ | CH | |
| CH₃ | NHCH₂CH₂F | H | OCH₃ | Cl | CH | |
| CH₃ | NHCH₂CH₂F | H | CH₃ | CH₃ | CH | |
| CH₃ | NHCH₂CH₂F | H | OCH₃ | OCH₃ | N | |
| CH₃ | NHCH₂CH₂F | H | OCH₃ | CH₃ | N | |
| CH₃ | NHCH₂CHF₂ | H | OCH₃ | OCH₃ | CH | |
| CH₃ | NHCH₂CHF₂ | H | OCH₃ | CH₃ | CH | |
| CH₃ | NHCH₂CHF₂ | H | OCH₃ | Cl | CH | |
| CH₃ | NHCH₂CHF₂ | H | CH₃ | CH₃ | CH | |
| CH₃ | NHCH₂CHF₂ | H | OCH₃ | OCH₃ | N | |
| CH₃ | NHCH₂CHF₂ | H | OCH₃ | CH₃ | N | |
| CH₃ | NHCH₂CF₃ | H | OCH₃ | OCH₃ | CH | |
| CH₃ | NHCH₂CF₃ | H | OCH₃ | CH₃ | CH | |
| CH₃ | NHCH₂CF₃ | H | OCH₃ | Cl | CH | |
| CH₃ | NHCH₂CF₃ | H | CH₃ | CH₃ | CH | |
| CH₃ | NHCH₂CF₃ | H | OCH₃ | OCH₃ | N | |
| CH₂CH₃ | NHCH₂CF₃ | H | OCH₃ | CH₃ | N | |
| CH₃ | NHCH₂CH₂OH | H | OCH₃ | OCH₃ | CH | |
| CH₃ | NHCH₂CH₂OH | H | OCH₃ | CH₃ | CH | |
| CH₃ | NHCH₂CH₂OH | H | OCH₃ | Cl | CH | |
| CH₃ | NHCH₂CH₂OH | H | CH₃ | CH₃ | CH | |
| CH₃ | NHCH₂CH₂OH | H | OCH₃ | OCH₃ | N | |
| CH₃ | NHCH₂CH₂OH | H | OCH₃ | CH₃ | N | |
| CH₃ | NHCH₂CH₂NH₂ | H | OCH₃ | OCH₃ | CH | |
| CH₃ | NHCH₂CH₂NH₂ | H | OCH₃ | CH₃ | CH | |
| CH₃ | NHCH₂CH₂NH₂ | H | OCH₃ | Cl | CH | |
| CH₃ | NHCH₂CH₂NH₂ | H | CH₃ | CH₃ | CH | |
| CH₃ | NHCH₂CH₂NH₂ | H | OCH₃ | OCH₃ | N | |
| CH₃ | NHCH₂CH₂NH₂ | H | OCH₃ | CH₃ | N | |
| CH₃ | NHCH₃ | H | OCH₃ | OCH₃ | CH | 184–193 |
| CH₃ | NHCH₃ | H | OCH₃ | CH₃ | CH | 180–185 |
| CH₃ | NHCH₃ | H | OCH₃ | Cl | CH | 148–163 |
| CH₃ | NHCH₃ | H | CH₃ | CH₃ | CH | 179–186 |
| CH₃ | NHCH₃ | H | OCH₃ | OCH₃ | N | 124–145 |
| CH₃ | NHCH₃ | H | OCH₃ | CH₃ | N | 138–186 |
| CH₃ | NHCH₃ | H | OCH₂CH₃ | NHCH₃ | N | 160–194 |
| C₂H₅ | NHCH₃ | H | OCH₃ | OCH₃ | CH | 180–186 |
| C₂H₅ | NHCH₃ | H | OCH₃ | CH₃ | CH | 169–170 |
| C₂H₅ | NHCH₃ | H | OCH₃ | Cl | CH | tacky solid |
| C₂H₅ | NHCH₃ | H | CH₃ | CH₃ | CH | 178–182 |
| C₂H₅ | NHCH₃ | H | OCH₃ | OCH₃ | N | 140–143 |
| C₂H₅ | NHCH₃ | H | OCH₃ | CH₃ | N | 135–178 |
| C₂H₅ | NHCH₃ | H | OCH₂CH₃ | NHCH₃ | N | 115–170 |
| CH₃ | NHCH₂CH₂SCH₃ | H | OCH₃ | OCH₃ | CH | |
| CH₃ | NHCH₂CH₂SCH₃ | H | OCH₃ | CH₃ | CH | |
| CH₃ | NHCH₂CH₂SCH₃ | H | OCH₃ | Cl | CH | |
| CH₃ | NHCH₂CH₂SCH₃ | H | CH₃ | CH₃ | CH | |
| CH₃ | NHCH₂CH₂SCH₃ | H | OCH₃ | OCH₃ | N | |
| CH₃ | NHCH₂CH₂SCH₃ | H | OCH₃ | CH₃ | N | |
| CH₃ | NHCH₂CH₂S(O)CH₃ | H | OCH₃ | OCH₃ | CH | |
| CH₃ | NHCH₂CH₂S(O)CH₃ | H | OCH₃ | CH₃ | CH | |
| CH₃ | NHCH₂CH₂S(O)CH₃ | H | OCH₃ | Cl | CH | |
| CH₃ | NHCH₂CH₂S(O)CH₃ | H | CH₃ | CH₃ | CH | |
| CH₃ | NHCH₂CH₂S(O)CH₃ | H | OCH₃ | OCH₃ | N | |
| CH₃ | NHCH₂CH₂S(O)CH₃ | H | OCH₃ | CH₃ | N | |
| CH₃ | NHCH₂CH₂S(O)₂CH₃ | H | OCH₃ | OCH₃ | CH | |
| CH₃ | NHCH₂CH₂S(O)₂CH₃ | H | OCH₃ | CH₃ | CH | |
| CH₃ | NHCH₂CH₂S(O)₂CH₃ | H | OCH₃ | Cl | CH | |
| CH₃ | NHCH₂CH₂S(O)₂CH₃ | H | CH₃ | CH₃ | CH | |
| CH₃ | NHCH₂CH₂S(O)₂CH₃ | H | OCH₃ | OCH₃ | N | |
| CH₃ | NHCH₂CH₂S(O)₂CH₃ | H | OCH₃ | CH₃ | N | |
| CH₃ | CH₂O-cyclopropyl | H | OCH₃ | OCH₃ | CH | |
| CH₃ | CH₂O-cyclopropyl | H | OCH₃ | CH₃ | CH | |
| CH₃ | CH₂O-cyclopropyl | H | OCH₃ | Cl | CH | |
| CH₃ | CH₂O-cyclopropyl | H | CH₃ | CH₃ | CH | |
| CH₃ | CH₂O-cyclopropyl | H | OCH₃ | OCH₃ | N | |
| CH₃ | CH₂O-cyclopropyl | H | OCH₃ | CH₃ | N | |
| CH₃ | CH₂OCH₂-cyclopropyl | H | OCH₃ | OCH₃ | CH | |
| CH₃ | CH₂OCH₂-cyclopropyl | H | OCH₃ | CH₃ | CH | |

TABLE Ia-continued

| | | | | | |
|---|---|---|---|---|---|
| CH$_3$ | CH$_2$OCH$_2$-cyclopropyl | H | OCH$_3$ | Cl | CH |
| CH$_3$ | CH$_2$OCH$_2$-cyclopropyl | H | CH$_3$ | CH$_3$ | CH |
| CH$_3$ | CH$_2$OCH$_2$-cyclopropyl | H | OCH$_3$ | OCH$_3$ | N |
| CH$_3$ | CH$_2$OCH$_2$-cyclopropyl | H | OCH$_3$ | CH$_3$ | N |
| CH$_3$ | CH$_2$O-cyclobutyl | H | OCH$_3$ | OCH$_3$ | CH |
| CH$_3$ | CH$_2$O-cyclobutyl | H | OCH$_3$ | CH$_3$ | CH |
| CH$_3$ | CH$_2$O-cyclobutyl | H | OCH$_3$ | Cl | CH |
| CH$_3$ | CH$_2$O-cyclobutyl | H | CH$_3$ | CH$_3$ | CH |
| CH$_3$ | CH$_2$O-cyclobutyl | H | OCH$_3$ | OCH$_3$ | N |
| CH$_2$CH$_3$ | CH$_2$O-cyclobutyl | H | OCH$_3$ | CH$_3$ | N |
| CH$_3$ | CH$_2$OCH$_2$CF$_2$CF$_3$ | H | OCH$_3$ | OCH$_3$ | CH |
| CH$_3$ | CH$_2$OCH$_2$CF$_2$CF$_3$ | H | OCH$_3$ | CH$_3$ | CH |
| CH$_3$ | CH$_2$OCH$_2$CF$_2$CF$_3$ | H | OCH$_3$ | Cl | CH |
| CH$_3$ | CH$_2$OCH$_2$CF$_2$CF$_3$ | H | CH$_3$ | CH$_3$ | CH |
| CH$_3$ | CH$_2$OCH$_2$CF$_2$CF$_3$ | H | OCH$_3$ | OCH$_3$ | N |
| CH$_3$ | CH$_2$OCH$_2$CF$_2$CF$_3$ | H | OCH$_3$ | CH$_3$ | N |
| CH$_3$ | CH$_2$OCH(CF$_3$)CH$_3$ | H | OCH$_3$ | OCH$_3$ | CH |
| CH$_3$ | CH$_2$OCH(CF$_3$)CH$_3$ | H | OCH$_3$ | CH$_3$ | CH |
| CH$_3$ | CH$_2$OCH(CF$_3$)CH$_3$ | H | OCH$_3$ | Cl | CH |
| CH$_3$ | CH$_2$OCH(CF$_3$)CH$_3$ | H | CH$_3$ | CH$_3$ | CH |
| CH$_3$ | CH$_2$OCH(CF$_3$)CH$_3$ | H | OCH$_3$ | OCH$_3$ | N |
| CH$_3$ | CH$_2$OCH(CF$_3$)CH$_3$ | H | OCH$_3$ | CH$_3$ | N |
| CH$_3$ | CH$_2$OCH$_2$CF$_2$CF$_2$H | H | OCH$_3$ | OCH$_3$ | CH |
| CH$_3$ | CH$_2$OCH$_2$CF$_2$CF$_2$H | H | OCH$_3$ | CH$_3$ | CH |
| CH$_3$ | CH$_2$OCH$_2$CF$_2$CF$_2$H | H | OCH$_3$ | Cl | CH |
| CH$_3$ | CH$_2$OCH$_2$CF$_2$CF$_2$H | H | CH$_3$ | CH$_3$ | CH |
| CH$_3$ | CH$_2$OCH$_2$CF$_2$CF$_2$H | H | OCH$_3$ | OCH$_3$ | N |
| CH$_2$CH$_3$ | CH$_2$OCH$_2$CF$_2$CF$_2$H | H | OCH$_3$ | CH$_3$ | N |
| CH$_3$ | CH$_2$OCH(CH$_2$F)$_2$ | H | OCH$_3$ | OCH$_3$ | CH |
| CH$_3$ | CH$_2$OCH(CH$_2$F)$_2$ | H | OCH$_3$ | CH$_3$ | CH |
| CH$_3$ | CH$_2$OCH(CH$_2$F)$_2$ | H | OCH$_3$ | Cl | CH |
| CH$_3$ | CH$_2$OCH(CH$_2$F)$_2$ | H | CH$_3$ | CH$_3$ | CH |
| CH$_3$ | CH$_2$OCH(CH$_2$F)$_2$ | H | OCH$_3$ | OCH$_3$ | N |
| CH$_3$ | CH$_2$OCH(CH$_2$F)$_2$ | H | OCH$_3$ | CH$_3$ | N |
| CH$_3$ | CH$_2$OCH(CH$_2$F)CH$_3$ | H | OCH$_3$ | OCH$_3$ | CH |
| CH$_3$ | CH$_2$OCH(CH$_2$F)CH$_3$ | H | OCH$_3$ | CH$_3$ | CH |
| CH$_3$ | CH$_2$OCH(CH$_2$F)CH$_3$ | H | OCH$_3$ | Cl | CH |
| CH$_3$ | CH$_2$OCH(CH$_2$F)CH$_3$ | H | CH$_3$ | CH$_3$ | CH |
| CH$_3$ | CH$_2$OCH(CH$_2$F)CH$_3$ | H | OCH$_3$ | OCH$_3$ | N |
| CH$_3$ | CH$_2$OCH(CH$_2$F)CH$_3$ | H | OCH$_3$ | CH$_3$ | N |
| CH$_3$ | CH$_2$O(CH$_2$)$_3$CH$_2$Cl | H | OCH$_3$ | OCH$_3$ | CH |
| CH$_3$ | CH$_2$O(CH$_2$)$_3$CH$_2$Cl | H | OCH$_3$ | CH$_3$ | CH |
| CH$_3$ | CH$_2$O(CH$_2$)$_3$CH$_2$Cl | H | OCH$_3$ | Cl | CH |
| CH$_3$ | CH$_2$O(CH$_2$)$_3$CH$_2$Cl | H | CH$_3$ | CH$_3$ | CH |
| CH$_3$ | CH$_2$O(CH$_2$)$_3$CH$_2$Cl | H | OCH$_3$ | OCH$_3$ | N |
| CH$_2$CH$_3$ | CH$_2$O(CH$_2$)$_3$CH$_2$Cl | H | OCH$_3$ | CH$_3$ | N |
| CH$_3$ | CH$_2$OCH$_2$C(Cl)CH$_2$ | H | OCH$_3$ | OCH$_3$ | CH |
| CH$_3$ | CH$_2$OCH$_2$C(Cl)CH$_2$ | H | OCH$_3$ | CH$_3$ | CH |
| CH$_3$ | CH$_2$OCH$_2$C(Cl)CH$_2$ | H | OCH$_3$ | Cl | CH |
| CH$_3$ | CH$_2$OCH$_2$C(Cl)CH$_2$ | H | CH$_3$ | CH$_3$ | CH |
| CH$_3$ | CH$_2$OCH$_2$C(Cl)CH$_2$ | H | OCH$_3$ | OCH$_3$ | N |
| CH$_3$ | CH$_2$OCH$_2$C(Cl)CH$_2$ | H | OCH$_3$ | CH$_3$ | N |
| CH$_3$ | CH$_2$OCH$_2$CCCH$_2$Cl | H | OCH$_3$ | OCH$_3$ | CH |
| CH$_3$ | CH$_2$OCH$_2$CCCH$_2$Cl | H | OCH$_3$ | CH$_3$ | CH |
| CH$_3$ | CH$_2$OCH$_2$CCCH$_2$Cl | H | OCH$_3$ | Cl | CH |
| CH$_3$ | CH$_2$OCH$_2$CCCH$_2$Cl | H | CH$_3$ | CH$_3$ | CH |
| CH$_3$ | CH$_2$OCH$_2$CCCH$_2$Cl | H | OCH$_3$ | OCH$_3$ | N |
| CH$_2$CH$_3$ | CH$_2$OCH$_2$CCCH$_2$Cl | H | OCH$_3$ | CH$_3$ | N |
| CH$_3$ | CH$_2$OCH$_2$OCH$_3$ | H | OCH$_3$ | OCH$_3$ | CH |
| CH$_3$ | CH$_2$OCH$_2$OCH$_3$ | H | OCH$_3$ | CH$_3$ | CH |
| CH$_3$ | CH$_2$OCH$_2$OCH$_3$ | H | OCH$_3$ | Cl | CH |
| CH$_3$ | CH$_2$OCH$_2$OCH$_3$ | H | CH$_3$ | CH$_3$ | CH |
| CH$_3$ | CH$_2$OCH$_2$OCH$_3$ | H | OCH$_3$ | OCH$_3$ | N |
| CH$_3$ | CH$_2$OCH$_2$OCH$_3$ | H | OCH$_3$ | CH$_3$ | N |
| CH$_3$ | CH$_2$OCH$_2$OCH$_2$CF$_3$ | H | OCH$_3$ | OCH$_3$ | CH |
| CH$_3$ | CH$_2$OCH$_2$OCH$_2$CF$_3$ | H | OCH$_3$ | CH$_3$ | CH |
| CH$_3$ | CH$_2$OCH$_2$OCH$_2$CF$_3$ | H | OCH$_3$ | Cl | CH |
| CH$_3$ | CH$_2$OCH$_2$OCH$_2$CF$_3$ | H | CH$_3$ | CH$_3$ | CH |
| CH$_3$ | CH$_2$OCH$_2$OCH$_2$CF$_3$ | H | OCH$_3$ | OCH$_3$ | N |
| CH$_3$ | CH$_2$OCH$_2$OCH$_2$CF$_3$ | H | OCH$_3$ | CH$_3$ | N |
| CH$_3$ | CH$_2$OCH$_2$SCH$_3$ | H | OCH$_3$ | OCH$_3$ | CH |
| CH$_3$ | CH$_2$OCH$_2$SCH$_3$ | H | OCH$_3$ | CH$_3$ | CH |
| CH$_3$ | CH$_2$OCH$_2$SCH$_3$ | H | OCH$_3$ | Cl | CH |
| CH$_3$ | CH$_2$OCH$_2$SCH$_3$ | H | CH$_3$ | CH$_3$ | CH |
| CH$_3$ | CH$_2$OCH$_2$SCH$_3$ | H | OCH$_3$ | OCH$_3$ | N |
| CH$_2$CH$_3$ | CH$_2$OCH$_2$SCH$_3$ | H | OCH$_3$ | CH$_3$ | N |
| CH$_3$ | CH$_2$OCH$_2$CN | H | OCH$_3$ | OCH$_3$ | CH |
| CH$_3$ | CH$_2$OCH$_2$CN | H | OCH$_3$ | CH$_3$ | CH |
| CH$_3$ | CH$_2$OCH$_2$CN | H | OCH$_3$ | Cl | CH |
| CH$_3$ | CH$_2$OCH$_2$CN | H | CH$_3$ | CH$_3$ | CH |
| CH$_3$ | CH$_2$OCH$_2$CN | H | OCH$_3$ | OCH$_3$ | N |
| CH$_3$ | CH$_2$OCH$_2$CN | H | OCH$_3$ | CH$_3$ | N |

TABLE Ia-continued

| | | | | | | |
|---|---|---|---|---|---|---|
| CH$_3$ | CH$_2$OCH$_2$CH$_2$N(CH$_3$)$_2$ | H | OCH$_3$ | OCH$_3$ | CH | |
| CH$_3$ | CH$_2$OCH$_2$CH$_2$N(CH$_3$)$_2$ | H | OCH$_3$ | CH$_3$ | CH | |
| CH$_3$ | CH$_2$OCH$_2$CH$_2$N(CH$_3$)$_2$ | H | OCH$_3$ | Cl | CH | |
| CH$_3$ | CH$_2$OCH$_2$CH$_2$N(CH$_3$)$_2$ | H | CH$_3$ | CH$_3$ | CH | |
| CH$_3$ | CH$_2$OCH$_2$CH$_2$N(CH$_3$)$_2$ | H | OCH$_3$ | OCH$_3$ | N | |
| CH$_2$CH$_3$ | CH$_2$OCH$_2$CH$_2$N(CH$_3$)$_2$ | H | OCH$_3$ | CH$_3$ | N | |
| CH$_3$ | CH$_2$OCH$_2$CH$_2$F | H | OCH$_3$ | OCH$_3$ | CH | 92–95 |
| CH$_3$ | CH$_2$OCH$_2$CH$_2$F | H | OCH$_3$ | CH$_3$ | CH | 115–117 |
| CH$_3$ | CH$_2$OCH$_2$CH$_2$F | H | OCH$_3$ | Cl | CH | |
| CH$_3$ | CH$_2$OCH$_2$CH$_2$F | H | CH$_3$ | CH$_3$ | CH | |
| CH$_3$ | CH$_2$OCH$_2$CH$_2$F | H | OCH$_3$ | OCH$_3$ | N | 150–152 |
| CH$_3$ | CH$_2$OCH$_2$CH$_2$F | H | OCH$_3$ | CH$_3$ | N | 100–103 |
| CH$_2$CH$_3$ | CH$_2$OCH$_2$CH$_2$F | H | OCH$_3$ | OCH$_3$ | CH | 81–83 |
| CH$_2$CH$_3$ | CH$_2$OCH$_2$CH$_2$F | H | OCH$_3$ | CH$_3$ | CH | 100–101 |
| CH$_2$CH$_3$ | CH$_2$OCH$_2$CH$_2$F | H | OCH$_3$ | Cl | CH | |
| CH$_2$CH$_3$ | CH$_2$OCH$_2$CH$_2$F | H | CH$_3$ | CH$_3$ | CH | |
| CH$_2$CH$_3$ | CH$_2$OCH$_2$CH$_2$F | H | OCH$_3$ | OCH$_3$ | N | 125–127 |
| CH$_2$CH$_3$ | CH$_2$OCH$_2$CH$_2$F | H | OCH$_3$ | CH$_3$ | N | 142–144 |
| CH$_3$ | CH$_2$OCH$_2$CHF$_2$ | H | OCH$_3$ | OCH$_3$ | CH | |
| CH$_3$ | CH$_2$OCH$_2$CHF$_2$ | H | OCH$_3$ | CH$_3$ | CH | |
| CH$_3$ | CH$_2$OCH$_2$CHF$_2$ | H | OCH$_3$ | Cl | CH | |
| CH$_3$ | CH$_2$OCH$_2$CHF$_2$ | H | CH$_3$ | CH$_3$ | CH | |
| CH$_3$ | CH$_2$OCH$_2$CHF$_2$ | H | OCH$_3$ | OCH$_3$ | N | |
| CH$_3$ | CH$_2$OCH$_2$CHF$_2$ | H | OCH$_3$ | CH$_3$ | N | |
| CH$_3$ | CH$_2$OCH$_2$CF$_3$ | H | OCH$_3$ | OCH$_3$ | CH | 118–120 |
| CH$_3$ | CH$_2$OCH$_2$CF$_3$ | H | OCH$_3$ | CH$_3$ | CH | 139–141 |
| CH$_3$ | CH$_2$OCH$_2$CF$_3$ | H | OCH$_3$ | Cl | CH | 124–125 |
| CH$_3$ | CH$_2$OCH$_2$CF$_3$ | H | CH$_3$ | CH$_3$ | CH | 159–161 |
| CH$_3$ | CH$_2$OCH$_2$CF$_3$ | H | OCH$_3$ | OCH$_3$ | N | 128–130 |
| CH$_3$ | CH$_2$OCH$_2$CF$_3$ | H | OCH$_3$ | CH$_3$ | N | 106–109 |
| CH$_2$CH$_3$ | CH$_2$OCH$_2$CF$_3$ | H | OCH$_3$ | OCH$_3$ | CH | 85–89 |
| CH$_2$CH$_3$ | CH$_2$OCH$_2$CF$_3$ | H | OCH$_3$ | CH$_3$ | CH | 110–113 |
| CH$_2$CH$_3$ | CH$_2$OCH$_2$CF$_3$ | H | OCH$_3$ | Cl | CH | 106–110 |
| CH$_2$CH$_3$ | CH$_2$OCH$_2$CF$_3$ | H | CH$_3$ | CH$_3$ | CH | 134–136 |
| CH$_2$CH$_3$ | CH$_2$OCH$_2$CF$_3$ | H | OCH$_3$ | OCH$_3$ | N | >250 |
| CH$_2$CH$_3$ | CH$_2$OCH$_2$CF$_3$ | H | OCH$_3$ | CH$_3$ | N | 126–128 |
| CH$_3$ | CH$_2$OCH$_2$CCH | H | OCH$_3$ | OCH$_3$ | CH | |
| CH$_3$ | CH$_2$OCH$_2$CCH | H | OCH$_3$ | CH$_3$ | CH | |
| CH$_3$ | CH$_2$OCH$_2$CCH | H | OCH$_3$ | Cl | CH | |
| CH$_3$ | CH$_2$OCH$_2$CCH | H | CH$_3$ | CH$_3$ | CH | |
| CH$_3$ | CH$_2$OCH$_2$CCH | H | OCH$_3$ | OCH$_3$ | N | |
| CH$_3$ | CH$_2$OCH$_2$CCH | H | OCH$_3$ | CH$_3$ | N | |
| CH$_3$ | CH$_2$OC(O)CH$_3$ | H | OCH$_3$ | OCH$_3$ | CH | 100–103 |
| CH$_3$ | CH$_2$OC(O)CH$_3$ | H | OCH$_3$ | CH$_3$ | CH | 165–167 |
| CH$_3$ | CH$_2$OC(O)CH$_3$ | H | OCH$_3$ | Cl | CH | |
| CH$_3$ | CH$_2$OC(O)CH$_3$ | H | CH$_3$ | CH$_3$ | CH | |
| CH$_3$ | CH$_2$OC(O)CH$_3$ | H | OCH$_3$ | OCH$_3$ | N | |
| CH$_3$ | CH$_2$OC(O)CH$_3$ | H | OCH$_3$ | CH$_3$ | N | 127–130 |
| CH$_3$ | CH$_2$OC(O)CH$_2$Cl | H | OCH$_3$ | OCH$_3$ | CH | |
| CH$_3$ | CH$_2$OC(O)CH$_2$Cl | H | OCH$_3$ | CH$_3$ | CH | |
| CH$_3$ | CH$_2$OC(O)CH$_2$Cl | H | OCH$_3$ | Cl | CH | |
| CH$_3$ | CH$_2$OC(O)CH$_2$Cl | H | CH$_3$ | CH$_3$ | CH | |
| CH$_3$ | CH$_2$OC(O)CH$_2$Cl | H | OCH$_3$ | OCH$_3$ | N | |
| CH$_2$CH$_3$ | CH$_2$OC(O)CH$_2$Cl | H | OCH$_3$ | CH$_3$ | N | |
| CH$_3$ | CH$_2$OC(O)OCH$_3$ | H | OCH$_3$ | OCH$_3$ | CH | |
| CH$_3$ | CH$_2$OC(O)OCH$_3$ | H | OCH$_3$ | CH$_3$ | CH | |
| CH$_3$ | CH$_2$OC(O)OCH$_3$ | H | OCH$_3$ | Cl | CH | |
| CH$_3$ | CH$_2$OC(O)OCH$_3$ | H | CH$_3$ | CH$_3$ | CH | |
| CH$_3$ | CH$_2$OC(O)OCH$_3$ | H | OCH$_3$ | OCH$_3$ | N | |
| CH$_3$ | CH$_2$OC(O)OCH$_3$ | H | OCH$_3$ | CH$_3$ | N | |
| CH$_3$ | CH$_2$OH | H | OCH$_3$ | OCH$_3$ | CH | 154–157 |
| CH$_3$ | CH$_2$OH | H | OCH$_3$ | CH$_3$ | CH | |
| CH$_3$ | CH$_2$OH | H | OCH$_3$ | Cl | CH | |
| CH$_3$ | CH$_2$OH | H | CH$_3$ | CH$_3$ | CH | |
| CH$_3$ | CH$_2$OH | H | OCH$_3$ | OCH$_3$ | N | |
| CH$_3$ | CH$_2$OH | H | OCH$_3$ | CH$_3$ | N | |
| CH$_3$ | CH$_2$OP(O)(OCH$_3$)$_2$ | H | OCH$_3$ | OCH$_3$ | CH | |
| CH$_3$ | CH$_2$OP(O)(OCH$_3$)$_2$ | H | OCH$_3$ | CH$_3$ | CH | |
| CH$_3$ | CH$_2$OP(O)(OCH$_3$)$_2$ | H | OCH$_3$ | Cl | CH | |
| CH$_3$ | CH$_2$OP(O)(OCH$_3$)$_2$ | H | CH$_3$ | CH$_3$ | CH | |
| CH$_3$ | CH$_2$OP(O)(OCH$_3$)$_2$ | H | OCH$_3$ | OCH$_3$ | N | |
| CH$_2$CH$_3$ | CH$_2$OP(O)(OCH$_3$)$_2$ | H | OCH$_3$ | CH$_3$ | N | |
| CH$_3$ | CH$_2$OSO$_2$CH$_3$ | H | OCH$_3$ | OCH$_3$ | CH | |
| CH$_3$ | CH$_2$OSO$_2$CH$_3$ | H | OCH$_3$ | CH$_3$ | CH | |
| CH$_3$ | CH$_2$OSO$_2$CH$_3$ | H | OCH$_3$ | Cl | CH | |
| CH$_3$ | CH$_2$OSO$_2$CH$_3$ | H | CH$_3$ | CH$_3$ | CH | |
| CH$_3$ | CH$_2$OSO$_2$CH$_3$ | H | OCH$_3$ | OCH$_3$ | N | |
| CH$_3$ | CH$_2$OSO$_2$CH$_3$ | H | OCH$_3$ | CH$_3$ | N | |
| CH$_3$ | CH$_2$OC(O)NHCH$_3$ | H | OCH$_3$ | OCH$_3$ | CH | |
| CH$_3$ | CH$_2$OC(O)NHCH$_3$ | H | OCH$_3$ | CH$_3$ | CH | |
| CH$_3$ | CH$_2$OC(O)NHCH$_3$ | H | OCH$_3$ | Cl | CH | |
| CH$_3$ | CH$_2$OC(O)NHCH$_3$ | H | CH$_3$ | CH$_3$ | CH | |

TABLE Ia-continued

| | | | | | | |
|---|---|---|---|---|---|---|
| CH$_3$ | CH$_2$OC(O)NHCH$_3$ | H | OCH$_3$ | OCH$_3$ | N | |
| CH$_3$ | CH$_2$OC(O)NHCH$_3$ | H | OCH$_3$ | CH$_3$ | N | |
| CH$_3$ | CH$_2$OC(O)N(CH$_3$)$_2$ | H | OCH$_3$ | OCH$_3$ | CH | |
| CH$_3$ | CH$_2$OC(O)N(CH$_3$)$_2$ | H | OCH$_3$ | CH$_3$ | CH | |
| CH$_3$ | CH$_2$OC(O)N(CH$_3$)$_2$ | H | OCH$_3$ | Cl | CH | |
| CH$_3$ | CH$_2$OC(O)N(CH$_3$)$_2$ | H | CH$_3$ | CH$_3$ | CH | |
| CH$_3$ | CH$_2$OC(O)N(CH$_3$)$_2$ | H | OCH$_3$ | OCH$_3$ | N | |
| CH$_2$CH$_3$ | CH$_2$OC(O)N(CH$_3$)$_2$ | H | OCH$_3$ | CH$_3$ | N | |
| CH$_3$ | CH$_2$OSi(CH$_3$)$_3$ | H | OCH$_3$ | OCH$_3$ | CH | |
| CH$_3$ | CH$_2$OSi(CH$_3$)$_3$ | H | OCH$_3$ | CH$_3$ | CH | |
| CH$_3$ | CH$_2$OSi(CH$_3$)$_3$ | H | OCH$_3$ | Cl | CH | |
| CH$_3$ | CH$_2$OSi(CH$_3$)$_3$ | H | CH$_3$ | CH$_3$ | CH | |
| CH$_3$ | CH$_2$OSi(CH$_3$)$_3$ | H | OCH$_3$ | OCH$_3$ | N | |
| CH$_3$ | CH$_2$OSi(CH$_3$)$_3$ | H | OCH$_3$ | CH$_3$ | N | |
| CH$_3$ | CH$_2$OCH$_2$CH$_2$OCH$_3$ | H | OCH$_3$ | OCH$_3$ | CH | 168–170 |
| CH$_3$ | CH$_2$OCH$_2$CH$_2$OCH$_3$ | H | OCH$_3$ | CH$_3$ | CH | 90–91 |
| CH$_3$ | CH$_2$OCH$_2$CH$_2$OCH$_3$ | H | OCH$_3$ | Cl | CH | 109–111 |
| CH$_3$ | CH$_2$OCH$_2$CH$_2$OCH$_3$ | H | CH$_3$ | CH$_3$ | CH | 120–122 |
| CH$_3$ | CH$_2$OCH$_2$CH$_2$OCH$_3$ | H | OCH$_3$ | OCH$_3$ | N | 135–137 |
| CH$_3$ | CH$_2$OCH$_2$CH$_2$OCH$_3$ | H | OCH$_3$ | CH$_3$ | N | 139–141 |
| CH$_3$ | CH$_2$OCH$_2$C(H)CH$_2$ | H | OCH$_3$ | OCH$_3$ | CH | |
| CH$_3$ | CH$_2$OCH$_2$C(H)CH$_2$ | H | OCH$_3$ | CH$_3$ | CH | |
| CH$_3$ | CH$_2$OCH$_2$C(H)CH$_2$ | H | OCH$_3$ | Cl | CH | |
| CH$_3$ | CH$_2$OCH$_2$C(H)CH$_2$ | H | CH$_3$ | CH$_3$ | CH | |
| CH$_3$ | CH$_2$OCH$_2$C(H)CH$_2$ | H | OCH$_3$ | OCH$_3$ | N | |
| CH$_3$ | CH$_2$OCH$_2$C(H)CH$_2$ | H | OCH$_3$ | CH$_3$ | N | |
| CH$_3$ | CH$_2$OCH$_2$C(Cl)CH$_2$ | H | OCH$_3$ | OCH$_3$ | CH | |
| CH$_3$ | CH$_2$OCH$_2$C(Cl)CH$_2$ | H | OCH$_3$ | CH$_3$ | CH | |
| CH$_3$ | CH$_2$OCH$_2$C(Cl)CH$_2$ | H | OCH$_3$ | Cl | CH | |
| CH$_3$ | CH$_2$OCH$_2$C(Cl)CH$_2$ | H | CH$_3$ | CH$_3$ | CH | |
| CH$_3$ | CH$_2$OCH$_2$C(Cl)CH$_2$ | H | OCH$_3$ | OCH$_3$ | N | |
| CH$_2$CH$_3$ | CH$_2$OCH$_2$C(Cl)CH$_2$ | H | OCH$_3$ | CH$_3$ | N | |
| CH$_3$ | CH$_2$S-cyclopropyl | H | OCH$_3$ | OCH$_3$ | CH | |
| CH$_3$ | CH$_2$S-cyclopropyl | H | OCH$_3$ | CH$_3$ | CH | |
| CH$_3$ | CH$_2$S-cyclopropyl | H | OCH$_3$ | Cl | CH | |
| CH$_3$ | CH$_2$S-cyclopropyl | H | CH$_3$ | CH$_3$ | CH | |
| CH$_3$ | CH$_2$S-cyclopropyl | H | OCH$_3$ | OCH$_3$ | N | |
| CH$_3$ | CH$_2$S-cyclopropyl | H | OCH$_3$ | CH$_3$ | N | |
| CH$_3$ | CH$_2$SCH$_2$-cyclopropyl | H | OCH$_3$ | OCH$_3$ | CH | |
| CH$_3$ | CH$_2$SCH$_2$-cyclopropyl | H | OCH$_3$ | CH$_3$ | CH | |
| CH$_3$ | CH$_2$SCH$_2$-cyclopropyl | H | OCH$_3$ | Cl | CH | |
| CH$_3$ | CH$_2$SCH$_2$-cyclopropyl | H | CH$_3$ | CH$_3$ | CH | |
| CH$_3$ | CH$_2$SCH$_2$-cyclopropyl | H | OCH$_3$ | OCH$_3$ | N | |
| CH$_3$ | CH$_2$SCH$_2$-cyclopropyl | H | OCH$_3$ | CH$_3$ | N | |
| CH$_3$ | CH$_2$S-cyclobutyl | H | OCH$_3$ | OCH$_3$ | CH | |
| CH$_3$ | CH$_2$S-cyclobutyl | H | OCH$_3$ | CH$_3$ | CH | |
| CH$_3$ | CH$_2$S-cyclobutyl | H | OCH$_3$ | Cl | CH | |
| CH$_3$ | CH$_2$S-cyclobutyl | H | CH$_3$ | CH$_3$ | CH | |
| CH$_3$ | CH$_2$S-cyclobutyl | H | OCH$_3$ | OCH$_3$ | N | |
| CH$_2$CH$_3$ | CH$_2$S-cyclobutyl | H | OCH$_3$ | CH$_3$ | N | |
| CH$_3$ | CH$_2$SCH$_2$CF$_2$CF$_3$ | H | OCH$_3$ | OCH$_3$ | CH | |
| CH$_3$ | CH$_2$SCH$_2$CF$_2$CF$_3$ | H | OCH$_3$ | CH$_3$ | CH | |
| CH$_3$ | CH$_2$SCH$_2$CF$_2$CF$_3$ | H | OCH$_3$ | Cl | CH | |
| CH$_3$ | CH$_2$SCH$_2$CF$_2$CF$_3$ | H | CH$_3$ | CH$_3$ | CH | |
| CH$_3$ | CH$_2$SCH$_2$CF$_2$CF$_3$ | H | OCH$_3$ | OCH$_3$ | N | |
| CH$_3$ | CH$_2$SCH$_2$CF$_2$CF$_3$ | H | OCH$_3$ | CH$_3$ | N | |
| CH$_3$ | CH$_2$SCH(CF$_3$)CH$_3$ | H | OCH$_3$ | OCH$_3$ | CH | |
| CH$_3$ | CH$_2$SCH(CF$_3$)CH$_3$ | H | OCH$_3$ | CH$_3$ | CH | |
| CH$_3$ | CH$_2$SCH(CF$_3$)CH$_3$ | H | OCH$_3$ | Cl | CH | |
| CH$_3$ | CH$_2$SCH(CF$_3$)CH$_3$ | H | CH$_3$ | CH$_3$ | CH | |
| CH$_3$ | CH$_2$SCH(CF$_2$)CH$_3$ | H | OCH$_3$ | OCH$_3$ | N | |
| CH$_3$ | CH$_2$SCH(CF$_3$)CH$_3$ | H | OCH$_3$ | CH$_3$ | N | |
| CH$_3$ | CH$_2$SCH$_2$CF$_2$CF$_2$H | H | OCH$_3$ | OCH$_3$ | CH | |
| CH$_3$ | CH$_2$SCH$_2$CF$_2$CF$_2$H | H | OCH$_3$ | CH$_3$ | CH | |
| CH$_3$ | CH$_2$SCH$_2$CF$_2$CF$_2$H | H | OCH$_3$ | Cl | CH | |
| CH$_3$ | CH$_2$SCH$_2$CF$_2$CF$_2$H | H | CH$_3$ | CH$_3$ | CH | |
| CH$_3$ | CH$_2$SCH$_2$CF$_2$CF$_2$H | H | OCH$_3$ | OCH$_3$ | N | |
| CH$_2$CH$_3$ | CH$_2$SCH$_2$CF$_2$CF$_2$H | H | OCH$_3$ | CH$_3$ | N | |
| CH$_3$ | CH$_2$SCH(CH$_2$F)$_2$ | H | OCH$_3$ | OCH$_3$ | CH | |
| CH$_3$ | CH$_2$SCH(CH$_2$F)$_2$ | H | OCH$_3$ | CH$_3$ | CH | |
| CH$_3$ | CH$_2$SCH(CH$_2$F)$_2$ | H | OCH$_3$ | Cl | CH | |
| CH$_3$ | CH$_2$SCH(CH$_2$F)$_2$ | H | CH$_3$ | CH$_3$ | CH | |
| CH$_3$ | CH$_2$SCH(CH$_2$F)$_2$ | H | OCH$_3$ | OCH$_3$ | N | |
| CH$_3$ | CH$_2$SCH(CH$_2$F)$_2$ | H | OCH$_3$ | CH$_3$ | N | |
| CH$_3$ | CH$_2$SCH(CH$_2$F)CH$_3$ | H | OCH$_3$ | OCH$_3$ | CH | |
| CH$_3$ | CH$_2$SCH(CH$_2$F)CH$_3$ | H | OCH$_3$ | CH$_3$ | CH | |
| CH$_3$ | CH$_2$SCH(CH$_2$F)CH$_3$ | H | OCH$_3$ | Cl | CH | |
| CH$_3$ | CH$_2$SCH(CH$_2$F)CH$_3$ | H | CH$_3$ | CH$_3$ | CH | |
| CH$_3$ | CH$_2$SCH(CH$_2$F)CH$_3$ | H | OCH$_3$ | OCH$_3$ | N | |
| CH$_3$ | CH$_2$SCH(CH$_2$F)CH$_3$ | H | OCH$_3$ | CH$_3$ | N | |
| CH$_3$ | CH$_2$S(CH$_2$)$_3$CH$_2$Cl | H | OCH$_3$ | OCH$_3$ | CH | |
| CH$_3$ | CH$_2$S(CH$_2$)$_3$CH$_2$Cl | H | OCH$_3$ | CH$_3$ | CH | |

TABLE Ia-continued

| | | | | | |
|---|---|---|---|---|---|
| CH$_3$ | CH$_2$S(CH$_2$)$_3$CH$_2$Cl | H | OCH$_3$ | Cl | CH |
| CH$_3$ | CH$_2$S(CH$_2$)$_3$CH$_2$Cl | H | CH$_3$ | CH$_3$ | CH |
| CH$_3$ | CH$_2$S(CH$_2$)$_3$CH$_2$Cl | H | OCH$_3$ | OCH$_3$ | N |
| CH$_2$CH$_3$ | CH$_2$S(CH$_2$)$_3$CH$_2$Cl | H | OCH$_3$ | CH$_3$ | N |
| CH$_3$ | CH$_2$SCH$_2$CH$_2$OCH$_3$ | H | OCH$_3$ | OCH$_3$ | CH |
| CH$_3$ | CH$_2$SCH$_2$CH$_2$OCH$_3$ | H | OCH$_3$ | CH$_3$ | CH |
| CH$_3$ | CH$_2$SCH$_2$CH$_2$OCH$_3$ | H | OCH$_3$ | Cl | CH |
| CH$_3$ | CH$_2$SCH$_2$CH$_2$OCH$_3$ | H | CH$_3$ | CH$_3$ | CH |
| CH$_3$ | CH$_2$SCH$_2$CH$_2$OCH$_3$ | H | OCH$_3$ | OCH$_3$ | N |
| CH$_3$ | CH$_2$SCH$_2$CH$_2$OCH$_3$ | H | OCH$_3$ | CH$_3$ | N |
| CH$_3$ | CH$_2$SCH$_2$C(Cl)CH$_2$ | H | OCH$_3$ | OCH$_3$ | CH |
| CH$_3$ | CH$_2$SCH$_2$C(Cl)CH$_2$ | H | OCH$_3$ | CH$_3$ | CH |
| CH$_3$ | CH$_2$SCH$_2$C(Cl)CH$_2$ | H | OCH$_3$ | Cl | CH |
| CH$_3$ | CH$_2$SCH$_2$C(Cl)CH$_2$ | H | CH$_3$ | CH$_3$ | CH |
| CH$_3$ | CH$_2$SCH$_2$C(Cl)CH$_2$ | H | OCH$_3$ | OCH$_3$ | N |
| CH$_3$ | CH$_2$SCH$_2$C(Cl)CH$_2$ | H | OCH$_3$ | CH$_3$ | N |
| CH$_3$ | CH$_2$SCH$_2$CCCH$_2$Cl | H | OCH$_3$ | OCH$_3$ | CH |
| CH$_3$ | CH$_2$SCH$_2$CCCH$_2$Cl | H | OCH$_3$ | CH$_3$ | CH |
| CH$_3$ | CH$_2$SCH$_2$CCCH$_2$Cl | H | OCH$_3$ | Cl | CH |
| CH$_3$ | CH$_2$SCH$_2$CCCH$_2$Cl | H | CH$_3$ | CH$_3$ | CH |
| CH$_3$ | CH$_2$SCH$_2$CCCH$_2$Cl | H | OCH$_3$ | OCH$_3$ | N |
| CH$_2$CH$_3$ | CH$_2$SCH$_2$CCCH$_2$Cl | H | OCH$_3$ | CH$_3$ | N |
| CH$_3$ | CH$_2$SCH$_2$OCH$_3$ | H | OCH$_3$ | OCH$_3$ | CH |
| CH$_3$ | CH$_2$SCH$_2$OCH$_3$ | H | OCH$_3$ | CH$_3$ | CH |
| CH$_3$ | CH$_2$SCH$_2$OCH$_3$ | H | OCH$_3$ | Cl | CH |
| CH$_3$ | CH$_2$SCH$_2$OCH$_3$ | H | CH$_3$ | CH$_3$ | CH |
| CH$_3$ | CH$_2$SCH$_2$OCH$_3$ | H | OCH$_3$ | OCH$_3$ | N |
| CH$_3$ | CH$_2$SCH$_2$OCH$_3$ | H | OCH$_3$ | CH$_3$ | N |
| CH$_3$ | CH$_2$SCH$_2$OCH$_2$CF$_3$ | H | OCH$_3$ | OCH$_3$ | CH |
| CH$_3$ | CH$_2$SCH$_2$OCH$_2$CF$_3$ | H | OCH$_3$ | CH$_3$ | CH |
| CH$_3$ | CH$_2$SCH$_2$OCH$_2$CF$_3$ | H | OCH$_3$ | Cl | CH |
| CH$_3$ | CH$_2$SCH$_2$OCH$_2$CF$_3$ | H | CH$_3$ | CH$_3$ | CH |
| CH$_3$ | CH$_2$SCH$_2$OCH$_2$CF$_3$ | H | OCH$_3$ | OCH$_3$ | N |
| CH$_3$ | CH$_2$SCH$_2$OCH$_2$CF$_3$ | H | OCH$_3$ | CH$_3$ | N |
| CH$_3$ | CH$_2$SCH$_2$SCH$_3$ | H | OCH$_3$ | OCH$_3$ | CH |
| CH$_3$ | CH$_2$SCH$_2$SCH$_3$ | H | OCH$_3$ | CH$_3$ | CH |
| CH$_3$ | CH$_2$SCH$_2$SCH$_3$ | H | OCH$_3$ | Cl | CH |
| CH$_3$ | CH$_2$SCH$_2$SCH$_3$ | H | CH$_3$ | CH$_3$ | CH |
| CH$_3$ | CH$_2$SCH$_2$SCH$_3$ | H | OCH$_3$ | OCH$_3$ | N |
| CH$_3$ | CH$_2$SCH$_2$SCH$_3$ | H | OCH$_3$ | CH$_3$ | N |
| CH$_3$ | CH$_2$SCH$_2$CN | H | OCH$_3$ | OCH$_3$ | CH |
| CH$_3$ | CH$_2$SCH$_2$CN | H | OCH$_3$ | CH$_3$ | CH |
| CH$_3$ | CH$_2$SCH$_2$CN | H | OCH$_3$ | Cl | CH |
| CH$_3$ | CH$_2$SCH$_2$CN | H | CH$_3$ | CH$_3$ | CH |
| CH$_3$ | CH$_2$SCH$_2$CN | H | OCH$_3$ | OCH$_3$ | N |
| CH$_3$ | CH$_2$SCH$_2$CN | H | OCH$_3$ | CH$_3$ | N |
| CH$_3$ | CH$_2$SCH$_2$CH$_2$N(CH$_3$)$_2$ | H | OCH$_3$ | OCH$_3$ | CH |
| CH$_3$ | CH$_2$SCH$_2$CH$_2$N(CH$_3$)$_2$ | H | OCH$_3$ | CH$_3$ | CH |
| CH$_3$ | CH$_2$SCH$_2$CH$_2$N(CH$_3$)$_2$ | H | OCH$_3$ | Cl | CH |
| CH$_3$ | CH$_2$SCH$_2$CH$_2$N(CH$_3$)$_2$ | H | CH$_3$ | CH$_3$ | CH |
| CH$_3$ | CH$_2$SCH$_2$CH$_2$N(CH$_3$)$_2$ | H | OCH$_3$ | OCH$_3$ | N |
| CH$_2$CH$_3$ | CH$_2$SCH$_2$CH$_2$N(CH$_3$)$_2$ | H | OCH$_3$ | CH$_3$ | N |
| CH$_3$ | CH$_2$SCH$_2$CH$_2$F | H | OCH$_3$ | OCH$_3$ | CH |
| CH$_3$ | CH$_2$SCH$_2$CH$_2$F | H | OCH$_3$ | CH$_3$ | CH |
| CH$_3$ | CH$_2$SCH$_2$CH$_2$F | H | OCH$_3$ | Cl | CH |
| CH$_3$ | CH$_2$SCH$_2$CH$_2$F | H | CH$_3$ | CH$_3$ | CH |
| CH$_3$ | CH$_2$SCH$_2$CH$_2$F | H | OCH$_3$ | OCH$_3$ | N |
| CH$_3$ | CH$_2$SCH$_2$CH$_2$F | H | OCH$_3$ | CH$_3$ | N |
| CH$_3$ | CH$_2$SCH$_2$CHF$_2$ | H | OCH$_3$ | OCH$_3$ | CH |
| CH$_3$ | CH$_2$SCH$_2$CHF$_2$ | H | OCH$_3$ | CH$_3$ | CH |
| CH$_3$ | CH$_2$SCH$_2$CHF$_2$ | H | OCH$_3$ | Cl | CH |
| CH$_3$ | CH$_2$SCH$_2$CHF$_2$ | H | CH$_3$ | CH$_3$ | CH |
| CH$_3$ | CH$_2$SCH$_2$CHF$_2$ | H | OCH$_3$ | OCH$_3$ | N |
| CH$_3$ | CH$_2$SCH$_2$CHF$_2$ | H | OCH$_3$ | CH$_3$ | N |
| CH$_3$ | CH$_2$SCH$_2$CF$_3$ | H | OCH$_3$ | OCH$_3$ | CH |
| CH$_3$ | CH$_2$SCH$_2$CF$_3$ | H | OCH$_3$ | CH$_3$ | CH |
| CH$_3$ | CH$_2$SCH$_2$CF$_3$ | H | OCH$_3$ | Cl | CH |
| CH$_3$ | CH$_2$SCH$_2$CF$_3$ | H | CH$_3$ | CH$_3$ | CH |
| CH$_3$ | CH$_2$SCH$_2$CF$_3$ | H | OCH$_3$ | OCH$_3$ | N |
| CH$_2$CH$_3$ | CH$_2$SCH$_2$CF$_3$ | H | OCH$_3$ | CH$_3$ | N |
| CH$_3$ | CH$_2$SCH$_2$CCH | H | OCH$_3$ | OCH$_3$ | CH |
| CH$_3$ | CH$_2$SCH$_2$CCH | H | OCH$_3$ | CH$_3$ | CH |
| CH$_3$ | CH$_2$SCH$_2$CCH | H | OCH$_3$ | Cl | CH |
| CH$_3$ | CH$_2$SCH$_2$CCH | H | CH$_3$ | CH$_3$ | CH |
| CH$_3$ | CH$_2$SCH$_2$CCH | H | OCH$_3$ | OCH$_3$ | N |
| CH$_3$ | CH$_2$SCH$_2$CCH | H | OCH$_3$ | CH$_3$ | N |
| CH$_3$ | CH$_2$SH | H | OCH$_3$ | OCH$_3$ | CH |
| CH$_3$ | CH$_2$SH | H | OCH$_3$ | CH$_3$ | CH |
| CH$_3$ | CH$_2$SH | H | OCH$_3$ | Cl | CH |
| CH$_3$ | CH$_2$SH | H | CH$_3$ | CH$_3$ | CH |
| CH$_3$ | CH$_2$SH | H | OCH$_3$ | OCH$_3$ | N |
| CH$_3$ | CH$_2$SH | H | OCH$_3$ | CH$_3$ | N |

TABLE Ia-continued

| | | | | | |
|---|---|---|---|---|---|
| CH$_3$ | CH$_2$SP(O)(OCH$_3$)$_2$ | H | OCH$_3$ | OCH$_3$ | CH |
| CH$_3$ | CH$_2$SP(O)(OCH$_3$)$_2$ | H | OCH$_3$ | CH$_3$ | CH |
| CH$_3$ | CH$_2$SP(O)(OCH$_3$)$_2$ | H | OCH$_3$ | Cl | CH |
| CH$_3$ | CH$_2$SP(O)(OCH$_3$)$_2$ | H | CH$_3$ | CH$_3$ | CH |
| CH$_3$ | CH$_2$SP(O)(OCH$_3$)$_2$ | H | OCH$_3$ | OCH$_3$ | N |
| CH$_2$CH$_3$ | CH$_2$SP(O)(OCH$_3$)$_2$ | H | OCH$_3$ | CH$_3$ | N |
| CH$_3$ | CH$_2$SCH$_2$CH$_2$OCH$_3$ | H | OCH$_3$ | OCH$_3$ | CH |
| CH$_3$ | CH$_2$SCH$_2$CH$_2$OCH$_3$ | H | OCH$_3$ | CH$_3$ | CH |
| CH$_3$ | CH$_2$SCH$_2$CH$_2$OCH$_3$ | H | OCH$_3$ | Cl | CH |
| CH$_3$ | CH$_2$SCH$_2$CH$_2$OCH$_3$ | H | CH$_3$ | CH$_3$ | CH |
| CH$_3$ | CH$_2$SCH$_2$CH$_2$OCH$_3$ | H | OCH$_3$ | OCH$_3$ | N |
| CH$_3$ | CH$_2$SCH$_2$CH$_2$OCH$_3$ | H | OCH$_3$ | CH$_3$ | N |
| CH$_3$ | CH$_2$SCH$_2$C(H)CH$_2$ | H | OCH$_3$ | OCH$_3$ | CH |
| CH$_3$ | CH$_2$SCH$_2$C(H)CH$_2$ | H | OCH$_3$ | CH$_3$ | CH |
| CH$_3$ | CH$_2$SCH$_2$C(H)CH$_2$ | H | OCH$_3$ | Cl | CH |
| CH$_3$ | CH$_2$SCH$_2$C(H)CH$_2$ | H | CH$_3$ | CH$_3$ | CH |
| CH$_3$ | CH$_2$SCH$_2$C(H)CH$_2$ | H | OCH$_3$ | OCH$_3$ | N |
| CH$_3$ | CH$_2$SCH$_2$C(H)CH$_2$ | H | OCH$_3$ | CH$_3$ | N |
| CH$_3$ | CH$_2$SCH$_2$C(Cl)CH$_2$ | H | OCH$_3$ | OCH$_3$ | CH |
| CH$_3$ | CH$_2$SCH$_2$C(Cl)CH$_2$ | H | OCH$_3$ | CH$_3$ | CH |
| CH$_3$ | CH$_2$SCH$_2$C(Cl)CH$_2$ | H | OCH$_3$ | Cl | CH |
| CH$_3$ | CH$_2$SCH$_2$C(Cl)CH$_2$ | H | CH$_3$ | CH$_3$ | CH |
| CH$_3$ | CH$_2$SCH$_2$C(Cl)CH$_2$ | H | OCH$_3$ | OCH$_3$ | N |
| CH$_3$ | CH$_2$SCH$_2$C(Cl)CH$_2$ | H | OCH$_3$ | CH$_3$ | N |
| CH$_3$ | CH$_2$S(O)-cyclopropyl | H | OCH$_3$ | OCH$_3$ | CH |
| CH$_3$ | CH$_2$S(O)-cyclopropyl | H | OCH$_3$ | CH$_3$ | CH |
| CH$_3$ | CH$_2$S(O)-cyclopropyl | H | OCH$_3$ | Cl | CH |
| CH$_3$ | CH$_2$S(O)-cyclopropyl | H | CH$_3$ | CH$_3$ | CH |
| CH$_3$ | CH$_2$S(O)-cyclopropyl | H | OCH$_3$ | OCH$_3$ | N |
| CH$_3$ | CH$_2$S(O)-cyclopropyl | H | OCH$_3$ | CH$_3$ | N |
| CH$_3$ | CH$_2$S(O)CH$_2$-cyclopropyl | H | OCH$_3$ | OCH$_3$ | CH |
| CH$_3$ | CH$_2$S(O)CH$_2$-cyclopropyl | H | OCH$_3$ | CH$_3$ | CH |
| CH$_3$ | CH$_2$S(O)CH$_2$-cyclopropyl | H | OCH$_3$ | Cl | CH |
| CH$_3$ | CH$_2$S(O)CH$_2$-cyclopropyl | H | CH$_3$ | CH$_3$ | CH |
| CH$_3$ | CH$_2$S(O)CH$_2$-cyclopropyl | H | OCH$_3$ | OCH$_3$ | N |
| CH$_3$ | CH$_2$S(O)CH$_2$-cyclopropyl | H | OCH$_3$ | CH$_3$ | N |
| CH$_3$ | CH$_2$S(O)-cyclobutyl | H | OCH$_3$ | OCH$_3$ | CH |
| CH$_3$ | CH$_2$S(O)-cyclobutyl | H | OCH$_3$ | CH$_3$ | CH |
| CH$_3$ | CH$_2$S(O)-cyclobutyl | H | OCH$_3$ | Cl | CH |
| CH$_3$ | CH$_2$S(O)-cyclobutyl | H | CH$_3$ | CH$_3$ | CH |
| CH$_3$ | CH$_2$S(O)-cyclobutyl | H | OCH$_3$ | OCH$_3$ | N |
| CH$_2$CH$_3$ | CH$_2$S(O)-cyclobutyl | H | OCH$_3$ | CH$_3$ | N |
| CH$_3$ | CH$_2$S(O)CH$_2$CF$_2$CF$_3$ | H | OCH$_3$ | OCH$_3$ | CH |
| CH$_3$ | CH$_2$S(O)CH$_2$CF$_2$CF$_3$ | H | OCH$_3$ | CH$_3$ | CH |
| CH$_3$ | CH$_2$S(O)CH$_2$CF$_2$CF$_3$ | H | OCH$_3$ | Cl | CH |
| CH$_3$ | CH$_2$S(O)CH$_2$CF$_2$CF$_3$ | H | CH$_3$ | CH$_3$ | CH |
| CH$_3$ | CH$_2$S(O)CH$_2$CF$_2$CF$_3$ | H | OCH$_3$ | OCH$_3$ | N |
| CH$_3$ | CH$_2$S(O)CH$_2$CF$_2$CF$_3$ | H | OCH$_3$ | CH$_3$ | N |
| CH$_3$ | CH$_2$S(O)CH$_3$)CH$_3$ | H | OCH$_3$ | OCH$_3$ | CH |
| CH$_3$ | CH$_2$S(O)CH(CF$_3$)CH$_3$ | H | OCH$_3$ | CH$_3$ | CH |
| CH$_3$ | CH$_2$S(O)CH(CF$_3$)CH$_3$ | H | OCH$_3$ | Cl | CH |
| CH$_3$ | CH$_2$S(O)CH(CF$_3$)CH$_3$ | H | CH$_3$ | CH$_3$ | CH |
| CH$_3$ | CH$_2$S(O)CH(CF$_3$)CH$_3$ | H | OCH$_3$ | OCH$_3$ | N |
| CH$_3$ | CH$_2$S(O)CH(CF$_3$)CH$_3$ | H | OCH$_3$ | CH$_3$ | N |
| CH$_3$ | CH$_2$S(O)CH$_2$CF$_2$CF$_2$H | H | OCH$_3$ | OCH$_3$ | CH |
| CH$_3$ | CH$_2$S(O)CH$_2$CF$_2$CF$_2$H | H | OCH$_3$ | CH$_3$ | CH |
| CH$_3$ | CH$_2$S(O)CH$_2$CF$_2$CF$_2$H | H | OCH$_3$ | Cl | CH |
| CH$_3$ | CH$_2$S(O)CH$_2$CF$_2$CF$_2$H | H | CH$_3$ | CH$_3$ | CH |
| CH$_3$ | CH$_2$S(O)CH$_2$CF$_2$CF$_2$H | H | OCH$_3$ | OCH$_3$ | N |
| CH$_2$CH$_3$ | CH$_2$S(O)CH$_2$CF$_2$CF$_2$H | H | OCH$_3$ | CH$_3$ | N |
| CH$_3$ | CH$_2$S(O)CH(CH$_2$F)$_2$ | H | OCH$_3$ | OCH$_3$ | CH |
| CH$_3$ | CH$_2$S(O)CH(CH$_2$F)$_2$ | H | OCH$_3$ | CH$_3$ | CH |
| CH$_3$ | CH$_2$S(O)CH(CH$_2$F)$_2$ | H | OCH$_3$ | Cl | CH |
| CH$_3$ | CH$_2$S(O)CH(CH$_2$F)$_2$ | H | CH$_3$ | CH$_3$ | CH |
| CH$_3$ | CH$_2$S(O)CH(CH$_2$F)$_2$ | H | OCH$_3$ | OCH$_3$ | N |
| CH$_3$ | CH$_2$S(O)CH(CH$_2$F)$_2$ | H | OCH$_3$ | CH$_3$ | N |
| CH$_3$ | CH$_2$S(O)CH(CH$_2$F)CH$_3$ | H | OCH$_3$ | OCH$_3$ | CH |
| CH$_3$ | CH$_2$S(O)CH(CH$_2$F)CH$_3$ | H | OCH$_3$ | CH$_3$ | CH |
| CH$_3$ | CH$_2$S(O)CH(CH$_2$F)CH$_3$ | H | OCH$_3$ | Cl | CH |
| CH$_3$ | CH$_2$S(O)CH(CH$_2$F)CH$_3$ | H | CH$_3$ | CH$_3$ | CH |
| CH$_3$ | CH$_2$S(O)CH(CH$_2$F)CH$_3$ | H | OCH$_3$ | OCH$_3$ | N |
| CH$_3$ | CH$_2$S(O)CH(CH$_2$F)CH$_3$ | H | OCH$_3$ | CH$_3$ | N |
| CH$_3$ | CH$_2$S(O)(CH$_2$)$_3$CH$_2$Cl | H | OCH$_3$ | OCH$_3$ | CH |
| CH$_3$ | CH$_2$S(O)(CH$_2$)$_3$CH$_2$Cl | H | OCH$_3$ | CH$_3$ | CH |
| CH$_3$ | CH$_2$S(O)(CH$_2$)$_3$CH$_2$Cl | H | OCH$_3$ | Cl | CH |
| CH$_3$ | CH$_2$S(O)(CH$_2$)$_3$CH$_2$Cl | H | CH$_3$ | CH$_3$ | CH |
| CH$_3$ | CH$_2$S(O)(CH$_2$)$_3$CH$_2$Cl | H | OCH$_3$ | OCH$_3$ | N |
| CH$_2$CH$_3$ | CH$_2$S(O)CH$_2$)$_3$CH$_2$Cl | H | OCH$_3$ | CH$_3$ | N |
| CH$_3$ | CH$_2$S(O)CH$_2$CH$_2$OCH$_3$ | H | OCH$_3$ | OCH$_3$ | CH |
| CH$_3$ | CH$_2$S(O)CH$_2$CH$_2$OCH$_3$ | H | OCH$_3$ | CH$_3$ | CH |
| CH$_3$ | CH$_2$S(O)CH$_2$CH$_2$OCH$_3$ | H | OCH$_3$ | Cl | CH |
| CH$_3$ | CH$_2$S(O)CH$_2$CH$_2$OCH$_3$ | H | CH$_3$ | CH$_3$ | CH |

TABLE Ia-continued

| | | | | | | |
|---|---|---|---|---|---|---|
| CH$_3$ | CH$_2$S(O)CH$_2$CH$_2$OCH$_3$ | H | OCH$_3$ | OCH$_3$ | N | |
| CH$_3$ | CH$_2$S(O)CH$_2$CH$_2$OCH$_3$ | H | OCH$_3$ | CH$_3$ | N | |
| CH$_3$ | CH$_2$S(O)CH$_2$C(Cl)CH$_2$ | H | OCH$_3$ | OCH$_3$ | CH | |
| CH$_3$ | CH$_2$S(O)CH$_2$C(Cl)CH$_2$ | H | OCH$_3$ | CH$_3$ | CH | |
| CH$_3$ | CH$_2$S(O)CH$_2$C(Cl)CH$_2$ | H | OCH$_3$ | Cl | CH | |
| CH$_3$ | CH$_2$S(O)CH$_2$C(Cl)CH$_2$ | H | CH$_3$ | CH$_3$ | CH | |
| CH$_3$ | CH$_2$S(O)CH$_2$C(Cl)CH$_2$ | H | OCH$_3$ | OCH$_3$ | N | |
| CH$_3$ | CH$_2$S(O)CH$_2$C(Cl)CH$_2$ | H | OCH$_3$ | CH$_3$ | N | |
| CH$_3$ | CH$_2$S(O)CH$_2$CCCH$_2$Cl | H | OCH$_3$ | OCH$_3$ | CH | |
| CH$_3$ | CH$_2$S(O)CH$_2$CCCH$_2$Cl | H | OCH$_3$ | CH$_3$ | CH | |
| CH$_3$ | CH$_2$S(O)CH$_2$CCCH$_2$Cl | 2 | H | OCH$_3$ | Cl | CH |
| CH$_3$ | CH$_2$S(O)CH$_2$CCCH$_2$Cl | H | CH$_3$ | CH$_3$ | CH | |
| CH$_3$ | CH$_2$S(O)CH$_2$CCCH$_2$Cl | H | OCH$_3$ | OCH$_3$ | N | |
| CH$_2$CH$_3$ | CH$_2$S(O)CH$_2$CCCH$_2$Cl | H | OCH$_3$ | CH$_3$ | N | |
| CH$_3$ | CH$_2$S(O)CH$_2$CN | H | OCH$_3$ | OCH$_3$ | CH | |
| CH$_3$ | CH$_2$S(O)CH$_2$CN | H | OCH$_3$ | CH$_3$ | CH | |
| CH$_3$ | CH$_2$S(O)CH$_2$CN | H | OCH$_3$ | Cl | CH | |
| CH$_3$ | CH$_2$S(O)CH$_2$CN | H | CH$_3$ | CH$_3$ | CH | |
| CH$_3$ | CH$_2$S(O)CH$_2$CN | H | OCH$_3$ | OCH$_3$ | N | |
| CH$_3$ | CH$_2$S(O)CH$_2$CN | H | OCH$_3$ | CH$_3$ | N | |
| CH$_3$ | CH$_2$S(O)CH$_2$CH$_2$N(CH$_3$)$_2$ | H | OCH$_3$ | OCH$_3$ | CH | |
| CH$_3$ | CH$_2$S(O)CH$_2$CH$_2$N(CH$_3$)$_2$ | H | OCH$_3$ | CH$_3$ | CH | |
| CH$_3$ | CH$_2$S(O)CH$_2$CH$_2$N(CH$_3$)$_2$ | H | OCH$_3$ | Cl | CH | |
| CH$_3$ | CH$_2$S(O)CH$_2$CH$_2$N(CH$_3$)$_2$ | H | CH$_3$ | CH$_3$ | CH | |
| CH$_3$ | CH$_2$S(O)CH$_2$CH$_2$N(CH$_3$)$_2$ | H | OCH$_3$ | OCH$_3$ | N | |
| CH$_2$CH$_3$ | CH$_2$S(O)CH$_2$CH$_2$N(CH$_3$)$_2$ | H | OCH$_3$ | CH$_3$ | N | |
| CH$_3$ | CH$_2$S(O)CH$_2$CH$_2$F | H | OCH$_3$ | OCH$_3$ | CH | |
| CH$_3$ | CH$_2$S(O)CH$_2$CH$_2$F | H | OCH$_3$ | CH$_3$ | CH | |
| CH$_3$ | CH$_2$S(O)CH$_2$CH$_2$F | H | OCH$_3$ | Cl | CH | |
| CH$_3$ | CH$_2$S(O)CH$_2$CH$_2$F | H | CH$_3$ | CH$_3$ | CH | |
| CH$_3$ | CH$_2$S(O)CH$_2$CH$_2$F | H | OCH$_3$ | OCH$_3$ | N | |
| CH$_3$ | CH$_2$S(O)CH$_2$CH$_2$F | H | OCH$_3$ | CH$_3$ | N | |
| CH$_3$ | CH$_2$S(O)CH$_2$CHF$_2$ | H | OCH$_3$ | OCH$_3$ | CH | |
| CH$_3$ | CH$_2$S(O)CH$_2$CHF$_2$ | H | OCH$_3$ | CH$_3$ | CH | |
| CH$_3$ | CH$_2$S(O)CH$_2$CHF$_2$ | H | OCH$_3$ | Cl | CH | |
| CH$_3$ | CH$_2$S(O)CH$_2$CHF$_2$ | H | CH$_3$ | CH$_3$ | CH | |
| CH$_3$ | CH$_2$S(O)CH$_2$CHF$_2$ | H | OCH$_3$ | OCH$_3$ | N | |
| CH$_3$ | CH$_2$S(O)CH$_2$CHF$_2$ | H | OCH$_3$ | CH$_3$ | N | |
| CH$_3$ | CH$_2$S(O)CH$_2$CF$_3$ | H | OCH$_3$ | OCH$_3$ | CH | |
| CH$_3$ | CH$_2$S(O)CH$_2$CF$_3$ | H | OCH$_3$ | CH$_3$ | CH | |
| CH$_3$ | CH$_2$S(O)CH$_2$CF$_3$ | H | OCH$_3$ | Cl | CH | |
| CH$_3$ | CH$_2$S(O)CH$_2$CF$_3$ | H | CH$_H$ | CH$_3$ | CH | |
| CH$_3$ | CH$_2$S(O)CH$_2$CF$_3$ | H | OCH$_3$ | OCH$_3$ | N | |
| CH$_2$CH$_3$ | CH$_2$S(O)CH$_2$CF$_3$ | H | OCH$_3$ | CH$_3$ | N | |
| CH$_3$ | CH$_2$S(O)CH$_2$CCH | H | OCH$_3$ | OCH$_3$ | CH | |
| CH$_3$ | CH$_2$S(O)CH$_2$CCH | H | OCH$_3$ | CH$_3$ | CH | |
| CH$_3$ | CH$_2$S(O)CH$_2$CCH | H | OCH$_3$ | Cl | CH | |
| CH$_3$ | CH$_2$S(O)CH$_2$CCH | H | CH$_3$ | CH$_3$ | CH | |
| CH$_3$ | CH$_2$S(O)CH$_2$CCH | H | OCH$_3$ | OCH$_3$ | N | |
| CH$_3$ | CH$_2$S(O)CH$_2$CCH | H | OCH$_3$ | CH$_3$ | N | |
| CH$_3$ | CH$_2$S(O)CH$_2$CH$_2$OCH$_3$ | H | OCH$_3$ | OCH$_3$ | CH | |
| CH$_3$ | CH$_2$S(O)CH$_2$CH$_2$OCH$_3$ | H | OCH$_3$ | CH$_3$ | CH | |
| CH$_3$ | CH$_2$S(O)CH$_2$CH$_2$OCH$_3$ | H | OCH$_3$ | Cl | CH | |
| CH$_3$ | CH$_2$S(O)CH$_2$CH$_2$OCH$_3$ | H | CH$_3$ | CH$_3$ | CH | |
| CH$_3$ | CH$_2$S(O)CH$_2$CH$_2$OCH$_3$ | H | OCH$_3$ | OCH$_3$ | N | |
| CH$_3$ | CH$_2$S(O)CH$_2$CH$_2$OCH$_3$ | H | OCH$_3$ | CH$_3$ | N | |
| CH$_3$ | CH$_2$S(O)CH$_2$C(H)CH$_2$ | H | OCH$_3$ | OCH$_3$ | CH | |
| CH$_3$ | CH$_2$S(O)CH$_2$C(H)CH$_2$ | H | OCH$_3$ | CH$_3$ | CH | |
| CH$_3$ | CH$_2$S(O)CH$_2$C(H)CH$_2$ | H | OCH$_3$ | Cl | CH | |
| CH$_3$ | CH$_2$S(O)CH$_2$C(H)CH$_2$ | H | CH$_3$ | CH$_3$ | CH | |
| CH$_3$ | CH$_2$S(O)CH$_2$C(H)CH$_2$ | H | OCH$_3$ | OCH$_3$ | N | |
| CH$_3$ | CH$_2$S(O)CH$_2$C(H)CH$_2$ | H | OCH$_3$ | CH$_3$ | N | |
| CH$_3$ | CH$_2$S(O)CH$_2$C(Cl)CH$_2$ | H | OCH$_3$ | OCH$_3$ | CH | |
| CH$_3$ | CH$_2$S(O)CH$_2$C(Cl)CH$_2$ | H | OCH$_3$ | CH$_3$ | CH | |
| CH$_3$ | CH$_2$S(O)CH$_2$C(Cl)CH$_2$ | H | OCH$_3$ | Cl | CH | |
| CH$_3$ | CH$_2$S(O)CH$_2$C(Cl)CH$_2$ | H | CH$_3$ | CH$_3$ | CH | |
| CH$_3$ | CH$_2$S(O)CH$_2$C(Cl)CH$_2$ | H | OCH$_3$ | OCH$_3$ | N | |
| CH$_3$ | CH$_2$S(O)CH$_2$C(Cl)CH$_2$ | H | OCH$_3$ | CH$_3$ | N | |
| CH$_3$ | CH$_2$S(O)$_2$-cyclopropyl | H | OCH$_3$ | OCH$_3$ | CH | |
| CH$_3$ | CH$_2$S(O)$_2$-cyclopropyl | H | OCH$_3$ | CH$_3$ | CH | |
| CH$_3$ | CH$_2$S(O)$_2$-cyclopropyl | H | OCH$_3$ | Cl | CH | |
| CH$_3$ | CH$_2$S(O)$_2$-cyclopropyl | H | CH$_3$ | CH$_3$ | CH | |
| CH$_3$ | CH$_2$S(O)$_2$-cyclopropyl | H | OCH$_3$ | OCH$_3$ | N | |
| CH$_3$ | CH$_2$S(O)$_2$-cyclopropyl | H | OCH$_3$ | CH$_3$ | N | |
| CH$_3$ | CH$_2$S(O)$_2$CH$_2$-cyclopropyl | H | OCH$_3$ | OCH$_3$ | CH | |
| CH$_3$ | CH$_2$S(O)$_2$CH$_2$-cyclopropyl | H | OCH$_3$ | CH$_3$ | CH | |
| CH$_3$ | CH$_2$S(O)$_2$CH$_2$-cyclopropyl | H | OCH$_3$ | Cl | CH | |
| CH$_3$ | CH$_2$S(O)$_2$CH$_2$-cyclopropyl | H | CH$_3$ | CH$_3$ | CH | |
| CH$_3$ | CH$_2$S(O)$_2$CH$_2$-cyclopropyl | H | OCH$_3$ | OCH$_3$ | N | |
| CH$_3$ | CH$_2$S(O)$_2$CH$_2$-cyclopropyl | H | OCH$_3$ | CH$_3$ | N | |
| CH$_3$ | CH$_2$S(O)$_2$-cyclobutyl | H | OCH$_3$ | OCH$_3$ | CH | |

TABLE Ia-continued

| | | | | | |
|---|---|---|---|---|---|
| CH$_3$ | CH$_2$S(O)$_2$-cyclobutyl | H | OCH$_3$ | CH$_3$ | CH |
| CH$_3$ | CH$_2$S(O)$_2$-cyclobutyl | H | OCH$_3$ | Cl | CH |
| CH$_3$ | CH$_2$S(O)$_2$-cyclobutyl | H | CH$_3$ | CH$_3$ | CH |
| CH$_3$ | CH$_2$S(O)$_2$-cyclobutyl | H | OCH$_3$ | OCH$_3$ | N |
| CH$_3$ | CH$_2$S(O)$_2$-cyclobutyl | H | OCH$_3$ | CH$_3$ | N |
| CH$_3$ | CH$_2$S(O)$_2$CH$_2$CF$_2$CF$_3$ | H | OCH$_3$ | OCH$_3$ | CH |
| CH$_3$ | CH$_2$S(O)$_2$CH$_2$CF$_2$CF$_3$ | H | OCH$_3$ | CH$_3$ | CH |
| CH$_3$ | CH$_2$S(O)$_2$CH$_2$CF$_2$CF$_3$ | H | OCH$_3$ | Cl | CH |
| CH$_3$ | CH$_2$S(O)$_2$CH$_2$CF$_2$CF$_3$ | H | CH$_3$ | CH$_3$ | CH |
| CH$_3$ | CH$_2$S(O)$_2$CH$_2$CF$_2$CF$_3$ | H | OCH$_3$ | OCH$_3$ | N |
| CH$_3$ | CH$_2$S(O)$_2$CH$_2$CF$_2$CF$_3$ | H | OCH$_3$ | CH$_3$ | N |
| CH$_3$ | CH$_2$S(O)$_2$CH(CF$_3$)CH$_3$ | H | OCH$_3$ | OCH$_3$ | CH |
| CH$_3$ | CH$_2$S(O)$_2$CH(CF$_3$)CH$_3$ | H | OCH$_3$ | CH$_3$ | CH |
| CH$_3$ | CH$_2$S(O)$_2$CH(CF$_3$)CH$_3$ | H | OCH$_3$ | Cl | CH |
| CH$_3$ | CH$_2$S(O)$_2$CH(CF$_3$)CH$_3$ | H | CH$_3$ | CH$_3$ | CH |
| CH$_3$ | CH$_2$S(O)$_2$CH(CF$_3$)CH$_3$ | H | OCH$_3$ | OCH$_3$ | N |
| CH$_3$ | CH$_2$S(O)$_2$CH(CF$_3$)CH$_3$ | H | OCH$_3$ | CH$_3$ | N |
| CH$_3$ | CH$_2$S(O)$_2$CH$_2$CF$_2$CF$_2$H | H | OCH$_3$ | OCH$_3$ | CH |
| CH$_3$ | CH$_2$S(O)$_2$CH$_2$CF$_2$CF$_2$H | H | OCH$_3$ | CH$_3$ | CH |
| CH$_3$ | CH$_2$S(O)$_2$CH$_2$CF$_2$CF$_2$H | H | OCH$_3$ | Cl | CH |
| CH$_3$ | CH$_2$S(O)$_2$CH$_2$CF$_2$CF$_2$H | H | CH$_3$ | CH$_3$ | CH |
| CH$_3$ | CH$_2$S(O)$_2$CH$_2$CF$_2$CF$_2$H | H | OCH$_3$ | OCH$_3$ | N |
| CH$_3$ | CH$_2$S(O)$_2$CH$_2$CF$_2$CF$_2$H | H | OCH$_3$ | CH$_3$ | N |
| CH$_3$ | CH$_2$S(O)$_2$CH(CH$_2$F)$_2$ | H | OCH$_3$ | OCH$_3$ | CH |
| CH$_3$ | CH$_2$S(O)$_2$CH(CH$_2$F)$_2$ | H | OCH$_3$ | CH$_3$ | CH |
| CH$_3$ | CH$_2$S(O)$_2$CH(CH$_2$F)$_2$ | H | OCH$_3$ | Cl | CH |
| CH$_3$ | CH$_2$S(O)$_2$CH(CH$_2$F)$_2$ | H | CH$_3$ | CH$_3$ | CH |
| CH$_3$ | CH$_2$S(O)$_2$CH(CH$_2$F)$_2$ | H | OCH$_3$ | OCH$_3$ | N |
| CH$_3$ | CH$_2$S(O)$_2$CH(CH$_2$F)$_2$ | H | OCH$_3$ | CH$_3$ | N |
| CH$_3$ | CH$_2$S(O)$_2$CH(CH$_2$F)CH$_3$ | H | OCH$_3$ | OCH$_3$ | CH |
| CH$_3$ | CH$_2$S(O)$_2$CH(CH$_2$F)CH$_3$ | H | OCH$_3$ | CH$_3$ | CH |
| CH$_3$ | CH$_2$S(O)$_2$CH(CH$_2$F)CH$_3$ | H | OCH$_3$ | Cl | CH |
| CH$_3$ | CH$_2$S(O)$_2$CH(CH$_2$F)CH$_3$ | H | CH$_3$ | CH$_3$ | CH |
| CH$_3$ | CH$_2$S(O)$_2$CH(CH$_2$F)CH$_3$ | H | OCH$_3$ | OCH$_3$ | N |
| CH$_3$ | CH$_2$S(O)$_2$CH(CH$_2$F)CH$_3$ | H | OCH$_3$ | CH$_3$ | N |
| CH$_3$ | CH$_2$S(O)$_2$(CH$_2$)$_3$CH$_2$Cl | H | OCH$_3$ | OCH$_3$ | CH |
| CH$_3$ | CH$_2$S(O)$_2$(CH$_2$)$_3$CH$_2$Cl | H | OCH$_3$ | CH$_3$ | CH |
| CH$_3$ | CH$_2$S(O)$_2$(CH$_2$)$_3$CH$_2$Cl | H | OCH$_3$ | Cl | CH |
| CH$_3$ | CH$_2$S(O)$_2$(CH$_2$)$_3$CH$_2$Cl | H | CH$_3$ | CH$_3$ | CH |
| CH$_3$ | CH$_2$S(O)$_2$(CH$_2$)$_3$CH$_2$Cl | H | OCH$_3$ | OCH$_3$ | N |
| CH$_2$CH$_3$ | CH$_2$S(O)$_2$(CH$_2$)$_3$CH$_2$Cl | H | OCH$_3$ | CH$_3$ | N |
| CH$_3$ | CH$_2$S(O)CH$_2$CH$_2$OCH$_3$ | H | OCH$_3$ | OCH$_3$ | CH |
| CH$_3$ | CH$_2$S(O)CH$_2$CH$_2$OCH$_3$ | H | OCH$_3$ | CH$_3$ | CH |
| CH$_3$ | CH$_2$S(O)CH$_2$CH$_2$OCH$_3$ | H | OCH$_3$ | Cl | CH |
| CH$_3$ | CH$_2$S(O)CH$_2$CH$_2$OCH$_3$ | H | CH$_3$ | CH$_3$ | CH |
| CH$_3$ | CH$_2$S(O)CH$_2$CH$_2$OCH$_3$ | H | OCH$_3$ | OCH$_3$ | N |
| CH$_3$ | CH$_2$S(O)CH$_2$CH$_2$OCH$_3$ | H | OCH$_3$ | CH$_3$ | N |
| CH$_3$ | CH$_2$S(O)$_2$CH$_2$C(Cl)CH$_2$ | H | OCH$_3$ | OCH$_3$ | CH |
| CH$_3$ | CH$_2$S(O)$_2$CH$_2$C(Cl)CH$_2$ | H | OCH$_3$ | CH$_3$ | CH |
| CH$_3$ | CH$_2$S(O)$_2$CH$_2$C(Cl)CH$_2$ | H | OCH$_3$ | Cl | CH |
| CH$_3$ | CH$_2$S(O)$_2$CH$_2$C(Cl)CH$_2$ | H | CH$_3$ | CH$_3$ | CH |
| CH$_3$ | CH$_2$S(O)$_2$CH$_2$C(Cl)CH$_2$ | H | OCH$_3$ | OCH$_3$ | N |
| CH$_3$ | CH$_2$S(O)$_2$CH$_2$C(Cl)CH$_2$ | H | OCH$_3$ | CH$_3$ | N |
| CH$_3$ | CH$_2$S(O)$_2$CH$_2$CCCH$_2$Cl | H | OCH$_3$ | OCH$_3$ | CH |
| CH$_3$ | CH$_2$S(O)$_2$CH$_2$CCCH$_2$Cl | H | OCH$_3$ | CH$_3$ | CH |
| CH$_3$ | CH$_2$S(O)$_2$CH$_2$CCCH$_2$Cl | H | CH$_3$ | Cl | CH |
| CH$_3$ | CH$_2$S(O)$_2$CH$_2$CCCH$_2$Cl | H | CH$_3$ | CH$_3$ | CH |
| CH$_3$ | CH$_2$S(O)$_2$CH$_2$CCCH$_2$Cl | H | OCH$_3$ | OCH$_3$ | N |
| CH$_2$CH$_3$ | CH$_2$S(O)$_2$CH$_2$CCCH$_2$Cl | H | OCH$_3$ | CH$_3$ | N |
| CH$_3$ | CH$_2$S(O)$_2$CH$_2$CCH | H | OCH$_3$ | OCH$_3$ | CH |
| CH$_3$ | CH$_2$S(O)$_2$CH$_2$CCH | H | OCH$_3$ | CH$_3$ | CH |
| CH$_3$ | CH$_2$S(O)$_2$CH$_2$CCH | H | OCH$_3$ | Cl | CH |
| CH$_3$ | CH$_2$S(O)$_2$CH$_2$CCH | H | CH$_3$ | CH$_3$ | CH |
| CH$_3$ | CH$_2$S(O)$_2$CH$_2$CCH | H | OCH$_3$ | OCH$_3$ | N |
| CH$_3$ | CH$_2$S(O)$_2$CH$_2$CCH | H | OCH$_3$ | CH$_3$ | N |
| CH$_3$ | CH$_2$S(O)$_2$CH$_2$CN | H | OCH$_3$ | OCH$_3$ | CH |
| CH$_3$ | CH$_2$S(O)$_2$CH$_2$CN | H | OCH$_3$ | CH$_3$ | CH |
| CH$_3$ | CH$_2$S(O)$_2$CH$_2$CN | H | OCH$_3$ | Cl | CH |
| CH$_3$ | CH$_2$S(O)$_2$CH$_2$CN | H | CH$_3$ | CH$_3$ | CH |
| CH$_3$ | CH$_2$S(O)$_2$CH$_2$CN | H | OCH$_3$ | OCH$_3$ | N |
| CH$_3$ | CH$_2$S(O)$_2$CH$_2$CN | H | OCH$_3$ | CH$_3$ | N |
| CH$_3$ | CH$_2$S(O)$_2$CH$_2$CH$_2$N(CH$_3$)$_2$ | H | OCH$_3$ | OCH$_3$ | CH |
| CH$_3$ | CH$_2$S(O)$_2$CH$_2$CH$_2$N(CH$_3$)$_2$ | H | OCH$_3$ | CH$_3$ | CH |
| CH$_3$ | CH$_2$S(O)$_2$CH$_2$CH$_2$N(CH$_3$)$_2$ | H | OCH$_3$ | Cl | CH |
| CH$_3$ | CH$_2$S(O)$_2$CH$_2$CH$_2$N(CH$_3$)$_2$ | H | CH$_3$ | CH$_3$ | CH |
| CH$_3$ | CH$_2$S(O)$_2$CH$_2$CH$_2$N(CH$_3$)$_2$ | H | OCH$_3$ | OCH$_3$ | N |
| CH$_2$Ch$_3$ | CH$_2$S(O)$_2$CH$_2$CH$_2$N(CH$_3$)$_2$ | H | OCH$_3$ | CH$_3$ | N |
| CH$_3$ | CH$_2$S(O)$_2$CH$_2$CH$_2$F | H | OCH$_3$ | OCH$_3$ | CH |
| CH$_3$ | CH$_2$S(O)$_2$CH$_2$CH$_2$F | H | OCH$_3$ | CH$_3$ | CH |
| CH$_3$ | CH$_3$S(O)$_2$CH$_2$CH$_2$F | H | OCH$_3$ | Cl | CH |
| CH$_3$ | CH$_2$S(O)$_2$CH$_2$CH$_2$F | H | CH$_3$ | CH$_3$ | CH |
| CH$_3$ | CH$_2$S(O)$_2$CH$_2$CH$_2$F | H | OCH$_3$ | OCH$_3$ | N |

TABLE Ia-continued

| | | | | | | |
|---|---|---|---|---|---|---|
| CH$_3$ | CH$_2$S(O)$_2$CH$_2$CH$_2$F | H | OCH$_3$ | CH$_3$ | N | |
| CH$_3$ | CH$_2$S(O)$_2$CH$_2$CHF$_2$ | H | OCH$_3$ | OCH$_3$ | CH | |
| CH$_3$ | CH$_2$S(O)$_2$CH$_2$CHF$_2$ | H | OCH$_3$ | CH$_3$ | CH | |
| CH$_3$ | CH$_2$S(O)$_2$CH$_2$CHF$_2$ | H | OCH$_3$ | Cl | CH | |
| CH$_3$ | CH$_2$S(O)$_2$CH$_2$CHF$_2$ | H | CH$_3$ | CH$_3$ | CH | |
| CH$_3$ | CH$_2$S(O)$_2$CH$_2$CHF$_2$ | H | OCH$_3$ | OCH$_3$ | N | |
| CH$_3$ | CH$_2$S(O)$_2$CH$_2$CHF$_2$ | H | OCH$_3$ | CH$_3$ | N | |
| CH$_3$ | CH$_2$S(O)$_2$CH$_2$CF$_3$ | H | OCH$_3$ | OCH$_3$ | CH | |
| CH$_3$ | CH$_2$S(O)$_2$CH$_2$CF$_3$ | H | OCH$_3$ | CH$_3$ | CH | |
| CH$_3$ | CH$_2$S(O)$_2$CH$_2$CF$_3$ | H | OCH$_3$ | Cl | CH | |
| CH$_3$ | CH$_2$S(O)$_2$CH$_2$CF$_3$ | H | CH$_3$ | CH$_3$ | CH | |
| CH$_3$ | CH$_2$S(O)$_2$CH$_2$CF$_3$ | H | OCH$_3$ | OCH$_3$ | N | |
| CH$_2$CH$_3$ | CH$_2$S(O)$_2$CH$_2$CF$_3$ | H | OCH$_3$ | CH$_3$ | N | |
| CH$_3$ | CH$_2$S(O)$_2$CH$_2$CH$_2$OCH$_3$ | H | OCH$_3$ | OCH$_3$ | CH | |
| CH$_3$ | CH$_2$S(O)$_2$CH$_2$CH$_2$OCH$_3$ | H | OCH$_3$ | CH$_3$ | CH | |
| CH$_3$ | CH$_2$S(O)$_2$CH$_2$CH$_2$OCH$_3$ | H | OCH$_3$ | Cl | CH | |
| CH$_3$ | CH$_2$S(O)$_2$CH$_2$CH$_2$OCH$_3$ | H | CH$_3$ | CH$_3$ | CH | |
| CH$_3$ | CH$_2$S(O)$_2$CH$_2$CH$_2$OCH$_3$ | H | OCH$_3$ | OCH$_3$ | N | |
| CH$_3$ | CH$_2$S(O)$_2$CH$_2$CH$_2$OCH$_3$ | H | OCH$_3$ | CH$_3$ | N | |
| CH$_3$ | CH$_2$S(O)$_2$CH$_2$C(H)CH$_2$ | H | OCH$_3$ | OCH$_3$ | CH | |
| CH$_3$ | CH$_2$S(O)$_2$CH$_2$C(H)CH$_2$ | H | OCH$_3$ | CH$_3$ | CH | |
| CH$_3$ | CH$_2$S(O)$_2$CH$_2$C(H)CH$_2$ | H | OCH$_3$ | Cl | CH | |
| CH$_3$ | CH$_2$S(O)$_2$CH$_2$C(H)CH$_2$ | H | CH$_3$ | CH$_3$ | CH | |
| CH$_3$ | CH$_2$S(O)$_2$CH$_2$C(H)CH$_2$ | H | OCH$_3$ | OCH$_3$ | N | |
| CH$_3$ | CH$_2$S(O)$_2$CH$_2$C(H)CH$_2$ | H | OCH$_3$ | CH$_3$ | N | |
| CH$_3$ | CH$_2$S(O)$_2$CH$_2$C(Cl)CH$_2$ | H | OCH$_3$ | OCH$_3$ | CH | |
| CH$_3$ | CH$_2$S(O)$_2$CH$_2$C(Cl)CH$_2$ | H | OCH$_3$ | CH$_3$ | CH | |
| CH$_3$ | CH$_2$S(O)$_2$CH$_2$C(Cl)CH$_2$ | H | OCH$_3$ | Cl | CH | |
| CH$_3$ | CH$_2$S(O)$_2$CH$_2$C(Cl)CH$_2$ | H | CH$_3$ | CH$_3$ | CH | |
| CH$_3$ | CH$_2$S(O)$_2$CH$_2$C(Cl)CH$_2$ | H | OCH$_3$ | OCH$_3$ | N | |
| CH$_2$CH$_3$ | CH$_2$S(O)$_2$CH$_2$C(Cl)CH$_2$ | H | OCH$_3$ | CH$_3$ | N | |
| CH$_3$ | C(H)CH$_2$ | H | OCH$_3$ | OCH$_3$ | CH | |
| CH$_3$ | C(H)CH$_2$ | H | OCH$_3$ | CH$_3$ | CH | |
| CH$_3$ | C(H)CH$_2$ | H | OCH$_3$ | Cl | CH | |
| CH$_3$ | C(H)CH$_2$ | H | CH$_3$ | CH$_3$ | CH | |
| CH$_3$ | C(H)CH$_2$ | H | OCH$_3$ | OCH$_3$ | N | |
| CH$_3$ | C(H)CH$_2$ | H | OCH$_3$ | CH$_3$ | N | |
| CH$_3$ | CCH | H | OCH$_3$ | OCH$_3$ | CH | |
| CH$_3$ | CCH | H | OCH$_3$ | CH$_3$ | CH | |
| CH$_3$ | CCH | H | OCH$_3$ | Cl | CH | |
| CH$_3$ | CCH | H | CH$_3$ | CH$_3$ | CH | |
| CH$_3$ | CCH | H | OCH$_3$ | OCH$_3$ | N | |
| CH$_3$ | CCH | H | OCH$_3$ | CH$_3$ | N | |
| CH$_3$ | C(Cl)CH$_2$ | H | OCH$_3$ | OCH$_3$ | CH | |
| CH$_3$ | C(Cl)CH$_2$ | H | OCH$_3$ | CH$_3$ | CH | |
| CH$_3$ | C(Cl)CH$_2$ | H | OCH$_3$ | Cl | CH | |
| CH$_3$ | C(Cl)CH$_2$ | H | CH$_3$ | CH$_3$ | CH | |
| CH$_3$ | C(Cl)CH$_2$ | H | OCH$_3$ | OCH$_3$ | N | |
| CH$_3$ | C(Cl)CH$_2$ | H | OCH$_3$ | CH$_3$ | N | |
| CH$_3$ | CH$_2$C(O)NHCH$_3$ | H | OCH$_3$ | OCH$_3$ | CH | |
| CH$_3$ | CH$_2$C(O)NHCH$_3$ | H | OCH$_3$ | CH$_3$ | CH | |
| CH$_3$ | CH$_2$C(O)NHCH$_3$ | H | OCH$_3$ | Cl | CH | |
| CH$_3$ | CH$_2$C(O)NHCH$_3$ | H | CH$_3$ | CH$_3$ | CH | |
| CH$_3$ | CH$_2$C(O)NHCH$_3$ | H | OCH$_3$ | OCH$_3$ | N | |
| CH$_3$ | CH$_2$C(O)NHCH$_3$ | H | OCH$_3$ | CH$_3$ | N | |
| CH$_3$ | CH$_2$C(O)N(CH$_3$)$_2$ | H | OCH$_3$ | OCH$_3$ | CH | |
| CH$_3$ | CH$_2$C(O)N(CH$_3$)$_2$ | H | OCH$_3$ | CH$_3$ | CH | |
| CH$_3$ | CH$_2$C(O)N(CH$_3$)$_2$ | H | OCH$_3$ | Cl | CH | |
| CH$_3$ | CH$_2$C(O)N(CH$_3$)$_2$ | H | CH$_3$ | CH$_3$ | CH | |
| CH$_3$ | CH$_2$C(O)N(CH$_3$)$_2$ | H | OCH$_3$ | OCH$_3$ | N | |
| CH$_3$ | CH$_2$C(O)N(CH$_3$)$_2$ | H | OCH$_3$ | CH$_3$ | N | |
| CH$_3$ | CCF$_3$ | H | CH$_3$ | OCH$_3$ | CH | |
| CH$_3$ | OCF$_3$ | H | OCH$_3$ | OCH$_3$ | CH | |
| CH$_3$ | OCF$_3$ | H | Cl | OCH$_3$ | CH | |
| CH$_3$ | OCF$_3$ | H | CH$_3$ | OCH$_3$ | N | |
| CH$_3$ | OCF$_3$ | H | OCH$_3$ | OCH$_3$ | N | |
| CH$_3$ | SCF$_3$ | H | CH$_3$ | OCH$_3$ | CH | |
| CH$_3$ | SCF$_3$ | H | OCH$_3$ | OCH$_3$ | CH | |
| CH$_3$ | SCF$_3$ | H | Cl | OCH$_3$ | CH | |
| CH$_3$ | SCF$_3$ | H | CH$_3$ | OCH$_3$ | N | |
| CH$_3$ | SCF$_3$ | H | OCH$_3$ | OCH$_3$ | N | |
| CH$_3$ | OCH$_2$CH$_2$Br | H | CH$_3$ | OCH$_3$ | CH | |
| CH$_3$ | OCH$_2$CH$_2$I | H | OCH$_3$ | OCH$_3$ | CH | |
| CH$_3$ | C≡CI | H | CH$_3$ | OCH$_3$ | N | |
| CH$_3$ | CH$_2$CBr$_3$ | H | OCH$_3$ | OCH$_3$ | CH | |
| CH$_3$ | C(CH$_3$)(CH$_2$CH$_3$) | H | CH$_3$ | OCH$_3$ | CH | |
| CH$_3$ | CH$_2$Cl | H | CH$_3$ | CH$_3$ | CH | 176–180 (d) |
| CH$_3$ | CH$_2$Cl | H | CH$_3$ | OCH$_3$ | CH | 167–170 |
| CH$_3$ | CH$_2$Cl | H | OCH$_3$ | OCH$_3$ | CH | 149–153 (d) |
| CH$_3$ | CH$_2$Cl | H | Cl | OCH$_3$ | CH | 164–166 |
| CH$_3$ | CH$_2$Cl | H | CH$_3$ | OCH$_3$ | N | 148–150 |
| CH$_3$ | CH$_2$Cl | H | OCH$_3$ | OCH$_3$ | N | 161–162 |

TABLE Ia-continued

| | | | | | | |
|---|---|---|---|---|---|---|
| CH₂CH₃ | CH₂Cl | H | CH₃ | CH₃ | CH | 158-162 |
| CH₂CH₃ | CH₂Cl | H | CH₃ | OCH₃ | CH | |
| CH₂CH₃ | CH₂Cl | H | OCH₃ | OCH₃ | CH | 141-144 |
| CH₂CH₃ | CH₂Cl | H | Cl | OCH₃ | CH | 158-162 |
| CH₂CH₃ | CH₂Cl | H | CH₃ | OCH₃ | N | 134-142 |
| CH₂CH₃ | CH₂Cl | H | OCH₃ | OCH₃ | N | Gum |
| CH₂CH₃ | CHBr₂ | H | OCH₃ | OCH₃ | CH | 181-182 |
| CH₃ | CHBr₂ | H | OCH₃ | OCH₃ | CH | |
| CH₃ | CH₂Br | H | OCH₃ | OCH₃ | CH | |
| CH₃ | CHCl₂ | H | OCH₃ | OCH₃ | CH | |
| CH₃ | OC(O)CH₃ | H | CH₃ | CH₃ | CH | |
| CH₃ | OC(O)CH₃ | H | CH₃ | OCH₃ | CH | |
| CH₃ | OC(O)CH₃ | H | OCH₃ | OCH₃ | CH | 188-190 |
| CH₃ | OC(O)CH₃ | H | Cl | OCH₃ | CH | |
| CH₃ | OC(O)CH₃ | H | CH₃ | OCH₃ | N | |
| CH₃ | OC(O)CH₃ | H | OCH₃ | OCH₃ | N | |
| CH(CH₃)₂ | CH₂Cl | H | OCH₃ | OCH₃ | CH | 146-148 |
| CH(CH₃)₂ | CH₂Cl | H | OCH₃ | CH₃ | CH | 147-148 |
| CH(CH₃)₂ | CH₂Cl | H | Cl | OCH₃ | CH | 171-173 |
| CH(CH₃)₂ | CH₂Cl | H | CH₃ | CH₃ | CH | 166-169 |
| CH(CH₃)₂ | CH₂Cl | H | OCH₃ | OCH₃ | N | 76-81 |
| CH(CH₃)₂ | CH₂Cl | H | OCH₃ | CH₃ | N | 57-60 |
| CH₂CH₂CH₃ | CH₂Cl | H | OCH₃ | OCH₃ | CH | 122-128 |
| CH₂CH₂CH₃ | CH₂Cl | H | OCH₃ | CH₃ | CH | 126-128 |
| CH₂CH₂CH₃ | CH₂Cl | H | Cl | OCH₃ | CH | 169-170 |
| CH₂CH₂CH₃ | CH₂Cl | H | CH₃ | CH₃ | CH | 154-156 |
| CH₂CH₂CH₃ | CH₂Cl | H | OCH₃ | OCH₃ | N | 104-106 |
| CH₂CH₂CH₃ | CH₂Cl | H | OCH₃ | CH₃ | N | oil |

TABLE Ib

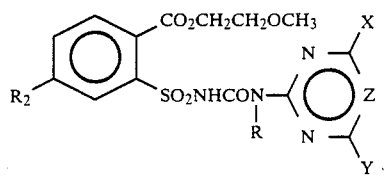

| R₂ | R | X | Y | Z | m.p. (°C.) |
|---|---|---|---|---|---|
| OC₂H₅ | H | CH₃ | CH₃ | CH | |
| OC₂H₅ | H | OCH₃ | CH₃ | CH | |
| OC₂H₅ | H | OCH₃ | | CH | |
| OC₂H₅ | H | Cl | OCH₃ | CH | |
| OC₂H₅ | H | OCH₃ | N(CH₃)₂ | CH | |
| OC₂H₅ | H | CH₃ | CH₃ | N | |
| OC₂H₅ | H | OCH₃ | CH₃ | N | |
| OC₂H₅ | H | OCH₃ | OCH₃ | N | |
| OC₂H₅ | H | OCH₃ | N(CH₃)₂ | N | |
| OC₂H₅ | H | OCH₃ | OCH₂CF₃ | N | |
| OC₂H₅ | CH₃ | OCH₃ | CH₃ | N | |
| OC₂H₅ | CH₃ | OCH₃ | OCH₃ | N | |
| OC₂H₅ | CH₃ | CH₃ | OCH₃ | CH | |
| OC₂H₅ | CH₃ | OCH₃ | OCH₃ | CH | |
| OC₂H₅ | H | Br | OCH₃ | CH | |
| OC₂H₅ | CH₃ | OCH₃ | N(CH₃)₂ | N | |
| OC₂H₅ | H | CH₃ | OCH₂CF₃ | N | |
| OC₂H₅ | H | OCH₃ | OCH₂CF₃ | CH | |
| OC₂H₅ | H | OCH₃ | C₂H₅ | CH | |
| OC₂H₅ | H | OCH₃ | C₂H₅ | N | |

TABLE Ib-continued

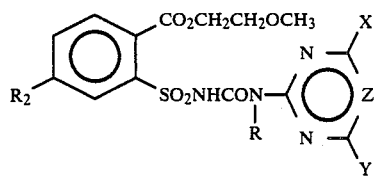

| R2 | R | X | Y | Z | m.p. (°C.) |
|---|---|---|---|---|---|
| OC2H5 | H | OCH3 | NHCH3 | CH | |
| OC2H5 | H | OCH3 | NHCH3 | N | |
| OC2H5 | H | CH3 | OC2H5 | CH | |
| OC2H5 | H | OCH3 | OC2H5 | CH | |
| OC2H5 | H | CH3 | OC2H5 | N | |
| OC2H5 | H | OCH3 | OC2H5 | N | |
| OC2H5 | H | CH3 | OCH2CHF2 | CH | |
| OC2H5 | H | OCH3 | OCH2CHF2 | CH | |
| OC2H5 | H | CH3 | OCH2CHF2 | N | |
| OC2H5 | H | OCH3 | OCH2CHF2 | N | |
| OC2H5 | H | CH3 | OCH2CH2F | CH | |
| OC2H5 | H | OCH3 | OCH2CH2F | CH | |
| OC2H5 | H | CH3 | OCH2CH2F | N | |
| OC2H5 | CH3 | OCH3 | OCH2CH2F | N | |
| OC2H5 | CH3 | OCH3 | OCH3 | CH | |
| OC2H5 | H | Cl | N(CH3)2 | CH | |
| OC2H5 | H | Cl | OC2H5 | CH | |
| SC2H5 | H | CH3 | CH3 | CH | |
| SC2H5 | H | OCH3 | CH3 | CH | |
| SC2H5 | H | OCH3 | OCH3 | CH | |
| SC2H5 | H | Cl | OCH3 | CH | |
| SC2H5 | H | OCH3 | N(CH3)2 | CH | |
| SC2H5 | H | CH3 | CH3 | N | |
| SC2H5 | H | OCH3 | CH3 | N | |
| SC2H5 | H | OCH3 | OCH3 | N | |
| SC2H5 | H | OCH3 | N(CH3)2 | N | |
| SC2H5 | H | OCH3 | OCH2CF3 | N | |
| SC2H5 | CH3 | OCH3 | CH3 | N | |
| SC2H5 | CH3 | OCH3 | OCH3 | N | |
| SC2H5 | CH3 | CH3 | OCH3 | CH | |
| SC2H5 | CH3 | OCH3 | OCH3 | CH | |
| SC2H5 | H | Br | OCH3 | CH | |
| SC2H5 | CH3 | OCH3 | N(CH3)2 | N | |
| SC2H5 | H | CH3 | OCH2CF3 | N | |
| SC2H5 | H | CH3 | OCH2CF3 | CH | |
| SC2H5 | H | OCH3 | OCH2CF3 | CH | |
| SC2H5 | H | OCH3 | C2H5 | CH | |
| SC2H5 | H | OCH3 | C2H5 | N | |
| SC2H5 | H | OCH3 | NHCH3 | CH | |
| SC2H5 | H | OCH3 | NHCH3 | N | |
| SC2H5 | H | CH3 | OC2H5 | CH | |
| SC2H5 | H | OCH3 | OC2H5 | CH | |
| SC2H5 | H | CH3 | OC2H5 | N | |
| SC2H5 | H | OCH3 | OC2H5 | N | |
| SC2H5 | H | CH3 | OCH2CHF2 | CH | |
| SC2H5 | H | OCH3 | OCH2CHF2 | CH | |
| SC2H5 | H | CH3 | OCH2CHF2 | N | |
| SC2H5 | H | OCH3 | OCH2CHF2 | N | |
| SC2H5 | H | CH3 | OCH2CH2F | CH | |
| SC2H5 | H | OCH3 | OCH2CH2F | CH | |
| SC2H5 | H | CH3 | OCH2CH2F | N | |
| SC2H5 | CH3 | OCH3 | OCH2CH2F | N | |
| SC2H5 | CH3 | Cl | OCH3 | CH | |
| SC2H5 | H | Cl | N(CH3)2 | CH | |
| SC2H5 | H | Cl | OC2H5 | CH | |
| S(CH2)5CH3 | H | CH3 | CH3 | CH | |
| S(CH2)5CH3 | H | OCH3 | CH3 | CH | |
| S(CH2)5CH3 | H | OCH3 | OCH3 | CH | |
| S(CH2)5CH3 | H | Cl | OCH3 | CH | |
| S(CH2)5CH3 | H | CH3 | CH3 | N | |
| S(CH2)5CH3 | H | OCH3 | CH3 | N | |
| S(CH2)5CH3 | H | OCH3 | OCH3 | N | |
| S(CH2)5CH3 | H | OCH3 | N(CH3)2 | CH | |
| S(CH2)5CH3 | H | OCH3 | N(CH3)2 | N | |
| S(CH2)5CH3 | H | OCH3 | OCH2CF3 | N | |
| S(CH2)5CH3 | CH3 | OCH3 | CH3 | N | |
| S(CH2)5CH3 | CH3 | OCH3 | OCH3 | N | |
| S(CH2)5CH3 | CH3 | CH3 | OCH3 | CH | |
| S(CH2)5CH3 | CH3 | OCH3 | OCH3 | CH | |
| S(CH2)5CH3 | H | Br | OCH3 | CH | |

TABLE Ib-continued

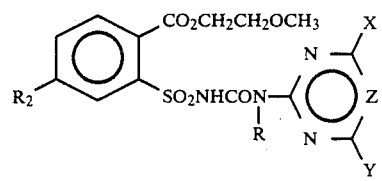

| R₂ | R | X | Y | Z | m.p. (°C.) |
|---|---|---|---|---|---|
| S(CH₂)₅CH₃ | H | CH₃ | OCH₂CF₃ | N | |
| S(CH₂)₅CH₃ | H | CH₃ | OCH₂CF₃ | CH | |
| S(CH₂)₅CH₃ | H | OCH₃ | OCH₂CF₃ | CH | |
| S(CH₂)₅CH₃ | H | OCH₃ | NHCH₃ | N | |
| S(O)(CH₃) | H | CH₃ | CH₃ | CH | |
| S(O)(CH₃) | H | OCH₃ | CH₃ | CH | |
| S(O)(CH₃) | H | OCH₃ | OCH₃ | CH | |
| S(O)(CH₃) | H | Cl | OCH₃ | CH | |
| S(O)(CH₃) | H | OCH₃ | N(CH₃)₂ | CH | |
| S(O)(CH₃) | H | CH₃ | CH₃ | N | |
| S(O)(CH₃) | H | OCH₃ | CH₃ | N | |
| S(O)(CH₃) | H | OCH₃ | OCH₃ | N | |
| S(O)(CH₃) | H | OCH₃ | N(CH₃)₂ | N | |
| S(O)(CH₃) | H | OCH₃ | OCH₂CF₃ | N | |
| S(O)(CH₃) | CH₃ | OCH₃ | CH₃ | N | |
| S(O)(CH₃) | CH₃ | OCH₃ | OCH₃ | N | |
| S(O)(CH₃) | CH₃ | CH₃ | OCH₃ | CH | |
| S(O)(CH₃) | CH₃ | OCH₃ | OCH₃ | CH | |
| S(O)(CH₃) | H | Br | OCH₃ | CH | |
| S(O)(CH₃) | H | OCH₃ | N(CH₃)₂ | CH | |
| S(O)(CH₃) | CH₃ | OCH₃ | N(CH₃)₂ | N | |
| S(O)(CH₃) | H | CH₃ | OCH₂CF₃ | N | |
| S(O)(CH₃) | H | CH₃ | OCH₂CF₃ | CH | |
| S(O)(CH₃) | H | OCH₃ | OCH₂CF₃ | CH | |
| S(O)(CH₃) | H | OCH₃ | C₂H₅ | CH | |
| S(O)(CH₃) | H | OCH₃ | C₂H₅ | N | |
| S(O)(CH₃) | H | OCH₃ | NHCH₃ | CH | |
| S(O)(CH₃) | H | OCH₃ | NHCH₃ | N | |
| S(O)(CH₃) | H | CH₃ | OC₂H₅ | CH | |
| S(O)(CH₃) | H | OCH₃ | OC₂H₅ | CH | |
| S(O)(CH₃) | H | CH₃ | OC₂H₅ | N | |
| S(O)(CH₃) | H | OCH₃ | OC₂H₅ | N | |
| S(O)(CH₃) | H | CH₃ | OCH₂CHF₂ | CH | |
| S(O)(CH₃) | H | OCH₃ | OCH₂CHF₂ | CH | |
| S(O)(CH₃) | H | CH₃ | OCH₂CHF₂ | N | |
| S(O)(CH₃) | H | OCH₃ | OCH₂CHF₂ | N | |
| S(O)(CH₃) | H | CH₃ | OCH₂CHF₂ | CH | |
| S(O)(CH₃) | H | OCH₃ | OCH₂CHF₂ | CH | |
| S(O)(CH₃) | H | CH₃ | OCH₂CHF₂ | N | |
| S(O)(CH₃) | H | OCH₃ | OCH₂CHF₂ | N | |
| S(O)(CH₃) | CH₃ | Cl | OCH₃ | CH | |
| S(O)(CH₃) | H | Cl | N(CH₃)₂ | CH | |
| S(O)(CH₃) | H | Cl | OC₂H₅ | CH | |
| OCH₂CH=CH₂ | H | CH₃ | CH₃ | CH | |
| OCH₂CH=CH₂ | H | OCH₃ | CH₃ | CH | |
| OCH₂CH=CH₂ | H | OCH₃ | OCH₃ | CH | |
| OCH₂CH=CH₂ | H | Cl | OCH₃ | CH | |
| OCH₂CH=CH₂ | H | OCH₃ | N(CH₃)₂ | CH | |
| OCH₂CH=CH₂ | H | CH₂ | CH₃ | N | |
| OCH₂CH=CH₂ | H | OCH₃ | CH₃ | N | |
| OCH₂CH=CH₂ | H | OCH₃ | OCH₃ | N | |
| OCH₂CH=CH₂ | H | OCH₃ | N(CH₃)₂ | N | |
| OCH₂CH=CH₂ | H | OCH₃ | OCH₂CF₃ | N | |
| OCH₂CH=CH₂ | CH₃ | OCH₃ | CH₃ | N | |
| OCH₂CH=CH₂ | CH₃ | OCH₃ | OCH₃ | N | |
| OCH₂CH=CH₂ | CH₃ | CH₃ | OCH₃ | CH | |
| OCH₂CH=CH₂ | CH₃ | OCH₃ | OCH₃ | CH | |
| OCH₂CH=CH₂ | H | Br | OCH₃ | CH | |
| OCH₂CH=CH₂ | CH₃ | OCH₃ | N(CH₃)₂ | N | |
| OCH₂CH=CH₂ | H | CH₃ | OCH₂CF₃ | N | |
| OCH₂CH=CH₂ | H | CH₃ | OCH₂CF₃ | CH | |
| OCH₂CH=CH₂ | H | OCH₃ | OCH₂CF₃ | CH | |
| OCH₂CH=CH₂ | H | OCH₃ | C₂H₅ | CH | |
| OCH₂CH=CH₂ | H | OCH₃ | C₂H₅ | N | |
| OCH₂CH=CH₂ | H | OCH₃ | NHCH₃ | CH | |
| OCH₂CH=CH₂ | H | OCH₃ | NHCH₃ | N | |
| OCH₂CH=CH₂ | H | CH₃ | OC₂H₅ | CH | |
| OCH₂CH=CH₂ | H | OCH₃ | OC₂H₅ | CH | |
| OCH₂CH=CH₂ | H | CH₃ | OC₂H₅ | N | |
| OCH₂CH=CH₂ | H | OCH₃ | OC₂H₅ | N | |

TABLE Ib-continued

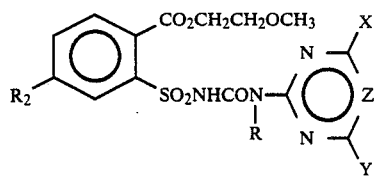

| R₂ | R | X | Y | Z | m.p. (°C.) |
|---|---|---|---|---|---|
| OCH₂CH=CH₂ | H | CH₃ | OCH₂CHF₂ | CH | |
| OCH₂CH=CH₂ | H | OCH₃ | OCH₂CHF₂ | CH | |
| OCH₂CH=CH₂ | H | CH₃ | OCH₂CHF₂ | N | |
| OCH₂CH=CH₂ | H | OCH₃ | OCH₂CHF₂ | N | |
| OCH₂CH=CH₂ | H | CH₃ | OCH₂CH₂F | CH | |
| OCH₂CH=CH₂ | H | OCH₃ | OCH₂CH₂F | CH | |
| OCH₂CH=CH₂ | H | CH₃ | OCH₂CH₂F | N | |
| OCH₂CH=CH₂ | CH₃ | OCH₃ | OCH₂CH₂F | N | |
| OCH₂CH=CH₂ | CH₃ | Cl | OCH₃ | CH | |
| OCH₂CH=CH₂ | H | Cl | N(CH₃)₂ | CH | |
| OCH₂CH=CH₂ | H | Cl | OC₂H₅ | CH | |
| OCH₂C≡CH | H | CH₃ | CH₃ | CH | |
| OCH₂C≡CH | H | OCH₃ | CH₃ | CH | |
| OCH₂C≡CH | H | OCH₃ | OCH₃ | CH | |
| OCH₂C≡CH | H | Cl | OCH₃ | CH | |
| OCH₂C≡CH | H | OCH₃ | N(CH₃)₂ | CH | |
| OCH₂C≡CH | H | CH₃ | CH₃ | N | |
| OCH₂C≡CH | H | OCH₃ | CH₃ | N | |
| OCH₂C≡CH | H | OCH₃ | OCH₃ | N | |
| OCH₂C≡CH | H | OCH₃ | N(CH₃)₂ | N | |
| OCH₂C≡CH | H | OCH₃ | OCH₂CF₃ | N | |
| OCH₂C≡CH | H | OCH₃ | CH₃ | N | |
| OCH₂C≡CH | CH₃ | OCH₃ | OCH₃ | N | |
| OCH₂C≡CH | CH₃ | CH₃ | OCH₃ | CH | |
| OCH₂C≡CH | CH₃ | OCH₃ | OCH₃ | CH | |
| OCH₂C≡CH | H | Br | OCH₃ | CH | |
| OCH₂C≡CH | CH₃ | OCH₃ | N(CH₃)₂ | N | |
| OCH₂C≡CH | H | CH₃ | OCH₂CF₃ | N | |
| OCH₂C≡CH | H | CH₃ | OCH₂CF₃ | CH | |
| OCH₂C≡CH | H | OCH₃ | OCH₂CF₃ | CH | |
| OCH₂C≡CH | H | OCH₃ | C₂H₅ | CH | |
| OCH₂C≡CH | H | OCH₃ | C₂H₅ | N | |
| OCH₂C≡CH | H | OCH₃ | NHCH₃ | CH | |
| OCH₂C≡CH | H | OCH₃ | NHCH₃ | N | |
| OCH₂C≡CH | H | CH₃ | OC₂H₅ | CH | |
| OCH₂C≡CH | H | OCH₃ | OC₂H₅ | CH | |
| OCH₂C≡CH | H | CH₃ | OC₂H₅ | N | |
| OCH₂C≡CH | H | OCH₃ | OC₂H₅ | N | |
| OCH₂C≡CH | H | CH₃ | OCH₂CHF₂ | CH | |
| OCH₂C≡CH | H | OCH₃ | OCH₂CHF₂ | CH | |
| OCH₂C≡CH | H | CH₃ | OCH₂CHF₂ | N | |
| OCH₂C≡CH | H | OCH₃ | OCH₂CHF₂ | N | |
| OCH₂C≡CH | H | CH₃ | OCH₂CH₂F | CH | |
| OCH₂C≡CH | H | OCH₃ | OCH₂CH₂F | CH | |
| OCH₂C≡CH | H | CH₃ | OCH₂CF₃ | N | |
| OCH₂C≡CH | CH₃ | OCH₃ | OCH₂CF₃ | N | |
| OCH₂C≡CH | CH₃ | Cl | OCH₃ | CH | |
| OCH₂C≡CH | H | Cl | N(CH₃)₂ | CH | |
| OCH₂C≡CH | H | Cl | OC₂H₅ | CH | |
| SCH₂CH=CH₂ | H | CH₃ | CH₃ | CH | |
| SCH₂CH=CH₂ | H | OCH₃ | CH₃ | CH | |
| SCH₂CH=CH₂ | H | OCH₃ | OCH₃ | CH | |
| SCH₂CH=CH₂ | H | Cl | OCH₃ | CH | |
| SCH₂CH=CH₂ | H | OCH₃ | N(CH₃)₂ | N | |
| SCH₂CH=CH₂ | H | CH₃ | CH₃ | N | |
| SCH₂CH=CH₂ | H | OCH₃ | CH₃ | N | |
| SCH₂CH=CH₂ | H | OCH₃ | OCH₃ | N | |
| SCH₂CH=CH₂ | H | OCH₃ | N(CH₃)₂ | N | |
| SCH₂CH=CH₂ | H | OCH₃ | OCH₂CF₃ | N | |
| SCH₂CH=CH₂ | CH₃ | OCH₃ | CH₃ | N | |
| SCH₂CH=CH₂ | CH₃ | OCH₃ | OCH₃ | N | |
| SCH₂CH=CH₂ | CH₃ | CH₃ | OCH₃ | CH | |
| SCH₂CH=CH₂ | CH₃ | OCH₃ | OCH₃ | CH | |
| SCH₂CH=CH₂ | H | Br | OCH₃ | CH | |
| SCH₂CH=CH₂ | CH₃ | OCH₃ | N(CH₃)₂ | N | |
| SCH₂CH=CH₂ | H | CH₃ | OCH₂CF₃ | N | |
| SCH₂CH=CH₂ | H | CH₃ | OCH₂CF₃ | CH | |
| SCH₂CH=CH₂ | H | OCH₃ | OCH₂CF₃ | CH | |
| SCH₂CH=CH₂ | H | OCH₃ | C₂H₅ | CH | |
| SCH₂CH=CH₂ | H | OCH₃ | C₂H₅ | CH | |

TABLE Ib-continued

[Structure: benzene ring with CO₂CH₂CH₂OCH₃ group, R₂ substituent, SO₂NHCON(R)- linked to pyrimidine/triazine ring with X, Y, Z substituents]

| R₂ | R | X | Y | Z | m.p. (°C.) |
|---|---|---|---|---|---|
| SCH₂CH=CH₂ | H | OCH₃ | NHCH₃ | CH | |
| SCH₂CH=CH₂ | H | OCH₃ | NHCH₃ | N | |
| SCH₂CH=CH₂ | H | CH₃ | OC₂H₅ | CH | |
| SCH₂CH=CH₂ | H | OCH₃ | OC₂H₅ | CH | |
| SCH₂CH=CH₂ | H | CH₃ | OC₂H₅ | N | |
| SCH₂CH=CH₂ | H | OCH₃ | OC₂H₅ | N | |
| SCH₂CH=CH₃ | H | CH₃ | OCH₂CHF₂ | CH | |
| SCH₂CH=CH₂ | H | OCH₃ | OCH₂CHF₂ | CH | |
| SCH₂CH=CH₂ | H | CH₃ | OCH₂CHF₂ | N | |
| SCH₂CH=CH₂ | H | OCH₃ | OCH₂CHF₂ | N | |
| SCH₂CH=CH₂ | H | CH₃ | OCH₂CH₂F | CH | |
| SCH₂CH=CH₂ | H | OCH₃ | OCH₂CH₂F | CH | |
| SCH₂CH=CH₂ | H | CH₃ | OCH₂CH₂F | N | |
| SCH₂CH=CH₂ | H | OCH₃ | OCH₂CH₂F | N | |
| SCH₂CH=CH₂ | CH₃ | Cl | OCH₃ | CH | |
| SCH₂CH=CH₂ | H | Cl | N(CH₃)₂ | CH | |
| SCH₂CH=CH₂ | H | Cl | OC₂H₅ | CH | |
| SCH₂C≡CH | H | CH₃ | CH₃ | CH | |
| SCH₂C≡CH | H | OCH₃ | CH₃ | CH | |
| SCH₂C≡CH | H | OCH₃ | OCH₃ | CH | |
| SCH₂C≡CH | H | Cl | OCH₃ | CH | |
| SCH₂C≡CH | H | OCH₃ | N(CH₃)₂ | N | |
| SCH₂C≡CH | H | CH₃ | CH₃ | N | |
| SCH₂C≡CH | H | OCH₃ | CH₃ | N | |
| SCH₂C≡CH | H | OCH₃ | OCH₃ | N | |
| SCH₂C≡CH | H | OCH₃ | N(CH₃)₂ | N | |
| SCH₂C≡CH | H | OCH₃ | OCH₂CF₃ | N | |
| SCH₂C≡CH | CH₃ | OCH₃ | CH₃ | N | |
| SCH₂C≡CH | CH₃ | OCH₃ | OCH₃ | N | |
| SCH₂C≡CH | CH₃ | CH₃ | OCH₃ | CH | |
| SCH₂C≡CH | CH₃ | OCH₃ | OCH₃ | CH | |
| SCH₂C≡CH | H | Br | OCH₃ | CH | |
| SCH₂C≡CH | CH₃ | OCH₃ | N(CH₃)₂ | N | |
| SCH₂C≡CH | H | CH₃ | OCH₂CF₃ | N | |
| SCH₂C≡CH | H | CH₃ | OCH₂CF₃ | CH | |
| SCH₂C≡CH | H | OCH₃ | OCH₂CF₃ | CH | |
| SCH₂C≡CH | H | OCH₃ | C₂H₅ | CH | |
| SCH₂C≡CH | H | OCH₃ | C₂H₅ | CH | |
| SCH₂C≡CH | H | OCH₃ | NHCH₃ | CH | |
| SCH₂C≡CH | H | OCH₃ | NHCH₃ | N | |
| SCH₂C≡CH | H | CH₃ | OC₂H₅ | CH | |
| SCH₂C≡CH | H | OCH₃ | OC₂H₅ | CH | |
| SCH₂C≡CH | H | CH₃ | OC₂H₅ | N | |
| SCH₂C≡CH | H | OCH₃ | OC₂H₅ | N | |
| SCH₂C≡CH | H | CH₃ | OCH₂CHF₂ | CH | |
| SCH₂C≡CH | H | OCH₃ | OCH₂CHF₂ | CH | |
| SCH₂C≡CH | H | CH₃ | OCH₂CHF₂ | N | |
| SCH₂C≡CH | H | OCH₃ | OCH₂CHF₂ | N | |
| SCH₂C≡CH | H | CH₃ | OCH₂CH₂F | CH | |
| SCH₂C≡CH | H | OCH₃ | OCH₂CH₂F | CH | |
| SCH₂C≡CH | H | CH₃ | OCH₂CH₂F | N | |
| SCH₂C≡CH | H | OCH₃ | OCH₂CH₂F | N | |
| SCH₂C≡CH | CH₃ | Cl | OCH₃ | CH | |
| SCH₂C≡CH | H | Cl | N(CH₃)₂ | CH | |
| SCH₂C≡CH | H | Cl | OC₂H₅ | CH | |
| CH₂CH₂F | H | CH₃ | CH₃ | CH | |
| CH₂CH₂F | H | OCH₃ | CH₃ | CH | |
| CH₂CH₂F | H | OCH₃ | OCH₃ | CH | |
| CH₂CH₂F | H | Cl | OCH₃ | CH | |
| CH₂CH₂F | H | OCH₃ | N(CH₃)₂ | CH | |
| CH₂CH₂F | H | CH₃ | CH₃ | N | |
| CH₂CH₂F | H | OCH₃ | CH₃ | N | |
| CH₂CH₂F | H | OCH₃ | OCH₃ | N | |
| CH₂CH₂F | H | OCH₃ | N(CH₃)₂ | N | |
| CH₂CH₂F | H | OCH₃ | OCH₂CF₂ | N | |
| CH₂CH₂F | CH₃ | OCH₃ | CH₃ | N | |
| CH₂CH₂F | CH₃ | OCH₃ | OCH₃ | N | |
| CH₂CH₂F | CH₃ | CH₃ | OCH₃ | CH | |
| CH₂CH₂F | CH₃ | OCH₃ | OCH₃ | CH | |
| CH₂CH₂F | H | Br | OCH₃ | CH | |

TABLE Ib-continued

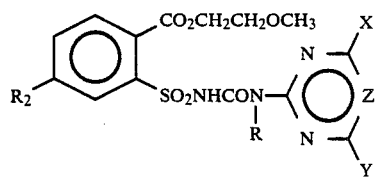

| R2 | R | X | Y | Z | m.p. (°C.) |
|---|---|---|---|---|---|
| CH2CH2F | CH3 | OCH3 | N(CH3)2 | N | |
| CH2CH2F | H | CH3 | OCH2CF3 | N | |
| CH2CH2F | H | CH3 | OCH2CF3 | CH | |
| CH2CH2F | H | OCH3 | OCH2CF3 | CH | |
| CH2CH2F | H | OCH3 | C2H5 | CH | |
| CH2CH2F | H | OCH3 | C2H5 | N | |
| CH2CH2F | H | OCH3 | NHCH3 | CH | |
| CH2CH2F | H | OCH3 | NHCH3 | N | |
| CH2CH2F | H | CH3 | OC2H5 | CH | |
| CH2CH2F | H | OCH3 | OC2H5 | CH | |
| CH2CH2F | H | CH3 | OC2H5 | N | |
| CH2CH2F | H | OCH3 | OC2H5 | N | |
| CH2CH2F | H | CH3 | OCH2CHF2 | CH | |
| CH2CH2F | H | OCH3 | OCH2CHF2 | CH | |
| CH2CH2F | H | CH3 | OCH2CHF2 | N | |
| CH2CH2F | H | OCH3 | OCH2CHF2 | N | |
| CH2CH2F | H | CH3 | OCH2CH2F | CH | |
| CH2CH2F | H | OCH3 | OCH2CH2F | CH | |
| CH2CH2F | H | CH3 | OCH2CF3 | N | |
| CH2CH2F | CH3 | OCH3 | OCH2CF3 | N | |
| CH2CH2F | CH3 | Cl | OCH3 | CH | |
| CH2CH2F | H | Cl | N(CH3)2 | CH | |
| CH2CH2F | H | Cl | OC2H5 | CH | |
| CH2CF3 | H | CH3 | CH3 | CH | |
| CH2CF3 | H | OCH3 | CH3 | CH | |
| CH2CF3 | H | OCH3 | OCH3 | CH | |
| CH2CF3 | H | Cl | OCH3 | CH | |
| CH2CF3 | H | OCH3 | N(CH3)2 | CH | |
| CH2CF3 | H | CH3 | CH3 | N | |
| CH2CF3 | H | OCH3 | CH3 | N | |
| CH2CF3 | H | OCH3 | OCH3 | N | |
| CH2CF3 | H | OCH3 | N(CH3)2 | N | |
| CH2CF3 | H | OCH3 | OCH2CF3 | N | |
| CH2CF3 | CH3 | OCH3 | CH3 | N | |
| CH2CF3 | CH3 | OCH3 | OCH3 | N | |
| CH2CF3 | CH3 | CH3 | OCH3 | CH | |
| CH2CF3 | CH3 | OCH3 | OCH3 | CH | |
| CH2CF3 | H | Br | OCH3 | CH | |
| CH2CF3 | CH3 | OCH3 | N(CH3)2 | N | |
| CH2CF3 | H | CH3 | OCH2CF3 | N | |
| CH2CF3 | H | CH3 | OCH2CF3 | CH | |
| CH2CF3 | H | OCH3 | OCH2CF3 | CH | |
| CH2CF3 | H | OCH3 | C2H5 | CH | |
| CH2CF3 | H | OCH3 | C2H5 | N | |
| CH2CF3 | H | OCH3 | NHCH3 | CH | |
| CH2CF3 | H | OCH3 | NHCH3 | N | |
| CH2CF3 | H | CH3 | OC2H5 | CH | |
| CH2CF3 | H | OCH3 | OC2H5 | CH | |
| CH2CF3 | H | CH3 | OC2H5 | N | |
| CH2CF3 | H | OCH3 | OC2H5 | N | |
| CH2CF3 | H | CH3 | OCH2CHF2 | CH | |
| CH2CF3 | H | OCH3 | OCH2CHF2 | CH | |
| CH2CF3 | H | CH3 | OCH2CHF2 | N | |
| CH2CF3 | H | OCH3 | OCH2CHF2 | N | |
| CH2CF3 | H | CH3 | OCH2CH2F | CH | |
| CH2CF3 | H | OCH3 | OCH2CH2F | CH | |
| CH2CF3 | H | CH3 | OCH2CH2F | N | |
| CH2CF3 | CH3 | OCH3 | OCH2CH2F | N | |
| CH2CF3 | CH3 | Cl | OCH3 | CH | |
| CH2CF3 | H | Cl | N(CH3)2 | CH | |
| CH2CF3 | H | Cl | OC2H5 | CH | |
| CHFCH3 | H | CH3 | CH3 | CH | |
| CHFCH3 | H | OCH3 | CH3 | CH | |
| CHFCH3 | H | OCH3 | OCH3 | CH | |
| CHFCH3 | H | Cl | OCH3 | CH | |
| CHFCH3 | H | OCH3 | N(CH3)2 | CH | |
| CHFCH3 | H | CH3 | CH3 | N | |
| CHFCH3 | H | OCH3 | CH3 | N | |
| CHFCH3 | H | OCH3 | OCH3 | N | |
| CHFCH3 | H | OCH3 | N(CH3)2 | N | |

TABLE Ib-continued

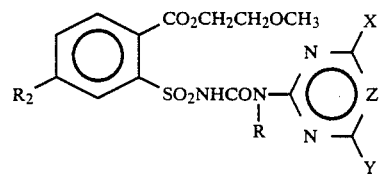

| R₂ | R | X | Y | Z | m.p. (°C.) |
|---|---|---|---|---|---|
| CHFCH₃ | H | OCH₃ | OCH₂CF₃ | N | |
| CHFCH₃ | CH₃ | OCH₃ | CH₃ | N | |
| CHFCH₃ | CH₃ | OCH₃ | OCH₃ | N | |
| CHFCH₃ | CH₃ | CH₃ | OCH₃ | CH | |
| CHFCH₃ | CH₃ | OCH₃ | OCH₃ | CH | |
| CHFCH₃ | H | Br | OCH₃ | CH | |
| CHFCH₃ | CH₃ | OCH₃ | N(CH₃)₂ | N | |
| CHFCH₃ | H | CH₃ | OCH₂CF₃ | N | |
| CHFCH₃ | H | CH₃ | OCH₂CF₃ | CH | |
| CHFCH₃ | H | OCH₃ | OCH₂CF₃ | CH | |
| CHFCH₃ | H | OCH₃ | C₂H₅ | CH | |
| CHFCH₃ | H | OCH₃ | C₂H₅ | N | |
| CHFCH₃ | H | OCH₃ | NHCH₃ | CH | |
| CHFCH₃ | H | OCH₃ | NHCH₃ | N | |
| CHFCH₃ | H | CH₃ | OC₂H₅ | CH | |
| CHFCH₃ | H | OCH₃ | OC₂H₅ | CH | |
| CHFCH₃ | H | CH₃ | OC₂H₅ | N | |
| CHFCH₃ | H | OCH₃ | OC₂H₅ | N | |
| CHFCH₃ | H | CH₃ | OCH₂CHF₂ | CH | |
| CHFCH₃ | H | OCH₃ | OCH₂CHF₂ | CH | |
| CHFCH₃ | H | CH₃ | OCH₂CHF₂ | N | |
| CHFCH₃ | H | OCH₃ | OCH₂CHF₂ | N | |
| CHFCH₃ | H | CH₃ | OCH₂CH₂F | CH | |
| CHFCH₃ | H | OCH₃ | OCH₂CH₂F | CH | |
| CHFCH₃ | H | CH₃ | OCH₂CF₃ | N | |
| CHFCH₃ | CH₃ | OCH₃ | OCH₂CF₃ | N | |
| CHFCH₃ | CH₃ | Cl | OCH₃ | CH | |
| CHFCH₃ | H | Cl | N(CH₃)₂ | CH | |
| CHFCH₃ | H | Cl | OC₂H₅ | CH | |
| CH₂F | H | CH₃ | CH₃ | CH | |
| CH₂F | H | OCH₃ | CH₃ | CH | |
| CH₂F | H | OCH₃ | OCH₃ | CH | |
| CH₂F | H | Cl | OCH₃ | CH | |
| CH₂F | H | OCH₃ | N(CH₃)₂ | CH | |
| CH₂F | H | CH₃ | CH₃ | N | |
| CH₂F | H | OCH₃ | CH₃ | N | |
| CH₂F | H | OCH₃ | OCH₃ | N | |
| CH₂F | H | OCH₃ | N(CH₃)₂ | N | |
| CH₂F | H | OCH₃ | OCH₂CF₃ | N | |
| CH₂F | CH₃ | OCH₃ | CH₃ | N | |
| CH₂F | CH₃ | OCH₃ | OCH₃ | N | |
| CH₂F | CH₃ | CH₃ | OCH₃ | CH | |
| CH₂F | CH₃ | OCH₃ | OCH₃ | CH | |
| CH₂F | H | Br | OCH₃ | CH | |
| CH₂F | CH₃ | OCH₃ | N(CH₃)₂ | N | |
| CH₂F | H | CH₃ | OCH₂CF₃ | N | |
| CH₂F | H | CH₃ | OCH₂CF₃ | CH | |
| CH₂F | H | OCH₃ | OCH₂CF₃ | CH | |
| CH₂F | H | OCH₃ | C₂H₅ | CH | |
| CH₂F | H | OCH₃ | C₂H₅ | N | |
| CH₂F | H | OCH₃ | NHCH₃ | CH | |
| CH₂F | H | OCH₃ | NHCH₃ | N | |
| CH₂F | H | CH₃ | OC₂H₅ | CH | |
| CH₂F | H | OCH₃ | OC₂H₅ | CH | |
| CH₂F | H | CH₃ | OC₂H₅ | N | |
| CH₂F | H | OCH₃ | OC₂H₅ | N | |
| CH₂F | H | CH₃ | OCH₂CHF₂ | CH | |
| CH₂F | H | OCH₃ | OCH₂CHF₂ | CH | |
| CH₂F | H | CH₃ | OCH₂CHF₂ | N | |
| CH₂F | H | OCH₃ | OCH₂CHF₂ | N | |
| CH₂F | H | CH₃ | OCH₂CH₂F | CH | |
| CH₂F | H | OCH₃ | OCH₂CH₂F | CH | |
| CH₂F | H | CH₃ | OCH₂CH₂F | N | |
| CH₂F | CH₃ | OCH₃ | OCH₂CH₂F | N | |
| CH₂F | CH₃ | Cl | OCH₃ | CH | |
| CH₂F | H | Cl | N(CH₃)₂ | CH | |
| CH₂F | H | Cl | OC₂H₅ | CH | |
| CHF₂ | H | CH₃ | CH₃ | CH | |
| CHF₂ | H | OCH₃ | CH₃ | CH | |
| CHF₂ | H | OCH₃ | OCH₃ | CH | |

TABLE Ib-continued

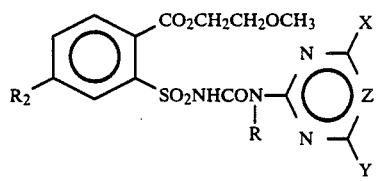

| $R_2$ | R | X | Y | Z | m.p. (°C.) |
|---|---|---|---|---|---|
| $CHF_2$ | H | Cl | $OCH_3$ | CH | |
| $CHF_2$ | H | $OCH_3$ | $N(CH_3)_2$ | CH | |
| $CHF_2$ | H | $CH_3$ | $CH_3$ | N | |
| $CHF_2$ | H | $OCH_3$ | $CH_3$ | N | |
| $CHF_2$ | H | $OCH_3$ | $OCH_3$ | N | |
| $CHF_2$ | H | $OCH_3$ | $N(CH_3)_2$ | N | |
| $CHF_2$ | H | $OCH_3$ | $OCH_2CF_3$ | N | |
| $CHF_2$ | $CH_3$ | $OCH_3$ | $CH_3$ | N | |
| $CHF_2$ | $CH_3$ | $OCH_3$ | $OCH_3$ | N | |
| $CHF_2$ | $CH_3$ | $CH_3$ | $OCH_3$ | CH | |
| $CHF_2$ | $CH_3$ | $OCH_3$ | $OCH_3$ | CH | |
| $CHF_2$ | H | Br | $OCH_3$ | CH | |
| $CHF_2$ | $CH_3$ | $OCH_3$ | $N(CH_3)_2$ | N | |
| $CHF_2$ | H | $CH_3$ | $OCH_2CF_3$ | N | |
| $CHF_2$ | H | $CH_3$ | $OCH_2CF_3$ | CH | |
| $CHF_2$ | H | $OCH_3$ | $OCH_2CF_3$ | CH | |
| $CHF_2$ | H | $OCH_3$ | $C_2H_5$ | CH | |
| $CHF_2$ | H | $OCH_3$ | $C_2H_5$ | N | |
| $CHF_2$ | H | $OCH_3$ | $NHCH_3$ | CH | |
| $CHF_2$ | H | $OCH_3$ | $NHCH_3$ | N | |
| $CHF_2$ | H | $CH_3$ | $OC_2H_5$ | CH | |
| $CHF_2$ | H | $OCH_3$ | $OC_2H_5$ | CH | |
| $CHF_2$ | H | $CH_3$ | $OC_2H_5$ | N | |
| $CHF_2$ | H | $OCH_3$ | $OC_2H_5$ | N | |
| $CHF_2$ | H | $CH_3$ | $OCH_2CHF_2$ | CH | |
| $CHF_2$ | H | $OCH_3$ | $OCH_2CHF_2$ | CH | |
| $CHF_2$ | H | $CH_3$ | $OCH_2CHF_2$ | N | |
| $CHF_2$ | H | $OCH_3$ | $OCH_2CHF_2$ | N | |
| $CHF_2$ | H | $CH_3$ | $OCH_2CH_2F$ | CH | |
| $CHF_2$ | H | $OCH_3$ | $OCH_2CH_2F$ | CH | |
| $CHF_2$ | H | $CH_3$ | $OCH_2CH_2F$ | N | |
| $CHF_2$ | $CH_3$ | $OCH_3$ | $OCH_2CH_2F$ | N | |
| $CHF_2$ | $CH_3$ | Cl | $OCH_3$ | CH | |
| $CHF_2$ | H | Cl | $N(CH_3)_2$ | CH | |
| $CHF_2$ | H | Cl | $OC_2H_5$ | CH | |
| $CH_2OCH_3$ | H | $CH_3$ | $CH_3$ | CH | |
| $CH_2OCH_3$ | H | $OCH_3$ | $CH_3$ | CH | |
| $CH_2OCH_3$ | H | $OCH_3$ | $OCH_3$ | CH | |
| $CH_2OCH_3$ | H | Cl | $OCH_3$ | CH | |
| $CH_2OCH_3$ | H | $OCH_3$ | $N(CH_3)_2$ | CH | |
| $CH_2OCH_3$ | H | $CH_3$ | $CH_3$ | N | |
| $CH_2OCH_3$ | H | $OCH_3$ | $CH_3$ | N | |
| $CH_2OCH_3$ | H | $OCH_3$ | $OCH_3$ | N | |
| $CH_2OCH_3$ | H | $OCH_3$ | $N(CH_3)_2$ | N | |
| $CH_2OCH_3$ | H | $OCH_3$ | $OCH_2CF_3$ | N | |
| $CH_2OCH_3$ | $CH_3$ | $OCH_3$ | $CH_3$ | N | |
| $CH_2OCH_3$ | $CH_3$ | $OCH_3$ | $OCH_3$ | N | |
| $CH_2OCH_3$ | $CH_3$ | $CH_3$ | $OCH_3$ | CH | |
| $CH_2OCH_3$ | $CH_3$ | $OCH_3$ | $OCH_3$ | CH | |
| $CH_2OCH_3$ | H | Br | $OCH_3$ | CH | |
| $CH_2OCH_3$ | $CH_3$ | $OCH_3$ | $N(CH_3)_2$ | N | |
| $CH_2OCH_3$ | H | $CH_3$ | $OCH_2CF_3$ | N | |
| $CH_2OCH_3$ | H | $CH_3$ | $OCH_2CF_3$ | CH | |
| $CH_2OCH_3$ | H | $OCH_3$ | $OCH_2CF_3$ | CH | |
| $CH_2OCH_3$ | H | $OCH_3$ | $C_2H_5$ | CH | |
| $CH_2OCH_3$ | H | $OCH_3$ | $C_2H_5$ | N | |
| $CH_2OCH_3$ | H | $OCH_3$ | $NHCH_3$ | CH | |
| $CH_2OCH_3$ | H | $OCH_3$ | $NHCH_3$ | N | |
| $CH_2OCH_3$ | H | $CH_3$ | $OC_2H_5$ | CH | |
| $CH_2OCH_3$ | H | $OCH_3$ | $OC_2H_5$ | CH | |
| $CH_2OCH_3$ | H | $CH_3$ | $OC_2H_5$ | N | |
| $CH_2OCH_3$ | H | $OCH_3$ | $OC_2H_5$ | N | |
| $CH_2OCH_3$ | H | $CH_3$ | $OCH_2CHF_2$ | CH | |
| $CH_2OCH_3$ | H | $OCH_3$ | $OCH_2CHF_2$ | CH | |
| $CH_2OCH_3$ | H | $CH_3$ | $OCH_2CHF_2$ | N | |
| $CH_2OCH_3$ | H | $OCH_3$ | $OCH_2CHF_2$ | N | |
| $CH_2OCH_3$ | H | $CH_3$ | $OCH_2CH_2F$ | CH | |
| $CH_2OCH_3$ | H | $OCH_3$ | $OCH_2CH_2F$ | CH | |
| $CH_2OCH_3$ | H | $CH_3$ | $OCH_2CF_3$ | N | |
| $CH_2OCH_3$ | $CH_3$ | $OCH_3$ | $OCH_2CF_3$ | N | |

TABLE Ib-continued

[Structure: benzene ring with CO₂CH₂CH₂OCH₃ group, R₂ substituent, SO₂NHCON(R)- linked to a pyrimidine/triazine ring with X, Y, Z substituents]

| R₂ | R | X | Y | Z | m.p. (°C.) |
|---|---|---|---|---|---|
| CH₂OCH₃ | CH₃ | Cl | OCH₃ | CH | |
| CH₂OCH₃ | H | Cl | N(CH₃)₂ | CH | |
| CH₂OCH₃ | H | Cl | OC₂H₅ | CH | |
| CH₂SCH₃ | H | CH₃ | CH₃ | CH | |
| CH₂SCH₃ | H | OCH₃ | CH₃ | CH | |
| CH₂SCH₃ | H | OCH₃ | OCH₃ | CH | |
| CH₂SCH₃ | H | Cl | OCH₃ | CH | |
| CH₂SCH₃ | H | OCH₃ | N(CH₃)₂ | CH | |
| CH₂SCH₃ | H | CH₃ | CH₃ | N | |
| CH₂SCH₃ | H | OCH₃ | CH₃ | N | |
| CH₂SCH₃ | H | OCH₃ | OCH₃ | N | |
| CH₂SCH₃ | H | OCH₃ | N(CH₃)₂ | N | |
| CH₂SCH₃ | H | OCH₃ | OCH₂CF₃ | N | |
| CH₂SCH₃ | CH₃ | OCH₃ | CH₃ | N | |
| CH₂SCH₃ | CH₃ | OCH₃ | OCH₃ | N | |
| CH₂SCH₃ | CH₃ | CH₃ | OCH₃ | CH | |
| CH₂SCH₃ | CH₃ | OCH₃ | OCH₃ | CH | |
| CH₂SCH₃ | H | Br | OCH₃ | CH | |
| CH₂SCH₃ | CH₃ | OCH₃ | N(CH₃)₂ | N | |
| CH₂SCH₃ | H | CH₃ | OCH₂CF₃ | N | |
| CH₂SCH₃ | H | CH₃ | OCH₂CF₃ | CH | |
| CH₂SCH₃ | H | OCH₃ | OCH₂CF₃ | CH | |
| CH₂SCH₃ | H | OCH₃ | C₂H₅ | CH | |
| CH₂SCH₃ | H | OCH₃ | C₂H₅ | N | |
| CH₂SCH₃ | H | OCH₃ | NHCH₃ | CH | |
| CH₂SCH₃ | H | OCH₃ | NHCH₃ | N | |
| CH₂SCH₃ | H | CH₃ | OC₂H₅ | CH | |
| CH₂SCH₃ | H | OCH₃ | OC₂H₅ | CH | |
| CH₂SCH₃ | H | CH₃ | OC₂H₅ | N | |
| CH₂SCH₃ | H | OCH₃ | OC₂H₅ | N | |
| CH₂SCH₃ | H | CH₃ | OCH₂CHF₂ | CH | |
| CH₂SCH₃ | H | OCH₃ | OCH₂CHF₂ | CH | |
| CH₂SCH₃ | H | CH₃ | OCH₂CHF₂ | N | |
| CH₂SCH₃ | H | OCH₃ | OCH₂CHF₂ | N | |
| CH₂SCH₃ | H | CH₃ | OCH₂CH₂F | CH | |
| CH₂SCH₃ | H | OCH₃ | OCH₂CH₂F | CH | |
| CH₂SCH₃ | H | CH₃ | OCH₂CH₂F | N | |
| CH₂SCH₃ | CH₃ | OCH₃ | OCH₂CH₂F | N | |
| CH₂SCH₃ | CH₃ | Cl | OCH₃ | CH | |
| CH₂SCH₃ | H | Cl | N(CH₃)₂ | CH | |
| CH₂SCH₃ | H | Cl | OC₂H₅ | CH | |
| OCF₂H | H | CH₃ | CH₃ | CH | |
| OCF₂H | H | OCH₃ | CH₃ | CH | 126–128 |
| OCF₂H | H | OCH₃ | OCH₃ | CH | 121–125 |
| OCF₂H | H | Cl | OCH₃ | CH | 133–134 |
| OCF₂H | H | OC₂H₅ | NHCH₃ | N | 170–180 |
| OCF₂H | H | CH₃ | CH₃ | N | |
| OCF₂H | H | OCH₃ | CH₃ | N | |
| OCF₂H | H | OCH₃ | OCH₃ | N | |
| OCF₂H | H | OCH₃ | N(CH₃)₂ | CH | |
| OCF₂H | H | OCH₃ | OCH₂CF₃ | N | |
| OCF₂H | CH₃ | OCH₃ | CH₃ | N | |
| OCF₂H | CH₃ | OCH₃ | OCH₃ | N | |
| OCF₂H | CH₃ | CH₃ | OCH₃ | CH | |
| OCF₂H | CH₃ | OCH₃ | OCH₃ | CH | |
| OCF₂H | H | Br | OCH₃ | CH | |
| OCF₂H | CH₃ | OCH₃ | N(CH₃)₂ | N | |
| OCF₂H | H | CH₃ | OCH₂CF₃ | N | |
| OCF₂H | H | CH₃ | OCH₂CF₃ | CH | |
| OCF₂H | H | OCH₃ | OCH₂CF₃ | CH | |
| OCF₂H | H | OCH₃ | C₂H₅ | CH | |
| OCF₂H | H | OCH₃ | C₂H₅ | N | |
| OCF₂H | H | OCH₃ | NHCH₃ | CH | |
| OCF₂H | H | OCH₃ | NHCH₃ | N | |
| OCF₂H | H | CH₃ | OC₂H₅ | CH | |
| OCF₂H | H | OCH₃ | OC₂H₅ | CH | |

TABLE Ib-continued

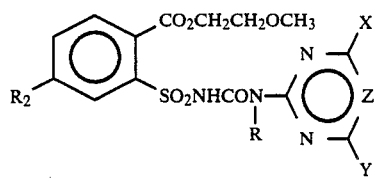

| R₂ | R | X | Y | Z | m.p. (°C.) |
|---|---|---|---|---|---|
| OCF₂H | H | CH₃ | OC₂H₅ | N | |
| OCF₂H | H | OCH₃ | OC₂H₅ | N | |
| OCF₂H | H | CH₃ | OCH₂CHF₂ | CH | |
| OCF₂H | H | OCH₃ | OCH₂CHF₂ | CH | |
| OCF₂H | H | CH₃ | OCH₂CHF₂ | N | |
| OCF₂H | H | OCH₃ | OCH₂CHF₂ | N | |
| OCF₂H | H | CH₃ | OCH₂CH₂F | CH | |
| OCF₂H | H | OCH₃ | OCH₂CH₂F | CH | |
| OCF₂H | H | CH₃ | OCH₂CH₂F | N | |
| OCF₂H | CH₃ | OCH₃ | OCH₂CH₂F | N | |
| OCF₂H | CH₃ | Cl | OCH₃ | CH | |
| OCF₂H | H | Cl | N(CH₃)₂ | CH | |
| OCF₂H | H | Cl | OC₂H₅ | CH | |
| OCH₂CH₂F | H | CH₃ | CH₃ | CH | |
| OCH₂CH₂F | H | OCH₃ | CH₃ | CH | |
| OCH₂CH₂F | H | OCH₃ | OCH₃ | CH | |
| OCH₂CH₂F | H | Cl | OCH₃ | CH | |
| OCH₂CH₂F | H | OCH₃ | N(CH₃)₂ | CH | |
| OCH₂CH₂F | H | CH₃ | CH₃ | N | |
| OCH₂CH₂F | H | OCH₃ | CH₃ | N | |
| OCH₂CH₂F | H | OCH₃ | OCH₃ | N | |
| OCH₂CH₂F | H | OCH₃ | N(CH₃)₂ | N | |
| OCH₂CH₂F | H | OCH₃ | OCH₂CF₃ | N | |
| OCH₂CH₂F | CH₃ | OCH₃ | CH₃ | N | |
| OCH₂CH₂F | CH₃ | OCH₃ | OCH₃ | N | |
| OCH₂CH₂F | CH₃ | CH₃ | OCH₃ | CH | |
| OCH₂CH₂F | CH₃ | OCH₃ | OCH₃ | CH | |
| OCH₂CH₂F | H | Br | OCH₃ | CH | |
| OCH₂CH₂F | CH₃ | OCH₃ | N(CH₃)₂ | N | |
| OCH₂CH₂F | H | CH₃ | OCH₂CF₃ | N | |
| OCH₂CH₂F | H | CH₃ | OCH₂CF₃ | CH | |
| OCH₂CH₂F | H | OCH₃ | OCH₂CF₃ | CH | |
| OCH₂CH₂F | H | OCH₃ | C₂H₅ | CH | |
| OCH₂CH₂F | H | OCH₃ | C₂H₅ | N | |
| OCH₂CH₂F | H | OCH₃ | NHCH₃ | CH | |
| OCH₂CH₂F | H | OCH₃ | NHCH₃ | N | |
| OCH₂CH₂F | H | CH₃ | OC₂H₅ | CH | |
| OCH₂CH₂F | H | OCH₃ | OC₂H₅ | CH | |
| OCH₂CH₂F | H | CH₃ | OC₂H₅ | N | |
| OCH₂CH₂F | H | OCH₃ | OC₂H₅ | N | |
| OCH₂CH₂F | H | CH₃ | OCH₂CHF₂ | CH | |
| OCH₂CH₂F | H | OCH₃ | OCH₂CHF₂ | CH | |
| OCH₂CH₂F | H | CH₃ | OCH₂CHF₂ | N | |
| OCH₂CH₂F | H | OCH₃ | OCH₂CHF₂ | N | |
| OCH₂CH₂F | H | CH₃ | OCH₂CH₂F | CH | |
| OCH₂CH₂F | H | OCH₃ | OCH₂CH₂F | CH | |
| OCH₂CH₂F | H | CH₃ | OCH₂CH₂F | N | |
| OCH₂CH₂F | CH₃ | OCH₃ | OCH₂CH₂F | N | |
| OCH₂CH₂F | CH₃ | Cl | OCH₃ | CH | |
| OCH₂CH₂F | H | Cl | N(CH₃)₂ | CH | |
| OCH₂CH₂F | H | Cl | OC₂H₅ | CH | |
| OCH₂CF₃ | H | CH₃ | CH₃ | CH | 170-171 |
| OCH₂CF₃ | H | OCH₃ | CH₃ | CH | 144-145 |
| OCH₂CF₃ | H | OCH₃ | OCH₃ | CH | 135-166 |
| OCH₂CF₃ | H | Cl | OCH₃ | CH | 159-162 |
| OCH₂CF₃ | H | OCH₃ | N(CH₃)₂ | CH | |
| OCH₂CF₃ | H | CH₃ | CH₃ | N | |
| OCH₂CF₃ | H | OCH₃ | CH₃ | N | 140-142 |
| OCH₂CF₃ | H | OCH₃ | OCH₃ | N | 180-187 |
| OCH₂CF₃ | H | OCH₃ | N(CH₃)₂ | N | |
| OCH₂CF₃ | H | OCH₃ | OCH₂CF₃ | N | |
| OCH₂CF₃ | H | OC₂H₅ | NHCH₃ | N | 187-190 |
| OCH₂CF₃ | CH₃ | OCH₃ | CH₃ | N | |

TABLE Ib-continued

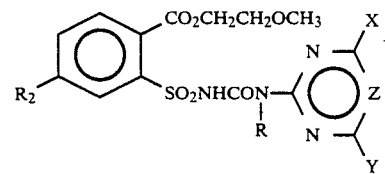

| $R_2$ | R | X | Y | Z | m.p. (°C.) |
|---|---|---|---|---|---|
| $OCH_2CF_3$ | $CH_3$ | $OCH_3$ | $OCH_3$ | N | |
| $OCH_2CF_3$ | $CH_3$ | $CH_3$ | $OCH_3$ | CH | |
| $OCH_2CF_3$ | $CH_3$ | $OCH_3$ | $OCH_3$ | CH | |
| $OCH_2CF_3$ | H | Br | $OCH_3$ | CH | |
| $OCH_2CF_3$ | $CH_3$ | $OCH_3$ | $N(CH_3)_2$ | N | |
| $OCH_2CF_3$ | H | $CH_3$ | $OCH_2CF_3$ | N | |
| $OCH_2CF_3$ | H | $CH_3$ | $OCH_2CF_3$ | CH | |
| $OCH_2CF_3$ | H | $OCH_3$ | $OCH_2CF_3$ | CH | |
| $OCH_2CF_3$ | H | $OCH_3$ | $C_2H_5$ | CH | |
| $OCH_2CF_3$ | H | $OCH_3$ | $C_2H_5$ | N | |
| $OCH_2CF_3$ | H | $OCH_3$ | $NHCH_3$ | CH | |
| $OCH_2CF_3$ | H | $OCH_3$ | $NHCH_3$ | N | |
| $OCH_2CF_3$ | H | $CH_3$ | $OC_2H_5$ | CH | |
| $OCH_2CF_3$ | H | $OCH_3$ | $OC_2H_5$ | CH | |
| $OCH_2CF_3$ | H | $CH_3$ | $OC_2H_5$ | N | |
| $OCH_2CF_3$ | H | $OCH_3$ | $OC_2H_5$ | N | |
| $OCH_2CF_3$ | H | $CH_3$ | $OCH_2CHF_2$ | CH | |
| $OCH_2CF_3$ | H | $OCH_3$ | $OCH_2CHF_2$ | CH | |
| $OCH_2CF_3$ | H | $CH_3$ | $OCH_2CHF_2$ | N | |
| $OCH_2CF_3$ | H | $OCH_3$ | $OCH_2CHF_2$ | N | |
| $OCH_2CF_3$ | H | $CH_3$ | $OCH_2CH_2F$ | CH | |
| $OCH_2CF_3$ | H | $OCH_3$ | $OCH_2CH_2F$ | CH | |
| $OCH_2CF_3$ | H | $CH_3$ | $OCH_2CH_2F$ | N | |
| $OCH_2CF_3$ | $CH_3$ | $OCH_3$ | $OCH_2CH_2F$ | N | |
| $OCH_2CF_3$ | $CH_3$ | Cl | $OCH_3$ | CH | |
| $OCH_2CF_3$ | H | Cl | $N(CH_3)_2$ | CH | |
| $OCH_2CF_3$ | H | Cl | $OC_2H_5$ | CH | |
| $OCH_2CH_2OCH_3$ | H | $CH_3$ | $CH_3$ | CH | |
| $OCH_2CH_2OCH_3$ | H | $OCH_3$ | $CH_3$ | CH | |
| $OCH_2CH_2OCH_3$ | H | $OCH_3$ | $OCH_3$ | CH | |
| $OCH_2CH_2OCH_3$ | H | Cl | $OCH_3$ | CH | |
| $OCH_2CH_2OCH_3$ | H | $OCH_3$ | $N(CH_3)_2$ | CH | |
| $OCH_2CH_2OCH_3$ | H | $CH_3$ | $CH_3$ | N | |
| $OCH_2CH_2OCH_3$ | H | $OCH_3$ | $CH_3$ | N | |
| $OCH_2CH_2OCH_3$ | H | $OCH_3$ | $OCH_3$ | N | |
| $OCH_2CH_2OCH_3$ | H | $OCH_3$ | $N(CH_3)_2$ | N | |
| $OCH_2CH_2OCH_3$ | H | $OCH_3$ | $OCH_2CF_3$ | N | |
| $OCH_2CH_2OCH_3$ | $CH_3$ | $OCH_3$ | $CH_3$ | N | |
| $OCH_2CH_2OCH_3$ | $CH_3$ | $OCH_3$ | $OCH_3$ | N | |
| $OCH_2CH_2OCH_3$ | $CH_3$ | $CH_3$ | $OCH_3$ | CH | |
| $OCH_2CH_2OCH_3$ | $CH_3$ | $OCH_3$ | $OCH_3$ | CH | |
| $OCH_2CH_2OCH_3$ | H | Br | $OCH_3$ | CH | |
| $OCH_2CH_2OCH_3$ | H | $CH_3$ | $OCH_2CF_3$ | N | |
| $OCH_2CH_2OCH_3$ | H | $CH_3$ | $OCH_2CF_3$ | CH | |
| $OCH_2CH_2OCH_3$ | H | $OCH_3$ | $OCH_2CF_3$ | CH | |
| $OCH_2CH_2OCH_3$ | H | $OCH_3$ | $C_2H_5$ | CH | |
| $OCH_2CH_2OCH_3$ | H | $OCH_3$ | $C_2H_5$ | N | |
| $OCH_2CH_2OCH_3$ | H | $OCH_3$ | $NHCH_3$ | CH | |
| $OCH_2CH_2OCH_3$ | H | $OCH_3$ | $NHCH_3$ | N | |
| $OCH_2CH_2OCH_3$ | H | $CH_3$ | $OC_2H_5$ | CH | |
| $OCH_2CH_2OCH_3$ | H | $OCH_3$ | $OC_2H_5$ | CH | |
| $OCH_2CH_2OCH_3$ | H | $CH_3$ | $OC_2H_5$ | N | |
| $OCH_2CH_2OCH_3$ | H | $OCH_3$ | $OC_2H_5$ | N | |
| $OCH_2CH_2OCH_3$ | H | $CH_3$ | $OCH_2CHF_2$ | CH | |
| $OCH_2CH_2OCH_3$ | H | $OCH_3$ | $OCH_2CHF_2$ | CH | |
| $OCH_2CH_2OCH_3$ | H | $CH_3$ | $OCH_2CHF_2$ | N | |
| $OCH_2CH_2OCH_3$ | H | $OCH_3$ | $OCH_2CHF_2$ | N | |
| $OCH_2CH_2OCH_3$ | H | $CH_3$ | $OCH_2CH_2F$ | CH | |
| $OCH_2CH_2OCH_3$ | H | $OCH_3$ | $OCH_2CH_2F$ | CH | |
| $OCH_2CH_2OCH_3$ | H | $CH_3$ | $OCH_2CF_3$ | N | |
| $OCH_2CH_2OCH_3$ | $CH_3$ | $OCH_3$ | $OCH_2CF_3$ | N | |
| $OCH_2CH_2OCH_3$ | $CH_3$ | Cl | $OCH_3$ | CH | |
| $OCH_2CH_2OCH_3$ | H | Cl | $N(CH_3)_2$ | CH | |
| $OCH_2CH_2OCH_3$ | H | Cl | $OC_2H_5$ | CH | |
| O-cyclopropyl | H | $CH_3$ | $CH_3$ | CH | |
| O-cyclopropyl | H | $OCH_3$ | $CH_3$ | CH | |
| O-cyclopropyl | H | $OCH_3$ | $OCH_3$ | CH | |
| O-cyclopropyl | H | Cl | $OCH_3$ | CH | |
| O-cyclopropyl | H | $OCH_3$ | $N(CH_3)_2$ | CH | |
| O-cyclopropyl | H | $CH_3$ | $CH_3$ | N | |

TABLE Ib-continued

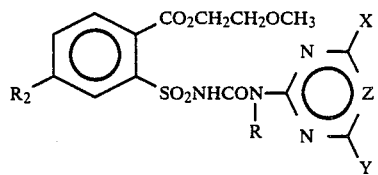

| R₂ | R | X | Y | Z | m.p. (°C.) |
|---|---|---|---|---|---|
| O-cyclopropyl | H | OCH₃ | CH₃ | N | |
| O-cyclopropyl | H | OCH₃ | OCH₃ | N | |
| O-cyclopropyl | H | OCH₃ | N(CH₃)₂ | N | |
| O-cyclopropyl | H | OCH₃ | OCH₂CF₃ | N | |
| O-cyclopropyl | CH₃ | OCH₃ | CH₃ | N | |
| O-cyclopropyl | CH₃ | OCH₃ | OCH₃ | N | |
| O-cyclopropyl | CH₃ | CH₃ | OCH₃ | CH | |
| O-cyclopropyl | CH₃ | OCH₃ | OCH₃ | CH | |
| O-cyclopropyl | H | Br | OCH₃ | CH | |
| O-cyclopropyl | CH₃ | OCH₃ | N(CH₃)₂ | N | |
| O-cyclopropyl | H | CH₃ | OCH₂CF₃ | N | |
| O-cyclopropyl | H | CH₃ | OCH₂CF₃ | CH | |
| O-cyclopropyl | H | OCH₃ | OCH₂CF₃ | CH | |
| O-cyclopropyl | H | OCH₃ | C₂H₅ | CH | |
| O-cyclopropyl | H | OCH₃ | C₂H₅ | N | |
| O-cyclopropyl | H | OCH₃ | NHCH₃ | CH | |
| O-cyclopropyl | H | OCH₃ | NHCH₃ | N | |
| O-cyclopropyl | H | CH₃ | OC₂H₅ | CH | |
| O-cyclopropyl | H | OCH₃ | OC₂H₅ | CH | |
| O-cyclopropyl | H | CH₃ | OC₂H₅ | N | |
| O-cyclopropyl | H | OCH₃ | OC₂H₅ | N | |
| O-cyclopropyl | H | CH₃ | OCH₂CHF₂ | CH | |
| O-cyclopropyl | H | OCH₃ | OCH₂CHF₂ | CH | |
| O-cyclopropyl | H | CH₃ | OCH₂CHF₂ | N | |
| O-cyclopropyl | H | OCH₃ | OCH₂CHF₂ | N | |
| O-cyclopropyl | H | CH₃ | OCH₂CH₂F | CH | |
| O-cyclopropyl | H | OCH₃ | OCH₂CH₂F | CH | |
| O-cyclopropyl | H | CH₃ | OCH₂CH₂F | N | |
| O-cyclopropyl | CH₃ | OCH₃ | OCH₂CH₂F | N | |
| O-cyclopropyl | CH₃ | Cl | OCH₃ | CH | |
| O-cyclopropyl | H | Cl | N(CH₃)₂ | CH | |
| O-cyclopropyl | H | Cl | OC₂H₅ | CH | |
| OCF₂CF₂H | H | OCH₃ | Cl | CH | |
| OCF₂CF₂H | H | CH₃ | CH₃ | CH | |
| OCF₂CF₂H | H | OCH₃ | OCH₃ | N | |
| S-cyclopropyl | H | OCH₃ | OCH₃ | CH | |
| S-cyclopropyl | H | OCH₃ | CH₃ | CH | |
| S-cyclopropyl | H | OCH₃ | Cl | CH | |
| S-cyclopropyl | H | CH₃ | CH₃ | CH | |
| S-cyclopropyl | H | OCH₃ | OCH₃ | N | |
| S-cyclopropyl | H | OCH₃ | CH₃ | N | |
| SCH₂-cyclopropyl | H | OCH₃ | OCH₃ | CH | |
| SCH₂-cyclopropyl | H | OCH₃ | CH₃ | CH | |
| SCH₂-cyclopropyl | H | OCH₃ | Cl | CH | |
| SCH₂-cyclopropyl | H | CH₃ | CH₃ | CH | |
| SCH₂-cyclopropyl | H | OCH₃ | OCH₃ | N | |
| NHCH₂-cyclopropyl | H | OCH₃ | OCH₃ | CH | |
| NHCH₂-cyclopropyl | H | OCH₃ | CH₃ | CH | |
| NHCH₂-cyclopropyl | H | OCH₃ | Cl | CH | |
| NHCH₂-cyclopropyl | H | CH₃ | CH₃ | CH | |
| NHCH₂-cyclopropyl | H | OCH₃ | OCH₃ | N | |
| NHCH₂-cyclopropyl | H | OCH₃ | CH₃ | N | |
| NHCH₂CHF₂ | H | OCH₃ | CH₃ | N | |
| NHCH₂CF₃ | H | OCH₃ | OCH₃ | CH | |
| NHCH₂CF₃ | H | OCH₃ | CH₃ | CH | |
| NHCH₂CF₃ | H | OCH₃ | Cl | CH | |
| NHCH₂CF₃ | H | CH₃ | CH₃ | CH | |
| NHCH₂CF₃ | H | OCH₃ | OCH₃ | N | |
| NHCH₃ | H | OCH₃ | OCH₃ | CH | |
| NHCH₃ | H | OCH₃ | CH₃ | CH | |
| NHCH₃ | H | OCH₃ | Cl | CH | |
| NHCH₃ | H | CH₃ | CH₃ | CH | |
| NHCH₃ | H | OCH₃ | OCH₃ | N | |
| NHCH₂CH₂SCH₃ | H | OCH₃ | OCH₃ | CH | |
| NHCH₂CH₂SCH₃ | H | OCH₃ | CH₃ | CH | |
| NHCH₂CH₂SCH₃ | H | OCH₃ | Cl | CH | |
| NHCH₂CH₂SCH₃ | H | CH₃ | CH₃ | CH | |
| NHCH₂CH₂SCH₃ | H | OCH₃ | OCH₃ | N | |

TABLE Ib-continued

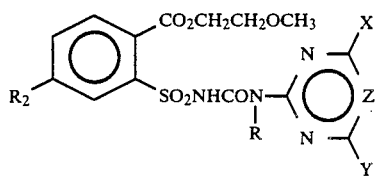

| R2 | R | X | Y | Z | m.p. (°C.) |
|---|---|---|---|---|---|
| NHCH2CH2SCH3 | H | OCH3 | CH3 | N | |

15

TABLE Ic

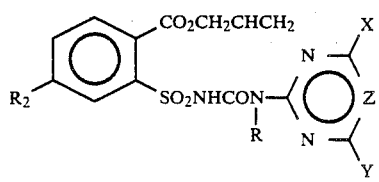

| R2 | R | X | Y | Z | m.p. (°C. |
|---|---|---|---|---|---|
| OC2H5 | H | CH3 | CH3 | CH | |
| OC2H5 | H | OCH3 | CH3 | CH | |
| OC2H5 | H | OCH3 | OCH3 | CH | |
| OC2H5 | H | Cl | OCH3 | CH | |
| OC2H5 | H | OCH3 | N(CH3)2 | CH | |
| OC2H5 | H | CH3 | CH3 | N | |
| OC2H5 | H | OCH3 | CH3 | N | |
| OC2H5 | H | OCH3 | OCH3 | N | |
| OC2H5 | H | OCH3 | N(CH3)2 | N | |
| OC2H5 | H | OCH3 | OCH2CF3 | N | |
| OC2H5 | CH3 | OCH3 | CH3 | N | |
| OC2H5 | CH3 | OCH3 | OCH3 | N | |
| OC2H5 | CH3 | CH3 | OCH3 | CH | |
| OC2H5 | CH3 | OCH3 | OCH3 | CH | |
| OC2H5 | H | Br | OCH3 | CH | |
| OC2H5 | CH3 | OCH3 | N(CH3)2 | N | |
| OC2H5 | H | CH3 | OCH2CF3 | N | |
| OC2H5 | H | CH3 | OCH2CF3 | CH | |
| OC2H5 | H | OCH3 | OCH2CF3 | CH | |
| OC2H5 | H | OCH3 | C2H5 | CH | |
| OC2H5 | H | OCH3 | C2H5 | N | |
| OC2H5 | H | OCH3 | NHCH3 | CH | |
| OC2H5 | H | OCH3 | NHCH3 | N | |
| OC2H5 | H | CH3 | OC2H5 | CH | |
| OC2H5 | H | OCH3 | OC2H5 | CH | |
| OC2H5 | H | CH3 | OC2H5 | N | |
| OC2H5 | H | OCH3 | OC2H5 | N | |
| OC2H5 | H | CH3 | OCH2CHF2 | CH | |
| OC2H5 | H | OCH3 | OCH2CHF2 | CH | |
| OC2H5 | H | CH3 | OCH2CHF2 | N | |
| OC2H5 | H | OCH3 | OCH2CHF2 | N | |
| OC2H5 | H | CH3 | OCH2CH2F | CH | |
| OC2H5 | H | OCH3 | OCH2CH2F | CH | |
| OC2H5 | H | CH3 | OCH2CH2F | N | |
| OC2H5 | CH3 | OCH3 | OCH2CH2F | N | |
| OC2H5 | CH3 | Cl | OCH3 | CH | |
| OC2H5 | H | Cl | N(CH3)2 | CH | |
| OC2H5 | H | Cl | OC2H5 | CH | |
| SC2H5 | H | CH3 | CH3 | CH | |
| SC2H5 | H | OCH3 | CH3 | CH | |
| SC2H5 | H | Cl | OCH3 | CH | |
| SC2H5 | H | OCH3 | N(CH3)2 | CH | |
| SC2H5 | H | CH3 | CH3 | N | |
| SC2H5 | H | OCH3 | CH3 | N | |
| SC2H5 | H | OCH3 | OCH3 | N | |
| SC2H5 | H | OCH3 | N(CH3)2 | N | |
| SC2H5 | H | OCH3 | OCH2CF3 | N | |

TABLE Ic-continued

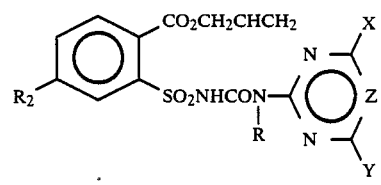

| R₂ | R | X | Y | Z | m.p. (°C.) |
|---|---|---|---|---|---|
| SC₂H₅ | CH₃ | OCH₃ | CH₃ | N | |
| SC₂H₅ | CH₃ | OCH₃ | OCH₃ | N | |
| SC₂H₅ | CH₃ | CH₃ | OCH₃ | CH | |
| SC₂H₅ | CH₃ | OCH₃ | OCH₃ | CH | |
| SC₂H₅ | H | Br | OCH₃ | CH | |
| SC₂H₅ | CH₃ | OCH₃ | N(CH₃)₂ | N | |
| SC₂H₅ | H | CH₃ | OCH₂CF₃ | N | |
| SC₂H₅ | H | CH₃ | OCH₂CF₃ | CH | |
| SC₂H₅ | H | OCH₃ | OCH₂CF₃ | CH | |
| SC₂H₅ | H | OCH₃ | C₂H₅ | CH | |
| SC₂H₅ | H | OCH₃ | C₂H₅ | N | |
| SC₂H₅ | H | OCH₃ | NHCH₃ | CH | |
| SC₂H₅ | H | OCH₃ | NHCH₃ | N | |
| SC₂H₅ | H | CH₃ | OC₂H₅ | CH | |
| SC₂H₅ | H | OCH₃ | OC₂H₅ | CH | |
| SC₂H₅ | H | CH₃ | OC₂H₅ | N | |
| SC₂H₅ | H | OCH₃ | OC₂H₅ | N | |
| SC₂H₅ | H | CH₃ | OCH₂CHF₂ | CH | |
| SC₂H₅ | H | OCH₃ | OCH₂CHF₂ | CH | |
| SC₂H₅ | H | CH₃ | OCH₂CHF₂ | N | |
| SC₂H₅ | H | OCH₃ | OCH₂CHF₂ | N | |
| SC₂H₅ | H | CH₃ | OCH₂CH₂F | CH | |
| SC₂H₅ | H | OCH₃ | OCH₂CH₂F | CH | |
| SC₂H₅ | H | CH₃ | OCH₂CH₂F | N | |
| SC₂H₅ | CH₃ | OCH₃ | OCH₂CH₂F | N | |
| SC₂H₅ | CH₃ | Cl | OCH₃ | CH | |
| SC₂H₅ | H | Cl | N(CH₃)₂ | CH | |
| SC₂H₅ | H | Cl | OC₂H₅ | CH | |
| S(CH₂)₅CH₃ | H | CH₃ | CH₃ | CH | |
| S(CH₂)₅CH₃ | H | OCH₃ | CH₃ | CH | |
| S(CH₂)₅CH₃ | H | OCH₃ | OCH₃ | CH | |
| S(CH₂)₅CH₃ | H | Cl | OCH₃ | CH | |
| S(CH₂)₅CH₃ | H | CH₃ | CH₃ | N | |
| S(CH₂)₅CH₃ | H | OCH₃ | CH₃ | N | |
| S(CH₂)₅CH₃ | H | OCH₃ | OCH₃ | N | |
| S(CH₂)₅CH₃ | H | OCH₃ | N(CH₃)₂ | CH | |
| S(CH₂)₅CH₃ | H | OCH₃ | N(CH₃)₂ | N | |
| S(CH₂)₅CH₃ | H | OCH₃ | OCH₂CF₃ | N | |
| S(CH₂)₅CH₃ | CH₃ | OCH₃ | CH₃ | N | |
| S(CH₂)₅CH₃ | CH₃ | OCH₃ | OCH₃ | N | |
| S(CH₂)₅CH₃ | CH₃ | CH₃ | OCH₃ | CH | |
| S(CH₂)₅CH₃ | CH₃ | OCH₃ | OCH₃ | CH | |
| S(CH₂)₅CH₃ | H | Br | OCH₃ | CH | |
| S(CH₂)₅CH₃ | H | CH₃ | OCH₂CF₃ | N | |
| S(CH₂)₅CH₃ | H | CH₃ | OCH₂CF₃ | CH | |
| S(CH₂)₅CH₃ | H | OCH₃ | OCH₂CF₃ | CH | |
| S(CH₂)₅CH₃ | H | OCH₃ | NHCH₃ | N | |
| S(O)(CH₃) | H | CH₃ | CH₃ | CH | |
| S(O)(CH₃) | H | OCH₃ | CH₃ | CH | |
| S(O)(CH₃) | H | OCH₃ | OCH₃ | CH | |
| S(O)(CH₃) | H | Cl | OCH₃ | CH | |
| S(O)(CH₃) | H | OCH₃ | N(CH₃)₂ | CH | |
| S(O)(CH₃) | H | CH₃ | CH₃ | N | |
| S(O)(CH₃) | H | OCH₃ | CH₃ | N | |
| S(O)(CH₃) | H | OCH₃ | OCH₃ | N | |
| S(O)(CH₃) | H | OCH₃ | N(CH₃)₂ | N | |
| S(O)(CH₃) | H | OCH₃ | OCH₂CF₃ | N | |
| S(O)(CH₃) | CH₃ | OCH₃ | CH₃ | N | |
| S(O)(CH₃) | CH₃ | OCH₃ | OCH₃ | N | |
| S(O)(CH₃) | CH₃ | CH₃ | OCH₃ | CH | |
| S(O)(CH₃) | CH₃ | OCH₃ | OCH₃ | CH | |
| S(O)(CH₃) | H | Br | OCH₃ | CH | |
| S(O)(CH₃) | H | OCH₃ | N(CH₃)₂ | CH | |
| S(O)(CH₃) | CH₃ | OCH₃ | N(CH₃)₂ | N | |
| S(O)(CH₃) | H | CH₃ | OCH₂CF₃ | N | |
| S(O)(CH₃) | H | CH₃ | OCH₂CF₃ | CH | |
| S(O)(CH₃) | H | OCH₃ | OCH₂CF₃ | CH | |
| S(O)(CH₃) | H | OCH₃ | C₂H₅ | CH | |
| S(O)(CH₃) | H | OCH₃ | C₂H₅ | N | |
| S(O)(CH₃) | H | OCH₃ | NHCH₃ | CH | |

TABLE Ic-continued

Structure: benzene ring with $CO_2CH_2CHCH_2$ (ortho), $R_2$ substituent, and $SO_2NHCON(R)$— linked to a heterocyclic ring with substituents X, Y, Z (N, Z, N positions around ring with X and Y).

| $R_2$ | R | X | Y | Z | m.p. (°C.) |
|---|---|---|---|---|---|
| $S(O)(CH_3)$ | H | $OCH_3$ | $NHCH_3$ | N | |
| $S(O)(CH_3)$ | H | $CH_3$ | $OC_2H_5$ | CH | |
| $S(O)(CH_3)$ | H | $OCH_3$ | $OC_2H_5$ | CH | |
| $S(O)(CH_3)$ | H | $CH_3$ | $OC_2H_5$ | N | |
| $S(O)(CH_3)$ | H | $OCH_3$ | $OC_2H_5$ | N | |
| $S(O)(CH_3)$ | H | $CH_3$ | $OCH_2CHF_2$ | CH | |
| $S(O)(CH_3)$ | H | $OCH_3$ | $OCH_2CHF_2$ | CH | |
| $S(O)(CH_3)$ | H | $CH_3$ | $OCH_2CHF_2$ | N | |
| $S(O)(CH_3)$ | H | $OCH_3$ | $OCH_2CHF_2$ | N | |
| $S(O)(CH_3)$ | H | $CH_3$ | $OCH_2CHF_2$ | CH | |
| $S(O)(CH_3)$ | H | $OCH_3$ | $OCH_2CHF_2$ | CH | |
| $S(O)(CH_3)$ | H | $CH_3$ | $OCH_2CHF_2$ | N | |
| $S(O)(CH_3)$ | H | $OCH_3$ | $OCH_2CHF_2$ | N | |
| $S(O)(CH_3)$ | $CH_3$ | Cl | $OCH_3$ | CH | |
| $S(O)(CH_3)$ | H | Cl | $N(CH_3)_2$ | CH | |
| $S(O)(CH_3)$ | H | Cl | $OC_2H_5$ | CH | |
| $OCH_2CH=CH_2$ | H | $CH_3$ | $CH_3$ | CH | |
| $OCH_2CH=CH_2$ | H | $OCH_3$ | $CH_3$ | CH | |
| $OCH_2CH=CH_2$ | H | $OCH_3$ | $OCH_3$ | CH | |
| $OCH_2CH=CH_2$ | H | Cl | $OCH_3$ | CH | |
| $OCH_2CH=CH_2$ | H | $OCH_3$ | $N(CH_3)_2$ | CH | |
| $OCH_2CH=CH_2$ | H | $CH_3$ | $CH_3$ | N | |
| $OCH_2CH=CH_2$ | H | $OCH_3$ | $CH_3$ | N | |
| $OCH_2CH=CH_2$ | H | $OCH_3$ | $OCH_3$ | N | |
| $OCH_2CH=CH_2$ | H | $OCH_3$ | $N(CH_3)_2$ | N | |
| $OCH_2CH=CH_2$ | H | $OCH_3$ | $OCH_2CF_3$ | N | |
| $OCH_2CH=CH_2$ | $CH_3$ | $OCH_3$ | $CH_3$ | N | |
| $OCH_2CH=CH_2$ | $CH_3$ | $OCH_3$ | $OCH_3$ | N | |
| $OCH_2CH=CH_2$ | $CH_3$ | $CH_3$ | $OCH_3$ | CH | |
| $OCH_2CH=CH_2$ | $CH_3$ | $OCH_3$ | $OCH_3$ | CH | |
| $OCH_2CH=CH_2$ | H | Br | $OCH_3$ | CH | |
| $OCH_2CH=CH_2$ | $CH_3$ | $OCH_3$ | $N(CH_3)_2$ | N | |
| $OCH_2CH=CH_2$ | H | $CH_3$ | $OCH_2CF_3$ | N | |
| $OCH_2CH=CH_2$ | H | $CH_3$ | $OCH_2CF_3$ | CH | |
| $OCH_2CH=CH_2$ | H | $OCH_3$ | $OCH_2CF_3$ | CH | |
| $OCH_2CH=CH_2$ | H | $OCH_3$ | $C_2H_5$ | CH | |
| $OCH_2CH=CH_2$ | H | $OCH_3$ | $C_2H_5$ | N | |
| $OCH_2CH=CH_2$ | H | $OCH_3$ | $NHCH_3$ | CH | |
| $OCH_2CH=CH_2$ | H | $OCH_3$ | $NHCH_3$ | N | |
| $OCH_2CH=CH_2$ | H | $CH_3$ | $OC_2H_5$ | CH | |
| $OCH_2CH=CH_2$ | H | $OCH_3$ | $OC_2H_5$ | CH | |
| $OCH_2CH=CH_2$ | H | $CH_3$ | $OC_2H_5$ | N | |
| $OCH_2CH=CH_2$ | H | $OCH_3$ | $OC_2H_5$ | N | |
| $OCH_2CH=CH_2$ | H | $CH_3$ | $OCH_2CHF_2$ | CH | |
| $OCH_2CH=CH_2$ | H | $OCH_3$ | $OCH_2CHF_2$ | CH | |
| $OCH_2CH=CH_2$ | H | $CH_3$ | $OCH_2CHF_2$ | N | |
| $OCH_2CH=CH_2$ | H | $OCH_3$ | $OCH_2CHF_2$ | N | |
| $OCH_2CH=CH_2$ | H | $CH_3$ | $OCH_2CH_2F$ | CH | |
| $OCH_2CH=CH_2$ | H | $OCH_3$ | $OCH_2CH_2F$ | CH | |
| $OCH_2CH=CH_2$ | H | $CH_3$ | $OCH_2CH_2F$ | N | |
| $OCH_2CH=CH_2$ | $CH_3$ | $OCH_3$ | $OCH_2CH_2F$ | N | |
| $OCH_2CH=CH_2$ | $CH_3$ | Cl | $OCH_3$ | CH | |
| $OCH_2CH=CH_2$ | H | Cl | $N(CH_3)_2$ | CH | |
| $OCH_2CH=CH_2$ | H | Cl | $OC_2H_5$ | CH | |
| $OCH_2C\equiv CH$ | H | $CH_3$ | $CH_3$ | CH | |
| $OCH_2C\equiv CH$ | H | $OCH_3$ | $CH_3$ | CH | |
| $OCH_2C\equiv CH$ | H | $OCH_3$ | $OCH_3$ | CH | |
| $OCH_2C\equiv CH$ | H | Cl | $OCH_3$ | CH | |
| $OCH_2C\equiv CH$ | H | $OCH_3$ | $N(CH_3)_2$ | CH | |
| $OCH_2C\equiv CH$ | H | $CH_3$ | $CH_3$ | N | |
| $OCH_2C\equiv CH$ | H | $OCH_3$ | $CH_3$ | N | |
| $OCH_2C\equiv CH$ | H | $OCH_3$ | $OCH_3$ | N | |
| $OCH_2C\equiv CH$ | H | $OCH_3$ | $N(CH_3)_2$ | N | |
| $OCH_2C\equiv CH$ | H | $OCH_3$ | $OCH_2CF_3$ | N | |
| $OCH_2C\equiv CH$ | $CH_3$ | $OCH_3$ | $CH_3$ | N | |
| $OCH_2C\equiv CH$ | $CH_3$ | $OCH_3$ | $OCH_3$ | N | |
| $OCH_2C\equiv CH$ | $CH_3$ | $CH_3$ | $OCH_3$ | CH | |
| $OCH_2C\equiv CH$ | $CH_3$ | $OCH_3$ | $OCH_3$ | CH | |
| $OCH_2C\equiv CH$ | H | Br | $OCH_3$ | CH | |
| $OCH_2C\equiv CH$ | $CH_3$ | $OCH_3$ | $N(CH_3)_2$ | N | |

TABLE Ic-continued

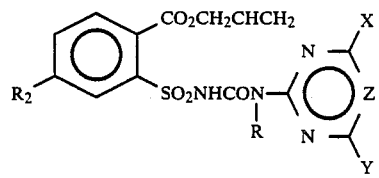

| R₂ | R | X | Y | Z | m.p. (°C.) |
|---|---|---|---|---|---|
| OCH₂C≡CH | H | CH₃ | OCH₂CF₃ | N | |
| OCH₂C≡CH | H | CH₃ | OCH₂CF₃ | CH | |
| OCH₂C≡CH | H | OCH₃ | OCH₂CF₃ | CH | |
| OCH₂C≡CH | H | OCH₃ | C₂H₅ | CH | |
| OCH₂C≡CH | H | OCH₃ | C₂H₅ | N | |
| OCH₂C≡CH | H | OCH₃ | NHCH₃ | CH | |
| OCH₂C≡CH | H | OCH₃ | NHCH₃ | N | |
| OCH₂C≡CH | H | CH₃ | OC₂H₅ | CH | |
| OCH₂C≡CH | H | OCH₃ | OC₂H₅ | CH | |
| OCH₂C≡CH | H | CH₃ | OC₂H₅ | N | |
| OCH₂C≡CH | H | OCH₃ | OC₂H₅ | N | |
| OCH₂C≡CH | H | CH₃ | OCH₂CHF₂ | CH | |
| OCH₂C≡CH | H | OCH₃ | OCH₂CHF₂ | CH | |
| OCH₂C≡CH | H | CH₃ | OCH₂CHF₂ | N | |
| OCH₂C≡CH | H | OCH₃ | OCH₂CHF₂ | N | |
| OCH₂C≡CH | H | CH₃ | OCH₂CH₂F | CH | |
| OCH₂C≡CH | H | OCH₃ | OCH₂CH₂F | CH | |
| OCH₂C≡CH | H | CH₃ | OCH₂CF₃ | N | |
| OCH₂C≡CH | CH₃ | OCH₃ | OCH₂CF₃ | N | |
| OCH₂C≡CH | CH₃ | Cl | OCH₃ | CH | |
| OCH₂C≡CH | H | Cl | N(CH₃)₂ | CH | |
| OCH₂C≡CH | H | Cl | OC₂H₅ | CH | |
| SCH₂CH=CH₂ | H | CH₃ | CH₃ | CH | |
| SCH₂CH=CH₂ | H | OCH₃ | CH₃ | CH | |
| SCH₂CH=CH₂ | H | OCH₃ | OCH₃ | CH | |
| SCH₂CH=CH₂ | H | Cl | OCH₃ | CH | |
| SCH₂CH=CH₂ | H | OCH₃ | N(CH₃)₂ | N | |
| SCH₂CH=CH₂ | H | CH₃ | CH₃ | N | |
| SCH₂CH=CH₂ | H | OCH₃ | CH₃ | N | |
| SCH₂CH=CH₂ | H | OCH₃ | OCH₃ | N | |
| SCH₂CH=CH₂ | H | OCH₃ | N(CH₃)₂ | N | |
| SCH₂CH=CH₂ | H | OCH₃ | OCH₂CF₃ | N | |
| SCH₂CH=CH₂ | CH₃ | OCH₃ | CH₃ | N | |
| SCH₂CH=CH₂ | CH₃ | OCH₃ | OCH₃ | N | |
| SCH₂CH=CH₂ | CH₃ | CH₃ | OCH₃ | CH | |
| SCH₂CH=CH₂ | CH₃ | OCH₃ | OCH₃ | CH | |
| SCH₂CH=CH₂ | H | Br | OCH₃ | CH | |
| SCH₂CH=CH₂ | CH₃ | OCH₃ | N(CH₃)₂ | N | |
| SCH₂CH=CH₂ | H | CH₃ | OCH₂CF₃ | N | |
| SCH₂CH=CH₂ | H | CH₃ | OCH₂CF₃ | CH | |
| SCH₂CH=CH₂ | H | OCH₃ | OCH₂CF₃ | CH | |
| SCH₂CH=CH₂ | H | OCH₃ | C₂H₅ | CH | |
| SCH₂CH=CH₂ | H | OCH₃ | C₂H₅ | CH | |
| SCH₂CH=CH₂ | H | OCH₃ | NHCH₃ | CH | |
| SCH₂CH=CH₂ | H | OCH₃ | NHCH₃ | N | |
| SCH₂CH=CH₂ | H | CH₃ | OC₂H₅ | CH | |
| SCH₂CH=CH₂ | H | OCH₃ | OC₂H₅ | CH | |
| SCH₂CH=CH₂ | H | CH₃ | OC₂H₅ | N | |
| SCH₂CH=CH₂ | H | OCH₃ | OC₂H₅ | N | |
| SCH₂CH=CH₂ | H | CH₃ | OCH₂CHF₂ | CH | |
| SCH₂CH=CH₂ | H | OCH₃ | OCH₂CHF₂ | CH | |
| SCH₂CH=CH₂ | H | CH₃ | OCH₂CHF₂ | N | |
| SCH₂CH=CH₂ | H | OCH₃ | OCH₂CHF₂ | N | |
| SCH₂CH=CH₂ | H | CH₃ | OCH₂CH₂F | CH | |
| SCH₂CH=CH₂ | H | OCH₃ | OCH₂CH₂F | CH | |
| SCH₂CH=CH₂ | H | CH₃ | OCH₂CH₂F | N | |
| SCH₂CH=CH₂ | H | OCH₃ | OCH₂CH₂F | N | |
| SCH₂CH=CH₂ | CH₃ | Cl | OCH₃ | CH | |
| SCH₂CH=CH₂ | H | Cl | N(CH₃)₂ | CH | |
| SCH₂CH=CH₂ | H | Cl | OC₂H₅ | CH | |
| SCH₂C≡CH | H | CH₃ | CH₃ | CH | |
| SCH₂C≡CH | H | OCH₃ | CH₃ | CH | |
| SCH₂C≡CH | H | OCH₃ | OCH₃ | CH | |
| SCH₂C≡CH | H | Cl | OCH₃ | CH | |
| SCH₂C≡CH | H | OCH₃ | N(CH₃)₂ | N | |
| SCH₂C≡CH | H | CH₃ | CH₃ | N | |
| SCH₂C≡CH | H | OCH₃ | CH₃ | N | |
| SCH₂C≡CH | H | OCH₃ | OCH₃ | N | |
| SCH₂C≡CH | H | OCH₃ | N(CH₃)₂ | N | |
| SCH₂C≡CH | H | OCH₃ | OCH₂CF₃ | N | |

TABLE Ic-continued

Structure: benzene ring with CO₂CH₂CHCH₂ at one position, SO₂NHCON(R)- linked to a heterocyclic ring with X, Y, Z and N positions, and R₂ substituent.

| R₂ | R | X | Y | Z | m.p. (°C.) |
|---|---|---|---|---|---|
| SCH₂C≡CH | CH₃ | OCH₃ | CH₃ | N | |
| SCH₂C≡CH | CH₃ | OCH₃ | OCH₃ | N | |
| SCH₂C≡CH | CH₃ | CH₃ | OCH₃ | CH | |
| SCH₂C≡CH | CH₃ | OCH₃ | OCH₃ | CH | |
| SCH₂C≡CH | H | Br | OCH₃ | CH | |
| SCH₂C≡CH | CH₃ | OCH₃ | N(CH₃)₂ | N | |
| SCH₂C≡CH | H | CH₃ | OCH₂CF₃ | N | |
| SCH₂C≡CH | H | CH₃ | OCH₂CF₃ | CH | |
| SCH₂C≡CH | H | OCH₃ | OCH₂CF₃ | CH | |
| SCH₂C≡CH | H | OCH₃ | C₂H₅ | CH | |
| SCH₂C≡CH | H | OCH₃ | C₂H₅ | CH | |
| SCH₂C≡CH | H | OCH₃ | NHCH₃ | CH | |
| SCH₂C≡CH | H | OCH₃ | NHCH₃ | N | |
| SCH₂C≡CH | H | CH₃ | OC₂H₅ | CH | |
| SCH₂C≡CH | H | OCH₃ | OC₂H₅ | CH | |
| SCH₂C≡CH | H | CH₃ | OC₂H₅ | N | |
| SCH₂C≡CH | H | OCH₃ | OC₂H₅ | N | |
| SCH₂C≡CH | H | CH₃ | OCH₂CHF₂ | CH | |
| SCH₂C≡CH | H | OCH₃ | OCH₂CHF₂ | CH | |
| SCH₂C≡CH | H | CH₃ | OCH₂CHF₂ | N | |
| SCH₂C≡CH | H | OCH₃ | OCH₂CHF₂ | N | |
| SCH₂C≡CH | H | CH₃ | OCH₂CH₂F | CH | |
| SCH₂C≡CH | H | OCH₃ | OCH₂CH₂F | CH | |
| SCH₂C≡CH | H | CH₃ | OCH₂CH₂F | N | |
| SCH₂C≡CH | H | OCH₃ | OCH₂CH₂F | N | |
| SCH₂C≡CH | CH₃ | Cl | OCH₃ | CH | |
| SCH₂C≡CH | H | Cl | N(CH₃)₂ | CH | |
| SCH₂C≡CH | H | Cl | OC₂H₅ | CH | |
| CH₂CH₂F | H | CH₃ | CH₃ | CH | |
| CH₂CH₂F | H | OCH₃ | CH₃ | CH | |
| CH₂CH₂F | H | OCH₃ | OCH₃ | CH | |
| CH₂CH₂F | H | Cl | OCH₃ | CH | |
| CH₂CH₂F | H | OCH₃ | N(CH₃)₂ | CH | |
| CH₂CH₂F | H | CH₃ | CH₃ | N | |
| CH₂CH₂F | H | OCH₃ | OCH₃ | N | |
| CH₂CH₂F | H | OCH₃ | N(CH₃)₂ | N | |
| CH₂CH₂F | H | OCH₃ | OCH₂CF₃ | N | |
| CH₂CH₂F | CH₃ | OCH₃ | CH₃ | N | |
| CH₂CH₂F | CH₃ | OCH₃ | OCH₃ | N | |
| CH₂CH₂F | CH₃ | CH₃ | OCH₃ | CH | |
| CH₂CH₂F | CH₃ | OCH₃ | OCH₃ | CH | |
| CH₂CH₂F | H | Br | OCH₃ | CH | |
| CH₂CH₂F | CH₃ | OCH₃ | N(CH₃)₂ | N | |
| CH₂CH₂F | H | CH₃ | OCH₂CF₃ | N | |
| CH₂CH₂F | H | CH₃ | OCH₂CF₃ | CH | |
| CH₂CH₂F | H | OCH₃ | OCH₂CF₃ | CH | |
| CH₂CH₂F | H | OCH₃ | C₂H₅ | CH | |
| CH₂CH₂F | H | OCH₃ | C₂H₅ | N | |
| CH₂CH₂F | H | OCH₃ | NHCH₃ | CH | |
| CH₂CH₂F | H | OCH₃ | NHCH₃ | N | |
| CH₂CH₂F | H | CH₃ | OC₂H₅ | CH | |
| CH₂CH₂F | H | OCH₃ | OC₂H₅ | CH | |
| CH₂CH₂F | H | CH₃ | OC₂H₅ | N | |
| CH₂CH₂F | H | OCH₃ | OC₂H₅ | N | |
| CH₂CH₂F | H | CH₃ | OCH₂CHF₂ | CH | |
| CH₂CH₂F | H | OCH₃ | OCH₂CHF₂ | CH | |
| CH₂CH₂F | H | CH₃ | OCH₂CHF₂ | N | |
| CH₂CH₂F | H | OCH₃ | OCH₂CHF₂ | N | |
| CH₂CH₂F | H | CH₃ | OCH₂CH₂F | CH | |
| CH₂CH₂F | H | OCH₃ | OCH₂CH₂F | CH | |
| CH₂CH₂F | H | CH₃ | OCH₂CF₃ | N | |
| CH₂CH₂F | CH₃ | OCH₃ | OCH₂CF₃ | N | |
| CH₂CH₂F | CH₃ | Cl | OCH₃ | CH | |
| CH₂CH₂F | H | Cl | N(CH₃)₂ | CH | |
| CH₂CH₂F | H | Cl | OC₂H₅ | CH | |
| CH₂CF₃ | H | CH₃ | CH₃ | CH | |
| CH₂CF₃ | H | OCH₃ | CH₃ | CH | |
| CH₂CF₃ | H | OCH₃ | OCH₃ | CH | |
| CH₂CF₃ | H | Cl | OCH₃ | CH | |

TABLE Ic-continued

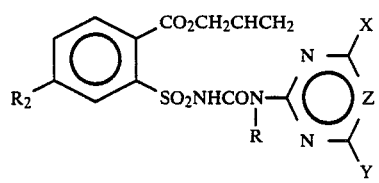

| $R_2$ | R | X | Y | Z | m.p. (°C.) |
|---|---|---|---|---|---|
| $CH_2CF_3$ | H | $OCH_3$ | $N(CH_3)_2$ | CH | |
| $CH_2CF_3$ | H | $CH_3$ | $CH_3$ | N | |
| $CH_2CF_3$ | H | $OCH_3$ | $CH_3$ | N | |
| $CH_2CF_3$ | H | $OCH_3$ | $OCH_3$ | N | |
| $CH_2CF_3$ | H | $OCH_3$ | $N(CH_3)_2$ | N | |
| $CH_2CF_3$ | H | $OCH_3$ | $OCH_2CF_3$ | N | |
| $CH_2CF_3$ | $CH_3$ | $OCH_3$ | $CH_3$ | N | |
| $CH_2CF_3$ | $CH_3$ | $OCH_3$ | $OCH_3$ | N | |
| $CH_2CF_3$ | $CH_3$ | $CH_3$ | $OCH_3$ | CH | |
| $CH_2CF_3$ | $CH_3$ | $OCH_3$ | $OCH_3$ | CH | |
| $CH_2CF_3$ | H | Br | $OCH_3$ | CH | |
| $CH_2CF_3$ | $CH_3$ | $OCH_3$ | $N(CH_3)_2$ | N | |
| $CH_2CF_3$ | H | $CH_3$ | $OCH_2CF_3$ | N | |
| $CH_2CF_3$ | H | $CH_3$ | $OCH_2CF_3$ | CH | |
| $CH_2CF_3$ | H | $OCH_3$ | $OCH_2CF_3$ | CH | |
| $CH_2CF_3$ | H | $OCH_3$ | $C_2H_5$ | CH | |
| $CH_2CF_3$ | H | $OCH_3$ | $C_2H_5$ | N | |
| $CH_2CF_3$ | H | $OCH_3$ | $NHCH_3$ | CH | |
| $CH_2CF_3$ | H | $OCH_3$ | $NHCH_3$ | N | |
| $CH_2CF_3$ | H | $CH_3$ | $OC_2H_5$ | CH | |
| $CH_2CF_3$ | H | $OCH_3$ | $OC_2H_5$ | CH | |
| $CH_2CF_3$ | H | $CH_3$ | $OC_2H_5$ | N | |
| $CH_2CF_3$ | H | $OCH_3$ | $OC_2H_5$ | N | |
| $CH_2CF_3$ | H | $CH_3$ | $OCH_2CHF_2$ | CH | |
| $CH_2CF_3$ | H | $OCH_3$ | $OCH_2CHF_2$ | CH | |
| $CH_2CF_3$ | H | $CH_3$ | $OCH_2CHF_2$ | N | |
| $CH_2CF_3$ | H | $OCH_3$ | $OCH_2CHF_2$ | N | |
| $CH_2CF_3$ | H | $CH_3$ | $OCH_2CH_2F$ | CH | |
| $CH_2CF_3$ | H | $OCH_3$ | $OCH_2CH_2F$ | CH | |
| $CH_2CF_3$ | H | $CH_3$ | $OCH_2CH_2F$ | N | |
| $CH_2CF_3$ | $CH_3$ | $OCH_3$ | $OCH_2CH_2F$ | N | |
| $CH_2CF_3$ | $CH_3$ | Cl | $OCH_3$ | CH | |
| $CH_2CF_3$ | H | Cl | $N(CH_3)_2$ | CH | |
| $CH_2CF_3$ | H | Cl | $OC_2H_5$ | CH | |
| $CHFCH_3$ | H | $CH_3$ | $CH_3$ | CH | |
| $CHFCH_3$ | H | $OCH_3$ | $CH_3$ | CH | |
| $CHFCH_3$ | H | $OCH_3$ | $OCH_3$ | CH | |
| $CHFCH_3$ | H | Cl | $OCH_3$ | CH | |
| $CHFCH_3$ | H | $OCH_3$ | $N(CH_3)_2$ | CH | |
| $CHFCH_3$ | H | $CH_3$ | $CH_3$ | N | |
| $CHFCH_3$ | H | $OCH_3$ | $CH_3$ | N | |
| $CHFCH_3$ | H | $OCH_3$ | $OCH_3$ | N | |
| $CHFCH_3$ | H | $OCH_3$ | $N(CH_3)_2$ | N | |
| $CHFCH_3$ | H | $OCH_3$ | $OCH_2CF_3$ | N | |
| $CHFCH_3$ | $CH_3$ | $OCH_3$ | $CH_3$ | N | |
| $CHFCH_3$ | $CH_3$ | $OCH_3$ | $OCH_3$ | N | |
| $CHFCH_3$ | $CH_3$ | $CH_3$ | $OCH_3$ | CH | |
| $CHFCH_3$ | $CH_3$ | $OCH_3$ | $OCH_3$ | CH | |
| $CHFCH_3$ | H | Br | $OCH_3$ | CH | |
| $CHFCH_3$ | $CH_3$ | $OCH_3$ | $N(CH_3)_2$ | N | |
| $CHFCH_3$ | H | $CH_3$ | $OCH_2CF_3$ | N | |
| $CHFCH_3$ | H | $CH_3$ | $OCH_2CF_3$ | CH | |
| $CHFCH_3$ | H | $OCH_3$ | $OCH_2CF_3$ | CH | |
| $CHFCH_3$ | H | $OCH_3$ | $C_2H_5$ | CH | |
| $CHFCH_3$ | H | $OCH_3$ | $C_2H_5$ | N | |
| $CHFCH_3$ | H | $OCH_3$ | $NHCH_3$ | CH | |
| $CHFCH_3$ | H | $OCH_3$ | $NHCH_3$ | N | |
| $CHFCH_3$ | H | $CH_3$ | $OC_2H_5$ | CH | |
| $CHFCH_3$ | H | $OCH_3$ | $OC_2H_5$ | CH | |
| $CHFCH_3$ | H | $CH_3$ | $OC_2H_5$ | N | |
| $CHFCH_3$ | H | $OCH_3$ | $OC_2H_5$ | N | |
| $CHFCH_3$ | H | $CH_3$ | $OCH_2CHF_2$ | CH | |
| $CHFCH_3$ | H | $OCH_3$ | $OCH_2CHF_2$ | CH | |
| $CHFCH_3$ | H | $CH_3$ | $OCH_2CHF_2$ | N | |
| $CHFCH_3$ | H | $OCH_3$ | $OCH_2CHF_2$ | N | |
| $CHFCH_3$ | H | $CH_3$ | $OCH_2CH_2F$ | CH | |
| $CHFCH_3$ | H | $OCH_3$ | $OCH_2CH_2F$ | CH | |
| $CHFCH_3$ | H | $CH_3$ | $OCH_2CF_3$ | N | |
| $CHFCH_3$ | $CH_3$ | $OCH_3$ | $OCH_2CF_3$ | N | |
| $CHFCH_3$ | $CH_3$ | Cl | $OCH_3$ | CH | |

TABLE Ic-continued

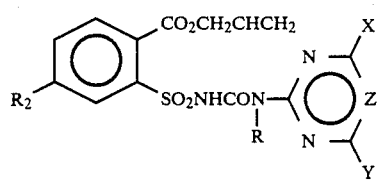

| $R_2$ | R | X | Y | Z | m.p. (°C.) |
|---|---|---|---|---|---|
| $CHFCH_3$ | H | Cl | $N(CH_3)_2$ | CH | |
| $CHFCH_3$ | H | Cl | $OC_2H_5$ | CH | |
| $CH_2F$ | H | $CH_3$ | $CH_3$ | CH | |
| $CH_2F$ | H | $OCH_3$ | $CH_3$ | CH | |
| $CH_2F$ | H | $OCH_3$ | $OCH_3$ | CH | |
| $CH_2F$ | H | Cl | $OCH_3$ | CH | |
| $CH_2F$ | H | $OCH_3$ | $N(CH_3)_2$ | CH | |
| $CH_2F$ | H | $CH_3$ | $CH_3$ | N | |
| $CH_2F$ | H | $OCH_3$ | $CH_3$ | N | |
| $CH_2F$ | H | $OCH_3$ | $OCH_3$ | N | |
| $CH_2F$ | H | $OCH_3$ | $N(CH_3)_2$ | N | |
| $CH_2F$ | H | $OCH_3$ | $OCH_2CF_3$ | N | |
| $CH_2F$ | $CH_3$ | $OCH_3$ | $CH_3$ | N | |
| $CH_2F$ | $CH_3$ | $OCH_3$ | $OCH_3$ | N | |
| $CH_2F$ | $CH_3$ | $CH_3$ | $OCH_3$ | CH | |
| $CH_2F$ | $CH_3$ | $OCH_3$ | $OCH_3$ | CH | |
| $CH_2F$ | H | Br | $OCH_3$ | CH | |
| $CH_2F$ | $CH_3$ | $OCH_3$ | $N(CH_3)_2$ | N | |
| $CH_2F$ | H | $CH_3$ | $OCH_2CF_3$ | N | |
| $CH_2F$ | H | $CH_3$ | $OCH_2CF_3$ | CH | |
| $CH_2F$ | H | $OCH_3$ | $OCH_2CF_3$ | CH | |
| $CH_2F$ | H | $OCH_3$ | $C_2H_5$ | CH | |
| $CH_2F$ | H | $OCH_3$ | $C_2H_5$ | N | |
| $CH_2F$ | H | $OCH_3$ | $NHCH_3$ | CH | |
| $CH_2F$ | H | $OCH_3$ | $NHCH_3$ | N | |
| $CH_2F$ | H | $CH_3$ | $OC_2H_5$ | CH | |
| $CH_2F$ | H | $OCH_3$ | $OC_2H_5$ | CH | |
| $CH_2F$ | H | $CH_3$ | $OC_2H_5$ | N | |
| $CH_2F$ | H | $OCH_3$ | $OC_2H_5$ | N | |
| $CH_2F$ | H | $CH_3$ | $OCH_2CHF_2$ | CH | |
| $CH_2F$ | H | $OCH_3$ | $OCH_2CHF_2$ | CH | |
| $CH_2F$ | H | $CH_3$ | $OCH_2CHF_2$ | N | |
| $CH_2F$ | H | $OCH_3$ | $OCH_2CHF_2$ | N | |
| $CH_2F$ | H | $CH_3$ | $OCH_2CH_2F$ | CH | |
| $CH_2F$ | H | $OCH_3$ | $OCH_2CH_2F$ | CH | |
| $CH_2F$ | H | $CH_3$ | $OCH_2CH_2F$ | N | |
| $CH_2F$ | $CH_3$ | $OCH_3$ | $OCH_2CH_2F$ | N | |
| $CH_2F$ | $CH_3$ | Cl | $OCH_3$ | CH | |
| $CH_2F$ | H | Cl | $N(CH_3)_2$ | CH | |
| $CH_2F$ | H | Cl | $OC_2H_5$ | CH | |
| $CHF_2$ | H | $CH_3$ | $CH_3$ | CH | |
| $CHF_2$ | H | $OCH_3$ | $CH_3$ | CH | |
| $CHF_2$ | H | $OCH_3$ | $OCH_3$ | CH | |
| $CHF_2$ | H | Cl | $OCH_3$ | CH | |
| $CHF_2$ | H | $OCH_3$ | $N(CH_3)_2$ | CH | |
| $CHF_2$ | H | $CH_3$ | $CH_3$ | N | |
| $CHF_2$ | H | $OCH_3$ | $CH_3$ | N | |
| $CHF_2$ | H | $OCH_3$ | $OCH_3$ | N | |
| $CHF_2$ | H | $OCH_3$ | $N(CH_3)_2$ | N | |
| $CHF_2$ | H | $OCH_3$ | $OCH_2CF_3$ | N | |
| $CHF_2$ | $CH_3$ | $OCH_3$ | $CH_3$ | N | |
| $CHF_2$ | $CH_3$ | $OCH_3$ | $OCH_3$ | N | |
| $CHF_2$ | $CH_3$ | $CH_3$ | $OCH_3$ | CH | |
| $CHF_2$ | $CH_3$ | $OCH_3$ | $OCH_3$ | CH | |
| $CHF_2$ | H | Br | $OCH_3$ | CH | |
| $CHF_2$ | $CH_3$ | $OCH_3$ | $N(CH_3)_2$ | N | |
| $CHF_2$ | H | $CH_3$ | $OCH_2CF_3$ | N | |
| $CHF_2$ | H | $CH_3$ | $OCH_2CF_3$ | CH | |
| $CHF_2$ | H | $OCH_3$ | $OCH_2CF_3$ | CH | |
| $CHF_2$ | H | $OCH_3$ | $C_2H_5$ | CH | |
| $CHF_2$ | H | $OCH_3$ | $C_2H_5$ | N | |
| $CHF_2$ | H | $OCH_3$ | $NHCH_3$ | CH | |
| $CHF_2$ | H | $OCH_3$ | $NHCH_3$ | N | |
| $CHF_2$ | H | $CH_3$ | $OC_2H_5$ | CH | |
| $CHF_2$ | H | $OCH_3$ | $OC_2H_5$ | CH | |
| $CHF_2$ | H | $CH_3$ | $OC_2H_5$ | N | |
| $CHF_2$ | H | $OCH_3$ | $OC_2H_5$ | N | |
| $CHF_2$ | H | $CH_3$ | $OCH_2CHF_2$ | CH | |
| $CHF_2$ | H | $OCH_3$ | $OCH_2CHF_2$ | CH | |
| $CHF_2$ | H | $CH_3$ | $OCH_2CHF_2$ | N | |

TABLE Ic-continued

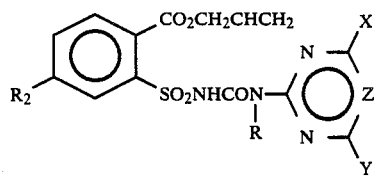

| R$_2$ | R | X | Y | Z | m.p. (°C.) |
|---|---|---|---|---|---|
| CHF$_2$ | H | OCH$_3$ | OCH$_2$CHF$_2$ | N | |
| CHF$_2$ | H | CH$_3$ | OCH$_2$CH$_2$F | CH | |
| CHF$_2$ | H | OCH$_3$ | OCH$_2$CH$_2$F | CH | |
| CHF$_2$ | H | CH$_3$ | OCH$_2$CH$_2$F | N | |
| CHF$_2$ | CH$_3$ | OCH$_3$ | OCH$_2$CH$_2$F | N | |
| CHF$_2$ | CH$_3$ | Cl | OCH$_3$ | CH | |
| CHF$_2$ | H | Cl | N(CH$_3$)$_2$ | CH | |
| CHF$_2$ | H | Cl | OC$_2$H$_5$ | CH | |
| CH$_2$OCH$_3$ | H | CH$_3$ | CH$_3$ | CH | |
| CH$_2$OCH$_3$ | H | OCH$_3$ | CH$_3$ | CH | |
| CH$_2$OCH$_3$ | H | OCH$_3$ | OCH$_3$ | CH | |
| CH$_2$OCH$_3$ | H | Cl | OCH$_3$ | CH | |
| CH$_2$OCH$_3$ | H | OCH$_3$ | N(CH$_3$)$_2$ | CH | |
| CH$_2$OCH$_3$ | H | CH$_3$ | CH$_3$ | N | |
| CH$_2$OCH$_3$ | H | OCH$_3$ | CH$_3$ | N | |
| CH$_2$OCH$_3$ | H | OCH$_3$ | OCH$_3$ | N | |
| CH$_2$OCH$_3$ | H | OCH$_3$ | N(CH$_3$)$_2$ | N | |
| CH$_2$OCH$_3$ | H | OCH$_3$ | OCH$_2$CF$_3$ | N | |
| CH$_2$OCH$_3$ | CH$_3$ | OCH$_3$ | CH$_3$ | N | |
| CH$_2$OCH$_3$ | CH$_3$ | OCH$_3$ | OCH$_3$ | N | |
| CH$_2$OCH$_3$ | CH$_3$ | CH$_3$ | OCH$_3$ | CH | |
| CH$_2$OCH$_3$ | CH$_3$ | OCH$_3$ | OCH$_3$ | CH | |
| CH$_2$OCH$_3$ | H | Br | OCH$_3$ | CH | |
| CH$_2$OCH$_3$ | H | OCH$_3$ | N(CH$_3$)$_2$ | CH | |
| CH$_2$OCH$_3$ | CH$_3$ | OCH$_3$ | N(CH$_3$)$_2$ | N | |
| CH$_2$OCH$_3$ | H | CH$_3$ | OCH$_2$CF$_3$ | N | |
| CH$_2$OCH$_3$ | H | CH$_3$ | OCH$_2$CF$_3$ | CH | |
| CH$_2$OCH$_3$ | H | OCH$_3$ | OCH$_2$CF$_3$ | CH | |
| CH$_2$OCH$_3$ | H | OCH$_3$ | C$_2$H$_5$ | CH | |
| CH$_2$OCH$_3$ | H | OCH$_3$ | C$_2$H$_5$ | N | |
| CH$_2$OCH$_3$ | H | OCH$_3$ | NHCH$_3$ | CH | |
| CH$_2$OCH$_3$ | H | OCH$_3$ | NHCH$_3$ | N | |
| CH$_2$OCH$_3$ | H | CH$_3$ | OC$_2$H$_5$ | CH | |
| CH$_2$OCH$_3$ | H | OCH$_3$ | OC$_2$H$_5$ | CH | |
| CH$_2$OCH$_3$ | H | CH$_3$ | OC$_2$H$_5$ | N | |
| CH$_2$OCH$_3$ | H | OCH$_3$ | OC$_2$H$_5$ | N | |
| CH$_2$OCH$_3$ | H | CH$_3$ | OCH$_2$CHF$_2$ | CH | |
| CH$_2$OCH$_3$ | H | OCH$_3$ | OCH$_2$CHF$_2$ | CH | |
| CH$_2$OCH$_3$ | H | CH$_3$ | OCH$_2$CHF$_2$ | N | |
| CH$_2$OCH$_3$ | H | OCH$_3$ | OCH$_2$CHF$_2$ | N | |
| CH$_2$OCH$_3$ | H | CH$_3$ | OCH$_2$CH$_2$F | CH | |
| CH$_2$OCH$_3$ | H | OCH$_3$ | OCH$_2$CH$_2$F | CH | |
| CH$_2$OCH$_3$ | H | CH$_3$ | OCH$_2$CF$_3$ | N | |
| CH$_2$OCH$_3$ | CH$_3$ | OCH$_3$ | OCH$_2$CF$_3$ | N | |
| CH$_2$OCH$_3$ | CH$_3$ | Cl | OCH$_3$ | CH | |
| CH$_2$OCH$_3$ | H | Cl | N(CH$_3$)$_2$ | CH | |
| CH$_2$OCH$_3$ | H | Cl | OC$_2$H$_5$ | CH | |
| CH$_2$SCH$_3$ | H | CH$_3$ | CH$_3$ | CH | |
| CH$_2$SCH$_3$ | H | OCH$_3$ | CH$_3$ | CH | |
| CH$_2$SCH$_3$ | H | OCH$_3$ | OCH$_3$ | CH | |
| CH$_2$SCH$_3$ | H | Cl | OCH$_3$ | CH | |
| CH$_2$SCH$_3$ | H | OCH$_3$ | N(CH$_3$)$_2$ | CH | |
| CH$_2$SCH$_3$ | H | CH$_3$ | CH$_3$ | N | |
| CH$_2$SCH$_3$ | H | OCH$_3$ | CH$_3$ | N | |
| CH$_2$SCH$_3$ | H | OCH$_3$ | OCH$_3$ | N | |
| CH$_2$SCH$_3$ | H | OCH$_3$ | N(CH$_3$)$_2$ | N | |
| CH$_2$SCH$_3$ | H | OCH$_3$ | OCH$_2$CF$_3$ | N | |
| CH$_2$SCH$_3$ | CH$_3$ | OCH$_3$ | CH$_3$ | N | |
| CH$_2$SCH$_3$ | CH$_3$ | OCH$_3$ | OCH$_3$ | N | |
| CH$_2$SCH$_3$ | CH$_3$ | CH$_3$ | OCH$_3$ | CH | |
| CH$_2$SCH$_3$ | CH$_3$ | OCH$_3$ | OCH$_3$ | CH | |
| CH$_2$SCH$_3$ | H | Br | OCH$_3$ | CH | |
| CH$_2$SCH$_3$ | CH$_3$ | OCH$_3$ | N(CH$_3$)$_2$ | N | |
| CH$_2$SCH$_3$ | H | CH$_3$ | OCH$_2$CF$_3$ | N | |
| CH$_2$SCH$_3$ | H | CH$_3$ | OCH$_2$CF$_3$ | CH | |
| CH$_2$SCH$_3$ | H | OCH$_3$ | OCH$_2$CF$_3$ | CH | |
| CH$_2$SCH$_3$ | H | OCH$_3$ | C$_2$H$_5$ | CH | |
| CH$_2$SCH$_3$ | H | OCH$_3$ | C$_2$H$_5$ | N | |
| CH$_2$SCH$_3$ | H | OCH$_3$ | NHCH$_3$ | CH | |
| CH$_2$SCH$_3$ | H | OCH$_3$ | NHCH$_3$ | N | |

TABLE Ic-continued

| R₂ | R | X | Y | Z | m.p. (°C.) |
|---|---|---|---|---|---|
| CH₂SCH₃ | H | CH₃ | OC₂H₅ | CH | |
| CH₂SCH₃ | H | OCH₃ | OC₂H₅ | CH | |
| CH₂SCH₃ | H | CH₃ | OC₂H₅ | N | |
| CH₂SCH₃ | H | OCH₃ | OC₂H₅ | N | |
| CH₂SCH₃ | H | CH₃ | OCH₂CHF₂ | CH | |
| CH₂SCH₃ | H | OCH₃ | OCH₂CHF₂ | CH | |
| CH₂SCH₃ | H | CH₃ | OCH₂CHF₂ | N | |
| CH₂SCH₃ | H | OCH₃ | OCH₂CHF₂ | N | |
| CH₂SCH₃ | H | CH₃ | OCH₂CH₂F | CH | |
| CH₂SCH₃ | H | OCH₃ | OCH₂CH₂F | CH | |
| CH₂SCH₃ | H | CH₃ | OCH₂CH₂F | N | |
| CH₂SCH₃ | CH₃ | OCH₃ | OCH₂CH₂F | N | |
| CH₂SCH₃ | CH₃ | Cl | OCH₃ | CH | |
| CH₂SCH₃ | H | Cl | N(CH₃)₂ | CH | |
| CH₂SCH₃ | H | Cl | OC₂H₅ | CH | |
| OCF₂H | H | CH₃ | CH₃ | CH | |
| OCF₂H | H | OCH₃ | CH₃ | CH | |
| OCF₂H | H | OCH₃ | OCH₃ | CH | |
| OCF₂H | H | Cl | OCH₃ | CH | |
| OCF₂H | H | OCH₃ | N(CH₃)₂ | CH | |
| OCF₂H | H | CH₃ | CH₃ | N | |
| OCF₂H | H | OCH₃ | CH₃ | N | |
| OCF₂H | H | OCH₃ | OCH₃ | N | |
| OCF₂H | H | OCH₃ | N(CH₃)₂ | N | |
| OCF₂H | H | OCH₃ | OCH₂CF₃ | N | |
| OCF₂H | CH₃ | OCH₃ | CH₃ | N | |
| OCF₂H | CH₃ | OCH₃ | OCH₃ | N | |
| OCF₂H | CH₃ | CH₃ | OCH₃ | CH | |
| OCF₂H | CH₃ | OCH₃ | OCH₃ | CH | |
| OCF₂H | H | Br | OCH₃ | CH | |
| OCF₂H | CH₃ | OCH₃ | N(CH₃)₂ | N | |
| OCF₂H | H | CH₃ | OCH₂CF₃ | N | |
| OCF₂H | H | CH₃ | OCH₂CF₃ | CH | |
| OCF₂H | H | OCH₃ | OCH₂CF₃ | CH | |
| OCF₂H | H | OCH₃ | C₂H₅ | CH | |
| OCF₂H | H | OCH₃ | C₂H₅ | N | |
| OCF₂H | H | OCH₃ | NHCH₃ | CH | |
| OCF₂H | H | OCH₃ | NHCH₃ | N | |
| OCF₂H | H | CH₃ | OC₂H₅ | CH | |
| OCF₂H | H | OCH₃ | OC₂H₅ | CH | |
| OCF₂H | H | CH₃ | OC₂H₅ | N | |
| OCF₂H | H | OCH₃ | OC₂H₅ | N | |
| OCF₂H | H | CH₃ | OCH₂CHF₂ | CH | |
| OCF₂H | H | OCH₃ | OCH₂CHF₂ | CH | |
| OCF₂H | H | CH₃ | OCH₂CHF₂ | N | |
| OCF₂H | H | OCH₃ | OCH₂CHF₂ | N | |
| OCF₂H | H | CH₃ | OCH₂CH₂F | CH | |
| OCF₂H | H | OCH₃ | OCH₂CH₂F | CH | |
| OCF₂H | H | CH₃ | OCH₂CH₂F | N | |
| OCF₂H | CH₃ | OCH₃ | OCH₂CH₂F | N | |
| OCF₂H | CH₃ | Cl | OCH₃ | CH | |
| OCF₂H | H | Cl | N(CH₃)₂ | CH | |
| OCF₂H | H | Cl | OC₂H₅ | CH | |
| OCH₂CH₂F | H | CH₃ | CH₃ | CH | |
| OCH₂CH₂F | H | OCH₃ | CH₃ | CH | |
| OCH₂CH₂F | H | OCH₃ | OCH₃ | CH | |
| OCH₂CH₂F | H | Cl | OCH₃ | CH | |
| OCH₂CH₂F | H | OCH₃ | N(CH₃)₂ | CH | |
| OCH₂CH₂F | H | CH₃ | CH₃ | N | |
| OCH₂CH₂F | H | OCH₃ | CH₃ | N | |
| OCH₂CH₂F | H | OCH₃ | OCH₃ | N | |
| OCH₂CH₂F | H | OCH₃ | N(CH₃)₂ | N | |
| OCH₂CH₂F | H | OCH₃ | OCH₂CF₃ | N | |
| OCH₂CH₂F | CH₃ | OCH₃ | CH₃ | N | |
| OCH₂CH₂F | CH₃ | OCH₃ | OCH₃ | N | |
| OCH₂CH₂F | CH₃ | CH₃ | OCH₃ | CH | |
| OCH₂CH₂F | CH₃ | OCH₃ | OCH₃ | CH | |
| OCH₂CH₂F | H | Br | OCH₃ | CH | |
| OCH₂CH₂F | CH₃ | OCH₃ | N(CH₃)₂ | N | |
| OCH₂CH₂F | H | CH₃ | OCH₂CF₃ | N | |

TABLE Ic-continued

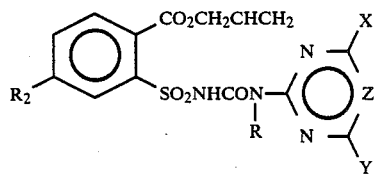

| R₂ | R | X | Y | Z | m.p. (°C.) |
|---|---|---|---|---|---|
| OCH₂CH₂F | H | CH₃ | OCH₂CF₃ | CH | |
| OCH₂CH₂F | H | OCH₃ | OCH₂CF₃ | CH | |
| OCH₂CH₂F | H | OCH₃ | C₂H₅ | CH | |
| OCH₂CH₂F | H | OCH₃ | C₂H₅ | N | |
| OCH₂CH₂F | H | OCH₃ | NHCH₃ | CH | |
| OCH₂CH₂F | H | OCH₃ | NHCH₃ | N | |
| OCH₂CH₂F | H | CH₃ | OC₂H₅ | CH | |
| OCH₂CH₂F | H | OCH₃ | OC₂H₅ | CH | |
| OCH₂CH₂F | H | CH₃ | OC₂H₅ | N | |
| OCH₂CH₂F | H | OCH₃ | OC₂H₅ | N | |
| OCH₂CH₂F | H | CH₃ | OCH₂CHF₂ | CH | |
| OCH₂CH₂F | H | OCH₃ | OCH₂CHF₂ | CH | |
| OCH₂CH₂F | H | CH₃ | OCH₂CHF₂ | N | |
| OCH₂CH₂F | H | OCH₃ | OCH₂CHF₂ | N | |
| OCH₂CH₂F | H | CH₃ | OCH₂CH₂F | CH | |
| OCH₂CH₂F | H | OCH₃ | OCH₂CH₂F | CH | |
| OCH₂CH₂F | H | CH₃ | OCH₂CH₂F | N | |
| OCH₂CH₂F | CH₃ | OCH₃ | OCH₂CH₂F | N | |
| OCH₂CH₂F | CH₃ | Cl | OCH₃ | CH | |
| OCH₂CH₂F | H | Cl | N(CH₃)₂ | CH | |
| OCH₂CH₂F | H | Cl | OC₂H₅ | CH | |
| OCH₂CF₃ | H | CH₃ | CH₃ | CH | |
| OCH₂CF₃ | H | OCH₃ | CH₃ | CH | |
| OCH₂CF₃ | H | OCH₃ | OCH₃ | CH | |
| OCH₂CF₃ | H | Cl | OCH₃ | CH | |
| OCH₂CF₃ | H | OCH₃ | N(CH₃)₂ | CH | |
| OCH₂CF₃ | H | CH₃ | CH₃ | N | |
| OCH₂CF₃ | H | OCH₃ | CH₃ | N | |
| OCH₂CF₃ | H | OCH₃ | OCH₃ | N | |
| OCH₂CF₃ | H | OCH₃ | N(CH₃)₂ | N | |
| OCH₂CF₃ | H | OCH₃ | OCH₂CF₃ | N | |
| OCH₂CF₃ | H | OC₂H₅ | NHCH₃ | N | |
| OCH₂CF₃ | CH₃ | OCH₃ | CH₃ | N | |
| OCH₂CF₃ | CH₃ | OCH₃ | OCH₃ | N | |
| OCH₂CF₃ | CH₃ | CH₃ | OCH₃ | CH | |
| OCH₂CF₃ | CH₃ | OCH₃ | OCH₃ | CH | |
| OCH₂CF₃ | H | Br | OCH₃ | CH | |
| OCH₂CF₃ | CH₃ | OCH₃ | N(CH₃)₂ | N | |
| OCH₂CF₃ | H | CH₃ | OCH₂CF₃ | N | |
| OCH₂CF₃ | H | CH₃ | OCH₂CF₃ | CH | |
| OCH₂CF₃ | H | OCH₃ | OCH₂CF₃ | CH | |
| OCH₂CF₃ | H | OCH₃ | C₂H₅ | CH | |
| OCH₂CF₃ | H | OCH₃ | C₂H₅ | N | |
| OCH₂CF₃ | H | OCH₃ | NHCH₃ | CH | |
| OCH₂CF₃ | H | OCH₃ | NHCH₃ | N | |
| OCH₂CF₃ | H | CH₃ | OC₂H₅ | CH | |
| OCH₂CF₃ | H | OCH₃ | OC₂H₅ | CH | |
| OCH₂CF₃ | H | CH₃ | OC₂H₅ | N | |
| OCH₂CF₃ | H | OCH₃ | OC₂H₅ | N | |
| OCH₂CF₃ | H | CH₃ | OCH₂CHF₂ | CH | |
| OCH₂CF₃ | H | OCH₃ | OCH₂CHF₂ | CH | |
| OCH₂CF₃ | H | CH₃ | OCH₂CHF₂ | N | |
| OCH₂CF₃ | H | OCH₃ | OCH₂CHF₂ | N | |
| OCH₂CF₃ | H | CH₃ | OCH₂CH₂F | CH | |
| OCH₂CF₃ | H | OCH₃ | OCH₂CH₂F | CH | |
| OCH₂CF₃ | H | CH₃ | OCH₂CH₂F | N | |
| OCH₂CF₃ | CH₃ | OCH₃ | OCH₂CH₂F | N | |
| OCH₂CF₃ | CH₃ | Cl | OCH₃ | CH | |
| OCH₂CF₃ | H | Cl | N(CH₃)₂ | CH | |
| OCH₂CF₃ | H | Cl | OC₂H₅ | CH | |
| OCH₂CH₂OCH₃ | H | CH₃ | CH₃ | CH | |
| OCH₂CH₂OCH₃ | H | OCH₃ | CH₃ | CH | |
| OCH₂CH₂OCH₃ | H | OCH₃ | OCH₃ | CH | |
| OCH₂CH₂OCH₃ | H | Cl | OCH₃ | CH | |
| OCH₂CH₂OCH₃ | H | OCH₃ | N(CH₃)₂ | CH | |
| OCH₂CH₂OCH₃ | H | CH₃ | CH₃ | N | |
| OCH₂CH₂OCH₃ | H | OCH₃ | CH₃ | N | |
| OCH₂CH₂OCH₃ | H | OCH₃ | OCH₃ | N | |
| OCH₂CH₂OCH₃ | H | OCH₃ | N(CH₃)₂ | N | |
| OCH₂CH₂OCH₃ | H | OCH₃ | OCH₂CF₃ | N | |

TABLE Ic-continued

[Structure: benzene ring with CO₂CH₂CHCH₂ group, R₂ substituent, SO₂NHCON(R)- linked to a triazine/pyrimidine ring with substituents X, Y, Z and N positions]

| R₂ | R | X | Y | Z | m.p. (°C.) |
|---|---|---|---|---|---|
| OCH₂CH₂OCH₃ | CH₃ | OCH₃ | CH₃ | N | |
| OCH₂CH₂OCH₃ | CH₃ | OCH₃ | OCH₃ | N | |
| OCH₂CH₂OCH₃ | CH₃ | CH₃ | OCH₃ | CH | |
| OCH₂CH₂OCH₃ | CH₃ | OCH₃ | OCH₃ | CH | |
| OCH₂CH₂OCH₃ | H | Br | OCH₃ | CH | |
| OCH₂CH₂OCH₃ | H | CH₃ | OCH₂CF₃ | N | |
| OCH₂CH₂OCH₃ | H | CH₃ | OCH₂CF₃ | CH | |
| OCH₂CH₂OCH₃ | H | OCH₃ | OCH₂CF₃ | CH | |
| OCH₂CH₂OCH₃ | H | OCH₃ | C₂H₅ | CH | |
| OCH₂CH₂OCH₃ | H | OCH₃ | C₂H₅ | N | |
| OCH₂CH₂OCH₃ | H | OCH₃ | NHCH₃ | CH | |
| OCH₂CH₂OCH₃ | H | OCH₃ | NHCH₃ | N | |
| OCH₂CH₂OCH₃ | H | CH₃ | OC₂H₅ | CH | |
| OCH₂CH₂OCH₃ | H | OCH₃ | OC₂H₅ | CH | |
| OCH₂CH₂OCH₃ | H | CH₃ | OC₂H₅ | N | |
| OCH₂CH₂OCH₃ | H | OCH₃ | OC₂H₅ | N | |
| OCH₂CH₂OCH₃ | H | CH₃ | OCH₂CHF₂ | CH | |
| OCH₂CH₂OCH₃ | H | OCH₃ | OCH₂CHF₂ | CH | |
| OCH₂CH₂OCH₃ | H | CH₃ | OCH₂CHF₂ | N | |
| OCH₂CH₂OCH₃ | H | OCH₃ | OCH₂CHF₂ | N | |
| OCH₂CH₂OCH₃ | H | CH₃ | OCH₂CH₂F | CH | |
| OCH₂CH₂OCH₃ | H | OCH₃ | OCH₂CH₂F | CH | |
| OCH₂CH₂OCH₃ | H | CH₃ | OCH₂CF₃ | N | |
| OCH₂CH₂OCH₃ | CH₃ | OCH₃ | OCH₂CF₃ | N | |
| OCH₂CH₂OCH₃ | CH₃ | Cl | OCH₃ | CH | |
| OCH₂CH₂OCH₃ | H | Cl | N(CH₃)₂ | CH | |
| OCH₂CH₂OCH₃ | H | Cl | OC₂H₅ | CH | |
| O-cyclopropyl | H | CH₃ | CH₃ | CH | |
| O-cyclopropyl | H | OCH₃ | CH₃ | CH | |
| O-cyclopropyl | H | OCH₃ | OCH₃ | CH | |
| O-cyclopropyl | H | Cl | OCH₃ | CH | |
| O-cyclopropyl | H | OCH₃ | N(CH₃)₂ | CH | |
| O-cyclopropyl | H | CH₃ | CH₃ | N | |
| O-cyclopropyl | H | OCH₃ | CH₃ | N | |
| O-cyclopropyl | H | OCH₃ | OCH₃ | N | |
| O-cyclopropyl | H | OCH₃ | N(CH₃)₂ | N | |
| O-cyclopropyl | H | OCH₃ | OCH₂CF₃ | N | |
| O-cyclopropyl | CH₃ | OCH₃ | CH₃ | N | |
| O-cyclopropyl | CH₃ | OCH₃ | OCH₃ | N | |
| O-cyclopropyl | CH₃ | CH₃ | OCH₃ | CH | |
| O-cyclopropyl | CH₃ | OCH₃ | OCH₃ | CH | |
| O-cyclopropyl | H | Br | OCH₃ | CH | |
| O-cyclopropyl | CH₃ | OCH₃ | N(CH₃)₂ | N | |
| O-cyclopropyl | H | CH₃ | OCH₂CF₃ | N | |
| O-cyclopropyl | H | CH₃ | OCH₂CF₃ | CH | |
| O-cyclopropyl | H | OCH₃ | OCH₂CF₃ | CH | |
| O-cyclopropyl | H | OCH₃ | C₂H₅ | CH | |
| O-cyclopropyl | H | OCH₃ | C₂H₅ | N | |
| O-cyclopropyl | H | OCH₃ | NHCH₃ | CH | |
| O-cyclopropyl | H | OCH₃ | NHCH₃ | N | |
| O-cyclopropyl | H | CH₃ | OC₂H₅ | CH | |
| O-cyclopropyl | H | OCH₃ | OC₂H₅ | CH | |
| O-cyclopropyl | H | CH₃ | OC₂H₅ | N | |
| O-cyclopropyl | H | OCH₃ | OC₂H₅ | N | |
| O-cyclopropyl | H | CH₃ | OCH₂CHF₂ | CH | |
| O-cyclopropyl | H | OCH₃ | OCH₂CHF₂ | CH | |
| O-cyclopropyl | H | CH₃ | OCH₂CHF₂ | N | |
| O-cyclopropyl | H | OCH₃ | OCH₂CHF₂ | N | |
| O-cyclopropyl | H | CH₃ | OCH₂CH₂F | CH | |
| O-cyclopropyl | H | OCH₃ | OCH₂CH₂F | CH | |
| O-cyclopropyl | H | CH₃ | OCH₂CH₂F | N | |
| O-cyclopropyl | CH₃ | OCH₃ | OCH₂CH₂F | N | |
| O-cyclopropyl | CH₃ | Cl | OCH₃ | CH | |
| O-cyclopropyl | H | Cl | N(CH₃)₂ | CH | |
| O-cyclopropyl | H | Cl | OC₂H₅ | CH | |
| OCF₂CF₂H | H | OCH₃ | Cl | CH | |
| OCF₂CF₂H | H | CH₃ | CH₃ | CH | |
| OCF₂CF₂H | H | OCH₃ | OCH₃ | N | |
| S-cyclopropyl | H | OCH₃ | OCH₃ | CH | |
| S-cyclopropyl | H | OCH₃ | CH₃ | CH | |

TABLE Ic-continued

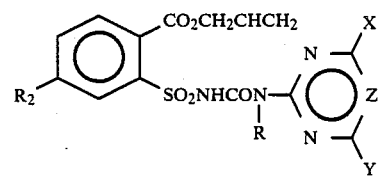

| R2 | R | X | Y | Z | m.p. (°C.) |
|---|---|---|---|---|---|
| S-cyclopropyl | H | OCH$_3$ | Cl | CH | |
| S-cyclopropyl | H | CH$_3$ | CH$_3$ | CH | |
| S-cyclopropyl | H | OCH$_3$ | OCH$_3$ | N | |
| S-cyclopropyl | H | OCH$_3$ | CH$_3$ | N | |
| SCH$_2$-cyclopropyl | H | OCH$_3$ | OCH$_3$ | CH | |
| SCH$_2$-cyclopropyl | H | OCH$_3$ | CH$_3$ | CH | |
| SCH$_2$-cyclopropyl | H | OCH$_3$ | Cl | CH | |
| SCH$_2$-cyclopropyl | H | CH$_3$ | CH$_3$ | CH | |
| SCH$_2$-cyclopropyl | H | OCH$_3$ | OCH$_3$ | N | |
| NHCH$_2$-cyclopropyl | H | OCH$_3$ | OCH$_3$ | CH | |
| NHCH$_2$-cyclopropyl | H | OCH$_3$ | CH$_3$ | CH | |
| NHCH$_2$-cyclopropyl | H | OCH$_3$ | Cl | CH | |
| NHCH$_2$-cyclopropyl | H | CH$_3$ | CH$_3$ | CH | |
| NHCH$_2$-cyclopropyl | H | OCH$_3$ | OCH$_3$ | N | |
| NHCH$_2$-cyclopropyl | H | OCH$_3$ | CH$_3$ | N | |
| NHCH$_2$CF$_2$CF$_3$ | H | OCH$_3$ | OCH$_3$ | CH | |
| NHCH$_2$CF$_2$CF$_3$ | H | OCH$_3$ | CH$_3$ | CH | |
| NHCH$_2$CF$_2$CF$_3$ | H | OCH$_3$ | Cl | CH | |
| NHCH$_2$CF$_2$CF$_3$ | H | CH$_3$ | CH$_3$ | CH | |
| NHCH$_2$CF$_2$CF$_3$ | H | OCH$_3$ | OCH$_3$ | N | |
| NHCH$_2$CF$_2$CF$_3$ | H | OCH$_3$ | CH$_3$ | N | |
| NHCH(CF$_3$)CH$_3$ | H | OCH$_3$ | OCH$_3$ | CH | |
| NHCH(CF$_3$)CH$_3$ | H | OCH$_3$ | CH$_3$ | CH | |
| NHCH$_2$CHF$_2$ | H | OCH$_3$ | CH$_3$ | N | |
| NHCH$_2$CF$_3$ | H | OCH$_3$ | OCH$_3$ | CH | |
| NHCH$_2$CF$_3$ | H | OCH$_3$ | CH$_3$ | CH | |
| NHCH$_2$CF$_3$ | H | OCH$_3$ | Cl | CH | |
| NHCH$_2$CF$_3$ | H | CH$_3$ | CH$_3$ | CH | |
| NHCH$_2$CF$_3$ | H | OCH$_3$ | OCH$_3$ | N | |
| NHCH$_3$ | H | OCH$_3$ | OCH$_3$ | CH | |
| NHCH$_3$ | H | OCH$_3$ | CH$_3$ | CH | |
| NHCH$_3$ | H | OCH$_3$ | Cl | CH | |
| NHCH$_3$ | H | CH$_3$ | CH$_3$ | CH | |
| NHCH$_3$ | H | OCH$_3$ | OCH$_3$ | N | |

TABLE Id

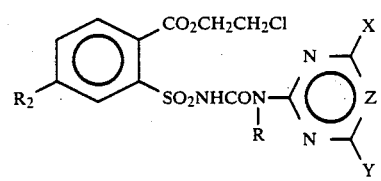

| R2 | R | X | Y | Z | m.p. (°C.) |
|---|---|---|---|---|---|
| OC$_2$H$_5$ | H | CH$_3$ | CH$_3$ | CH | |
| OC$_2$H$_5$ | H | OCH$_3$ | CH$_3$ | CH | |
| OC$_2$H$_5$ | H | OCH$_3$ | OCH$_3$ | CH | |
| OC$_2$H$_5$ | H | Cl | OCH$_3$ | CH | |
| OC$_2$H$_5$ | H | OCH$_3$ | N(CH$_3$)$_2$ | CH | |
| OC$_2$H$_5$ | H | CH$_3$ | CH$_3$ | N | |
| OC$_2$H$_5$ | H | OCH$_3$ | CH$_3$ | N | |
| OC$_2$H$_5$ | H | OCH$_3$ | OCH$_3$ | N | |
| OC$_2$H$_5$ | H | OCH$_3$ | N(CH$_3$)$_2$ | N | |
| OC$_2$H$_5$ | H | OCH$_3$ | OCH$_2$CF$_3$ | N | |
| OC$_2$H$_5$ | CH$_3$ | OCH$_3$ | CH$_3$ | N | |
| OC$_2$H$_5$ | CH$_3$ | OCH$_3$ | OCH$_3$ | N | |
| OC$_2$H$_5$ | CH$_3$ | CH$_3$ | OCH$_3$ | CH | |
| OC$_2$H$_5$ | CH$_3$ | OCH$_3$ | OCH$_3$ | CH | |
| OC$_2$H$_5$ | H | Br | OCH$_3$ | CH | |

TABLE Id-continued

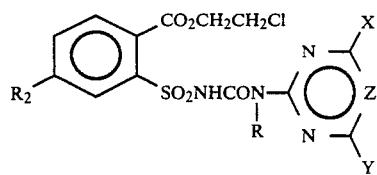

| R₂ | R | X | Y | Z | m.p. (°C.) |
|---|---|---|---|---|---|
| OC₂H₅ | CH₃ | OCH₃ | N(CH₃)₂ | N | |
| OC₂H₅ | H | CH₃ | OCH₂CF₃ | N | |
| OC₂H₅ | H | CH₃ | OCH₂CF₃ | CH | |
| OC₂H₅ | H | OCH₃ | OCH₂CF₃ | CH | |
| OC₂H₅ | H | OCH₃ | C₂H₅ | CH | |
| OC₂H₅ | H | OCH₃ | C₂H₅ | N | |
| OC₂H₅ | H | OCH₃ | NHCH₃ | CH | |
| OC₂H₅ | H | OCH₃ | NHCH₃ | N | |
| OC₂H₅ | H | CH₃ | OC₂H₅ | CH | |
| OC₂H₅ | H | OCH₃ | OC₂H₅ | CH | |
| OC₂H₅ | H | CH₃ | OC₂H₅ | N | |
| OC₂H₅ | H | OCH₃ | OC₂H₅ | N | |
| OC₂H₅ | H | CH₃ | OCH₂CHF₂ | CH | |
| OC₂H₅ | H | OCH₃ | OCH₂CHF₂ | CH | |
| OC₂H₅ | H | CH₃ | OCH₂CHF₂ | N | |
| OC₂H₅ | H | OCH₃ | OCH₂CHF₂ | N | |
| OC₂H₅ | H | CH₃ | OCH₂CH₂F | CH | |
| OC₂H₅ | H | OCH₃ | OCH₂CH₂F | CH | |
| OC₂H₅ | H | CH₃ | OCH₂CH₂F | N | |
| OC₂H₅ | CH₃ | OCH₃ | OCH₂CH₂F | N | |
| OC₂H₅ | CH₃ | Cl | OCH₃ | CH | |
| OC₂H₅ | H | Cl | N(CH₃)₂ | CH | |
| OC₂H₅ | H | Cl | OC₂H₅ | CH | |
| SC₂H₅ | H | CH₃ | CH₃ | CH | |
| SC₂H₅ | H | OCH₃ | CH₃ | CH | |
| SC₂H₅ | H | OCH₃ | OCH₃ | CH | |
| SC₂H₅ | H | Cl | OCH₃ | CH | |
| SC₂H₅ | H | OCH₃ | N(CH₃)₂ | CH | |
| SC₂H₅ | H | CH₃ | CH₃ | N | |
| SC₂H₅ | H | OCH₃ | CH₃ | N | |
| SC₂H₅ | H | OCH₃ | OCH₃ | N | |
| SC₂H₅ | H | OCH₃ | N(CH₃)₂ | N | |
| SC₂H₅ | H | OCH₃ | OCH₂CF₃ | N | |
| SC₂H₅ | CH₃ | OCH₃ | CH₃ | N | |
| SC₂H₅ | CH₃ | OCH₃ | OCH₃ | N | |
| SC₂H₅ | CH₃ | CH₃ | OCH₃ | CH | |
| SC₂H₅ | CH₃ | OCH₃ | OCH₃ | CH | |
| SC₂H₅ | H | Br | OCH₃ | CH | |
| SC₂H₅ | CH₃ | OCH₃ | N(CH₃)₂ | N | |
| SC₂H₅ | H | CH₃ | OCH₂CF₃ | N | |
| SC₂H₅ | H | CH₃ | OCH₂CF₃ | CH | |
| SC₂H₅ | H | OCH₃ | OCH₂CF₃ | CH | |
| SC₂H₅ | H | OCH₃ | C₂H₅ | CH | |
| SC₂H₅ | H | OCH₃ | C₂H₅ | N | |
| SC₂H₅ | H | OCH₃ | NHCH₃ | CH | |
| SC₂H₅ | H | OCH₃ | NHCH₃ | N | |
| SC₂H₅ | H | CH₃ | OC₂H₅ | CH | |
| SC₂H₅ | H | OCH₃ | OC₂H₅ | CH | |
| SC₂H₅ | H | CH₃ | OC₂H₅ | N | |
| SC₂H₅ | H | OCH₃ | OC₂H₅ | N | |
| SC₂H₅ | H | CH₃ | OCH₂CHF₂ | CH | |
| SC₂H₅ | H | OCH₃ | OCH₂CHF₂ | CH | |
| SC₂H₅ | H | CH₃ | OCH₂CHF₂ | N | |
| SC₂H₅ | H | OCH₃ | OCH₂CHF₂ | N | |
| SC₂H₅ | H | CH₃ | OCH₂CH₂F | CH | |
| SC₂H₅ | H | OCH₃ | OCH₂CH₂F | CH | |
| SC₂H₅ | H | CH₃ | OCH₂CH₂F | N | |
| SC₂H₅ | CH₃ | OCH₃ | OCH₂CH₂F | N | |
| SC₂H₅ | CH₃ | Cl | OCH₃ | CH | |
| SC₂H₅ | H | Cl | N(CH₃)₂ | CH | |
| SC₂H₅ | H | Cl | OC₂H₅ | CH | |
| S(CH₂)₅CH₃ | H | CH₃ | CH₃ | CH | |
| S(CH₂)₅CH₃ | H | OCH₃ | CH₃ | CH | |
| S(CH₂)₅CH₃ | H | OCH₃ | OCH₃ | CH | |
| S(CH₂)₅CH₃ | H | Cl | OCH₃ | CH | |
| S(CH₂)₅CH₃ | H | CH₃ | CH₃ | N | |
| S(CH₂)₅CH₃ | H | OCH₃ | CH₃ | N | |
| S(CH₂)₅CH₃ | H | OCH₃ | OCH₃ | N | |
| S(O)(CH₃) | H | CH₃ | CH₃ | CH | |
| S(O)(CH₃) | H | OCH₃ | CH₃ | CH | |

TABLE Id-continued

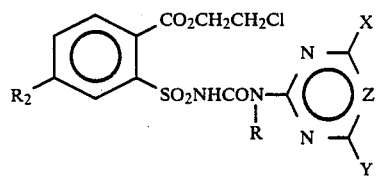

| $R_2$ | R | X | Y | Z | m.p. (°C.) |
|---|---|---|---|---|---|
| $S(O)(CH_3)$ | H | $OCH_3$ | $OCH_3$ | CH | |
| $S(O)(CH_3)$ | H | Cl | $OCH_3$ | CH | |
| $S(O)(CH_3)$ | H | $OCH_3$ | $N(CH_3)_2$ | CH | |
| $S(O)(CH_3)$ | H | $CH_3$ | $CH_3$ | N | |
| $S(O)(CH_3)$ | H | $OCH_3$ | $CH_3$ | N | |
| $S(O)(CH_3)$ | H | $OCH_3$ | $OCH_3$ | N | |
| $S(O)(CH_3)$ | H | $OCH_3$ | $N(CH_3)_2$ | N | |
| $S(O)(CH_3)$ | H | $OCH_3$ | $OCH_2CF_3$ | N | |
| $S(O)(CH_3)$ | $CH_3$ | $OCH_3$ | $CH_3$ | N | |
| $S(O)(CH_3)$ | $CH_3$ | $OCH_3$ | $OCH_3$ | N | |
| $S(O)(CH_3)$ | $CH_3$ | $CH_3$ | $OCH_3$ | CH | |
| $S(O)(CH_3)$ | $CH_3$ | $OCH_3$ | $OCH_3$ | CH | |
| $S(O)(CH_3)$ | H | Br | $OCH_3$ | CH | |
| $S(O)(CH_3)$ | H | $OCH_3$ | $N(CH_3)_2$ | CH | |
| $S(O)(CH_3)$ | $CH_3$ | $OCH_3$ | $N(CH_3)_2$ | N | |
| $S(O)(CH_3)$ | H | $CH_3$ | $OCH_2CF_3$ | N | |
| $S(O)(CH_3)$ | H | $CH_3$ | $OCH_2CF_3$ | CH | |
| $S(O)(CH_3)$ | H | $OCH_3$ | $OCH_2CF_3$ | CH | |
| $S(O)(CH_3)$ | H | $OCH_3$ | $C_2H_5$ | CH | |
| $S(O)(CH_3)$ | H | $OCH_3$ | $C_2H_5$ | N | |
| $S(O)(CH_3)$ | H | $OCH_3$ | $NHCH_3$ | CH | |
| $S(O)(CH_3)$ | H | $OCH_3$ | $NHCH_3$ | N | |
| $S(O)(CH_3)$ | H | $CH_3$ | $OC_2H_5$ | CH | |
| $S(O)(CH_3)$ | H | $OCH_3$ | $OC_2H_5$ | CH | |
| $S(O)(CH_3)$ | H | $CH_3$ | $OC_2H_5$ | N | |
| $S(O)(CH_3)$ | H | $OCH_3$ | $OC_2H_5$ | N | |
| $S(O)(CH_3)$ | H | $CH_3$ | $OCH_2CHF_2$ | CH | |
| $S(O)(CH_3)$ | H | $OCH_3$ | $OCH_2CHF_2$ | CH | |
| $S(O)(CH_3)$ | H | $CH_3$ | $OCH_2CHF_2$ | N | |
| $S(O)(CH_3)$ | H | $OCH_3$ | $OCH_2CHF_2$ | N | |
| $S(O)(CH_3)$ | H | $CH_3$ | $OCH_2CHF_2$ | CH | |
| $S(O)(CH_3)$ | H | $OCH_3$ | $OCH_2CHF_2$ | CH | |
| $S(O)(CH_3)$ | H | $CH_3$ | $OCH_2CHF_2$ | N | |
| $S(O)(CH_3)$ | H | $OCH_3$ | $OCH_2CHF_2$ | N | |
| $S(O)(CH_3)$ | $CH_3$ | Cl | $OCH_3$ | CH | |
| $S(O)(CH_3)$ | H | Cl | $N(CH_3)_2$ | CH | |
| $S(O)(CH_3)$ | H | Cl | $OC_2H_5$ | CH | |
| $OCH_2CH=CH_2$ | H | $CH_3$ | $CH_3$ | CH | |
| $OCH_2CH=CH_2$ | H | $OCH_3$ | $CH_3$ | CH | |
| $OCH_2CH=CH_2$ | H | $OCH_3$ | $OCH_3$ | CH | |
| $OCH_2CH=CH_2$ | H | Cl | $OCH_3$ | CH | |
| $OCH_2CH=CH_2$ | H | $OCH_3$ | $N(CH_3)_2$ | CH | |
| $OCH_2CH=CH_2$ | H | $CH_3$ | $CH_3$ | N | |
| $OCH_2CH=CH_2$ | H | $OCH_3$ | $CH_3$ | N | |
| $OCH_2CH=CH_2$ | H | $OCH_3$ | $OCH_3$ | N | |
| $OCH_2CH=CH_2$ | H | $OCH_3$ | $N(CH_3)_2$ | N | |
| $OCH_2CH=CH_2$ | H | $OCH_3$ | $OCH_2CF_3$ | N | |
| $OCH_2CH=CH_2$ | $CH_3$ | $OCH_3$ | $CH_3$ | N | |
| $OCH_2CH=CH_2$ | $CH_3$ | $OCH_3$ | $OCH_3$ | N | |
| $OCH_2CH=CH_2$ | $CH_3$ | $CH_3$ | $OCH_3$ | CH | |
| $OCH_2CH=CH_2$ | $CH_3$ | $OCH_3$ | $OCH_3$ | CH | |
| $OCH_2CH=CH_2$ | H | Br | $OCH_3$ | CH | |
| $OCH_2CH=CH_2$ | $CH_3$ | $OCH_3$ | $N(CH_3)_2$ | N | |
| $OCH_2CH=CH_2$ | H | $CH_3$ | $OCH_2CF_3$ | N | |
| $OCH_2CH=CH_2$ | H | $CH_3$ | $OCH_2CF_3$ | CH | |
| $OCH_2CH=CH_2$ | H | $OCH_3$ | $OCH_2CF_3$ | CH | |
| $OCH_2CH=CH_2$ | H | $OCH_3$ | $C_2H_5$ | CH | |
| $OCH_2CH=CH_2$ | H | $OCH_3$ | $C_2H_5$ | N | |
| $OCH_2CH=CH_2$ | H | $OCH_3$ | $NHCH_3$ | CH | |
| $OCH_2CH=CH_2$ | H | $OCH_3$ | $NHCH_3$ | N | |
| $OCH_2CH=CH_2$ | H | $CH_3$ | $OC_2H_5$ | CH | |
| $OCH_2CH=CH_2$ | H | $OCH_3$ | $OC_2H_5$ | CH | |
| $OCH_2CH=CH_2$ | H | $CH_3$ | $OC_2H_5$ | N | |
| $OCH_2CH=CH_2$ | H | $OCH_3$ | $OC_2H_5$ | N | |
| $OCH_2CH=CH_2$ | H | $CH_3$ | $OCH_2CHF_2$ | CH | |
| $OCH_2CH=CH_2$ | H | $OCH_3$ | $OCH_2CHF_2$ | CH | |
| $OCH_2CH=CH_2$ | H | $CH_3$ | $OCH_2CHF_2$ | N | |
| $OCH_2CH=CH_2$ | H | $OCH_3$ | $OCH_2CHF_2$ | N | |
| $OCH_2CH=CH_2$ | H | $CH_3$ | $OCH_2CH_2F$ | CH | |
| $OCH_2CH=CH_2$ | H | $OCH_3$ | $OCH_2CH_2F$ | CH | |

TABLE Id-continued

| R₂ | R | X | Y | Z | m.p. (°C.) |
|---|---|---|---|---|---|
| OCH₂CH=CH₂ | H | CH₃ | OCH₂CH₂F | N | |
| OCH₂CH=CH₂ | CH₃ | OCH₃ | OCH₂CH₂F | N | |
| OCH₂CH=CH₂ | CH₃ | Cl | OCH₃ | CH | |
| OCH₂CH=CH₂ | H | Cl | N(CH₃)₂ | CH | |
| OCH₂CH=CH₂ | H | Cl | OC₂H₅ | CH | |
| OCH₂C≡CH | H | CH₃ | CH₃ | CH | |
| OCH₂C≡CH | H | OCH₃ | CH₃ | CH | |
| OCH₂C≡CH | H | OCH₃ | OCH₃ | CH | |
| OCH₂C≡CH | H | Cl | OCH₃ | CH | |
| OCH₂C≡CH | H | OCH₃ | N(CH₃)₂ | CH | |
| OCH₂C≡CH | H | CH₃ | CH₃ | N | |
| OCH₂C≡CH | H | OCH₃ | CH₃ | N | |
| OCH₂C≡CH | H | OCH₃ | OCH₃ | N | |
| OCH₂C≡CH | H | OCH₃ | N(CH₃)₂ | N | |
| OCH₂C≡CH | H | OCH₃ | OCH₂CF₃ | N | |
| OCH₂C≡CH | CH₃ | OCH₃ | CH₃ | N | |
| OCH₂C≡CH | CH₃ | OCH₃ | OCH₃ | N | |
| OCH₂C≡CH | CH₃ | CH₃ | OCH₃ | CH | |
| OCH₂C≡CH | CH₃ | OCH₃ | OCH₃ | CH | |
| OCH₂C≡CH | H | Br | OCH₃ | CH | |
| OCH₂C≡CH | CH₃ | OCH₃ | N(CH₃)₂ | N | |
| OCH₂C≡CH | H | CH₃ | OCH₂CF₃ | N | |
| OCH₂C≡CH | H | CH₃ | OCH₂CF₃ | CH | |
| OCH₂C≡CH | H | OCH₃ | OCH₂CF₃ | CH | |
| OCH₂C≡CH | H | OCH₃ | C₂H₅ | CH | |
| OCH₂C≡CH | H | OCH₃ | C₂H₅ | N | |
| OCH₂C≡CH | H | OCH₃ | NHCH₃ | CH | |
| OCH₂C≡CH | H | OCH₃ | NHCH₃ | N | |
| OCH₂C≡CH | H | CH₃ | OC₂H₅ | CH | |
| OCH₂C≡CH | H | OCH₃ | OC₂H₅ | CH | |
| OCH₂C≡CH | H | CH₃ | OC₂H₅ | N | |
| OCH₂C≡CH | H | OCH₃ | OC₂H₅ | N | |
| OCH₂C≡CH | H | CH₃ | OCH₂CHF₂ | CH | |
| OCH₂C≡CH | H | OCH₃ | OCH₂CHF₂ | CH | |
| OCH₂C≡CH | H | CH₃ | OCH₂CHF₂ | N | |
| OCH₂C≡CH | H | OCH₃ | OCH₂CHF₂ | N | |
| OCH₂C≡CH | H | CH₃ | OCH₂CH₂F | CH | |
| OCH₂C≡CH | H | OCH₃ | OCH₂CH₂F | CH | |
| OCH₂C≡CH | H | CH₃ | OCH₂CF₃ | N | |
| OCH₂C≡CH | CH₃ | OCH₃ | OCH₂CF₃ | N | |
| OCH₂C≡CH | CH₃ | Cl | OCH₃ | CH | |
| OCH₂C≡CH | H | Cl | N(CH₃)₂ | CH | |
| OCH₂C≡CH | H | Cl | OC₂H₅ | CH | |
| SCH₂CH=CH₂ | H | CH₃ | CH₃ | CH | |
| SCH₂CH=CH₂ | H | OCH₃ | CH₃ | CH | |
| SCH₂CH=CH₂ | H | OCH₃ | OCH₃ | CH | |
| SCH₂CH=CH₂ | H | Cl | OCH₃ | CH | |
| SCH₂CH=CH₂ | H | OCH₃ | N(CH₃)₂ | N | |
| SCH₂CH=CH₂ | H | CH₃ | CH₃ | N | |
| SCH₂CH=CH₂ | H | OCH₃ | CH₃ | N | |
| SCH₂CH=CH₂ | H | OCH₃ | OCH₃ | N | |
| SCH₂CH=CH₂ | H | OCH₃ | N(CH₃)₂ | N | |
| SCH₂CH=CH₂ | H | OCH₃ | OCH₂CF₃ | N | |
| SCH₂CH=CH₂ | CH₃ | OCH₃ | CH₃ | N | |
| SCH₂CH=CH₂ | CH₃ | OCH₃ | OCH₃ | N | |
| SCH₂CH=CH₂ | CH₃ | CH₃ | OCH₃ | CH | |
| SCH₂CH=CH₂ | CH₃ | OCH₃ | OCH₃ | CH | |
| SCH₂CH=CH₂ | H | Br | OCH₃ | CH | |
| SCH₂CH=CH₂ | CH₃ | OCH₃ | N(CH₃)₂ | N | |
| SCH₂CH=CH₂ | H | CH₃ | OCH₂CF₃ | N | |
| SCH₂CH=CH₂ | H | CH₃ | OCH₂CF₃ | CH | |
| SCH₂CH=CH₂ | H | OCH₃ | OCH₂CF₃ | CH | |
| SCH₂CH=CH₂ | H | OCH₃ | C₂H₅ | CH | |
| SCH₂CH=CH₂ | H | OCH₃ | C₂H₅ | N | |
| SCH₂CH=CH₂ | H | OCH₃ | NHCH₃ | CH | |
| SCH₂CH=CH₂ | H | OCH₃ | NHCH₃ | N | |
| SCH₂CH=CH₂ | H | CH₃ | OC₂H₅ | CH | |
| SCH₂CH=CH₂ | H | OCH₃ | OC₂H₅ | CH | |
| SCH₂CH=CH₂ | H | CH₃ | OC₂H₅ | N | |
| SCH₂CH=CH₂ | H | OCH₃ | OC₂H₅ | N | |

TABLE Id-continued

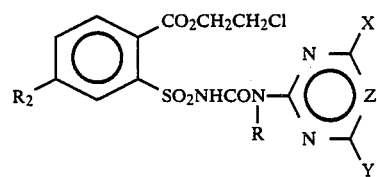

| R₂ | R | X | Y | Z | m.p. (°C.) |
|---|---|---|---|---|---|
| SCH₂CH=CH₂ | H | CH₃ | OCH₂CHF₂ | CH | |
| SCH₂CH=CH₂ | H | OCH₃ | OCH₂CHF₂ | CH | |
| SCH₂CH=CH₂ | H | CH₃ | OCH₂CHF₂ | N | |
| SCH₂CH=CH₂ | H | OCH₃ | OCH₂CHF₂ | N | |
| SCH₂CH=CH₂ | H | CH₃ | OCH₂CH₂F | CH | |
| SCH₂CH=CH₂ | H | OCH₃ | OCH₂CH₂F | CH | |
| SCH₂CH=CH₂ | H | CH₃ | OCH₂CH₂F | N | |
| SCH₂CH=CH₂ | H | OCH₃ | OCH₂CH₂F | N | |
| SCH₂CH=CH₂ | CH₃ | Cl | OCH₃ | CH | |
| SCH₃CH=CH₃ | H | Cl | N(CH₃)₂ | CH | |
| SCH₂CH=CH₂ | H | Cl | OC₂H₅ | CH | |
| SCH₂C≡CH | H | CH₃ | CH₃ | CH | |
| SCH₂C≡CH | H | OCH₃ | CH₃ | CH | |
| SCH₂C≡CH | H | OCH₃ | OCH₃ | CH | |
| SCH₂C≡CH | H | Cl | OCH₃ | CH | |
| SCH₂C≡CH | H | OCH₃ | N(CH₃)₂ | N | |
| SCH₂C≡CH | H | CH₃ | CH₃ | N | |
| SCH₂C≡CH | H | OCH₃ | CH₃ | N | |
| SCH₂C≡CH | H | OCH₃ | OCH₃ | N | |
| SCH₂C≡CH | H | OCH₃ | N(CH₃)₂ | N | |
| SCH₂C≡CH | H | OCH₃ | OCH₂CF₃ | N | |
| SCH₂C≡CH | CH₃ | OCH₃ | CH₃ | N | |
| SCH₂C≡CH | CH₃ | OCH₃ | OCH₃ | N | |
| SCH₂C≡CH | CH₃ | CH₃ | OCH₃ | CH | |
| SCH₂C≡CH | CH₃ | OCH₃ | OCH₃ | CH | |
| SCH₂C≡CH | H | Br | OCH₃ | CH | |
| SCH₂C≡CH | CH₃ | OCH₃ | N(CH₃)₂ | N | |
| SCH₂C≡CH | H | CH₃ | OCH₂CF₃ | N | |
| SCH₂C≡CH | H | CH₃ | OCH₂CF₃ | CH | |
| SCH₂C≡CH | H | OCH₃ | OCH₂CF₃ | CH | |
| SCH₂C≡CH | H | OCH₃ | C₂H₅ | CH | |
| SCH₂C≡CH | H | OCH₃ | C₂H₅ | CH | |
| SCH₂C≡CH | H | OCH₃ | NHCH₃ | CH | |
| SCH₂C≡CH | H | OCH₃ | NHCH₃ | N | |
| SCH₂C≡CH | H | CH₃ | OC₂H₅ | CH | |
| SCH₂C≡CH | H | OCH₃ | OC₂H₅ | CH | |
| SCH₂C≡CH | H | CH₃ | OC₂H₅ | N | |
| SCH₂C≡CH | H | OCH₃ | OC₂H₅ | N | |
| SCH₂C≡CH | H | CH₃ | OCH₂CHF₂ | CH | |
| SCH₂C≡CH | H | OCH₃ | OCH₂CHF₂ | CH | |
| SCH₂C≡CH | H | CH₃ | OCH₂CHF₂ | N | |
| SCH₂C≡CH | H | OCH₃ | OCH₂CHF₂ | N | |
| SCH₂C≡CH | H | CH₃ | OCH₂CH₂F | CH | |
| SCH₂C≡CH | H | OCH₃ | OCH₂CH₂F | CH | |
| SCH₂C≡CH | H | CH₃ | OCH₂CH₂F | N | |
| SCH₂C≡CH | H | OCH₃ | OCH₂CH₂F | N | |
| SCH₂C≡CH | CH₃ | Cl | OCH₃ | CH | |
| SCH₂C≡CH | H | Cl | N(CH₃)₂ | CH | |
| SCH₂C≡CH | H | Cl | OC₂H₅ | CH | |
| CH₂CH₂F | H | CH₃ | CH₃ | CH | |
| CH₂CH₂F | H | OCH₃ | CH₃ | CH | |
| CH₂CH₂F | H | OCH₃ | OCH₃ | CH | |
| CH₂CH₂F | H | Cl | OCH₃ | CH | |
| CH₂CH₂F | H | OCH₃ | N(CH₃)₂ | CH | |
| CH₂CH₂F | H | CH₃ | CH₃ | N | |
| CH₂CH₂F | H | OCH₃ | CH₃ | N | |
| CH₂CH₂F | H | OCH₃ | OCH₃ | N | |
| CH₂CH₂F | H | OCH₃ | N(CH₃)₂ | N | |
| CH₂CH₂F | H | OCH₃ | OCH₂CF₃ | N | |
| CH₂CH₂F | CH₃ | OCH₃ | CH₃ | N | |
| CH₂CH₂F | CH₃ | OCH₃ | OCH₃ | N | |
| CH₂CH₂F | CH₃ | CH₃ | OCH₃ | CH | |
| CH₂CH₂F | CH₃ | OCH₃ | OCH₃ | CH | |
| CH₂CH₂F | H | Br | OCH₃ | CH | |
| CH₂CH₂F | CH₃ | OCH₃ | N(CH₃)₂ | N | |
| CH₂CH₂F | H | CH₃ | OCH₂CF₃ | N | |
| CH₂CH₂F | H | CH₃ | OCH₂CF₃ | CH | |
| CH₂CH₂F | H | OCH₃ | OCH₂CF₃ | CH | |
| CH₂CH₂F | H | OCH₃ | C₂H₅ | CH | |
| CH₂CH₂F | H | OCH₃ | C₂H₅ | N | |

TABLE Id-continued

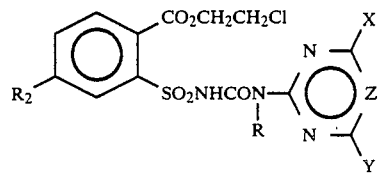

| R₂ | R | X | Y | Z | m.p. (°C.) |
|---|---|---|---|---|---|
| CH₂CH₂F | H | OCH₃ | NHCH₃ | CH | |
| CH₂CH₂F | H | OCH₃ | NHCH₃ | N | |
| CH₂CH₂F | H | CH₃ | OC₂H₅ | CH | |
| CH₂CH₂F | H | OCH₃ | OC₂H₅ | CH | |
| CH₂CH₂F | H | CH₃ | OC₂H₅ | N | |
| CH₂CH₂F | H | OCH₃ | OC₂H₅ | N | |
| CH₂CH₂F | H | CH₃ | OCH₂CHF₂ | CH | |
| CH₂CH₂F | H | OCH₃ | OCH₂CHF₂ | CH | |
| CH₂CH₂F | H | CH₃ | OCH₂CHF₂ | N | |
| CH₂CH₂F | H | OCH₃ | OCH₂CHF₂ | N | |
| CH₂CH₂F | H | CH₃ | OCH₂CH₂F | CH | |
| CH₂CH₂F | H | OCH₃ | OCH₂CH₂F | CH | |
| CH₂CH₂F | H | CH₃ | OCH₂CF₃ | N | |
| CH₂CH₂F | CH₃ | OCH₃ | OCH₂CF₃ | N | |
| CH₂CH₂F | CH₃ | Cl | OCH₃ | CH | |
| CH₂CH₂F | H | Cl | N(CH₃)₂ | CH | |
| CH₂CH₂F | H | Cl | OC₂H₅ | CH | |
| CH₂CF₃ | H | CH₃ | CH₃ | CH | |
| CH₂CF₃ | H | OCH₃ | CH₃ | CH | |
| CH₂CF₃ | H | OCH₃ | OCH₃ | CH | |
| CH₂CF₃ | H | Cl | OCH₃ | CH | |
| CH₂CF₃ | H | OCH₃ | N(CH₃)₂ | CH | |
| CH₂CF₃ | H | CH₃ | CH₃ | N | |
| CH₂CF₃ | H | OCH₃ | CH₃ | N | |
| CH₂CF₃ | H | OCH₃ | OCH₃ | N | |
| CH₂CF₃ | H | OCH₃ | N(CH₃)₂ | N | |
| CH₂CF₃ | H | OCH₃ | OCH₂CF₃ | N | |
| CH₂CF₃ | CH₃ | OCH₃ | CH₃ | N | |
| CH₂CF₃ | CH₃ | OCH₃ | OCH₃ | N | |
| CH₂CF₃ | CH₃ | CH₃ | OCH₃ | CH | |
| CH₂CF₃ | CH₃ | OCH₃ | OCH₃ | CH | |
| CH₂CF₃ | H | Br | OCH₃ | CH | |
| CH₂CF₃ | CH₃ | OCH₃ | N(CH₃)₂ | N | |
| CH₂CF₃ | H | CH₃ | OCH₂CF₃ | N | |
| CH₂CF₃ | H | CH₃ | OCH₂CF₃ | CH | |
| CH₂CF₃ | H | OCH₃ | OCH₂CF₃ | CH | |
| CH₂CF₃ | H | OCH₃ | C₂H₅ | CH | |
| CH₂CF₃ | H | OCH₃ | C₂H₅ | N | |
| CH₂CF₃ | H | OCH₃ | NHCH₃ | CH | |
| CH₂CF₃ | H | OCH₃ | NHCH₃ | N | |
| CH₂CF₃ | H | CH₃ | OC₂H₅ | CH | |
| CH₂CF₃ | H | OCH₃ | OC₂H₅ | CH | |
| CH₂CF₃ | H | CH₃ | OC₂H₅ | N | |
| CH₂CF₃ | H | OCH₃ | OC₂H₅ | N | |
| CH₂CF₃ | H | CH₃ | OCH₂CHF₂ | CH | |
| CH₂CF₃ | H | OCH₃ | OCH₂CHF₂ | CH | |
| CH₂CF₃ | H | CH₃ | OCH₂CHF₂ | N | |
| CH₂CF₃ | H | OCH₃ | OCH₂CHF₂ | N | |
| CH₂CF₃ | H | CH₃ | OCH₂CH₂F | CH | |
| CH₂CF₃ | H | OCH₃ | OCH₂CH₂F | CH | |
| CH₂CF₃ | H | CH₃ | OCH₂CH₂F | N | |
| CH₂CF₃ | CH₃ | OCH₃ | OCH₂CH₂F | N | |
| CH₂CF₃ | CH₃ | Cl | OCH₃ | CH | |
| CH₂CF₃ | H | Cl | N(CH₃)₂ | CH | |
| CH₂CF₃ | H | Cl | OC₂H₅ | CH | |
| CHFCH₃ | H | CH₃ | CH₃ | CH | |
| CHFCH₃ | H | OCH₃ | CH₃ | CH | |
| CHFCH₃ | H | OCH₃ | OCH₃ | CH | |
| CHFCH₃ | H | Cl | OCH₃ | CH | |
| CHFCH₃ | H | OCH₃ | N(CH₃)₂ | CH | |
| CHFCH₃ | H | CH₃ | CH₃ | N | |
| CHFCH₃ | H | OCH₃ | CH₃ | N | |
| CHFCH₃ | H | OCH₃ | OCH₃ | N | |
| CHFCH₃ | H | OCH₃ | N(CH₃)₂ | N | |
| CHFCH₃ | H | OCH₃ | OCH₂CF₃ | N | |
| CHFCH₃ | CH₃ | OCH₃ | CH₃ | N | |
| CHFCH₃ | CH₃ | OCH₃ | OCH₃ | N | |
| CHFCH₃ | CH₃ | CH₃ | OCH₃ | CH | |
| CHFCH₃ | CH₃ | OCH₃ | OCH₃ | CH | |
| CHFCH₃ | H | Br | OCH₃ | CH | |

TABLE Id-continued

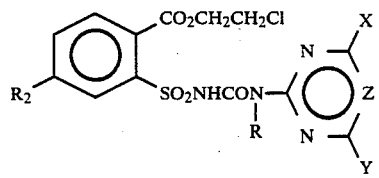

| R₂ | R | X | Y | Z | m.p. (°C.) |
|---|---|---|---|---|---|
| CHFCH₃ | CH₃ | OCH₃ | N(CH₃)₂ | N | |
| CHFCH₃ | H | CH₃ | OCH₂CF₃ | N | |
| CHFCH₃ | H | CH₃ | OCH₂CF₃ | CH | |
| CHFCH₃ | H | OCH₃ | OCH₂CF₃ | CH | |
| CHFCH₃ | H | OCH₃ | C₂H₅ | CH | |
| CHFCH₃ | H | OCH₃ | C₂H₅ | N | |
| CHFCH₃ | H | OCH₃ | NHCH₃ | CH | |
| CHFCH₃ | H | OCH₃ | NHCH₃ | N | |
| CHFCH₃ | H | CH₃ | OC₂H₅ | CH | |
| CHFCH₃ | H | OCH₃ | OC₂H₅ | CH | |
| CHFCH₃ | H | CH₃ | OC₂H₅ | N | |
| CHFCH₃ | H | OCH₃ | OC₂H₅ | N | |
| CHFCH₃ | H | CH₃ | OCH₂CHF₂ | CH | |
| CHFCH₃ | H | OCH₃ | OCH₂CHF₂ | CH | |
| CHFCH₃ | H | CH₃ | OCH₂CHF₂ | N | |
| CHFCH₃ | H | OCH₃ | OCH₂CHF₂ | N | |
| CHFCH₃ | H | CH₃ | OCH₂CH₂F | CH | |
| CHFCH₃ | H | OCH₃ | OCH₂CH₂F | CH | |
| CHFCH₃ | H | CH₃ | OCH₂CF₃ | N | |
| CHFCH₃ | CH₃ | OCH₃ | OCH₂CF₃ | N | |
| CHFCH₃ | CH₃ | Cl | OCH₃ | CH | |
| CHFCH₃ | H | Cl | N(CH₂)₂ | CH | |
| CHFCH₃ | H | Cl | OC₂H₅ | CH | |
| CH₂F | H | CH₃ | CH₃ | CH | |
| CH₂F | H | OCH₃ | CH₃ | CH | |
| CH₂F | H | OCH₃ | OCH₃ | CH | |
| CH₂F | H | Cl | OCH₃ | CH | |
| CH₂F | H | OCH₃ | N(CH₃)₂ | CH | |
| CH₂F | H | CH₃ | CH₃ | N | |
| CH₂F | H | OCH₃ | CH₃ | N | |
| CH₂F | H | OCH₃ | OCH₃ | N | |
| CH₂F | H | OCH₃ | N(CH₃)₂ | N | |
| CH₂F | H | OCH₃ | OCH₂CF₃ | N | |
| CH₂F | CH₃ | OCH₃ | CH₃ | N | |
| CH₂F | CH₃ | OCH₃ | OCH₃ | N | |
| CH₂F | CH₃ | OCH₃ | OCH₃ | CH | |
| CH₂F | CH₃ | OCH₃ | OCH₃ | CH | |
| CH₂F | H | Br | OCH₃ | CH | |
| CH₂F | CH₃ | OCH₃ | N(CH₃)₂ | N | |
| CH₂F | H | CH₃ | OCH₂CF₃ | CH | |
| CH₂F | H | OCH₃ | OCH₂CF₃ | CH | |
| CH₂F | H | OCH₃ | C₂H₅ | CH | |
| CH₂F | H | OCH₃ | C₂H₅ | N | |
| CH₂F | H | OCH₃ | NHCH₃ | CH | |
| CH₂F | H | OCH₃ | NHCH₃ | N | |
| CH₂F | H | CH₃ | OC₂H₅ | CH | |
| CH₂F | H | OCH₃ | OC₂H₅ | CH | |
| CH₂F | H | CH₃ | OC₂H₅ | N | |
| CH₂F | H | OCH₃ | OC₂H₅ | N | |
| CH₂F | H | CH₃ | OCH₂CH₂F | CH | |
| CH₂F | H | OCH₃ | OCH₂CH₂F | CH | |
| CH₂F | H | CH₃ | OCH₂CH₂F | N | |
| CH₂F | H | OCH₃ | OCH₂CH₂F | N | |
| CH₂F | H | CH₃ | OCH₂CH₂F | CH | |
| CH₂F | H | OCH₃ | OCH₂CH₂F | CH | |
| CH₂F | H | CH₃ | OCH₂CH₂F | N | |
| CH₂F | CH₃ | OCH₃ | OCH₂CH₂F | N | |
| CH₂F | CH₃ | Cl | OCH₃ | CH | |
| CH₂F | H | Cl | N(CH₃)₂ | CH | |
| CH₂F | H | Cl | OC₂H₅ | CH | |
| CHF₂ | H | CH₃ | CH₃ | CH | |
| CHF₂ | H | OCH₃ | CH₃ | CH | |
| CHF₂ | H | OCH₃ | OCH₃ | CH | |
| CHF₂ | H | Cl | OCH₃ | CH | |
| CHF₂ | H | OCH₃ | N(CH₃)₂ | CH | |
| CHF₂ | H | CH₃ | CH₃ | N | |
| CHF₂ | H | OCH₃ | CH₃ | N | |
| CHF₂ | H | OCH₃ | OCH₃ | N | |
| CHF₂ | H | OCH₃ | N(CH₃)₂ | N | |

TABLE Id-continued

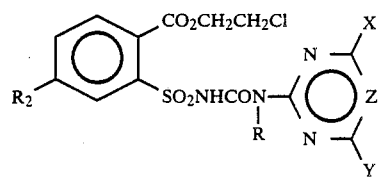

| $R_2$ | R | X | Y | Z | m.p. (°C.) |
|---|---|---|---|---|---|
| $CHF_2$ | H | $OCH_3$ | $OCH_2CF_3$ | N | |
| $CHF_2$ | $CH_3$ | $OCH_3$ | $CH_3$ | N | |
| $CHF_2$ | $CH_3$ | $OCH_3$ | $OCH_3$ | N | |
| $CHF_2$ | $CH_3$ | $OCH_3$ | $OCH_3$ | CH | |
| $CHF_2$ | $CH_3$ | $OCH_3$ | $OCH_3$ | CH | |
| $CHF_2$ | H | Br | $OCH_3$ | CH | |
| $CHF_2$ | $CH_3$ | $OCH_3$ | $N(CH_3)_2$ | N | |
| $CHF_2$ | H | $CH_3$ | $OCH_2CF_3$ | N | |
| $CHF_2$ | H | $CH_3$ | $OCH_2CF_3$ | CH | |
| $CHF_2$ | H | $OCH_3$ | $OCH_2CF_3$ | CH | |
| $CHF_2$ | H | $OCH_3$ | $C_2H_5$ | CH | |
| $CHF_2$ | H | $OCH_3$ | $C_2H_5$ | N | |
| $CHF_2$ | H | $OCH_3$ | $NHCH_3$ | CH | |
| $CHF_2$ | H | $OCH_3$ | $NHCH_3$ | N | |
| $CHF_2$ | H | $CH_3$ | $OC_2H_5$ | CH | |
| $CHF_2$ | H | $OCH_3$ | $OC_2H_5$ | CH | |
| $CHF_2$ | H | $CH_3$ | $OC_2H_5$ | N | |
| $CHF_2$ | H | $OCH_3$ | $OC_2H_5$ | N | |
| $CHF_2$ | H | $CH_3$ | $OCH_2CHF_2$ | CH | |
| $CHF_2$ | H | $OCH_3$ | $OCH_2CHF_2$ | CH | |
| $CHF_2$ | H | $CH_3$ | $OCH_2CHF_2$ | N | |
| $CHF_2$ | H | $OCH_3$ | $OCH_2CHF_2$ | N | |
| $CHF_2$ | H | $CH_3$ | $OCH_2CH_2F$ | CH | |
| $CHF_2$ | H | $OCH_3$ | $OCH_2CH_2F$ | CH | |
| $CHF_2$ | H | $CH_3$ | $OCH_2CH_2F$ | N | |
| $CHF_2$ | $CH_3$ | $OCH_3$ | $OCH_2CH_2F$ | N | |
| $CHF_2$ | $CH_3$ | Cl | $OCH_3$ | CH | |
| $CHF_2$ | H | Cl | $N(CH_3)_2$ | CH | |
| $CHF_2$ | H | Cl | $OC_2H_5$ | CH | |
| $CH_2OCH_3$ | H | $CH_3$ | $CH_3$ | CH | |
| $CH_2OCH_3$ | H | $OCH_3$ | $CH_3$ | CH | |
| $CH_2OCH_3$ | H | $OCH_3$ | $OCH_3$ | CH | |
| $CH_2OCH_3$ | H | Cl | $OCH_3$ | CH | |
| $CH_2OCH_3$ | H | $OCH_3$ | $N(CH_3)_2$ | CH | |
| $CH_2OCH_3$ | H | $CH_3$ | $CH_3$ | N | |
| $CH_2OCH_3$ | H | $OCH_3$ | $CH_3$ | N | |
| $CH_2OCH_3$ | H | $OCH_3$ | $OCH_3$ | N | |
| $CH_2OCH_3$ | H | $OCH_3$ | $N(CH_3)_2$ | N | |
| $CH_2OCH_3$ | H | $OCH_3$ | $OCH_2CF_3$ | N | |
| $CH_2OCH_3$ | $CH_3$ | $OCH_3$ | $CH_3$ | N | |
| $CH_2OCH_3$ | $CH_3$ | $OCH_3$ | $OCH_3$ | N | |
| $CH_2OCH_3$ | $CH_3$ | $CH_3$ | $OCH_3$ | CH | |
| $CH_2OCH_3$ | $CH_3$ | $OCH_3$ | $OCH_3$ | CH | |
| $CH_2OCH_3$ | H | Br | $OCH_3$ | CH | |
| $CH_2OCH_3$ | H | $OCH_3$ | $N(CH_3)_2$ | CH | |
| $CH_2OCH_3$ | $CH_3$ | $OCH_3$ | $N(CH_3)_2$ | N | |
| $CH_2OCH_3$ | H | $CH_3$ | $OCH_2CF_3$ | N | |
| $CH_2OCH_3$ | H | $CH_3$ | $OCH_2CF_3$ | CH | |
| $CH_2OCH_3$ | H | $OCH_3$ | $OCH_2CF_3$ | CH | |
| $CH_2OCH_3$ | H | $OCH_3$ | $C_2H_5$ | CH | |
| $CH_2OCH_3$ | H | $OCH_3$ | $C_2H_5$ | N | |
| $CH_2OCH_3$ | H | $OCH_3$ | $NHCH_3$ | CH | |
| $CH_2OCH_3$ | H | $OCH_3$ | $NHCH_3$ | N | |
| $CH_2OCH_3$ | H | $CH_3$ | $OC_2H_5$ | CH | |
| $CH_2OCH_3$ | H | $OCH_3$ | $OC_2H_5$ | CH | |
| $CH_2OCH_3$ | H | $CH_3$ | $OC_2H_5$ | N | |
| $CH_2OCH_3$ | H | $OCH_3$ | $OC_2H_5$ | N | |
| $CH_2OCH_3$ | H | $CH_3$ | $OCH_2CHF_2$ | CH | |
| $CH_2OCH_3$ | H | $OCH_3$ | $OCH_2CHF_2$ | CH | |
| $CH_2OCH_3$ | H | $CH_3$ | $OCH_2CHF_2$ | N | |
| $CH_2OCH_3$ | H | $OCH_3$ | $OCH_2CHF_2$ | N | |
| $CH_2OCH_3$ | H | $CH_3$ | $OCH_2CH_2F$ | CH | |
| $CH_2OCH_3$ | H | $OCH_3$ | $OCH_2CH_2F$ | CH | |
| $CH_2OCH_3$ | H | $CH_3$ | $OCH_2CF_3$ | N | |
| $CH_2OCH_3$ | $CH_3$ | $OCH_3$ | $OCH_2CF_3$ | N | |
| $CH_2OCH_3$ | $CH_3$ | Cl | $OCH_3$ | CH | |
| $CH_2OCH_3$ | H | Cl | $N(CH_3)_2$ | CH | |
| $CH_2OCH_3$ | H | Cl | $OC_2H_5$ | CH | |
| $CH_2SCH_3$ | H | $CH_3$ | $CH_3$ | CH | |
| $CH_2SCH_3$ | H | $OCH_3$ | $CH_3$ | CH | |

TABLE Id-continued

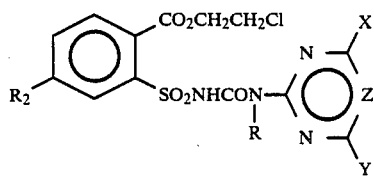

| $R_2$ | R | X | Y | Z | m.p. (°C.) |
|---|---|---|---|---|---|
| $CH_2SCH_3$ | H | $OCH_3$ | $OCH_3$ | CH | |
| $CH_2SCH_3$ | H | Cl | $OCH_3$ | CH | |
| $CH_2SCH_3$ | H | $OCH_3$ | $N(CH_3)_2$ | CH | |
| $CH_2SCH_3$ | H | $CH_3$ | $CH_3$ | N | |
| $CH_2SCH_3$ | H | $OCH_3$ | $CH_3$ | N | |
| $CH_2SCH_3$ | H | $OCH_3$ | $OCH_3$ | N | |
| $CH_2SCH_3$ | H | $OCH_3$ | $N(CH_3)_2$ | N | |
| $CH_2SCH_3$ | H | $OCH_3$ | $OCH_2CF_3$ | N | |
| $CH_2SCH_3$ | $CH_3$ | $OCH_3$ | $CH_3$ | N | |
| $CH_2SCH_3$ | $CH_3$ | $OCH_3$ | $OCH_3$ | N | |
| $CH_2SCH_3$ | $CH_3$ | $CH_3$ | $OCH_3$ | CH | |
| $CH_2SCH_3$ | $CH_3$ | $OCH_3$ | $OCH_3$ | CH | |
| $CH_2SCH_3$ | H | Br | $OCH_3$ | CH | |
| $CH_2SCH_3$ | $CH_3$ | $OCH_3$ | $N(CH_3)_2$ | N | |
| $CH_2SCH_3$ | H | $CH_3$ | $OCH_2CF_3$ | N | |
| $CH_2SCH_3$ | H | $CH_3$ | $OCH_2CF_3$ | CH | |
| $CH_2SCH_3$ | H | $OCH_3$ | $OCH_2CF_3$ | CH | |
| $CH_2SCH_3$ | H | $OCH_3$ | $C_2H_5$ | CH | |
| $CH_2SCH_3$ | H | $OCH_3$ | $C_2H_5$ | N | |
| $CH_2SCH_3$ | H | $OCH_3$ | $NHCH_3$ | CH | |
| $CH_2SCH_3$ | H | $OCH_3$ | $NHCH_3$ | N | |
| $CH_2SCH_3$ | H | $CH_3$ | $OC_2H_5$ | CH | |
| $CH_2SCH_3$ | H | $OCH_3$ | $OC_2H_5$ | CH | |
| $CH_2SCH_3$ | H | $CH_3$ | $OC_2H_5$ | N | |
| $CH_2SCH_3$ | H | $OCH_3$ | $OC_2H_5$ | N | |
| $CH_2SCH_3$ | H | $CH_3$ | $OCH_2CHF_2$ | CH | |
| $CH_2SCH_3$ | H | $OCH_3$ | $OCH_2CHF_2$ | CH | |
| $CH_2SCH_3$ | H | $CH_3$ | $OCH_2CHF_2$ | N | |
| $CH_2SCH_3$ | H | $OCH_3$ | $OCH_2CHF_2$ | N | |
| $CH_2SCH_3$ | H | $CH_3$ | $OCH_2CH_2F$ | CH | |
| $CH_2SCH_3$ | H | $OCH_3$ | $OCH_2CH_2F$ | CH | |
| $CH_2SCH_3$ | H | $CH_3$ | $OCH_2CH_2F$ | N | |
| $CH_2SCH_3$ | $CH_3$ | $OCH_3$ | $OCH_2CH_2F$ | N | |
| $CH_2SCH_3$ | $CH_3$ | Cl | $OCH_3$ | CH | |
| $CH_2SCH_3$ | H | Cl | $N(CH_3)_2$ | CH | |
| $CH_2SCH_3$ | H | Cl | $OC_2H_5$ | CH | |
| $OCF_2H$ | H | $CH_3$ | $CH_3$ | CH | |
| $OCF_2H$ | H | $OCH_3$ | $CH_3$ | CH | |
| $OCF_2H$ | H | $OCH_3$ | $OCH_3$ | CH | |
| $OCF_2H$ | H | Cl | $OCH_3$ | CH | |
| $OCF_2H$ | H | $OCH_3$ | $N(CH_3)_2$ | CH | |
| $OCF_2H$ | H | $CH_3$ | $CH_3$ | N | |
| $OCF_2H$ | H | $OCH_3$ | $CH_3$ | N | |
| $OCF_2H$ | H | $OCH_3$ | $OCH_3$ | N | |
| $OCF_2H$ | H | $OCH_3$ | $N(CH_3)_2$ | N | |
| $OCF_2H$ | H | $OCH_3$ | $OCH_2CF_3$ | N | |
| $OCF_2H$ | $CH_3$ | $OCH_3$ | $CH_3$ | N | |
| $OCF_2H$ | $CH_3$ | $OCH_3$ | $OCH_3$ | N | |
| $OCF_2H$ | $CH_3$ | $CH_3$ | $OCH_3$ | CH | |
| $OCF_2H$ | $CH_3$ | $OCH_3$ | $OCH_3$ | CH | |
| $OCF_2H$ | H | Br | $OCH_3$ | CH | |
| $OCF_2H$ | $CH_3$ | $OCH_3$ | $N(CH_3)_2$ | N | |
| $OCF_2H$ | H | $CH_3$ | $OCH_2CF_3$ | N | |
| $OCF_2H$ | H | $CH_3$ | $OCH_2CF_3$ | CH | |
| $OCF_2H$ | H | $OCH_3$ | $OCH_2CF_3$ | CH | |
| $OCF_2H$ | H | $OCH_3$ | $C_2H_5$ | CH | |
| $OCF_2H$ | H | $OCH_3$ | $C_2H_5$ | N | |
| $OCF_2H$ | H | $OCH_3$ | $NHCH_3$ | CH | |
| $OCF_2H$ | H | $OCH_3$ | $NHCH_3$ | N | |
| $OCF_2H$ | H | $CH_3$ | $OC_2H_5$ | CH | |
| $OCF_2H$ | H | $OCH_3$ | $OC_2H_5$ | CH | |
| $OCF_2H$ | H | $CH_3$ | $OC_2H_5$ | N | |
| $OCF_2H$ | H | $OCH_3$ | $OC_2H_5$ | N | |
| $OCF_2H$ | H | $CH_3$ | $OCH_2CHF_2$ | CH | |
| $OCF_2H$ | H | $OCH_3$ | $OCH_2CHF_2$ | CH | |
| $OCF_2H$ | H | $CH_3$ | $OCH_2CHF_2$ | N | |
| $OCF_2H$ | H | $OCH_3$ | $OCH_2CHF_2$ | N | |
| $OCF_2H$ | H | $CH_3$ | $OCH_2CH_2F$ | CH | |
| $OCF_2H$ | H | $OCH_3$ | $OCH_2CH_2F$ | CH | |
| $OCF_2H$ | H | $CH_3$ | $OCH_2CH_2F$ | N | |

TABLE Id-continued

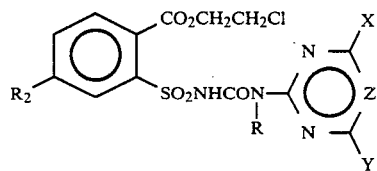

| R₂ | R | X | Y | Z | m.p. (°C.) |
|---|---|---|---|---|---|
| OCF₂H | CH₃ | OCH₃ | OCH₂CH₂F | N | |
| OCF₂H | CH₃ | Cl | OCH₃ | CH | |
| OCF₂H | H | Cl | N(CH₃)₂ | CH | |
| OCF₂H | H | Cl | OC₂H₅ | CH | |
| OCH₂CH₂F | H | CH₃ | CH₃ | CH | |
| OCH₂CH₂F | H | OCH₃ | CH₃ | CH | |
| OCH₂CH₂F | H | OCH₃ | OCH₃ | CH | |
| OCH₂CH₂F | H | Cl | OCH₃ | CH | |
| OCH₂CH₂F | H | OCH₃ | N(CH₃)₂ | CH | |
| OCH₂CH₂F | H | CH₃ | CH₃ | N | |
| OCH₂CH₂F | H | OCH₃ | CH₃ | N | |
| OCH₂CH₂F | H | OCH₃ | OCH₃ | N | |
| OCH₂CH₂F | H | OCH₃ | N(CH₃)₂ | N | |
| OCH₂CH₂F | H | OCH₃ | OCH₂CF₃ | N | |
| OCH₂CH₂F | CH₃ | OCH₃ | CH₃ | N | |
| OCH₂CH₂F | CH₃ | OCH₃ | OCH₃ | N | |
| OCH₂CH₂F | CH₃ | CH₃ | OCH₃ | CH | |
| OCH₂CH₂F | CH₃ | OCH₃ | OCH₃ | CH | |
| OCH₂CH₂F | H | Br | OCH₃ | CH | |
| OCH₂CH₂F | CH₃ | OCH₃ | N(CH₃)₂ | N | |
| OCH₂CH₂F | H | CH₃ | OCH₂CF₃ | N | |
| OCH₂CH₂F | H | CH₃ | OCH₂CF₃ | CH | |
| OCH₂CH₂F | H | OCH₃ | OCH₂CF₃ | CH | |
| OCH₂CH₂F | H | OCH₃ | C₂H₅ | CH | |
| OCH₂CH₂F | H | OCH₃ | C₂H₅ | N | |
| OCH₂CH₂F | H | OCH₃ | NHCH₃ | CH | |
| OCH₂CH₂F | H | OCH₃ | NHCH₃ | N | |
| OCH₂CH₂F | H | CH₃ | OC₂H₅ | CH | |
| OCH₂CH₂F | H | OCH₃ | OC₂H₅ | CH | |
| OCH₂CH₂F | H | CH₃ | OC₂H₅ | N | |
| OCH₂CH₂F | H | OCH₃ | OC₂H₅ | N | |
| OCH₂CH₂F | H | CH₃ | OCH₂CHF₂ | CH | |
| OCH₂CH₂F | H | OCH₃ | OCH₂CHF₂ | CH | |
| OCH₂CH₂F | H | CH₃ | OCH₂CHF₂ | N | |
| OCH₂CH₂F | H | OCH₃ | OCH₂CHF₂ | N | |
| OCH₂CH₂F | H | CH₃ | OCH₂CH₂F | CH | |
| OCH₂CH₂F | H | OCH₃ | OCH₂CH₂F | CH | |
| OCH₂CH₂F | H | CH₃ | OCH₂CH₂F | N | |
| OCH₂CH₂F | CH₃ | OCH₃ | OCH₂CH₂F | N | |
| OCH₂CH₂F | CH₃ | Cl | OCH₃ | CH | |
| OCH₂CH₂F | H | Cl | N(CH₃)₂ | CH | |
| OCH₂CH₂F | H | Cl | OC₂H₅ | CH | |
| OCH₂CF₃ | H | CH₃ | CH₃ | CH | |
| OCH₂CF₃ | H | OCH₃ | CH₃ | CH | |
| OCH₂CF₃ | H | OCH₃ | OCH₃ | CH | |
| OCH₂CF₃ | H | Cl | OCH₃ | CH | |
| OCH₂CF₃ | H | OCH₃ | N(CH₃)₂ | CH | |
| OCH₂CF₃ | H | CH₃ | CH₃ | N | |
| OCH₂CF₃ | H | OCH₃ | CH₃ | N | |
| OCH₂CF₃ | H | OCH₃ | OCH₃ | N | |
| OCH₂CF₃ | H | OCH₃ | N(CH₃)₂ | N | |
| OCH₂CF₃ | H | OCH₃ | OCH₂CF₃ | N | |
| OCH₂CF₃ | H | OC₂H₅ | NHCH₃ | N | |
| OCH₂CF₃ | CH₃ | OCH₃ | CH₃ | N | |
| OCH₂CF₃ | CH₃ | OCH₃ | OCH₃ | N | |
| OCH₂CF₃ | CH₃ | CH₃ | OCH₃ | CH | |
| OCH₂CF₃ | CH₃ | OCH₃ | OCH₃ | CH | |
| OCH₂CF₃ | H | Br | OCH₃ | CH | |
| OCH₂CF₃ | CH₃ | OCH₃ | N(CH₃)₂ | N | |
| OCH₂CF₃ | H | CH₃ | OCH₂CF₃ | N | |
| OCH₂CF₃ | H | CH₃ | OCH₂CF₃ | CH | |
| OCH₂CF₃ | H | OCH₃ | OCH₂CF₃ | CH | |
| OCH₂CF₃ | H | OCH₃ | C₂H₅ | CH | |
| OCH₂CF₃ | H | OCH₃ | C₂H₅ | N | |
| OCH₂CF₃ | H | OCH₃ | NHCH₃ | CH | |
| OCH₂CF₃ | H | OCH₃ | NHCH₃ | N | |
| OCH₂CF₃ | H | CH₃ | OC₂H₅ | CH | |
| OCH₂CF₃ | H | OCH₃ | OC₂H₅ | CH | |
| OCH₂CF₃ | H | CH₃ | OC₂H₅ | N | |
| OCH₂CF₃ | H | OCH₃ | OC₂H₅ | N | |

TABLE Id-continued

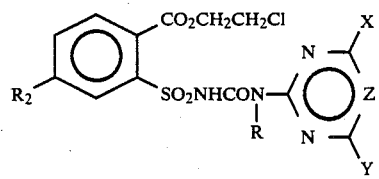

| R₂ | R | X | Y | Z | m.p. (°C.) |
|---|---|---|---|---|---|
| OCH₂CF₃ | H | CH₃ | OCH₂CHF₂ | CH | |
| OCH₂CF₃ | H | OCH₃ | OCH₂CHF₂ | CH | |
| OCH₂CF₃ | H | CH₃ | OCH₂CHF₂ | N | |
| OCH₂CF₃ | H | OCH₃ | OCH₂CHF₂ | N | |
| OCH₂CF₃ | H | CH₃ | OCH₂CH₂F | CH | |
| OCH₂CF₃ | H | OCH₃ | OCH₂CH₂F | CH | |
| OCH₂CF₃ | H | CH₃ | OCH₂CH₂F | N | |
| OCH₂CF₃ | CH₃ | OCH₃ | OCH₂CH₂F | N | |
| OCH₂CF₃ | CH₃ | Cl | OCH₃ | CH | |
| OCH₂CF₃ | H | Cl | N(CH₃)₂ | CH | |
| OCH₂CF₃ | H | Cl | OC₂H₅ | CH | |
| OCH₂CH₂OCH₃ | H | CH₃ | CH₃ | CH | |
| OCH₂CH₂OCH₃ | H | OCH₃ | CH₃ | CH | |
| OCH₂CH₂OCH₃ | H | OCH₃ | OCH₃ | CH | |
| OCH₂CH₂OCH₃ | H | Cl | OCH₃ | CH | |
| OCH₂CH₂OCH₃ | H | OCH₃ | N(CH₃)₂ | CH | |
| OCH₂CH₂OCH₃ | H | CH₃ | CH₃ | N | |
| OCH₂CH₂OCH₃ | H | OCH₃ | CH₃ | N | |
| OCH₂CH₂OCH₃ | H | OCH₃ | OCH₃ | N | |
| OCH₂CH₂OCH₃ | H | OCH₃ | N(CH₃)₂ | N | |
| OCH₂CH₂OCH₃ | H | OCH₃ | OCH₂CF₃ | N | |
| OCH₂CH₂OCH₃ | CH₃ | OCH₃ | CH₃ | N | |
| OCH₂CH₂OCH₃ | CH₃ | OCH₃ | OCH₃ | N | |
| OCH₂CH₂OCH₃ | CH₃ | CH₃ | OCH₃ | CH | |
| OCH₂CH₂OCH₃ | CH₃ | OCH₃ | OCH₃ | CH | |
| OCH₂CH₂OCH₃ | H | Br | OCH₃ | CH | |
| OCH₂CH₂OCH₃ | H | CH₃ | OCH₂CF₃ | N | |
| OCH₂CH₂OCH₃ | H | CH₃ | OCH₂CF₃ | CH | |
| OCH₂CH₂OCH₃ | H | OCH₃ | OCH₂CF₃ | CH | |
| OCH₂CH₂OCH₃ | H | OCH₃ | C₂H₅ | CH | |
| OCH₂CH₂OCH₃ | H | OCH₃ | C₂H₅ | N | |
| OCH₂CH₂OCH₃ | H | OCH₃ | NHCH₃ | CH | |
| OCH₂CH₂OCH₃ | H | OCH₃ | NHCH₃ | N | |
| OCH₂CH₂OCH₃ | H | CH₃ | OC₂H₅ | CH | |
| OCH₂CH₂OCH₃ | H | OCH₃ | OC₂H₅ | CH | |
| OCH₂CH₂OCH₃ | H | CH₃ | OC₂H₅ | N | |
| OCH₂CH₂OCH₃ | H | OCH₃ | OC₂H₅ | N | |
| OCH₂CH₂OCH₃ | H | CH₃ | OCH₂CHF₂ | CH | |
| OCH₂CH₂OCH₃ | H | OCH₃ | OCH₂CHF₂ | CH | |
| OCH₂CH₂OCH₃ | H | CH₃ | OCH₂CHF₂ | N | |
| OCH₂CH₂OCH₃ | H | OCH₃ | OCH₂CHF₂ | N | |
| OCH₂CH₂OCH₃ | H | CH₃ | OCH₂CH₂F | CH | |
| OCH₂CH₂OCH₃ | H | OCH₃ | OCH₂CH₂F | CH | |
| OCH₂CH₂OCH₃ | H | CH₃ | OCH₂CF₃ | N | |
| OCH₂CH₂OCH₃ | CH₃ | OCH₃ | OCH₂CF₃ | N | |
| OCH₂CH₂OCH₃ | CH₃ | Cl | OCH₃ | CH | |
| OCH₂CH₂OCH₃ | H | Cl | N(CH₃)₂ | CH | |
| OCH₂CH₂OCH₃ | H | Cl | OC₂H₅ | CH | |
| O-cyclopropyl | H | CH₃ | CH₃ | CH | |
| O-cyclopropyl | H | OCH₃ | CH₃ | CH | |
| O-cyclopropyl | H | OCH₃ | OCH₃ | CH | |
| O-cyclopropyl | H | Cl | OCH₃ | CH | |
| O-cyclopropyl | H | OCH₃ | N(CH₃)₂ | CH | |
| O-cyclopropyl | H | CH₃ | CH₃ | N | |
| O-cyclopropyl | H | OCH₃ | CH₃ | N | |
| O-cyclopropyl | H | OCH₃ | OCH₃ | N | |
| O-cyclopropyl | H | OCH₃ | N(CH₃)₂ | N | |
| O-cyclopropyl | H | OCH₃ | OCH₂CF₃ | N | |
| O-cyclopropyl | CH₃ | OCH₃ | CH₃ | N | |
| O-cyclopropyl | CH₃ | OCH₃ | OCH₃ | N | |
| O-cyclopropyl | CH₃ | CH₃ | OCH₃ | CH | |
| O-cyclopropyl | CH₃ | OCH₃ | OCH₃ | CH | |
| O-cyclopropyl | H | Br | OCH₃ | CH | |
| O-cyclopropyl | CH₃ | OCH₃ | N(CH₃)₂ | N | |
| O-cyclopropyl | H | CH₃ | OCH₂CF₃ | N | |
| O-cyclopropyl | H | CH₃ | OCH₂CF₃ | CH | |
| O-cyclopropyl | H | OCH₃ | OCH₂CF₃ | CH | |
| O-cyclopropyl | H | OCH₃ | C₂H₅ | CH | |
| O-cyclopropyl | H | OCH₃ | C₂H₅ | N | |
| O-cyclopropyl | H | OCH₃ | NHCH₃ | CH |

TABLE Id-continued

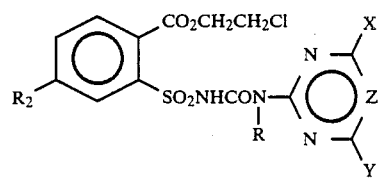

| $R_2$ | R | X | Y | Z | m.p. (°C.) |
|---|---|---|---|---|---|
| O-cyclopropyl | H | $OCH_3$ | $NHCH_3$ | N | |
| O-cyclopropyl | H | $CH_3$ | $OC_2H_5$ | CH | |
| O-cyclopropyl | H | $OCH_3$ | $OC_2H_5$ | CH | |
| O-cyclopropyl | H | $CH_3$ | $OC_2H_5$ | N | |
| O-cyclopropyl | H | $OCH_3$ | $OC_2H_5$ | N | |
| O-cyclopropyl | H | $CH_3$ | $OCH_2CHF_2$ | CH | |
| O-cyclopropyl | H | $OCH_3$ | $OCH_2CHF_2$ | CH | |
| O-cyclopropyl | H | $CH_3$ | $OCH_2CHF_2$ | N | |
| O-cyclopropyl | H | $OCH_3$ | $OCH_2CHF_2$ | N | |
| O-cyclopropyl | H | $CH_3$ | $OCH_2CH_2F$ | CH | |
| O-cyclopropyl | H | $OCH_3$ | $OCH_2CH_2F$ | CH | |
| O-cyclopropyl | H | $CH_3$ | $OCH_2CH_2F$ | N | |
| O-cyclopropyl | $CH_3$ | $OCH_3$ | $OCH_2CH_2F$ | N | |
| O-cyclopropyl | $CH_3$ | Cl | $OCH_3$ | CH | |
| O-cyclopropyl | H | Cl | $N(CH_3)_2$ | CH | |
| O-cyclopropyl | H | Cl | $OC_2H_5$ | CH | |
| $OCF_2CF_2H$ | H | $OCH_3$ | Cl | CH | |
| $OCF_2CF_2H$ | H | $CH_3$ | $CH_3$ | CH | |
| $OCF_2CF_2H$ | H | $OCH_3$ | $OCH_3$ | N | |
| S-cyclopropyl | H | $OCH_3$ | $OCH_3$ | CH | |
| S-cyclopropyl | H | $OCH_3$ | Cl | CH | |
| S-cyclopropyl | H | $CH_3$ | $CH_3$ | CH | |
| S-cyclopropyl | H | $OCH_3$ | $OCH_3$ | N | |
| S-cyclopropyl | H | $OCH_3$ | $CH_3$ | N | |
| $SCH_2$-cyclopropyl | H | $OCH_3$ | $OCH_3$ | CH | |
| $SCH_2$-cyclopropyl | H | $OCH_3$ | $CH_3$ | CH | |
| $SCH_2$-cyclopropyl | H | $OCH_3$ | Cl | CH | |
| $SCH_2$-cyclopropyl | H | $CH_3$ | $CH_3$ | CH | |
| $SCH_2$-cyclopropyl | H | $OCH_3$ | $OCH_3$ | N | |
| $NHCH_2$-cyclopropyl | H | $OCH_3$ | $OCH_3$ | CH | |
| $NHCH_2$-cyclopropyl | H | $OCH_3$ | $CH_3$ | CH | |
| $NHCH_2$-cyclopropyl | H | $OCH_3$ | Cl | CH | |
| $NHCH_2$-cyclopropyl | H | $CH_3$ | $CH_3$ | CH | |
| $NHCH_2$-cyclopropyl | H | $OCH_3$ | $OCH_3$ | N | |
| $NHCH_2$-cyclopropyl | H | $OCH_3$ | $CH_3$ | N | |
| $NHCH_2CF_2CF_3$ | H | $OCH_3$ | $OCH_3$ | CH | |
| $NHCH_2CF_2CF_3$ | H | $OCH_3$ | $CH_3$ | CH | |
| $NHCH_2CF_2CF_3$ | H | $OCH_3$ | Cl | CH | |
| $NHCH_2CF_2CF_3$ | H | $CH_3$ | $CH_3$ | CH | |
| $NHCH_2CF_2CF_3$ | H | $OCH_3$ | $OCH_3$ | N | |
| $NHCH_2CF_2CF_3$ | H | $OCH_3$ | $CH_3$ | N | |
| $NHCH(CF_3)CH_3$ | H | $OCH_3$ | $OCH_3$ | CH | |
| $NHCH(CF_3)CH_3$ | H | $OCH_3$ | $CH_3$ | CH | |
| $NHCH_2CHF_2$ | H | $OCH_3$ | $CH_3$ | N | |
| $NHCH_2CF_3$ | H | $OCH_3$ | $OCH_3$ | CH | |
| $NHCH_2CF_3$ | H | $OCH_3$ | $CH_3$ | CH | |
| $NHCH_2CF_3$ | H | $OCH_3$ | Cl | CH | |
| $NHCH_2CF_3$ | H | $CH_3$ | $CH_3$ | CH | |
| $NHCH_2CF_3$ | H | $OCH_3$ | $OCH_3$ | N | |
| $NHCH_3$ | H | $OCH_3$ | $OCH_3$ | CH | |
| $NHCH_3$ | H | $OCH_3$ | $CH_3$ | CH | |
| $NHCH_3$ | H | $OCH_3$ | Cl | CH | |
| $NHCH_3$ | H | $CH_3$ | $CH_3$ | CH | |
| $NHCH_3$ | H | $OCH_3$ | $OCH_3$ | N | |

TABLE Ie

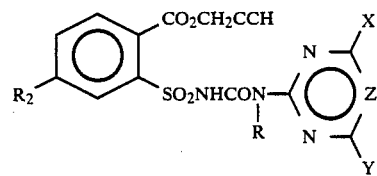

| R₂ | R | X | Y | Z | m.p. (°C.) |
|---|---|---|---|---|---|
| OC₂H₅ | H | CH₃ | CH₃ | CH | |
| OC₂H₅ | H | OCH₃ | CH₃ | CH | |
| OC₂H₅ | H | OCH₃ | OCH₃ | CH | |
| OC₂H₅ | H | Cl | OCH₃ | CH | |
| OC₂H₅ | H | OCH₃ | N(CH₃)₂ | CH | |
| OC₂H₅ | H | CH₃ | CH₃ | N | |
| OC₂H₅ | H | OCH₃ | CH₃ | N | |
| OC₂H₅ | H | OCH₃ | OCH₃ | N | |
| OC₂H₅ | H | OCH₃ | N(CH₃)₂ | N | |
| OC₂H₅ | H | OCH₃ | OCH₂CF₃ | N | |
| OC₂H₅ | CH₃ | OCH₃ | CH₃ | N | |
| OC₂H₅ | CH₃ | OCH₃ | OCH₃ | N | |
| OC₂H₅ | CH₃ | CH₃ | OCH₃ | CH | |
| OC₂H₅ | CH₃ | OCH₃ | OCH₃ | CH | |
| OC₂H₅ | H | Br | OCH₃ | CH | |
| OC₂H₅ | CH₃ | OCH₃ | N(CH₃)₂ | N | |
| OC₂H₅ | H | CH₃ | OCH₂CF₃ | N | |
| OC₂H₅ | H | CH₃ | OCH₂CF₃ | CH | |
| OC₂H₅ | H | OCH₃ | OCH₂CF₃ | CH | |
| OC₂H₅ | H | OCH₃ | C₂H₅ | CH | |
| OC₂H₅ | H | OCH₃ | C₂H₅ | N | |
| OC₂H₅ | H | OCH₃ | NHCH₃ | CH | |
| OC₂H₅ | H | OCH₃ | NHCH₃ | N | |
| OC₂H₅ | H | CH₃ | OC₂H₅ | CH | |
| OC₂H₅ | H | OCH₃ | OC₂H₅ | CH | |
| OC₂H₅ | H | CH₃ | OC₂H₅ | N | |
| OC₂H₅ | H | OCH₃ | OC₂H₅ | N | |
| OC₂H₅ | H | CH₃ | OCH₂CHF₂ | CH | |
| OC₂H₅ | H | OCH₃ | OCH₂CHF₂ | CH | |
| OC₂H₅ | H | CH₃ | OCH₂CHF₂ | N | |
| OC₂H₅ | H | OCH₃ | OCH₂CHF₂ | N | |
| OC₂H₅ | H | CH₃ | OCH₂CH₂F | CH | |
| OC₂H₅ | H | OCH₃ | OCH₂CH₂F | CH | |
| OC₂H₅ | H | CH₃ | OCH₂CH₂F | N | |
| OC₂H₅ | CH₃ | OCH₃ | OCH₂CH₂F | N | |
| OC₂H₅ | CH₃ | Cl | OCH₃ | CH | |
| OC₂H₅ | H | Cl | N(CH₃)₂ | CH | |
| OC₂H₅ | H | Cl | OC₂H₅ | CH | |
| SC₂H₅ | H | CH₃ | CH₃ | CH | |
| SC₂H₅ | H | OCH₃ | CH₃ | CH | |
| SC₂H₅ | H | OCH₃ | OCH₃ | CH | |
| SC₂H₅ | H | Cl | OCH₃ | CH | |
| SC₂H₅ | H | OCH₃ | N(CH₃)₂ | CH | |
| SC₂H₅ | H | CH₃ | CH₃ | N | |
| SC₂H₅ | H | OCH₃ | CH₃ | N | |
| SC₂H₅ | H | OCH₃ | OCH₃ | N | |
| SC₂H₅ | H | OCH₃ | N(CH₃)₂ | N | |
| SC₂H₅ | H | OCH₃ | OCH₂CF₃ | N | |
| SC₂H₅ | CH₃ | OCH₃ | CH₃ | N | |
| SC₂H₅ | CH₃ | OCH₃ | OCH₃ | N | |
| SC₂H₅ | CH₃ | CH₃ | OCH₃ | CH | |
| SC₂H₅ | CH₃ | OCH₃ | OCH₃ | CH | |
| SC₂H₅ | H | Br | OCH₃ | CH | |
| SC₂H₅ | CH₃ | OCH₃ | N(CH₃)₂ | N | |
| SC₂H₅ | H | CH₃ | OCH₂CF₃ | N | |
| SC₂H₅ | H | OCH₃ | OCH₂CF₃ | CH | |
| SC₂H₅ | H | OCH₃ | C₂H₅ | CH | |
| SC₂H₅ | H | OCH₃ | C₂H₅ | N | |
| SC₂H₅ | H | OCH₃ | NHCH₃ | CH | |
| SC₂H₅ | H | OCH₃ | NHCH₃ | N | |
| SC₂H₅ | H | CH₃ | OC₂H₅ | CH | |
| SC₂H₅ | H | OCH₃ | OC₂H₅ | CH | |
| SC₂H₅ | H | CH₃ | OC₂H₅ | N | |
| SC₂H₅ | H | OCH₃ | OC₂H₅ | N | |
| SC₂H₅ | H | CH₃ | OCH₂CHF₂ | CH | |
| SC₂H₅ | H | OCH₃ | OCH₂CHF₂ | CH | |
| SC₂H₅ | H | CH₃ | OCH₂CHF₂ | N | |
| SC₂H₅ | H | OCH₃ | OCH₂CHF₂ | N | |
| SC₂H₅ | H | CH₃ | OCH₂CH₂F | CH | |

TABLE Ie-continued

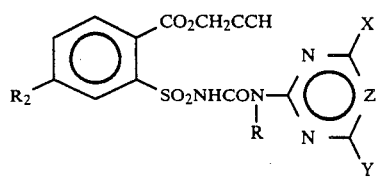

| $R_2$ | R | X | Y | Z | m.p. (°C.) |
|---|---|---|---|---|---|
| $SC_2H_5$ | H | $OCH_3$ | $OCH_2CH_2F$ | CH | |
| $SC_2H_5$ | H | $CH_3$ | $OCH_2CH_2F$ | N | |
| $SC_2H_5$ | $CH_3$ | $OCH_3$ | $OCH_2CH_2F$ | N | |
| $SC_2H_5$ | $CH_3$ | Cl | $OCH_3$ | CH | |
| $SC_2H_5$ | H | Cl | $N(CH_3)_2$ | CH | |
| $SC_2H_5$ | H | Cl | $OC_2H_5$ | CH | |
| $S(CH_2)_5CH_3$ | H | $CH_3$ | $CH_3$ | CH | |
| $S(CH_2)_5CH_3$ | H | $OCH_3$ | $CH_3$ | CH | |
| $S(CH_2)_5CH_3$ | H | $OCH_3$ | $OCH_3$ | CH | |
| $S(CH_2)_5CH_3$ | H | Cl | $OCH_3$ | CH | |
| $S(CH_2)_5CH_3$ | H | $CH_3$ | $CH_3$ | N | |
| $S(CH_2)_5CH_3$ | H | $OCH_3$ | $CH_3$ | N | |
| $S(CH_2)_5CH_3$ | H | $OCH_3$ | $OCH_3$ | N | |
| $S(O)(CH_3)$ | H | $CH_3$ | $CH_3$ | CH | |
| $S(O)(CH_3)$ | H | $OCH_3$ | $CH_3$ | CH | |
| $S(O)(CH_3)$ | H | $OCH_3$ | $OCH_3$ | CH | |
| $S(O)(CH_3)$ | H | Cl | $OCH_3$ | CH | |
| $S(O)(CH_3)$ | H | $OCH_3$ | $N(CH_3)_2$ | CH | |
| $S(O)(CH_3)$ | H | $CH_3$ | $CH_3$ | N | |
| $S(O)(CH_3)$ | H | $OCH_3$ | $CH_3$ | N | |
| $S(O)(CH_3)$ | H | $OCH_3$ | $OCH_3$ | N | |
| $S(O)(CH_3)$ | H | $OCH_3$ | $N(CH_3)_2$ | N | |
| $S(O)(CH_3)$ | H | $OCH_3$ | $OCH_2CF_3$ | N | |
| $S(O)(CH_3)$ | $CH_3$ | $OCH_3$ | $CH_3$ | N | |
| $S(O)(CH_3)$ | $CH_3$ | $OCH_3$ | $OCH_3$ | N | |
| $S(O)(CH_3)$ | $CH_3$ | $CH_3$ | $OCH_3$ | CH | |
| $S(O)(CH_3)$ | $CH_3$ | $OCH_3$ | $OCH_3$ | CH | |
| $S(O)(CH_3)$ | H | Br | $OCH_3$ | CH | |
| $S(O)(CH_3)$ | H | $OCH_3$ | $N(CH_3)_2$ | CH | |
| $S(O)(CH_3)$ | $CH_3$ | $OCH_3$ | $N(CH_3)_2$ | N | |
| $S(O)(CH_3)$ | H | $CH_3$ | $OCH_2CF_3$ | N | |
| $S(O)(CH_3)$ | H | $CH_3$ | $OCH_2CF_3$ | CH | |
| $S(O)(CH_3)$ | H | $OCH_3$ | $OCH_2CF_3$ | CH | |
| $S(O)(CH_3)$ | H | $OCH_3$ | $C_2H_5$ | CH | |
| $S(O)(CH_3)$ | H | $OCH_3$ | $C_2H_5$ | N | |
| $S(O)(CH_3)$ | H | $OCH_3$ | $NHCH_3$ | CH | |
| $S(O)(CH_3)$ | H | $OCH_3$ | $NHCH_3$ | N | |
| $S(O)(CH_3)$ | H | $CH_3$ | $OC_2H_5$ | CH | |
| $S(O)(CH_3)$ | H | $OCH_3$ | $OC_2H_5$ | CH | |
| $S(O)(CH_3)$ | H | $CH_3$ | $OC_2H_5$ | N | |
| $S(O)(CH_3)$ | H | $OCH_3$ | $OC_2H_5$ | N | |
| $S(O)(CH_3)$ | H | $CH_3$ | $OCH_2CHF_2$ | CH | |
| $S(O)(CH_3)$ | H | $OCH_3$ | $OCH_2CHF_2$ | CH | |
| $S(O)(CH_3)$ | H | $CH_3$ | $OCH_2CHF_2$ | N | |
| $S(O)(CH_3)$ | H | $OCH_3$ | $OCH_2CHF_2$ | N | |
| $S(O)(CH_3)$ | H | $CH_3$ | $OCH_2CHF_2$ | CH | |
| $S(O)(CH_3)$ | H | $OCH_3$ | $OCH_2CHF_2$ | CH | |
| $S(O)(CH_3)$ | H | $CH_3$ | $OCH_2CHF_2$ | N | |
| $S(O)(CH_3)$ | H | $OCH_3$ | $OCH_2CHF_2$ | N | |
| $S(O)(CH_3)$ | $CH_3$ | Cl | $OCH_3$ | CH | |
| $S(O)(CH_3)$ | H | Cl | $N(CH_3)_2$ | CH | |
| $S(O)(CH_3)$ | H | Cl | $OC_2H_5$ | CH | |
| $CH_2F$ | H | $CH_3$ | $CH_3$ | CH | |
| $CH_2F$ | H | $OCH_3$ | $CH_3$ | CH | |
| $CH_2F$ | H | $OCH_3$ | $OCH_3$ | CH | |
| $CH_2F$ | H | Cl | $OCH_3$ | CH | |
| $CH_2F$ | H | $OCH_3$ | $N(CH_3)_2$ | CH | |
| $CH_2F$ | H | $CH_3$ | $CH_3$ | N | |
| $CH_2F$ | H | $OCH_3$ | $CH_3$ | N | |
| $CH_2F$ | H | $OCH_3$ | $OCH_3$ | N | |
| $CH_2F$ | H | $OCH_3$ | $N(CH_3)_2$ | N | |
| $CH_2F$ | H | $OCH_3$ | $OCH_2CF_3$ | N | |
| $CH_2F$ | $CH_3$ | $OCH_3$ | $CH_3$ | N | |
| $CH_2F$ | $CH_3$ | $OCH_3$ | $OCH_3$ | N | |
| $CH_2F$ | $CH_3$ | $CH_3$ | $OCH_3$ | CH | |
| $CH_2F$ | $CH_3$ | $OCH_3$ | $OCH_3$ | CH | |
| $CH_2F$ | H | Br | $OCH_3$ | CH | |
| $CH_2F$ | $CH_3$ | $OCH_3$ | $N(CH_3)_2$ | N | |
| $CH_2F$ | H | $CH_3$ | $OCH_2CF_3$ | N | |
| $CH_2F$ | H | $CH_3$ | $OCH_2CF_3$ | CH | |

TABLE Ie-continued

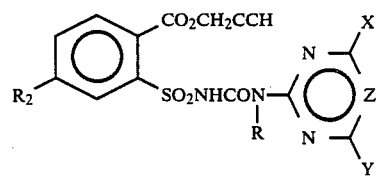

| $R_2$ | R | X | Y | Z | m.p. (°C.) |
|---|---|---|---|---|---|
| $CH_2F$ | H | $OCH_3$ | $OCH_2CF_3$ | CH | |
| $CH_2F$ | H | $OCH_3$ | $C_2H_5$ | CH | |
| $CH_2F$ | H | $OCH_3$ | $C_2H_5$ | N | |
| $CH_2F$ | H | $OCH_3$ | $NHCH_3$ | CH | |
| $CH_2F$ | H | $OCH_3$ | $NHCH_3$ | N | |
| $CH_2F$ | H | $CH_3$ | $OC_2H_5$ | CH | |
| $CH_2F$ | H | $OCH_3$ | $OC_2H_5$ | CH | |
| $CH_2F$ | H | $CH_3$ | $OC_2H_5$ | N | |
| $CH_2F$ | H | $OCH_3$ | $OC_2H_5$ | N | |
| $CH_2F$ | H | $CH_3$ | $OCH_2CHF_2$ | CH | |
| $CH_2F$ | H | $OCH_3$ | $OCH_2CHF_2$ | CH | |
| $CH_2F$ | H | $CH_3$ | $OCH_2CHF_2$ | N | |
| $CH_2F$ | H | $OCH_3$ | $OCH_2CHF_2$ | N | |
| $CH_2F$ | H | $CH_3$ | $OCH_2CH_2F$ | CH | |
| $CH_2F$ | H | $OCH_3$ | $OCH_2CH_2F$ | CH | |
| $CH_2F$ | H | $CH_3$ | $OCH_2CH_2F$ | N | |
| $CH_2F$ | $CH_3$ | $OCH_3$ | $OCH_2CH_2F$ | N | |
| $CH_2F$ | $CH_3$ | Cl | $OCH_3$ | CH | |
| $CH_2F$ | H | Cl | $N(CH_3)_2$ | CH | |
| $CH_2F$ | H | Cl | $OC_2H_5$ | CH | |
| $CH_2OCH_3$ | H | $CH_3$ | $CH_3$ | CH | |
| $CH_2OCH_3$ | H | $OCH_3$ | $CH_3$ | CH | |
| $CH_2OCH_3$ | H | $OCH_3$ | $OCH_3$ | CH | |
| $CH_2OCH_3$ | H | Cl | $OCH_3$ | CH | |
| $CH_2OCH_3$ | H | $OCH_3$ | $N(CH_3)_2$ | CH | |
| $CH_2OCH_3$ | H | $CH_3$ | $CH_3$ | N | |
| $CH_2OCH_3$ | H | $OCH_3$ | $CH_3$ | N | |
| $CH_2OCH_3$ | H | $OCH_3$ | $OCH_3$ | N | |
| $CH_2OCH_3$ | H | $OCH_3$ | $N(CH_3)_2$ | N | |
| $CH_2OCH_3$ | H | $OCH_3$ | $OCH_2CF_3$ | N | |
| $CH_2OCH_3$ | $CH_3$ | $OCH_3$ | $CH_3$ | N | |
| $CH_2OCH_3$ | $CH_3$ | $OCH_3$ | $OCH_3$ | N | |
| $CH_2OCH_3$ | $CH_3$ | $CH_3$ | $OCH_3$ | CH | |
| $CH_2OCH_3$ | $CH_3$ | $OCH_3$ | $OCH_3$ | CH | |
| $CH_2OCH_3$ | H | Br | $OCH_3$ | CH | |
| $CH_2OCH_3$ | H | $OCH_3$ | $N(CH_3)_2$ | CH | |
| $CH_2OCH_3$ | $CH_3$ | $OCH_3$ | $N(CH_3)_2$ | N | |
| $CH_2OCH_3$ | H | $CH_3$ | $OCH_2CF_3$ | N | |
| $CH_2OCH_3$ | H | $CH_3$ | $OCH_2CF_3$ | CH | |
| $CH_2OCH_3$ | H | $OCH_3$ | $OCH_2CF_3$ | CH | |
| $CH_2OCH_3$ | H | $OCH_3$ | $C_2H_5$ | CH | |
| $CH_2OCH_3$ | H | $OCH_3$ | $C_2H_5$ | N | |
| $CH_2OCH_3$ | H | $OCH_3$ | $NHCH_3$ | CH | |
| $CH_2OCH_3$ | H | $OCH_3$ | $NHCH_3$ | N | |
| $CH_2OCH_3$ | H | $CH_3$ | $OC_2H_5$ | CH | |
| $CH_2OCH_3$ | H | $OCH_3$ | $OC_2H_5$ | CH | |
| $CH_2OCH_3$ | H | $CH_3$ | $OC_2H_5$ | N | |
| $CH_2OCH_3$ | H | $OCH_3$ | $OC_2H_5$ | N | |
| $CH_2OCH_3$ | H | $CH_3$ | $OCH_2CHF_2$ | CH | |
| $CH_2OCH_3$ | H | $OCH_3$ | $OCH_2CHF_2$ | CH | |
| $CH_2OCH_3$ | H | $CH_3$ | $OCH_2CHF_2$ | N | |
| $CH_2OCH_3$ | H | $OCH_3$ | $OCH_2CHF_2$ | N | |
| $CH_2OCH_3$ | H | $CH_3$ | $OCH_2CH_2F$ | CH | |
| $CH_2OCH_3$ | H | $OCH_3$ | $OCH_2CH_2F$ | CH | |
| $CH_2OCH_3$ | H | $CH_3$ | $OCH_2CF_3$ | N | |
| $CH_2OCH_3$ | $CH_3$ | $OCH_3$ | $OCH_2CF_3$ | N | |
| $CH_2OCH_3$ | $CH_3$ | Cl | $OCH_3$ | CH | |
| $CH_2OCH_3$ | H | Cl | $N(CH_3)_2$ | CH | |
| $CH_2OCH_3$ | H | Cl | $OC_2H_5$ | CH | |
| $CH_2SCH_3$ | H | $CH_3$ | $CH_3$ | CH | |
| $CH_2SCH_3$ | H | $OCH_3$ | $CH_3$ | CH | |
| $CH_2SCH_3$ | H | $OCH_3$ | $OCH_3$ | CH | |
| $CH_2SCH_3$ | H | Cl | $OCH_3$ | CH | |
| $CH_2SCH_3$ | H | $OCH_3$ | $N(CH_3)_2$ | CH | |
| $CH_2SCH_3$ | H | $CH_3$ | $CH_3$ | N | |
| $CH_2SCH_3$ | H | $OCH_3$ | $CH_3$ | N | |
| $CH_2SCH_3$ | H | $OCH_3$ | $OCH_3$ | N | |
| $CH_2SCH_3$ | H | $OCH_3$ | $N(CH_3)_2$ | N | |
| $CH_2SCH_3$ | H | $OCH_3$ | $OCH_2CF_3$ | N | |
| $CH_2SCH_3$ | $CH_3$ | $OCH_3$ | $CH_3$ | N | |

TABLE Ie-continued

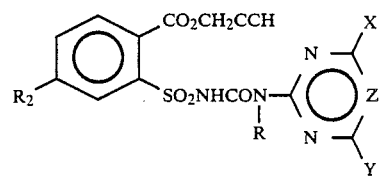

| R₂ | R | X | Y | Z | m.p. (°C.) |
|---|---|---|---|---|---|
| $CH_2SCH_3$ | $CH_3$ | $OCH_3$ | $OCH_3$ | N | |
| $CH_2SCH_3$ | $CH_3$ | $CH_3$ | $OCH_3$ | CH | |
| $CH_2SCH_3$ | $CH_3$ | $OCH_3$ | $OCH_3$ | CH | |
| $CH_2SCH_3$ | H | Br | $OCH_3$ | CH | |
| $CH_2SCH_3$ | $CH_3$ | $OCH_3$ | $N(CH_3)_2$ | N | |
| $CH_2SCH_3$ | H | $CH_3$ | $OCH_2CF_3$ | N | |
| $CH_2SCH_3$ | H | $CH_3$ | $OCH_2CF_3$ | CH | |
| $CH_2SCH_3$ | H | $OCH_3$ | $OCH_2CF_3$ | CH | |
| $CH_2SCH_3$ | H | $OCH_3$ | $C_2H_5$ | CH | |
| $CH_2SCH_3$ | H | $OCH_3$ | $C_2H_5$ | N | |
| $CH_2SCH_3$ | H | $OCH_3$ | $NHCH_3$ | CH | |
| $CH_2SCH_3$ | H | $OCH_3$ | $NHCH_3$ | N | |
| $CH_2SCH_3$ | H | $CH_3$ | $OC_2H_5$ | CH | |
| $CH_2SCH_3$ | H | $OCH_3$ | $OC_2H_5$ | CH | |
| $CH_2SCH_3$ | H | $CH_3$ | $OC_2H_5$ | N | |
| $CH_2SCH_3$ | H | $OCH_3$ | $OC_2H_5$ | N | |
| $CH_2SCH_3$ | H | $CH_3$ | $OCH_2CHF_2$ | CH | |
| $CH_2SCH_3$ | H | $OCH_3$ | $OCH_2CHF_2$ | CH | |
| $CH_2SCH_3$ | H | $CH_3$ | $OCH_2CHF_2$ | N | |
| $CH_2SCH_3$ | H | $OCH_3$ | $OCH_2CHF_2$ | N | |
| $CH_2SCH_3$ | H | $CH_3$ | $OCH_2CH_2F$ | CH | |
| $CH_2SCH_3$ | H | $OCH_3$ | $OCH_2CH_2F$ | CH | |
| $CH_2SCH_3$ | H | $CH_3$ | $OCH_2CH_2F$ | N | |
| $CH_2SCH_3$ | $CH_3$ | $OCH_3$ | $OCH_2CH_2F$ | N | |
| $CH_2SCH_3$ | $CH_3$ | Cl | $OCH_3$ | CH | |
| $CH_2SCH_3$ | H | Cl | $N(CH_3)_2$ | CH | |
| $CH_2SCH_3$ | H | Cl | $OC_2H_5$ | CH | |
| $OCF_2H$ | H | $CH_3$ | $CH_3$ | CH | |
| $OCF_2H$ | H | $OCH_3$ | $CH_3$ | CH | |
| $OCF_2H$ | H | $OCH_3$ | $OCH_3$ | CH | |
| $OCF_2H$ | H | Cl | $OCH_3$ | CH | |
| $OCF_2H$ | H | $OCH_3$ | $N(CH_3)_2$ | CH | |
| $OCF_2H$ | H | $CH_3$ | $CH_3$ | N | |
| $OCF_2H$ | H | $OCH_3$ | $CH_3$ | N | |
| $OCF_2H$ | H | $OCH_3$ | $OCH_3$ | N | |
| $OCF_2H$ | H | $OCH_3$ | $N(CH_3)_2$ | N | |
| $OCF_2H$ | H | $OCH_3$ | $OCH_2CF_3$ | N | |
| $OCF_2H$ | $CH_3$ | $OCH_3$ | $CH_3$ | N | |
| $OCF_2H$ | $CH_3$ | $OCH_3$ | $OCH_3$ | N | |
| $OCF_2H$ | $CH_3$ | $CH_3$ | $OCH_3$ | CH | |
| $OCF_2H$ | $CH_3$ | $OCH_3$ | $OCH_3$ | CH | |
| $OCF_2H$ | H | Br | $OCH_3$ | CH | |
| $OCF_2H$ | $CH_3$ | $OCH_3$ | $N(CH_3)_2$ | N | |
| $OCF_2H$ | H | $CH_3$ | $OCH_2CF_3$ | N | |
| $OCF_2H$ | H | $CH_3$ | $OCH_2CF_3$ | CH | |
| $OCF_2H$ | H | $OCH_3$ | $OCH_2CF_3$ | CH | |
| $OCF_2H$ | H | $OCH_3$ | $C_2H_5$ | CH | |
| $OCF_2H$ | H | $OCH_3$ | $C_2H_5$ | N | |
| $OCF_2H$ | H | $OCH_3$ | $NHCH_3$ | CH | |
| $OCF_2H$ | H | $OCH_3$ | $NHCH_3$ | N | |
| $OCF_2H$ | H | $CH_3$ | $OC_2H_5$ | CH | |
| $OCF_2H$ | H | $OCH_3$ | $OC_2H_5$ | CH | |
| $OCF_2H$ | H | $CH_3$ | $OC_2H_5$ | N | |
| $OCF_2H$ | H | $OCH_3$ | $OC_2H_5$ | N | |
| $OCF_2H$ | H | $CH_3$ | $OCH_2CHF_2$ | CH | |
| $OCF_2H$ | H | $OCH_3$ | $OCH_2CHF_2$ | CH | |
| $OCF_2H$ | H | $CH_3$ | $OCH_2CHF_2$ | N | |
| $OCF_2H$ | H | $OCH_3$ | $OCH_2CHF_2$ | N | |
| $OCF_2H$ | H | $CH_3$ | $OCH_2CH_2F$ | CH | |
| $OCF_2H$ | H | $OCH_3$ | $OCH_2CH_2F$ | CH | |
| $OCF_2H$ | H | $CH_3$ | $OCH_2CH_2F$ | N | |
| $OCF_2H$ | $CH_3$ | $OCH_3$ | $OCH_2CH_2F$ | N | |
| $OCF_2H$ | $CH_3$ | Cl | $OCH_3$ | CH | |
| $OCF_2H$ | H | Cl | $N(CH_3)_2$ | CH | |
| $OCF_2H$ | H | Cl | $OC_2H_5$ | CH | |
| $OCH_2CF_3$ | H | $CH_3$ | $CH_3$ | CH | |
| $OCH_2CF_3$ | H | $OCH_3$ | $CH_3$ | CH | |
| $OCH_2CF_3$ | H | $OCH_3$ | $OCH_3$ | CH | |
| $OCH_2CF_3$ | H | Cl | $OCH_3$ | CH | |
| $OCH_2CF_3$ | H | $OCH_3$ | $N(CH_3)_2$ | CH | |

TABLE Ie-continued

[Structure: benzene ring with CO₂CH₂CCH group, R₂ substituent, SO₂NHCON(R)- linked to a 6-membered heterocycle with N, X, Z, Y, N positions]

| R₂ | R | X | Y | Z | m.p. (°C.) |
|---|---|---|---|---|---|
| OCH₂CF₃ | H | CH₃ | CH₃ | N | |
| OCH₂CF₃ | H | OCH₃ | CH₃ | N | |
| OCH₂CF₃ | H | OCH₃ | OCH₃ | N | |
| OCH₂CF₃ | H | OCH₃ | N(CH₃)₂ | N | |
| OCH₂CF₃ | H | OCH₃ | OCH₂CF₃ | N | |
| OCH₂CF₃ | H | OC₂H₅ | NHCH₃ | N | |
| OCH₂CF₃ | CH₃ | OCH₃ | CH₃ | N | |
| OCH₂CF₃ | CH₃ | OCH₃ | OCH₃ | N | |
| OCH₂CF₃ | CH₃ | CH₃ | OCH₃ | CH | |
| OCH₂CF₃ | CH₃ | OCH₃ | OCH₃ | CH | |
| OCH₂CF₃ | H | Br | OCH₃ | CH | |
| OCH₂CF₃ | CH₃ | OCH₃ | N(CH₃)₂ | N | |
| OCH₂CF₃ | H | CH₃ | OCH₂CF₃ | N | |
| OCH₂CF₃ | H | CH₃ | OCH₂CF₃ | CH | |
| OCH₂CF₃ | H | OCH₃ | OCH₂CF₃ | CH | |
| OCH₂CF₃ | H | OCH₃ | C₂H₅ | CH | |
| OCH₂CF₃ | H | OCH₃ | C₂H₅ | N | |
| OCH₂CF₃ | H | OCH₃ | NHCH₃ | CH | |
| OCH₂CF₃ | H | OCH₃ | NHCH₃ | N | |
| OCH₂CF₃ | H | CH₃ | OC₂H₅ | CH | |
| OCH₂CF₃ | H | OCH₃ | OC₂H₅ | CH | |
| OCH₂CF₃ | H | CH₃ | OC₂H₅ | N | |
| OCH₂CF₃ | H | OCH₃ | OC₂5 | N | |
| OCH₂CF₃ | H | CH₃ | OCH₂CHF₂ | CH | |
| OCH₂CF₃ | H | OCH₃ | OCH₂CHF₂ | CH | |
| OCH₂CF₃ | H | CH₃ | OCH₂CHF₂ | N | |
| OCH₂CF₃ | H | OCH₃ | OCH₂CHF₂ | N | |
| OCH₂CF₃ | H | CH₃ | OCH₂CH₂F | CH | |
| OCH₂CF₃ | H | OCH₃ | OCH₂CH₂F | CH | |
| OCH₂CF₃ | H | CH₃ | OCH₂CH₂F | N | |
| OCH₂CF₃ | CH₃ | OCH₃ | OCH₂CH₂F | N | |
| OCH₂CF₃ | CH₃ | Cl | OCH₃ | CH | |
| OCH₂CF₃ | H | Cl | N(CH₃)₂ | CH | |
| OCH₂CF₃ | H | Cl | OC₂H₅ | CH | |
| OCH₂CH₂OCH₃ | H | CH₃ | CH₃ | CH | |
| OCH₂CH₂OCH₃ | H | OCH₃ | CH₃ | CH | |
| OCH₂CH₂OCH₃ | H | OCH₃ | OCH₃ | CH | |
| OCH₂CH₂OCH₃ | H | Cl | OCH₃ | CH | |
| OCH₂CH₂OCH₃ | H | OCH₃ | N(CH₃)₂ | CH | |
| OCH₂CH₂OCH₃ | H | CH₃ | CH₃ | N | |
| OCH₂CH₂OCH₃ | H | OCH₃ | CH₃ | N | |
| OCH₂CH₂OCH₃ | H | OCH₃ | OCH₃ | N | |
| OCH₂CH₂OCH₃ | H | OCH₃ | N(CH₃)₂ | N | |
| OCH₂CH₂OCH₃ | H | OCH₃ | OCH₂CF₃ | N | |
| OCH₂CH₂OCH₃ | CH₃ | OCH₃ | CH₃ | N | |
| OCH₂CH₂OCH₃ | CH₃ | OCH₃ | OCH₃ | N | |
| OCH₂CH₂OCH₃ | CH₃ | CH₃ | OCH₃ | CH | |
| OCH₂CH₂OCH₃ | CH₃ | OCH₃ | OCH₃ | CH | |
| OCH₂CH₂OCH₃ | H | Br | OCH₃ | CH | |
| OCH₂CH₂OCH₃ | H | CH₃ | OCH₂CF₃ | N | |
| OCH₂CH₂OCH₃ | H | CH₃ | OCH₂CF₃ | CH | |
| OCH₂CH₂OCH₃ | H | OCH₃ | OCH₂CF₃ | CH | |
| OCH₂CH₂OCH₃ | H | OCH₃ | C₂H₅ | CH | |
| OCH₂CH₂OCH₃ | H | OCH₃ | C₂H₅ | N | |
| OCH₂CH₂OCH₃ | H | OCH₃ | NHCH₃ | CH | |
| OCH₂CH₂OCH₃ | H | OCH₃ | NHCH₃ | N | |
| OCH₂CH₂OCH₃ | H | CH₃ | OC₂H₅ | CH | |
| OCH₂CH₂OCH₃ | H | OCH₃ | OC₂H₅ | CH | |
| OCH₂CH₂OCH₃ | H | CH₃ | OC₂H₅ | N | |
| OCH₂CH₂OCH₃ | H | OCH₃ | OC₂H₅ | N | |
| OCH₂CH₂OCH₃ | H | CH₃ | OCH₂CHF₂ | CH | |
| OCH₂CH₂OCH₃ | H | OCH₃ | OCH₂CHF₂ | CH | |
| OCH₂CH₂OCH₃ | H | CH₃ | OCH₂CHF₂ | N | |
| OCH₂CH₂OCH₃ | H | OCH₃ | OCH₂CHF₂ | N | |
| OCH₂CH₂OCH₃ | H | CH₃ | OCH₂CH₂F | CH | |
| OCH₂CH₂OCH₃ | H | OCH₃ | OCH₂CH₂F | CH | |
| OCH₂CH₂OCH₃ | H | CH₃ | OCH₂CF₃ | N | |
| OCH₂CH₂OCH₃ | CH₃ | OCH₃ | OCH₂CF₃ | N | |
| OCH₂CH₂OCH₃ | CH₃ | Cl | OCH₃ | CH | |
| OCH₂CH₂OCH₃ | H | Cl | N(CH₃)₂ | CH | |

TABLE Ie-continued

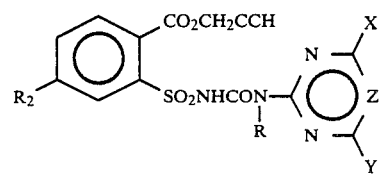

| R₂ | R | X | Y | Z | m.p. (°C.) |
|---|---|---|---|---|---|
| OCH₂CH₂OCH₃ | H | Cl | OC₂H₅ | CH | |
| O-cyclopropyl | H | CH₃ | CH₃ | CH | |
| O-cyclopropyl | H | OCH₃ | CH₃ | CH | |
| O-cyclopropyl | H | OCH₃ | OCH₃ | CH | |
| O-cyclopropyl | H | Cl | OCH₃ | CH | |
| O-cyclopropyl | H | OCH₃ | N(CH₃)₂ | CH | |
| O-cyclopropyl | H | OCH₃ | CH₃ | N | |
| O-cyclopropyl | H | OCH₃ | CH₃ | N | |
| O-cyclopropyl | H | OCH₃ | OCH₃ | N | |
| O-cyclopropyl | H | OCH₃ | N(CH₃)₂ | N | |
| O-cyclopropyl | H | OCH₃ | OCH₂CF₃ | N | |
| O-cyclopropyl | CH₃ | OCH₃ | CH₃ | N | |
| O-cyclopropyl | CH₃ | OCH₃ | OCH₃ | N | |
| O-cyclopropyl | CH₃ | CH₃ | OCH₃ | CH | |
| O-cyclopropyl | CH₃ | OCH₃ | OCH₃ | CH | |
| O-cyclopropyl | H | Br | OCH₃ | CH | |
| O-cyclopropyl | CH₃ | OCH₃ | N(CH₃)₂ | N | |
| O-cyclopropyl | H | CH₃ | OCH₂CF₃ | N | |
| O-cyclopropyl | H | CH₃ | OCH₂CF₃ | CH | |
| O-cyclopropyl | H | OCH₃ | OCH₂CF₃ | CH | |
| O-cyclopropyl | H | OCH₃ | C₂H₅ | CH | |
| O-cyclopropyl | H | OCH₃ | C₂H₅ | N | |
| O-cyclopropyl | H | OCH₃ | NHCH₃ | CH | |
| O-cyclopropyl | H | OCH₃ | NHCH₃ | N | |
| O-cyclopropyl | H | CH₃ | OC₂H₅ | CH | |
| O-cyclopropyl | H | OCH₃ | OC₂H₅ | CH | |
| O-cyclopropyl | H | CH₃ | OC₂H₅ | N | |
| O-cyclopropyl | H | OCH₃ | OC₂H₅ | N | |
| O-cyclopropyl | H | CH₃ | OCH₂CHF₂ | CH | |
| O-cyclopropyl | H | OCH₃ | OCH₂CHF₂ | CH | |
| O-cyclopropyl | H | CH₃ | OCH₂CHF₂ | N | |
| O-cyclopropyl | H | OCH₃ | OCH₂CHF₂ | N | |
| O-cyclopropyl | H | CH₃ | OCH₂CH₂F | CH | |
| O-cyclopropyl | H | OCH₃ | OCH₂CH₂F | CH | |
| O-cyclopropyl | H | CH₃ | OCH₂CH₂F | N | |
| O-cyclopropyl | CH₃ | OCH₃ | OCH₂CH₂F | N | |
| O-cyclopropyl | CH₃ | Cl | OCH₃ | CH | |
| O-cyclopropyl | H | Cl | N(CH₃)₂ | CH | |
| O-cyclopropyl | H | Cl | OC₂H₅ | CH | |
| NHCH₂CHF₂ | H | OCH₃ | CH₃ | N | |
| NHCH₂CHF₂ | H | OCH₃ | OCH₃ | CH | |
| NHCH₂CHF₂ | H | OCH₃ | CH₃ | CH | |
| NHCH₂CHF₂ | H | OCH₃ | Cl | CH | |
| NHCH₂CHF₂ | H | CH₃ | CH₃ | CH | |
| NHCH₂CHF₂ | H | OCH₃ | OCH₃ | N | |
| NHCH₃ | H | OCH₃ | OCH₃ | CH | |
| NHCH₃ | H | OCH₃ | CH₃ | CH | |
| NHCH₃ | H | OCH₃ | Cl | CH | |
| NHCH₃ | H | CH₃ | CH₃ | CH | |
| NHCH₃ | H | OCH₃ | OCH₃ | N | |

TABLE If

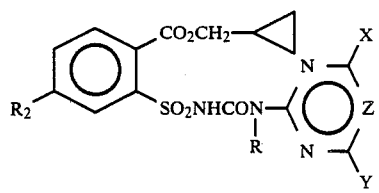

| R₂ | R | X | Y | Z | m.p. (°C.) |
|---|---|---|---|---|---|
| OC₂H₅ | H | CH₃ | CH₃ | CH | |
| OC₂H₅ | H | OCH₃ | CH₃ | CH | |
| OC₂H₅ | H | OCH₃ | OCH₃ | CH | |
| OC₂H₅ | H | Cl | OCH₃ | CH | |
| OC₂H₅ | H | OCH₃ | N(CH₃)₂ | CH | |
| OC₂H₅ | H | CH₃ | CH₃ | N | |
| OC₂H₅ | H | OCH₃ | CH₃ | N | |
| OC₂H₅ | H | OCH₃ | OCH₃ | N | |
| OC₂H₅ | H | OCH₃ | N(CH₃)₂ | N | |
| OC₂H₅ | H | OCH₃ | OCH₂CF₃ | N | |
| OC₂H₅ | CH₃ | OCH₃ | CH₃ | N | |
| OC₂H₅ | CH₃ | OCH₃ | OCH₃ | N | |
| OC₂H₅ | CH₃ | CH₃ | OCH₃ | CH | |
| OC₂H₅ | CH₃ | OCH₃ | OCH₃ | CH | |
| OC₂H₅ | H | Br | OCH₃ | CH | |
| OC₂H₅ | CH₃ | OCH₃ | N(CH₃)₂ | N | |
| OC₂H₅ | H | CH₃ | OCH₂CF₃ | N | |
| OC₂H₅ | H | CH₃ | OCH₂CF₃ | CH | |
| OC₂H₅ | H | OCH₃ | OCH₂CF₃ | CH | |
| OC₂H₅ | H | OCH₃ | C₂H₅ | CH | |
| OC₂H₅ | H | OCH₃ | C₂H₅ | N | |
| OC₂H₅ | H | OCH₃ | NHCH₃ | CH | |
| OC₂H₅ | H | OCH₃ | NHCH₃ | N | |
| OC₂H₅ | H | CH₃ | OC₂H₅ | CH | |
| OC₂H₅ | H | OCH₃ | OC₂H₅ | CH | |
| OC₂H₅ | H | CH₃ | OC₂H₅ | N | |
| OC₂H₅ | H | OCH₃ | OC₂H₅ | N | |
| OC₂H₅ | H | CH₃ | OCH₂CHF₂ | CH | |
| OC₂H₅ | H | OCH₃ | OCH₂CHF₂ | CH | |
| OC₂H₅ | H | CH₃ | OCH₂CHF₂ | N | |
| OC₂H₅ | H | OCH₃ | OCH₂CHF₂ | N | |
| OC₂H₅ | H | CH₃ | OCH₂CH₂F | CH | |
| OC₂H₅ | H | OCH₃ | OCH₂CH₂F | CH | |
| OC₂H₅ | H | CH₃ | OCH₂CH₂F | N | |
| OC₂H₅ | CH₃ | OCH₃ | OCH₂CH₂F | N | |
| OC₂H₅ | CH₃ | Cl | OCH₃ | CH | |
| OC₂H₅ | H | Cl | N(CH₃)₂ | CH | |
| OC₂H₅ | H | Cl | OC₂H₅ | CH | |
| SC₂H₅ | H | CH₃ | CH₃ | CH | |
| SC₂H₅ | H | OCH₃ | CH₃ | CH | |
| SC₂H₅ | H | OCH₃ | OCH₃ | CH | |
| SC₂H₅ | H | Cl | OCH₃ | CH | |
| SC₂H₅ | H | OCH₃ | N(CH₃)₂ | CH | |
| SC₂H₅ | H | CH₃ | CH₃ | N | |
| SC₂H₅ | H | OCH₃ | CH₃ | N | |
| SC₂H₅ | H | OCH₃ | OCH₃ | N | |
| SC₂H₅ | H | OCH₃ | N(CH₃)₂ | N | |
| SC₂H₅ | H | OCH₃ | OCH₂CF₃ | N | |
| SC₂H₅ | CH₃ | OCH₃ | CH₃ | N | |
| SC₂H₅ | CH₃ | OCH₃ | OCH₃ | N | |
| SC₂H₅ | CH₃ | CH₃ | OCH₃ | CH | |
| SC₂H₅ | CH₃ | OCH₃ | OCH₃ | CH | |
| SC₂H₅ | H | Br | OCH₃ | CH | |
| SC₂H₅ | CH₃ | OCH₃ | N(CH₃)₂ | N | |
| SC₂H₅ | H | CH₃ | OCH₂CF₃ | N | |
| SC₂H₅ | H | CH₃ | OCH₂CF₃ | CH | |
| SC₂H₅ | H | OCH₃ | OCH₂CF₃ | CH | |
| SC₂H₅ | H | OCH₃ | C₂H₅ | CH | |
| SC₂H₅ | H | OCH₃ | C₂H₅ | N | |
| SC₂H₅ | H | OCH₃ | NHCH₃ | CH | |
| SC₂H₅ | H | OCH₃ | NHCH₃ | N | |
| SC₂H₅ | H | CH₃ | OC₂H₅ | CH | |
| SC₂H₅ | H | OCH₃ | OC₂H₅ | CH | |
| SC₂H₅ | H | CH₃ | OC₂H₅ | N | |
| SC₂H₅ | H | OCH₃ | OC₂H₅ | N | |
| SC₂H₅ | H | CH₃ | OCH₂CHF₂ | CH | |
| SC₂H₅ | H | OCH₃ | OCH₂CHF₂ | CH | |
| SC₂H₅ | H | CH₃ | OCH₂CHF₂ | N | |
| SC₂H₅ | H | OCH₃ | OCH₂CHF₂ | N | |

TABLE If-continued

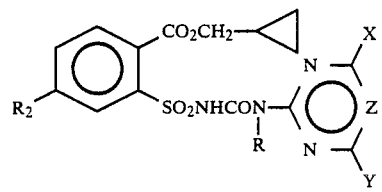

| R₂ | R | X | Y | Z | m.p. (°C.) |
|---|---|---|---|---|---|
| SC₂H₅ | H | CH₃ | OCH₂CH₂F | CH | |
| SC₂H₅ | H | OCH₃ | OCH₂CH₂F | CH | |
| SC₂H₅ | H | CH₃ | OCH₂CH₂F | N | |
| SC₂H₅ | CH₃ | OCH₃ | OCH₂CH₂F | N | |
| SC₂H₅ | CH₃ | Cl | OCH₃ | CH | |
| SC₂H₅ | H | Cl | N(CH₃)₂ | CH | |
| SC₂H₅ | H | Cl | OC₂H₅ | CH | |
| S(CH₂)₅CH₃ | H | CH₃ | CH₃ | CH | |
| S(CH₂)₅CH₃ | H | OCH₃ | CH₃ | CH | |
| S(CH₂)₅CH₃ | H | OCH₃ | OCH₃ | CH | |
| S(CH₂)₅CH₃ | H | Cl | OCH₃ | CH | |
| S(CH₂)₅CH₃ | H | CH₃ | CH₃ | N | |
| S(CH₂)₅CH₃ | H | OCH₃ | CH₃ | N | |
| S(CH₂)₅CH₃ | H | OCH₃ | OCH₃ | N | |
| S(O)(CH₃) | H | CH₃ | CH₃ | CH | |
| S(O)(CH₃) | H | OCH₃ | CH₃ | CH | |
| S(O)(CH₃) | H | OCH₃ | OCH₃ | CH | |
| S(O)(CH₃) | H | Cl | OCH₃ | CH | |
| S(O)(CH₃) | H | OCH₃ | N(CH₃)₂ | CH | |
| S(O)(CH₃) | H | CH₃ | CH₃ | N | |
| S(O)(CH₃) | H | OCH₃ | CH₃ | N | |
| S(O)(CH₃) | H | OCH₃ | OCH₃ | N | |
| S(O)(CH₃) | H | OCH₃ | N(CH₃)₂ | N | |
| S(O)(CH₃) | H | OCH₃ | OCH₂CF₃ | N | |
| S(O)(CH₃) | CH₃ | OCH₃ | CH₃ | N | |
| S(O)(CH₃) | CH₃ | OCH₃ | OCH₃ | N | |
| S(O)(CH₃) | CH₃ | CH₃ | OCH₃ | CH | |
| S(O)(CH₃) | CH₃ | OCH₃ | OCH₃ | CH | |
| S(O)(CH₃) | H | Br | OCH₃ | CH | |
| S(O)(CH₃) | H | OCH₃ | N(CH₃)₂ | CH | |
| S(O)(CH₃) | CH₃ | OCH₃ | N(CH₃)₂ | N | |
| S(O)(CH₃) | H | CH₃ | OCH₂CF₃ | N | |
| S(O)(CH₃) | H | CH₃ | OCH₂CF₃ | CH | |
| S(O)(CH₃) | H | OCH₃ | OCH₂CF₃ | CH | |
| S(O)(CH₃) | H | OCH₃ | C₂H₅ | CH | |
| S(O)(CH₃) | H | OCH₃ | C₂H₅ | N | |
| S(O)(CH₃) | H | OCH₃ | NHCH₃ | CH | |
| S(O)(CH₃) | H | OCH₃ | NHCH₃ | N | |
| S(O)(CH₃) | H | CH₃ | OC₂H₅ | CH | |
| S(O)(CH₃) | H | OCH₃ | OC₂H₅ | CH | |
| S(O)(CH₃) | H | CH₃ | OC₂H₅ | N | |
| S(O)(CH₃) | H | OCH₃ | OC₂H₅ | N | |
| S(O)(CH₃) | H | CH₃ | OCH₂CHF₂ | CH | |
| S(O)(CH₃) | H | OCH₃ | OCH₂CHF₂ | CH | |
| S(O)(CH₃) | H | CH₃ | OCH₂CHF₂ | N | |
| S(O)(CH₃) | H | OCH₃ | OCH₂CHF₂ | N | |
| S(O)(CH₃) | H | CH₃ | OCH₂CHF₂ | CH | |
| S(O)(CH₃) | H | OCH₃ | OCH₂CHF₂ | CH | |
| S(O)(CH₃) | H | CH₃ | OCH₂CHF₂ | N | |
| S(O)(CH₃) | H | OCH₃ | OCH₂CHF₂ | N | |
| S(O)(CH₃) | CH₃ | Cl | OCH₃ | CH | |
| S(O)(CH₃) | H | Cl | N(CH₃)₂ | CH | |
| S(O)(CH₃) | H | Cl | OC₂H₅ | CH | |
| OCH₂CH=CH₂ | H | CH₃ | CH₃ | CH | |
| OCH₂CH=CH₂ | H | OCH₃ | CH₃ | CH | |
| OCH₂CH=CH₂ | H | OCH₃ | OCH₃ | CH | |
| OCH₂CH=CH₂ | H | Cl | OCH₃ | CH | |
| OCH₂CH=CH₂ | H | OCH₃ | N(CH₃)₂ | CH | |
| OCH₂CH=CH₂ | H | CH₃ | CH₃ | N | |
| OCH₂CH=CH₂ | H | OCH₃ | CH₃ | N | |
| OCH₂CH=CH₂ | H | OCH₃ | OCH₃ | N | |
| OCH₂CH=CH₂ | H | OCH₃ | N(CH₃)₂ | N | |
| OCH₂CH=CH₂ | H | OCH₃ | OCH₂CF₃ | N | |
| OCH₂CH=CH₂ | CH₃ | OCH₃ | CH₃ | N | |
| OCH₂CH=CH₂ | CH₃ | OCH₃ | OCH₃ | N | |
| OCH₂CH=CH₂ | CH₃ | CH₃ | OCH₃ | CH | |
| OCH₂CH=CH₂ | CH₃ | OCH₃ | OCH₃ | CH | |
| OCH₂CH=CH₂ | H | Br | OCH₃ | CH | |
| OCH₂CH=CH₂ | CH₃ | OCH₃ | N(CH₃)₂ | N | |

TABLE If-continued

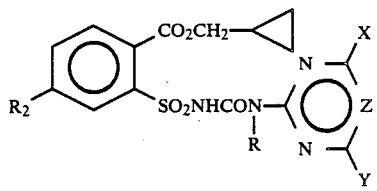

| R₂ | R | X | Y | Z | m.p. (°C.) |
|---|---|---|---|---|---|
| OCH₂CH=CH₂ | H | CH₃ | OCH₂CF₃ | N | |
| OCH₂CH=CH₂ | H | CH₃ | OCH₂CF₃ | CH | |
| OCH₂CH=CH₂ | H | OCH₃ | OCH₂CF₃ | CH | |
| OCH₂CH=CH₂ | H | OCH₃ | C₂H₅ | CH | |
| OCH₂CH=CH₂ | H | OCH₃ | C₂H₅ | N | |
| OCH₂CH=CH₂ | H | OCH₃ | NHCH₃ | CH | |
| OCH₂CH=CH₂ | H | OCH₃ | NHCH₃ | N | |
| OCH₂CH=CH₂ | H | CH₃ | OC₂H₅ | CH | |
| OCH₂CH=CH₂ | H | OCH₃ | OC₂H₅ | CH | |
| OCH₂CH=CH₂ | H | CH₃ | OC₂H₅ | N | |
| OCH₂CH=CH₂ | H | OCH₃ | OC₂H₅ | N | |
| OCH₂CH=CH₂ | H | CH₃ | OCH₂CHF₂ | CH | |
| OCH₂CH=CH₂ | H | OCH₃ | OCH₂CHF₂ | CH | |
| OCH₂CH=CH₂ | H | CH₃ | OCH₂CHF₂ | N | |
| OCH₂CH=CH₂ | H | OCH₃ | OCH₂CHF₂ | N | |
| OCH₂CH=CH₂ | H | CH₃ | OCH₂CH₂F | CH | |
| OCH₂CH=CH₂ | H | OCH₃ | OCH₂CH₂F | CH | |
| OCH₂CH=CH₂ | H | CH₃ | OCH₂CH₂F | N | |
| OCH₂CH=CH₂ | CH₃ | OCH₃ | OCH₂CH₂F | N | |
| OCH₂CH=CH₂ | CH₃ | Cl | OCH₃ | CH | |
| OCH₂CH=CH₂ | H | Cl | N(CH₃)₂ | CH | |
| OCH₂CH=CH₂ | H | Cl | OC₂H₅ | CH | |
| OCH₂C≡CH | H | CH₃ | CH₃ | CH | |
| OCH₂C≡CH | H | OCH₃ | CH₃ | CH | |
| OCH₂C≡CH | H | OCH₃ | OCH₃ | CH | |
| OCH₂C≡CH | H | Cl | OCH₃ | CH | |
| OCH₂C≡CH | H | OCH₃ | N(CH₃)₂ | CH | |
| OCH₂C≡CH | H | CH₃ | CH₃ | N | |
| OCH₂C≡CH | H | OCH₃ | CH₃ | N | |
| OCH₂C≡CH | H | OCH₃ | OCH₃ | N | |
| OCH₂C≡CH | H | OCH₃ | N(CH₃)₂ | N | |
| OCH₂C≡CH | H | OCH₃ | OCH₂CF₃ | N | |
| OCH₂C≡CH | CH₃ | OCH₃ | CH₃ | N | |
| OCH₂C≡CH | CH₃ | OCH₃ | OCH₃ | N | |
| OCH₂C≡CH | CH₃ | CH₃ | OCH₃ | CH | |
| OCH₂C≡CH | CH₃ | OCH₃ | OCH₃ | CH | |
| OCH₂C≡CH | H | Br | OCH₃ | CH | |
| OCH₂C≡CH | CH₃ | OCH₃ | N(CH₃)₂ | N | |
| OCH₂C≡CH | H | CH₃ | OCH₂CF₃ | N | |
| OCH₂C≡CH | H | CH₃ | OCH₂CF₃ | CH | |
| OCH₂C≡CH | H | OCH₃ | OCH₂CF₃ | CH | |
| OCH₂C≡CH | H | OCH₃ | C₂H₅ | CH | |
| OCH₂C≡CH | H | OCH₃ | C₂H₅ | N | |
| OCH₂C≡CH | H | OCH₃ | NHCH₃ | CH | |
| OCH₂C≡CH | H | OCH₃ | NHCH₃ | N | |
| OCH₂C≡CH | H | CH₃ | OC₂H₅ | CH | |
| OCH₂C≡CH | H | OCH₃ | OC₂H₅ | CH | |
| OCH₂C≡CH | H | CH₃ | OC₂H₅ | N | |
| OCH₂C≡CH | H | OCH₃ | OC₂H₅ | N | |
| OCH₂C≡CH | H | CH₃ | OCH₂CHF₂ | CH | |
| OCH₂C≡CH | H | OCH₃ | OCH₂CHF₂ | CH | |
| OCH₂C≡CH | H | CH₃ | OCH₂CHF₂ | N | |
| OCH₂C≡CH | H | OCH₃ | OCH₂CHF₂ | N | |
| OCH₂C≡CH | H | CH₃ | OCH₂CH₂F | CH | |
| OCH₂C≡CH | H | OCH₃ | OCH₂CH₂F | CH | |
| OCH₂C≡CH | H | CH₃ | OCH₂CF₃ | N | |
| OCH₂C≡CH | CH₃ | OCH₃ | OCH₂CF₃ | N | |
| OCH₂C≡CH | CH₃ | Cl | OCH₃ | CH | |
| OCH₂C≡CH | H | Cl | N(CH₃)₂ | CH | |
| OCH₂C≡CH | H | Cl | OC₂H₅ | CH | |
| SCH₂CH=CH₂ | H | CH₃ | CH₃ | CH | |
| SCH₂CH=CH₂ | H | OCH₃ | CH₃ | CH | |
| SCH₂CH=CH₂ | H | OCH₃ | OCH₃ | CH | |
| SCH₂CH=CH₂ | H | Cl | OCH₃ | CH | |
| SCH₂CH=CH₂ | H | OCH₃ | N(CH₃)₂ | N | |
| SCH₂CH=CH₂ | H | CH₃ | CH₃ | N | |
| SCH₂CH=CH₂ | H | OCH₃ | CH₃ | N | |
| SCH₂CH=CH₂ | H | OCH₃ | OCH₃ | N | |
| SCH₂CH=CH₂ | H | OCH₃ | N(CH₃)₂ | N | |

TABLE If-continued

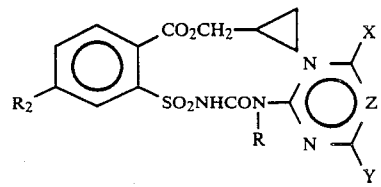

| $R_2$ | R | X | Y | Z | m.p. (°C.) |
|---|---|---|---|---|---|
| $SCH_2CH=CH_2$ | H | $OCH_3$ | $OCH_2CF_3$ | N | |
| $SCH_2CH=CH_2$ | $CH_3$ | $OCH_3$ | $CH_3$ | N | |
| $SCH_2CH=CH_2$ | $CH_3$ | $OCH_3$ | $OCH_3$ | N | |
| $SCH_2CH=CH_2$ | $CH_3$ | $CH_3$ | $OCH_3$ | CH | |
| $SCH_2CH=CH_2$ | $CH_3$ | $OCH_3$ | $OCH_3$ | CH | |
| $SCH_2CH=CH_2$ | H | Br | $OCH_3$ | CH | |
| $SCH_2CH=CH_2$ | $CH_3$ | $OCH_3$ | $N(CH_3)_2$ | N | |
| $SCH_2CH=CH_2$ | H | $CH_3$ | $OCH_2CF_3$ | N | |
| $SCH_2CH=CH_2$ | H | $CH_3$ | $OCH_2CF_3$ | CH | |
| $SCH_2CH=CH_2$ | H | $OCH_3$ | $OCH_2CF_3$ | CH | |
| $SCH_2CH=CH_2$ | H | $OCH_3$ | $C_2H_5$ | CH | |
| $SCH_2CH=CH_2$ | H | $OCH_3$ | $C_2H_5$ | CH | |
| $SCH_2CH=CH_2$ | H | $OCH_3$ | $NHCH_3$ | CH | |
| $SCH_2CH=CH_2$ | H | $OCH_3$ | $NHCH_3$ | N | |
| $SCH_2CH=CH_2$ | H | $CH_3$ | $OC_2H_5$ | CH | |
| $SCH_2CH=CH_2$ | H | $OCH_3$ | $OC_2H_5$ | CH | |
| $SCH_2CH=CH_2$ | H | $CH_3$ | $OC_2H_5$ | N | |
| $SCH_2CH=CH_2$ | H | $OCH_3$ | $OC_2H_5$ | N | |
| $SCH_2CH=CH_2$ | H | $CH_3$ | $OCH_2CHF_2$ | CH | |
| $SCH_2CH=CH_2$ | H | $OCH_3$ | $OCH_2CHF_2$ | CH | |
| $SCH_2CH=CH_2$ | H | $CH_3$ | $OCH_2CHF_2$ | N | |
| $SCH_2CH=CH_2$ | H | $OCH_3$ | $OCH_2CHF_2$ | N | |
| $SCH_2CH=CH_2$ | H | $CH_3$ | $OCH_2CH_2F$ | CH | |
| $SCH_2CH=CH_2$ | H | $OCH_3$ | $OCH_2CH_2F$ | CH | |
| $SCH_2CH=CH_2$ | H | $CH_3$ | $OCH_2CH_2F$ | N | |
| $SCH_2CH=CH_2$ | H | $OCH_3$ | $OCH_2CH_2F$ | N | |
| $SCH_2CH=CH_2$ | $CH_3$ | Cl | $OCH_3$ | CH | |
| $SCH_2CH=CH_2$ | H | Cl | $N(CH_3)_2$ | CH | |
| $SCH_2CH=CH_2$ | H | Cl | $OC_2H_5$ | CH | |
| $SCH_2C\equiv CH$ | H | $CH_3$ | $CH_3$ | CH | |
| $SCH_2C\equiv CH$ | H | $OCH_3$ | $CH_3$ | CH | |
| $SCH_2C\equiv CH$ | H | $OCH_3$ | $OCH_3$ | CH | |
| $SCH_2C\equiv CH$ | H | Cl | $OCH_3$ | CH | |
| $SCH_2C\equiv CH$ | H | $OCH_3$ | $N(CH_3)_2$ | N | |
| $SCH_2C\equiv CH$ | H | $CH_3$ | $CH_3$ | N | |
| $SCH_2C\equiv CH$ | H | $OCH_3$ | $CH_3$ | N | |
| $SCH_2C\equiv CH$ | H | $OCH_3$ | $OCH_3$ | N | |
| $SCH_2C\equiv CH$ | H | $OCH_3$ | $N(CH_3)_2$ | N | |
| $SCH_2C\equiv CH$ | H | $OCH_3$ | $OCH_2CF_3$ | N | |
| $SCH_2C\equiv CH$ | $CH_3$ | $OCH_3$ | $CH_3$ | N | |
| $SCH_2C\equiv CH$ | $CH_3$ | $OCH_3$ | $OCH_3$ | N | |
| $SCH_2C\equiv CH$ | $CH_3$ | $CH_3$ | $OCH_3$ | CH | |
| $SCH_2C\equiv CH$ | $CH_3$ | $OCH_3$ | $OCH_3$ | CH | |
| $SCH_2C\equiv CH$ | H | Br | $OCH_3$ | CH | |
| $SCH_2C\equiv CH$ | $CH_3$ | $OCH_3$ | $N(CH_3)_2$ | N | |
| $SCH_2C\equiv CH$ | H | $CH_3$ | $OCH_2CF_3$ | N | |
| $SCH_2C\equiv CH$ | H | $CH_3$ | $OCH_2CF_3$ | CH | |
| $SCH_2C\equiv CH$ | H | $OCH_3$ | $OCH_2CF_3$ | CH | |
| $SCH_2C\equiv CH$ | H | $OCH_3$ | $C_2H_5$ | CH | |
| $SCH_2C\equiv CH$ | H | $OCH_3$ | $C_2H_5$ | CH | |
| $SCH_2C\equiv CH$ | H | $OCH_3$ | $NHCH_3$ | CH | |
| $SCH_2C\equiv CH$ | H | $OCH_3$ | $NHCH_3$ | N | |
| $SCH_2C\equiv CH$ | H | $CH_3$ | $OC_2H_5$ | CH | |
| $SCH_2C\equiv CH$ | H | $OCH_3$ | $OC_2H_5$ | CH | |
| $SCH_2C\equiv CH$ | H | $CH_3$ | $OC_2H_5$ | N | |
| $SCH_2C\equiv CH$ | H | $OCH_3$ | $OC_2H_5$ | N | |
| $SCH_2C\equiv CH$ | H | $CH_3$ | $OCH_2CHF_2$ | CH | |
| $SCH_2C\equiv CH$ | H | $OCH_3$ | $OCH_2CHF_2$ | CH | |
| $SCH_2C\equiv CH$ | H | $CH_3$ | $OCH_2CHF_2$ | N | |
| $SCH_2C\equiv CH$ | H | $OCH_3$ | $OCH_2CHF_2$ | N | |
| $SCH_2C\equiv CH$ | H | $CH_3$ | $OCH_2CH_2F$ | CH | |
| $SCH_2C\equiv CH$ | H | $OCH_3$ | $OCH_2CH_2F$ | CH | |
| $SCH_2C\equiv CH$ | H | $CH_3$ | $OCH_2CH_2F$ | N | |
| $SCH_2C\equiv CH$ | H | $OCH_3$ | $OCH_2CH_2F$ | N | |
| $SCH_2C\equiv CH$ | $CH_3$ | Cl | $OCH_3$ | CH | |
| $SCH_2C\equiv CH$ | H | Cl | $N(CH_3)_2$ | CH | |
| $SCH_2C\equiv CH$ | H | Cl | $OC_2H_5$ | CH | |
| $CH_2CH_2F$ | H | $CH_3$ | $CH_3$ | CH | |
| $CH_2CH_2F$ | H | $OCH_3$ | $CH_3$ | CH | |

TABLE If-continued

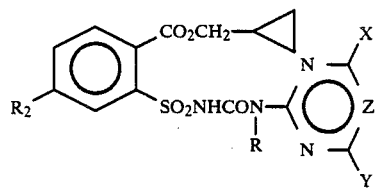

| R₂ | R | X | Y | Z | m.p. (°C.) |
|---|---|---|---|---|---|
| CH₂CH₂F | H | OCH₃ | OCH₃ | CH | |
| CH₂CH₂F | H | Cl | OCH₃ | CH | |
| CH₂CH₂F | H | OCH₃ | N(CH₃)₂ | CH | |
| CH₂CH₂F | H | CH₃ | CH₃ | N | |
| CH₂CH₂F | H | OCH₃ | CH₃ | N | |
| CH₂CH₂F | H | OCH₃ | OCH₃ | N | |
| CH₂CH₂F | H | OCH₃ | N(CH₃)₂ | N | |
| CH₂CH₂F | H | OCH₃ | OCH₂CF₃ | N | |
| CH₂CH₂F | CH₃ | OCH₃ | CH₃ | N | |
| CH₂CH₂F | CH₃ | OCH₃ | OCH₃ | N | |
| CH₂CH₂F | CH₃ | CH₃ | OCH₃ | CH | |
| CH₂CH₂F | CH₃ | OCH₃ | OCH₃ | CH | |
| CH₂CH₂F | H | Br | OCH₃ | CH | |
| CH₂CH₂F | CH₃ | OCH₃ | N(CH₃)₂ | N | |
| CH₂CH₂F | H | CH₃ | OCH₂CF₃ | N | |
| CH₂CH₂F | H | CH₃ | OCH₂CF₃ | CH | |
| CH₂CH₂F | H | OCH₃ | OCH₂CF₃ | CH | |
| CH₂CH₂F | H | OCH₃ | C₂H₅ | CH | |
| CH₂CH₂F | H | OCH₃ | C₂H₅ | N | |
| CH₂CH₂F | H | OCH₃ | NHCH₃ | CH | |
| CH₂CH₂F | H | OCH₃ | NHCH₃ | N | |
| CH₂CH₂F | H | CH₃ | OC₂H₅ | CH | |
| CH₂CH₂F | H | OCH₃ | OC₂H₅ | CH | |
| CH₂CH₂F | H | CH₃ | OC₂H₅ | N | |
| CH₂CH₂F | H | OCH₃ | OC₂H₅ | N | |
| CH₂CH₂F | H | CH₃ | OCH₂CHF₂ | CH | |
| CH₂CH₂F | H | OCH₃ | OCH₂CHF₂ | CH | |
| CH₂CH₂F | H | CH₃ | OCH₂CHF₂ | N | |
| CH₂CH₂F | H | OCH₃ | OCH₂CHF₂ | N | |
| CH₂CH₂F | H | CH₃ | OCH₂CH₂F | CH | |
| CH₂CH₂F | H | OCH₃ | OCH₂CH₂F | CH | |
| CH₂CH₂F | H | CH₃ | OCH₂CF₃ | N | |
| CH₂CH₂F | CH₃ | OCH₃ | OCH₂CF₃ | N | |
| CH₂CH₂F | CH₃ | Cl | OCH₃ | CH | |
| CH₂CH₂F | H | Cl | N(CH₃)₂ | CH | |
| CH₂CH₂F | H | Cl | OC₂H₅ | CH | |
| CH₂CF₃ | H | CH₃ | CH₃ | CH | |
| CH₂CF₃ | H | OCH₃ | CH₃ | CH | |
| CH₂CF₃ | H | OCH₃ | OCH₃ | CH | |
| CH₂CF₃ | H | Cl | OCH₃ | CH | |
| CH₂CF₃ | H | OCH₃ | N(CH₃)₂ | CH | |
| CH₂CF₃ | H | CH₃ | CH₃ | N | |
| CH₂CF₃ | H | OCH₃ | CH₃ | N | |
| CH₂CF₃ | H | OCH₃ | OCH₃ | N | |
| CH₂CF₃ | H | OCH₃ | N(CH₃)₂ | N | |
| CH₂CF₃ | H | OCH₃ | OCH₂CF₃ | N | |
| CH₂CF₃ | CH₃ | OCH₃ | CH₃ | N | |
| CH₂CF₃ | CH₃ | OCH₃ | OCH₃ | N | |
| CH₂CF₃ | CH₃ | CH₃ | OCH₃ | CH | |
| CH₂CF₃ | CH₃ | OCH₃ | OCH₃ | CH | |
| CH₂CF₃ | H | Br | OCH₃ | CH | |
| CH₂CF₃ | CH₃ | OCH₃ | N(CH₃)₂ | N | |
| CH₂CF₃ | H | CH₃ | OCH₂CF₃ | N | |
| CH₂CF₃ | H | CH₃ | OCH₂CF₃ | CH | |
| CH₂CF₃ | H | OCH₃ | OCH₂CF₃ | CH | |
| CH₂CF₃ | H | OCH₃ | C₂H₅ | CH | |
| CH₂CF₃ | H | OCH₃ | C₂H₅ | N | |
| CH₂CF₃ | H | OCH₃ | NHCH₃ | CH | |
| CH₂CF₃ | H | OCH₃ | NHCH₃ | N | |
| CH₂CF₃ | H | CH₃ | OC₂H₅ | CH | |
| CH₂CF₃ | H | OCH₃ | OC₂H₅ | CH | |
| CH₂CF₃ | H | CH₃ | OC₂H₅ | N | |
| CH₂CF₃ | H | OCH₃ | OC₂H₅ | N | |
| CH₂CF₃ | H | CH₃ | OCH₂CHF₂ | CH | |
| CH₂CF₃ | H | OCH₃ | OCH₂CHF₂ | CH | |
| CH₂CF₃ | H | CH₃ | OCH₂CHF₂ | N | |
| CH₂CF₃ | H | OCH₃ | OCH₂CHF₂ | N | |
| CH₂CF₃ | H | CH₃ | OCH₂CH₂F | CH | |
| CH₂CF₃ | H | OCH₃ | OCH₂CH₂F | CH | |

TABLE If-continued

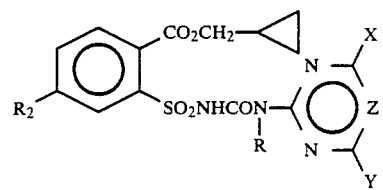

| R2 | R | X | Y | Z | m.p. (°C.) |
|---|---|---|---|---|---|
| CH2CF3 | H | CH3 | OCH2CH2F | N | |
| CH2CF3 | CH3 | OCH3 | OCH2CH2F | N | |
| CH2CF3 | CH3 | Cl | OCH3 | CH | |
| CH2CF3 | H | Cl | N(CH3)2 | CH | |
| CH2CF3 | H | Cl | OC2H5 | CH | |
| CHFCH3 | H | CH3 | CH3 | CH | |
| CHFCH3 | H | OCH3 | CH3 | CH | |
| CHFCH3 | H | OCH3 | OCH3 | CH | |
| CHFCH3 | H | Cl | OCH3 | CH | |
| CHFCH3 | H | OCH3 | N(CH3)2 | CH | |
| CHFCH3 | H | CH3 | CH3 | N | |
| CHFCH3 | H | OCH3 | CH3 | N | |
| CHFCH3 | H | OCH3 | OCH3 | N | |
| CHFCH3 | H | OCH3 | N(CH3)2 | N | |
| CHFCH3 | H | OCH3 | OCH2CF3 | N | |
| CHFCH3 | CH3 | OCH3 | CH3 | N | |
| CHFCH3 | CH3 | OCH3 | OCH3 | N | |
| CHFCH3 | CH3 | CH3 | OCH3 | CH | |
| CHFCH3 | CH3 | OCH3 | OCH3 | CH | |
| CHFCH3 | H | Br | OCH3 | CH | |
| CHFCH3 | CH3 | OCH3 | N(CH3)2 | N | |
| CHFCH3 | H | CH3 | OCH2CF3 | N | |
| CHFCH3 | H | CH3 | OCH2CF3 | CH | |
| CHFCH3 | H | OCH3 | OCH2CF3 | CH | |
| CHFCH3 | H | OCH3 | C2H5 | CH | |
| CHFCH3 | H | OCH3 | C2H5 | N | |
| CHFCH3 | H | OCH3 | NHCH3 | CH | |
| CHFCH3 | H | OCH3 | NHCH3 | N | |
| CHFCH3 | H | CH3 | OC2H5 | CH | |
| CHFCH3 | H | OCH3 | OC2H5 | CH | |
| CHFCH3 | H | CH3 | OC2H5 | N | |
| CHFCH3 | H | OCH3 | OC2H5 | N | |
| CHFCH3 | H | CH3 | OCH2CHF2 | CH | |
| CHFCH3 | H | OCH3 | OCH2CHF2 | CH | |
| CHFCH3 | H | CH3 | OCH2CHF2 | N | |
| CHFCH3 | H | OCH3 | OCH2CHF2 | N | |
| CHFCH3 | H | CH3 | OCH2CH2F | CH | |
| CHFCH3 | H | OCH3 | OCH2CH2F | CH | |
| CHFCH3 | H | CH3 | OCH2CF3 | N | |
| CHFCH3 | H | OCH3 | OCH2CF3 | N | |
| CHFCH3 | CH3 | Cl | OCH3 | CH | |
| CHFCH3 | H | Cl | N(CH3)2 | CH | |
| CHFCH3 | H | Cl | OC2H5 | CH | |
| CH2F | H | CH3 | CH3 | CH | |
| CH2F | H | OCH3 | CH3 | CH | |
| CH2F | H | OCH3 | OCH3 | CH | |
| CH2F | H | Cl | OCH3 | CH | |
| CH2F | H | OCH3 | N(CH3)2 | CH | |
| CH2F | H | CH3 | CH3 | N | |
| CH2F | H | OCH3 | CH3 | N | |
| CH2F | H | OCH3 | OCH3 | N | |
| CH2F | H | OCH3 | N(CH3)2 | N | |
| CH2F | H | OCH3 | OCH2CF3 | N | |
| CH2F | CH3 | OCH3 | CH3 | N | |
| CH2F | CH3 | OCH3 | OCH3 | N | |
| CH2F | CH3 | CH3 | OCH3 | CH | |
| CH2F | CH3 | OCH3 | OCH3 | CH | |
| CH2F | H | Br | OCH3 | CH | |
| CH2F | CH3 | OCH3 | N(CH3)2 | N | |
| CH2F | H | CH3 | OCH2CF3 | N | |
| CH2F | H | OCH3 | OCH2CF3 | CH | |
| CH2F | H | OCH3 | C2H5 | CH | |
| CH2F | H | OCH3 | C2H5 | N | |
| CH2F | H | OCH3 | NHCH3 | CH | |
| CH2F | H | OCH3 | NHCH3 | N | |
| CH2F | H | CH3 | OC2H5 | CH | |
| CH2F | H | OCH3 | OC2H5 | CH | |
| CH2F | H | CH3 | OC2H5 | N | |

TABLE If-continued

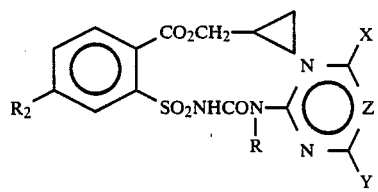

| R₂ | R | X | Y | Z | m.p. (°C.) |
|---|---|---|---|---|---|
| CH₂F | H | OCH₃ | OC₂H₅ | N | |
| CH₂F | CH₃ | CH₃ | OCH₂CHF₂ | CH | |
| CH₂F | H | OCH₃ | OCH₂CHF₂ | CH | |
| CH₂F | H | CH₃ | OCH₂CHF₂ | N | |
| CH₂F | H | OCH₃ | OCH₂CHF₂ | N | |
| CH₂F | H | CH₃ | OCH₂CH₂F | CH | |
| CH₂F | H | OCH₃ | OCH₂CH₂F | CH | |
| CH₂F | H | CH₃ | OCH₂CH₂F | N | |
| CH₂F | CH₃ | OCH₃ | OCH₂CH₂F | N | |
| CH₂F | CH₃ | Cl | OCH₃ | CH | |
| CH₂F | H | Cl | N(CH₃)₂ | CH | |
| CH₂F | H | Cl | OC₂H₅ | CH | |
| CHF₂ | H | CH₃ | CH₃ | CH | |
| CHF₂ | H | OCH₃ | CH₃ | CH | |
| CHF₂ | H | Cl | OCH₃ | CH | |
| CHF₂ | H | OCH₃ | N(CH₃)₂ | CH | |
| CHF₂ | H | CH₃ | CH₃ | N | |
| CHF₂ | H | OCH₃ | CH₃ | N | |
| CHF₂ | H | OCH₃ | OCH₃ | N | |
| CHF₂ | H | OCH₃ | N(CH₃)₂ | N | |
| CHF₂ | H | OCH₃ | OCH₂CF₃ | N | |
| CHF₂ | CH₃ | OCH₃ | CH₃ | N | |
| CHF₂ | CH₃ | OCH₃ | OCH₃ | N | |
| CHF₂ | CH₃ | CH₃ | OCH₃ | CH | |
| CHF₂ | CH₃ | OCH₃ | OCH₃ | CH | |
| CHF₂ | H | Br | OCH₃ | CH | |
| CHF₂ | CH₃ | OCH₃ | N(CH₃)₂ | N | |
| CHF₂ | H | CH₃ | OCH₂CF₃ | N | |
| CHF₂ | H | CH₃ | OCH₂CF₃ | CH | |
| CHF₂ | H | OCH₃ | OCH₂CF₃ | CH | |
| CHF₂ | H | OCH₃ | C₂H₅ | CH | |
| CHF₂ | H | OCH₃ | C₂H₅ | N | |
| CHF₂ | H | OCH₃ | NHCH₃ | CH | |
| CHF₂ | H | OCH₃ | NHCH₃ | N | |
| CHF₂ | H | CH₃ | OC₂H₅ | CH | |
| CHF₂ | H | OCH₃ | OC₂H₅ | CH | |
| CHF₂ | H | CH₃ | OC₂H₅ | N | |
| CHF₂ | H | OCH₃ | OC₂H₅ | N | |
| CHF₂ | H | CH₃ | OCH₂CHF₂ | CH | |
| CHF₂ | H | OCH₃ | OCH₂CHF₂ | CH | |
| CHF₂ | H | CH₃ | OCH₂CHF₂ | N | |
| CHF₂ | H | OCH₃ | OCH₂CHF₂ | N | |
| CHF₂ | H | CH₃ | OCH₂CH₂F | CH | |
| CHF₂ | H | OCH₃ | OCH₂CH₂F | CH | |
| CHF₂ | H | CH₃ | OCH₂CH₂F | N | |
| CHF₂ | CH₃ | OCH₃ | OCH₂CH₂F | N | |
| CHF₂ | CH₃ | Cl | OCH₃ | CH | |
| CHF₂ | H | Cl | N(CH₃)₂ | CH | |
| CHF₂ | H | Cl | OC₂H₅ | CH | |
| CH₂OCH₃ | H | CH₃ | CH₃ | CH | |
| CH₂OCH₃ | H | OCH₃ | CH₃ | CH | |
| CH₂OCH₃ | H | OCH₃ | OCH₃ | CH | |
| CH₂OCH₃ | H | Cl | OCH₃ | CH | |
| CH₂OCH₃ | H | OCH₃ | N(CH₃)₂ | CH | |
| CH₂OCH₃ | H | CH₃ | CH₃ | N | |
| CH₂OCH₃ | H | OCH₃ | CH₃ | N | |
| CH₂OCH₃ | H | OCH₃ | OCH₃ | N | |
| CH₂OCH₃ | H | OCH₃ | N(CH₃)₂ | N | |
| CH₂OCH₃ | H | OCH₃ | OCH₂CF₃ | N | |
| CH₂OCH₃ | CH₃ | OCH₃ | CH₃ | N | |
| CH₂OCH₃ | CH₃ | OCH₃ | OCH₃ | N | |
| CH₂OCH₃ | CH₃ | CH₃ | OCH₃ | CH | |
| CH₂OCH₃ | CH₃ | OCH₃ | OCH₃ | CH | |
| CH₂OCH₃ | H | Br | OCH₃ | CH | |
| CH₂OCH₃ | H | OCH₃ | N(CH₃)₂ | CH | |
| CH₂OCH₃ | CH₃ | OCH₃ | N(CH₃)₂ | N | |
| CH₂OCH₃ | H | CH₃ | OCH₂CF₃ | N | |
| CH₂OCH₃ | H | CH₃ | OCH₂CF₃ | CH | |

TABLE If-continued

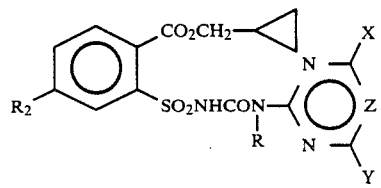

| $R_2$ | R | X | Y | Z | m.p. (°C.) |
|---|---|---|---|---|---|
| $CH_2OCH_3$ | H | $OCH_3$ | $OCH_2CF_3$ | CH | |
| $CH_2OCH_3$ | H | $OCH_3$ | $C_2H_5$ | CH | |
| $CH_2OCH_3$ | H | $OCH_3$ | $C_2H_5$ | N | |
| $CH_2OCH_3$ | H | $OCH_3$ | $NHCH_3$ | CH | |
| $CH_2OCH_3$ | H | $OCH_3$ | $NHCH_3$ | N | |
| $CH_2OCH_3$ | H | $CH_3$ | $OC_2H_5$ | CH | |
| $CH_2OCH_3$ | H | $OCH_3$ | $OC_2H_5$ | CH | |
| $CH_2OCH_3$ | H | $CH_3$ | $OC_2H_5$ | N | |
| $CH_2OCH_3$ | H | $OCH_3$ | $OC_2H_5$ | N | |
| $CH_2OCH_3$ | H | $CH_3$ | $OCH_2CHF_2$ | CH | |
| $CH_2OCH_3$ | H | $OCH_3$ | $OCH_2CHF_2$ | CH | |
| $CH_2OCH_3$ | H | $CH_3$ | $OCH_2CHF_2$ | N | |
| $CH_2OCH_3$ | H | $OCH_3$ | $OCH_2CHF_2$ | N | |
| $CH_2OCH_3$ | H | $CH_3$ | $OCH_2CH_2F$ | CH | |
| $CH_2OCH_3$ | H | $OCH_3$ | $OCH_2CH_2F$ | CH | |
| $CH_2OCH_3$ | H | $CH_3$ | $OCH_2CF_3$ | N | |
| $CH_2OCH_3$ | $CH_3$ | $OCH_3$ | $OCH_2CF_3$ | N | |
| $CH_2OCH_3$ | $CH_3$ | Cl | $OCH_3$ | CH | |
| $CH_2OCH_3$ | H | Cl | $N(CH_3)_2$ | CH | |
| $CH_2OCH_3$ | H | Cl | $OC_2H_5$ | CH | |
| $CH_2SCH_3$ | H | $CH_3$ | $CH_3$ | CH | |
| $CH_2SCH_3$ | H | $OCH_3$ | $CH_3$ | CH | |
| $CH_2SCH_3$ | H | $OCH_3$ | $OCH_3$ | CH | |
| $CH_2SCH_3$ | H | Cl | $OCH_3$ | CH | |
| $CH_2SCH_3$ | H | $OCH_3$ | $N(CH_3)_2$ | CH | |
| $CH_2SCH_3$ | H | $CH_3$ | $CH_3$ | N | |
| $CH_2SCH_3$ | H | $OCH_3$ | $CH_3$ | N | |
| $CH_2SCH_3$ | H | $OCH_3$ | $OCH_3$ | N | |
| $CH_2SCH_3$ | H | $OCH_3$ | $N(CH_3)_2$ | N | |
| $CH_2SCH_3$ | H | $OCH_3$ | $OCH_2CF_3$ | N | |
| $CH_2SCH_3$ | $CH_3$ | $OCH_3$ | $CH_3$ | N | |
| $CH_2SCH_3$ | $CH_3$ | $OCH_3$ | $OCH_3$ | N | |
| $CH_2SCH_3$ | $CH_3$ | $CH_3$ | $OCH_3$ | CH | |
| $CH_2SCH_3$ | $CH_3$ | $OCH_3$ | $OCH_3$ | CH | |
| $CH_2SCH_3$ | H | Br | $OCH_3$ | CH | |
| $CH_2SCH_3$ | $CH_3$ | $OCH_3$ | $N(CH_3)_2$ | N | |
| $CH_2SCH_3$ | H | $CH_3$ | $OCH_2CF_3$ | N | |
| $CH_2SCH_3$ | H | $OCH_3$ | $OCH_2CF_3$ | CH | |
| $CH_2SCH_3$ | H | $OCH_3$ | $C_2H_5$ | CH | |
| $CH_2SCH_3$ | H | $OCH_3$ | $C_2H_5$ | N | |
| $CH_2SCH_3$ | H | $OCH_3$ | $NHCH_3$ | CH | |
| $CH_2SCH_3$ | H | $OCH_3$ | $NHCH_3$ | N | |
| $CH_2SCH_3$ | H | $CH_3$ | $OC_2H_5$ | CH | |
| $CH_2SCH_3$ | H | $OCH_3$ | $OC_2H_5$ | CH | |
| $CH_2SCH_3$ | H | $CH_3$ | $OC_2H_5$ | N | |
| $CH_2SCH_3$ | H | $OCH_3$ | $OC_2H_5$ | N | |
| $CH_2SCH_3$ | H | $CH_3$ | $OCH_2CHF_2$ | CH | |
| $CH_2SCH_3$ | H | $OCH_3$ | $OCH_2CHF_2$ | CH | |
| $CH_2SCH_3$ | H | $CH_3$ | $OCH_2CHF_2$ | N | |
| $CH_2SCH_3$ | H | $OCH_3$ | $OCH_2CHF_2$ | N | |
| $CH_2SCH_3$ | H | $CH_3$ | $OCH_2CH_2F$ | CH | |
| $CH_2SCH_3$ | H | $OCH_3$ | $OCH_2CH_2F$ | CH | |
| $CH_2SCH_3$ | H | $CH_3$ | $OCH_2CH_2F$ | N | |
| $CH_2SCH_3$ | $CH_3$ | $OCH_3$ | $OCH_2CH_2F$ | N | |
| $CH_2SCH_3$ | $CH_3$ | Cl | $OCH_3$ | CH | |
| $CH_2SCH_3$ | H | Cl | $N(CH_3)_2$ | CH | |
| $CH_2SCH_3$ | H | Cl | $OC_2H_5$ | CH | |
| $OCF_2H$ | H | $CH_3$ | $CH_3$ | CH | |
| $OCF_2H$ | H | $OCH_3$ | $CH_3$ | CH | |
| $OCF_2H$ | H | $OCH_3$ | $OCH_3$ | CH | |
| $OCF_2H$ | H | Cl | $OCH_3$ | CH | |
| $OCF_2H$ | H | $OCH_3$ | $N(CH_3)_2$ | CH | |
| $OCF_2H$ | H | $CH_3$ | $CH_3$ | N | |
| $OCF_2H$ | H | $OCH_3$ | $CH_3$ | N | |
| $OCF_2H$ | H | $OCH_3$ | $OCH_3$ | N | |
| $OCF_2H$ | H | $OCH_3$ | $N(CH_3)_2$ | N | |
| $OCF_2H$ | H | $OCH_3$ | $OCH_2CF_3$ | N | |
| $OCF_2H$ | $CH_3$ | $OCH_3$ | $CH_3$ | N | |

TABLE If-continued

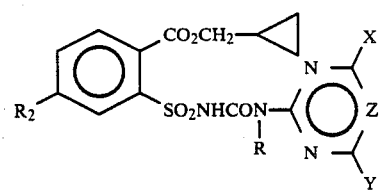

| $R_2$ | R | X | Y | Z | m.p. (°C.) |
|---|---|---|---|---|---|
| $OCF_2H$ | $CH_3$ | $OCH_3$ | $OCH_3$ | N | |
| $OCF_2H$ | $CH_3$ | $CH_3$ | $OCH_3$ | CH | |
| $OCF_2H$ | $CH_3$ | $OCH_3$ | $OCH_3$ | CH | |
| $OCF_2H$ | H | Br | $OCH_3$ | CH | |
| $OCF_2H$ | $CH_3$ | $OCH_3$ | $N(CH_3)_2$ | N | |
| $OCF_2H$ | H | $CH_3$ | $OCH_2CF_3$ | N | |
| $OCF_2H$ | H | $CH_3$ | $OCH_2CF_3$ | CH | |
| $OCF_2H$ | H | $OCH_3$ | $OCH_2CF_3$ | CH | |
| $OCF_2H$ | H | $OCH_3$ | $C_2H_5$ | CH | |
| $OCF_2H$ | H | $OCH_3$ | $C_2H_5$ | N | |
| $OCF_2H$ | H | $OCH_3$ | $NHCH_3$ | CH | |
| $OCF_2H$ | H | $OCH_3$ | $NHCH_3$ | N | |
| $OCF_2H$ | H | $CH_3$ | $OC_2H_5$ | CH | |
| $OCF_2H$ | H | $OCH_3$ | $OC_2H_5$ | CH | |
| $OCF_2H$ | H | $CH_3$ | $OC_2H_5$ | N | |
| $OCF_2H$ | H | $OCH_3$ | $OC_2H_5$ | N | |
| $OCF_2H$ | H | $CH_3$ | $OCH_2CHF_2$ | CH | |
| $OCF_2H$ | H | $OCH_3$ | $OCH_2CHF_2$ | CH | |
| $OCF_2H$ | H | $CH_3$ | $OCH_2CHF_2$ | N | |
| $OCF_2H$ | H | $OCH_3$ | $OCH_2CHF_2$ | N | |
| $OCF_2H$ | H | $CH_3$ | $OCH_2CH_2F$ | CH | |
| $OCF_2H$ | H | $OCH_3$ | $OCH_2CH_2F$ | CH | |
| $OCF_2H$ | H | $CH_3$ | $OCH_2CH_2F$ | N | |
| $OCF_2H$ | $CH_3$ | $OCH_3$ | $OCH_2CH_2F$ | N | |
| $OCF_2H$ | $CH_3$ | Cl | $OCH_3$ | CH | |
| $OCF_2H$ | H | Cl | $N(CH_3)_2$ | CH | |
| $OCF_2H$ | H | Cl | $OC_2H_5$ | CH | |
| $OCH_2CH_2F$ | H | $CH_3$ | $CH_3$ | CH | |
| $OCH_2CH_2F$ | H | $OCH_3$ | $CH_3$ | CH | |
| $OCH_2CH_2F$ | H | $OCH_3$ | $OCH_3$ | CH | |
| $OCH_2CH_2F$ | H | Cl | $OCH_3$ | CH | |
| $OCH_2CH_2F$ | H | $OCH_3$ | $N(CH_3)_2$ | CH | |
| $OCH_2CH_2F$ | H | $CH_3$ | $CH_3$ | N | |
| $OCH_2CH_2F$ | H | $OCH_3$ | $CH_3$ | N | |
| $OCH_2CH_2F$ | H | $OCH_3$ | $OCH_3$ | N | |
| $OCH_2CH_2F$ | H | $OCH_3$ | $N(CH_3)_2$ | N | |
| $OCH_2CH_2F$ | H | $OCH_3$ | $OCH_2CF_3$ | N | |
| $OCH_2CH_2F$ | $CH_3$ | $OCH_3$ | $CH_3$ | N | |
| $OCH_2CH_2F$ | $CH_3$ | $OCH_3$ | $OCH_3$ | N | |
| $OCH_2CH_2F$ | $CH_3$ | $CH_3$ | $OCH_3$ | CH | |
| $OCH_2CH_2F$ | $CH_3$ | $OCH_3$ | $OCH_3$ | CH | |
| $OCH_2CH_2F$ | H | Br | $OCH_3$ | CH | |
| $OCH_2CH_2F$ | $CH_3$ | $OCH_3$ | $N(CH_3)_2$ | N | |
| $OCH_2CH_2F$ | H | $CH_3$ | $OCH_2CF_3$ | N | |
| $OCH_2CH_2F$ | H | $CH_3$ | $OCH_2CF_3$ | CH | |
| $OCH_2CH_2F$ | H | $OCH_3$ | $OCH_2CF_3$ | CH | |
| $OCH_2CH_2F$ | H | $OCH_3$ | $C_2H_5$ | CH | |
| $OCH_2CH_2F$ | H | $OCH_3$ | $C_2H_5$ | N | |
| $OCH_2CH_2F$ | H | $OCH_3$ | $NHCH_3$ | CH | |
| $OCH_2CH_2F$ | H | $OCH_3$ | $NHCH_3$ | N | |
| $OCH_2CH_2F$ | H | $CH_3$ | $OC_2H_5$ | CH | |
| $OCH_2CH_2F$ | H | $OCH_3$ | $OC_2H_5$ | CH | |
| $OCH_2CH_2F$ | H | $CH_3$ | $OC_2H_5$ | N | |
| $OCH_2CH_2F$ | H | $OCH_3$ | $OC_2H_5$ | N | |
| $OCH_2CH_2F$ | H | $CH_3$ | $OCH_2CHF_2$ | CH | |
| $OCH_2CH_2F$ | H | $OCH_3$ | $OCH_2CHF_2$ | CH | |
| $OCH_2CH_2F$ | H | $CH_3$ | $OCH_2CHF_2$ | N | |
| $OCH_2CH_2F$ | H | $OCH_3$ | $OCH_2CHF_2$ | N | |
| $OCH_2CH_2F$ | H | $CH_3$ | $OCH_2CH_2F$ | CH | |
| $OCH_2CH_2F$ | H | $OCH_3$ | $OCH_2CH_2F$ | CH | |
| $OCH_2CH_2F$ | H | $CH_3$ | $OCH_2CH_2F$ | N | |
| $OCH_2CH_2F$ | $CH_3$ | $OCH_3$ | $OCH_2CH_2F$ | N | |
| $OCH_2CH_2F$ | $CH_3$ | Cl | $OCH_3$ | CH | |
| $OCH_2CH_2F$ | H | Cl | $N(CH_3)_2$ | CH | |
| $OCH_2CH_2F$ | H | Cl | $OC_2H_5$ | CH | |
| $OCH_2CF_3$ | H | $CH_3$ | $CH_3$ | CH | 177–178 |
| $OCH_2CF_3$ | H | $OCH_3$ | $CH_3$ | CH | 158–161 |

TABLE If-continued

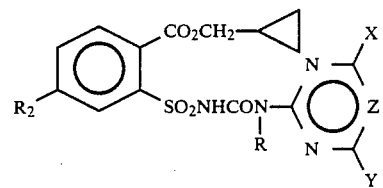

| R₂ | R | X | Y | Z | m.p. (°C.) |
|---|---|---|---|---|---|
| OCH₂CF₃ | H | OCH₃ | OCH₃ | CH | 174–175 |
| OCH₂CF₃ | H | Cl | OCH₃ | CH | 161–163 |
| OCH₂CF₃ | H | OCH₃ | N(CH₃)₂ | CH | |
| OCH₂CF₃ | H | CH₃ | CH₃ | N | |
| OCH₂CF₃ | H | OCH₃ | CH₃ | N | 147–148 |
| OCH₂CF₃ | H | OCH₃ | OCH₃ | N | 174–175 |
| OCH₂CF₃ | H | OCH₃ | N(CH₃)₂ | N | |
| OCH₂CF₃ | H | OCH₃ | OCH₂CF₃ | N | |
| OCH₂CF₃ | H | OC₂H₅ | NHCH₃ | N | |
| OCH₂CF₃ | CH₃ | OCH₃ | CH₃ | N | |
| OCH₂CF₃ | CH₃ | OCH₃ | OCH₃ | N | |
| OCH₂CF₃ | CH₃ | CH₃ | OCH₃ | CH | |
| OCH₂CF₃ | CH₃ | OCH₃ | OCH₃ | CH | |
| OCH₂CF₃ | H | Br | OCH₃ | CH | |
| OCH₂CF₃ | CH₃ | OCH₃ | N(CH₃)₂ | N | |
| OCH₂CF₃ | H | CH₃ | OCH₂CF₃ | N | |
| OCH₂CF₃ | H | CH₃ | OCH₂CF₃ | CH | |
| OCH₂CF₃ | H | OCH₃ | OCH₂CF₃ | CH | |
| OCH₂CF₃ | H | OCH₃ | C₂H₅ | CH | |
| OCH₂CF₃ | H | OCH₃ | C₂H₅ | N | |
| OCH₂CF₃ | H | OCH₃ | NHCH₃ | CH | |
| OCH₂CF₃ | H | OCH₃ | NHCH₃ | N | |
| OCH₂CF₃ | H | CH₃ | OC₂H₅ | CH | |
| OCH₂CF₃ | H | OCH₃ | OC₂H₅ | CH | |
| OCH₂CF₃ | H | CH₃ | OC₂H₅ | N | |
| OCH₂CF₃ | H | OCH₃ | OC₂H₅ | N | |
| OCH₂CF₃ | H | CH₃ | OCH₂CHF₂ | CH | |
| OCH₂CF₃ | H | OCH₃ | OCH₂CHF₂ | CH | |
| OCH₂CF₃ | H | CH₃ | OCH₂CHF₂ | N | |
| OCH₂CF₃ | H | OCH₃ | OCH₂CHF₂ | N | |
| OCH₂CF₃ | H | CH₃ | OCH₂CH₂F | CH | |
| OCH₂CF₃ | H | OCH₃ | OCH₂CH₂F | CH | |
| OCH₂CF₃ | H | CH₃ | OCH₂CH₂F | N | |
| OCH₂CF₃ | H | OCH₃ | OCH₂CH₂F | N | |
| OCH₂CF₃ | CH₃ | Cl | OCH₃ | CH | |
| OCH₂CF₃ | H | Cl | N(CH₃)₂ | CH | |
| OCH₂CF₃ | H | Cl | OC₂H₅ | CH | |
| OCH₂CH₂OCH₃ | H | CH₃ | CH₃ | CH | |
| OCH₂CH₂OCH₃ | H | OCH₃ | CH₃ | CH | |
| OCH₂CH₂OCH₃ | H | OCH₃ | OCH₃ | CH | |
| OCH₂CH₂OCH₃ | H | Cl | OCH₃ | CH | |
| OCH₂CH₂OCH₃ | H | OCH₃ | N(CH₃)₂ | CH | |
| OCH₂CH₂OCH₃ | H | CH₃ | CH₃ | N | |
| OCH₂CH₂OCH₃ | H | OCH₃ | CH₃ | N | |
| OCH₂CH₂OCH₃ | H | OCH₃ | OCH₃ | N | |
| OCH₂CH₂OCH₃ | H | OCH₃ | N(CH₃)₂ | N | |
| OCH₂CH₂OCH₃ | H | OCH₃ | OCH₂CF₃ | N | |
| OCH₂CH₂OCH₃ | CH₃ | OCH₃ | CH₃ | N | |
| OCH₂CH₂OCH₃ | CH₃ | OCH₃ | OCH₃ | N | |
| OCH₂CH₂OCH₃ | CH₃ | CH₃ | OCH₃ | CH | |
| OCH₂CH₂OCH₃ | CH₃ | OCH₃ | OCH₃ | CH | |
| OCH₂CH₂OCH₃ | H | Br | OCH₃ | CH | |
| OCH₂CH₂OCH₃ | H | CH₃ | OCH₂CF₃ | N | |
| OCH₂CH₂OCH₃ | H | CH₃ | OCH₂CF₃ | CH | |
| OCH₂CH₂OCH₃ | H | OCH₃ | OCH₂CF₃ | CH | |
| OCH₂CH₂OCH₃ | H | OCH₃ | C₂H₅ | CH | |
| OCH₂CH₂OCH₃ | H | OCH₃ | C₂H₅ | N | |
| OCH₂CH₂OCH₃ | H | OCH₃ | NHCH₃ | CH | |
| OCH₂CH₂OCH₃ | H | OCH₃ | NHCH₃ | N | |
| OCH₂CH₂OCH₃ | H | CH₃ | OC₂H₅ | CH | |
| OCH₂CH₂OCH₃ | H | OCH₃ | OC₂H₅ | CH | |
| OCH₂CH₂OCH₃ | H | CH₃ | OC₂H₅ | N | |
| OCH₂CH₂OCH₃ | H | OCH₃ | OC₂H₅ | N | |
| OCH₂CH₂OCH₃ | H | CH₃ | OCH₂CHF₂ | CH | |
| OCH₂CH₂OCH₃ | H | OCH₃ | OCH₂CHF₂ | CH | |

TABLE If-continued

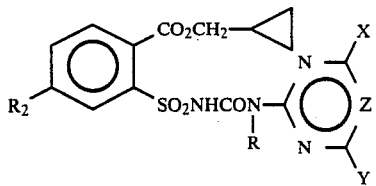

| $R_2$ | R | X | Y | Z | m.p. (°C.) |
|---|---|---|---|---|---|
| $OCH_2CH_2OCH_3$ | H | $CH_3$ | $OCH_2CHF_2$ | N | |
| $OCH_2CH_2OCH_3$ | H | $OCH_3$ | $OCH_2CHF_2$ | N | |
| $OCH_2CH_2OCH_3$ | H | $CH_3$ | $OCH_2CH_2F$ | CH | |
| $OCH_2CH_2OCH_3$ | H | $OCH_3$ | $OCH_2CH_2F$ | CH | |
| $OCH_2CH_2OCH_3$ | H | $CH_3$ | $OCH_2CF_3$ | N | |
| $OCH_2CH_2OCH_3$ | $CH_3$ | $OCH_3$ | $OCH_2CF_3$ | N | |
| $OCH_2CH_2OCH_3$ | $CH_3$ | Cl | $OCH_3$ | CH | |
| $OCH_2CH_2OCH_3$ | H | Cl | $N(CH_3)_2$ | CH | |
| $OCH_2CH_2OCH_3$ | H | Cl | $OC_2H_5$ | CH | |
| O-cyclopropyl | H | $CH_3$ | $CH_3$ | CH | |
| O-cyclopropyl | H | $OCH_3$ | $CH_3$ | CH | |
| O-cyclopropyl | H | $OCH_3$ | $OCH_3$ | CH | |
| O-cyclopropyl | H | Cl | $OCH_3$ | CH | |
| O-cyclopropyl | H | $OCH_3$ | $N(CH_3)_2$ | CH | |
| O-cyclopropyl | H | $CH_3$ | $CH_3$ | N | |
| O-cyclopropyl | H | $OCH_3$ | $CH_3$ | N | |
| O-cyclopropyl | H | $OCH_3$ | $OCH_3$ | N | |
| O-cyclopropyl | H | $OCH_3$ | $N(CH_3)_2$ | N | |
| O-cyclopropyl | H | $OCH_3$ | $OCH_2CF_3$ | N | |
| O-cyclopropyl | $CH_3$ | $OCH_3$ | $CH_3$ | N | |
| O-cyclopropyl | $CH_3$ | $OCH_3$ | $OCH_3$ | N | |
| O-cyclopropyl | $CH_3$ | $CH_3$ | $OCH_3$ | CH | |
| O-cyclopropyl | $CH_3$ | $OCH_3$ | $OCH_3$ | CH | |
| O-cyclopropyl | H | Br | $OCH_3$ | CH | |
| O-cyclopropyl | $CH_3$ | $OCH_3$ | $N(CH_3)_2$ | N | |
| O-cyclopropyl | H | $CH_3$ | $OCH_2CF_3$ | N | |
| O-cyclopropyl | H | $CH_3$ | $OCH_2CF_3$ | CH | |
| O-cyclopropyl | H | $OCH_3$ | $OCH_2CF_3$ | CH | |
| O-cyclopropyl | H | $OCH_3$ | $C_2H_5$ | CH | |
| O-cyclopropyl | H | $OCH_3$ | $C_2H_5$ | N | |
| O-cyclopropyl | H | $OCH_3$ | $NHCH_3$ | CH | |
| O-cyclopropyl | H | $OCH_3$ | $NHCH_3$ | N | |
| O-cyclopropyl | H | $CH_3$ | $OC_2H_5$ | CH | |
| O-cyclopropyl | H | $OCH_3$ | $OC_2H_5$ | CH | |
| O-cyclopropyl | H | $CH_3$ | $OC_2H_5$ | N | |
| O-cyclopropyl | H | $OCH_3$ | $OC_2H_5$ | N | |
| O-cyclopropyl | H | $CH_3$ | $OCH_2CHF_2$ | CH | |
| O-cyclopropyl | H | $OCH_3$ | $OCH_2CHF_2$ | CH | |
| O-cyclopropyl | H | $CH_3$ | $OCH_2CHF_2$ | N | |
| O-cyclopropyl | H | $OCH_3$ | $OCH_2CHF_2$ | N | |
| O-cyclopropyl | H | $CH_3$ | $OCH_2CH_2F$ | CH | |
| O-cyclopropyl | H | $OCH_3$ | $OCH_2CH_2F$ | CH | |
| O-cyclopropyl | H | $CH_3$ | $OCH_2CH_2F$ | N | |
| O-cyclopropyl | $CH_3$ | $OCH_3$ | $OCH_2CH_2F$ | N | |
| O-cyclopropyl | $CH_3$ | Cl | $OCH_3$ | CH | |
| O-cyclopropyl | H | Cl | $N(CH_3)_2$ | CH | |
| O-cyclopropyl | H | Cl | $OC_2H_5$ | CH | |
| $OCF_2CF_2H$ | H | $OCH_3$ | Cl | CH | |
| $OCF_2CF_2H$ | H | $CH_3$ | $CH_3$ | CH | |
| $OCF_2CF_2H$ | H | $OCH_3$ | $OCH_3$ | N | |
| S-cyclopropyl | H | $OCH_3$ | $OCH_3$ | CH | |
| S-cyclopropyl | H | $OCH_3$ | $CH_3$ | CH | |
| S-cyclopropyl | H | $OCH_3$ | Cl | CH | |
| S-cyclopropyl | H | $CH_3$ | $CH_3$ | CH | |
| S-cyclopropyl | H | $OCH_3$ | $OCH_3$ | N | |
| S-cyclopropyl | H | $OCH_3$ | $CH_3$ | N | |
| $SCH_2$-cyclopropyl | H | $OCH_3$ | $OCH_3$ | CH | |
| $SCH_2$-cyclopropyl | H | $OCH_3$ | $CH_3$ | CH | |
| $SCH_2$-cyclopropyl | H | $OCH_3$ | Cl | CH | |
| $SCH_2$-cyclopropyl | H | $CH_3$ | $CH_3$ | CH | |
| $SCH_2$-cyclopropyl | H | $OCH_3$ | $OCH_3$ | N | |
| $NHCH_2$-cyclopropyl | H | $OCH_3$ | $OCH_3$ | CH | |
| $NHCH_2$-cyclopropyl | H | $OCH_3$ | $CH_3$ | CH | |
| $NHCH_2$-cyclopropyl | H | $OCH_3$ | Cl | CH | |
| $NHCH_2$-cyclopropyl | H | $CH_3$ | $CH_3$ | CH | |
| $NHCH_2$-cyclopropyl | H | $OCH_3$ | $OCH_3$ | N | |
| $NHCH_2$-cyclopropyl | H | $OCH_3$ | $CH_3$ | N | |
| $NHCH_2CF_2CF_3$ | H | $OCH_3$ | $OCH_3$ | CH | |
| $NHCH_2CF_2CF_3$ | H | $OCH_3$ | $CH_3$ | CH | |

TABLE If-continued

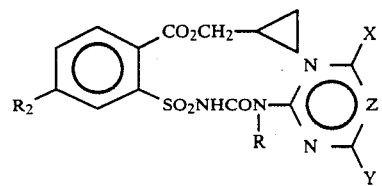

| R₂ | R | X | Y | Z | m.p. (°C.) |
|---|---|---|---|---|---|
| NHCH₂CF₂CF₃ | H | OCH₃ | Cl | CH | |
| NHCH₂CF₂CF₃ | H | CH₃ | CH₃ | CH | |
| NHCH₂CF₂CF₃ | H | OCH₃ | OCH₃ | N | |
| NHCH₂CF₂CF₃ | H | OCH₃ | CH₃ | N | |
| NHCH(CF₃)CH₃ | H | OCH₃ | OCH₃ | CH | |
| NHCH(CF₃)CH₃ | H | OCH₃ | CH₃ | CH | |
| NHCH₂CHF₂ | H | OCH₃ | CH₃ | N | |
| NHCH₂CHF₂ | H | OCH₃ | OCH₃ | CH | |
| NHCH₂CHF₂ | H | OCH₃ | CH₃ | CH | |
| NHCH₂CHF₂ | H | OCH₃ | Cl | CH | |
| NHCH₂CHF₂ | H | CH₃ | CH₃ | CH | |
| NHCH₂CHF₂ | H | OCH₃ | OCH₃ | N | |
| NHCH₃ | H | OCH₃ | OCH₃ | CH | |
| NHCH₃ | H | OCH₃ | CH₃ | CH | |
| NHCH₃ | H | OCH₃ | Cl | CH | |
| NHCH₃ | H | CH₃ | CH₃ | CH | |
| NHCH₃ | H | OCH₃ | OCH₃ | N | |

TABLE Ig

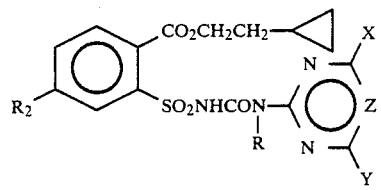

| R₂ | R | X | Y | Z | m.p. (°C.) |
|---|---|---|---|---|---|
| OC₂H₅ | H | CH₃ | CH₃ | CH | |
| OC₂H₅ | H | OCH₃ | CH₃ | CH | |
| OC₂H₅ | H | OCH₃ | OCH₃ | CH | |
| OC₂H₅ | H | Cl | OCH₃ | CH | |
| OC₂H₅ | H | OCH₃ | N(CH₃)₂ | CH | |
| OC₂H₅ | H | CH₃ | CH₃ | N | |
| OC₂H₅ | H | OCH₃ | CH₃ | N | |
| OC₂H₅ | H | OCH₃ | OCH₃ | N | |
| OC₂H₅ | H | OCH₃ | N(CH₃)₂ | N | |
| OC₂H₅ | H | OCH₃ | OCH₂CF₃ | N | |
| OC₂H₅ | CH₃ | OCH₃ | CH₃ | N | |
| OC₂H₅ | CH₃ | OCH₃ | OCH₃ | N | |
| OC₂H₅ | CH₃ | CH₃ | OCH₃ | CH | |
| OC₂H₅ | CH₃ | OCH₃ | OCH₃ | CH | |
| OC₂H₅ | H | Br | OCH₃ | CH | |
| OC₂H₅ | CH₃ | OCH₃ | N(CH₃)₂ | N | |
| OC₂H₅ | H | CH₃ | OCH₂CF₃ | N | |
| OC₂H₅ | H | CH₃ | OCH₂CF₃ | CH | |
| OC₂H₅ | H | OCH₃ | OCH₂CF₃ | CH | |
| OC₂H₅ | H | OCH₃ | C₂H₅ | CH | |
| OC₂H₅ | H | OCH₃ | C₂H₅ | N | |
| OC₂H₅ | H | OCH₃ | NHCH₃ | CH | |
| OC₂H₅ | H | OCH₃ | NHCH₃ | N | |
| OC₂H₅ | H | CH₃ | OC₂H₅ | CH | |
| OC₂H₅ | H | OCH₃ | OC₂H₅ | CH | |
| OC₂H₅ | H | CH₃ | OC₂H₅ | N | |
| OC₂H₅ | H | OCH₃ | OC₂H₅ | N | |
| OC₂H₅ | H | CH₃ | OCH₂CHF₂ | CH | |
| OC₂H₅ | H | CH₃ | OCH₂CHF₂ | N | |
| OC₂H₅ | H | OCH₃ | OCH₂CHF₂ | N | |
| OC₂H₅ | H | CH₃ | OCH₂CH₂F | CH | |

TABLE Ig-continued

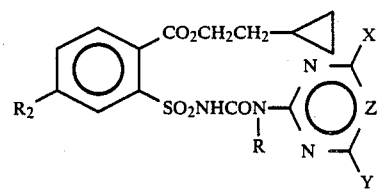

| R₂ | R | X | Y | Z | m.p. (°C.) |
|---|---|---|---|---|---|
| OC₂H₅ | H | OCH₃ | OCH₂CH₂F | CH | |
| OC₂H₅ | H | CH₃ | OCH₂CH₂F | N | |
| OC₂H₅ | CH₃ | OCH₃ | OCH₂CH₂F | N | |
| OC₂H₅ | CH₃ | Cl | OCH₃ | CH | |
| OC₂H₅ | H | Cl | N(CH₃)₂ | CH | |
| OC₂H₅ | H | Cl | OC₂H₅ | CH | |
| SC₂H₅ | H | CH₃ | CH₃ | CH | |
| SC₂H₅ | H | OCH₃ | CH₃ | CH | |
| SC₂H₅ | H | OCH₃ | OCH₃ | CH | |
| SC₂H₅ | H | Cl | OCH₃ | CH | |
| SC₂H₅ | H | OCH₃ | N(CH₃)₂ | CH | |
| SC₂H₅ | H | CH₃ | CH₃ | N | |
| SC₂H₅ | H | OCH₃ | CH₃ | N | |
| SC₂H₅ | H | OCH₃ | OCH₃ | N | |
| SC₂H₅ | H | OCH₃ | N(CH₃)₂ | N | |
| SC₂H₅ | H | OCH₃ | OCH₂CF₃ | N | |
| SC₂H₅ | CH₃ | OCH₃ | CH₃ | N | |
| SC₂H₅ | CH₃ | OCH₃ | OCH₃ | N | |
| SC₂H₅ | CH₃ | CH₃ | OCH₃ | CH | |
| SC₂H₅ | CH₃ | OCH₃ | OCH₃ | CH | |
| SC₂H₅ | H | Br | OCH₃ | CH | |
| SC₂H₅ | CH₃ | OCH₃ | N(CH₃)₂ | N | |
| SC₂H₅ | H | CH₃ | OCH₂CF₃ | N | |
| SC₂H₅ | H | CH₃ | OCH₂CF₃ | CH | |
| SC₂H₅ | H | OCH₃ | OCH₂CF₃ | CH | |
| SC₂H₅ | H | OCH₃ | C₂H₅ | CH | |
| SC₂H₅ | H | OCH₃ | C₂H₅ | N | |
| SC₂H₅ | H | OCH₃ | NHCH₃ | CH | |
| SC₂H₅ | H | OCH₃ | NHCH₃ | N | |
| SC₂H₅ | H | CH₃ | OC₂H₅ | CH | |
| SC₂H₅ | H | OCH₃ | OC₂H₅ | CH | |
| SC₂H₅ | H | CH₃ | OC₂H₅ | N | |
| SC₂H₅ | H | OCH₃ | OC₂H₅ | N | |
| SC₂H₅ | H | CH₃ | OCH₂CHF₂ | CH | |
| SC₂H₅ | H | OCH₃ | OCH₂CHF₂ | CH | |
| SC₂H₅ | H | CH₃ | OCH₂CHF₂ | N | |
| SC₂H₅ | H | OCH₃ | OCH₂CHF₂ | N | |
| SC₂H₅ | H | CH₃ | OCH₂CH₂F | CH | |
| SC₂H₅ | H | OCH₃ | OCH₂CH₂F | CH | |
| SC₂H₅ | H | CH₃ | OCH₂CH₂F | N | |
| SC₂H₅ | CH₃ | OCH₃ | OCH₂CH₂F | N | |
| SC₂H₅ | CH₃ | Cl | OCH₃ | CH | |
| SC₂H₅ | H | Cl | N(CH₃)₂ | CH | |
| SC₂H₅ | H | Cl | OC₂H₅ | CH | |
| S(CH₂)₅CH₃ | H | CH₃ | CH₃ | CH | |
| S(CH₂)₅CH₃ | H | OCH₃ | CH₃ | CH | |
| S(CH₂)₅CH₃ | H | OCH₃ | OCH₃ | CH | |
| S(CH₂)₅CH₃ | H | Cl | OCH₃ | CH | |
| S(CH₂)₅CH₃ | H | CH₃ | CH₃ | N | |
| S(CH₂)₅CH₃ | H | OCH₃ | CH₃ | N | |
| S(CH₂)₅CH₃ | H | OCH₃ | OCH₃ | N | |
| S(O)(CH₃) | H | CH₃ | CH₃ | CH | |
| S(O)(CH₃) | H | OCH₃ | CH₃ | CH | |
| S(O)(CH₃) | H | OCH₃ | OCH₃ | CH | |
| S(O)(CH₃) | H | Cl | OCH₃ | CH | |
| S(O)(CH₃) | H | OCH₃ | N(CH₃)₂ | CH | |
| S(O)(CH₃) | H | CH₃ | CH₃ | N | |
| S(O)(CH₃) | H | OCH₃ | CH₃ | N | |
| S(O)(CH₃) | H | OCH₃ | OCH₃ | N | |
| S(O)(CH₃) | H | OCH₃ | N(CH₃)₂ | N | |
| S(O)(CH₃) | H | OCH₃ | OCH₂CF₃ | N | |
| S(O)(CH₃) | CH₃ | OCH₃ | CH₃ | N | |
| S(O)(CH₃) | CH₃ | OCH₃ | OCH₃ | N | |
| S(O)(CH₃) | CH₃ | CH₃ | OCH₃ | CH | |
| S(O)(CH₃) | CH₃ | OCH₃ | OCH₃ | CH | |
| S(O)(CH₃) | H | Br | OCH₃ | CH | |
| S(O)(CH₃) | H | OCH₃ | N(CH₃)₂ | CH | |
| S(O)(CH₃) | CH₃ | OCH₃ | N(CH₃)₂ | N | |
| S(O)(CH₃) | H | CH₃ | OCH₂CF₃ | N | |
| S(O)(CH₃) | H | CH₃ | OCH₂CF₃ | CH | |

TABLE Ig-continued

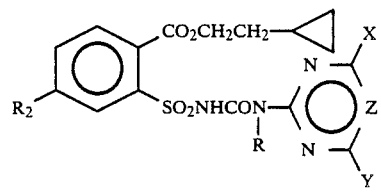

| R₂ | R | X | Y | Z | m.p. (°C.) |
|---|---|---|---|---|---|
| S(O)(CH₃) | H | OCH₃ | OCH₂CF₃ | CH | |
| S(O)(CH₃) | H | OCH₃ | C₂H₅ | CH | |
| S(O)(CH₃) | H | OCH₃ | C₂H₅ | N | |
| S(O)(CH₃) | H | OCH₃ | NHCH₃ | CH | |
| S(O)(CH₃) | H | OCH₃ | NHCH₃ | N | |
| S(O)(CH₃) | H | CH₃ | OC₂H₅ | CH | |
| S(O)(CH₃) | H | OCH₃ | OC₂H₅ | CH | |
| S(O)(CH₃) | H | CH₃ | OC₂H₅ | N | |
| S(O)(CH₃) | H | OCH₃ | OC₂H₅ | N | |
| S(O)(CH₃) | H | CH₃ | OCH₂CHF₂ | CH | |
| S(O)(CH₃) | H | OCH₃ | OCH₂CHF₂ | CH | |
| S(O)(CH₃) | H | CH₃ | OCH₂CHF₂ | N | |
| S(O)(CH₃) | H | OCH₃ | OCH₂CHF₂ | N | |
| S(O)(CH₃) | H | CH₃ | OCH₂CHF₂ | CH | |
| S(O)(CH₃) | H | OCH₃ | OCH₂CHF₂ | CH | |
| S(O)(CH₃) | H | CH₃ | OCH₂CHF₂ | N | |
| S(O)(CH₃) | H | OCH₃ | OCH₂CHF₂ | N | |
| S(O)(CH₃) | CH₃ | Cl | OCH₃ | CH | |
| S(O)(CH₃) | H | Cl | N(CH₃)₂ | CH | |
| S(O)(CH₃) | H | Cl | OC₂H₅ | CH | |
| OCH₂CH=CH₂ | H | CH₃ | CH₃ | CH | |
| OCH₂CH=CH₂ | H | OCH₃ | CH₃ | CH | |
| OCH₂CH=CH₂ | H | OCH₃ | OCH₃ | CH | |
| OCH₂CH=CH₂ | H | Cl | OCH₃ | CH | |
| OCH₂CH=CH₂ | H | OCH₃ | N(CH₃)₂ | CH | |
| OCH₂CH=CH₂ | H | CH₃ | CH₃ | N | |
| OCH₂CH=CH₂ | H | OCH₃ | CH₃ | N | |
| OCH₂CH=CH₂ | H | OCH₃ | OCH₃ | N | |
| OCH₂CH=CH₂ | H | OCH₃ | N(CH₃)₂ | N | |
| OCH₂CH=CH₂ | H | OCH₃ | OCH₂CF₃ | N | |
| OCH₂CH=CH₂ | CH₃ | OCH₃ | CH₃ | N | |
| OCH₂CH=CH₂ | CH₃ | OCH₃ | OCH₃ | N | |
| OCH₂CH=CH₂ | CH₃ | CH₃ | OCH₃ | CH | |
| OCH₂CH=CH₂ | CH₃ | OCH₃ | OCH₃ | CH | |
| OCH₂CH=CH₂ | H | Br | OCH₃ | CH | |
| OCH₂CH=CH₂ | CH₃ | OCH₃ | N(CH₃)₂ | N | |
| OCH₂CH=CH₂ | H | CH₃ | OCH₂CF₃ | N | |
| OCH₂CH=CH₂ | H | CH₃ | OCH₂CF₃ | CH | |
| OCH₂CH=CH₂ | H | OCH₃ | OCH₂CF₃ | CH | |
| OCH₂CH=CH₂ | H | OCH₃ | C₂H₅ | CH | |
| OCH₂CH=CH₂ | H | OCH₃ | C₂H₅ | N | |
| OCH₂CH=CH₂ | H | OCH₃ | NHCH₃ | CH | |
| OCH₂CH=CH₂ | H | OCH₃ | NHCH₃ | N | |
| OCH₂CH=CH₂ | H | CH₃ | OC₂H₅ | CH | |
| OCH₂CH=CH₂ | H | OCH₃ | OC₂H₅ | CH | |
| OCH₂CH=CH₂ | H | CH₃ | OC₂H₅ | N | |
| OCH₂CH=CH₂ | H | OCH₃ | OC₂H₅ | N | |
| OCH₂CH=CH₂ | H | CH₃ | OCH₂CHF₂ | CH | |
| OCH₂CH=CH₂ | H | OCH₃ | OCH₂CHF₂ | CH | |
| OCH₂CH=CH₂ | H | CH₃ | OCH₂CHF₂ | N | |
| OCH₂CH=CH₂ | H | OCH₃ | OCH₂CHF₂ | N | |
| OCH₂CH=CH₂ | H | CH₃ | OCH₂CH₂F | CH | |
| OCH₂CH=CH₂ | H | OCH₃ | OCH₂CH₂F | CH | |
| OCH₂CH=CH₂ | H | CH₃ | OCH₂CH₂F | N | |
| OCH₂CH=CH₂ | CH₃ | OCH₃ | OCH₂CH₂F | N | |
| OCH₂CH=CH₂ | CH₃ | Cl | OCH₃ | CH | |
| OCH₂CH=CH₂ | H | Cl | N(CH₃)₂ | CH | |
| OCH₂CH=CH₂ | H | Cl | OC₂H₅ | CH | |
| OCH₂C≡CH | H | CH₃ | CH₃ | CH | |
| OCH₂C≡CH | H | OCH₃ | CH₃ | CH | |
| OCH₂C≡CH | H | OCH₃ | OCH₃ | CH | |
| OCH₂C≡CH | H | Cl | OCH₃ | CH | |
| OCH₂C≡CH | H | OCH₃ | N(CH₃)₂ | CH | |
| OCH₂C≡CH | H | CH₃ | CH₃ | N | |
| OCH₂C≡CH | H | OCH₃ | CH₃ | N | |
| OCH₂C≡CH | H | OCH₃ | OCH₃ | N | |
| OCH₂C≡CH | H | OCH₃ | N(CH₃)₂ | N | |
| OCH₂C≡CH | H | OCH₃ | OCH₂CF₃ | N | |
| OCH₂C≡CH | CH₃ | OCH₃ | CH₃ | N | |
| OCH₂C≡CH | CH₃ | OCH₃ | OCH₃ | N | |

TABLE Ig-continued

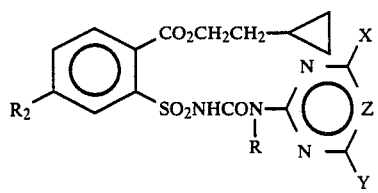

| R₂ | R | X | Y | Z | m.p. (°C.) |
|---|---|---|---|---|---|
| OCH₂C≡CH | CH₃ | CH₃ | OCH₃ | CH | |
| OCH₂C≡CH | CH₃ | OCH₃ | OCH₃ | CH | |
| OCH₂C≡CH | H | Br | OCH₃ | CH | |
| OCH₂C≡CH | CH₃ | OCH₃ | N(CH₃)₂ | N | |
| OCH₂C≡CH | H | CH₃ | OCH₂CF₃ | N | |
| OCH₂C≡CH | H | CH₃ | OCH₂CF₃ | CH | |
| OCH₂C≡CH | H | OCH₃ | OCH₂CF₃ | CH | |
| OCH₂C≡CH | H | OCH₃ | C₂H₅ | CH | |
| OCH₂C≡CH | H | OCH₃ | C₂H₅ | N | |
| OCH₂C≡CH | H | OCH₃ | NHCH₃ | CH | |
| OCH₂C≡CH | H | OCH₃ | NHCH₃ | N | |
| OCH₂C≡CH | H | CH₃ | OC₂H₅ | CH | |
| OCH₂C≡CH | H | OCH₃ | OC₂H₅ | CH | |
| OCH₂C≡CH | H | CH₃ | OC₂H₅ | N | |
| OCH₂C≡CH | H | OCH₃ | OC₂H₅ | N | |
| OCH₂C≡CH | H | CH₃ | OCH₂CHF₂ | CH | |
| OCH₂C≡CH | H | OCH₃ | OCH₂CHF₂ | CH | |
| OCH₂C≡CH | H | CH₃ | OCH₂CHF₂ | N | |
| OCH₂C≡CH | H | OCH₃ | OCH₂CHF₂ | N | |
| OCH₂C≡CH | H | CH₃ | OCH₂CH₂F | CH | |
| OCH₂C≡CH | H | OCH₃ | OCH₂CH₂F | CH | |
| OCH₂C≡CH | H | CH₃ | OCH₂CF₃ | N | |
| OCH₂C≡CH | CH₃ | OCH₃ | OCH₂CF₃ | N | |
| OCH₂C≡CH | CH₃ | Cl | OCH₃ | CH | |
| OCH₂C≡CH | H | Cl | N(CH₃)₂ | CH | |
| OCH₂C≡CH | H | Cl | OC₂H₅ | CH | |
| SCH₂CH=CH₂ | H | CH₃ | CH₃ | CH | |
| SCH₂CH=CH₂ | H | OCH₃ | CH₃ | CH | |
| SCH₂CH=CH₂ | H | OCH₃ | OCH₃ | CH | |
| SCH₂CH=CH₂ | H | Cl | OCH₃ | CH | |
| SCH₂CH=CH₂ | H | OCH₃ | N(CH₃)₂ | N | |
| SCH₂CH=CH₂ | H | CH₃ | CH₃ | N | |
| SCH₂CH=CH₂ | H | OCH₃ | CH₃ | N | |
| SCH₂CH=CH₂ | H | OCH₃ | OCH₃ | N | |
| SCH₂CH=CH₂ | H | OCH₃ | N(CH₃)₂ | N | |
| SCH₂CH=CH₂ | H | OCH₃ | OCH₂CF₃ | N | |
| SCH₂CH=CH₂ | CH₃ | OCH₃ | CH₃ | N | |
| SCH₂CH=CH₂ | CH₃ | OCH₃ | OCH₃ | N | |
| SCH₂CH=CH₂ | CH₃ | CH₃ | OCH₃ | CH | |
| SCH₂CH=CH₂ | CH₃ | OCH₃ | OCH₃ | CH | |
| SCH₂CH=CH₂ | H | Br | OCH₃ | CH | |
| SCH₂CH=CH₂ | CH₃ | OCH₃ | N(CH₃)₂ | N | |
| SCH₂CH=CH₂ | H | CH₃ | OCH₂CF₃ | N | |
| SCH₂CH=CH₂ | H | CH₃ | OCH₂CF₃ | CH | |
| SCH₂CH=CH₂ | H | OCH₃ | OCH₂CF₃ | CH | |
| SCH₂CH=CH₂ | H | OCH₃ | C₂H₅ | CH | |
| SCH₂CH=CH₂ | H | OCH₃ | C₂H₅ | CH | |
| SCH₂CH=CH₂ | H | OCH₃ | NHCH₃ | CH | |
| SCH₂CH=CH₂ | H | OCH₃ | NHCH₃ | N | |
| SCH₂CH=CH₂ | H | CH₃ | OC₂H₅ | CH | |
| SCH₂CH=CH₂ | H | OCH₃ | OC₂H₅ | CH | |
| SCH₂CH=CH₂ | H | CH₃ | OC₂H₅ | N | |
| SCH₂CH=CH₂ | H | OCH₃ | OC₂H₅ | N | |
| SCH₂CH=CH₂ | H | CH₃ | OCH₂CHF₂ | CH | |
| SCH₂CH=CH₂ | H | OCH₃ | OCH₂CHF₂ | CH | |
| SCH₂CH=CH₂ | H | CH₃ | OCH₂CHF₂ | N | |
| SCH₂CH=CH₂ | H | OCH₃ | OCH₂CHF₂ | N | |
| SCH₂CH=CH₂ | H | CH₃ | OCH₂CH₂F | CH | |
| SCH₂CH=CH₂ | H | OCH₃ | OCH₂CH₂F | CH | |
| SCH₂CH=CH₂ | H | CH₃ | OCH₂CH₂F | N | |
| SCH₂CH=CH₂ | H | OCH₃ | OCH₂CH₂F | N | |
| SCH₂CH=CH₂ | CH₃ | Cl | OCH₃ | CH | |
| SCH₂CH=CH₂ | H | Cl | N(CH₃)₂ | CH | |
| SCH₂CH=CH₂ | H | Cl | OC₂H₅ | CH | |
| SCH₂C≡CH | H | CH₃ | CH₃ | CH | |
| SCH₂C≡CH | H | OCH₃ | CH₃ | CH | |
| SCH₂C≡CH | H | OCH₃ | OCH₃ | CH | |
| SCH₂C≡CH | H | Cl | OCH₃ | CH | |
| SCH₂C≡CH | H | OCH₃ | N(CH₃)₂ | N | |
| SCH₂C≡CH | H | CH₃ | CH₃ | N | |

TABLE Ig-continued

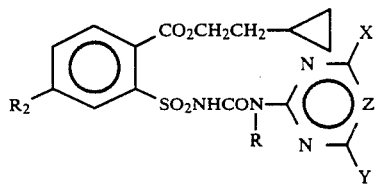

| R₂ | R | X | Y | Z | m.p. (°C.) |
|---|---|---|---|---|---|
| SCH₂C≡CH | H | OCH₃ | CH₃ | N | |
| SCH₂C≡CH | H | OCH₃ | OCH₃ | N | |
| SCH₂C≡CH | H | OCH₃ | N(CH₃)₂ | N | |
| SCH₂C≡CH | H | OCH₃ | OCH₂CF₃ | N | |
| SCH₂C≡CH | CH₃ | OCH₃ | CH₃ | N | |
| SCH₂C≡CH | CH₃ | OCH₃ | OCH₃ | N | |
| SCH₂C≡CH | CH₃ | CH₃ | OCH₃ | CH | |
| SCH₂C≡CH | CH₃ | OCH₃ | OCH₃ | CH | |
| SCH₂C≡CH | H | Br | OCH₃ | CH | |
| SCH₂C≡CH | CH₃ | OCH₃ | N(CH₃)₂ | N | |
| SCH₂C≡CH | H | CH₃ | OCH₂CF₃ | N | |
| SCH₂C≡CH | H | CH₃ | OCH₂CF₃ | CH | |
| SCH₂C≡CH | H | OCH₃ | OCH₂CF₃ | CH | |
| SCH₂C≡CH | H | OCH₃ | C₂H₅ | CH | |
| SCH₂C≡CH | H | OCH₃ | C₂H₅ | CH | |
| SCH₂C≡CH | H | OCH₃ | NHCH₃ | CH | |
| SCH₂C≡CH | H | OCH₃ | NHCH₃ | N | |
| SCH₂C≡CH | H | CH₃ | OC₂H₅ | CH | |
| SCH₂C≡CH | H | OCH₃ | OC₂H₅ | CH | |
| SCH₂C≡CH | H | CH₃ | OC₂H₅ | N | |
| SCH₂C≡CH | H | OCH₃ | OC₂H₅ | N | |
| SCH₂C≡CH | H | CH₃ | OCH₂CHF₂ | CH | |
| SCH₂C≡CH | H | OCH₃ | OCH₂CHF₂ | CH | |
| SCH₂C≡CH | H | CH₃ | OCH₂CHF₂ | N | |
| SCH₂C≡CH | H | OCH₃ | OCH₂CHF₂ | N | |
| SCH₂C≡CH | H | CH₃ | OCH₂CH₂F | CH | |
| SCH₂C≡CH | H | OCH₃ | OCH₂CH₂F | CH | |
| SCH₂C≡CH | H | CH₃ | OCH₂CH₂F | N | |
| SCH₂C≡CH | H | OCH₃ | OCH₂CH₂F | N | |
| SCH₂C≡CH | CH₃ | Cl | OCH₃ | CH | |
| SCH₂C≡CH | H | Cl | N(CH₃)₂ | CH | |
| SCH₂C≡CH | H | Cl | OC₂H₅ | CH | |
| CH₂CH₂F | H | CH₃ | CH₃ | CH | |
| CH₂CH₂F | H | OCH₃ | CH₃ | CH | |
| CH₂CH₂F | H | OCH₃ | OCH₃ | CH | |
| CH₂CH₂F | H | Cl | OCH₃ | CH | |
| CH₂CH₂F | H | OCH₃ | N(CH₃)₂ | CH | |
| CH₂CH₂F | H | CH₃ | CH₃ | N | |
| CH₂CH₂F | H | OCH₃ | CH₃ | N | |
| CH₂CH₂F | H | OCH₃ | OCH₃ | N | |
| CH₂CH₂F | H | OCH₃ | N(CH₃)₂ | N | |
| CH₂CH₂F | H | OCH₃ | OCH₂CF₃ | N | |
| CH₂CH₂F | CH₃ | OCH₃ | CH₃ | N | |
| CH₂CH₂F | CH₃ | OCH₃ | OCH₃ | N | |
| CH₂CH₂F | CH₃ | CH₃ | OCH₃ | CH | |
| CH₂CH₂F | CH₃ | OCH₃ | OCH₃ | CH | |
| CH₂CH₂F | H | Br | OCH₃ | CH | |
| CH₂CH₂F | CH₃ | OCH₃ | N(CH₃)₂ | N | |
| CH₂CH₂F | H | CH₃ | OCH₂CF₃ | N | |
| CH₂CH₂F | H | CH₃ | OCH₂CF₃ | CH | |
| CH₂CH₂F | H | OCH₃ | OCH₂CF₃ | CH | |
| CH₂CH₂F | H | OCH₃ | C₂H₅ | CH | |
| CH₂CH₂F | H | OCH₃ | C₂H₅ | N | |
| CH₂CH₂F | H | OCH₃ | NHCH₃ | CH | |
| CH₂CH₂F | H | OCH₃ | NHCH₃ | N | |
| CH₂CH₂F | H | CH₃ | OC₂H₅ | CH | |
| CH₂CH₂F | H | OCH₃ | OC₂H₅ | CH | |
| CH₂CH₂F | H | CH₃ | OC₂H₅ | N | |
| CH₂CH₂F | H | OCH₃ | OC₂H₅ | N | |
| CH₂CH₂F | H | CH₃ | OCH₂CHF₂ | CH | |
| CH₂CH₂F | H | OCH₃ | OCH₂CHF₂ | CH | |
| CH₂CH₂F | H | CH₃ | OCH₂CHF₂ | N | |
| CH₂CH₂F | H | OCH₃ | OCH₂CHF₂ | N | |
| CH₂CH₂F | H | CH₃ | OCH₂CH₂F | CH | |
| CH₂CH₂F | H | OCH₃ | OCH₂CH₂F | CH | |
| CH₂CH₂F | H | CH₃ | OCH₂CF₃ | N | |
| CH₂CH₂F | CH₃ | OCH₃ | OCH₂CF₃ | N | |
| CH₂CH₂F | CH₃ | Cl | OCH₃ | CH | |
| CH₂CH₂F | H | Cl | N(CH₃)₂ | CH | |
| CH₂CH₂F | H | Cl | OC₂H₅ | CH | |

TABLE Ig-continued

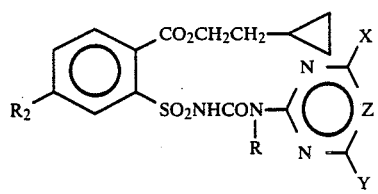

| R₂ | R | X | Y | Z | m.p. (°C.) |
|---|---|---|---|---|---|
| CH₂CF₃ | H | CH₃ | CH₃ | CH | |
| CH₂CF₃ | H | OCH₃ | CH₃ | CH | |
| CH₂CF₃ | H | OCH₃ | OCH₃ | CH | |
| CH₂CF₃ | H | Cl | OCH₃ | CH | |
| CH₂CF₃ | H | OCH₃ | N(CH₃)₂ | CH | |
| CH₂CF₃ | H | CH₃ | CH₃ | N | |
| CH₂CF₃ | H | OCH₃ | CH₃ | N | |
| CH₂CF₃ | H | OCH₃ | OCH₃ | N | |
| CH₂CF₃ | H | OCH₃ | N(CH₃)₂ | N | |
| CH₂CF₃ | H | OCH₃ | OCH₂CF₃ | N | |
| CH₂CF₃ | CH₃ | OCH₃ | CH₃ | N | |
| CH₂CF₃ | CH₃ | OCH₃ | OCH₃ | N | |
| CH₂CF₃ | CH₃ | CH₃ | OCH₃ | CH | |
| CH₂CF₃ | CH₃ | OCH₃ | OCH₃ | CH | |
| CH₂CF₃ | H | Br | OCH₃ | CH | |
| CH₂CF₃ | CH₃ | OCH₃ | N(CH₃)₂ | N | |
| CH₂CF₃ | H | CH₃ | OCH₂CF₃ | N | |
| CH₂CF₃ | H | CH₃ | OCH₂CF₃ | CH | |
| CH₂CF₃ | H | OCH₃ | OCH₂CF₃ | CH | |
| CH₂CF₃ | H | OCH₃ | C₂H₅ | CH | |
| CH₂CF₃ | H | OCH₃ | C₂H₅ | N | |
| CH₂CF₃ | H | OCH₃ | NHCH₃ | CH | |
| CH₂CF₃ | H | OCH₃ | NHCH₃ | N | |
| CH₂CF₃ | H | CH₃ | OC₂H₅ | CH | |
| CH₂CF₃ | H | OCH₃ | OC₂H₅ | CH | |
| CH₂CF₃ | H | CH₃ | OC₂H₅ | N | |
| CH₂CF₃ | H | OCH₃ | OC₂H₅ | N | |
| CH₂CF₃ | H | CH₃ | OCH₂CHF₂ | CH | |
| CH₂CF₃ | H | OCH₃ | OCH₂CHF₂ | CH | |
| CH₂CF₃ | H | CH₃ | OCH₂CHF₂ | N | |
| CH₂CF₃ | H | OCH₃ | OCH₂CHF₂ | N | |
| CH₂CF₃ | H | CH₃ | OCH₂CH₂F | CH | |
| CH₂CF₃ | H | OCH₃ | OCH₂CH₂F | CH | |
| CH₂CF₃ | H | CH₃ | OCH₂CH₂F | N | |
| CH₂CF₃ | CH₃ | OCH₃ | OCH₂CH₂F | N | |
| CH₂CF₃ | CH₃ | Cl | OCH₃ | CH | |
| CH₂CF₃ | H | Cl | N(CH₃)₂ | CH | |
| CH₂CF₃ | H | Cl | OC₂H₅ | CH | |
| CHFCH₃ | H | CH₃ | CH₃ | CH | |
| CHFCH₃ | H | OCH₃ | CH₃ | CH | |
| CHFCH₃ | H | OCH₃ | OCH₃ | CH | |
| CHFCH₃ | H | Cl | OCH₃ | CH | |
| CHFCH₃ | H | OCH₃ | N(CH₃)₂ | CH | |
| CHFCH₃ | H | CH₃ | CH₃ | N | |
| CHFCH₃ | H | OCH₃ | CH₃ | N | |
| CHFCH₃ | H | OCH₃ | OCH₃ | N | |
| CHFCH₃ | H | OCH₃ | N(CH₃)₂ | N | |
| CHFCH₃ | H | OCH₃ | OCH₂CF₃ | N | |
| CHFCH₃ | CH₃ | OCH₃ | CH₃ | N | |
| CHFCH₃ | CH₃ | OCH₃ | OCH₃ | N | |
| CHFCH₃ | CH₃ | CH₃ | OCH₃ | CH | |
| CHFCH₃ | CH₃ | OCH₃ | OCH₃ | CH | |
| CHFCH₃ | H | Br | OCH₃ | CH | |
| CHFCH₃ | CH₃ | OCH₃ | N(CH₃)₂ | N | |
| CHFCH₃ | H | CH₃ | OCH₂CF₃ | N | |
| CHFCH₃ | H | CH₃ | OCH₂CF₃ | CH | |
| CHFCH₃ | H | OCH₃ | OCH₂CF₃ | CH | |
| CHFCH₃ | H | OCH₃ | C₂H₅ | CH | |
| CHFCH₃ | H | OCH₃ | C₂H₅ | N | |
| CHFCH₃ | H | OCH₃ | NHCH₃ | CH | |
| CHFCH₃ | H | OCH₃ | NHCH₃ | N | |
| CHFCH₃ | H | CH₃ | OC₂H₅ | CH | |
| CHFCH₃ | H | OCH₃ | OC₂H₅ | CH | |
| CHFCH₃ | H | CH₃ | OC₂H₅ | N | |
| CHFCH₃ | H | OCH₃ | OC₂H₅ | N | |
| CHFCH₃ | H | CH₃ | OCH₂CHF₂ | CH | |
| CHFCH₃ | H | OCH₃ | OCH₂CHF₂ | CH | |
| CHFCH₃ | H | CH₃ | OCH₂CHF₂ | N | |
| CHFCH₃ | H | OCH₃ | OCH₂CHF₂ | N | |
| CHFCH₃ | H | CH₃ | OCH₂CH₂F | CH | |

TABLE Ig-continued

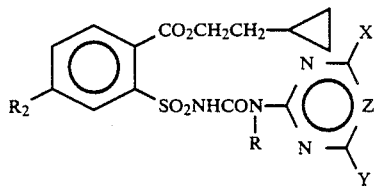

| $R_2$ | R | X | Y | Z | m.p. (°C.) |
|---|---|---|---|---|---|
| $CHFCH_3$ | H | $OCH_3$ | $OCH_2CH_2F$ | CH | |
| $CHFCH_3$ | H | $CH_3$ | $OCH_2CF_3$ | N | |
| $CHFCH_3$ | $CH_3$ | $OCH_3$ | $OCH_2CF_3$ | N | |
| $CHFCH_3$ | $CH_3$ | Cl | $OCH_3$ | CH | |
| $CHFCH_3$ | H | Cl | $N(CH_3)_2$ | CH | |
| $CHFCH_3$ | H | Cl | $OC_2H_5$ | CH | |
| $CH_2F$ | H | $CH_3$ | $CH_3$ | CH | |
| $CH_2F$ | H | $OCH_3$ | $OCH_3$ | CH | |
| $CH_2F$ | H | Cl | $OCH_3$ | CH | |
| $CH_2F$ | H | $OCH_3$ | $N(CH_3)_2$ | CH | |
| $CH_2F$ | H | $CH_3$ | $CH_3$ | N | |
| $CH_2F$ | H | $OCH_3$ | $CH_3$ | N | |
| $CH_2F$ | H | $OCH_3$ | $OCH_3$ | N | |
| $CH_2F$ | H | $OCH_3$ | $N(CH_3)_2$ | N | |
| $CH_2F$ | H | $OCH_3$ | $OCH_2CF_3$ | N | |
| $CH_2F$ | $CH_3$ | $OCH_3$ | $CH_3$ | N | |
| $CH_2F$ | $CH_3$ | $OCH_3$ | $OCH_3$ | N | |
| $CH_2F$ | $CH_3$ | $CH_3$ | $OCH_3$ | CH | |
| $CH_2F$ | $CH_3$ | $OCH_3$ | $OCH_3$ | CH | |
| $CH_2F$ | H | Br | $OCH_3$ | CH | |
| $CH_2F$ | $CH_3$ | $OCH_3$ | $N(CH_3)_2$ | N | |
| $CH_2F$ | H | $CH_3$ | $OCH_2CF_3$ | N | |
| $CH_2F$ | H | $CH_3$ | $OCH_2CF_3$ | CH | |
| $CH_2F$ | H | $OCH_3$ | $OCH_2CF_3$ | CH | |
| $CH_2F$ | H | $OCH_3$ | $C_2H_5$ | CH | |
| $CH_2F$ | H | $OCH_3$ | $C_2H_5$ | N | |
| $CH_2F$ | H | $OCH_3$ | $NHCH_3$ | CH | |
| $CH_2F$ | H | $OCH_3$ | $NHCH_3$ | N | |
| $CH_2F$ | H | $CH_3$ | $OC_2H_5$ | CH | |
| $CH_2F$ | H | $OCH_3$ | $OC_2H_5$ | CH | |
| $CH_2F$ | H | $CH_3$ | $OC_2H_5$ | N | |
| $CH_2F$ | H | $OCH_3$ | $OC_2H_5$ | N | |
| $CH_2F$ | H | $CH_3$ | $OCH_2CHF_2$ | CH | |
| $CH_2F$ | H | $OCH_3$ | $OCH_2CHF_2$ | CH | |
| $CH_2F$ | H | $CH_3$ | $OCH_2CHF_2$ | N | |
| $CH_2F$ | H | $OCH_3$ | $OCH_2CHF_2$ | N | |
| $CH_2F$ | H | $CH_3$ | $OCH_2CH_2F$ | CH | |
| $CH_2F$ | H | $OCH_3$ | $OCH_2CH_2F$ | CH | |
| $CH_2F$ | H | $CH_3$ | $OCH_2CH_2F$ | N | |
| $CH_2F$ | $CH_3$ | $OCH_3$ | $OCH_2CH_2F$ | N | |
| $CH_2F$ | $CH_3$ | Cl | $OCH_3$ | CH | |
| $CH_2F$ | H | Cl | $N(CH_3)_2$ | CH | |
| $CH_2F$ | H | Cl | $OC_2H_5$ | CH | |
| $CHF_2$ | H | $CH_3$ | $CH_3$ | CH | |
| $CHF_2$ | H | $OCH_3$ | $CH_3$ | CH | |
| $CHF_2$ | H | $OCH_3$ | $OCH_3$ | CH | |
| $CHF_2$ | H | Cl | $OCH_3$ | CH | |
| $CHF_2$ | H | $OCH_3$ | $N(CH_3)_2$ | CH | |
| $CHF_2$ | H | $CH_3$ | $CH_3$ | N | |
| $CHF_2$ | H | $OCH_3$ | $CH_3$ | N | |
| $CHF_2$ | H | $OCH_3$ | $OCH_3$ | N | |
| $CHF_2$ | H | $OCH_3$ | $N(CH_3)_2$ | N | |
| $CHF_2$ | H | $OCH_3$ | $OCH_2CF_3$ | N | |
| $CHF_2$ | $CH_3$ | $OCH_3$ | $CH_3$ | N | |
| $CHF_2$ | $CH_3$ | $OCH_3$ | $OCH_3$ | N | |
| $CHF_2$ | $CH_3$ | $CH_3$ | $OCH_3$ | CH | |
| $CHF_2$ | $CH_3$ | $OCH_3$ | $OCH_3$ | CH | |
| $CHF_2$ | H | Br | $OCH_3$ | CH | |
| $CHF_2$ | $CH_3$ | $OCH_3$ | $N(CH_3)_2$ | N | |
| $CHF_2$ | H | $CH_3$ | $OCH_2CF_3$ | N | |
| $CHF_2$ | H | $CH_3$ | $OCH_2CF_3$ | CH | |
| $CHF_2$ | H | $OCH_3$ | $OCH_2CF_3$ | CH | |
| $CHF_2$ | H | $OCH_3$ | $C_2H_5$ | CH | |
| $CHF_2$ | H | $OCH_3$ | $C_2H_5$ | N | |
| $CHF_2$ | H | $OCH_3$ | $NHCH_3$ | CH | |
| $CHF_2$ | H | $OCH_3$ | $NHCH_3$ | N | |
| $CHF_2$ | H | $CH_3$ | $OC_2H_5$ | CH | |
| $CHF_2$ | H | $OCH_3$ | $OC_2H_5$ | CH | |
| $CHF_2$ | H | $CH_3$ | $OC_2H_5$ | N | |
| $CHF_2$ | H | $OCH_3$ | $OC_2H_5$ | N | |

TABLE Ig-continued

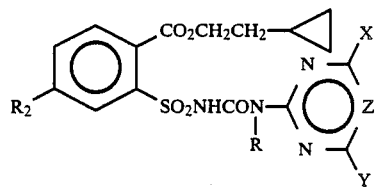

| R₂ | R | X | Y | Z | m.p. (°C.) |
|---|---|---|---|---|---|
| CHF₂ | H | CH₃ | OCH₂CHF₂ | CH | |
| CHF₂ | H | OCH₃ | OCH₂CHF₂ | CH | |
| CHF₂ | H | CH₃ | OCH₂CHF₂ | N | |
| CHF₂ | H | OCH₃ | OCH₂CHF₂ | N | |
| CHF₂ | H | CH₃ | OCH₂CH₂F | CH | |
| CHF₂ | H | OCH₃ | OCH₂CH₂F | CH | |
| CHF₂ | H | CH₃ | OCH₂CH₂F | N | |
| CHF₂ | CH₃ | OCH₃ | OCH₂CH₂F | N | |
| CHF₂ | CH₃ | Cl | OCH₃ | CH | |
| CHF₂ | H | Cl | N(CH₃)₂ | CH | |
| CHF₂ | H | Cl | OC₂H₅ | CH | |
| CH₂OCH₃ | H | CH₃ | CH₃ | CH | |
| CH₂OCH₃ | H | OCH₃ | CH₃ | CH | |
| CH₂OCH₃ | H | OCH₃ | OCH₃ | CH | |
| CH₂OCH₃ | H | Cl | OCH₃ | CH | |
| CH₂OCH₃ | H | OCH₃ | N(CH₃)₂ | CH | |
| CH₂OCH₃ | H | CH₃ | CH₃ | N | |
| CH₂OCH₃ | H | OCH₃ | CH₃ | N | |
| CH₂OCH₃ | H | OCH₃ | OCH₃ | N | |
| CH₂OCH₃ | H | OCH₃ | N(CH₃)₂ | N | |
| CH₂OCH₃ | H | OCH₃ | OCH₂CF₃ | N | |
| CH₂OCH₃ | CH₃ | OCH₃ | CH₃ | N | |
| CH₂OCH₃ | CH₃ | OCH₃ | OCH₃ | N | |
| CH₂OCH₃ | CH₃ | CH₃ | OCH₃ | CH | |
| CH₂OCH₃ | CH₃ | OCH₃ | OCH₃ | CH | |
| CH₂OCH₃ | H | Br | OCH₃ | CH | |
| CH₂OCH₃ | H | OCH₃ | N(CH₃)₂ | CH | |
| CH₂OCH₃ | CH₃ | OCH₃ | N(CH₃)₂ | N | |
| CH₂OCH₃ | H | CH₃ | OCH₂CF₃ | N | |
| CH₂OCH₃ | H | CH₃ | OCH₂CF₃ | CH | |
| CH₂OCH₃ | H | OCH₃ | OCH₂CF₃ | CH | |
| CH₂OCH₃ | H | OCH₃ | C₂H₅ | CH | |
| CH₂OCH₃ | H | OCH₃ | C₂H₅ | N | |
| CH₂OCH₃ | H | OCH₃ | NHCH₃ | CH | |
| CH₂OCH₃ | H | OCH₃ | NHCH₃ | N | |
| CH₂OCH₃ | H | CH₃ | OC₂H₅ | CH | |
| CH₂OCH₃ | H | OCH₃ | OC₂H₅ | CH | |
| CH₂OCH₃ | H | CH₃ | OC₂H₅ | N | |
| CH₂OCH₃ | H | OCH₃ | OC₂H₅ | N | |
| CH₂OCH₃ | H | CH₃ | OCH₂CHF₂ | CH | |
| CH₂OCH₃ | H | OCH₃ | OCH₂CHF₂ | CH | |
| CH₂OCH₃ | H | CH₃ | OCH₂CHF₂ | N | |
| CH₂OCH₃ | H | OCH₃ | OCH₂CHF₂ | N | |
| CH₂OCH₃ | H | CH₃ | OCH₂CH₂F | CH | |
| CH₂OCH₃ | H | OCH₃ | OCH₂CH₂F | CH | |
| CH₂OCH₃ | H | CH₃ | OCH₂CF₃ | N | |
| CH₂OCH₃ | CH₃ | OCH₃ | OCH₂CF₃ | N | |
| CH₂OCH₃ | CH₃ | Cl | OCH₃ | CH | |
| CH₂OCH₃ | H | Cl | N(CH₃)₂ | CH | |
| CH₂OCH₃ | H | Cl | OC₂H₅ | CH | |
| CH₂SCH₃ | H | CH₃ | CH₃ | CH | |
| CH₂SCH₃ | H | OCH₃ | CH₃ | CH | |
| CH₂SCH₃ | H | OCH₃ | OCH₃ | CH | |
| CH₂SCH₃ | H | Cl | OCH₃ | CH | |
| CH₂SCH₃ | H | OCH₃ | N(CH₃)₂ | CH | |
| CH₂SCH₃ | H | CH₃ | CH₃ | N | |
| CH₂SCH₃ | H | OCH₃ | CH₃ | N | |
| CH₂SCH₃ | H | OCH₃ | OCH₃ | N | |
| CH₂SCH₃ | H | OCH₃ | N(CH₃)₂ | N | |
| CH₂SCH₃ | H | OCH₃ | OCH₂CF₃ | N | |
| CH₂SCH₃ | CH₃ | OCH₃ | CH₃ | N | |
| CH₂SCH₃ | CH₃ | OCH₃ | OCH₃ | N | |
| CH₂SCH₃ | CH₃ | CH₃ | OCH₃ | CH | |
| CH₂SCH₃ | CH₃ | OCH₃ | OCH₃ | CH | |
| CH₂SCH₃ | H | Br | OCH₃ | CH | |
| CH₂SCH₃ | CH₃ | OCH₃ | N(CH₃)₂ | N | |
| CH₂SCH₃ | H | CH₃ | OCH₂CF₃ | N | |
| CH₂SCH₃ | H | CH₃ | OCH₂CF₃ | CH | |
| CH₂SCH₃ | H | OCH₃ | OCH₂CF₃ | CH | |
| CH₂SCH₃ | H | OCH₃ | C₂H₅ | CH | |

TABLE Ig-continued

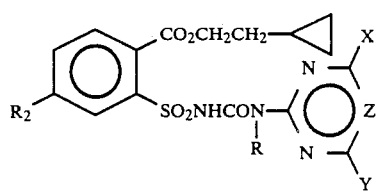

| R₂ | R | X | Y | Z | m.p. (°C.) |
|---|---|---|---|---|---|
| CH₂SCH₃ | H | OCH₃ | C₂H₅ | N | |
| CH₂SCH₃ | H | OCH₃ | NHCH₃ | CH | |
| CH₂SCH₃ | H | OCH₃ | NHCH₃ | N | |
| CH₂SCH₃ | H | CH₃ | OC₂H₅ | CH | |
| CH₂SCH₃ | H | OCH₃ | OC₂H₅ | CH | |
| CH₂SCH₃ | H | CH₃ | OC₂H₅ | N | |
| CH₂SCH₃ | H | OCH₃ | OC₂H₅ | N | |
| CH₂SCH₃ | H | CH₃ | OCH₂CHF₂ | CH | |
| CH₂SCH₃ | H | OCH₃ | OCH₂CHF₂ | CH | |
| CH₂SCH₃ | H | CH₃ | OCH₂CHF₂ | N | |
| CH₂SCH₃ | H | OCH₃ | OCH₂CHF₂ | N | |
| CH₂SCH₃ | H | CH₃ | OCH₂CH₂F | CH | |
| CH₂SCH₃ | H | OCH₃ | OCH₂CH₂F | CH | |
| CH₂SCH₃ | H | CH₃ | OCH₂CH₂F | N | |
| CH₂SCH₃ | CH₃ | OCH₃ | OCH₂CH₂F | N | |
| CH₂SCH₃ | CH₃ | Cl | OCH₃ | CH | |
| CH₂SCH₃ | H | Cl | N(CH₃)₂ | CH | |
| CH₂SCH₃ | H | Cl | OC₂H₅ | CH | |
| OCF₂H | H | CH₃ | CH₃ | CH | |
| OCF₂H | H | OCH₃ | CH₃ | CH | |
| OCF₂H | H | OCH₃ | OCH₃ | CH | |
| OCF₂H | H | Cl | OCH₃ | CH | |
| OCF₂H | H | OCH₃ | N(CH₃)₂ | CH | |
| OCF₂H | H | CH₃ | CH₃ | N | |
| OCF₂H | H | OCH₃ | CH₃ | N | |
| OCF₂H | H | OCH₃ | OCH₃ | N | |
| OCF₂H | H | OCH₃ | N(CH₃)₂ | N | |
| OCF₂H | H | OCH₃ | OCH₂CF₃ | N | |
| OCF₂H | CH₃ | OCH₃ | CH₃ | N | |
| OCF₂H | CH₃ | OCH₃ | OCH₃ | N | |
| OCF₂H | CH₃ | CH₃ | OCH₃ | CH | |
| OCF₂H | CH₃ | OCH₃ | OCH₃ | CH | |
| OCF₂H | H | Br | OCH₃ | CH | |
| OCF₂H | CH₃ | OCH₃ | N(CH₃)₂ | N | |
| OCF₂H | H | CH₃ | OCH₂CF₃ | N | |
| OCF₂H | H | CH₃ | OCH₂CF₃ | CH | |
| OCF₂H | H | OCH₃ | OCH₂CF₃ | CH | |
| OCF₂H | H | OCH₃ | C₂H₅ | CH | |
| OCF₂H | H | OCH₃ | C₂H₅ | N | |
| OCF₂H | H | OCH₃ | NHCH₃ | CH | |
| OCF₂H | H | OCH₃ | NHCH₃ | N | |
| OCF₂H | H | CH₃ | OC₂H₅ | CH | |
| OCF₂H | H | OCH₃ | OC₂H₅ | CH | |
| OCF₂H | H | CH₃ | OC₂H₅ | N | |
| OCF₂H | H | OCH₃ | OC₂H₅ | N | |
| OCF₂H | H | CH₃ | OCH₂CHF₂ | CH | |
| OCF₂H | H | OCH₃ | OCH₂CHF₂ | CH | |
| OCF₂H | H | CH₃ | OCH₂CHF₂ | N | |
| OCF₂H | H | OCH₃ | OCH₂CHF₂ | N | |
| OCF₂H | H | CH₃ | OCH₂CH₂F | CH | |
| OCF₂H | H | OCH₃ | OCH₂CH₂F | CH | |
| OCF₂H | H | CH₃ | OCH₂CH₂F | N | |
| OCF₂H | CH₃ | OCH₃ | OCH₂CH₂F | N | |
| OCF₂H | CH₃ | Cl | OCH₃ | CH | |
| OCF₂H | H | Cl | N(CH₃)₂ | CH | |
| OCF₂H | H | Cl | OC₂H₅ | CH | |
| OCH₂CH₂F | H | CH₃ | CH₃ | CH | |
| OCH₂CH₂F | H | OCH₃ | CH₃ | CH | |
| OCH₂CH₂F | H | OCH₃ | OCH₃ | CH | |
| OCH₂CH₂F | H | Cl | OCH₃ | CH | |
| OCH₂CH₂F | H | OCH₃ | N(CH₃)₂ | CH | |
| OCH₂CH₂F | H | CH₃ | CH₃ | N | |
| OCH₂CH₂F | H | OCH₃ | CH₃ | N | |
| OCH₂CH₂F | H | OCH₃ | OCH₃ | N | |
| OCH₂CH₂F | H | OCH₃ | N(CH₃)₂ | N | |
| OCH₂CH₂F | H | OCH₃ | OCH₂CF₃ | N | |
| OCH₂CH₂F | CH₃ | OCH₃ | CH₃ | N | |
| OCH₂CH₂F | CH₃ | OCH₃ | OCH₃ | N | |
| OCH₂CH₂F | CH₃ | CH₃ | OCH₃ | CH | |
| OCH₂CH₂F | CH₃ | OCH₃ | OCH₃ | CH | |

TABLE Ig-continued

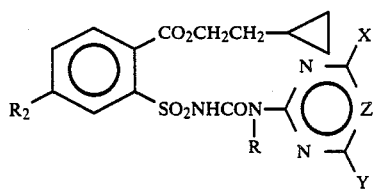

| $R_2$ | R | X | Y | Z | m.p. (°C.) |
|---|---|---|---|---|---|
| $OCH_2CH_2F$ | H | Br | $OCH_3$ | CH | |
| $OCH_2CH_2F$ | $CH_3$ | $OCH_3$ | $N(CH_3)_2$ | N | |
| $OCH_2CH_2F$ | H | $CH_3$ | $OCH_2CF_3$ | N | |
| $OCH_2CH_2F$ | H | $CH_3$ | $OCH_2CF_3$ | CH | |
| $OCH_2CH_2F$ | H | $OCH_3$ | $OCH_2CF_3$ | CH | |
| $OCH_2CH_2F$ | H | $OCH_3$ | $C_2H_5$ | CH | |
| $OCH_2CH_2F$ | H | $OCH_3$ | $C_2H_5$ | N | |
| $OCH_2CH_2F$ | H | $OCH_3$ | $NHCH_3$ | CH | |
| $OCH_2CH_2F$ | H | $OCH_3$ | $NHCH_3$ | N | |
| $OCH_2CH_2F$ | H | $CH_3$ | $OC_2H_5$ | CH | |
| $OCH_2CH_2F$ | H | $OCH_3$ | $OC_2H_5$ | CH | |
| $OCH_2CH_2F$ | H | $CH_3$ | $OC_2H_5$ | N | |
| $OCH_2CH_2F$ | H | $OCH_3$ | $OC_2H_5$ | N | |
| $OCH_2CH_2F$ | H | $CH_3$ | $OCH_2CHF_2$ | CH | |
| $OCH_2CH_2F$ | H | $OCH_3$ | $OCH_2CHF_2$ | CH | |
| $OCH_2CH_2F$ | H | $CH_3$ | $OCH_2CHF_2$ | N | |
| $OCH_2CH_2F$ | H | $OCH_3$ | $OCH_2CHF_2$ | N | |
| $OCH_2CH_2F$ | H | $CH_3$ | $OCH_2CH_2F$ | CH | |
| $OCH_2CH_2F$ | H | $OCH_3$ | $OCH_2CH_2F$ | CH | |
| $OCH_2CH_2F$ | H | $CH_3$ | $OCH_2CH_2F$ | N | |
| $OCH_2CH_2F$ | $CH_3$ | $OCH_3$ | $OCH_2CH_2F$ | N | |
| $OCH_2CH_2F$ | $CH_3$ | Cl | $OCH_3$ | CH | |
| $OCH_2CH_2F$ | H | Cl | $N(CH_3)_2$ | CH | |
| $OCH_2CH_2F$ | H | Cl | $OC_2H_5$ | CH | |
| $OCH_2CF_3$ | H | $CH_3$ | $CH_3$ | CH | |
| $OCH_2CF_3$ | H | $OCH_3$ | $CH_3$ | CH | |
| $OCH_2CF_3$ | H | $OCH_3$ | $OCH_3$ | CH | |
| $OCH_2CF_3$ | H | Cl | $OCH_3$ | CH | |
| $OCH_2CF_3$ | H | $OCH_3$ | $N(CH_3)_2$ | CH | |
| $OCH_2CF_3$ | H | $CH_3$ | $CH_3$ | N | |
| $OCH_2CF_3$ | H | $OCH_3$ | $CH_3$ | N | |
| $OCH_2CF_3$ | H | $OCH_3$ | $OCH_3$ | N | |
| $OCH_2CF_3$ | H | $OCH_3$ | $N(CH_3)_2$ | N | |
| $OCH_2CF_3$ | H | $OCH_3$ | $OCH_2CF_3$ | N | |
| $OCH_2CF_3$ | H | $OC_2H_5$ | $NHCH_3$ | N | |
| $OCH_2CF_3$ | $CH_3$ | $OCH_3$ | $CH_3$ | N | |
| $OCH_2CF_3$ | $CH_3$ | $OCH_3$ | $OCH_3$ | N | |
| $OCH_2CF_3$ | $CH_3$ | $CH_3$ | $OCH_3$ | CH | |
| $OCH_2CF_3$ | $CH_3$ | $OCH_3$ | $OCH_3$ | CH | |
| $OCH_2CF_3$ | H | Br | $OCH_3$ | CH | |
| $OCH_2CF_3$ | $CH_3$ | $OCH_3$ | $N(CH_3)_2$ | N | |
| $OCH_2CF_3$ | H | $CH_3$ | $OCH_2CF_3$ | N | |
| $OCH_2CF_3$ | H | $CH_3$ | $OCH_2CF_3$ | CH | |
| $OCH_2CF_3$ | H | $OCH_3$ | $OCH_2CF_3$ | CH | |
| $OCH_2CF_3$ | H | $OCH_3$ | $C_2H_5$ | CH | |
| $OCH_2CF_3$ | H | $OCH_3$ | $C_2H_5$ | N | |
| $OCH_2CF_3$ | H | $OCH_3$ | $NHCH_3$ | CH | |
| $OCH_2CF_3$ | H | $OCH_3$ | $NHCH_3$ | N | |
| $OCH_2CF_3$ | H | $CH_3$ | $OC_2H_5$ | CH | |
| $OCH_2CF_3$ | H | $OCH_3$ | $OC_2H_5$ | CH | |
| $OCH_2CF_3$ | H | $CH_3$ | $OC_2H_5$ | N | |
| $OCH_2CF_3$ | H | $OCH_3$ | $OC_2H_5$ | N | |
| $OCH_2CF_3$ | H | $CH_3$ | $OCH_2CHF_2$ | CH | |
| $OCH_2CF_3$ | H | $OCH_3$ | $OCH_2CHF_2$ | CH | |
| $OCH_2CF_3$ | H | $CH_3$ | $OCH_2CHF_2$ | N | |
| $OCH_2CF_3$ | H | $OCH_3$ | $OCH_2CHF_2$ | N | |
| $OCH_2CF_3$ | H | $CH_3$ | $OCH_2CH_2F$ | CH | |
| $OCH_2CF_3$ | H | $OCH_3$ | $OCH_2CH_2F$ | CH | |
| $OCH_2CF_3$ | H | $CH_3$ | $OCH_2CH_2F$ | N | |
| $OCH_2CF_3$ | $CH_3$ | $OCH_3$ | $OCH_2CH_2F$ | N | |
| $OCH_2CF_3$ | $CH_3$ | Cl | $OCH_3$ | CH | |
| $OCH_2CF_3$ | H | Cl | $N(CH_3)_2$ | CH | |
| $OCH_2CF_3$ | H | Cl | $OC_2H_5$ | CH | |
| $OCH_2CH_2OCH_3$ | H | $CH_3$ | $CH_3$ | CH | |
| $OCH_2CH_2OCH_3$ | H | $OCH_3$ | $CH_3$ | CH | |
| $OCH_2CH_2OCH_3$ | H | $OCH_3$ | $OCH_3$ | CH | |
| $OCH_2CH_2OCH_3$ | H | Cl | $OCH_3$ | CH | |
| $OCH_2CH_2OCH_3$ | H | $OCH_3$ | $N(CH_3)_2$ | CH | |
| $OCH_2CH_2OCH_3$ | H | $CH_3$ | $CH_3$ | N | |
| $OCH_2CH_2OCH_3$ | H | $OCH_3$ | $CH_3$ | N | |

TABLE Ig-continued

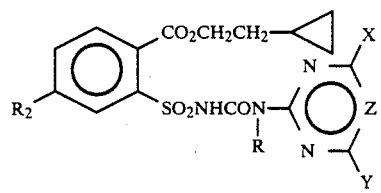

| R₂ | R | X | Y | Z | m.p. (°C.) |
|---|---|---|---|---|---|
| OCH₂CH₂OCH₃ | H | OCH₃ | OCH₃ | N | |
| OCH₂CH₂OCH₃ | H | OCH₃ | N(CH₃)₂ | N | |
| OCH₂CH₂OCH₃ | H | OCH₃ | OCH₂CF₃ | N | |
| OCH₂CH₂OCH₃ | CH₃ | OCH₃ | CH₃ | N | |
| OCH₂CH₂OCH₃ | CH₃ | OCH₃ | OCH₃ | N | |
| OCH₂CH₂OCH₃ | CH₃ | CH₃ | OCH₃ | CH | |
| OCH₂CH₂OCH₃ | CH₃ | OCH₃ | OCH₃ | CH | |
| OCH₂CH₂OCH₃ | H | Br | OCH₃ | CH | |
| OCH₂CH₂OCH₃ | H | CH₃ | OCH₂CF₃ | N | |
| OCH₂CH₂OCH₃ | H | CH₃ | OCH₂CF₃ | CH | |
| OCH₂CH₂OCH₃ | H | OCH₃ | OCH₂CF₃ | CH | |
| OCH₂CH₂OCH₃ | H | OCH₃ | C₂H₅ | CH | |
| OCH₂CH₂OCH₃ | H | OCH₃ | C₂H₅ | N | |
| OCH₂CH₂OCH₃ | H | OCH₃ | NHCH₃ | CH | |
| OCH₂CH₂OCH₃ | H | OCH₃ | NHCH₃ | N | |
| OCH₂CH₂OCH₃ | H | CH₃ | OC₂H₅ | CH | |
| OCH₂CH₂OCH₃ | H | OCH₃ | OC₂H₅ | CH | |
| OCH₂CH₂OCH₃ | H | CH₃ | OC₂H₅ | N | |
| OCH₂CH₂OCH₃ | H | OCH₃ | OC₂H₅ | N | |
| OCH₂CH₂OCH₃ | H | CH₃ | OCH₂CHF₂ | CH | |
| OCH₂CH₂OCH₃ | H | OCH₃ | OCH₂CHF₂ | CH | |
| OCH₂CH₂OCH₃ | H | CH₃ | OCH₂CHF₂ | N | |
| OCH₂CH₂OCH₃ | H | OCH₃ | OCH₂CHF₂ | N | |
| OCH₂CH₂OCH₃ | H | CH₃ | OCH₂CH₂F | CH | |
| OCH₂CH₂OCH₃ | H | OCH₃ | OCH₂CH₂F | CH | |
| OCH₂CH₂OCH₃ | H | CH₃ | OCH₂CF₃ | N | |
| OCH₂CH₂OCH₃ | CH₃ | OCH₃ | OCH₂CF₃ | N | |
| OCH₂CH₂OCH₃ | CH₃ | Cl | OCH₃ | CH | |
| OCH₂CH₂OCH₃ | H | Cl | N(CH₃)₂ | CH | |
| OCH₂CH₂OCH₃ | H | Cl | OC₂H₅ | CH | |
| O-cyclopropyl | H | CH₃ | CH₃ | CH | |
| O-cyclopropyl | H | OCH₃ | CH₃ | CH | |
| O-cyclopropyl | H | OCH₃ | OCH₃ | CH | |
| O-cyclopropyl | H | Cl | OCH₃ | CH | |
| O-cyclopropyl | H | OCH₃ | N(CH₃)₂ | CH | |
| O-cyclopropyl | H | CH₃ | CH₃ | N | |
| O-cyclopropyl | H | OCH₃ | CH₃ | N | |
| O-cyclopropyl | H | OCH₃ | OCH₃ | N | |
| O-cyclopropyl | H | OCH₃ | N(CH₃)₂ | N | |
| O-cyclopropyl | H | OCH₃ | OCH₂CF₃ | N | |
| O-cyclopropyl | CH₃ | OCH₃ | CH₃ | N | |
| O-cyclopropyl | CH₃ | OCH₃ | OCH₃ | N | |
| O-cyclopropyl | CH₃ | CH₃ | OCH₃ | CH | |
| O-cyclopropyl | CH₃ | OCH₃ | OCH₃ | CH | |
| O-cyclopropyl | H | Br | OCH₃ | CH | |
| O-cyclopropyl | CH₃ | OCH₃ | N(CH₃)₂ | N | |
| O-cyclopropyl | H | CH₃ | OCH₂CF₃ | N | |
| O-cyclopropyl | H | CH₃ | OCH₂CF₃ | CH | |
| O-cyclopropyl | H | OCH₃ | OCH₂CF₃ | CH | |
| O-cyclopropyl | H | OCH₃ | C₂H₅ | CH | |
| O-cyclopropyl | H | OCH₃ | C₂H₅ | N | |
| O-cyclopropyl | H | OCH₃ | NHCH₃ | CH | |
| O-cyclopropyl | H | OCH₃ | NHCH₃ | N | |
| O-cyclopropyl | H | CH₃ | OC₂H₅ | CH | |
| O-cyclopropyl | H | OCH₃ | OC₂H₅ | CH | |
| O-cyclopropyl | H | CH₃ | OC₂H₅ | N | |
| O-cyclopropyl | H | OCH₃ | OC₂H₅ | N | |
| O-cyclopropyl | H | CH₃ | OCH₂CHF₂ | CH | |
| O-cyclopropyl | H | OCH₃ | OCH₂CHF₂ | CH | |
| O-cyclopropyl | H | CH₃ | OCH₂CHF₂ | N | |
| O-cyclopropyl | H | OCH₃ | OCH₂CHF₂ | N | |
| O-cyclopropyl | H | CH₃ | OCH₂CH₂F | CH | |
| O-cyclopropyl | H | OCH₃ | OCH₂CH₂F | CH | |
| O-cyclopropyl | H | CH₃ | OCH₂CH₂F | N | |
| O-cyclopropyl | CH₃ | OCH₃ | OCH₂CH₂F | N | |
| O-cyclopropyl | CH₃ | Cl | OCH₃ | CH | |
| O-cyclopropyl | H | Cl | N(CH₃)₂ | CH | |
| O-cyclopropyl | H | Cl | OC₂H₅ | CH | |
| OCF₂CF₂H | H | OCH₃ | Cl | CH | |
| OCF₂CF₂H | H | CH₃ | CH₃ | CH | |

TABLE Ig-continued

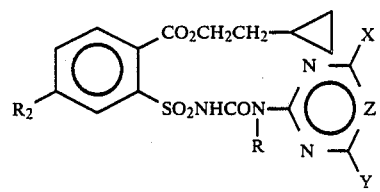

| R₂ | R | X | Y | Z | m.p. (°C.) |
|---|---|---|---|---|---|
| OCF$_2$CF$_2$H | H | OCH$_3$ | OCH$_3$ | N | |
| S-cyclopropyl | H | OCH$_3$ | OCH$_3$ | CH | |
| S-cyclopropyl | H | OCH$_3$ | CH$_3$ | CH | |
| S-cyclopropyl | H | OCH$_3$ | Cl | CH | |
| S-cyclopropyl | H | CH$_3$ | CH$_3$ | CH | |
| S-cyclopropyl | H | OCH$_3$ | OCH$_3$ | N | |
| S-cyclopropyl | H | OCH$_3$ | CH$_3$ | N | |
| SCH$_2$-cyclopropyl | H | OCH$_3$ | OCH$_3$ | CH | |
| SCH$_2$-cyclopropyl | H | OCH$_3$ | CH$_3$ | CH | |
| SCH$_2$-cyclopropyl | H | OCH$_3$ | Cl | CH | |
| SCH$_2$-cyclopropyl | H | CH$_3$ | CH$_3$ | CH | |
| SCH$_2$-cyclopropyl | H | OCH$_3$ | OCH$_3$ | N | |
| NHCH$_2$-cyclopropyl | H | OCH$_3$ | OCH$_3$ | CH | |
| NHCH$_2$-cyclopropyl | H | OCH$_3$ | CH$_3$ | CH | |
| NHCH$_2$-cyclopropyl | H | OCH$_3$ | Cl | CH | |
| NHCH$_2$-cyclopropyl | H | CH$_3$ | CH$_3$ | CH | |
| NHCH$_2$-cyclopropyl | H | OCH$_3$ | OCH$_3$ | N | |
| NHCH$_2$-cyclopropyl | H | OCH$_3$ | CH$_3$ | N | |
| NHCH$_2$CF$_2$CF$_3$ | H | OCH$_3$ | OCH$_3$ | CH | |
| NHCH$_2$CF$_2$CF$_3$ | H | OCH$_3$ | CH$_3$ | CH | |
| NHCH$_2$CF$_2$CF$_3$ | H | OCH$_3$ | Cl | CH | |
| NHCH$_2$CF$_2$CF$_3$ | H | CH$_3$ | CH$_3$ | CH | |
| NHCH$_2$CF$_2$CF$_3$ | H | OCH$_3$ | OCH$_3$ | N | |
| NHCH$_2$CF$_2$CF$_3$ | H | OCH$_3$ | CH$_3$ | N | |
| NHCH(CF$_3$)CH$_3$ | H | OCH$_3$ | OCH$_3$ | CH | |
| NHCH(CF$_3$)CH$_3$ | H | OCH$_3$ | CH$_3$ | CH | |
| NHCH$_2$CHF$_2$ | H | OCH$_3$ | CH$_3$ | N | |
| NHCH$_2$CF$_3$ | H | OCH$_3$ | OCH$_3$ | CH | |
| NHCH$_2$CF$_3$ | H | OCH$_3$ | CH$_3$ | CH | |
| NHCH$_2$CF$_3$ | H | OCH$_3$ | Cl | CH | |
| NHCH$_2$CF$_3$ | H | CH$_3$ | CH$_3$ | CH | |
| NHCH$_2$CF$_3$ | H | OCH$_3$ | OCH$_3$ | N | |
| NHCH$_3$ | H | OCH$_3$ | OCH$_3$ | CH | |
| NHCH$_3$ | H | OCH$_3$ | CH$_3$ | CH | |
| NHCH$_3$ | H | OCH$_3$ | Cl | CH | |
| NHCH$_3$ | H | CH$_3$ | CH$_3$ | CH | |
| NHCH$_3$ | H | OCH$_3$ | OCH$_3$ | N | |

TABLE I

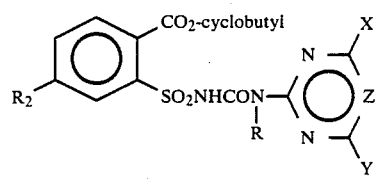

| R₂ | R | X | Y | Z | m.p. (°C.) |
|---|---|---|---|---|---|
| OC$_2$H$_5$ | H | CH$_3$ | CH$_3$ | CH | |
| OC$_2$H$_5$ | H | OCH$_3$ | CH$_3$ | CH | |
| OC$_2$H$_5$ | H | OCH$_3$ | OCH$_3$ | CH | |
| OC$_2$H$_5$ | H | Cl | OCH$_3$ | CH | |
| OC$_2$H$_5$ | H | OCH$_3$ | N(CH$_3$)$_2$ | CH | |
| OC$_2$H$_5$ | H | CH$_3$ | CH$_3$ | N | |
| OC$_2$H$_5$ | H | OCH$_3$ | CH$_3$ | N | |
| OC$_2$H$_5$ | H | OCH$_3$ | OCH$_3$ | N | |
| OC$_2$H$_5$ | H | OCH$_3$ | N(CH$_3$)$_2$ | N | |
| OC$_2$H$_5$ | H | OCH$_3$ | OCH$_2$CF$_3$ | N | |
| OC$_2$H$_5$ | CH$_3$ | OCH$_3$ | CH$_3$ | N | |
| OC$_2$H$_5$ | CH$_3$ | OCH$_3$ | OCH$_3$ | N | |

TABLE I-continued

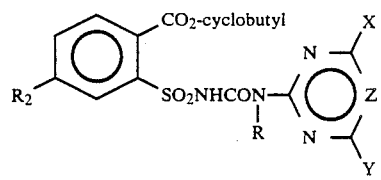

| $R_2$ | R | X | Y | Z | m.p. (°C.) |
|---|---|---|---|---|---|
| $OC_2H_5$ | $CH_3$ | $CH_3$ | $OCH_3$ | CH | |
| $OC_2H_5$ | $CH_3$ | $OCH_3$ | $OCH_3$ | CH | |
| $OC_2H_5$ | H | Br | $OCH_3$ | CH | |
| $OC_2H_5$ | $CH_3$ | $OCH_3$ | $N(CH_3)_2$ | N | |
| $OC_2H_5$ | H | $CH_3$ | $OCH_2CF_3$ | N | |
| $OC_2H_5$ | H | $CH_3$ | $OCH_2CF_3$ | CH | |
| $OC_2H_5$ | H | $OCH_3$ | $OCH_2CF_3$ | CH | |
| $OC_2H_5$ | H | $OCH_3$ | $C_2H_5$ | CH | |
| $OC_2H_5$ | H | $OCH_3$ | $C_2H_5$ | N | |
| $OC_2H_5$ | H | $OCH_3$ | $NHCH_3$ | CH | |
| $OC_2H_5$ | H | $OCH_3$ | $NHCH_3$ | N | |
| $OC_2H_5$ | H | $CH_3$ | $OC_2H_5$ | CH | |
| $OC_2H_5$ | H | $OCH_3$ | $OC_2H_5$ | CH | |
| $OC_2H_5$ | H | $CH_3$ | $OC_2H_5$ | N | |
| $OC_2H_5$ | H | $OCH_3$ | $OC_2H_5$ | N | |
| $OC_2H_5$ | H | $CH_3$ | Q | CH | |
| $OC_2H_5$ | H | $OCH_3$ | Q | CH | |
| $OC_2H_5$ | H | $CH_3$ | Q | N | |
| $OC_2H_5$ | H | $OCH_3$ | Q | N | |
| $OC_2H_5$ | H | $CH_3$ | Q | CH | |
| $OC_2H_5$ | H | $OCH_3$ | Q | CH | |
| $OC_2H_5$ | H | $CH_3$ | Q | N | |
| $OC_2H_5$ | $CH_3$ | $OCH_3$ | Q | N | |
| $OC_2H_5$ | $CH_3$ | Cl | $OCH_3$ | CH | |
| $OC_2H_5$ | H | Cl | $N(CH_3)_2$ | CH | |
| $OC_2H_5$ | H | Cl | $OC_2H_5$ | CH | |
| $SC_2H_5$ | H | $CH_3$ | $CH_3$ | CH | |
| $SC_2H_5$ | H | $OCH_3$ | $CH_3$ | CH | |
| $SC_2H_5$ | H | $OCH_3$ | $OCH_3$ | CH | |
| $SC_2H_5$ | H | Cl | $OCH_3$ | CH | |
| $SC_2H_5$ | H | $OCH_3$ | $N(CH_3)_2$ | CH | |
| $SC_2H_5$ | H | $CH_3$ | $CH_3$ | N | |
| $SC_2H_5$ | H | $OCH_3$ | $CH_3$ | N | |
| $SC_2H_5$ | H | $OCH_3$ | $OCH_3$ | N | |
| $SC_2H_5$ | H | $OCH_3$ | $N(CH_3)_2$ | N | |
| $SC_2H_5$ | H | $OCH_3$ | $OCH_2CF_3$ | N | |
| $SC_2H_5$ | $CH_3$ | $OCH_3$ | $CH_3$ | N | |
| $SC_2H_5$ | $CH_3$ | $OCH_3$ | $OCH_3$ | N | |
| $SC_2H_5$ | $CH_3$ | $CH_3$ | $OCH_3$ | CH | |
| $SC_2H_5$ | $CH_3$ | $OCH_3$ | $OCH_3$ | CH | |
| $SC_2H_5$ | H | Br | $OCH_3$ | CH | |
| $SC_2H_5$ | $CH_3$ | $OCH_3$ | $N(CH_3)_2$ | N | |
| $SC_2H_5$ | H | $CH_3$ | $OCH_2CF_3$ | N | |
| $SC_2H_5$ | H | $CH_3$ | $OCH_2CF_3$ | CH | |
| $SC_2H_5$ | H | $OCH_3$ | $OCH_2CF_3$ | CH | |
| $SC_2H_5$ | H | $OCH_3$ | $C_2H_5$ | CH | |
| $SC_2H_5$ | H | $OCH_3$ | $C_2H_5$ | N | |
| $SC_2H_5$ | H | $OCH_3$ | $NHCH_3$ | CH | |
| $SC_2H_5$ | H | $OCH_3$ | $NHCH_3$ | N | |
| $SC_2H_5$ | H | $CH_3$ | $OC_2H_5$ | CH | |
| $SC_2H_5$ | H | $OCH_3$ | $OC_2H_5$ | CH | |
| $SC_2H_5$ | H | $CH_3$ | $OC_2H_5$ | N | |
| $SC_2H_5$ | H | $OCH_3$ | $OC_2H_5$ | N | |
| $SC_2H_5$ | H | $CH_3$ | $OCH_2CHF_2$ | CH | |
| $SC_2H_5$ | H | $OCH_3$ | $OCH_2CHF_2$ | CH | |
| $SC_2H_5$ | H | $CH_3$ | $OCH_2CHF_2$ | N | |
| $SC_2H_5$ | H | $OCH_3$ | $OCH_2CHF_2$ | N | |
| $SC_2H_5$ | H | $CH_3$ | $OCH_2CHF_2$ | CH | |
| $SC_2H_5$ | H | $OCH_3$ | $OCH_2CHF_2$ | CH | |
| $SC_2H_5$ | H | $CH_3$ | $OCH_2CHF_2$ | N | |
| $SC_2H_5$ | $CH_3$ | $OCH_3$ | $OCH_2CHF_2$ | N | |
| $SC_2H_5$ | $CH_3$ | Cl | $OCH_3$ | CH | |
| $SC_2H_5$ | H | Cl | $N(CH_3)_2$ | CH | |
| $SC_2H_5$ | H | Cl | $OC_2H_5$ | CH | |
| $S(CH_2)_5CH_3$ | H | $CH_3$ | $CH_3$ | CH | |
| $S(CH_2)_5CH_3$ | H | $OCH_3$ | $CH_3$ | CH | |
| $S(CH_2)_5CH_3$ | H | $OCH_3$ | $OCH_3$ | CH | |
| $S(CH_2)_5CH_3$ | H | Cl | $OCH_3$ | CH | |
| $S(CH_2)_5CH_3$ | H | $CH_3$ | $CH_3$ | N | |
| $S(CH_2)_5CH_3$ | H | $OCH_3$ | $CH_3$ | N | |

TABLE I-continued

[Structure: benzene ring with CO₂-cyclobutyl and SO₂NHCON(R)- substituents, R₂ on ring; connected to a 6-membered N-heterocycle with X, Y, Z substituents]

| R₂ | R | X | Y | Z | m.p. (°C.) |
|---|---|---|---|---|---|
| S(CH₂)₅CH₃ | H | OCH₃ | OCH₃ | N | |
| S(O)(CH₃) | H | CH₃ | CH₃ | CH | |
| S(O)(CH₃) | H | OCH₃ | CH₃ | CH | |
| S(O)(CH₃) | H | OCH₃ | OCH₃ | CH | |
| S(O)(CH₃) | H | Cl | OCH₃ | CH | |
| S(O)(CH₃) | H | OCH₃ | N(CH₃)₂ | CH | |
| S(O)(CH₃) | H | CH₃ | CH₃ | N | |
| S(O)(CH₃) | H | OCH₃ | CH₃ | N | |
| S(O)(CH₃) | H | OCH₃ | OCH₃ | N | |
| S(O)(CH₃) | H | OCH₃ | N(CH₃)₂ | N | |
| S(O)(CH₃) | H | OCH₃ | OCH₂CF₃ | N | |
| S(O)(CH₃) | CH₃ | OCH₃ | CH₃ | N | |
| S(O)(CH₃) | CH₃ | OCH₃ | OCH₃ | N | |
| S(O)(CH₃) | CH₃ | CH₃ | OCH₃ | CH | |
| S(O)(CH₃) | CH₃ | OCH₃ | OCH₃ | CH | |
| S(O)(CH₃) | H | Br | OCH₃ | CH | |
| S(O)(CH₃) | H | OCH₃ | N(CH₃)₂ | CH | |
| S(O)(CH₃) | CH₃ | OCH₃ | N(CH₃)₂ | N | |
| S(O)(CH₃) | H | CH₃ | OCH₂CF₃ | N | |
| S(O)(CH₃) | H | CH₃ | OCH₂CF₂ | CH | |
| S(O)(CH₃) | H | OCH₃ | OCH₂CF₃ | CH | |
| S(O)(CH₃) | H | OCH₃ | C₂H₅ | CH | |
| S(O)(CH₃) | H | OCH₃ | C₂H₅ | N | |
| S(O)(CH₃) | H | OCH₃ | NHCH₃ | CH | |
| S(O)(CH₃) | H | OCH₃ | NHCH₃ | N | |
| S(O)(CH₃) | H | CH₃ | OC₂H₅ | CH | |
| S(O)(CH₃) | H | OCH₃ | OC₂H₅ | CH | |
| S(O)(CH₃) | H | CH₃ | OC₂H₅ | N | |
| S(O)(CH₃) | H | OCH₃ | OC₂H₅ | N | |
| S(O)(CH₃) | H | CH₃ | OCH₂CHF₂ | CH | |
| S(O)(CH₃) | H | OCH₃ | OCH₂CHF₂ | CH | |
| S(O)(CH₃) | H | CH₃ | OCH₂CHF₂ | N | |
| S(O)(CH₃) | H | OCH₃ | OCH₂CHF₂ | N | |
| S(O)(CH₃) | H | CH₃ | OCH₂CHF₂ | CH | |
| S(O)(CH₃) | H | OCH₃ | OCH₂CHF₂ | CH | |
| S(O)(CH₃) | H | CH₃ | OCH₂CHF₂ | N | |
| S(O)(CH₃) | H | OCH₃ | OCH₂CHF₂ | N | |
| S(O)(CH₃) | CH₃ | Cl | OCH₃ | CH | |
| S(O)(CH₃) | H | Cl | N(CH₃)₂ | CH | |
| S(O)(CH₃) | H | Cl | OC₂H₅ | CH | |
| OCH₂CH=CH₂ | H | CH₃ | CH₃ | CH | |
| OCH₂CH=CH₂ | H | OCH₃ | CH₃ | CH | |
| OCH₂CH=CH₂ | H | OCH₃ | OCH₃ | CH | |
| OCH₂CH=CH₂ | H | Cl | OCH₃ | CH | |
| OCH₂CH=CH₂ | H | OCH₃ | N(CH₃)₂ | CH | |
| OCH₂CH=CH₂ | H | CH₃ | CH₃ | N | |
| OCH₂CH=CH₂ | H | OCH₃ | CH₃ | N | |
| OCH₂CH=CH₂ | H | OCH₃ | OCH₃ | N | |
| OCH₂CH=CH₂ | H | OCH₃ | N(CH₃)₂ | N | |
| OCH₂CH=CH₂ | H | OCH₃ | OCH₂CF₃ | N | |
| OCH₂CH=CH₂ | CH₃ | OCH₃ | CH₃ | N | |
| OCH₂CH=CH₂ | CH₃ | OCH₃ | OCH₃ | N | |
| OCH₂CH=CH₂ | CH₃ | CH₃ | OCH₃ | CH | |
| OCH₂CH=CH₂ | CH₃ | OCH₃ | OCH₃ | CH | |
| OCH₂CH=CH₂ | H | Br | OCH₃ | CH | |
| OCH₂CH=CH₂ | CH₃ | OCH₃ | N(CH₃)₂ | N | |
| OCH₂CH=CH₂ | H | CH₃ | OCH₂CF₃ | N | |
| OCH₂CH=CH₂ | H | CH₃ | OCH₂CF₃ | CH | |
| OCH₂CH=CH₂ | H | OCH₃ | OCH₂CF₃ | CH | |
| OCH₂CH=CH₂ | H | OCH₃ | C₂H₅ | CH | |
| OCH₂CH=CH₂ | H | OCH₃ | C₂H₅ | N | |
| OCH₂CH=CH₂ | H | OCH₃ | NHCH₃ | CH | |
| OCH₂CH=CH₂ | H | OCH₃ | NHCH₃ | N | |
| OCH₂CH=CH₂ | H | CH₃ | OC₂H₅ | CH | |
| OCH₂CH=CH₂ | H | OCH₃ | OC₂H₅ | CH | |
| OCH₂CH=CH₂ | H | CH₃ | OC₂H₅ | N | |
| OCH₂CH=CH₂ | H | OCH₃ | OC₂H₅ | N | |
| OCH₂CH=CH₂ | H | CH₃ | OCH₂CHF₂ | CH | |
| OCH₂CH=CH₂ | H | OCH₃ | OCH₂CHF₂ | CH | |
| OCH₂CH=CH₂ | H | CH₃ | OCH₂CHF₂ | N | |

TABLE I-continued

[Structure: benzene ring with CO₂-cyclobutyl group, R₂ substituent, and SO₂NHCON(R)- linked to a pyrimidine/triazine ring bearing X, Y, Z substituents]

| R₂ | R | X | Y | Z | m.p. (°C.) |
|---|---|---|---|---|---|
| OCH₂CH=CH₂ | H | OCH₃ | OCH₂CHF₂ | N | |
| OCH₂CH=CH₂ | H | CH₃ | OCH₂CH₂F | CH | |
| OCH₂CH=CH₂ | H | OCH₃ | OCH₂CH₂F | CH | |
| OCH₂CH=CH₂ | H | CH₃ | OCH₂CH₂F | N | |
| OCH₂CH=CH₂ | CH₃ | OCH₃ | OCH₂CH₂F | N | |
| OCH₂CH=CH₂ | CH₃ | Cl | OCH₃ | CH | |
| OCH₂CH=CH₂ | H | CL | N(CH₃)₂ | CH | |
| OCH₂CH=CH₂ | H | Cl | OC₂H₅ | CH | |
| OCH₂C≡CH | H | CH₃ | CH₃ | CH | |
| OCH₂C≡CH | H | OCH₃ | CH₃ | CH | |
| OCH₂C≡CH | H | OCH₃ | OCH₃ | CH | |
| OCH₂C≡CH | H | Cl | OCH₃ | CH | |
| OCH₂C≡CH | H | OCH₃ | N(CH₃)₂ | CH | |
| OCH₂C≡CH | H | CH₃ | CH₃ | N | |
| OCH₂C≡CH | H | OCH₃ | CH₃ | N | |
| OCH₂C≡CH | H | OCH₃ | OCH₃ | N | |
| OCH₂C≡CH | H | OCH₃ | N(CH₃)₂ | N | |
| OCH₂C≡CH | H | OCH₃ | OCH₂CF₃ | N | |
| OCH₂C≡CH | CH₃ | OCH₃ | CH₃ | N | |
| OCH₂C≡CH | CH₃ | OCH₃ | OCH₃ | N | |
| OCH₂C≡CH | CH₃ | CH₃ | OCH₃ | CH | |
| OCH₂C≡CH | CH₃ | OCH₃ | OCH₃ | CH | |
| OCH₂C≡CH | H | Br | OCH₃ | CH | |
| OCH₂C≡CH | CH₃ | OCH₃ | N(CH₃)₂ | N | |
| OCH₂C≡CH | H | CH₃ | OCH₂CF₃ | N | |
| OCH₂C≡CH | H | CH₃ | OCH₂CF₃ | CH | |
| OCH₂C≡CH | H | OCH₃ | OCH₂CF₃ | CH | |
| OCH₂C≡CH | H | OCH₃ | C₂H₅ | CH | |
| OCH₂C≡CH | H | OCH₃ | C₂H₅ | N | |
| OCH₂C≡CH | H | OCH₃ | NHCH₃ | CH | |
| OCH₂C≡CH | H | OCH₃ | NHCH₃ | N | |
| OCH₂C≡CH | H | CH₃ | OC₂H₅ | CH | |
| OCH₂C≡CH | H | OCH₃ | OC₂H₅ | CH | |
| OCH₂C≡CH | H | CH₃ | OC₂H₅ | N | |
| OCH₂C≡CH | H | OCH₃ | OC₂H₅ | N | |
| OCH₂C≡CH | H | CH₃ | OCH₂CHF₂ | CH | |
| OCH₂C≡CH | H | OCH₃ | OCH₂CHF₂ | CH | |
| OCH₂C≡CH | H | CH₃ | OCH₂CHF₂ | N | |
| OCH₂C≡CH | H | OCH₃ | OCH₂CHF₂ | N | |
| OCH₂C≡CH | H | CH₃ | OCH₂CH₂F | CH | |
| OCH₂C≡CH | H | OCH₃ | OCH₂CH₂F | CH | |
| OCH₂C≡CH | H | CH₃ | OCH₂CF₃ | N | |
| OCH₂C≡CH | CH₃ | OCH₃ | OCH₂CF₃ | N | |
| OCH₂C≡CH | CH₃ | Cl | OCH₃ | CH | |
| OCH₂C≡CH | H | Cl | N(CH₃)₂ | CH | |
| OCH₂C≡CH | H | Cl | OC₂H₅ | CH | |
| SCH₂CH=CH₂ | H | CH₃ | CH₃ | CH | |
| SCH₂CH=CH₂ | H | OCH₃ | CH₃ | CH | |
| SCH₂CH=CH₂ | H | OCH₃ | OCH₃ | CH | |
| SCH₂CH=CH₂ | H | Cl | OCH₃ | CH | |
| SCH₂CH=CH₂ | H | OCH₃ | N(CH₃)₂ | N | |
| SCH₂CH=CH₂ | H | CH₃ | CH₃ | N | |
| SCH₂CH=CH₂ | H | OCH₃ | CH₃ | N | |
| SCH₂CH=CH₂ | H | OCH₃ | OCH₃ | N | |
| SCH₂CH=CH₂ | H | OCH₃ | N(CH₃)₂ | N | |
| SCH₂CH=CH₂ | H | OCH₃ | OCH₂CF₃ | N | |
| SCH₂CH=CH₂ | CH₃ | OCH₃ | CH₃ | N | |
| SCH₂CH=CH₂ | CH₃ | OCH₃ | OCH₃ | N | |
| SCH₂CH=CH₂ | CH₃ | CH₃ | OCH₃ | CH | |
| SCH₂CH=CH₂ | CH₃ | OCH₃ | OCH₃ | CH | |
| SCH₂CH=CH₂ | H | Br | OCH₃ | CH | |
| SCH₂CH=CH₂ | CH₃ | OCH₃ | N(CH₃)₂ | N | |
| SCH₂CH=CH₂ | H | CH₃ | OCH₂CF₃ | N | |
| SCH₂CH=CH₂ | H | CH₃ | OCH₂CF₃ | CH | |
| SCH₂CH=CH₂ | H | OCH₃ | OCH₂CF₃ | CH | |
| SCH₂CH=CH₂ | H | OCH₃ | C₂H₅ | CH | |
| SCH₂CH=CH₂ | H | OCH₃ | C₂H₅ | CH | |
| SCH₂CH=CH₂ | H | OCH₃ | NHCH₃ | CH | |
| SCH₂CH=CH₂ | H | OCH₃ | NHCH₃ | N | |
| SCH₂CH=CH₂ | H | CH₃ | OC₂H₅ | CH | |

TABLE I-continued

Structure: R₂-substituted phenyl with CO₂-cyclobutyl and SO₂NHCON(R)- linked to a heterocycle with substituents X, Y, Z (and N positions).

| R₂ | R | X | Y | Z | m.p. (°C.) |
|---|---|---|---|---|---|
| SCH₂CH=CH₂ | H | OCH₃ | OC₂H₅ | CH | |
| SCH₂CH=CH₂ | H | CH₃ | OC₂H₅ | N | |
| SCH₂CH=CH₂ | H | OCH₃ | OC₂H₅ | N | |
| SCH₂CH=CH₂ | H | CH₃ | OCH₂CHF₂ | CH | |
| SCH₂CH=CH₂ | H | OCH₃ | OCH₂CHF₂ | CH | |
| SCH₂CH=CH₂ | H | CH₃ | OCH₂CHF₂ | N | |
| SCH₂CH=CH₂ | H | OCH₃ | OCH₂CHF₂ | N | |
| SCH₂CH=CH₂ | H | CH₃ | OCH₂CH₂F | CH | |
| SCH₂CH=CH₂ | H | OCH₃ | OCH₂CH₂F | CH | |
| SCH₂CH=CH₂ | H | CH₃ | OCH₂CH₂F | N | |
| SCH₂CH=CH₂ | H | OCH₃ | OCH₂CH₂F | N | |
| SCH₂CH=CH₂ | CH₃ | Cl | OCH₃ | CH | |
| SCH₂CH=CH₂ | H | Cl | N(CH₃)₂ | CH | |
| SCH₂CH=CH₂ | H | Cl | OC₂H₅ | CH | |
| SCH₂C≡CH | H | CH₃ | CH₃ | CH | |
| SCH₂C≡CH | H | OCH₃ | CH₃ | CH | |
| SCH₂C≡CH | H | OCH₃ | OCH₃ | CH | |
| SCH₂C≡CH | H | Cl | OCH₃ | CH | |
| SCH₂C≡CH | H | OCH₃ | N(CH₃)₂ | N | |
| SCH₂C≡CH | H | CH₃ | CH₃ | N | |
| SCH₂C≡CH | H | OCH₃ | CH₃ | N | |
| SCH₂C≡CH | H | OCH₃ | OCH₃ | N | |
| SCH₂C≡CH | H | OCH₃ | N(CH₃)₂ | N | |
| SCH₂C≡CH | H | OCH₃ | OCH₂CF₃ | N | |
| SCH₂C≡CH | CH₃ | OCH₃ | CH₃ | N | |
| SCH₂C≡CH | CH₃ | OCH₃ | OCH₃ | N | |
| SCH₂C≡CH | CH₃ | CH₃ | OCH₃ | CH | |
| SCH₂C≡CH | CH₃ | OCH₃ | OCH₃ | CH | |
| SCH₂C≡CH | H | Br | OCH₃ | CH | |
| SCH₂C≡CH | CH₃ | OCH₃ | N(CH₃)₂ | N | |
| SCH₂C≡CH | H | CH₃ | OCH₂CF₃ | N | |
| SCH₂C≡CH | H | CH₃ | OCH₂CF₃ | CH | |
| SCH₂C≡CH | H | OCH₃ | OCH₂CF₃ | CH | |
| SCH₂C≡CH | H | OCH₃ | C₂H₅ | CH | |
| SCH₂C≡CH | H | OCH₃ | C₂H₅ | CH | |
| SCH₂C≡CH | H | OCH₃ | NHCH₃ | CH | |
| SCH₂C≡CH | H | OCH₃ | NHCH₃ | N | |
| SCH₂C≡CH | H | CH₃ | OC₂H₅ | CH | |
| SCH₂C≡CH | H | OCH₃ | OC₂H₅ | CH | |
| SCH₂C≡CH | H | CH₃ | OC₂H₅ | N | |
| SCH₂C≡CH | H | OCH₃ | OC₂H₅ | N | |
| SCH₂C≡CH | H | CH₃ | OCH₂CHF₂ | CH | |
| SCH₂C≡CH | H | OCH₃ | OCH₂CHF₂ | CH | |
| SCH₂C≡CH | H | CH₃ | OCH₂CHF₂ | N | |
| SCH₂C≡CH | H | OCH₃ | OCH₂CHF₂ | N | |
| SCH₂C≡CH | H | CH₃ | OCH₂CH₂F | CH | |
| SCH₂C≡CH | H | OCH₃ | OCH₂CH₂F | CH | |
| SCH₂C≡CH | H | CH₃ | OCH₂CH₂F | N | |
| SCH₂C≡CH | H | OCH₃ | OCH₂CH₂F | N | |
| SCH₂C≡CH | CH₃ | Cl | OCH₃ | CH | |
| SCH₂C≡CH | H | Cl | N(CH₃)₂ | CH | |
| SCH₂C≡CH | H | Cl | OC₂H₅ | CH | |
| CH₂CH₂F | H | CH₃ | CH₃ | CH | |
| CH₂CH₂F | H | OCH₃ | CH₃ | CH | |
| CH₂CH₂F | H | OCH₃ | OCH₃ | CH | |
| CH₂CH₂F | H | Cl | OCH₃ | CH | |
| CH₂CH₂F | H | OCH₃ | N(CH₃)₂ | CH | |
| CH₂CH₂F | H | CH₃ | CH₃ | N | |
| CH₂CH₂F | H | OCH₃ | CH₃ | N | |
| CH₂CH₂F | H | OCH₃ | OCH₃ | N | |
| CH₂CH₂F | H | OCH₃ | N(CH₃)₂ | N | |
| CH₂CH₂F | H | OCH₃ | OCH₂CF₃ | N | |
| CH₂CH₂F | CH₃ | OCH₃ | CH₃ | N | |
| CH₂CH₂F | CH₃ | OCH₃ | OCH₃ | N | |
| CH₂CH₂F | CH₃ | CH₃ | OCH₃ | CH | |
| CH₂CH₂F | CH₃ | OCH₃ | OCH₃ | CH | |
| CH₂CH₂F | H | Br | OCH₃ | CH | |
| CH₂CH₂F | CH₃ | OCH₃ | N(CH₃)₂ | N | |
| CH₂CH₂F | H | CH₃ | OCH₂CF₃ | N | |
| CH₂CH₂F | H | CH₃ | OCH₂CF₃ | CH | |

TABLE I-continued

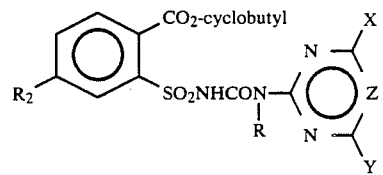

| $R_2$ | R | X | Y | Z | m.p. (°C.) |
|---|---|---|---|---|---|
| $CH_2CH_2F$ | H | $OCH_3$ | $OCH_2CF_3$ | CH | |
| $CH_2CH_2F$ | H | $OCH_3$ | $C_2H_5$ | CH | |
| $CH_2CH_2F$ | H | $OCH_3$ | $C_2H_5$ | N | |
| $CH_2CH_2F$ | H | $OCH_3$ | $NHCH_3$ | CH | |
| $CH_2CH_2F$ | H | $OCH_3$ | $NHCH_3$ | N | |
| $CH_2CH_2F$ | H | $CH_3$ | $OC_2H_5$ | CH | |
| $CH_2CH_2F$ | H | $OCH_3$ | $OC_2H_5$ | CH | |
| $CH_2CH_2F$ | H | $CH_3$ | $OC_2H_5$ | N | |
| $CH_2CH_2F$ | H | $OCH_3$ | $OC_2H_5$ | N | |
| $CH_2CH_2F$ | H | $CH_3$ | $OCH_2CHF_2$ | CH | |
| $CH_2CH_2F$ | H | $OCH_3$ | $OCH_2CHF_2$ | CH | |
| $CH_2CH_2F$ | H | $CH_3$ | $OCH_2CHF_2$ | N | |
| $CH_2CH_2F$ | H | $OCH_3$ | $OCH_2CHF_2$ | N | |
| $CH_2CH_2F$ | H | $CH_3$ | $OCH_2CH_2F$ | CH | |
| $CH_2CH_2F$ | H | $OCH_3$ | $OCH_2CH_2F$ | CH | |
| $CH_2CH_2F$ | H | $CH_3$ | $OCH_2CF_3$ | N | |
| $CH_2CH_2F$ | $CH_3$ | $OCH_3$ | $OCH_2CF_3$ | N | |
| $CH_2CH_2F$ | $CH_3$ | Cl | $OCH_3$ | CH | |
| $CH_2CH_2F$ | H | Cl | $N(CH_3)_2$ | CH | |
| $CH_2CH_2F$ | H | Cl | $OC_2H_5$ | CH | |
| $CH_2CF_3$ | H | $CH_3$ | $CH_3$ | CH | |
| $CH_2CF_3$ | H | $OCH_3$ | $CH_3$ | CH | |
| $CH_2CF_3$ | H | $OCH_3$ | $OCH_3$ | CH | |
| $CH_2CF_3$ | H | Cl | $OCH_3$ | CH | |
| $CH_2CF_3$ | H | $OCH_3$ | $N(CH_3)_2$ | CH | |
| $CH_2CF_3$ | H | $CH_3$ | $CH_3$ | N | |
| $CH_2CF_3$ | H | $OCH_3$ | $CH_3$ | N | |
| $CH_2CF_3$ | H | $OCH_3$ | $OCH_3$ | N | |
| $CH_2CF_3$ | H | $OCH_3$ | $N(CH_3)_2$ | N | |
| $CH_2CF_3$ | H | $OCH_3$ | $OCH_2CF_3$ | N | |
| $CH_2CF_3$ | $CH_3$ | $OCH_3$ | $CH_3$ | N | |
| $CH_2CF_3$ | $CH_3$ | $OCH_3$ | $OCH_3$ | N | |
| $CH_2CF_3$ | $CH_3$ | $CH_3$ | $OCH_3$ | CH | |
| $CH_2CF_3$ | $CH_3$ | $OCH_3$ | $OCH_3$ | CH | |
| $CH_2CF_3$ | H | Br | $OCH_3$ | CH | |
| $CH_2CF_3$ | $CH_3$ | $OCH_3$ | $N(CH_3)_2$ | N | |
| $CH_2CF_3$ | H | $CH_3$ | $OCH_2CF_3$ | N | |
| $CH_2CF_3$ | H | $CH_3$ | $OCH_2CF_3$ | CH | |
| $CH_2CF_3$ | H | $OCH_3$ | $OCH_2CF_3$ | CH | |
| $CH_2CF_3$ | H | $OCH_3$ | $C_2H_5$ | CH | |
| $CH_2CF_3$ | H | $OCH_3$ | $C_2H_5$ | N | |
| $CH_2CF_3$ | H | $OCH_3$ | $NHCH_3$ | CH | |
| $CH_2CF_3$ | H | $OCH_3$ | $NHCH_3$ | N | |
| $CH_2CF_3$ | H | $CH_3$ | $OC_2H_5$ | CH | |
| $CH_2CF_3$ | H | $OCH_3$ | $OC_2H_5$ | CH | |
| $CH_2CF_3$ | H | $CH_3$ | $OC_2H_5$ | N | |
| $CH_2CF_3$ | H | $OCH_3$ | $OC_2H_5$ | N | |
| $CH_2CF_3$ | H | $CH_3$ | $OCH_2CHF_2$ | CH | |
| $CH_2CF_3$ | H | $OCH_3$ | $OCH_2CHF_2$ | CH | |
| $CH_2CF_3$ | H | $CH_3$ | $OCH_2CHF_2$ | N | |
| $CH_2CF_3$ | H | $OCH_3$ | $OCH_2CHF_2$ | N | |
| $CH_2CF_3$ | H | $CH_3$ | $OCH_2CH_2F$ | CH | |
| $CH_2CF_3$ | H | $OCH_3$ | $OCH_2CH_2F$ | CH | |
| $CH_2CF_3$ | H | $CH_3$ | $OCH_2CH_2F$ | N | |
| $CH_2CF_3$ | $CH_3$ | $OCH_3$ | $OCH_2CH_2F$ | N | |
| $CH_2CF_3$ | $CH_3$ | Cl | $OCH_3$ | CH | |
| $CH_2CF_3$ | H | Cl | $N(CH_3)_2$ | CH | |
| $CH_2CF_3$ | H | Cl | $OC_2H_5$ | CH | |
| $CHFCH_3$ | H | $CH_3$ | $CH_3$ | CH | |
| $CHFCH_3$ | H | $OCH_3$ | $CH_3$ | CH | |
| $CHFCH_3$ | H | $OCH_3$ | $OCH_3$ | CH | |
| $CHFCH_3$ | H | Cl | $OCH_3$ | CH | |
| $CHFCH_3$ | H | $OCH_3$ | $N(CH_3)_2$ | CH | |
| $CHFCH_3$ | H | $CH_3$ | $CH_3$ | N | |
| $CHFCH_3$ | H | $OCH_3$ | $CH_3$ | N | |
| $CHFCH_3$ | H | $OCH_3$ | $OCH_3$ | N | |
| $CHFCH_3$ | H | $OCH_3$ | $N(CH_3)_2$ | N | |
| $CHFCH_3$ | H | $OCH_3$ | $OCH_2CF_3$ | N | |
| $CHFCH_3$ | $CH_3$ | $OCH_3$ | $CH_3$ | N | |
| $CHFCH_3$ | $CH_3$ | $OCH_3$ | $OCH_3$ | N | |

TABLE I-continued

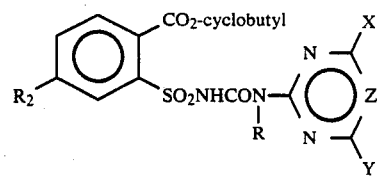

| R$_2$ | R | X | Y | Z | m.p. (°C.) |
|---|---|---|---|---|---|
| CHFCH$_3$ | CH$_3$ | CH$_3$ | OCH$_3$ | CH | |
| CHFCH$_3$ | CH$_3$ | OCH$_3$ | OCH$_3$ | CH | |
| CHFCH$_3$ | H | Br | OCH$_3$ | CH | |
| CHFCH$_3$ | CH$_3$ | OCH$_3$ | N(CH$_3$)$_2$ | N | |
| CHFCH$_3$ | H | CH$_3$ | OCH$_2$CF$_3$ | N | |
| CHFCH$_3$ | H | CH$_3$ | OCH$_2$CF$_3$ | CH | |
| CHFCH$_3$ | H | OCH$_3$ | OCH$_2$CF$_3$ | CH | |
| CHFCH$_3$ | H | OCH$_3$ | C$_2$H$_5$ | CH | |
| CHFCH$_3$ | H | OCH$_3$ | C$_2$H$_5$ | N | |
| CHFCH$_3$ | H | OCH$_3$ | NHCH$_3$ | CH | |
| CHFCH$_3$ | H | OCH$_3$ | NHCH$_3$ | N | |
| CHFCH$_3$ | H | CH$_3$ | OC$_2$H$_5$ | CH | |
| CHFCH$_3$ | H | OCH$_3$ | OC$_2$H$_5$ | CH | |
| CHFCH$_3$ | H | CH$_3$ | OC$_2$H$_5$ | N | |
| CHFCH$_3$ | H | OCH$_3$ | OC$_2$H$_5$ | N | |
| CHFCH$_3$ | H | CH$_3$ | OCH$_2$CHF$_2$ | CH | |
| CHFCH$_3$ | H | OCH$_3$ | OCH$_2$CHF$_2$ | CH | |
| CHFCH$_3$ | H | CH$_3$ | OCH$_2$CHF$_2$ | N | |
| CHFCH$_3$ | H | OCH$_3$ | OCH$_2$CHF$_2$ | N | |
| CHFCH$_3$ | H | CH$_3$ | OCH$_2$CH$_2$F | CH | |
| CHFCH$_3$ | H | OCH$_3$ | OCH$_2$CH$_2$F | CH | |
| CHFCH$_3$ | H | CH$_3$ | OCH$_2$CF$_3$ | N | |
| CHFCH$_3$ | CH$_3$ | OCH$_3$ | OCH$_2$CF$_3$ | N | |
| CHFCH$_3$ | CH$_3$ | Cl | OCH$_3$ | CH | |
| CHFCH$_3$ | H | Cl | N(CH$_3$)$_2$ | CH | |
| CHFCH$_3$ | H | Cl | OC$_2$H$_5$ | CH | |
| CH$_2$F | H | CH$_3$ | CH$_3$ | CH | |
| CH$_2$F | H | OCH$_3$ | CH$_3$ | CH | |
| CH$_2$F | H | OCH$_3$ | OCH$_3$ | CH | |
| CH$_2$F | H | Cl | OCH$_3$ | CH | |
| CH$_2$F | H | OCH$_3$ | N(CH$_3$)$_2$ | CH | |
| CH$_2$F | H | OCH$_3$ | CH$_3$ | N | |
| CH$_2$F | H | OCH$_3$ | OCH$_3$ | N | |
| CH$_2$F | H | OCH$_3$ | N(CH$_3$)$_2$ | N | |
| CH$_2$F | H | OCH$_3$ | OCH$_2$CF$_3$ | N | |
| CH$_2$F | CH$_3$ | OCH$_3$ | CH$_3$ | N | |
| CH$_2$F | CH$_3$ | OCH$_3$ | OCH$_3$ | N | |
| CH$_2$F | CH$_3$ | CH$_3$ | OCH$_3$ | CH | |
| CH$_2$F | CH$_3$ | OCH$_3$ | OCH$_3$ | CH | |
| CH$_2$F | H | Br | OCH$_3$ | CH | |
| CH$_2$F | CH$_3$ | OCH$_3$ | N(CH$_3$)$_2$ | N | |
| CH$_2$F | H | CH$_3$ | OCH$_2$CF$_3$ | N | |
| CH$_2$F | H | CH$_3$ | OCH$_2$CF$_3$ | CH | |
| CH$_2$F | H | OCH$_3$ | OCH$_2$CF$_3$ | CH | |
| CH$_2$F | H | OCH$_3$ | C$_2$H$_5$ | CH | |
| CH$_2$F | H | OCH$_3$ | C$_2$H$_5$ | N | |
| CH$_2$F | H | OCH$_3$ | NHCH$_3$ | CH | |
| CH$_2$F | H | OCH$_3$ | NHCH$_3$ | N | |
| CH$_2$F | H | OCH$_3$ | OC$_2$H$_5$ | CH | |
| CH$_2$F | H | OCH$_3$ | OC$_2$H$_5$ | CH | |
| CH$_2$F | H | CH$_3$ | OC$_2$H$_5$ | N | |
| CH$_2$F | H | OCH$_3$ | OC$_2$H$_5$ | N | |
| CH$_2$F | H | CH$_3$ | OCH$_2$CHF$_2$ | CH | |
| CH$_2$F | H | OCH$_3$ | OCH$_2$CHF$_2$ | CH | |
| CH$_2$F | H | CH$_3$ | OCH$_2$CHF$_2$ | N | |
| CH$_2$F | H | OCH$_3$ | OCH$_2$CHF$_2$ | N | |
| CH$_2$F | H | CH$_3$ | OCH$_2$CH$_2$F | CH | |
| CH$_2$F | H | OCH$_3$ | OCH$_2$CH$_2$F | CH | |
| CH$_2$F | H | CH$_3$ | OCH$_2$CH$_2$F | N | |
| CH$_2$F | CH$_3$ | OCH$_3$ | OCH$_2$CH$_2$F | N | |
| CH$_2$F | CH$_3$ | Cl | OCH$_3$ | CH | |
| CH$_2$F | H | Cl | N(CH$_3$)$_2$ | CH | |
| CH$_2$F | H | Cl | OC$_2$H$_5$ | CH | |
| CHF$_2$ | H | CH$_3$ | CH$_3$ | CH | |
| CHF$_2$ | H | OCH$_3$ | CH$_3$ | CH | |
| CHF$_2$ | H | OCH$_3$ | OCH$_3$ | CH | |
| CHF$_2$ | H | Cl | OCH$_3$ | CH | |
| CHF$_2$ | H | OCH$_3$ | N(CH$_3$)$_2$ | CH | |
| CHF$_2$ | H | CH$_3$ | CH$_3$ | N | |

TABLE I-continued

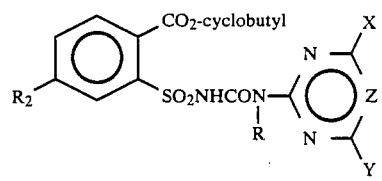

| R₂ | R | X | Y | Z | m.p. (°C.) |
|---|---|---|---|---|---|
| CHF₂ | H | OCH₃ | CH₃ | N | |
| CHF₂ | H | OCH₃ | OCH₃ | N | |
| CHF₂ | H | OCH₃ | N(CH₃)₂ | N | |
| CHF₂ | H | OCH₃ | OCH₂CF₃ | N | |
| CHF₂ | CH₃ | OCH₃ | CH₃ | N | |
| CHF₂ | CH₃ | OCH₃ | OCH₃ | N | |
| CHF₂ | CH₃ | CH₃ | OCH₃ | CH | |
| CHF₂ | CH₃ | OCH₃ | OCH₃ | CH | |
| CHF₂ | H | Br | OCH₃ | CH | |
| CHF₂ | CH₃ | OCH₃ | N(CH₃)₂ | N | |
| CHF₂ | H | CH₃ | OCH₂CF₃ | N | |
| CHF₂ | H | CH₃ | OCH₂CF₃ | CH | |
| CHF₂ | H | OCH₃ | OCH₂CF₃ | CH | |
| CHF₂ | H | OCH₃ | C₂H₅ | CH | |
| CHF₂ | H | OCH₃ | C₂H₅ | N | |
| CHF₂ | H | OCH₃ | NHCH₃ | CH | |
| CHF₂ | H | OCH₃ | NHCH₃ | N | |
| CHF₂ | H | CH₃ | OC₂H₅ | CH | |
| CHF₂ | H | OCH₃ | OC₂H₅ | CH | |
| CHF₂ | H | CH₃ | OC₂H₅ | N | |
| CHF₂ | H | OCH₃ | OC₂H₅ | N | |
| CHF₂ | H | CH₃ | OCH₂CHF₂ | CH | |
| CHF₂ | H | OCH₃ | OCH₂CHF₂ | CH | |
| CHF₂ | H | CH₃ | OCH₂CHF₂ | N | |
| CHF₂ | H | OCH₃ | OCH₂CHF₂ | N | |
| CHF₂ | H | CH₃ | OCH₂CH₂F | CH | |
| CHF₂ | H | OCH₃ | OCH₂CH₂F | CH | |
| CHF₂ | H | CH₃ | OCH₂CH₂F | N | |
| CHF₂ | CH₃ | OCH₃ | OCH₂CH₂F | N | |
| CHF₂ | CH₃ | Cl | OCH₃ | CH | |
| CHF₂ | H | Cl | N(CH₃)₂ | CH | |
| CHF₂ | H | Cl | OC₂H₅ | CH | |
| CH₂OCH₃ | H | CH₃ | CH₃ | CH | |
| CH₂OCH₃ | H | OCH₃ | CH₃ | CH | |
| CH₂OCH₃ | H | OCH₃ | OCH₃ | CH | |
| CH₂OCH₃ | H | Cl | OCH₃ | CH | |
| CH₂OCH₃ | H | OCH₃ | N(CH₃)₂ | CH | |
| CH₂OCH₃ | H | CH₃ | CH₃ | N | |
| CH₂OCH₃ | H | OCH₃ | CH₃ | N | |
| CH₂OCH₃ | H | OCH₃ | OCH₃ | N | |
| CH₂OCH₃ | H | OCH₃ | N(CH₃)₂ | N | |
| CH₂OCH₃ | H | OCH₃ | OCH₂CF₃ | N | |
| CH₂OCH₃ | CH₃ | OCH₃ | CH₃ | N | |
| CH₂OCH₃ | CH₃ | OCH₃ | OCH₃ | N | |
| CH₂OCH₃ | CH₃ | CH₃ | OCH₃ | CH | |
| CH₂OCH₃ | CH₃ | OCH₃ | OCH₃ | CH | |
| CH₂OCH₃ | H | Br | OCH₃ | CH | |
| CH₂OCH₃ | H | OCH₃ | N(CH₃)₂ | CH | |
| CH₂OCH₃ | CH₃ | OCH₃ | N(CH₃)₂ | N | |
| CH₂OCH₃ | H | CH₃ | OCH₂CF₃ | N | |
| CH₂OCH₃ | H | CH₃ | OCH₂CF₃ | CH | |
| CH₂OCH₃ | H | OCH₃ | OCH₂CF₃ | CH | |
| CH₂OCH₃ | H | OCH₃ | C₂H₅ | CH | |
| CH₂OCH₃ | H | OCH₃ | C₂H₅ | N | |
| CH₂OCH₃ | H | OCH₃ | NHCH₃ | CH | |
| CH₂OCH₃ | H | OCH₃ | NHCH₃ | N | |
| CH₂OCH₃ | H | CH₃ | OC₂H₅ | CH | |
| CH₂OCH₃ | H | OCH₃ | OC₂H₅ | CH | |
| CH₂OCH₃ | H | CH₃ | OC₂H₅ | N | |
| CH₂OCH₃ | H | OCH₃ | OC₂H₅ | N | |
| CH₂OCH₃ | H | CH₃ | OCH₂CHF₂ | CH | |
| CH₂OCH₃ | H | OCH₃ | OCH₂CHF₂ | CH | |
| CH₂OCH₃ | H | CH₃ | OCH₂CHF₂ | N | |
| CH₂OCH₃ | H | OCH₃ | OCH₂CHF₂ | N | |
| CH₂OCH₃ | H | CH₃ | OCH₂CH₂F | CH | |
| CH₂OCH₃ | H | OCH₃ | OCH₂CH₂F | CH | |
| CH₂OCH₃ | H | CH₃ | OCH₂CF₃ | N | |
| CH₂OCH₃ | CH₃ | OCH₃ | OCH₂CF₃ | N | |
| CH₂OCH₃ | CH₃ | Cl | OCH₃ | CH | |
| CH₂OCH₃ | H | Cl | N(CH₃)₂ | CH | |

TABLE I-continued

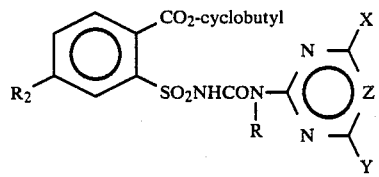

| $R_2$ | R | X | Y | Z | m.p. (°C.) |
|---|---|---|---|---|---|
| $CH_2OCH_3$ | H | Cl | $OC_2H_5$ | CH | |
| $CH_2SCH_3$ | H | $CH_3$ | $CH_3$ | CH | |
| $CH_2SCH_3$ | H | $OCH_3$ | $CH_3$ | CH | |
| $CH_2SCH_3$ | H | $OCH_3$ | $OCH_3$ | CH | |
| $CH_2SCH_3$ | H | Cl | $OCH_3$ | CH | |
| $CH_2SCH_3$ | H | $OCH_3$ | $N(CH_3)_2$ | CH | |
| $CH_2SCH_3$ | H | $CH_3$ | $CH_3$ | N | |
| $CH_2SCH_3$ | H | $OCH_3$ | $CH_3$ | N | |
| $CH_2SCH_3$ | H | $OCH_3$ | $OCH_3$ | N | |
| $CH_2SCH_3$ | H | $OCH_3$ | $N(CH_3)_2$ | N | |
| $CH_2SCH_3$ | H | $OCH_3$ | $OCH_2CF_3$ | N | |
| $CH_2SCH_3$ | $CH_3$ | $OCH_3$ | $CH_3$ | N | |
| $CH_2SCH_3$ | $CH_3$ | $OCH_3$ | $OCH_3$ | N | |
| $CH_2SCH_3$ | $CH_3$ | $CH_3$ | $OCH_3$ | CH | |
| $CH_2SCH_3$ | $CH_3$ | $OCH_3$ | $OCH_3$ | CH | |
| $CH_2SCH_3$ | H | Br | $OCH_3$ | CH | |
| $CH_2SCH_3$ | $CH_3$ | $OCH_3$ | $N(CH_3)_2$ | N | |
| $CH_2SCH_3$ | H | $CH_3$ | $OCH_2CF_3$ | N | |
| $CH_2SCH_3$ | H | $CH_3$ | $OCH_2CF_3$ | CH | |
| $CH_2SCH_3$ | H | $OCH_3$ | $OCH_2CF_3$ | CH | |
| $CH_2SCH_3$ | H | $OCH_3$ | $C_2H_5$ | CH | |
| $CH_2SCH_3$ | H | $OCH_3$ | $C_2H_5$ | N | |
| $CH_2SCH_3$ | H | $OCH_3$ | $NHCH_3$ | CH | |
| $CH_2SCH_3$ | H | $OCH_3$ | $NHCH_3$ | N | |
| $CH_2SCH_3$ | H | $CH_3$ | $OC_2H_5$ | CH | |
| $CH_2SCH_3$ | H | $OCH_3$ | $OC_2H_5$ | CH | |
| $CH_2SCH_3$ | H | $CH_3$ | $OC_2H_5$ | N | |
| $CH_2SCH_3$ | H | $OCH_3$ | $OC_2H_5$ | N | |
| $CH_2SCH_3$ | H | $CH_3$ | $OCH_2CHF_2$ | CH | |
| $CH_2SCH_3$ | H | $OCH_3$ | $OCH_2CHF_2$ | CH | |
| $CH_2SCH_3$ | H | $CH_3$ | $OCH_2CHF_2$ | N | |
| $CH_2SCH_3$ | H | $OCH_3$ | $OCH_2CHF_2$ | N | |
| $CH_2SCH_3$ | H | $CH_3$ | $OCH_2CH_2F$ | CH | |
| $CH_2SCH_3$ | H | $OCH_3$ | $OCH_2CH_2F$ | CH | |
| $CH_2SCH_3$ | H | $CH_3$ | $OCH_2CH_2F$ | N | |
| $CH_2SCH_3$ | $CH_3$ | $OCH_3$ | $OCH_2CH_2F$ | N | |
| $CH_2SCH_3$ | $CH_3$ | Cl | $OCH_3$ | CH | |
| $CH_2SCH_3$ | H | Cl | $N(CH_3)_2$ | CH | |
| $CH_2SCH_3$ | H | Cl | $OC_2H_5$ | CH | |
| $OCF_2H$ | H | $CH_3$ | $CH_3$ | CH | |
| $OCF_2H$ | H | $OCH_3$ | $CH_3$ | CH | |
| $OCF_2H$ | H | $OCH_3$ | $OCH_3$ | CH | |
| $OCF_2H$ | H | Cl | $OCH_3$ | CH | |
| $OCF_2H$ | H | $OCH_3$ | $N(CH_3)_2$ | CH | |
| $OCF_2H$ | H | $CH_3$ | $CH_3$ | N | |
| $OCF_2H$ | H | $OCH_3$ | $CH_3$ | N | |
| $OCF_2H$ | H | $OCH_3$ | $OCH_3$ | N | |
| $OCF_2H$ | H | $OCH_3$ | $N(CH_3)_2$ | N | |
| $OCF_2H$ | H | $OCH_3$ | $OCH_2CF_3$ | N | |
| $OCF_2H$ | $CH_3$ | $OCH_3$ | $CH_3$ | N | |
| $OCF_2H$ | $CH_3$ | $OCH_3$ | $OCH_3$ | N | |
| $OCF_2H$ | $CH_3$ | $CH_3$ | $OCH_3$ | CH | |
| $OCF_2H$ | $CH_3$ | $OCH_3$ | $OCH_3$ | CH | |
| $OCF_2H$ | H | Br | $OCH_3$ | CH | |
| $OCF_2H$ | $CH_3$ | $OCH_3$ | $N(CH_3)_2$ | N | |
| $OCF_2H$ | H | $CH_3$ | $OCH_2CF_3$ | N | |
| $OCF_2H$ | H | $CH_3$ | $OCH_2CF_3$ | CH | |
| $OCF_2H$ | H | $OCH_3$ | $OCH_2CF_3$ | CH | |
| $OCF_2H$ | H | $OCH_3$ | $C_2H_5$ | CH | |
| $OCF_2H$ | H | $OCH_3$ | $C_2H_5$ | N | |
| $OCF_2H$ | H | $OCH_3$ | $NHCH_3$ | CH | |
| $OCF_2H$ | H | $OCH_3$ | $NHCH_3$ | N | |
| $OCF_2H$ | H | $CH_3$ | $OC_2H_5$ | CH | |
| $OCF_2H$ | H | $OCH_3$ | $OC_2H_5$ | CH | |
| $OCF_2H$ | H | $CH_3$ | $OC_2H_5$ | N | |
| $OCF_2H$ | H | $OCH_3$ | $OC_2H_5$ | N | |
| $OCF_2H$ | H | $CH_3$ | $OCH_2CHF_2$ | CH | |
| $OCF_2H$ | H | $OCH_3$ | $OCH_2CHF_2$ | CH | |
| $OCF_2H$ | H | $CH_3$ | $OCH_2CHF_2$ | N | |
| $OCF_2H$ | H | $CH_3$ | $OCH_2CHF_2$ | N | |

TABLE I-continued

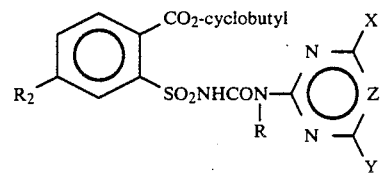

| R₂ | R | X | Y | Z | m.p. (°C.) |
|---|---|---|---|---|---|
| OCF₂H | H | CH₃ | OCH₂CH₂F | CH | |
| OCF₂H | H | OCH₃ | OCH₂CH₂F | CH | |
| OCF₂H | H | CH₃ | OCH₂CH₂F | N | |
| OCF₂H | CH₃ | OCH₃ | OCH₂CH₂F | N | |
| OCF₂H | CH₃ | Cl | OCH₃ | CH | |
| OCF₂H | H | Cl | N(CH₃)₂ | CH | |
| OCH₂CH₂F | H | Cl | OC₂H₅ | CH | |
| OCH₂CH₂F | H | CH₃ | CH₃ | CH | |
| OCH₂CH₂F | H | OCH₃ | CH₃ | CH | |
| OCH₂CH₂F | H | OCH₃ | OCH₃ | CH | |
| OCH₂CH₂F | H | Cl | OCH₃ | CH | |
| OCH₂CH₂F | H | OCH₃ | N(CH₃)₂ | CH | |
| OCH₂CH₂F | H | CH₃ | CH₃ | N | |
| OCH₂CH₂F | H | OCH₃ | CH₃ | N | |
| OCH₂CH₂F | H | OCH₃ | OCH₃ | N | |
| OCH₂CH₂F | H | OCH₃ | N(CH₃)₂ | N | |
| OCH₂CH₂F | H | OCH₃ | OCH₂CF₃ | N | |
| OCH₂CH₂F | CH₃ | OCH₃ | CH₃ | N | |
| OCH₂CH₂F | CH₃ | OCH₃ | OCH₃ | N | |
| OCH₂CH₂F | CH₃ | CH₃ | OCH₃ | CH | |
| OCH₂CH₂F | CH₃ | OCH₃ | OCH₃ | CH | |
| OCH₂CH₂F | H | Br | OCH₃ | CH | |
| OCH₂CH₂F | CH₃ | OCH₃ | N(CH₃)₂ | N | |
| OCH₂CH₂F | H | CH₃ | OCH₂CF₃ | N | |
| OCH₂CH₂F | H | CH₃ | OCH₂CF₃ | CH | |
| OCH₂CH₂F | H | OCH₃ | OCH₂CF₃ | CH | |
| OCH₂CH₂F | H | OCH₃ | C₂H₅ | CH | |
| OCH₂CH₂F | H | OCH₃ | C₂H₅ | N | |
| OCH₂CH₂F | H | OCH₃ | NHCH₃ | CH | |
| OCH₂CH₂F | H | OCH₃ | NHCH₃ | N | |
| OCH₂CH₂F | H | CH₃ | OC₂H₅ | CH | |
| OCH₂CH₂F | H | OCH₃ | OC₂H₅ | CH | |
| OCH₂CH₂F | H | CH₃ | OC₂H₅ | N | |
| OCH₂CH₂F | H | OCH₃ | OC₂H₅ | N | |
| OCH₂CH₂F | H | CH₃ | OCH₂CHF₂ | CH | |
| OCH₂CH₂F | H | OCH₃ | OCH₂CHF₂ | CH | |
| OCH₂CH₂F | H | CH₃ | OCH₂CHF₂ | N | |
| OCH₂CH₂F | H | OCH₃ | OCH₂CHF₂ | N | |
| OCH₂CH₂F | H | CH₃ | OCH₂CH₂F | CH | |
| OCH₂CH₂F | H | OCH₃ | OCH₂CH₂F | CH | |
| OCH₂CH₂F | H | CH₃ | OCH₂CH₂F | N | |
| OCH₂CH₂F | CH₃ | OCH₃ | OCH₂CH₂F | N | |
| OCH₂CH₂F | CH₃ | Cl | OCH₃ | CH | |
| OCH₂CH₂F | H | Cl | N(CH₃)₂ | CH | |
| OCH₂CH₂F | H | Cl | OC₂H₅ | CH | |
| OCH₂CF₃ | H | CH₃ | CH₃ | CH | |
| OCH₂CF₃ | H | OCH₃ | CH₃ | CH | |
| OCH₂CF₃ | H | OCH₃ | OCH₃ | CH | |
| OCH₂CF₃ | H | Cl | OCH₃ | CH | |
| OCH₂CF₃ | H | OCH₃ | N(CH₃)₂ | CH | |
| OCH₂CF₃ | H | CH₃ | CH₃ | N | |
| OCH₂CF₃ | H | OCH₃ | CH₃ | N | |
| OCH₂CF₃ | H | OCH₃ | OCH₃ | N | |
| OCH₂CF₃ | H | OCH₃ | N(CH₃)₂ | N | |
| OCH₂CF₃ | H | OCH₃ | OCH₂CF₃ | N | |
| OCH₂CF₃ | H | OC₂H₅ | NHCH₃ | N | |
| OCH₂CF₃ | CH₃ | OCH₃ | CH₃ | N | |
| OCH₂CF₃ | CH₃ | OCH₃ | OCH₃ | N | |
| OCH₂CF₃ | CH₃ | CH₃ | OCH₃ | CH | |
| OCH₂CF₃ | CH₃ | OCH₃ | OCH₃ | CH | |
| OCH₂CF₃ | H | Br | OCH₃ | CH | |
| OCH₂CF₃ | CH₃ | OCH₃ | N(CH₃)₂ | N | |
| OCH₂CF₃ | H | CH₃ | OCH₂CF₃ | N | |
| OCH₂CF₃ | H | CH₃ | OCH₂CF₃ | CH | |
| OCH₂CF₃ | H | OCH₃ | OCH₂CF₃ | CH | |
| OCH₂CF₃ | H | OCH₃ | C₂H₅ | CH | |
| OCH₂CF₃ | H | OCH₃ | C₂H₅ | N | |
| OCH₂CF₃ | H | OCH₃ | NHCH₃ | CH | |
| OCH₂CF₃ | H | OCH₃ | NHCH₃ | N | |
| OCH₂CF₃ | H | CH₃ | OC₂H₅ | CH | |

TABLE I-continued

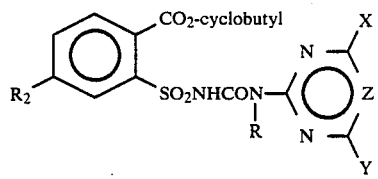

| $R_2$ | R | X | Y | Z | m.p. (°C.) |
|---|---|---|---|---|---|
| $OCH_2CF_3$ | H | $OCH_3$ | $OC_2H_5$ | CH | |
| $OCH_2CF_3$ | H | $CH_3$ | $OC_2H_5$ | N | |
| $OCH_2CF_3$ | H | $OCH_3$ | $OC_2H_5$ | N | |
| $OCH_2CF_3$ | H | $CH_3$ | $OCH_2CHF_2$ | CH | |
| $OCH_2CF_3$ | H | $OCH_3$ | $OCH_2CHF_2$ | CH | |
| $OCH_2CF_3$ | H | $CH_3$ | $OCH_2CHF_2$ | N | |
| $OCH_2CF_3$ | H | $OCH_3$ | $OCH_2CHF_2$ | N | |
| $OCH_2CF_3$ | H | $CH_3$ | $OCH_2CH_2F$ | CH | |
| $OCH_2CF_3$ | H | $OCH_3$ | $OCH_2CH_2F$ | CH | |
| $OCH_2CF_3$ | H | $CH_3$ | $OCH_2CH_2F$ | N | |
| $OCH_2CF_3$ | $CH_3$ | $OCH_3$ | $OCH_2CH_2F$ | N | |
| $OCH_2CF_3$ | $CH_3$ | Cl | $OCH_3$ | CH | |
| $OCH_2CF_3$ | H | Cl | $N(CH_3)_2$ | CH | |
| $OCH_2CF_3$ | H | Cl | $OC_2H_5$ | CH | |
| $OCH_2CH_2OCH_3$ | H | $CH_3$ | $CH_3$ | CH | |
| $OCH_2CH_2OCH_3$ | H | $OCH_3$ | $CH_3$ | CH | |
| $OCH_2CH_2OCH_3$ | H | $OCH_3$ | $OCH_3$ | CH | |
| $OCH_2CH_2OCH_3$ | H | Cl | $OCH_3$ | CH | |
| $OCH_2CH_2OCH_3$ | H | $OCH_3$ | $N(CH_3)_2$ | CH | |
| $OCH_2CH_2OCH_3$ | H | $CH_3$ | $CH_3$ | N | |
| $OCH_2CH_2OCH_3$ | H | $OCH_3$ | $CH_3$ | N | |
| $OCH_2CH_2OCH_3$ | H | $OCH_3$ | $OCH_3$ | N | |
| $OCH_2CH_2OCH_3$ | H | $OCH_3$ | $N(CH_3)_2$ | N | |
| $OCH_2CH_2OCH_3$ | H | $OCH_3$ | $OCH_2CF_3$ | N | |
| $OCH_2CH_2OCH_3$ | $CH_3$ | $OCH_3$ | $CH_3$ | N | |
| $OCH_2CH_2OCH_3$ | $CH_3$ | $OCH_3$ | $OCH_3$ | N | |
| $OCH_2CH_2OCH_3$ | $CH_3$ | $CH_3$ | $OCH_3$ | CH | |
| $OCH_2CH_2OCH_3$ | $CH_3$ | $OCH_3$ | $OCH_3$ | CH | |
| $OCH_2CH_2OCH_3$ | H | Br | $OCH_3$ | CH | |
| $OCH_2CH_2OCH_3$ | H | $CH_3$ | $OCH_2CF_3$ | N | |
| $OCH_2CH_2OCH_3$ | H | $CH_3$ | $OCH_2CF_3$ | CH | |
| $OCH_2CH_2OCH_3$ | H | $OCH_3$ | $OCH_2CF_3$ | CH | |
| $OCH_2CH_2OCH_3$ | H | $OCH_3$ | $C_2H_5$ | CH | |
| $OCH_2CH_2OCH_3$ | H | $OCH_3$ | $C_2H_5$ | N | |
| $OCH_2CH_2OCH_3$ | H | $OCH_3$ | $NHCH_3$ | CH | |
| $OCH_2CH_2OCH_3$ | H | $OCH_3$ | $NHCH_3$ | N | |
| $OCH_2CH_2OCH_3$ | H | $CH_3$ | $OC_2H_5$ | CH | |
| $OCH_2CH_2OCH_3$ | H | $OCH_3$ | $OC_2H_5$ | CH | |
| $OCH_2CH_2OCH_3$ | H | $CH_3$ | $OC_2H_5$ | N | |
| $OCH_2CH_2OCH_3$ | H | $OCH_3$ | $OC_2H_5$ | N | |
| $OCH_2CH_2OCH_3$ | H | $CH_3$ | $OCH_2CHF_2$ | CH | |
| $OCH_2CH_2OCH_3$ | H | $OCH_3$ | $OCH_2CHF_2$ | CH | |
| $OCH_2CH_2OCH_3$ | H | $CH_3$ | $OCH_2CHF_2$ | N | |
| $OCH_2CH_2OCH_3$ | H | $OCH_3$ | $OCH_2CHF_2$ | N | |
| $OCH_2CH_2OCH_3$ | H | $CH_3$ | $OCH_2CH_2F$ | CH | |
| $OCH_2CH_2OCH_3$ | H | $OCH_3$ | $OCH_2CH_2F$ | CH | |
| $OCH_2CH_2OCH_3$ | H | $CH_3$ | $OCH_2CF_3$ | N | |
| $OCH_2CH_2OCH_3$ | $CH_3$ | $OCH_3$ | $OCH_2CF_3$ | N | |
| $OCH_2CH_2OCH_3$ | $CH_3$ | Cl | $OCH_3$ | CH | |
| $OCH_2CH_2OCH_3$ | H | Cl | $N(CH_3)_2$ | CH | |
| $OCH_2CH_2OCH_3$ | H | Cl | $OC_2H_5$ | CH | |
| O-cyclopropyl | H | $CH_3$ | $CH_3$ | CH | |
| O-cyclopropyl | H | $OCH_3$ | $CH_3$ | CH | |
| O-cyclopropyl | H | $OCH_3$ | $OCH_3$ | CH | |
| O-cyclopropyl | H | Cl | $OCH_3$ | CH | |
| O-cyclopropyl | H | $OCH_3$ | $N(CH_3)_2$ | CH | |
| O-cyclopropyl | H | $CH_3$ | $CH_3$ | N | |
| O-cyclopropyl | H | $OCH_3$ | $CH_3$ | N | |
| O-cyclopropyl | H | $OCH_3$ | $OCH_3$ | N | |
| O-cyclopropyl | H | $OCH_3$ | $N(CH_3)_2$ | N | |
| O-cyclopropyl | H | $OCH_3$ | $OCH_2CF_3$ | N | |
| O-cyclopropyl | $CH_3$ | $OCH_3$ | $CH_3$ | N | |
| O-cyclopropyl | $CH_3$ | $OCH_3$ | $OCH_3$ | N | |
| O-cyclopropyl | $CH_3$ | $CH_3$ | $OCH_3$ | CH | |
| O-cyclopropyl | $CH_3$ | $OCH_3$ | $OCH_3$ | CH | |
| O-cyclopropyl | H | Br | $OCH_3$ | CH | |
| O-cyclopropyl | $CH_3$ | $OCH_3$ | $N(CH_3)_2$ | N | |
| O-cyclopropyl | H | $CH_3$ | $OCH_2CF_3$ | N | |
| O-cyclopropyl | H | $CH_3$ | $OCH_2CF_3$ | CH | |
| O-cyclopropyl | H | $OCH_3$ | $OCH_2CF_3$ | CH | |

TABLE I-continued

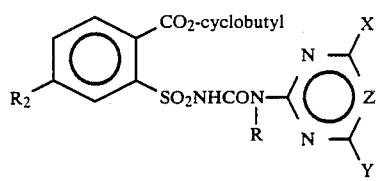

| $R_2$ | R | X | Y | Z | m.p. (°C.) |
|---|---|---|---|---|---|
| O-cyclopropyl | H | OCH$_3$ | C$_2$H$_5$ | CH | |
| O-cyclopropyl | H | OCH$_3$ | C$_2$H$_5$ | N | |
| O-cyclopropyl | H | OCH$_3$ | NHCH$_3$ | CH | |
| O-cyclopropyl | H | OCH$_3$ | NHCH$_3$ | N | |
| O-cyclopropyl | H | CH$_3$ | OC$_2$H$_5$ | CH | |
| O-cyclopropyl | H | OCH$_3$ | OC$_2$H$_5$ | CH | |
| O-cyclopropyl | H | CH$_3$ | OC$_2$H$_5$ | N | |
| O-cyclopropyl | H | OCH$_3$ | OC$_2$H$_5$ | N | |
| O-cyclopropyl | H | CH$_3$ | OCH$_2$CHF$_2$ | CH | |
| O-cyclopropyl | H | OCH$_3$ | OCH$_2$CHF$_2$ | CH | |
| O-cyclopropyl | H | CH$_3$ | OCH$_2$CHF$_2$ | N | |
| O-cyclopropyl | H | OCH$_3$ | OCH$_2$CHF$_2$ | N | |
| O-cyclopropyl | H | CH$_3$ | OCH$_2$CH$_2$F | CH | |
| O-cyclopropyl | H | OCH$_3$ | OCH$_2$CH$_2$F | CH | |
| O-cyclopropyl | H | CH$_3$ | OCH$_2$CH$_2$F | N | |
| O-cyclopropyl | CH$_3$ | OCH$_3$ | OCH$_2$CH$_2$F | N | |
| O-cyclopropyl | CH$_3$ | Cl | OCH$_3$ | CH | |
| O-cyclopropyl | H | Cl | N(CH$_3$)$_2$ | CH | |
| O-cyclopropyl | H | Cl | OC$_2$H$_5$ | CH | |
| OCF$_2$CF$_2$H | H | OCH$_3$ | Cl | CH | |
| OCF$_2$CF$_2$H | H | CH$_3$ | CH$_3$ | CH | |
| OCF$_2$CF$_2$H | H | OCH$_3$ | OCH$_3$ | N | |
| S-cyclopropyl | H | OCH$_3$ | OCH$_3$ | CH | |
| S-cyclopropyl | H | OCH$_3$ | CH$_3$ | CH | |
| S-cyclopropyl | H | OCH$_3$ | Cl | CH | |
| S-cyclopropyl | H | CH$_3$ | CH$_3$ | CH | |
| S-cyclopropyl | H | OCH$_3$ | OCH$_3$ | N | |
| S-cyclopropyl | H | OCH$_3$ | CH$_3$ | N | |
| SCH$_2$-cyclopropyl | H | OCH$_3$ | OCH$_3$ | CH | |
| SCH$_2$-cyclopropyl | H | OCH$_3$ | CH$_3$ | CH | |
| SCH$_2$-cyclopropyl | H | OCH$_3$ | Cl | CH | |
| SCH$_2$-cyclopropyl | H | CH$_3$ | CH$_3$ | CH | |
| SCH$_2$-cyclopropyl | H | OCH$_3$ | OCH$_3$ | N | |
| NHCH$_2$-cyclopropyl | OCH$_3$ | OCH$_3$ | CH | | |
| NHCH$_2$-cyclopropyl | H | OCH$_3$ | CH$_3$ | CH | |
| NHCH$_2$-cyclopropyl | H | OCH$_3$ | Cl | CH | |
| NHCH$_2$-cyclopropyl | H | CH$_3$ | CH$_3$ | CH | |
| NHCH$_2$-cyclopropyl | H | OCH$_3$ | OCH$_3$ | N | |
| NHCH$_2$-cyclopropyl | H | OCH$_3$ | CH$_3$ | N | |
| NHCH$_2$CF$_2$CF$_3$ | H | OCH$_3$ | OCH$_3$ | CH | |
| NHCH$_2$CF$_2$CF$_3$ | H | OCH$_3$ | CH$_3$ | CH | |
| NHCH$_2$CF$_2$CF$_3$ | H | OCH$_3$ | Cl | CH | |
| NHCH$_2$CF$_2$CF$_3$ | H | CH$_3$ | CH$_3$ | CH | |
| NHCH$_2$CF$_2$CF$_3$ | H | OCH$_3$ | OCH$_3$ | N | |
| NHCH$_2$CF$_2$CF$_3$ | H | OCH$_3$ | CH$_3$ | N | |
| NHCH(CF$_3$)CH$_3$ | H | OCH$_3$ | OCH$_3$ | CH | |
| NHCH(CF$_3$)CH$_3$ | H | OCH$_3$ | CH$_3$ | CH | |
| NHCH$_2$CHF$_2$ | H | OCH$_3$ | CH$_3$ | N | |
| NHCH$_2$CF$_3$ | H | OCH$_3$ | OCH$_3$ | CH | |
| NHCH$_2$CF$_3$ | H | OCH$_3$ | CH$_3$ | CH | |
| NHCH$_2$CF$_3$ | H | OCH$_3$ | Cl | CH | |
| NHCH$_2$CF$_3$ | H | CH$_3$ | CH$_3$ | CH | |
| NHCH$_2$CF$_3$ | H | OCH$_3$ | OCH$_3$ | N | |
| NHCH$_3$ | H | OCH$_3$ | OCH$_3$ | CH | |
| NHCH$_3$ | H | OCH$_3$ | CH$_3$ | CH | |
| NHCH$_3$ | H | OCH$_3$ | Cl | CH | |
| NHCH$_3$ | H | CH$_3$ | CH$_3$ | CH | |
| NHCH$_3$ | H | OCH$_3$ | OCH$_3$ | N | |

TABLE Ii

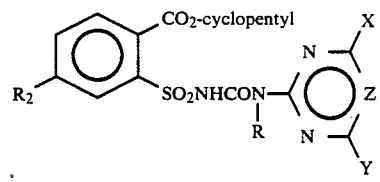

| $R_2$ | R | X | Y | Z | m.p. (°C.) |
|---|---|---|---|---|---|
| $OC_2H_5$ | H | $CH_3$ | $CH_3$ | CH | |
| $OC_2H_5$ | H | $OCH_3$ | $CH_3$ | CH | |
| $OC_2H_5$ | H | $OCH_3$ | $OCH_3$ | CH | |
| $OC_2H_5$ | H | Cl | $OCH_3$ | CH | |
| $OC_2H_5$ | H | $OCH_3$ | $N(CH_3)_2$ | CH | |
| $OC_2H_5$ | H | $CH_3$ | $CH_3$ | N | |
| $OC_2H_5$ | H | $OCH_3$ | $CH_3$ | N | |
| $OC_2H_5$ | H | $OCH_3$ | $OCH_3$ | N | |
| $OC_2H_5$ | H | $OCH_3$ | $N(CH_3)_2$ | N | |
| $OC_2H_5$ | H | $OCH_3$ | $OCH_2CF_3$ | N | |
| $OC_2H_5$ | $CH_3$ | $OCH_3$ | $CH_3$ | N | |
| $OC_2H_5$ | $CH_3$ | $OCH_3$ | $OCH_3$ | N | |
| $OC_2H_5$ | $CH_3$ | $CH_3$ | $OCH_3$ | CH | |
| $OC_2H_5$ | $CH_3$ | $OCH_3$ | $OCH_3$ | CH | |
| $OC_2H_5$ | H | Br | $OCH_3$ | CH | |
| $OC_2H_5$ | $CH_3$ | $OCH_3$ | $N(CH_3)_2$ | N | |
| $OC_2H_5$ | H | $CH_3$ | $OCH_2CF_3$ | N | |
| $OC_2H_5$ | H | $CH_3$ | $OCH_2CF_3$ | CH | |
| $OC_2H_5$ | H | $OCH_3$ | $OCH_2CF_3$ | CH | |
| $OC_2H_5$ | H | $OCH_3$ | $C_2H_5$ | CH | |
| $OC_2H_5$ | H | $OCH_3$ | $C_2H_5$ | N | |
| $OC_2H_5$ | H | $OCH_3$ | $NHCH_3$ | CH | |
| $OC_2H_5$ | H | $OCH_3$ | $NHCH_3$ | N | |
| $OC_2H_5$ | H | $CH_3$ | $OC_2H_5$ | CH | |
| $OC_2H_5$ | H | $OCH_3$ | $OC_2H_5$ | CH | |
| $OC_2H_5$ | H | $CH_3$ | $OC_2H_5$ | N | |
| $OC_2H_5$ | H | $OCH_3$ | $OC_2H_5$ | N | |
| $OC_2H_5$ | H | $CH_3$ | $OCH_2CHF_2$ | CH | |
| $OC_2H_5$ | H | $OCH_3$ | $OCH_2CHF_2$ | CH | |
| $OC_2H_5$ | H | $CH_3$ | $OCH_2CHF_2$ | N | |
| $OC_2H_5$ | H | $OCH_3$ | $OCH_2CHF_2$ | N | |
| $OC_2H_5$ | H | $CH_3$ | $OCH_2CH_2F$ | CH | |
| $OC_2H_5$ | H | $OCH_3$ | $OCH_2CH_2F$ | CH | |
| $OC_2H_5$ | H | $CH_3$ | $OCH_2CH_2F$ | N | |
| $OC_2H_5$ | $CH_3$ | $OCH_3$ | $OCH_2CH_2F$ | N | |
| $OC_2H_5$ | $CH_3$ | Cl | $OCH_3$ | CH | |
| $OC_2H_5$ | H | Cl | $N(CH_3)_2$ | CH | |
| $OC_2H_5$ | H | Cl | $OC_2H_5$ | CH | |
| $SC_2H_5$ | H | $CH_3$ | $CH_3$ | CH | |
| $SC_2H_5$ | H | $OCH_3$ | $CH_3$ | CH | |
| $SC_2H_5$ | H | $OCH_3$ | $OCH_3$ | CH | |
| $SC_2H_5$ | H | Cl | $OCH_3$ | CH | |
| $SC_2H_5$ | H | $OCH_3$ | $N(CH_3)_2$ | CH | |
| $SC_2H_5$ | H | $CH_3$ | $CH_3$ | N | |
| $SC_2H_5$ | H | $OCH_3$ | $CH_3$ | N | |
| $SC_2H_5$ | H | $OCH_3$ | $OCH_3$ | N | |
| $SC_2H_5$ | H | $OCH_3$ | $N(CH_3)_2$ | N | |
| $SC_2H_5$ | H | $OCH_3$ | $OCH_2CF_3$ | N | |
| $SC_2H_5$ | $CH_3$ | $OCH_3$ | $CH_3$ | N | |
| $SC_2H_5$ | $CH_3$ | $OCH_3$ | $OCH_3$ | N | |
| $SC_2H_5$ | $CH_3$ | $CH_3$ | $OCH_3$ | CH | |
| $SC_2H_5$ | $CH_3$ | $OCH_3$ | $OCH_3$ | CH | |
| $SC_2H_5$ | H | Br | $OCH_3$ | CH | |
| $SC_2H_5$ | $CH_3$ | $OCH_3$ | $N(CH_3)_2$ | N | |
| $SC_2H_5$ | H | $CH_3$ | $OCH_2CF_3$ | N | |
| $SC_2H_5$ | H | $CH_3$ | $OCH_2CF_3$ | CH | |
| $SC_2H_5$ | H | $OCH_3$ | $OCH_2CF_3$ | CH | |
| $SC_2H_5$ | H | $OCH_3$ | $C_2H_5$ | CH | |
| $SC_2H_5$ | H | $OCH_3$ | $C_2H_5$ | N | |
| $SC_2H_5$ | H | $OCH_3$ | $NHCH_3$ | CH | |
| $SC_2H_5$ | H | $OCH_3$ | $NHCH_3$ | N | |
| $SC_2H_5$ | H | $CH_3$ | $OC_2H_5$ | CH | |
| $SC_2H_5$ | H | $OCH_3$ | $OC_2H_5$ | CH | |
| $SC_2H_5$ | H | $CH_3$ | $OC_2H_5$ | N | |
| $SC_2H_5$ | H | $OCH_3$ | $OC_2H_5$ | N | |
| $SC_2H_5$ | H | $CH_3$ | $OCH_2CHF_2$ | CH | |
| $SC_2H_5$ | H | $OCH_3$ | $OCH_2CHF_2$ | CH | |
| $SC_2H_5$ | H | $CH_3$ | $OCH_2CHF_2$ | N | |
| $SC_2H_5$ | H | $OCH_3$ | $OCH_2CHF_2$ | N | |
| $SC_2H_5$ | H | $CH_3$ | $OCH_2CH_2F$ | CH | |
| $SC_2H_5$ | H | $OCH_3$ | $OCH_2CH_2F$ | CH | |

TABLE Ii-continued

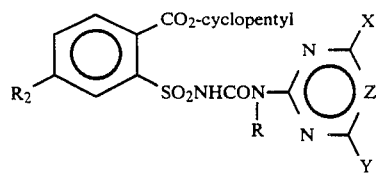

| $R_2$ | R | X | Y | Z | m.p. (°C.) |
|---|---|---|---|---|---|
| $SC_2H_5$ | H | $CH_3$ | $OCH_2CH_2F$ | N | |
| $SC_2H_5$ | $CH_3$ | $OCH_3$ | $OCH_2CH_2F$ | N | |
| $SC_2H_5$ | $CH_3$ | Cl | $OCH_3$ | CH | |
| $SC_2H_5$ | H | Cl | $N(CH_3)_2$ | CH | |
| $SC_2H_5$ | H | Cl | $OC_2H_5$ | CH | |
| $S(CH_2)_5CH_3$ | H | $CH_3$ | $CH_3$ | CH | |
| $S(CH_2)_5CH_3$ | H | $OCH_3$ | $CH_3$ | CH | |
| $S(CH_2)_5CH_3$ | H | $OCH_3$ | $OCH_3$ | CH | |
| $S(CH_2)_5CH_3$ | H | Cl | $OCH_3$ | CH | |
| $S(CH_2)_5CH_3$ | H | $CH_3$ | $CH_3$ | N | |
| $S(CH_2)_5CH_3$ | H | $OCH_3$ | $CH_3$ | N | |
| $S(CH_2)_5CH_3$ | H | $OCH_3$ | $OCH_3$ | N | |
| $S(O)(CH_3)$ | H | $CH_3$ | $CH_3$ | CH | |
| $S(O)(CH_3)$ | H | $OCH_3$ | $CH_3$ | CH | |
| $S(O)(CH_3)$ | H | $OCH_3$ | $OCH_3$ | CH | |
| $S(O)(CH_3)$ | H | Cl | $OCH_3$ | CH | |
| $S(O)(CH_3)$ | H | $OCH_3$ | $N(CH_3)_2$ | CH | |
| $S(O)(CH_3)$ | H | $CH_3$ | $CH_3$ | N | |
| $S(O)(CH_3)$ | H | $OCH_3$ | $CH_3$ | N | |
| $S(O)(CH_3)$ | H | $OCH_3$ | $OCH_3$ | N | |
| $S(O)(CH_3)$ | H | $OCH_3$ | $N(CH_3)_2$ | N | |
| $S(O)(CH_3)$ | H | $OCH_3$ | $OCH_2CF_3$ | N | |
| $S(O)(CH_3)$ | $CH_3$ | $OCH_3$ | $CH_3$ | N | |
| $S(O)(CH_3)$ | $CH_3$ | $OCH_3$ | $OCH_3$ | N | |
| $S(O)(CH_3)$ | $CH_3$ | $CH_3$ | $OCH_3$ | CH | |
| $S(O)(CH_3)$ | $CH_3$ | $OCH_3$ | $OCH_3$ | CH | |
| $S(O)(CH_3)$ | H | Br | $OCH_3$ | CH | |
| $S(O)(CH_3)$ | H | $OCH_3$ | $N(CH_3)_2$ | CH | |
| $S(O)(CH_3)$ | $CH_3$ | $OCH_3$ | $N(CH_3)_2$ | N | |
| $S(O)(CH_3)$ | H | $CH_3$ | $OCH_2CF_3$ | N | |
| $S(O)(CH_3)$ | H | $CH_3$ | $OCH_2CF_3$ | CH | |
| $S(O)(CH_3)$ | H | $OCH_3$ | $OCH_2CF_3$ | CH | |
| $S(O)(CH_3)$ | H | $OCH_3$ | $C_2H_5$ | CH | |
| $S(O)(CH_3)$ | H | $OCH_3$ | $C_2H_5$ | N | |
| $S(O)(CH_3)$ | H | $OCH_3$ | $NHCH_3$ | CH | |
| $S(O)(CH_3)$ | H | $OCH_3$ | $NHCH_3$ | N | |
| $S(O)(CH_3)$ | H | $CH_3$ | $OC_2H_5$ | CH | |
| $S(O)(CH_3)$ | H | $OCH_3$ | $OC_2H_5$ | CH | |
| $S(O)(CH_3)$ | H | $CH_3$ | $OC_2H_5$ | N | |
| $S(O)(CH_3)$ | H | $OCH_3$ | $OC_2H_5$ | N | |
| $S(O)(CH_3)$ | H | $CH_3$ | $OCH_2CHF_2$ | CH | |
| $S(O)(CH_3)$ | H | $OCH_3$ | $OCH_2CHF_2$ | CH | |
| $S(O)(CH_3)$ | H | $CH_3$ | $OCH_2CHF_2$ | N | |
| $S(O)(CH_3)$ | H | $OCH_3$ | $OCH_2CHF_2$ | N | |
| $S(O)(CH_3)$ | H | $CH_3$ | $OCH_2CHF_2$ | CH | |
| $S(O)(CH_3)$ | H | $OCH_3$ | $OCH_2CHF_2$ | CH | |
| $S(O)(CH_3)$ | H | $CH_3$ | $OCH_2CHF_2$ | N | |
| $S(O)(CH_3)$ | H | $OCH_3$ | $OCH_2CHF_2$ | N | |
| $S(O)(CH_3)$ | $CH_3$ | Cl | $OCH_3$ | CH | |
| $S(O)(CH_3)$ | H | Cl | $N(CH_3)_2$ | CH | |
| $S(O)(CH_3)$ | H | Cl | $OC_2H_5$ | CH | |
| $OCH_2CH=CH_2$ | H | $CH_3$ | $CH_3$ | CH | |
| $OCH_2CH=CH_2$ | H | $OCH_3$ | $CH_3$ | CH | |
| $OCH_2CH=CH_2$ | H | $OCH_3$ | $OCH_3$ | CH | |
| $OCH_2CH=CH_2$ | H | Cl | $OCH_3$ | CH | |
| $OCH_2CH=CH_2$ | H | $OCH_3$ | $N(CH_3)_2$ | CH | |
| $OCH_2CH=CH_2$ | H | $CH_3$ | $CH_3$ | N | |
| $OCH_2CH=CH_2$ | H | $OCH_3$ | $CH_3$ | N | |
| $OCH_2CH=CH_2$ | H | $OCH_3$ | $OCH_3$ | N | |
| $OCH_2CH=CH_2$ | H | $OCH_3$ | $N(CH_3)_2$ | N | |
| $OCH_2CH=CH_2$ | H | $OCH_3$ | $OCH_2CF_3$ | N | |
| $OCH_2CH=CH_2$ | $CH_3$ | $OCH_3$ | $CH_3$ | N | |
| $OCH_2CH=CH_2$ | $CH_3$ | $OCH_3$ | $OCH_3$ | N | |
| $OCH_2CH=CH_2$ | $CH_3$ | $CH_3$ | $OCH_3$ | CH | |
| $OCH_2CH=CH_2$ | $CH_3$ | $OCH_3$ | $OCH_3$ | CH | |
| $OCH_2CH=CH_2$ | H | Br | $OCH_3$ | CH | |
| $OCH_2CH=CH_2$ | $CH_3$ | $OCH_3$ | $N(CH_3)_2$ | N | |
| $OCH_2CH=CH_2$ | H | $CH_3$ | $OCH_2CF_3$ | N | |
| $OCH_2CH=CH_2$ | H | $CH_3$ | $OCH_2CF_3$ | CH | |
| $OCH_2CH=CH_2$ | H | $OCH_3$ | $OCH_2CF_3$ | CH | |
| $OCH_2CH=CH_2$ | H | $OCH_3$ | $C_2H_5$ | CH | |

TABLE Ii-continued

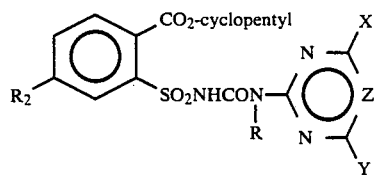

| R$_2$ | R | X | Y | Z | m.p. (°C.) |
|---|---|---|---|---|---|
| OCH$_2$CH=CH$_2$ | H | OCH$_3$ | C$_2$H$_5$ | N | |
| OCH$_2$CH=CH$_2$ | H | OCH$_3$ | NHCH$_3$ | CH | |
| OCH$_2$CH=CH$_2$ | H | OCH$_3$ | NHCH$_3$ | N | |
| OCH$_2$CH=CH$_2$ | H | CH$_3$ | OC$_2$H$_5$ | CH | |
| OCH$_2$CH=CH$_2$ | H | OCH$_3$ | OC$_2$H$_5$ | CH | |
| OCH$_2$CH=CH$_2$ | H | CH$_3$ | OC$_2$H$_5$ | N | |
| OCH$_2$CH=CH$_2$ | H | OCH$_3$ | OC$_2$H$_5$ | N | |
| OCH$_2$CH=CH$_2$ | H | CH$_3$ | OCH$_2$CHF$_2$ | CH | |
| OCH$_2$CH=CH$_2$ | H | OCH$_3$ | OCH$_2$CHF$_2$ | CH | |
| OCH$_2$CH=CH$_2$ | H | CH$_3$ | OCH$_2$CHF$_2$ | N | |
| OCH$_2$CH=CH$_2$ | H | OCH$_3$ | OCH$_2$CHF$_2$ | N | |
| OCH$_2$CH=CH$_2$ | H | CH$_3$ | OCH$_2$CH$_2$F | CH | |
| OCH$_2$CH=CH$_2$ | H | OCH$_3$ | OCH$_2$CH$_2$F | CH | |
| OCH$_2$CH=CH$_2$ | H | CH$_3$ | OCH$_2$CH$_2$F | N | |
| OCH$_2$CH=CH$_2$ | CH$_3$ | OCH$_3$ | OCH$_2$CH$_2$F | N | |
| OCH$_2$CH=CH$_2$ | CH$_3$ | Cl | OCH$_3$ | CH | |
| OCH$_2$CH=CH$_2$ | H | Cl | N(CH$_3$)$_2$ | CH | |
| OCH$_2$CH=CH$_2$ | H | Cl | OC$_2$H$_5$ | CH | |
| OCH$_2$C≡CH | H | CH$_3$ | CH$_3$ | CH | |
| OCH$_2$C≡CH | H | OCH$_3$ | CH$_3$ | CH | |
| OCH$_2$C≡CH | H | OCH$_3$ | OCH$_3$ | CH | |
| OCH$_2$C≡CH | H | Cl | OCH$_3$ | CH | |
| OCH$_2$C≡CH | H | OCH$_3$ | N(CH$_3$)$_2$ | CH | |
| OCH$_2$C≡CH | H | CH$_3$ | CH$_3$ | N | |
| OCH$_2$C≡CH | H | OCH$_3$ | CH$_3$ | N | |
| OCH$_2$C≡CH | H | OCH$_3$ | OCH$_3$ | N | |
| OCH$_2$C≡CH | H | OCH$_3$ | N(CH$_3$)$_2$ | N | |
| OCH$_2$C≡CH | H | OCH$_3$ | OCH$_2$CF$_3$ | N | |
| OCH$_2$C≡CH | CH$_3$ | OCH$_3$ | CH$_3$ | N | |
| OCH$_2$C≡CH | CH$_3$ | OCH$_3$ | OCH$_3$ | N | |
| OCH$_2$C≡CH | CH$_3$ | CH$_3$ | OCH$_3$ | CH | |
| OCH$_2$C≡CH | CH$_3$ | OCH$_3$ | OCH$_3$ | CH | |
| OCH$_2$C≡CH | H | Br | OCH$_3$ | CH | |
| OCH$_2$C≡CH | CH$_3$ | OCH$_3$ | N(CH$_3$)$_2$ | N | |
| OCH$_2$C≡CH | H | CH$_3$ | OCH$_2$CF$_3$ | N | |
| OCH$_2$C≡CH | H | CH$_3$ | OCH$_2$CF$_3$ | CH | |
| OCH$_2$C≡CH | H | OCH$_3$ | OCH$_2$CF$_3$ | CH | |
| OCH$_2$C≡CH | H | OCH$_3$ | C$_2$H$_5$ | CH | |
| OCH$_2$C≡CH | H | OCH$_3$ | C$_2$H$_5$ | N | |
| OCH$_2$C≡CH | H | OCH$_3$ | NHCH$_3$ | CH | |
| OCH$_2$C≡CH | H | OCH$_3$ | NHCH$_3$ | N | |
| OCH$_2$C≡CH | H | CH$_3$ | OC$_2$H$_5$ | CH | |
| OCH$_2$C≡CH | H | OCH$_3$ | OC$_2$H$_5$ | CH | |
| OCH$_2$C≡CH | H | CH$_3$ | OC$_2$H$_5$ | N | |
| OCH$_2$C≡CH | H | OCH$_3$ | OC$_2$H$_5$ | N | |
| OCH$_2$C≡CH | H | CH$_3$ | OCH$_2$CHF$_2$ | CH | |
| OCH$_2$C≡CH | H | OCH$_3$ | OCH$_2$CHF$_2$ | CH | |
| OCH$_2$C≡CH | H | CH$_3$ | OCH$_2$CHF$_2$ | N | |
| OCH$_2$C≡CH | H | OCH$_3$ | OCH$_2$CHF$_2$ | N | |
| OCH$_2$C≡CH | H | CH$_3$ | OCH$_2$CH$_2$F | CH | |
| OCH$_2$C≡CH | H | OCH$_3$ | OCH$_2$CH$_2$F | CH | |
| OCH$_2$C≡CH | H | CH$_3$ | OCH$_2$CF$_3$ | N | |
| OCH$_2$C≡CH | CH$_3$ | OCH$_3$ | OCH$_2$CF$_3$ | N | |
| OCH$_2$C≡CH | CH$_3$ | Cl | OCH$_3$ | CH | |
| OCH$_2$C≡CH | H | Cl | N(CH$_3$)$_2$ | CH | |
| OCH$_2$C≡CH | H | Cl | OC$_2$H$_5$ | CH | |
| SCH$_2$CH=CH$_2$ | H | CH$_3$ | CH$_3$ | CH | |
| SCH$_2$CH=CH$_2$ | H | OCH$_3$ | CH$_3$ | CH | |
| SCH$_2$CH=CH$_2$ | H | OCH$_3$ | OCH$_3$ | CH | |
| SCH$_2$CH=CH$_2$ | H | Cl | OCH$_3$ | CH | |
| SCH$_2$CH=CH$_2$ | H | OCH$_3$ | N(CH$_3$)$_2$ | N | |
| SCH$_2$CH=CH$_2$ | H | CH$_3$ | CH$_3$ | N | |
| SCH$_2$CH=CH$_2$ | H | OCH$_3$ | CH$_3$ | N | |
| SCH$_2$CH=CH$_2$ | H | OCH$_3$ | OCH$_3$ | N | |
| SCH$_2$CH=CH$_2$ | H | OCH$_3$ | N(CH$_3$)$_2$ | N | |
| SCH$_2$CH=CH$_2$ | H | OCH$_3$ | OCH$_2$CF$_3$ | N | |
| SCH$_2$CH=CH$_2$ | CH$_3$ | OCH$_3$ | CH$_3$ | N | |
| SCH$_2$CH=CH$_2$ | CH$_3$ | OCH$_3$ | OCH$_3$ | N | |
| SCH$_2$CH=CH$_2$ | CH$_3$ | CH$_3$ | OCH$_3$ | CH | |
| SCH$_2$CH=CH$_2$ | CH$_3$ | OCH$_3$ | OCH$_3$ | CH | |
| SCH$_2$CH=CH$_2$ | H | Br | OCH$_3$ | CH | |

TABLE Ii-continued

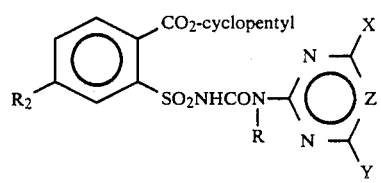

| R$_2$ | R | X | Y | Z | m.p. (°C.) |
|---|---|---|---|---|---|
| SCH$_2$CH=CH$_2$ | CH$_3$ | OCH$_3$ | N(CH$_3$)$_2$ | N | |
| SCH$_2$CH=CH$_2$ | H | CH$_3$ | OCH$_2$CF$_3$ | N | |
| SCH$_2$CH=CH$_2$ | H | CH$_3$ | OCH$_2$CF$_3$ | CH | |
| SCH$_2$CH=CH$_2$ | H | OCH$_3$ | OCH$_2$CF$_3$ | CH | |
| SCH$_2$CH=CH$_2$ | H | OCH$_3$ | C$_2$H$_5$ | CH | |
| SCH$_2$CH=CH$_2$ | H | OCH$_3$ | C$_2$H$_5$ | CH | |
| SCH$_2$CH=CH$_2$ | H | OCH$_3$ | NHCH$_3$ | CH | |
| SCH$_2$CH=CH$_2$ | H | OCH$_3$ | NHCH$_3$ | N | |
| SCH$_2$CH=CH$_2$ | H | CH$_3$ | OC$_2$H$_5$ | CH | |
| SCH$_2$CH=CH$_2$ | H | OCH$_3$ | OC$_2$H$_5$ | CH | |
| SCH$_2$CH=CH$_2$ | H | CH$_3$ | OC$_2$H$_5$ | N | |
| SCH$_2$CH=CH$_2$ | H | OCH$_3$ | OC$_2$H$_5$ | N | |
| SCH$_2$CH=CH$_2$ | H | CH$_3$ | OCH$_2$CHF$_2$ | CH | |
| SCH$_2$CH=CH$_2$ | H | OCH$_3$ | OCH$_2$CHF$_2$ | CH | |
| SCH$_2$CH=CH$_2$ | H | CH$_3$ | OCH$_2$CHF$_2$ | N | |
| SCH$_2$CH=CH$_2$ | H | OCH$_3$ | OCH$_2$CHF$_2$ | N | |
| SCH$_2$CH=CH$_2$ | H | CH$_3$ | OCH$_2$CH$_2$F | CH | |
| SCH$_2$CH=CH$_2$ | H | OCH$_3$ | OCH$_2$CH$_2$F | CH | |
| SCH$_2$CH=CH$_2$ | H | CH$_3$ | OCH$_2$CH$_2$F | N | |
| SCH$_2$CH=CH$_2$ | H | OCH$_3$ | OCH$_2$CH$_2$F | N | |
| SCH$_2$CH=CH$_2$ | CH$_3$ | Cl | OCH$_3$ | CH | |
| SCH$_2$CH=CH$_2$ | H | Cl | N(CH$_3$)$_2$ | CH | |
| SCH$_2$CH=CH$_2$ | H | Cl | OC$_2$H$_5$ | CH | |
| SCH$_2$C≡CH | H | CH$_3$ | CH$_3$ | CH | |
| SCH$_2$C≡CH | H | OCH$_3$ | CH$_3$ | CH | |
| SCH$_2$C≡CH | H | OCH$_3$ | OCH$_3$ | CH | |
| SCH$_2$C≡CH | H | Cl | OCH$_3$ | CH | |
| SCH$_2$C≡CH | H | OCH$_3$ | N(CH$_3$)$_2$ | N | |
| SCH$_2$C≡CH | H | CH$_3$ | CH$_3$ | N | |
| SCH$_2$C≡CH | H | OCH$_3$ | CH$_3$ | N | |
| SCH$_2$C≡CH | H | OCH$_3$ | OCH$_3$ | N | |
| SCH$_2$C≡CH | H | OCH$_3$ | N(CH$_3$)$_2$ | N | |
| SCH$_2$C≡CH | H | OCH$_3$ | OCH$_2$CF$_3$ | N | |
| SCH$_2$C≡CH | CH$_3$ | OCH$_3$ | CH$_3$ | N | |
| SCH$_2$C≡CH | CH$_3$ | OCH$_3$ | OCH$_3$ | N | |
| SCH$_2$C≡CH | CH$_3$ | CH$_3$ | OCH$_3$ | CH | |
| SCH$_2$C≡CH | CH$_3$ | OCH$_3$ | OCH$_3$ | CH | |
| SCH$_2$C≡CH | H | Br | OCH$_3$ | CH | |
| SCH$_2$C≡CH | CH$_3$ | OCH$_3$ | N(CH$_3$)$_2$ | N | |
| SCH$_2$C≡CH | H | CH$_3$ | OCH$_2$CF$_3$ | N | |
| SCH$_2$C≡CH | H | CH$_3$ | OCH$_2$CF$_3$ | CH | |
| SCH$_2$C≡CH | H | OCH$_3$ | OCH$_2$CF$_3$ | CH | |
| SCH$_2$C≡CH | H | OCH$_3$ | C$_2$H$_5$ | CH | |
| SCH$_2$C≡CH | H | OCH$_3$ | C$_2$H$_5$ | CH | |
| SCH$_2$C≡CH | H | OCH$_3$ | NHCH$_3$ | CH | |
| SCH$_2$C≡CH | H | OCH$_3$ | NHCH$_3$ | N | |
| SCH$_2$C≡CH | H | CH$_3$ | OC$_2$H$_5$ | CH | |
| SCH$_2$C≡CH | H | OCH$_3$ | OC$_2$H$_5$ | CH | |
| SCH$_2$C≡CH | H | CH$_3$ | OC$_2$H$_5$ | N | |
| SCH$_2$C≡CH | H | OCH$_3$ | OC$_2$H$_5$ | N | |
| SCH$_2$C≡CH | H | CH$_3$ | OCH$_2$CHF$_2$ | CH | |
| SCH$_2$C≡CH | H | OCH$_3$ | OCH$_2$CHF$_2$ | CH | |
| SCH$_2$C≡CH | H | CH$_3$ | OCH$_2$CHF$_2$ | N | |
| SCH$_2$C≡CH | H | OCH$_3$ | OCH$_2$CHF$_2$ | N | |
| SCH$_2$C≡CH | H | CH$_3$ | OCH$_2$CH$_2$F | CH | |
| SCH$_2$C≡CH | H | OCH$_3$ | OCH$_2$CH$_2$F | CH | |
| SCH$_2$C≡CH | H | CH$_3$ | OCH$_2$CH$_2$F | N | |
| SCH$_2$C≡CH | H | OCH$_3$ | OCH$_2$CH$_2$F | N | |
| SCH$_2$C≡CH | CH$_3$ | Cl | OCH$_3$ | CH | |
| SCH$_2$C≡CH | H | Cl | N(CH$_3$)$_2$ | CH | |
| SCH$_2$C≡CH | H | Cl | OC$_2$H$_5$ | CH | |
| CH$_2$CH$_2$F | H | CH$_3$ | CH$_3$ | CH | |
| CH$_2$CH$_2$F | H | OCH$_3$ | CH$_3$ | CH | |
| CH$_2$CH$_2$F | H | OCH$_3$ | OCH$_3$ | CH | |
| CH$_2$CH$_2$F | H | Cl | OCH$_3$ | CH | |
| CH$_2$CH$_2$F | H | OCH$_3$ | N(CH$_3$)$_2$ | CH | |
| CH$_2$CH$_2$F | H | CH$_3$ | CH$_3$ | N | |
| CH$_2$CH$_2$F | H | OCH$_3$ | CH$_3$ | N | |
| CH$_2$CH$_2$F | H | OCH$_3$ | OCH$_3$ | N | |
| CH$_2$CH$_2$F | H | OCH$_3$ | N(CH$_3$)$_2$ | N | |
| CH$_2$CH$_2$F | H | OCH$_3$ | OCH$_2$CF$_3$ | N | |

TABLE Ii-continued

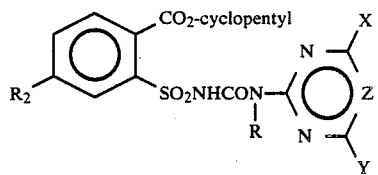

| R₂ | R | X | Y | Z | m.p. (°C.) |
|---|---|---|---|---|---|
| CH₂CH₂F | CH₃ | OCH₃ | CH₃ | N | |
| CH₂CH₂F | CH₃ | OCH₃ | OCH₃ | N | |
| CH₂CH₂F | CH₃ | CH₃ | OCH₃ | CH | |
| CH₂CH₂F | CH₃ | OCH₃ | OCH₃ | CH | |
| CH₂CH₂F | H | Br | OCH₃ | CH | |
| CH₂CH₂F | CH₃ | OCH₃ | N(CH₃)₂ | N | |
| CH₂CH₂F | H | CH₃ | OCH₂CF₃ | N | |
| CH₂CH₂F | H | CH₃ | OCH₂CF₃ | CH | |
| CH₂CH₂F | H | OCH₃ | OCH₂CF₃ | CH | |
| CH₂CH₂F | H | OCH₃ | C₂H₅ | CH | |
| CH₂CH₂F | H | OCH₃ | C₂H₅ | N | |
| CH₂CH₂F | H | OCH₃ | NHCH₃ | CH | |
| CH₂CH₂F | H | OCH₃ | NHCH₃ | N | |
| CH₂CH₂F | H | CH₃ | OC₂H₅ | CH | |
| CH₂CH₂F | H | OCH₃ | OC₂H₅ | CH | |
| CH₂CH₂F | H | CH₃ | OC₂H₅ | N | |
| CH₂CH₂F | H | OCH₃ | OC₂H₅ | N | |
| CH₂CH₂F | H | CH₃ | OCH₂CHF₂ | CH | |
| CH₂CH₂F | H | OCH₃ | OCH₂CHF₂ | CH | |
| CH₂CH₂F | H | CH₃ | OCH₂CHF₂ | N | |
| CH₂CH₂F | H | OCH₃ | OCH₂CHF₂ | N | |
| CH₂CH₂F | H | CH₃ | OCH₂CH₂F | CH | |
| CH₂CH₂F | H | OCH₃ | OCH₂CH₂F | CH | |
| CH₂CH₂F | H | CH₃ | OCH₂CF₃ | N | |
| CH₂CH₂F | CH₃ | OCH₃ | OCH₂CF₃ | N | |
| CH₂CH₂F | CH₃ | Cl | OCH₃ | CH | |
| CH₂CH₂F | H | Cl | N(CH₃)₂ | CH | |
| CH₂CH₂F | H | Cl | OC₂H₅ | CH | |
| CH₂CF₃ | H | CH₃ | CH₃ | CH | |
| CH₂CF₃ | H | OCH₃ | CH₃ | CH | |
| CH₂CF₃ | H | OCH₃ | OCH₃ | CH | |
| CH₂CF₃ | H | Cl | OCH₃ | CH | |
| CH₂CF₃ | H | OCH₃ | N(CH₃)₂ | CH | |
| CH₂CF₃ | H | CH₃ | CH₃ | N | |
| CH₂CF₃ | H | OCH₃ | CH₃ | N | |
| CH₂CF₃ | H | OCH₃ | OCH₃ | N | |
| CH₂CF₃ | H | OCH₃ | N(CH₃)₂ | N | |
| CH₂CF₃ | H | OCH₃ | OCH₂CF₃ | N | |
| CH₂CF₃ | CH₃ | OCH₃ | CH₃ | N | |
| CH₂CF₃ | CH₃ | OCH₃ | OCH₃ | N | |
| CH₂CF₃ | CH₃ | CH₃ | OCH₃ | CH | |
| CH₂CF₃ | CH₃ | OCH₃ | OCH₃ | CH | |
| CH₂CF₃ | H | Br | OCH₃ | CH | |
| CH₂CF₃ | CH₃ | OCH₃ | N(CH₃)₂ | N | |
| CH₂CF₃ | H | CH₃ | OCH₂CF₃ | N | |
| CH₂CF₃ | H | CH₃ | OCH₂CF₃ | CH | |
| CH₂CF₃ | H | OCH₃ | OCH₂CF₃ | CH | |
| CH₂CF₃ | H | OCH₃ | C₂H₅ | CH | |
| CH₂CF₃ | H | OCH₃ | C₂H₅ | N | |
| CH₂CF₃ | H | OCH₃ | NHCH₃ | CH | |
| CH₂CF₃ | H | OCH₃ | NHCH₃ | N | |
| CH₂CF₃ | H | CH₃ | OC₂H₅ | CH | |
| CH₂CF₃ | H | OCH₃ | OC₂H₅ | CH | |
| CH₂CF₃ | H | CH₃ | OC₂H₅ | N | |
| CH₂CF₃ | H | OCH₃ | OC₂H₅ | N | |
| CH₂CF₃ | H | CH₃ | OCH₂CHF₂ | CH | |
| CH₂CF₃ | H | OCH₃ | OCH₂CHF₂ | CH | |
| CH₂CF₃ | H | CH₃ | OCH₂CHF₂ | N | |
| CH₂CF₃ | H | OCH₃ | OCH₂CHF₂ | N | |
| CH₂CF₃ | H | CH₃ | OCH₂CH₂F | CH | |
| CH₂CF₃ | H | OCH₃ | OCH₂CH₂F | CH | |
| CH₂CF₃ | H | CH₃ | OCH₂CH₂F | N | |
| CH₂CF₃ | CH₃ | OCH₃ | OCH₂CH₂F | N | |
| CH₂CF₃ | CH₃ | Cl | OCH₃ | CH | |
| CH₂CF₃ | H | Cl | N(CH₃)₂ | CH | |
| CH₂CF₃ | H | Cl | OC₂H₅ | CH | |
| CHFCH₃ | H | CH₃ | CH₃ | CH | |
| CHFCH₃ | H | OCH₃ | CH₃ | CH | |
| CHFCH₃ | H | OCH₃ | OCH₃ | CH | |
| CHFCH₃ | H | Cl | OCH₃ | CH | |
| CHFCH₃ | H | OCH₃ | N(CH₃)₂ | CH | |

TABLE Ii-continued

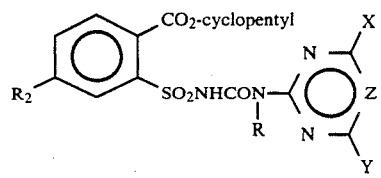

| $R_2$ | R | X | Y | Z | m.p. (°C.) |
|---|---|---|---|---|---|
| $CHFCH_3$ | H | $CH_3$ | $CH_3$ | N | |
| $CHFCH_3$ | H | $OCH_3$ | $CH_3$ | N | |
| $CHFCH_3$ | H | $OCH_3$ | $OCH_3$ | N | |
| $CHFCH_3$ | H | $OCH_3$ | $N(CH_3)_2$ | N | |
| $CHFCH_3$ | H | $OCH_3$ | $OCH_2CF_3$ | N | |
| $CHFCH_3$ | $CH_3$ | $OCH_3$ | $CH_3$ | N | |
| $CHFCH_3$ | $CH_3$ | $OCH_3$ | $OCH_3$ | N | |
| $CHFCH_3$ | $CH_3$ | $CH_3$ | $OCH_3$ | CH | |
| $CHFCH_3$ | $CH_3$ | $OCH_3$ | $OCH_3$ | CH | |
| $CHFCH_3$ | H | Br | $OCH_3$ | CH | |
| $CHFCH_3$ | $CH_3$ | $OCH_3$ | $N(CH_3)_2$ | N | |
| $CHFCH_3$ | H | $CH_3$ | $OCH_2CF_3$ | N | |
| $CHFCH_3$ | H | $CH_3$ | $OCH_2CF_3$ | CH | |
| $CHFCH_3$ | H | $OCH_3$ | $OCH_2CF_3$ | CH | |
| $CHFCH_3$ | H | $OCH_3$ | $C_2H_5$ | CH | |
| $CHFCH_3$ | H | $OCH_3$ | $C_2H_5$ | N | |
| $CHFCH_3$ | H | $OCH_3$ | $NHCH_3$ | CH | |
| $CHFCH_3$ | H | $OCH_3$ | $NHCH_3$ | N | |
| $CHFCH_3$ | H | $CH_3$ | $OC_2H_5$ | CH | |
| $CHFCH_3$ | H | $OCH_3$ | $OC_2H_5$ | CH | |
| $CHFCH_3$ | H | $CH_3$ | $OC_2H_5$ | N | |
| $CHFCH_3$ | H | $OCH_3$ | $OC_2H_5$ | N | |
| $CHFCH_3$ | H | $CH_3$ | $OCH_2CHF_2$ | CH | |
| $CHFCH_3$ | H | $OCH_3$ | $OCH_2CHF_2$ | CH | |
| $CHFCH_3$ | H | $CH_3$ | $OCH_2CHF_2$ | N | |
| $CHFCH_3$ | H | $OCH_3$ | $OCH_2CHF_2$ | N | |
| $CHFCH_3$ | H | $CH_3$ | $OCH_2CH_2F$ | CH | |
| $CHFCH_3$ | H | $OCH_3$ | $OCH_2CH_2F$ | CH | |
| $CHFCH_3$ | H | $CH_3$ | $OCH_2CF_3$ | N | |
| $CHFCH_3$ | $CH_3$ | $OCH_3$ | $OCH_2CF_3$ | N | |
| $CHFCH_3$ | $CH_3$ | Cl | $OCH_3$ | CH | |
| $CHFCH_3$ | H | Cl | $N(CH_3)_2$ | CH | |
| $CHFCH_3$ | H | Cl | $OC_2H_5$ | CH | |
| $CH_2F$ | H | $CH_3$ | $CH_3$ | CH | |
| $CH_2F$ | H | $OCH_3$ | $CH_3$ | CH | |
| $CH_2F$ | H | $OCH_3$ | $OCH_3$ | CH | |
| $CH_2F$ | H | Cl | $OCH_3$ | CH | |
| $CH_2F$ | H | $OCH_3$ | $N(CH_3)_2$ | CH | |
| $CH_2F$ | H | $CH_3$ | $CH_3$ | N | |
| $CH_2F$ | H | $OCH_3$ | $CH_3$ | N | |
| $CH_2F$ | H | $OCH_3$ | $OCH_3$ | N | |
| $CH_2F$ | H | $OCH_3$ | $N(CH_3)_2$ | N | |
| $CH_2F$ | H | $OCH_3$ | $OCH_2CF_3$ | N | |
| $CH_2F$ | $CH_3$ | $OCH_3$ | $CH_3$ | N | |
| $CH_2F$ | $CH_3$ | $OCH_3$ | $OCH_3$ | N | |
| $CH_2F$ | $CH_3$ | $CH_3$ | $OCH_3$ | CH | |
| $CH_2F$ | $CH_3$ | $OCH_3$ | $OCH_3$ | CH | |
| $CH_2F$ | H | Br | $OCH_3$ | CH | |
| $CH_2F$ | $CH_3$ | $OCH_3$ | $N(CH_3)_2$ | N | |
| $CH_2F$ | H | $CH_3$ | $OCH_2CF_3$ | N | |
| $CH_2F$ | H | $CH_3$ | $OCH_2CF_3$ | CH | |
| $CH_2F$ | H | $OCH_3$ | $OCH_2CF_3$ | CH | |
| $CH_2F$ | H | $OCH_3$ | $C_2H_5$ | CH | |
| $CH_2F$ | H | $OCH_3$ | $C_2H_5$ | N | |
| $CH_2F$ | H | $OCH_3$ | $NHCH_3$ | CH | |
| $CH_2F$ | H | $OCH_3$ | $NHCH_3$ | N | |
| $CH_2F$ | H | $CH_3$ | $OC_2H_5$ | CH | |
| $CH_2F$ | H | $OCH_3$ | $OC_2H_5$ | CH | |
| $CH_2F$ | H | $CH_3$ | $OC_2H_5$ | N | |
| $CH_2F$ | H | $OCH_3$ | $OC_2H_5$ | N | |
| $CH_2F$ | H | $CH_3$ | $OCH_2CHF_2$ | CH | |
| $CH_2F$ | H | $OCH_3$ | $OCH_2CHF_2$ | CH | |
| $CH_2F$ | H | $CH_3$ | $OCH_2CHF_2$ | N | |
| $CH_2F$ | H | $OCH_3$ | $OCH_2CHF_2$ | N | |
| $CH_2F$ | H | $CH_3$ | $OCH_2CH_2F$ | CH | |
| $CH_2F$ | H | $OCH_3$ | $OCH_2CH_2F$ | CH | |
| $CH_2F$ | H | $CH_3$ | $OCH_2CH_2F$ | N | |
| $CH_2F$ | $CH_3$ | $OCH_3$ | $OCH_2CH_2F$ | N | |
| $CH_2F$ | $CH_3$ | Cl | $OCH_3$ | CH | |
| $CH_2F$ | H | Cl | $N(CH_3)_2$ | CH | |
| $CH_2F$ | H | Cl | $OC_2H_5$ | CH | |

TABLE Ii-continued

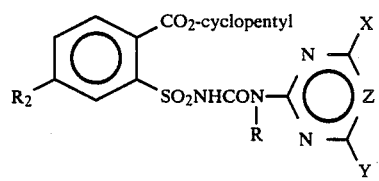

| $R_2$ | R | X | Y | Z | m.p. (°C.) |
|---|---|---|---|---|---|
| $CHF_2$ | H | $CH_3$ | $CH_3$ | CH | |
| $CHF_2$ | H | $OCH_3$ | $CH_3$ | CH | |
| $CHF_2$ | H | $OCH_3$ | $OCH_3$ | CH | |
| $CHF_2$ | H | Cl | $OCH_3$ | CH | |
| $CHF_2$ | H | $OCH_3$ | $N(CH_3)_2$ | CH | |
| $CHF_2$ | H | $CH_3$ | $CH_3$ | N | |
| $CHF_2$ | H | $OCH_3$ | $CH_3$ | N | |
| $CHF_2$ | H | $OCH_3$ | $OCH_3$ | N | |
| $CHF_2$ | H | $OCH_3$ | $N(CH_3)_2$ | N | |
| $CHF_2$ | H | $OCH_3$ | $OCH_2CF_3$ | N | |
| $CHF_2$ | $CH_3$ | $OCH_3$ | $CH_3$ | N | |
| $CHF_2$ | $CH_3$ | $OCH_3$ | $OCH_3$ | N | |
| $CHF_2$ | $CH_3$ | $CH_3$ | $OCH_3$ | CH | |
| $CHF_2$ | $CH_3$ | $OCH_3$ | $OCH_3$ | CH | |
| $CHF_2$ | H | Br | $OCH_3$ | CH | |
| $CHF_2$ | $CH_3$ | $OCH_3$ | $N(CH_3)_2$ | N | |
| $CHF_2$ | H | $CH_3$ | $OCH_2CF_3$ | N | |
| $CHF_2$ | H | $CH_3$ | $OCH_2CF_3$ | CH | |
| $CHF_2$ | H | $OCH_3$ | $OCH_2CF_3$ | CH | |
| $CHF_2$ | H | $OCH_3$ | $C_2H_5$ | CH | |
| $CHF_2$ | H | $OCH_3$ | $C_2H_5$ | N | |
| $CHF_2$ | H | $OCH_3$ | $NHCH_3$ | CH | |
| $CHF_2$ | H | $OCH_3$ | $NHCH_3$ | N | |
| $CHF_2$ | H | $CH_3$ | $OC_2H_5$ | CH | |
| $CHF_2$ | H | $OCH_3$ | $OC_2H_5$ | CH | |
| $CHF_2$ | H | $CH_3$ | $OC_2H_5$ | N | |
| $CHF_2$ | H | $OCH_3$ | $OC_2H_5$ | N | |
| $CHF_2$ | H | $CH_3$ | $OCH_2CHF_2$ | CH | |
| $CHF_2$ | H | $OCH_3$ | $OCH_2CHF_2$ | CH | |
| $CHF_2$ | H | $CH_3$ | $OCH_2CHF_2$ | N | |
| $CHF_2$ | H | $OCH_3$ | $OCH_2CHF_2$ | N | |
| $CHF_2$ | H | $CH_3$ | $OCH_2CH_2F$ | CH | |
| $CHF_2$ | H | $OCH_3$ | $OCH_2CH_2F$ | CH | |
| $CHF_2$ | H | $CH_3$ | $OCH_2CH_2F$ | N | |
| $CHF_2$ | $CH_3$ | $OCH_3$ | $OCH_2CH_2F$ | N | |
| $CHF_2$ | $CH_3$ | Cl | $OCH_3$ | CH | |
| $CHF_2$ | H | Cl | $N(CH_3)_2$ | CH | |
| $CHF_2$ | H | Cl | $OC_2H_5$ | CH | |
| $CH_2OCH_3$ | H | $CH_3$ | $CH_3$ | CH | |
| $CH_2OCH_3$ | H | $OCH_3$ | $CH_3$ | CH | |
| $CH_2OCH_3$ | H | $OCH_3$ | $OCH_3$ | CH | |
| $CH_2OCH_3$ | H | Cl | $OCH_3$ | CH | |
| $CH_2OCH_3$ | H | $OCH_3$ | $N(CH_3)_2$ | CH | |
| $CH_2OCH_3$ | H | $CH_3$ | $CH_3$ | N | |
| $CH_2OCH_3$ | H | $OCH_3$ | $CH_3$ | N | |
| $CH_2OCH_3$ | H | $OCH_3$ | $OCH_3$ | N | |
| $CH_2OCH_3$ | H | $OCH_3$ | $N(CH_3)_2$ | N | |
| $CH_2OCH_3$ | H | $OCH_3$ | $OCH_2CF_3$ | N | |
| $CH_2OCH_3$ | $CH_3$ | $OCH_3$ | $CH_3$ | N | |
| $CH_2OCH_3$ | $CH_3$ | $OCH_3$ | $OCH_3$ | N | |
| $CH_2OCH_3$ | $CH_3$ | $CH_3$ | $OCH_3$ | CH | |
| $CH_2OCH_3$ | $CH_3$ | $OCH_3$ | $OCH_3$ | CH | |
| $CH_2OCH_3$ | H | Br | $OCH_3$ | CH | |
| $CH_2OCH_3$ | H | $OCH_3$ | $N(CH_3)_2$ | CH | |
| $CH_2OCH_3$ | $CH_3$ | $OCH_3$ | $N(CH_3)_2$ | N | |
| $CH_2OCH_3$ | H | $CH_3$ | $OCH_2CF_3$ | N | |
| $CH_2OCH_3$ | H | $CH_3$ | $OCH_2CF_3$ | CH | |
| $CH_2OCH_3$ | H | $OCH_3$ | $OCH_2CF_3$ | CH | |
| $CH_2OCH_3$ | H | $OCH_3$ | $C_2H_5$ | CH | |
| $CH_2OCH_3$ | H | $OCH_3$ | $C_2H_5$ | N | |
| $CH_2OCH_3$ | H | $OCH_3$ | $NHCH_3$ | CH | |
| $CH_2OCH_3$ | H | $OCH_3$ | $NHCH_3$ | N | |
| $CH_2OCH_3$ | H | $CH_3$ | $OC_2H_5$ | CH | |
| $CH_2OCH_3$ | H | $OCH_3$ | $OC_2H_5$ | CH | |
| $CH_2OCH_3$ | H | $CH_3$ | $OC_2H_5$ | N | |
| $CH_2OCH_3$ | H | $OCH_3$ | $OC_2H_5$ | N | |
| $CH_2OCH_3$ | H | $CH_3$ | $OCH_2CHF_2$ | CH | |
| $CH_2OCH_3$ | H | $OCH_3$ | $OCH_2CHF_2$ | CH | |
| $CH_2OCH_3$ | H | $CH_3$ | $OCH_2CHF_2$ | N | |
| $CH_2OCH_3$ | H | $OCH_3$ | $OCH_2CHF_2$ | N | |
| $CH_2OCH_3$ | H | $CH_3$ | $OCH_2CH_2F$ | CH | |

TABLE Ii-continued

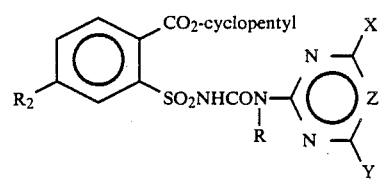

| $R_2$ | R | X | Y | Z | m.p. (°C.) |
|---|---|---|---|---|---|
| $CH_2OCH_3$ | H | $OCH_3$ | $OCH_2CH_2F$ | CH | |
| $CH_2OCH_3$ | H | $CH_3$ | $OCH_2CF_3$ | N | |
| $CH_2OCH_3$ | $CH_3$ | $OCH_3$ | $OCH_2CF_3$ | N | |
| $CH_2OCH_3$ | $CH_3$ | Cl | $OCH_3$ | CH | |
| $CH_2OCH_3$ | H | Cl | $N(CH_3)_2$ | CH | |
| $CH_2OCH_3$ | H | Cl | $OC_2H_5$ | CH | |
| $CH_2SCH_3$ | H | $CH_3$ | $CH_3$ | CH | |
| $CH_2SCH_3$ | H | $OCH_3$ | $CH_3$ | CH | |
| $CH_2SCH_3$ | H | $OCH_3$ | $OCH_3$ | CH | |
| $CH_2SCH_3$ | H | Cl | $OCH_3$ | CH | |
| $CH_2SCH_3$ | H | $OCH_3$ | $N(CH_3)_2$ | CH | |
| $CH_2SCH_3$ | H | $CH_3$ | $CH_3$ | N | |
| $CH_2SCH_3$ | H | $OCH_3$ | $CH_3$ | N | |
| $CH_2SCH_3$ | H | $OCH_3$ | $OCH_3$ | N | |
| $CH_2SCH_3$ | H | $OCH_3$ | $N(CH_3)_2$ | N | |
| $CH_2SCH_3$ | H | $OCH_3$ | $OCH_2CF_3$ | N | |
| $CH_2SCH_3$ | $CH_3$ | $OCH_3$ | $CH_3$ | N | |
| $CH_2SCH_3$ | $CH_3$ | $OCH_3$ | $OCH_3$ | N | |
| $CH_2SCH_3$ | $CH_3$ | $CH_3$ | $OCH_3$ | CH | |
| $CH_2SCH_3$ | $CH_3$ | $OCH_3$ | $OCH_3$ | CH | |
| $CH_2SCH_3$ | H | Br | $OCH_3$ | CH | |
| $CH_2SCH_3$ | $CH_3$ | $OCH_3$ | $N(CH_3)_2$ | N | |
| $CH_2SCH_3$ | H | $CH_3$ | $OCH_2CF_3$ | N | |
| $CH_2SCH_3$ | H | $CH_3$ | $OCH_2CF_3$ | CH | |
| $CH_2SCH_3$ | H | $OCH_3$ | $OCH_2CF_3$ | CH | |
| $CH_2SCH_3$ | H | $OCH_3$ | $C_2H_5$ | CH | |
| $CH_2SCH_3$ | H | $OCH_3$ | $C_2H_5$ | N | |
| $CH_2SCH_3$ | H | $OCH_3$ | $NHCH_3$ | CH | |
| $CH_2SCH_3$ | H | $OCH_3$ | $NHCH_3$ | N | |
| $CH_2SCH_3$ | H | $CH_3$ | $OC_2H_5$ | CH | |
| $CH_2SCH_3$ | H | $OCH_3$ | $OC_2H_5$ | CH | |
| $CH_2SCH_3$ | H | $CH_3$ | $OC_2H_5$ | N | |
| $CH_2SCH_3$ | H | $OCH_3$ | $OC_2H_5$ | N | |
| $CH_2SCH_3$ | H | $CH_3$ | $OCH_2CHF_2$ | CH | |
| $CH_2SCH_3$ | H | $OCH_3$ | $OCH_2CHF_2$ | CH | |
| $CH_2SCH_3$ | H | $CH_3$ | $OCH_2CHF_2$ | N | |
| $CH_2SCH_3$ | H | $OCH_3$ | $OCH_2CHF_2$ | N | |
| $CH_2SCH_3$ | H | $CH_3$ | $OCH_2CH_2F$ | CH | |
| $CH_2SCH_3$ | H | $OCH_3$ | $OCH_2CH_2F$ | CH | |
| $CH_2SCH_3$ | H | $CH_3$ | $OCH_2CH_2F$ | N | |
| $CH_2SCH_3$ | $CH_3$ | $OCH_3$ | $OCH_2CH_2F$ | N | |
| $CH_2SCH_3$ | $CH_3$ | Cl | $OCH_3$ | CH | |
| $CH_2SCH_3$ | H | Cl | $N(CH_3)_2$ | CH | |
| $CH_2SCH_3$ | H | Cl | $OC_2H_5$ | CH | |
| $OCF_2H$ | H | $CH_3$ | $CH_3$ | CH | |
| $OCF_2H$ | H | $OCH_3$ | $CH_3$ | CH | |
| $OCF_2H$ | H | $OCH_3$ | $OCH_3$ | CH | |
| $OCF_2H$ | H | Cl | $OCH_3$ | CH | |
| $OCF_2H$ | H | $OCH_3$ | $N(CH_3)_2$ | CH | |
| $OCF_2H$ | H | $CH_3$ | $CH_3$ | N | |
| $OCF_2H$ | H | $OCH_3$ | $CH_3$ | N | |
| $OCF_2H$ | H | $OCH_3$ | $OCH_3$ | N | |
| $OCF_2H$ | H | $OCH_3$ | $N(CH_3)_2$ | N | |
| $OCF_2H$ | H | $OCH_3$ | $OCH_2CF_3$ | N | |
| $OCF_2H$ | $CH_3$ | $OCH_3$ | $CH_3$ | N | |
| $OCF_2H$ | $CH_3$ | $OCH_3$ | $OCH_3$ | N | |
| $OCF_2H$ | $CH_3$ | $CH_3$ | $OCH_3$ | CH | |
| $OCF_2H$ | $CH_3$ | $OCH_3$ | $OCH_3$ | CH | |
| $OCF_2H$ | H | Br | $OCH_3$ | CH | |
| $OCF_2H$ | $CH_3$ | $OCH_3$ | $N(CH_3)_2$ | N | |
| $OCF_2H$ | H | $CH_3$ | $OCH_2CF_3$ | N | |
| $OCF_2H$ | H | $CH_3$ | $OCH_2CF_3$ | CH | |
| $OCF_2H$ | H | $OCH_3$ | $OCH_2CF_3$ | CH | |
| $OCF_2H$ | H | $OCH_3$ | $C_2H_5$ | CH | |
| $OCF_2H$ | H | $OCH_3$ | $C_2H_5$ | N | |
| $OCF_2H$ | H | $OCH_3$ | $NHCH_3$ | CH | |
| $OCF_2H$ | H | $OCH_3$ | $NHCH_3$ | N | |
| $OCF_2H$ | H | $CH_3$ | $OC_2H_5$ | CH | |
| $OCF_2H$ | H | $OCH_3$ | $OC_2H_5$ | CH | |
| $OCF_2H$ | H | $CH_3$ | $OC_2H_5$ | N | |
| $OCF_2H$ | H | $OCH_3$ | $OC_2H_5$ | N | |

TABLE Ii-continued

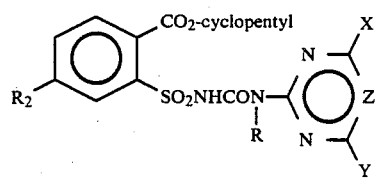

| R₂ | R | X | Y | Z | m.p. (°C.) |
|---|---|---|---|---|---|
| OCF₂H | H | CH₃ | OCH₂CHF₂ | CH | |
| OCF₂H | H | OCH₃ | OCH₂CHF₂ | CH | |
| OCF₂H | H | CH₃ | OCH₂CHF₂ | N | |
| OCF₂H | H | OCH₃ | OCH₂CHF₂ | N | |
| OCF₂H | H | CH₃ | OCH₂CH₂F | CH | |
| OCF₂H | H | OCH₃ | OCH₂CH₂F | CH | |
| OCF₂H | H | CH₃ | OCH₂CH₂F | N | |
| OCF₂H | CH₃ | OCH₃ | OCH₂CH₂F | N | |
| OCF₂H | CH₃ | OCH₃ | OCH₃ | CH | |
| OCF₂H | H | Cl | N(CH₃)₂ | CH | |
| OCF₂H | H | Cl | OC₂H₅ | CH | |
| OCH₂CH₂F | H | CH₃ | CH₃ | CH | |
| OCH₂CH₂F | H | OCH₃ | CH₃ | CH | |
| OCH₂CH₂F | H | OCH₃ | OCH₃ | CH | |
| OCH₂CH₂F | H | Cl | OCH₃ | CH | |
| OCH₂CH₂F | H | OCH₃ | N(CH₃)₂ | CH | |
| OCH₂CH₂F | H | CH₃ | CH₃ | N | |
| OCH₂CH₂F | H | OCH₃ | CH₃ | N | |
| OCH₂CH₂F | H | OCH₃ | OCH₃ | N | |
| OCH₂CH₂F | H | OCH₃ | N(CH₃)₂ | N | |
| OCH₂CH₂F | H | OCH₃ | OCH₂CF₃ | N | |
| OCH₂CH₂F | CH₃ | OCH₃ | CH₃ | N | |
| OCH₂CH₂F | CH₃ | OCH₃ | OCH₃ | N | |
| OCH₂CH₂F | CH₃ | CH₃ | OCH₃ | CH | |
| OCH₂CH₂F | CH₃ | OCH₃ | OCH₃ | CH | |
| OCH₂CH₂F | H | Br | OCH₃ | CH | |
| OCH₂CH₂F | CH₃ | OCH₃ | N(CH₃)₂ | N | |
| OCH₂CH₂F | H | CH₃ | OCH₂CF₃ | N | |
| OCH₂CH₂F | H | CH₃ | OCH₂CF₃ | CH | |
| OCH₂CH₂F | H | OCH₃ | OCH₂CF₃ | CH | |
| OCH₂CH₂F | H | OCH₃ | C₂H₅ | CH | |
| OCH₂CH₂F | H | OCH₃ | C₂H₅ | N | |
| OCH₂CH₂F | H | OCH₃ | NHCH₃ | CH | |
| OCH₂CH₂F | H | OCH₃ | NHCH₃ | N | |
| OCH₂CH₂F | H | CH₃ | OC₂H₅ | CH | |
| OCH₂CH₂F | H | OCH₃ | OC₂H₅ | CH | |
| OCH₂CH₂F | H | CH₃ | OC₂H₅ | N | |
| OCH₂CH₂F | H | OCH₃ | OC₂H₅ | N | |
| OCH₂CH₂F | H | CH₃ | OCH₂CHF₂ | CH | |
| OCH₂CH₂F | H | OCH₃ | OCH₂CHF₂ | CH | |
| OCH₂CH₂F | H | CH₃ | OCH₂CHF₂ | N | |
| OCH₂CH₂F | H | OCH₃ | OCH₂CHF₂ | N | |
| OCH₂CH₂F | H | CH₃ | OCH₂CH₂F | CH | |
| OCH₂CH₂F | H | OCH₃ | OCH₂CH₂F | CH | |
| OCH₂CH₂F | H | CH₃ | OCH₂CH₂F | N | |
| OCH₂CH₂F | CH₃ | OCH₃ | OCH₂CH₂F | N | |
| OCH₂CH₂F | CH₃ | Cl | OCH₃ | CH | |
| OCH₂CH₂F | H | Cl | N(CH₃)₂ | CH | |
| OCH₂CH₂F | H | Cl | OC₂H₅ | CH | |
| OCH₂CF₃ | H | CH₃ | CH₃ | CH | |
| OCH₂CF₃ | H | OCH₃ | CH₃ | CH | |
| OCH₂CF₃ | H | OCH₃ | OCH₃ | CH | |
| OCH₂CF₃ | H | Cl | OCH₃ | CH | |
| OCH₂CF₃ | H | OCH₃ | N(CH₃)₂ | CH | |
| OCH₂CF₃ | H | CH₃ | CH₃ | N | |
| OCH₂CF₃ | H | OCH₃ | CH₃ | N | |
| OCH₂CF₃ | H | OCH₃ | OCH₃ | N | |
| OCH₂CF₃ | H | OCH₃ | N(CH₃)₂ | N | |
| OCH₂CF₃ | H | OCH₃ | OCH₂CF₃ | N | |
| OCH₂CF₃ | H | OC₂H₅ | NHCH₃ | N | |
| OCH₂CF₃ | CH₃ | OCH₃ | CH₃ | N | |
| OCH₂CF₃ | CH₃ | OCH₃ | OCH₃ | N | |
| OCH₂CF₃ | CH₃ | CH₃ | OCH₃ | CH | |
| OCH₂CF₃ | CH₃ | OCH₃ | OCH₃ | CH | |
| OCH₂CF₃ | H | Br | OCH₃ | CH | |
| OCH₂CF₃ | CH₃ | OCH₃ | N(CH₃)₂ | N | |
| OCH₂CF₃ | H | CH₃ | OCH₂CF₃ | N | |
| OCH₂CF₃ | H | CH₃ | OCH₂CF₃ | CH | |
| OCH₂CF₃ | H | OCH₃ | OCH₂CF₃ | CH | |
| OCH₂CF₃ | H | OCH₃ | C₂H₅ | CH | |
| OCH₂CF₃ | H | OCH₃ | C₂H₅ | N | |

TABLE Ii-continued

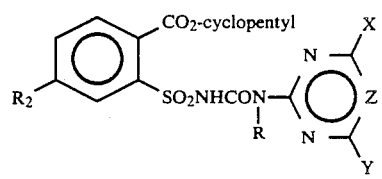

| $R_2$ | R | X | Y | Z | m.p. (°C.) |
|---|---|---|---|---|---|
| $OCH_2CF_3$ | H | $OCH_3$ | $NHCH_3$ | CH | |
| $OCH_2CF_3$ | H | $OCH_3$ | $NHCH_3$ | N | |
| $OCH_2CF_3$ | H | $CH_3$ | $OC_2H_5$ | CH | |
| $OCH_2CF_3$ | H | $OCH_3$ | $OC_2H_5$ | CH | |
| $OCH_2CF_3$ | H | $CH_3$ | $OC_2H_5$ | N | |
| $OCH_2CF_3$ | H | $OCH_3$ | $OC_2H_5$ | N | |
| $OCH_2CF_3$ | H | $CH_3$ | $OCH_2CHF_2$ | CH | |
| $OCH_2CF_3$ | H | $OCH_3$ | $OCH_2CHF_2$ | CH | |
| $OCH_2CF_3$ | H | $CH_3$ | $OCH_2CHF_2$ | N | |
| $OCH_2CF_3$ | H | $OCH_3$ | $OCH_2CHF_2$ | N | |
| $OCH_2CF_3$ | H | $CH_3$ | $OCH_2CH_2F$ | CH | |
| $OCH_2CF_3$ | H | $OCH_3$ | $OCH_2CH_2F$ | CH | |
| $OCH_2CF_3$ | H | $CH_3$ | $OCH_2CH_2F$ | N | |
| $OCH_2CF_3$ | $CH_3$ | $OCH_3$ | $OCH_2CH_2F$ | N | |
| $OCH_2CF_3$ | $CH_3$ | Cl | $OCH_3$ | CH | |
| $OCH_2CF_3$ | H | Cl | $N(CH_3)_2$ | CH | |
| $OCH_2CF_3$ | H | Cl | $OC_2H_5$ | CH | |
| $OCH_2CH_2OCH_3$ | H | $CH_3$ | $CH_3$ | CH | |
| $OCH_2CH_2OCH_3$ | H | $OCH_3$ | $CH_3$ | CH | |
| $OCH_2CH_2OCH_3$ | H | $OCH_3$ | $OCH_3$ | CH | |
| $OCH_2CH_2OCH_3$ | H | Cl | $OCH_3$ | CH | |
| $OCH_2CH_2OCH_3$ | H | $OCH_3$ | $N(CH_3)_2$ | CH | |
| $OCH_2CH_2OCH_3$ | H | $CH_3$ | $CH_3$ | N | |
| $OCH_2CH_2OCH_3$ | H | $OCH_3$ | $CH_3$ | N | |
| $OCH_2CH_2OCH_3$ | H | $OCH_3$ | $OCH_3$ | N | |
| $OCH_2CH_2OCH_3$ | H | $OCH_3$ | $N(CH_3)_2$ | N | |
| $OCH_2CH_2OCH_3$ | H | $OCH_3$ | $OCH_2CF_3$ | N | |
| $OCH_2CH_2OCH_3$ | $CH_3$ | $OCH_3$ | $CH_3$ | N | |
| $OCH_2CH_2OCH_3$ | $CH_3$ | $OCH_3$ | $OCH_3$ | N | |
| $OCH_2CH_2OCH_3$ | $CH_3$ | $CH_3$ | $OCH_3$ | CH | |
| $OCH_2CH_2OCH_3$ | $CH_3$ | $OCH_3$ | $OCH_3$ | CH | |
| $OCH_2CH_2OCH_3$ | H | Br | $OCH_3$ | CH | |
| $OCH_2CH_2OCH_3$ | H | $CH_3$ | $OCH_2CF_3$ | N | |
| $OCH_2CH_2OCH_3$ | H | $CH_3$ | $OCH_2CF_3$ | CH | |
| $OCH_2CH_2OCH_3$ | H | $OCH_3$ | $OCH_2CF_3$ | CH | |
| $OCH_2CH_2OCH_3$ | H | $OCH_3$ | $C_2H_5$ | CH | |
| $OCH_2CH_2OCH_3$ | H | $OCH_3$ | $C_2H_5$ | N | |
| $OCH_2CH_2OCH_3$ | H | $OCH_3$ | $NHCH_3$ | CH | |
| $OCH_2CH_2OCH_3$ | H | $OCH_3$ | $NHCH_3$ | N | |
| $OCH_2CH_2OCH_3$ | H | $CH_3$ | $OC_2H_5$ | CH | |
| $OCH_2CH_2OCH_3$ | H | $OCH_3$ | $OC_2H_5$ | CH | |
| $OCH_2CH_2OCH_3$ | H | $CH_3$ | $OC_2H_5$ | N | |
| $OCH_2CH_2OCH_3$ | H | $OCH_3$ | $OC_2H_5$ | N | |
| $OCH_2CH_2OCH_3$ | H | $CH_3$ | $OCH_2CHF_2$ | CH | |
| $OCH_2CH_2OCH_3$ | H | $OCH_3$ | $OCH_2CHF_2$ | CH | |
| $OCH_2CH_2OCH_3$ | H | $CH_3$ | $OCH_2CHF_2$ | N | |
| $OCH_2CH_2OCH_3$ | H | $OCH_3$ | $OCH_2CHF_2$ | N | |
| $OCH_2CH_2OCH_3$ | H | $CH_3$ | $OCH_2CH_2F$ | CH | |
| $OCH_2CH_2OCH_3$ | H | $OCH_3$ | $OCH_2CH_2F$ | CH | |
| $OCH_2CH_2OCH_3$ | H | $CH_3$ | $OCH_2CF_3$ | N | |
| $OCH_2CH_2OCH_3$ | $CH_3$ | $OCH_3$ | $OCH_2CF_3$ | N | |
| $OCH_2CH_2OCH_3$ | $CH_3$ | Cl | $OCH_3$ | CH | |
| $OCH_2CH_2OCH_3$ | H | Cl | $N(CH_3)_2$ | CH | |
| $OCH_2CH_2OCH_3$ | H | Cl | $OC_2H_5$ | CH | |
| O-cyclopropyl | H | $CH_3$ | $CH_3$ | CH | |
| O-cyclopropyl | H | $OCH_3$ | $CH_3$ | CH | |
| O-cyclopropyl | H | $OCH_3$ | $OCH_3$ | CH | |
| O-cyclopropyl | H | Cl | $OCH_3$ | CH | |
| O-cyclopropyl | H | $OCH_3$ | $N(CH_3)_2$ | CH | |
| O-cyclopropyl | H | $CH_3$ | $CH_3$ | N | |
| O-cyclopropyl | H | $OCH_3$ | $CH_3$ | N | |
| O-cyclopropyl | H | $OCH_3$ | $OCH_3$ | N | |
| O-cyclopropyl | H | $OCH_3$ | $N(CH_3)_2$ | N | |
| O-cyclopropyl | H | $OCH_3$ | $OCH_2CF_3$ | N | |
| O-cyclopropyl | $CH_3$ | $OCH_3$ | $CH_3$ | N | |
| O-cyclopropyl | $CH_3$ | $OCH_3$ | $OCH_3$ | N | |
| O-cyclopropyl | $CH_3$ | $CH_3$ | $OCH_3$ | CH | |
| O-cyclopropyl | $CH_3$ | $OCH_3$ | $OCH_3$ | CH | |
| O-cyclopropyl | H | Br | $OCH_3$ | CH | |
| O-cyclopropyl | $CH_3$ | $OCH_3$ | $N(CH_3)_2$ | N | |
| O-cyclopropyl | H | $CH_3$ | $OCH_2CF_3$ | N | |

TABLE Ii-continued $$\underset{R_2}{\phantom{xx}}\bigg\langle\!\!\!\!\!\!\!\!\!\!\!\!\!\!\!\!\!\!\!\!\!\bigg\rangle\!\!\!\overset{CO_2\text{-cyclopentyl}}{\underset{SO_2NHCON(R)}{\phantom{xx}}}\!\!-\!\!\overset{N=\!\!\!\underset{Y}{\overset{X}{\bigg\langle}}}{\underset{N}{\phantom{xx}}}\!\!\!\bigg\rangle\!\!Z$$

| $R_2$ | R | X | Y | Z | m.p. (°C.) |
|---|---|---|---|---|---|
| O-cyclopropyl | H | $CH_3$ | $OCH_2CF_3$ | CH | |
| O-cyclopropyl | H | $OCH_3$ | $OCH_2CF_3$ | CH | |
| O-cyclopropyl | H | $OCH_3$ | $C_2H_5$ | CH | |
| O-cyclopropyl | H | $OCH_3$ | $C_2H_5$ | N | |
| O-cyclopropyl | H | $OCH_3$ | $NHCH_3$ | CH | |
| O-cyclopropyl | H | $OCH_3$ | $NHCH_3$ | N | |
| O-cyclopropyl | H | $CH_3$ | $OC_2H_5$ | CH | |
| O-cyclopropyl | H | $OCH_3$ | $OC_2H_5$ | CH | |
| O-cyclopropyl | H | $CH_3$ | $OC_2H_5$ | N | |
| O-cyclopropyl | H | $OCH_3$ | $OC_2H_5$ | N | |
| O-cyclopropyl | H | $CH_3$ | $OCH_2CHF_2$ | CH | |
| O-cyclopropyl | H | $OCH_3$ | $OCH_2CHF_2$ | CH | |
| O-cyclopropyl | H | $CH_3$ | $OCH_2CHF_2$ | N | |
| O-cyclopropyl | H | $OCH_3$ | $OCH_2CHF_2$ | N | |
| O-cyclopropyl | H | $CH_3$ | $OCH_2CH_2F$ | CH | |
| O-cyclopropyl | H | $OCH_3$ | $OCH_2CH_2F$ | CH | |
| O-cyclopropyl | H | $CH_3$ | $OCH_2CH_2F$ | N | |
| O-cyclopropyl | $CH_3$ | $OCH_3$ | $OCH_2CH_2F$ | N | |
| O-cyclopropyl | $CH_3$ | Cl | $OCH_3$ | CH | |
| O-cyclopropyl | H | Cl | $N(CH_3)_2$ | CH | |
| O-cyclopropyl | H | Cl | $OC_2H_5$ | CH | |
| $OCF_2CF_2H$ | H | $OCH_3$ | Cl | CH | |
| $OCF_2CF_2H$ | H | $CH_3$ | $CH_3$ | CH | |
| $OCF_2CF_2H$ | H | $OCH_3$ | $OCH_3$ | N | |
| S-cyclopropyl | H | $OCH_3$ | $OCH_3$ | CH | |
| S-cyclopropyl | H | $OCH_3$ | $CH_3$ | CH | |
| S-cyclopropyl | H | $OCH_3$ | Cl | CH | |
| S-cyclopropyl | H | $CH_3$ | $CH_3$ | CH | |
| S-cyclopropyl | H | $OCH_3$ | $OCH_3$ | N | |
| S-cyclopropyl | H | $OCH_3$ | $CH_3$ | N | |
| $SCH_2$-cyclopropyl | H | $OCH_3$ | $OCH_3$ | CH | |
| $SCH_2$-cyclopropyl | H | $OCH_3$ | $CH_3$ | CH | |
| $SCH_2$-cyclopropyl | H | $OCH_3$ | Cl | CH | |
| $SCH_2$-cyclopropyl | H | $CH_3$ | $CH_3$ | CH | |
| $SCH_2$-cyclopropyl | H | $OCH_3$ | $OCH_3$ | N | |
| $NHCH_2$-cyclopropyl | H | $OCH_3$ | $OCH_3$ | CH | |
| $NHCH_2$-cyclopropyl | H | $OCH_3$ | $CH_3$ | CH | |
| $NHCH_2$-cyclopropyl | H | $OCH_3$ | Cl | CH | |
| $NHCH_2$-cyclopropyl | H | $CH_3$ | $CH_3$ | CH | |
| $NHCH_2$-cyclopropyl | H | $OCH_3$ | $OCH_3$ | N | |
| $NHCH_2$-cyclopropyl | H | $OCH_3$ | $CH_3$ | N | |
| $NHCH_2CF_2CF_3$ | H | $OCH_3$ | $OCH_3$ | CH | |
| $NHCH_2CF_2CF_3$ | H | $OCH_3$ | $CH_3$ | CH | |
| $NHCH_2CF_2CF_3$ | H | $OCH_3$ | Cl | CH | |
| $NHCH_2CF_2CF_3$ | H | $CH_3$ | $CH_3$ | CH | |
| $NHCH_2CF_2CF_3$ | H | $OCH_3$ | $OCH_3$ | N | |
| $NHCH_2CF_2CF_3$ | H | $OCH_3$ | $CH_3$ | N | |
| $NHCH(CF_3)CH_3$ | H | $OCH_3$ | $OCH_3$ | CH | |
| $NHCH(CF_3)CH_3$ | H | $OCH_3$ | $CH_3$ | CH | |
| $NHCH_2CHF_2$ | H | $OCH_3$ | $CH_3$ | N | |
| $NHCH_2CF_3$ | H | $OCH_3$ | $OCH_3$ | CH | |
| $NHCH_2CF_3$ | H | $OCH_3$ | $CH_3$ | CH | |
| $NHCH_2CF_3$ | H | $OCH_3$ | Cl | CH | |
| $NHCH_2CF_3$ | H | $CH_3$ | $CH_3$ | CH | |
| $NHCH_2CF_3$ | H | $OCH_3$ | $OCH_3$ | N | |
| $NHCH_3$ | H | $OCH_3$ | $OCH_3$ | CH | |
| $NHCH_3$ | H | $OCH_3$ | $CH_3$ | CH | |
| $NHCH_3$ | H | $OCH_3$ | Cl | CH | |
| $NHCH_3$ | H | $CH_3$ | $CH_3$ | CH | |
| $NHCH_3$ | H | $OCH_3$ | $OCH_3$ | N | |

Formulations

Useful formulations of the compounds of Formula I can be prepared in conventional ways. They include dusts, granules, pellets, solutions, suspensions, emulsions wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s) and (b) about 1% to 99.9% solid or liquid inert diluent(s). More specifically they will contain these ingredients in the following approximate proportions:

TABLE II

| | Weight Percent* | | |
|---|---|---|---|
| | Active Ingredient | Diluent(s) | Surfactant(s) |
| Wettable Powders | 20–90 | 0–74 | 1–10 |
| Oil Suspensions, Emulsions, Solutions, (including Emulsifiable Concentrates) | 3–50 | 40–95 | 0–15 |
| Aqueous Suspension | 10–50 | 40–84 | 1–20 |
| Dusts | 1–25 | 70–99 | 0–5 |
| Granules and Pellets | 0.1–95 | 5–99.9 | 0–15 |
| High Strength Compositions | 90–99 | 0–10 | 0–2 |

*Active ingredient plus at least one of a Surfactant or a Diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J., but other solids, either mined or manufactured, may be used. The more absorptive diluents are preferred for wettable powders and the denser ones for dusts. Typical liquid diluents and solvents are described in Marsden. "Solvents Guide," 2nd Ed., Interscience, N.Y., 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., N.Y., 1964, list surfactants and recommended uses. All formulations can contain minor amounts of additives to reduce foaming caking, corrosion microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example Littler U.S. Pat. No. 3,060,084). Granules and pellets may be made by spraying the active material upon preformed granular carriers or by agglomeration techniques. See J E. Browning "Agglomeration", Chemical Engineering, Dec. 4, 1967, pp. 147ff. and "Perry's Chemical Engineer's Handbook", 5th Ed., McGraw-Hill, N.Y., 1973. pp. 8–57ff.

For further information regarding the art of formulation see for example:

H. M. Loux, U.S. Pat. No. 3,235,361, Feb. 15, 1966, Col. 6, line 16 through Col. 7, line 19 and Examples 10 through 41;

R. W. Luckenbaugh, U.S. Pat. No. 3,309,192, Mar. 14, 1967. Col. 5, line 43 through Col. 7, line 62 and Examples 8, 12, 15, 39, 41, 52, 53, 58, 132, 138–140, 162–164, 166, 167 and 169–182;

H. Gysin and E. Knusli, U.S. Pat. No. 2,891,855, June 23, 1959, Col. 3, line 66 through Col. 5, line 17 and Examples 1–4;

G. C. Klingman, "Weed Control as a Science", John Wiley and Sons, Inc., N.Y., 1961, pp. 81–96; and J. D. Fryer and S. A. Evans, "Weed Control Handbook", 5th Ed., Blackwell Scientific Publications, Oxford, 1968, pp. 101–103.

In the following examples, all parts are by weight unless otherwise indicated.

EXAMPLE 16

| Wettable Powder | |
|---|---|
| 2-[[(4,6-dimethoxypyrimidin-2-yl)aminocarbonyl]aminosulfonyl]-4-(methylthio)benzoic acid, methyl ester | 80% |
| sodium alkylnaphthalenesulfonate | 2% |
| sodium ligninsulfonate | 2% |
| synthetic amorphous silica | 3% |
| kaolinite | 13% |

The ingredients are blended, hammer-milled until all the solids are essentially under 50 microns, reblended, and packaged.

EXAMPLE 17

| Wettable Powder | |
|---|---|
| 2-[[(4,6-dimethoxypyrimidin-2-yl)aminocarbonyl]aminosulfonyl]-4-(methylthio)benzoic acid, methyl ester | 50% |
| sodium alkylnaphthalenesulfonate | 2% |
| low viscosity methyl cellulose | 2% |
| diatomaceous earth | 46% |

The ingredients are blended, coarsely hammer-milled and then air-milled to produce particles essentially all below 10 microns in diameter. The product is reblended before packaging.

EXAMPLE 18

| Granule | |
|---|---|
| Wettable Powder of Example 17 | 5% |
| attapulgite granules (U.S.S. 20–40 mesh; 0.84–0.42 mm) | 95% |

A slurry of wettable powder containing 25% solids is sprayed on the surface of attapulgite granules in a double-cone blender. The granules are dried and packaged.

EXAMPLE 19

| Extruded Pellet | |
|---|---|
| 2-[[(4,6-dimethoxypyrimidin-2-yl)aminocarbonyl]aminosulfonyl]-4-(methylthio)benzoic acid, methyl ester | 25% |
| anhydrous sodium sulfate | 10% |
| crude calcium ligninsulfonate | 5% |
| sodium alkylnaphthalenesulfonate | 1% |
| calcium/magnesium bentonite | 59% |

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 20

| Oil Suspension | |
|---|---|
| 2-[[(4,6-dimethoxypyrimidin-2-yl)aminocarbonyl]-aminosulfonyl]-4-(methylthio)benzoic acid, methyl ester | 20% |
| Polyoxyethylene sorbitol hexaoleate | 5% |
| highly aliphatic hydrocarbon oil | 70% |

The ingredients are ground together is a sand mill until the solid particles have been reduced to under about 5 microns. The resulting thick suspension may be applied directly, but preferably after being extended with oils or emiulsified in water.

EXAMPLE 21

| Wettable Powder | |
|---|---|
| 2-[[(4,6-dimethoxypyrimidin-2-yl)aminocarbonyl]-aminosulfonyl]-4-(methylthio)benzoic acid, methyl ester | 20% |
| sodium alkylnaphthalenesulfonate | 4% |
| sodium ligninsulfonate | 4% |
| low viscosity methyl cellulose | 3% |
| attapulgite | 69% |

The ingredients are thoroughly blended. After grinding in a hammer-mill to produce particles essentially all below 100 microns, the material is reblended and sifted through a U.S.S. No. 50 sieve (0.3 mm opening) and packaged.

EXAMPLE 22

| Low Strength Granule | |
|---|---|
| 2-[[(4,6-dimethoxypyrimidin-2-yl)aminocarbonyl]-aminosulfonyl]-4-(methylthio)benzoic acid methyl ester | 1% |
| N,N-dimethylformamide | 9% |
| attapulgite granules (U.S.S. 20-40 sieve) | 90% |

The active ingredient is dissolved in the solvent and the solution is sprayed upon dedusted granules in a double cone blender. After spraying of the solution has been completed, the blender is allowed to run for a short period and then the granules are packaged.

EXAMPLE 23

| Aqueous Suspension | |
|---|---|
| 2-[[(4,6-dimethoxypyrimidin-2-yl)aminocarbonyl]-aminosulfonyl]-4-(methylthio)benzoic acid, methyl ester | 40% |
| polyacrylic acid thickener | 0.3% |
| dodecylphenol polyethylene glycol ether | 0.5% |
| disodium Phosphate | 1% |
| monosodium Phosphate | 0.5% |
| polyvinyl alcohol | 1.0% |
| water | 56.7% |

The ingredients are blended and ground together in a sand mill to produce particles essentially all under 5 microns in size.

EXAMPLE 24

| Solution | |
|---|---|
| 2-[[(4,6-dimethoxypyrimidin-2-yl)aminocarbonyl]-aminosulfonyl]-4-(methylthio)benzoic acid, methyl ester | 5% |
| water | 95% |

The salt is added directly to the water with stirring to produce the solution, which may then be packaged for use.

EXAMPLE 25

| Low Strength Granule | |
|---|---|
| 2-[[(4,6-dimethoxypyrimidin-2-yl)aminocarbonyl]-aminosulfonyl]-4-(methylthio)benzoic acid. methyl ester | 0.1% |
| attapulgite granules (U.S.S. 20-40 mesh) | 99.9% |

The active ingredient is dissolved in a solvent and the solution is sprayed upon dedusted granules in a double-cone blender. After spraying of the solution has been completed, the material is warmed to evaporate the solvent. The material is allowed to cool and then packaged.

EXAMPLE 26

| Granule | |
|---|---|
| 2-[[(4,6-dimethoxypyrimidin-2-yl)aminocarbonyl]-aminosulfonyl]-4-(methylthio)benzoic acid methyl ester | 80% |
| wetting agent | 1% |
| crude ligninsulfonate salt (containing 5-20% of the natural sugars) | 10% |
| attapulgite clay | 9% |

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water content is reduced to the desired level generally less than 1%. The material is then discharged, screened to the desired size range, generally 14-100 mesh (1410-149 microns), and packaged for use.

EXAMPLE 27

| High Strength Concentrate | |
|---|---|
| 2-[[(4,6-dimethoxypyrimidin-2-yl)aminocarbonyl]-aminosulfonyl]-4-(methylthio)benzoic acid, methyl ester | 99% |
| silica aerogel | 0.5% |
| synthetic amorphous silica | 0.5% |

The ingredients are blended and ground in a hammer-mill to produce a material essentially all passing a U.S.S. No. 50 screen (0.3 mm opening). The concentrate may be formulated further if necessary.

EXAMPLE 28

| Wettable Powder | |
|---|---|
| 2-[[(4,6-dimethoxypyrimidin-2-yl)aminocarbonyl]-aminosulfonyl]-4-(methylthio)benzoic acid, methyl ester | 90% |
| dioctyl sodium sulfosuccinate | 0.1% |
| synthetic fine silica | 9.9% |

The ingredients are blended and ground in a hammer-mill to produce particles essentially all below 100 microns. The material is sifted through a U.S.S. No. 50 screen and then packaged.

EXAMPLE 29

| Wettable Powder | |
|---|---|
| 2-[[(4,6-dimethoxypyrimidin-2-yl)aminocarbonyl]-aminosulfonyl]-4-(methylthio)benzoic acid methyl ester | 40% |
| sodium ligninsulfonate | 20% |
| montmorillonite clay | 40% |

The ingredients are thoroughly blended, coarsely hammer-milled and then air-milled to produce particles essentially all below 10 microns in size. The material is reblended and then packaged.

EXAMPLE 30

| Oil Suspension | |
|---|---|
| 2-[[(4,6-dimethoxypyrimidin-2-yl)aminocarbonyl]-aminosulfonyl]-4-(methylthio)benzoic acid, methyl ester | 35% |
| blend of polyalcohol carboxylic esters and oil soluble petroleum sulfonates | 6% |
| xylene | 59% |

The ingredients are combined and ground together in a sand mill to produce particles essentially all below 5 microns. The product can be used directly, extended with oils, or emulsified in water.

EXAMPLE 31

| Dust | |
|---|---|
| 2-[[(4,6-dimethoxypyrimidin-2-yl)aminocarbonyl]-aminosulfonyl]-4-(methylthio)benzoic acid methyl ester | 10% |
| attapulgite | 10% |
| pyrophyllite | 80% |

The active ingredient is blended with attapulgite and then passed through a hammer-mill to produce particles substantially all below 200 microns. The ground concentrate is then blended with powdered pyrophyllite until homogeneous.

EXAMPLE 32

| Emulsifiable Concentrate | |
|---|---|
| 2-[[(4,6-dimethoxypyrimidin-2-yl)aminocarbonyl]-aminosulfonyl]-4-(methylthio)benzoic acid, methyl ester | 20% |
| chlorobenzene | 74% |
| sorbitan monostearate and polyoxyethylene condensates thereof | 6% |

The ingredients are combined and stirred to produce a solution which can be emulsified in water for application.

UTILITY

Test results indicate that the compounds of the present invention are highly active preemergent or postemergent herbicides or plant growth regulants. Many of them have utility for broad-spectrum pre- and/or post-emergence weed control in areas where complete control of all vegetation is desired, such as around fuel storage tanks ammunition depots, industrial storage areas, parking lots, drive-in theaters, around billboards, highway and railroad structures. Some of the compounds have utility for selective weed control in crops such as wheat, barley, cotton, soybean, sugar beets, corn, rice, rape and alfalfa. Alternatively, the subject compounds are useful to modify plant growth.

The rates of application for the compounds of the invention are determined by a number of factors, including their use as plant growth modifiers or as herbicides, the crop species involved, the types of weeds to be controlled, weather and climate, formulations selected, mode of application, amount of foliage present, etc. In general terms, the subject compounds should be applied at levels of around 0.001 to 10 kg/ha, the lower rates being suggested for use on lighter soils and/or those having a low organic matter content, for plant growth modification or for situations where only short-term persistence is required.

The compounds of this invention may be used in combination with other commercial herbicides. They are particularly useful in combination with the following herbicides.

| Common Name | Chemical Name |
|---|---|
| acifluorfen | 5-[2-chloro-4-(trifluoromethyl)phenoxy]-2-nitrobenzoic acid |
| acrolein | acrolein |
| alachlor | 2-chloro-2',6'-diethyl-N-(methoxymethyl)-acetanilide |
| ametryn | 2-(ethylamino)-4-(isopropylamino)-6-methylthio)-s-triazine |
| amitrole | 3-amino-s-triazole |
| AMS | ammonium sulfamate |
| asulam | methyl sulfanilylcarbamate |
| atrazine | 2-chloro-4-(ethylamino)-6-(isopropyl-amino)-s-triazine |
| barban | 4-chloro-2-butynyl m-chlorocarbanilate |
| benefin | N-butyl-N-ethyl-α,α,α-trifluoro-2,6-dinitro-p-toluidine |
| bensulide | O,O-diisopropyl phosphorodithioate S-ester with N-(2-mercaptoethyl)-benzenesulfonamide |
| bentazon | 3-isopropyl-1H-2,1,3-benzothiadiazin-4(3H)-one 2,2-dioxide |
| benzipram | 3,5-dimethyl-N-(1-methylethyl)-N-(phenylmethyl)benzamide |
| benzoylprop | N-benzoyl-N-(3,4-dichlorophenyl)-DL-alaine |
| bifenox | methyl 5-(2,4-dichlorophenoxy)-2-nitrobenzoate |
| bromacil | 5-bromo-3-sec-butyl-6-methyluracil |
| bromoxynil | 3,5-dibromo-4-hydroxybenzonitrile |
| butachlor | N-(butoxymethyl)-2-chloro-2',6'-diethylacetanilide |
| butam | 2,2-dimethyl-N-(1-methylethyl)-N-(phenylmethyl)propanamide |

-continued

| | |
|---|---|
| buthidazole | 3-[5-(1,1-dimethylethyl)-1,3,4-thiadiazol-2-yl]-4-hydroxy-1-methyl-2-imidazolidinone |
| butralin | 4-(1,1-dimethylethyl)-N-(1-methylpropyl)-2,6-dinitrobenzenamine |
| butylate | S-ethyl-diisobutylthiocarbamate |
| cacodylic acid | hydroxydimethylarsine oxide |
| carbetamide | D-N-ethyllactamide carbanilate (ester) |
| CDAA | N-N-diallyl-2-chloroacetamide |
| CDEC | 2-chloroallyl diethyldithiocarbamate |
| chlorbromuron | 3-(4-bromo-3-chlorophenyl)-1-methoxy-1-methylurea |
| chloroxuron | 3-[p-(p-chlorophenoxy)phenyl]-1,1-dimethylurea |
| chlorpropham | isopropyl m-chlorocarbanilate |
| chlorsulfuron | 2-chloro-N-[(4-methoxy-6-methyl-1,3,5-triazin-2-yl)aminocarbonyl]benzenesulfonamide |
| chlortoluron | N'-(3-chloro-4-methylphenyl-N',N'-dimethylurea |
| cisanilide | cis-2,5-dimethyl-N-phenyl-1-pyrrolidinecarboxamide |
| CMA | calcium methanearsonate |
| cyanazine | 2-[[4-chloro-6-(ethylamino)-s-triazin-2-yl]amino]-2-methylpropionitrile |
| cycloate | S-ethyl N-ethylthiocyclohexanecarbamate |
| cycluron | 3-cyclooctyl-1,1-dimethylurea |
| cyperquat | 1-methyl-4-phenylpyridinium |
| cyprazine | 2-chloro-4-(cyclopropylamino)-6-(isopropylamino)-s-triazine |
| cyprazole | N-[5-(2-chloro-1,1-dimethylethyl)-1,3,4-thiadiazol-2-yl]cyclopropanecarboxamide |
| cypromid | 3',4'-dichlorocyclopropanecarboxanilide |
| dalapon | 2,2-dichloropropionic acid |
| dazomet | tetrahydro-3,5-dimethyl)-2H-1,3,5-thiadiazine-2-thione |
| DCPA | dimethyl tetrachloroterehthalate |
| desmetryn | 2-(isopropylamino)-4-(methylamino)-6-methylthio)-s-triazine |
| diallate | S-(2,3-dichloroallyl)diisopropylthiocarbamate |
| dicamba | 3,6-dichloro-o-anisic acid |
| dichlobenil | 2,6-dichlorobenzonitrile |
| dichlorprop | 2-(2,4-dichlorophenoxy)propionic acid |
| diclofop | 2-[4-(2,4-dichlorophenoxy)phenyl]-propanoic acid |
| diethatyl | N-(chloroacetyl)-N-(2,6-diethylphenyl)-glycine |
| difenzoquat | 1,2-dimethyl-3,5-diphenyl-1H-pyrazolium |
| dinitramine | $N^4,N^4$-diethyl-$\alpha,\alpha,\alpha$-trifluoro-3,5-dinitrotoluene-2,4-diamine |
| dinoseb | 2-sec-butyl-4,6-dinitrophenol |
| diphenamide | N,N-dimethyl-2,2-diphenylacetamide |
| dipropetryn | 2-(ethylthio)-4,6-bis(isopropylamino)-s-triazine |
| diquat | 6,7-dihydrodipyrido[1,2-a:2',1'-c]-pyrazinediium ion |
| diuron | 3-(3,4-dichlorophenyl)-1,1-dimethylurea |
| DSMA | disodium methanearsonate |
| endothall | 7-oxabicyclo[2.2.1]heptane-2,3-dicarboxylic acid |
| erbon | 2-(2,4,5-trichlorophenoxy)ethyl 2,2-dichloropropionate |
| ethafluralin | N-ethyl-N-(2-methyl-2-propenyl)-2,6-dinitro-4-(trifluoromethyl)benzenamine |
| ethofumesate | (±)-2-ethoxy-2,3-dihydro-3,3-dimethyl-5-benzofuranyl methanesulfonate |
| fenac | (2,3,6-trichlorophenyl)acetic acid |
| fenoxaprop ethyl | ethyl 2-(4-(6-chloro-2-benzoxazolyloxy)phenoxy)propanoate |
| fenuron | 1,1-dimethyl-3-phenylurea |
| fenuron TCA | 1,1-dimethyl-3-phenylurea mono(trichloroacetate) |
| flamprop | N-benzoyl-N-(3-chloro-4-fluorophenyl)-DL-alanine |
| fluchloralin | N-(2-chloroethyl)-2,6-dinitro-N-propyl-4-(trifluoromethyl)aniline |
| fluometuron | 1,1-dimethyl-3-($\alpha,\alpha,\alpha$-trifluoro-m-tolyl)-urea |
| fluorodifen | p-nitrophenyl $\alpha,\alpha,\alpha$-trifluoro-2-nitro-p-tolyl ether |
| fluridone | 1-methyl-3-phenyl-5-[3-(trifluoromethyl)phenyl]-4(1H)-pyridinone |
| fomesafen | 5-(2-chloro-4-trifluoromethylphenoxy)-N-methylsulfonyl-2-nitrobenzamide |
| fosamine | ethyl hydrogen (aminocarbonyl)phosphonate |
| glyphosate | N-(phosphonomethyl)glycine |
| hexaflurate | potassium hexafluoroarsenate |
| hexazinone | 3-cyclohexyl-6-(dimethylamino)-1-methyl-1,3,5-triazine-2,4(1H,3H)-dione |
| imazaquin | 2-(4,5-dihydro-4-methyl-4-(1-methylethyl)-5-oxo-1H-imidazol-2-yl)-3-quinolinecarboxylic acid |
| ioxynil | 4-hydroxy-3,5-diiodobenzonitrile |
| isopropalin | 2,6-dinitro-N,N-dipropylcumidine |
| karbutilate | tert-butylcarbamic acid ester with 3-(m-hydroxyphenyl)-1,1-dimethylurea |
| lactofen | 1'-(carboethoxy)ethyl-5-(2-chloro-4-(trifluoromethyl)phenoxy)-2-nitrobenzoate |
| lenacil | 3-cyclohexyl-6,7-dihydro-1H-cyclopentapyrimidine-2,4(3H,5H)-dione |
| linuron | 3-(3,4-dichlorophenyl)-1-methoxy-1-methylurea |
| MAA | methanearsonic acid |
| MAMA | monoammonium methanearsonate |
| MCPA | [(4-chloro-o-tolyl)oxy]acetic acid |
| MCPB | 4-[(4-chloro-o-tolyl)oxy]butyric acid |
| mecoprop | 2-[(4-chloro-o-tolyl)oxy]propionic acid |
| mefluidide | N-[(2,4-dimethyl-5-[[(trifluoromethyl)-sulfonyl]amino]phenyl]acetamide |
| methalpropalin | N-(2-methyl-2-propenyl)-2,6-dinitro-N-propyl-4-(trifluoromethyl)benzenamine |
| methabenzthiazuron | 1,3-dimethyl-3-(2-benzothiazolyl)urea |
| metham | sodium methyldithiocarbamate |
| methazole | 2-(3,4-dichlorophenyl)-4-methyl-1,2,4-oxadiazolidine-3,5-dione |
| methoxuron | N'-(3-chloro-4-methoxyphenyl)N,N-dimethylurea |
| metolachlor | 2-chloro-N-(2-ethyl-6-methylphenyl)-N-(2-methoxy-1-methylethyl)acetamide |
| metribuzin | 4-amino-6-tert-butyl-3-(methylthio)-as-triazine-5(4H)-one |
| metsulfuron methyl | 2-[[[(4-methoxy-6-methyl-1,3,5-triazine-2-yl)aminocarbonyl]aminosulfonyl]benzoic acid, methyl ester |
| molinate | S-ethyl hexahydro-1H-azepine-1-carbothioate |
| monolinuron | 3-(p-chlorophenyl)-1-methoxy-1-methylurea |
| monuron | 3-(p-chlorophenyl)-1,1-dimethylurea |
| monuron TCA | 3-(p-chlorophenyl)-1,1-dimethylurea mono(trichloroacetate) |
| MSMA | monosodium methanearsonate |
| napropamide | 2-($\alpha$-naphthoxy)-N,N-diethylpropionamide |
| naptalam | N-1-naphthylphthalamic acid |
| neburon | 1-butyl-3-(3,4-dichlorophenyl)-1-methylurea |
| nitralin | 4-(methylsulfonyl)-2,6-dinitro-N,N-dipropylaniline |
| nitrofen | 2,4-dichlorophenyl p-nitrophenyl ether |
| nitrofluorfen | 2-chloro-1-(4-nitrophenoxy)-4-(trifluoromethyl)benzene |
| norea | 3-(hexahydro-4,7-methanoindan-5-yl)-1,1-dimethylurea |
| norflurazon | 4-chloro-5-(methylamino)-2-($\alpha,\alpha,\alpha$-trifluoro-m-tolyl)-3(2H)-pyridazinone |
| oryzalin | 3,4-dinitro-N,N-dipropylsulfanilamide |
| oxadiazon | 2-tert-butyl-4-(2,4-dichloro-5-isopropoxyphenyl)$\Delta^2$-1,3,4-oxadiazolin-5-one |
| oxyfluorfen | 2-chloro-1-(3-ethoxy-4-nitrophenoxy)-4-(trifluoromethyl)benzene |
| paraquat | 1,1'-dimethyl-4,4'-bipyridinium ion |
| PBA | chlorinated benzoic acid |
| pendimethalin | N-(1-ethylpropyl)-3,4-dimethyl-2,6-dinitrobenzenamine |
| perfluidone | 1,1,1-trifluoro-N-[2-methyl-4-(phenylsulfonyl)phenyl]methanesulfonamide |

| | |
|---|---|
| picloram | 4-amino-3,5,6-trichloropicolinic acid |
| procyazine | 2-[[4-chloro-6-(cyclopropylamino)-1,3,5-triazine-2-yl]amino]-2-methylpropanenitrile |
| profluralin | N-(cyclopropylmethyl)-α,α,α-trifluoro-2,6-dinitro-N-propyl-p-toluidine |
| prometon | 2,4-bis(isopropylamino)-6-methoxy-s-triazine |
| prometryn | 2,4-bis(isopropylamino)-6-(methylthio)-s-triazine |
| pronamide | 3,5-dichloro N-(1,1-dimethyl-2-propynyl)benzamide |
| propachlor | 2-chloro-N-isopropylacetanilide |
| propanil | 3',4'-dichloropropionalide |
| propazine | 2-chloro-4,6-bis(isopropylamino)-s-triazine |
| propham | isopropyl carbanilate |
| prosulfalin | N-[[4-(dipropylamino)-3,5-dinitrophenyl]sulfonyl]-S,S-dimethylsulfilimine |
| prynachlor | 2-chloro-N-(1-methyl-2-propynyl)acetanilide |
| quinofop ethyl | 2-[4-(6-chloroquinoxalin-2-yloxy)phenoxypropanoic acid, ethyl ester |
| secbumeton | N-ethyl-6-methoxy-N'(1-methylpropyl)-1,3,5-triazine-2,4-diamine |
| sethoxydim | 2-[1-(ethoxyimino)butyl]-5-[2-(ethylthio)propyl]-3-hydroxy-2-cyclohexene-1-one |
| siduron | 1-(2-methylcyclohexyl)-3-phenylurea |
| simazine | 2-chloro-4,6-bis(ethylamino)-s-triazine |
| simetryn | 2,4-bis(ethylamino)-6-(methylthio)-s-triazine |
| supriox | 2-[1-(2,5-dimethylphenyl)ethylsulfonyl]-pyridine-N-oxide |
| TCA | trichloroacetic acid |
| tebuthiuron | N-[5-(1,1-dimethylethyl)-1,3,4-thiadiazol-2-yl]-N,N'-dimethylurea |
| terbacil | 3-tert-butyl-5-chloro-6-methyluracil |
| terbuchlor | N-(butoxymethyl)-2-chloro-N-[2-(1,1-dimethylethyl)-6-methylphenyl]-acetamide |
| terbuthylazine | 2-(tert-butylamino)-4-chloro-6-(ethylamino)-s-triazine |
| terbutol | 2,6-di-tert-butyl-p-tolyl methylcarbamate |
| terbutryn | 2-(tert-butylamino)-4-(ethylamino)-6-(methylthio)-s-triazine |
| tetrafluron | N,N-dimethyl-N'-[3-(1,1,2,2-tetrafluoroethoxy)phenyl]urea |
| thiobencarb | S-[(4-chlorophenyl)methyl] diethylcarbamothioate |
| triallate | S-(2,3,3-trichloroallyl)diisopropylthiocarbamate |
| trifluralin | α,α,α-trifluoro-2,6-dinitro-N,N-propyl-p-toluidine |
| trimeturon | 1-(p-chlorophenyl)-2,3,3-trimethylpseudourea |
| vernolate | S-propyl dipropylthiocarbamate |
| | ethyl 5-[2-chloro-4-(trifluoromethyl)-phenoxy]-2-nirrobenzoic acid |
| 2,3,6-TBA[b] | 2,3,6-trichlorobenzoic acid |
| 2,4-D | (2,4-dichlorophenoxy)acetic acid |
| 2,4-DB | 4-(2,4-dichlorophenoxy)butyric acid |
| 2,4-DEP | tris[2-(2,4-dichlorophenoxy)ethyl] phosphite |

| Trade Name or Code Number | Chemical Name |
|---|---|
| "Cinch" | exo-1-methyl-4-(1-methylethyl)-2-[(2-methylphenyl)methoxy]-7-oxabicyclo-[2.2.1]heptane |
| AC 263,499 | 2-[4,5-dihydro-4-methyl-4-(1-methylethyl)-5-oxo-1H-imidazol-2-yl]-5-ethyl-3-pyridinecarboxylic acid |
| Harmony ™ | 3-[[(4-methoxy-6-methyl-1,3,5-triazin-2-yl)aminocarbonyl]aminosulfonyl]-2-thiophenecarboxylic acid, methyl ester |
| PPG-1013 | 5-(2-chloro-4-(trifluoromethyl)phenoxy)-2-nitroacetophenone oxime-O-acetic acid, methyl ester |
| DOWCO 453 ME | 2-(4-(3-chloro-5-trifluoromethylpyridin-2-yloxy)phenoxy)propanoic acid, methyl ester |
| FMC 57020 | 2-(2'-chlorophenyl)methyl-4,4-dimethyl-3-isoxazolidinone |
| AC 222,293 | 6-(4-isopropyl-4-methyl-5-oxo-2-imidazolin-2-yl)-m-toluic acid, methyl ester and 6-(4-isopropyl-4-methyl-5-oxo-2-imidazolin-2-yl-p-toluic acid, methyl ester |
| AC 252,925 | 2-(4-isopropyl-4-methyl-5-oxo-2-imidazolin-2-yl)nicotinic acid with isopropyl amine (1:1) |
| DPX-L5300 | 2-[[N-(4-methoxy-6-methyl-1,3,5-triazine-2-yl)-N-methylaminocarbonyl]-aminosulfonyl]benzoic acid, methyl ester |
| — | 2-butyl-2,3-dihydro-N-[(4-methoxy-6-methylpyrimidin-2-yl)aminocarbonyl]-1,2-benzisothiazole-7-sulfonamide-1,1-dioxide |
| — | 2-butyl-2,3-dihydro-N-[(4,6-dimethoxypyrimidin-2-yl)aminocarbonyl]-1,2-benzisothiazole-7-sulfonamide-1,1-dioxide |

The herbicidal properties of the subject compounds were discovered in a number of greenhouse tests. The test procedures and results follow.

TEST A

Seeds of crabgrass (Digitaria sp.), barnyardgrass (Echinochloa crusgalli), wild oats (Avena fatua), cheatgrass (Bromus secalinus), sicklepod (Cassia obtusifolia) morning glory (Ipomoea sp. ), cocklebur (Xanthium sp. ), velvetleaf (Abutilon theophrasti), sorghum, corn, soybean, sugar beet, cotton, rice, wheat and purple nutsedge (Cyperus rotundus) tubers were planted and treated preemergence with the test chemicals dissolved in a non-phytotoxic solvent. At the same time, these crop and weed species were treated with a soil/foliage application. At the time of treatment, the plants ranged in height from 2 to 18 cm. Treated plants and controls were maintained in a greenhouse for sixteen days after which all species were compared to controls and visually rated for response to treatment. The ratings, summarized in Table 1, are based on a numerical scale extending from 0=no injury, to 10=complete kill. The accompanying descriptive symbols have the following meanings:

B=burn;
C=chlorosis/necrosis;
D=defoliation;
E=emergence inhibition;
G=growth retardation;
H=formative effects;
U=unusual pigmentation;
S=albinism; and
6Y=abscised buds or flowers.
-=no test Compounds

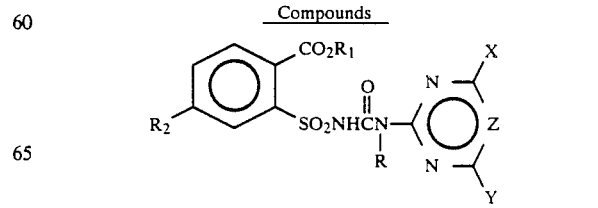

-continued

| Cmpd. | R | R₁ | R₂ | X | Y | Z |
|---|---|---|---|---|---|---|
| 1 | H | CH₃ | OC₂H₅ | OCH₃ | OCH₃ | CH |
| 2 | H | CH₃ | OC₂H₅ | OCH₃ | CH₃ | N |
| 3 | H | CH₃ | OC₂H₅ | CH₃ | CH₃ | N |
| 4 | H | CH₃ | OC₂H₅ | CH₃ | CH₃ | CH |
| 5 | H | CH₃ | OC₂H₅ | CH₃ | OCH₃ | CH |
| 6 | H | CH₃ | OC₂H₅ | OCH₃ | Cl | CH |
| 7 | H | CH₃ | OC₂H₅ | OCH₃ | OCH₃ | N |
| 8 | H | CH₃ | OC₂H₅ | OCH₃ | OCH₂CF₃ | N |
| 9 | H | CH₃ | OC₂H₅ | OCH₃ | N(CH₃)₂ | N |
| 10 | CH₃ | CH₃ | OC₂H₅ | OCH₃ | CH₃ | N |
| 11 | H | CH₃ | SCH₃ | OCH₃ | OCH₃ | CH |
| 12 | H | CH₃ | OC₂H₅ | OCH₃ | OCH₃ | CH |
| 13 | H | CH₃ | OC₂H₅ | OCH₃ | OCH₃ | N |
| 14 | H | CH₃ | OC₂H₅ | OCH₃ | N(CH₃)₂ | CH |
| 15 | H | CH₃ | OCH₂CH=CH₂ | OCH₃ | CH₃ | N |

TABLE 1

| Rate kg/ha | Cmpd. 1 0.05 | Cmpd. 2 0.05 | Cmpd. 3 0.05 | Cmpd. 4 0.05 | Cmpd. 5 0.05 | Cmpd. 6 0.05 | Cmpd. 7 0.05 | Cmpd. 8 0.05 |
|---|---|---|---|---|---|---|---|---|
| POSTEMERGENCE | | | | | | | | |
| Morningglory | 6C,9G | 10C | 9C | 9C | 6C,9G | 9C | 6C,9G | 10C |
| Cocklebur | 9C | 10C | 10C | 10C | 5C,9G | 10C | 10C | 9C |
| Sicklepod | 9C | 9C | 9C | 9C | 6C,9G | 4C,9G | 9C | 9C |
| Nutsedge | 2C,8G | 8G | 2C,8G | 2C,9G | 8G | 9G | 5G | 2C,8G |
| Crabgrass | 4G | 5G | 6G | 8G | 6G | 0 | 3G | 0 |
| Barnyardgrass | 5C,9H | 5C,9G | 5C,9G | 5C,9H | 5C,9H | 3C,5H | 3C,7H | 3H |
| Wild Oats | 3C,5G | 6C,9G | 2C,9G | 2C,9G | 2C,8G | 4G | 5C,9G | 4G |
| Wheat | 3C,6G | 7C,9G | 2C,9G | 3C,9G | 3C,8G | 2G | 5G | 4G |
| Corn | 2C,9G | 9G | 9G | 9G | 9G | 3C,7H | 2C,3H | 7H |
| Soybean | 5C,9G | 9C | 9C | 4C,9G | 6C,9G | 4C,9H | 4C,9G | 5C,9G |
| Rice | 5C,9G | 6C,9G | 5C,9G | 5C,9G | 5C,9G | 3C,9G | 5C,9G | 5C,9G |
| Sorghum | 4C,9H | 3C,9G | 2C,9G | 3C,9H | 3C,9G | 9H | 9G | 3C,8H |
| Sugar beet | 9C | 5C,9G | 5C,9G | 9C | 5C,9G | 5C,9G | 9C | 10C |
| Cotton | 9C | 9C | 9C | 9C | 9C | 9C | 9C | 3C,8G |
| Velvetleaf | — | — | — | — | — | — | — | — |
| Cheatgrass | — | — | — | — | — | — | — | — |
| PREEMERGENCE | | | | | | | | |
| Morningglory | 9G | 9G | 9G | 9G | 9G | 9G | 9G | 9G |
| Cocklebur | 9H | 5C,9H | 9H | 9H | 9H | 3C,8H | 9H | 8H |
| Sicklepod | 8G | 9G | 4C,8G | 8G | 2C,8G | 8G | 8G | 2C |
| Nutsedge | 9G | 8G | 7G | 10E | 8G | 10E | 8G | 0 |
| Crabgrass | 5G | 4G | 3G | 5G | 6G | 2G | 6G | 0 |
| Barnyardgrass | 2C,7G | 5G | 3C,6G | 9H | 5C,9H | 3C,5G | 3C,3G | 0 |
| Wild Oats | 2C,6G | 4C,8G | 3C,7H | 3C,8G | 4C,8G | 2C,4G | 4C,6G | 2C,6G |
| Wheat | 9H | 5C,9H | 3C,9H | 2C,9H | 3C,9H | 5G | 6G | 6G |
| Corn | 2C,8G | 8H | 8G | 9H | 9G | 7G | 1C,7G | 7G |
| Soybean | 2C,3H | 9H | 3C,6H | 8H | 9H | 7H | 8H | 4C,7H |
| Rice | 5C,9G | 10E | 10E | 10E | 10E | 9H | 10E | 4C,8H |
| Sorghum | 3C,9G | 7C,9H | 3C,9H | 4C,9H | 5C,9H | 5C,9H | 5C,9H | 3C,7G |
| Sugar beet | 3C,9G | 5C,9G | 5C,9G | 4C,9G | 4C,9G | 4C,8G | 4C,9G | 5C,9G |
| Cotton | 2C,9G | 9G | 9G | 9G | 9G | 9G | 9G | 3G |
| Velvetleaf | — | — | — | — | — | — | — | — |
| Cheatgrass | — | — | — | — | — | — | — | — |

| Rate kg/ha | Cmpd. 9 0.05 | Cmpd. 10 0.05 | Cmpd. 11 0.05 | Cmpd. 12 0.05 | Cmpd. 13 0.05 | Cmpd. 14 0.05 | Cmpd. 15 0.05 |
|---|---|---|---|---|---|---|---|
| POSTEMERGENCE | | | | | | | |
| Morningglory | 10C | 5C,9G | 9C | 3C,6G | 9C | 5C,9G | 10C |
| Cocklebur | 10C | 10C | 9C | 4G | 5C,9G | 2C,8H | 9C |
| SicklePod | 9C | 1C | 9C | 0 | 1C | 3C,3H | — |
| Nutsedge | 7G | 3G | 6C,9G | 0 | 0 | 0 | 4G |
| Crabgrass | 0 | 0 | 4C,9G | 0 | 0 | 2G | 5H |
| Barnyardgrass | 3H | 3H | 9C | 2H | 3C,3H | 2C,8H | 5C,8H |
| Wild Oats | 3C,9G | 2C,8G | 9C | 0 | 2C,6G | 6G | 9C |
| Wheat | 2C,8G | 5G | 9C | 0 | 2G | 0 | 10C |
| Corn | 2C,8H | 1H | 9C | 5G | 0 | 2C,8H | 10C |
| Soybean | 5C,9G | 5C,9G | 5C,9G | 3C,6G | 5C,9G | 3C,8G | 9C |
| Rice | 5C,9G | 6C,9G | 5C,9G | 4C,8G | 5C,9G | 2C,5G | 9C |
| Sorghum | 4C,9G | 2U,9H | 5C,9G | 3C,8G | 5G | 3C,8H | 9C |
| Sugar beet | 10C | 9C | 9C | 3C,8G | 9C | 5C,9G | 9C |
| Cotton | 10C | 5C,9G | 3C,9G | 9C | 9C | 5C,9G | 10C |
| Velvetleaf | — | — | — | — | — | — | 9C |
| Cheatgrass | — | — | — | — | — | — | 6C,9G |
| PREEMERGENCE | | | | | | | |
| Morningglory | 9G | 7G | 9G | 0 | 8G | 2C,6G | 9G |
| Cocklebur | 8G | 8G | 9H | 0 | 8H | 2C,5H | 9H |
| Sicklepod | 3G | 1C | 9G | 0 | 0 | 2C | — |
| Nutsedge | 0 | 0 | 10E | 0 | 0 | 10E | 8G |
| Crabgrass | 0 | 0 | 6C,9G | 0 | 0 | 3G | 2C,5G |
| Barnyardgrass | 3C,3H | 2C | 6C,9H | 0 | 1H | 3C,8H | 4C,5G |
| Wild Oats | 2C,7G | 3G | 6C,9G | 0 | 0 | 2C,7G | 3C,8G |
| Wheat | 6G | 3G | 9C | 0 | 0 | 2C,7G | 8G |
| Corn | 5G | 2G | 2C,9H | 0 | 5G | 2C,8G | 3U,6G |
| Soybean | 3G | 0 | 9H | 0 | 3C,2H | 3C,3H | 2C,6G |
| Rice | 3C,6G | 3C,8H | 10E | 2G | 3C,8H | 5G | 8H |
| Sorghum | 2C,8G | 2G | 4C,9H | 2G | 2C,5G | 3C,8G | 4U,8G |

TABLE 1-continued

| | | | | | | | |
|---|---|---|---|---|---|---|---|
| Sugar beet | 4C,9G | 3C,9G | 5C,9G | 2G | 8G | 9C | 9C |
| Cotton | 3G | 2G | 9G | 0 | 7G | 0 | 9G |
| Velvetleaf | — | — | — | — | — | — | 9C |
| Cheatgrass | — | — | — | — | — | — | 4C,8G |

TEST B

Postemergence

Two round pans (25 cm diameter by 12.5 cm deep) were filled with Woodstown sandy loam soil. One pan was planted with blackgrass (*Alopecurus myosuroides*), sugar beets, nutsedge (*Cyperus rotundus*) tubers, crabgrass (*Digitaria sanguinalis*), sicklepod (*Cassia obtusifolia*), teaweed (*Sida spinosa*), jimsonweed (*Datura stramonium*), velvetleaf (*Abutilon theophrasti*), and giant foxtail (*Setaria faberii*). The other pan was planted with wheat, cotton, rice, corn, soybean, wild oats (*Avena fatua*), cocklebur (*Xanthium pensylvanicum*), morningglory (*Ipomoea hederacea*), johnsongrass (*Sorghum halepense*) and barnyardgrass (*Echinochloa crusgalli*). The plants were grown for approximately fourteen days, then sprayed postemergence with the chemicals dissolved in a non-phytotoxic solvent.

Preemergence

Two round pans (25 cm diameter by 12.5 cm deep) were filled with Woodstown sandy loam soil. One pan was planted with blackgrass, sugar beets, nutsedge, crabgrass, sicklepod, teaweed, jimsonweed, velvetleaf, and giant foxtail. The other pan was planted with wheat, cotton, rice, corn, soybeans, wild oats, cocklebur, morningglory, johnsongrass, and barnyardgrass. The two pans were sprayed preemergence with the chemicals dissolved in a non-phytotoxic solvent.

Treated plants and controls were maintained in the greenhouse for 28 days, then all treated plants were compared to controls and visually rated for plant response.

Response ratings are based on a scale of 0 to 10: where 0=no effect, and 10 =complete control. The type of response is indicated by letters as described for Test 1 A dash (-) response means no test Response ratings are contained in Table 2.

TABLE 2

| | Compound 1 | | | | Compound 2 | | | | Compound 3 | | |
|---|---|---|---|---|---|---|---|---|---|---|---|
| Rate g/ha | 62 | 16 | 4 | 1 | 62 | 16 | 4 | 1 | 62 | 16 | 4 |
| POSTEMERGENCE | | | | | | | | | | | |
| Corn | 8G | 2G | 0 | 0 | 7G | 4G | 2G | 0 | 8G | 2G | 0 |
| Wheat | 0 | 0 | 0 | 0 | 9G | 5G | 0 | 0 | 5G | 0 | 0 |
| Rice | 8G | 2G | 0 | 0 | 10G | 10G | 5G | 0 | 10G | 9G | 5G |
| Soybean | 10G | 9G | 7G | 3G | 10G | 9G | 6 | 3G | 10G | 9G | 7G |
| Cotton | 10G | 9G | 9G | 3G | 10G | 10G | 9G | 2G | 10G | 9G | 5G |
| Sugar beet | 10G | 10G | 9G | 6G | 10G | 10G | 10G | 9G | 10G | 9G | 8G |
| Crabgrass | 7G | 4G | 0 | 0 | 7G | 3G | 0 | 0 | 7G | 6G | 2G |
| Johnsongrass | 10G | 9G | 8G | 3G | 10G | 9G | 8G | 2G | 10G | 8G | 2G |
| Blackgrass | 10G | 10G | 8G | 10G | 10G | 8G | 5G | 10G | 8G | 6G | |
| Barnyardgrass | 2G | 0 | 0 | 0 | 8G | 6G | 4G | 0 | 9G | 7G | 3G |
| Nutsedge | 7G | 3G | 0 | 0 | 8G | 6G | 3G | 0 | 6G | 0 | 0 |
| Giant Foxtail | 2G | 0 | 0 | 0 | 6G | 0 | 0 | 0 | 4G | 0 | 0 |
| Wild Oats | 0 | 0 | 0 | 0 | 10G | 9G | 4G | 0 | 9G | 8G | 0 |
| Cocklebur | 10G | 9G | 9G | 7G | 10G | 10G | 9G | 7G | 10G | 9G | 8G |
| Morningglory | 10G | 9G | 8G | 4G | 10G | 10G | 9G | 7G | 10G | 8G | 4G |
| Teaweed | 9G | 8G | 3G | 0 | 9G | 4G | 0 | 0 | 9G | 8G | 2G |
| Sicklepod | 10G | 9G | 5G | 0 | 10G | 9G | 8G | 2G | 9G | 8G | 3G |
| Jimsonweed | 10G | 8G | 6G | 2G | 10G | 10G | 9G | 3G | 9G | 9G | 3G |
| Velvetleaf | 10G | 10G | 8G | 5G | 10G | 9G | 9G | 5G | 9G | 8G | 7G |
| Rate g/ha | 250 | 62 | 16 | | 250 | 62 | 16 | 4 | 250 | 62 | 16 | 4 |
| PREEMERGENCE | | | | | | | | | | | |
| Corn | 6G | 3G | 0 | | 9 | 7G | 6G | 2G | 9G | 6G | 2G | 0 |
| Wheat | 5G | 0 | 0 | | 10G | 9G | 2G | 0 | 8G | 7G | 2G | 0 |
| Rice | 9G | 8G | 7G | | 10E | 10E | 10G | 9G | 10E | 10E | 9G | 7G |
| Soybean | 7G | 2G | 0 | | 10G | 9G | 8G | 2G | 9G | 7G | 5G | 3G |
| Cotton | 8G | 3G | 0 | | 10G | 8G | 3G | 0 | 10G | 9G | 6G | 3G |
| Sugar beet | 9G | 8G | 3G | | 10G | 10G | 10G | 7G | 10G | 9G | 9G | 7G |
| Crabgrass | 7G | 3G | 0 | | 8G | 3G | 0 | 0 | 6G | 0 | 0 | 0 |
| Johnsongrass | 9G | 9G | 5G | | 10G | 9G | 8G | 4G | 9G | 8G | 6G | 3G |
| Blackgrass | 9G | 9G | 8G | | 10E | 10G | 10G | 9G | 10G | 10G | 9G | 8G |
| Barnyardgrass | 6G | 2G | 0 | | 8G | 7G | 5G | 0 | 10G | 8G | 5G | 3G |
| Nutsedge | 8G | 2G | 0 | | 9G | 8G | 3G | 0 | 10G | 8G | 3G | 0 |
| Giant Foxtail | 9G | 4G | 0 | | 10G | 9G | 7G | 2G | 9G | 7G | 4G | 0 |
| Wild Oats | 7G | 2G | 0 | | 10G | 9G | 9G | 7G | 10G | 9G | 9G | 3G |
| Cocklebur | 8G | 4G | 2G | | 9G | 9G | 7G | 5G | 9G | 8G | 7G | 3G |
| Morningglory | 9G | 6G | 2G | | 10G | 9G | 6G | 3G | 9G | 9G | 5G | 2G |
| Teaweed | 9G | 8G | 2G | | 9G | 9G | 8G | 3G | 9G | 9G | 6G | 2G |
| SicklePod | 9G | 7G | 2G | | 10G | 9G | 7G | 2G | 10G | 9G | 3G | 0 |
| Jimsonweed | 9G | 4G | 0 | | 10G | 9G | 9G | 5G | 10G | 9G | 8G | 3G |
| Velvetleaf | 10G | 9G | 7G | | 10G | 10G | 9G | 5G | 10G | 10G | 9G | 5G |

| | Compound 4 | | | | Compound 6 | | | Compound 7 | | | |
|---|---|---|---|---|---|---|---|---|---|---|---|
| Rate g/ha | 62 | 16 | 4 | 1 | 62 | 16 | 4 | 62 | 16 | 4 | 1 |
| POSTEMERGENCE | | | | | | | | | | | |

TABLE 2-continued

| | | | | | | | | | | | |
|---|---|---|---|---|---|---|---|---|---|---|---|
| Corn | 8G | 5G | 0 | 0 | 2G | 0 | 0 | 2G | 0 | 0 | 0 |
| Wheat | 7G | 3G | 0 | 0 | 0 | 0 | 0 | 2G | 0 | 0 | 0 |
| Rice | 10G | 9G | 6G | 0 | 8G | 2G | 0 | 9G | 5G | 2G | 0 |
| Soybean | 10G | 10G | 7G | 3G | 7G | 4G | 2G | 10C | 9G | 8G | 4G |
| Cotton | 9G | 8G | 3G | 0 | 9G | 5G | 3G | 10C | 8G | 5G | 0 |
| Sugar beet | 10G | 10G | 8G | 6G | 10G | 10G | 6G | 10C | 10C | 10C | 7C |
| Crabgrass | 9G | 8G | 6G | 0 | 7G | 3G | 0 | 0 | 0 | 0 | 0 |
| Johnsongrass | 10G | 10G | 8G | 3G | 9G | 7G | 2G | 8G | 5G | 4G | 0 |
| Blackgrass | 10G | 10G | 8G | 7G | 10G | 9G | 6G | 10C | 8C | 5G | 0 |
| Barnyardgrass | 10G | 9G | 5G | 4G | 7G | 3G | 0 | 3G | 0 | 0 | 0 |
| Nutsedge | 9G | 7G | 3G | 0 | 0 | 0 | 0 | 0 | 0 | 0 | 0 |
| Giant Foxtail | 9G | 8G | 2G | 0 | 6G | 0 | 0 | 0 | 0 | 0 | 0 |
| Wild Oats | 9G | 8G | 0 | 0 | 0 | 0 | 0 | 5G | 3G | 0 | 0 |
| Cocklebur | 10G | 10G | 9G | 4G | 10G | 9G | 6G | 10G | 10G | 9G | 7G |
| Morningglory | 9G | 5G | 0 | 0 | 10G | 9G | 4G | 10C | 10C | 10G | 7G |
| Teaweed | 9G | 9G | 7G | 2G | 8G | 6G | 2G | 8G | 8G | 3G | 0 |
| SicklePod | 9G | 9G | 9G | 5G | 9G | 9G | 2G | 10C | 10G | 5G | 0 |
| Jimsonweed | 10G | 9G | 6G | 3G | 10G | 8G | 3G | 10G | 10G | 5G | 0 |
| Velvetleaf | 10G | 9G | 9G | 5G | 10G | 9G | 6G | 7G | 3G | 0 | 0 |
| Rate g/ha | 250 | 62 | 16 | 4 | 62 | 16 | | 250 | 62 | 16 | 4 |
| PREEMERGENCE | | | | | | | | | | | |
| Corn | 10G | 7G | 2G | 0 | 2G | 0 | | 2G | 0 | 0 | 0 |
| Wheat | 9G | 7G | 2G | 0 | 0 | 0 | | 4G | 2G | 0 | 0 |
| Rice | 10E | 9G | 9G | 6G | 9G | 7G | | 10E | 9G | 9G | 4G |
| Soybean | 10G | 8G | 5G | 2G | 0 | 0 | | 10G | 6G | 2C | 0 |
| Cotton | 9G | 9G | 8G | 0 | 4G | 0 | | 10G | 9G | 4G | 0 |
| Sugar beet | 10G | 9G | 7G | 2G | 7G | 2G | | 10G | 9G | 8G | 4G |
| Crabgrass | 9G | 8G | 5G | 0 | 0 | 0 | | 0 | 0 | 0 | 0 |
| Johnsongrass | 9G | 9G | 9G | 7G | 7G | 3G | | 7G | 4G | 0 | 0 |
| Blackgrass | 10G | 9G | 9G | 7G | 10G | 9G | | 10G | 9G | 7G | 3G |
| Barnyardgrass | 9G | 9G | 8G | 4G | 0 | 0 | | 2G | 0 | 0 | 0 |
| Nutsedge | 9G | 8G | 6G | 0 | 8G | 5G | | 3G | 0 | 0 | 0 |
| Giant Foxtail | 10E | 10E | 9G | 3G | 0 | 0 | | 0 | 0 | 0 | 0 |
| Wild Oats | 9G | 9G | 8G | 6G | 4G | 0 | | 8G | 7G | 3G | 0 |
| Cocklebur | 9G | 9G | 7G | 0 | 5G | 2G | | 10G | 9G | 8G | 4G |
| Morninglory | 9G | 8G | 6G | 0 | 7G | 2G | | 9G | 8G | 4G | 0 |
| Teaweed | 9G | 9G | 6G | 0 | 6G | 3G | | 10G | 9G | 5G | 0 |
| Sicklepod | 9G | 9G | 6G | 0 | 2G | 0 | | 10E | 9G | 5G | 0 |
| Jimsonweed | 9G | BG | 5G | 2G | 7G | 3G | | 10G | 8G | 4G | 0 |
| Velvetleaf | 10G | 9G | 7G | 5G | 8G | 6G | | 7G | 4G | 0 | 0 |

| | Compound 11 | | | | |
|---|---|---|---|---|---|
| Rate g/ha | 250 | 62 | 16 | 4 | 1 |
| POSTEMERGENCE | | | | | |
| Corn | 100 | 100 | 100 | 90 | 60 |
| Wheat | 100 | 100 | 90 | 50 | 0 |
| Rice | 100 | 100 | 100 | 90 | 60 |
| Soybean | 100 | 100 | 100 | 90 | 80 |
| Cotton | 100 | 70 | 20 | 0 | 0 |
| Sugar beet | 100 | 100 | 100 | 100 | 90 |
| Rape | 100 | 100 | 100 | 100 | 80 |
| Crabgrass | 100 | 90 | 70 | 20 | 0 |
| Johnsongrass | 100 | 100 | 100 | 90 | 80 |
| Blackgrass | 100 | 100 | 100 | 100 | 90 |
| Barnyardgrass | 100 | 100 | 100 | 80 | 0 |
| Nutsedge | 100 | 100 | 100 | 90 | 50 |
| Giant Foxtail | 100 | 100 | 100 | 70 | 0 |
| Wild Oats | 100 | 100 | 90 | 70 | 20 |
| Cocklebur | 100 | 100 | 90 | 60 | 20 |
| Morningglory | 100 | 100 | 100 | 100 | 90 |
| Teaweed | 100 | 70 | 20 | 0 | 0 |
| Sicklepod | 100 | 100 | 100 | 70 | 20 |
| Jimsonweed | 100 | 100 | 100 | 90 | 60 |
| Velvetleaf | 100 | 100 | 90 | 90 | 30 |
| Rate g/ha | | 62 | 16 | 4 | |
| PREEMERGENCE | | | | | |
| Corn | | 100 | 100 | 30 | |
| Wheat | | 100 | 90 | 30 | |
| Rice | | 100 | 100 | 90 | |
| Soybean | | 95 | 70 | 40 | |
| Cotton | | 40 | 20 | 0 | |
| Sugar beet | | 100 | 100 | 80 | |
| Rape | | 100 | 100 | 90 | |
| Crabgrass | | 100 | 90 | 50 | |
| Johnsongrass | | 100 | 100 | 90 | |
| Blackgrass | | 100 | 100 | 90 | |
| Barnyardgrass | | 100 | 100 | 70 | |
| Nutsedge | | 100 | 100 | 70 | |
| Giant Foxtail | | 100 | 100 | 90 | |

TABLE 2-continued

|  |  |  |  |
|---|---|---|---|
| Wild Oats | 100 | 90 | 40 |
| Cocklebur | 95 | 90 | 20 |
| Morningglory | 90 | 80 | 30 |
| Teaweed | 90 | 60 | 30 |
| Sicklepod | 90 | 60 | 30 |
| Jimsonweed | 100 | 100 | 30 |
| Velvetleaf | 100 | 60 | 30 |

TABLE 2

|  | Compound 1 | | | | Compound 2 | | | | Compound 3 | | | |
|---|---|---|---|---|---|---|---|---|---|---|---|---|
| Rate g/ha | 62 | 16 | 4 | 1 | 62 | 16 | 4 | 1 | 62 | 16 | 4 | |
| POSTEMERGENCE | | | | | | | | | | | | |
| Corn | 8G | 2G | 0 | 0 | 7G | 4G | 2G | 0 | 8G | 2G | 0 | |
| Wheat | 0 | 0 | 0 | 0 | 9G | 5G | 0 | 0 | 5G | 0 | 0 | |
| Rice | 8G | 2G | 0 | 0 | 10G | 10G | 5G | 0 | 10G | 9G | 5G | |
| Soybean | 10G | 9G | 7G | 3G | 10G | 9G | 6 | 3G | 10G | 9G | 7G | |
| Cotton | 10G | 9G | 9G | 3G | 10G | 10G | 9G | 2G | 10G | 9G | 5G | |
| Sugar beet | 10G | 10G | 9G | 6G | 10G | 10G | 10G | 9G | 10G | 9G | 8G | |
| Crabgrass | 7G | 4G | 0 | 0 | 7G | 3G | 0 | 0 | 7G | 6G | 2G | |
| Johnsongrass | 10G | 9G | 8G | 3G | 10G | 9G | 8G | 2G | 10G | 8G | 2G | |
| Blackgrass | 10G | 10G | 8G | 10G | 10G | 8G | 5G | 10G | 8G | 6G | | |
| Barnyardgrass | 2G | 0 | 0 | 0 | 8G | 6G | 4G | 0 | 9G | 7G | 3G | |
| Nutsedge | 7G | 3G | 0 | 0 | 8G | 6G | 3G | 0 | 6G | 0 | 0 | |
| Giant Foxtail | 2G | 0 | 0 | 0 | 6G | 0 | 0 | 0 | 4G | 0 | 0 | |
| Wild Oats | 0 | 0 | 0 | 0 | 10G | 9G | 4G | 0 | 9G | 8G | 0 | |
| Cocklebur | 10G | 9G | 9G | 7G | 10G | 10G | 9G | 7G | 10G | 9G | 8G | |
| Morningglory | 10G | 9G | 8G | 4G | 10G | 10G | 9G | 7G | 10G | 8G | 4G | |
| Teaweed | 9G | 8G | 3G | 0 | 9G | 4G | 0 | 0 | 9G | 8G | 2G | |
| Sicklepod | 10G | 9G | 5G | 0 | 10G | 9G | 8G | 2G | 9G | 8G | 3G | |
| Jimsonweed | 10G | 8G | 6G | 2G | 10G | 10G | 9G | 3G | 9G | 9G | 3G | |
| Velvetleaf | 10G | 10G | 8G | 5G | 10G | 9G | 9G | 5G | 9G | 8G | 7G | |
| PREEMERGENCE | | | | | | | | | | | | |
| Rate g/ha | 250 | 62 | 16 | | 250 | 62 | 16 | 4 | 250 | 62 | 16 | 4 |
| Corn | 6G | 3G | 0 | | 9 | 7G | 6G | 2G | 9G | 6G | 2G | 0 |
| Wheat | 5G | 0 | 0 | | 10G | 9G | 2G | 0 | 8G | 7G | 2G | 0 |
| Rice | 9G | 8G | 7G | | 10E | 10G | 10G | 9G | 10E | 10G | 9G | 7G |
| Soybean | 7G | 2G | 0 | | 10G | 9G | 8G | 2G | 9G | 7G | 5G | 3G |
| Cotton | 8G | 3G | 0 | | 10G | 8G | 3G | 0 | 10G | 9G | 6G | 3G |
| Sugar beet | 9G | 8G | 3G | | 10G | 10G | 10G | 7G | 10G | 9G | 9G | 7G |
| Crabgrass | 7G | 3G | 0 | | 8G | 3G | 0 | 0 | 6G | 0 | 0 | 0 |
| Johnsongrass | 9G | 9G | 5G | | 10G | 9G | 8G | 4G | 9G | 8G | 6G | 3G |
| Blackgrass | 9G | 9G | 8G | | 10E | 10G | 10G | 9G | 10G | 10G | 9G | 8G |
| Barnyardgrass | 6G | 2G | 0 | | 8G | 7G | 5G | 0 | 10G | 8G | 5G | 3G |
| Nutsedge | 8G | 2G | 0 | | 9G | 8G | 3G | 0 | 10G | 8G | 3G | 0 |
| Giant Foxtail | 9G | 4G | 0 | | 10G | 9G | 7G | 2G | 9G | 7G | 4G | 0 |
| Wild Oats | 7G | 2G | 0 | | 10G | 9G | 9G | 7G | 10G | 9G | 9G | 3G |
| Cocklebur | 8G | 4G | 2G | | 9G | 9G | 7G | 5G | 9G | 8G | 7G | 3G |
| Morningglory | 9G | 6G | 2G | | 10G | 9G | 6G | 3G | 9G | 9G | 5G | 2G |
| Teaweed | 9G | 8G | 2G | | 9G | 9G | 8G | 3G | 9G | 9G | 6G | 2G |
| SicklePod | 9G | 7G | 2G | | 10G | 9G | 7G | 2G | 10G | 9G | 3G | 0 |
| Jimsonweed | 9G | 4G | 0 | | 10G | 9G | 9G | 5G | 10G | 9G | 8G | 3G |
| Velvetleaf | 10G | 9G | 7G | | 10G | 10G | 9G | 5G | 10G | 10G | 9G | 5G |

|  | Compound 4 | | | | Compound 6 | | | Compound 7 | | | |
|---|---|---|---|---|---|---|---|---|---|---|---|
| Rate g/ha | 62 | 16 | 4 | 1 | 62 | 16 | 4 | 62 | 16 | 4 | 1 |
| POSTEMERGENCE | | | | | | | | | | | |
| Corn | 8G | 5G | 0 | 0 | 2G | 0 | 0 | 2G | 0 | 0 | 0 |
| Wheat | 7G | 3G | 0 | 0 | 0 | 0 | 0 | 2G | 0 | 0 | 0 |
| Rice | 10G | 9G | 6G | 0 | 8G | 2G | 0 | 9G | 5G | 2G | 0 |
| Soybean | 10G | 10G | 7G | 3G | 7G | 4G | 2G | 10C | 9G | 8G | 4G |
| Cotton | 9G | 8G | 3G | 0 | 9G | 5G | 3G | 10C | 8G | 5G | 0 |
| Sugar beet | 10G | 10G | 8G | 6G | 10G | 10G | 6G | 10C | 10C | 10C | 7C |
| Crabgrass | 9G | 8G | 6G | 0 | 7G | 3G | 0 | 0 | 0 | 0 | 0 |
| Johnsongrass | 10G | 10G | 8G | 3G | 9G | 7G | 2G | 8G | 5G | 4G | 0 |
| Blackgrass | 10G | 10G | 8G | 7G | 10G | 9G | 6G | 10C | 8C | 5G | 0 |
| Barnyardgrass | 10G | 9G | 5G | 4G | 7G | 3G | 0 | 3G | 0 | 0 | 0 |
| Nutsedge | 9G | 7G | 3G | 0 | 0 | 0 | 0 | 0 | 0 | 0 | 0 |
| Giant Foxtail | 9G | 8G | 2G | 0 | 6G | 0 | 0 | 0 | 0 | 0 | 0 |
| Wild Oats | 9G | 8G | 0 | 0 | 0 | 0 | 0 | 5G | 3G | 0 | 0 |
| Cocklebur | 10G | 10G | 9G | 4G | 10G | 9G | 6G | 10G | 10G | 9G | 7G |
| Morningglory | 9G | 5G | 0 | 0 | 10G | 9G | 4G | 10C | 10C | 10G | 7G |
| Teaweed | 9G | 9G | 7G | 2G | 8G | 6G | 2G | 8G | 8G | 3G | 0 |
| SicklePod | 9G | 9G | 9G | 5G | 9G | 9G | 2G | 10C | 10G | 5G | 0 |
| Jimsonweed | 10G | 9G | 6G | 3G | 10G | 8G | 3G | 10G | 10G | 5G | 0 |
| Velvetleaf | 10G | 9G | 9G | 5G | 10G | 9G | 6G | 7G | 3G | 0 | 0 |
| PREEMERGENCE | | | | | | | | | | | |
| Rate g/ha | 250 | 62 | 16 | 4 | 62 | 16 | | 250 | 62 | 16 | 4 |
| Corn | 10G | 7G | 2G | 0 | 2G | 0 | | 2G | 0 | 0 | 0 |

TABLE 2-continued

| | | | | | | | | | | |
|---|---|---|---|---|---|---|---|---|---|---|
| Wheat | 9G | 7G | 2G | 0 | 0 | 0 | 4G | 2G | 0 | 0 |
| Rice | 10E | 9G | 9G | 6G | 9G | 7G | 10E | 9G | 9G | 4G |
| Soybean | 10G | 8G | 5G | 2G | 0 | 0 | 10G | 6G | 2C | 0 |
| Cotton | 9G | 9G | 8G | 0 | 4G | 0 | 10G | 9G | 4G | 0 |
| Sugar beet | 10G | 9G | 7G | 2G | 7G | 2G | 10G | 9G | 8G | 4G |
| Crabgrass | 9G | 8G | 5G | 0 | 0 | 0 | 0 | 0 | 0 | 0 |
| Johnsongrass | 9G | 9G | 9G | 7G | 7G | 3G | 7G | 4G | 0 | 0 |
| Blackgrass | 10G | 9G | 9G | 7G | 10G | 9G | 10G | 9G | 7G | 3G |
| Barnyardgrass | 9G | 9G | 8G | 4G | 0 | 0 | 2G | 0 | 0 | 0 |
| Nutsedge | 9G | 8G | 6G | 0 | 8G | 5G | 3G | 0 | 0 | 0 |
| Giant Foxtail | 10E | 10E | 9G | 3G | 0 | 0 | 0 | 0 | 0 | 0 |
| Wild Oats | 9G | 9G | 8G | 6G | 4G | 0 | 8G | 7G | 3G | 0 |
| Cocklebur | 9G | 9G | 7G | 0 | 5G | 2G | 10G | 9G | 8G | 4G |
| Morninglory | 9G | 8G | 6G | 0 | 7G | 2G | 9G | 8G | 4G | 0 |
| Teaweed | 9G | 9G | 6G | 0 | 6G | 3G | 10G | 9G | 5G | 0 |
| Sicklepod | 9G | 9G | 6G | 0 | 2G | 0 | 10E | 9G | 5G | 0 |
| Jimsonweed | 9G | BG | 5G | 2G | 7G | 3G | 10G | 8G | 4G | 0 |
| Velvetleaf | 10G | 9G | 7G | 5G | 8G | 6G | 7G | 4G | 0 | 0 |

| | Compound 11 | | | | |
|---|---|---|---|---|---|
| Rate g/ha | 250 | 62 | 16 | 4 | 1 |
| POSTEMERGEMCE | | | | | |
| Corn | 100 | 100 | 100 | 90 | 60 |
| Wheat | 100 | 100 | 90 | 50 | 0 |
| Rice | 100 | 100 | 100 | 90 | 60 |
| Soybean | 100 | 100 | 100 | 90 | 80 |
| Cotton | 100 | 70 | 20 | 0 | 0 |
| Sugar beet | 100 | 100 | 100 | 100 | 90 |
| Rape | 100 | 100 | 100 | 100 | 80 |
| Crabgrass | 100 | 90 | 70 | 20 | 0 |
| Johnsongrass | 100 | 100 | 100 | 90 | 80 |
| Blackgrass | 100 | 100 | 100 | 100 | 90 |
| Barnyardgrass | 100 | 100 | 100 | 80 | 0 |
| Nutsedge | 100 | 100 | 100 | 90 | 50 |
| Giant Foxtail | 100 | 100 | 100 | 70 | 0 |
| Wild Oats | 100 | 100 | 90 | 70 | 20 |
| Cocklebur | 100 | 100 | 90 | 60 | 20 |
| Morningglory | 100 | 100 | 100 | 100 | 90 |
| Teaweed | 100 | 70 | 20 | 0 | 0 |
| Sicklepod | 100 | 100 | 100 | 70 | 20 |
| Jimsonweed | 100 | 100 | 100 | 90 | 60 |
| Velvetleaf | 100 | 100 | 90 | 90 | 30 |
| PREEMERGENCE | | | | | |
| Rate g/ha | 62 | 16 | 4 | | |
| Corn | 100 | 100 | 30 | | |
| Wheat | 100 | 90 | 30 | | |
| Rice | 100 | 100 | 90 | | |
| Soybean | 95 | 70 | 40 | | |
| Cotton | 40 | 20 | 0 | | |
| Sugar beet | 100 | 100 | 80 | | |
| Rape | 100 | 100 | 90 | | |
| Crabgrass | 100 | 90 | 50 | | |
| Johnsongrass | 100 | 100 | 90 | | |
| Blackgrass | 100 | 100 | 90 | | |
| Barnyardgrass | 100 | 100 | 70 | | |
| Nutsedge | 100 | 100 | 70 | | |
| Giant Foxtail | 100 | 100 | 90 | | |
| Wild Oats | 100 | 90 | 40 | | |
| Cocklebur | 95 | 90 | 20 | | |
| Morningglory | 90 | 80 | 30 | | |
| Teaweed | 90 | 60 | 30 | | |
| Sicklepod | 90 | 60 | 30 | | |
| Jimsonweed | 100 | 100 | 30 | | |
| Velvetleaf | 100 | 60 | 30 | | |

What is claimed is:

1. A compound of the structural formula:

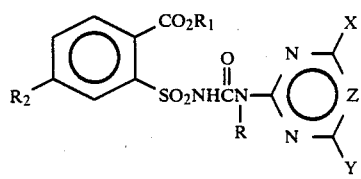

wherein

R is H or CH₃;

R₁ is C₁-C₃ alkyl, C₃-C₄ alkoxyalkyl, C₂-C₄ haloalkyl, C₃-C₄ alkenyl, C₃-C₄ alkynyl, C₄-C₆ cycloalkylalkyl or C₄-C₅ cycloalkyl;

R₂ is C₂-C₆ alkoxy, C₃-C₆ cycloalkoxy, C₄-C₆ cycloalkylalkoxy, OCF₂H, C₂-C₆ haloalkoxy, C₂-C₆ alkenyloxy, C₂-C₆ haloalkenyloxy, C₃-C₆ alkynyloxy, C₃-C₆ haloalkynyloxy, C₂-C₄ alkoxyalkoxy, C₂-C₄ haloalkoxyalkoxy, C₂-C₄ alkylthioalkoxy, C₂C₄ haloalkylthioalkoxy, C₂-C₄ alkylsulfinylalkoxy, C₂-C₄ haloalkylsulfinylalkoxy, C₂-C₄ alkylsulfonylalkoxy, C₂-C₄ haloalkylsulfonylalkoxy, C₂-C₄ cyanoalkoxy, OCH₂C(O)CH₃, OCH$_2$CH$_2$C(O)CH$_3$, C$_2$–C$_4$ aminoalkoxy, C$_2$–C$_8$ alkylthio, C$_3$–C$_6$ cycloalkylthio, C$_4$–C$_6$ cycloalkylalkythio, SCF$_2$H, C$_2$–C$_8$ haloalkylthio, C$_2$–C$_6$ alkenylthio, C$_2$–C$_6$ haloalkenylthio, C$_3$–C$_6$ alkynylthio, C$_3$–C$_6$ haloalkynylthio, C$_2$–C$_4$ alkoxyalkylthio, C$_2$–C$_4$ haloalkoxyalkylthio, C$_2$–C$_4$ alkylthioalkylthio, C$_2$–C$_4$ haloalkythioalkylthio, C$_2$–C$_4$ cyanoalkylthio, SCH$_2$C(O)CH$_3$, SCH$_2$CH$_2$C(O)CH$_3$, C$_2$–C$_4$ aminoalkylthio, SC$_6$H$_5$, SCH$_2$C$_6$H$_5$, C$_1$–C$_8$ alkylsulfinyl, C$_3$–C$_6$ cycloalkylsulfinyl, sulfinyl, C$_4$–C$_6$ cycloalkylalkylsulfinyl, C$_1$–C$_8$ haloalkylsulfinyl, C$_2$–C$_6$ alkenylsulfinyl, C$_2$–C$_6$ haloalkenylsulfinyl, C$_3$–C$_6$ alkynylsulfinyl, C$_3$–C$_6$ haloalkynylsulfinyl, C$_2$–C$_4$ alkoxyalkylsulfinyl, C$_2$–C$_4$ haloalkoxyalkylsulfinyl, C$_2$–C$_4$ cyanoalkylsulfinyl, S(O)CH$_2$C(O)CH$_3$, S(O)CH$_2$CH$_2$C(O)CH$_3$, C$_2$–C$_4$ aminoalkylsulfinyl, C$_3$–C$_6$ cycloalkylsulfonyl, C$_4$C$_6$ cycloalkylalkylsulfonyl, C$_1$–C$_8$ haloalkylsulfonyl, C$_2$–C$_6$ alkenylsulfonyl, C$_2$C$_6$ haloalkenylsulfonyl, C$_3$–C$_6$ alkynylsulfonyl, C$_3$–C$_6$ haloalkynylsulfonyl, C$_2$–C$_4$ alkoxyalklsulfonyl, C$_2$–C$_4$ haloalkoxyalkylsulfonyl, C$_2$–C$_4$ cyanoalkylsulfonyl, SO$_2$CH$_2$C(O)CH$_3$, SO$_2$CH$_2$CH$_2$C(O)CH$_3$, C$_2$–C$_4$ aminoalkylsulfonyl, CH$_2$F, CH$_2$, CH$_2$Cl, CHCl$_2$, CH$_2$Br, CHBr$_2$, C$_2$–C$_6$ substituted with 1–3 atoms of F, Cl or Br, C$_2$–C$_6$ alkenyl, C$_2$–C$_6$ haloalkenyl, C$_2$–C$_6$ haloalkynyl, OC(O)C$_1$–C$_4$ alkyl, CH$_2$C(O)NR$_a$R$_b$, NHC$_3$, NR$_b$R$_c$ or C$_1$–C$_4$ alkyl substituted with C$_1$–C$_4$ alkoxy, C$_3$–C$_4$ cycloalkoxy, cyclopropylmethoxy, C$_1$–C$_4$ haloalkoxy, C$_2$–C$_4$ alkenyloxy, C$_2$–C$_4$ haloalkenyloxy, C$_3$–C$_4$ alkynyloxy, C$_3$–C$_4$ haloalkynyloxy, C$_2$–C$_4$ alkoxyalkoxy, C$_2$–C$_4$ aminoalkoxy, C$_1$–C$_4$ alkylcarbonyloxy, C$_1$–C$_4$ haloalkylcarbonyloxy, C$_1$–C$_4$ carbamoyloxy, C$_1$C$_4$ alkoxycarbonyloxy, OH, OP(O)(OC$_1$–C$_2$ alkyl)$_2$, C$_1$–C$_4$ alkylsulfonyloxy, C$_1$–C$_2$ haloalkylsulfonyloxy, OSi(CH$_3$)$_3$, OSi(CH$_3$)$_2$C(CH$_3$)$_3$, C$_1$–C$_4$ alkylthio, C$_3$–C$_4$ cycloalkylthio, cyclopropylmethylthio, C$_1$–C$_4$ haloalkylthio, C$_2$–C$_4$ alkenylthio, C$_2$–C$_4$ haloalkenylthio, C$_3$–C$_4$ alkynylthio, C$_3$–C$_4$ haloalkynylthio, C$_2$–C$_4$ alkoxyalkylthio, C$_2$–C$_4$ aminoalkylthio, SH, SP(O)(OC$_1$–C$_2$ alkyl)$_2$, C$_1$–C$_4$ alkylsulfinyl, C$_3$–C$_4$ cycloalkylsulfonyl, cyclopropylmethylsulfinyl, C$_1$–C$_4$ haloalkylsulfinyl, C$_2$–C$_4$ alkenylsulfinyl, C$_2$–C$_4$ haloalkenylsulfinyl, C$_3$–C$_4$ alkynylsulfinyl, C$_3$–C$_4$ haloalkynylsulfinyl, C$_2$–C$_4$ alkoxyalkylsulfinyl, C$_2$–C$_4$ aminoalkylsulfinyl, C$_1$–C$_4$ alkylsulfonyl, C$_3$–C$_4$ cycloalkylsulfonyl, cyclopropylmethylsulfonyl, C$_1$–C$_4$ haloalkylsulfonyl, C$_2$–C$_4$ alkenylsulfonyl, C$_2$–C$_4$ haloalkenylsulfonyl, C$_3$–C$_4$ alkynylsulfonyl, C$_3$–C$_4$ haloalkynylsulfonyl, C$_2$–C$_4$ alkoxyalkylsulfonyl or C$_2$–C$_4$ aminoalkylsulfonyl;

R$_a$ and R$_b$ are independently H or C$_1$–C$_3$ alkyl;
R$_c$ is C$_2$–C$_4$ alkyl or cyclopropylmethyl;
X is CH$_3$, or OC$_2$H$_5$;
Y is C$_1$–C$_2$ alkyl, C$_1$–C$_2$ alkoxy, OCH$_2$CH$_2$F, OCH$_2$CHF$_2$, OCH$_2$CF$_3$, NHCH$_3$ or N(CH$_3$)$_2$; and
Z is N; and
their agriculturally suitable salts; provided that
(1) when R$_2$ is OCH$_2$CF$_3$ and R$_1$ is CH$_3$ or CH$_2$CH$_3$, then X and Y cannot simultaneously be OCH$_3$.

2. The compounds of claim 1 wherein R$_1$ is C$_1$–C$_3$ alkyl, C$_3$–C$_4$ alkoxyalkyl, C$_2$–C$_4$ haloalkyl, C$_3$–C$_4$ alkenyl or C$_3$–C$_4$ alkynyl.

3. Compounds of claim 1 wherein

R$_2$ is C$_2$–C$_6$ alkoxy, C$_2$–C$_8$ alkylthio, C$_1$–C$_8$ alkylsulfinyl, C$_2$–C$_8$ alkylsulfonyl, C$_3$–C$_6$ alkenyloxy, C$_3$–C$_6$ alkynyloxy, C$_3$–C$_6$ alkenylthio, C$_3$–C$_6$ alkenylsulfinyl, C$_3$–C$_6$ alkenylsulfonyl, C$_3$–C$_6$ alkynylthio, C$_3$–C$_6$ alkynylsulfinyl, C$_3$–C$_6$ alkynylsulfonyl, OCH$_2$CH$_2$OCH$_3$, OCH$_2$CH$_2$SCH$_3$, OCH$_2$CH$_2$S(O)CH$_3$, OCH$_2$CH$_2$SO$_2$CH$_3$, C$_2$–C$_6$ alkyl substituted with 1–3 atoms of F, Cl or Br, CH$_2$F, CHF$_2$, C$_1$–C$_4$ alkyl substituted with C$_1$–C$_2$ alkoxy, C$_1$–C$_2$ alkylthio, C$_1$–C$_2$ alkylsulfinyl or C$_1$–C$_2$ alkylsulfonyl, OCF$_2$H, OCH$_2$CH$_2$F, OCH$_2$CHF$_2$, OCH$_2$CF$_3$, OCH$_2$CH$_2$Cl, S-cyclohexyl, SC$_6$H$_5$ or SCH$_2$C$_6$H$_5$.

4. Compounds of claim 3 where
R$_2$ is C$_3$–C$_6$ alkenyloxy C$_3$–C$_6$ alkynyloxy, C$_3$–C$_6$ alkenylthio C$_3$–C$_6$ alkenylsulfinyl, C$_3$–C$_6$ alkenylsulfonyl C$_3$–C$_6$ alkynylthio, C$_3$–C$_6$ alkynylsulfinyl, C$_3$–C$_6$ alkynylsulfonyl, C$_2$–C$_6$ alkyl substituted with 1–3 atoms of F, Cl or Br, CH$_2$F, CHF$_2$, C$_1$–C$_4$ alkyl substituted in a nonbenzylic position with C$_1$–C$_2$ alkoxy, C$_1$–C$_2$ alkylthio, C$_1$–C$_2$ alkylsulfinyl or C$_1$–C$_2$ alkylsulfonyl, OCH$_2$CH$_2$OCH$_3$, OCH$_2$CH$_2$SCH$_3$, OCH$_2$CH$_2$S(O)CH$_3$, OCH$_2$CH$_2$SO$_2$CH$_3$, OCF$_2$H, OCH$_2$CH$_2$F, OCH$_2$CHF$_2$, OCH$_2$CF$_3$, OCH$_2$CH$_2$Cl, S-cyclohexyl, SC$_6$H$_5$ or SCH$_2$C$_6$H$_5$.

5. Compounds of claim 4 wherein R is H.

6. Compounds of claim 5 wherein
R$_2$ is C$_3$–C$_4$ alkenyloxy, C$_3$–C$_4$ alkenylthio, C$_3$–C$_4$ alkenylsulfinyl, C$_3$–C$_4$ alkenylsulfonyl, C$_2$–C$_3$ alkyl substituted with 1–3 atoms of F or Cl, CH$_2$F, CHF$_2$, OCHF$_2$, OCH$_2$CH$_2$F, OCH$_2$CF$_3$ or OCH$_2$CH$_2$Cl.

7. Compounds of claim 6 wherein
R$_1$ is CH$_3$ or CH$_2$CH$_3$;
X is CH$_3$, OCH$_3$ or Cl; and
Y is CH$_3$, OCH$_3$, C$_2$H$_5$ or OC$_2$H$_5$.

8. Compounds of claim 7 wherein
R$_2$ is allyloxy, allylthio, propargyloxy, propargylthio, CH$_2$F, OCHF$_2$, or OCH$_2$CH$_2$F.

9. Compounds of claim 3 wherein
R$_2$ is C$_2$–C$_6$ alkoxy. C$_2$–C$_8$ alkylthio, C$_2$–C$_8$ alkylsulfonyl, C$_1$–C$_8$ alkylsulfinyl, CH(H, C$_1$–C$_3$ alkyl)OC$_1$–C$_2$ alkyl, CH(H, C$_1$–C$_3$ alkyl) SC$_1$–C$_2$ alkyl, CH(H, C$_1$–C$_3$ alkyl)S(O)C$_1$–C$_2$ alkyl or CH(H, C$_1$–C$_3$ alkyl)SO$_2$C$_1$–C$_2$ alkyl.

10. Compounds of claim 9 wherein R is H.

11. Compounds of claim 10 wherein
R$_2$ is C$_2$–C$_4$ alkoxy, C$_2$–C$_4$ alkylthio, C$_2$–C$_4$ alkylsulfonyl, C$_1$–C$_4$ alkylsulfinyl, CH$_2$OC$_1$–C$_2$ alkyl, CH$_2$SC$_1$–C$_2$ alkyl, CH$_2$S(O)C$_1$–C$_2$ alkyl or CH$_2$SO$_2$C$_1$–C$_2$ alkyl.

12. Compounds of claim 11 wherein
R$_1$ is CH$_3$ or C$_2$H$_5$
X is CH$_3$ or OCH$_3$; and
Y is CH$_3$, OCH$_3$, C$_2$H$_5$ or OC$_2$H$_5$.

13. Compounds of claim 12 wherein
R$_2$ is C$_2$–C$_3$ alkoxy, C$_2$–C$_3$ alkylthio, C$_1$–C$_3$ alkylsulfinyl, CH$_2$OCH$_3$, CH$_2$SCH$_3$, CH$_2$S(O)CH$_3$ or CH$_2$SO$_2$CH$_3$.

14. Compounds of claim 1 wherein
R$_2$ is C$_2$–C$_6$ alkoxy, C$_3$–C$_6$ haloalkynyloxy, C$_2$–C$_8$ alkylthio, C$_7$–C$_8$ haloalkylthio, C$_3$–C$_6$ haloalkynylthio, C$_1$–C$_8$ alkylsulfinyl, C$_7$–C$_8$ haloalkylsulfinyl, C$_3$–C$_6$ haloalkynylsulfinyl, C$_2$–C$_8$ alkylsulfonyl, C$_7$–C$_8$ haloalkylsulfonyl, C$_3$–C$_6$ haloalkynylsulfonyl, C$_2$–C$_6$ alkenyl, CH$_2$C(O)NR$_a$R$_b$, NHCH$_3$, NR$_b$R$_c$, CH$_2$OC$_1$-C$_4$ alkyl, CH(CH$_3$)OC$_1$-C$_4$ alkyl C(CH$_3$)$_2$OC$_1$-C$_4$ alkyl, CH(CH$_2$CH$_3$)OC$_1$-C$_4$ alkyl C(CH$_3$)(CH$_2$CH$_3$)OC$_1$-C$_4$ alkyl, CH(CH$_2$CH$_2$CH$_3$)OC$_1$-C$_4$ alkyl, CH[CH(CH$_3$)$_2$]OC$_1$-C$_4$ alkyl CH$_2$OC$_1$-C$_4$ haloalkyl of at least 3 halogens, CH$_2$(CH$_3$)OC$_1$-C$_4$ haloalkyl of at least 3 halogens, C(CH$_3$)$_2$OC$_1$-C$_4$ haloalkyl of at least 3 halogens, CH(CH$_2$CH$_3$)OC$_1$-C$_4$ haloalkyl of at least 3 halogens, C(CH$_3$)(CH$_2$CH$_3$)OC$_1$-C$_4$ haloalkyl of at least 3 halogens, CH(CH$_2$CH$_2$CH$_3$)OC$_1$-C$_4$ haloalkyl of at least 3 halogens CH[CH(CH$_3$)$_2$]OC$_1$-C$_4$ haloalkyl of at least 3 halogens, CH$_2$CH$_2$OC$_2$-C$_4$ haloalkenyl, CH$_2$CH$_2$CH$_2$OC$_2$-C$_4$ haloalkenyl, CH$_2$CH$_2$CH$_2$Ch$_2$OC$_2$-C$_4$ haloalkenyl, CH(CH$_3$)CH$_2$OC$_2$-C$_4$ haloalkenyl, C(CH$_3$)$_2$CH$_2$OC$_2$-C$_4$ haloalkenyl, CH(CH$_2$CH$_3$)CH$_2$OC$_2$-C$_4$ haloalkenyl, CH$_2$CH(CH$_3$)OC$_2$-C$_4$ haloalkenyl, CH$_2$C(CH$_3$)$_2$OC$_2$-C$_4$ haloalkenyl, CH$_2$CH(CH$_2$CH$_3$)OC$_2$-C$_4$ haloalkenyl, CH(CH$_3$)CH(CH$_3$)OC$_2$-C$_4$ haloalkenyl, CH$_2$CH$_2$OC$_3$-C$_4$ alkynyl, CH$_2$CH$_2$CH$_2$OC$_3$-C$_4$ alkynyl, CH$_2$CH$_2$CH$_2$CH$_2$OC$_3$-C$_4$ alkynyl, CH(CH$_3$)CH$_2$OC$_3$-C$_4$ alkynyl, C(CH$_3$)$_2$CH$_2$OC$_3$-C$_4$ alkynyl, CH(CH$_2$CH$_3$)CH$_2$OC$_3$-C$_4$ alkynyl, CH$_2$CH(CH$_3$)OC$_3$-C$_4$ alkynyl, CH$_2$C(CH$_3$)$_2$OC$_3$-C$_4$ alkynyl, CH$_2$CH(CH$_2$CH$_3$)OC$_3$-C$_4$ alkynyl, CH(CH$_3$)CH(CH$_3$)OC$_3$-C$_4$ alkynyl, CH$_2$CH$_2$OC$_2$-C$_4$ alkoxyalkyl, CH$_2$CH$_2$CH$_2$OC$_2$-C$_4$ alkoxyalkyl, CH$_2$CH$_2$CH$_2$CH$_2$OC$_2$-C$_4$ alkoxyalkyl, CH(CH$_3$)CH$_2$OC$_2$-C$_4$ alkoxyalkyl, C(CH$_3$)$_2$CH$_2$OC$_2$-C$_4$ alkoxyalkyl, CH(CH$_2$CH$_3$)CH$_2$OC$_2$-C$_4$ alkoxyalkyl, CH$_2$CH(CH$_3$)OC$_2$-C$_4$ alkoxyalkyl CH$_2$C(CH$_3$)$_2$OC$_2$-C$_4$ alkoxyalkyl, CH$_2$CH(CH$_2$CH$_3$)OC$_2$-C$_4$ alkoxyalkyl, CH(CH$_3$)CH(CH$_3$)OC$_2$-C$_4$ alkoxyalkyl, CH$_2$OC$_1$-C$_4$ alkylcarbonyl, CH(CH$_3$)OC$_1$-C$_4$ alkylcarbonyl, C(CH$_3$)$_2$OC$_1$-C$_4$ alkylcarbonyl, CH(CH$_2$CH$_3$)OC$_1$-C$_4$ alkylcarbonyl, C(CH$_3$)(CH$_2$CH$_3$)OC$_1$-C$_4$ alkylcarbonyl, CH(CH$_2$CH$_2$CH$_3$)OC$_1$-C$_4$ alkylcarbonyl, CH[CH(CH$_3$)$_2$]OC$_1$-C$_4$ alkylcarbonyl, CH$_2$ OC$_1$-C$_4$ haloalkylcarbonyl, CH(CH$_3$)OC$_1$-C$_4$ haloalkylcarbonyl, C(CH$_3$)$_2$OC$_1$-C$_4$ haloalkylcarbonyl, CH(CH$_2$CH$_3$)OC$_1$-C$_4$ haloalkylcarbonyl, C(CH$_3$)(CH$_2$CH$_3$)OC$_1$-C$_4$ haloalkylcarbonyl, CH(CH$_2$CH$_2$CH$_3$)OC$_1$-C$_4$ haloalkylcarbonyl, CH[CH(CH$_3$)$_2$]OC$_1$-C$_4$ haloalkylcarbonyl, CH$_2$OC$_1$-C$_4$ alkoxycarbonyl, CH(CH$_3$)OC$_1$-C$_4$ alkoxycarbonyl, C(CH$_3$)$_2$OC$_1$-C$_4$ alkoxycarbonyl CH(CH$_2$CH$_3$)OC$_1$-C$_4$ alkoxycarbonyl, C(CH$_3$)(CH$_2$CH$_3$)OC$_1$-C$_4$ alkoxycarbonyl, CH(CH$_2$CH$_2$CH$_3$)OC$_1$-C$_4$ alkoxycarbonyl, CH[CH(CH$_3$)$_2$]OC$_1$-C$_4$ alkoxycarbonyl, CH$_2$OH, CH(CH$_3$)OH, C(CH$_3$)$_2$OH, CH(CH$_2$CH$_3$)OH, C(CH$_3$)(CH$_2$CH$_3$)OH, CH(CH$_2$CH$_2$CH$_3$)OH, CH[CH(CH$_3$)$_2$]OH, CH$_2$OC$_1$-C$_4$ alkylsulfonyl, CH(CH$_3$)OC$_1$-C$_4$ alkylsulfonyl, C(CH$_3$)$_2$OC$_1$-C$_4$ alkylsulfonyl, CH(CH$_2$CH$_3$)OC$_1$-C$_4$ alkylsulfonyl, C(CH$_3$)(CH$_2$CH$_3$)OC$_1$-C$_4$ alkylsulfonyl, CH(CH$_2$CH$_2$CH$_3$)OC$_1$-C$_4$ alkylsulfonyl, CH[CH(CH$_3$)$_2$]OC$_1$-C$_4$ alkylsulfonyl, Ch$_2$OC$_1$-C$_4$ haloalkylsulfonyl, CH(CH$_3$)OC$_1$-C$_4$ haloalkylsulfonyl, C(CH$_3$)$_2$OC$_1$-C$_4$ haloalkylsulfonyl, CH(CH$_2$CH$_3$)OC$_1$-C$_4$ haloalkylsulfonyl, C(CH$_3$)(CH$_2$CH$_3$)OC$_1$-C$_4$ haloalkylsulfonyl, CH(CH$_2$CH$_2$CH$_3$)OC$_1$-C$_4$ haloalkylsulfonyl, CH[CH(CH$_3$)$_2$]OC$_1$-C$_4$ haloalkylsulfonyl, CH$_2$SC$_1$-C$_4$ alkyl, CH(CH$_3$)SC$_1$-C$_4$ alkyl, C(CH$_3$)$_2$SC$_1$-C$_4$ alkyl, CH(CH$_2$CH$_3$)SC$_1$-C$_4$ alkyl, C(CH$_3$)(CH$_2$CH$_3$)SC$_1$-C$_4$ alkyl, CH(CH$_2$CH$_2$CH$_3$)SC$_1$-C$_4$ alkyl, CH[CH(CH$_3$)$_2$]SC$_1$-C$_4$ alkyl, CH$_2$SC$_1$-C$_4$ haloalkyl of at least 3 halogens, CH(CH$_3$)SC$_1$-C$_4$ haloalkyl of at least 3 halogens, C(CH$_3$)$_2$SC$_1$-C$_4$ haloalkyl of at least 3 halogens CH(CH$_2$CH$_3$)SC$_1$-C$_4$ haloalkyl of at least 3 halogens, C(CH$_3$)(CH$_2$CH$_3$)SC$_1$-C$_4$ haloalkyl of at least 3 halogens, CH(CH$_2$CH$_2$CH$_3$)SC$_1$-C$_4$ haloalkyl of at least 3 halogens, CH[CH(CH$_3$)$_2$]SC$_1$-C$_4$ haloalkyl of at least 3 halogens, CH$_2$CH$_2$SC$_2$-C$_4$ haloalkenyl, CH$_2$CH$_2$CH$_2$SC$_2$-C$_4$ haloalkenyl, CH$_2$CH$_2$CH$_2$CH$_2$SC$_2$-C$_4$ haloalkenyl, CH(CH$_3$)CH$_2$SC$_2$-C$_4$ haloalkenyl, C(CH$_3$)$_2$CH$_2$SC$_2$-C$_4$ haloalkenyl, CH(CH$_2$CH$_3$)CH$_2$SC$_2$-C$_4$ haloalkenyl, CH$_2$CH(CH$_3$)SC$_2$-C$_4$ haloalkenyl, CH$_2$C(CH$_3$)$_2$SC$_2$-C$_4$ haloalkenyl, CH$_2$CH(CH$_2$CH$_3$)SC$_2$-C$_4$ haloalkenyl, CH(CH$_3$)CH(CH$_3$)SC$_2$-C$_4$ haloalkenyl, CH$_2$CH$_2$SC$_3$-C$_4$ alkynyl, CH$_2$CH$_2$CH$_2$SC$_3$-C$_4$ alkynyl, CH$_2$CH$_2$CH$_2$Ch$_2$SC$_3$-C$_4$ alkynyl, CH(CH$_3$)CH$_2$SC$_3$-C$_4$ alkynyl, C(CH$_3$)$_2$CH$_2$SC$_3$-C$_4$ alkynyl CH(CH$_2$CH$_3$)CH$_2$SC$_3$-C$_4$ alkynyl. CH$_2$CH(CH$_3$)SC$_3$-C$_4$ alkynyl, CH$_2$C(CH$_3$)$_2$SC$_3$-C$_4$ alkynyl, CH$_2$CH(CH$_2$CH$_3$)SC$_3$-C$_4$ alkynyl, CH(CH$_3$)CH(CH$_3$)SC$_3$-C$_4$ alkynyl, CH$_2$CH$_2$SC$_2$-C$_4$ alkoxyalkyl, CH$_2$CH$_2$CH$_2$SC$_2$-C$_4$ alkoxyalkyl, CH$_2$CH$_2$CH$_2$SC$_2$-C$_4$ alkoxyalkyl, CH(CH$_3$)CH$_2$SC$_2$-C$_4$ alkoxyalkyl, C(CH$_3$)$_2$CH$_2$SC$_2$-C$_4$ alkoxyalkyl, CH(CH$_2$CH$_3$)CH$_2$SC$_2$-C$_4$ alkoxyalkyl, CH$_2$CH(CH$_3$)SC$_2$-C$_4$ alkoxyalkyl, CH$_2$C(CH$_3$)$_2$SC$_2$-C$_4$ alkoxyalkyl, CH$_2$CH(CH$_2$CH$_3$)SC$_2$ ∝ C$_4$ alkoxyalkyl, CH(CH$_3$)CH(CH$_3$)SC$_2$-C$_4$ alkoxyalkyl, CH$_2$S(O)C$_1$-C$_4$ alkyl, CH(CH$_3$)S(O)C$_1$-C$_4$ alkyl, C(CH$_3$)$_2$S(O)C$_1$-C$_4$ alkyl, CH(CH$_2$CH$_3$)S(O)C$_1$-C$_4$ alkyl C(CH$_3$)(CH$_2$CH$_3$)S(O)C$_1$-C$_4$ alkyl, CH(CH$_2$CH$_2$CH$_3$)S(O)C$_1$-C$_4$ alkyl, CH[CH(CH$_3$)$_2$]S(O)C$_1$-C$_4$ alkyl, CH$_2$S(O)C$_1$-C$_4$ alkyl, CH$_2$S(O)C$_1$-C$_4$ alkyl of at least 3 halogens, CH(CH$_3$)S(O)C$_1$-C$_4$ alkyl of at least 3 halogens, C(CH$_3$)$_2$S(O)C$_1$-C$_4$ alkyl of at least 3 halogens, CH(CH$_2$CH$_3$)S(O)C$_1$-C$_4$ alkyl of at least 3 halogens, C(CH$_3$)(CH$_2$CH$_3$S(O)C$_1$-C$_4$ alkyl of at least 3 halogens, CH(CH$_2$CH$_2$CH$_3$)S(O)C$_1$-C$_4$ alkyl of at least 3 halogens, CH[CH(CH$_3$)$_2$]S(O)C$_1$-C$_4$ alkyl of at least 3 halogens, CH$_2$CH$_2$S(O)C$_1$-C$_4$ haloalkyl, CH$_2$CH$_2$CH$_2$S(O)C$_1$-C$_4$ haloalkyl, CH$_2$CH(CH$_3$)S(O)C$_1$-C$_4$ haloalkyl, CH$_2$C(CH$_3$)$_2$S(O)C$_1$-C$_4$ haloalkyl, CH$_2$CH$_2$CH$_2$CH$_2$S(O)C$_1$-C$_4$ haloalkyl, CH(CH$_3$)CH$_2$S(O)C$_1$-C$_4$ haloalkyl, C(CH$_3$)$_2$CH$_2$S(O)C$_1$-C$_4$ haloalkyl, CH(CH$_2$CH$_3$)CH$_2$S(O)C$_1$-C$_4$ haloalkyl, CH$_2$CH(CH$_2$CH$_3$)S(O)C$_1$-C$_4$ haloalkyl, CH(CH$_3$)CH(CH$_3$)S(O)C$_1$-C$_4$ haloalkyl, CH$_2$CH$_2$S(O)C$_1$-C$_4$ haloalkenyl, CH$_2$CH$_2$CH$_2$S(O)C$_1$-C$_4$ haloalkenyl, CH$_2$CH(CH$_3$)S(O)C$_2$-C$_4$ haloalkenyl,
CH$_2$C(CH$_3$)$_2$S(O)C$_2$-C$_4$ haloalkenyl,
CH$_2$CH$_2$CH$_2$CH$_2$S(O)C$_2$-C$_4$ haloalkenyl,
CH(CH$_3$)CH$_2$S(O)C$_2$-C$_4$ haloalkenyl,
C(CH$_3$)$_2$CH$_2$S(O)C$_2$-C$_4$ haloalkenyl,
CH(CH$_2$CH$_3$)CH$_2$S(O)C$_2$-C$_4$ haloalkenyl,
CH$_2$CH(CH$_2$CH$_3$)S(O)C$_2$-C$_4$ haloalkenyl,
CH(CH$_3$)CH(CH$_3$)S(O)C$_2$-C$_4$ haloalkenyl,
CH$_2$CH$_2$S(O)C$_2$-C$_4$ alkynyl, CH$_2$CH$_2$CH$_2$S(O)C$_2$-C$_4$ alkynyl, CH$_2$CH(CH$_3$)S(O)C$_2$-C$_4$ alkynyl,
CH$_2$C(CH$_3$)$_2$S(O)C$_2$-C$_4$ alkynyl,
CH$_2$CH$_2$CH$_2$CH$_2$S(O)C$_2$-C$_4$ alkynyl,
CH(CH$_3$)CH$_2$S(O)C$_2$-C$_4$ alkynyl,
C(CH$_3$)$_2$CH$_2$S(O)C$_2$-C$_4$ alkynyl,
CH(CH$_2$CH$_3$)CH$_2$S(O)C$_2$-C$_4$ alkynyl,
CH$_2$CH(CH$_2$CH$_3$)S(O)C$_2$-C$_4$ alkynyl,
CH(CH$_3$)CH(CH$_3$)S(O)C$_2$-C$_4$ alkynyl,
CH$_2$CH$_2$S(O)C$_2$-C$_4$ alkoxyalkyl,
CH$_2$CH$_2$CH$_2$S(O)C$_2$-C$_4$ alkoxyalkyl,
CH$_2$CH(CH$_3$)S(O)C$_2$-C$_4$ alkoxyalkyl,
CH$_2$C(CH$_3$)$_2$S(O)C$_2$-C$_4$ alkoxyalkyl,
CH$_2$CH$_2$CH$_2$CH$_2$S(O)C$_2$-C$_4$ alkoxyalkyl,
CH(CH$_3$)CH$_2$S(O)C$_2$-C$_4$ alkoxyalkyl,
C(CH$_3$)$_2$CH$_2$S(O)C$_2$-C$_4$ alkoxyalkyl,
CH(CH$_2$CH$_3$)CH$_2$S(O)C$_2$-C$_4$ alkoxyalkyl,
CH$_2$CH(CH$_2$CH$_3$)S(O)C$_2$-C$_4$ alkoxyalkyl,
CH(CH$_3$)CH(CH$_3$)S(O)C$_2$-C$_4$ alkoxyalkyl,
CH$_2$SO$_2$C$_1$-C$_4$ alkyl, CH(CH$_3$)SO$_2$C$_1$-C$_4$ alkyl, C(CH$_3$)$_2$SO$_2$C$_1$-C$_4$ alkyl, CH(CH$_2$CH$_3$)SO$_2$C$_1$-C$_4$ alkyl, C(CH$_3$)(CH$_2$CH$_3$)SO$_2$C$_1$-C$_4$ alkyl, CH(CH$_2$CH$_2$CH$_3$)SO$_2$C$_1$-C$_4$ alkyl, CH[CH(CH$_3$)$_2$]SO$_2$C$_1$-C$_4$ alkyl, CH$_2$SO$_2$C$_1$-C$_4$ haloalkyl of at least 3 halogens, CH(CH$_3$)SO$_2$C$_1$-C$_4$ haloalkyl of at least 3 halogens, CH(CH$_3$)$_2$SO$_2$C$_1$-C$_4$ haloalkyl of at least 3 halogens, CH(CH$_2$CH$_3$)SO$_2$C$_1$-C$_4$ haloalkyl of at least 3 halogens, C(CH$_3$)(CH$_2$CH$_3$)SO$_2$C$_1$-C$_4$ haloalkyl of at least 3 halogens, CH(CH$_2$CH$_2$CH$_3$)SO$_2$C$_1$-C$_4$ haloalkyl of at least 3 halogens, CH[CH(CH$_3$)$_2$]SO$_2$C$_1$-C$_4$ haloalkyl of at least 3 halogens, CH$_2$CH$_2$SO$_2$C$_1$-C$_4$ haloalkyl,
CH$_2$CH$_2$CH$_2$SO$_2$C$_1$-C$_4$ haloalkyl,
CH$_2$CH(CH$_3$)SO$_2$C$_1$-C$_4$ haloalkyl,
CH$_2$C(CH$_3$)$_2$SO$_2$C$_1$-C$_4$ haloalkyl,
CH$_2$CH$_2$CH$_2$CH$_2$SO$_2$C$_1$-C$_4$ haloalkyl,
CH(CH$_3$)CH$_2$SO$_2$C$_1$-C$_4$ haloalkyl,
C(CH$_3$)$_2$CH$_2$SO$_2$C$_1$-C$_4$ haloalkyl,
CH(CH$_2$CH$_3$)CH$_2$SO$_2$C$_1$-C$_4$ haloalkyl,
CH$_2$CH(CH$_2$CH$_3$)SO$_2$C$_1$-C$_4$ haloalkyl,
CH(CH$_3$)CH(CH$_3$)SO$_2$C$_1$-C$_4$ haloalkyl,
CH$_2$CH$_2$SO$_2$C$_2$-C$_4$ haloalkenyl,
CH$_2$CH$_2$CH$_2$SO$_2$C$_2$-C$_4$ haloalkenyl,
CH$_2$CH(CH$_3$)SO$_2$C$_2$-C$_4$ haloalkenyl,
CH$_2$C(CH$_3$)$_2$SO$_2$C$_2$-C$_4$ haloalkenyl,
CH$_2$CH$_2$CH$_2$CH$_2$SO$_2$C$_2$-C$_4$ haloalkenyl,
CH(CH$_3$)CH$_2$SO$_2$C$_2$-C$_4$ haloalkenyl,
C(CH$_3$)$_2$CH$_2$SO$_2$C$_2$-C$_4$ haloalkenyl,
CH(CH$_2$CH$_3$)CH$_2$SO$_2$C$_2$-C$_4$ haloalkenyl,
CH$_2$CH(CH$_2$CH$_3$)SO$_2$C$_2$-C$_4$ haloalkenyl,
CH(CH$_3$)CH(CH$_3$)SO$_2$C$_2$-C$_4$ haloalkenyl,
CH$_2$CH$_2$SO$_2$C$_3$-C$_4$ alkynyl, CH$_2$CH$_2$CH$_2$SO$_2$C$_3$-C$_4$ alkynyl, CH$_2$CH(CH$_3$)SO$_2$C$_3$-C$_4$ alkynyl,
CH$_2$C(CH$_3$)$_2$SO$_2$C$_3$-C$_4$ alkynyl,
CH$_2$CH$_2$CH$_2$CH$_2$SO$_2$C$_3$-C$_4$ alkynyl,
CH(CH$_3$)CH$_2$SO$_2$C$_3$-C$_4$ alkynyl,
C(CH$_3$)$_2$CH$_2$SO$_2$C$_3$-C$_4$ alkynyl,
CH(CH$_2$CH$_3$)CH$_2$SO$_2$C$_3$-C$_4$ alkynyl,
CH$_2$CH(CH$_2$CH$_3$)SO$_2$C$_3$-C$_4$ alkynyl,
CH(CH$_3$)CH(CH$_3$)SO$_2$C$_3$-C$_4$ alkynyl,
CH$_2$CH$_2$SO$_2$C$_2$-C$_4$ alkoxyalkyl,
CH$_2$CH$_2$CH$_2$SO$_2$C$_2$-C$_4$ alkoxyalkyl,
CH$_2$CH(CH$_3$)SO$_2$C$_2$-C$_4$ alkoxyalkyl,
CH$_2$C(CH$_3$)$_2$SO$_2$C$_2$-C$_4$ alkoxyalkyl,
CH$_2$CH$_2$CH$_2$CH$_2$SO$_2$C$_2$-C$_4$ alkoxyalkyl,
CH(CH$_3$)CH$_2$SO$_2$C$_2$-C$_4$ alkoxyalkyl,
CH$_2$CH(CH$_2$CH$_3$)CH$_2$SO$_2$C$_2$-C$_4$ alkoxyalkyl,
CH$_2$CH(CH$_2$CH$_3$)SO$_2$C$_2$-C$_4$ alkoxyalkyl,
CH(CH$_3$)CH(CH$_3$)SO$_2$C$_2$-C$_4$ alkoxyalkyl,
C(CH$_3$)$_2$CH$_2$SO$_2$C$_2$-C$_4$ alkoxyalkyl, or C$_1$-C$_4$ alkyl substituted with C$_3$-C$_4$ cycloalkoxy, cyclopropylmethoxy C$_3$-C$_4$ haloalkynyloxy, C$_2$-C$_4$ aminoalkoxy, C$_1$-C$_4$ carbamoyloxy, OP(O)(OC$_1$-C$_2$ alkyl)$_2$, OSi(CH$_3$)$_3$, OSi(CH$_3$)$_2$C(CH$_3$)$_3$, C$_3$-C$_4$ cycloalkylthio, cyclopropylmethylthio, C$_2$-C$_4$ alkenylthio, C$_3$-C$_4$ haloalkynylthio, C$_2$-C$_4$ aminoalkylthio, SH, SP(O)(OC$_1$-C$_2$ alkyl)$_2$, C$_3$-C$_4$ cycloalkylsulfinyl, cyclopropylmethylsulfinyl, C$_3$-C$_4$ haloalkynylsulfinyl, C$_2$-C$_4$ aminoalkylsulfinyl, C$_3$-C$_4$ cycloalkylsulfonyl, cyclopropylmethylsulfonyl, C$_2$-C$_4$ alkenylsulfonyl, C$_3$-C$_4$ haloalkynylsulfonyl or C$_2$-C$_4$ aminoalkylsulfonyl.

15. Compounds of claim 14 wherein
R$_2$ is C$_2$-C$_4$ alkoxy, C$_3$-haloalkynyloxy. C$_2$-C$_4$ alkylthio, C$_3$-haloalkynylthio, C$_1$-C$_3$ alkylsulfinyl C$_3$-haloalkynylsulfinyl, C$_2$-C$_3$ alkylsulfonyl, C$_3$-haloalkynylsulfonyl, C$_2$-C$_3$ alkenyl, CH$_2$C(O)NR$_a$R$_b$, NHCH$_3$, NR$_b$R$_c$, CH$_2$OC$_1$-C$_2$ alkyl, CH$_2$OC$_1$-C$_2$ haloalkyl of at least 3 halogens, CH$_2$CH$_2$OC$_2$-C$_3$ haloalkenyl, CH$_2$CH$_2$OC$_3$-C$_4$ alkynyl, CH$_2$CH$_2$OC$_2$-C$_3$ alkoxyalkyl, CH$_2$OC$_1$-C$_2$ alkylcarbonyl, CH$_2$OC$_1$-C$_2$ alkoxycarbonyl, CH$_2$OH, CH$_2$OC$_1$-C$_2$ alkylsulfonyl, CH$_2$OC$_1$-C$_2$ haloalkylsulfonyl, CH$_2$SC$_1$-C$_2$ alkyl, CH$_2$SC$_1$-C$_2$ haloalkyl of at least 3 halogens, CH$_2$CH$_2$SC$_2$-C$_3$ haloalkenyl, CH$_2$CH$_2$SC$_3$-C$_4$ alkynyl, CH$_2$CH$_{SC2}$-C$_3$ alkoxyalkyl, CH$_2$S(O)C$_1$-C$_2$ alkyl, CH$_2$S(O)C$_1$-C$_2$ alkyl of at least 3 halogens, CH$_2$CH$_2$S(O)C$_1$-C$_2$ haloalkyl, CH$_2$CH$_2$S(O)C$_2$-C$_3$ haloalkenyl, CH$_2$CH$_2$S(O)C$_3$-C$_4$ alkynyl, CH$_2$CH$_2$S(O)C$_2$-C$_3$ alkoxyalkyl, CH$_2$SO$_2$C$_1$-C$_2$ alkyl, CH$_2$SO$_2$C$_1$-C$_2$ haloalkyl of at least 3 halogens, CH$_2$CH$_2$SO$_2$C$_1$-C$_2$ haloalkyl, CH$_2$CH$_2$SO$_2$C$_2$-C$_3$ haloalkenyl, CH$_2$CH$_2$SO$_2$C$_3$-C$_4$ alkynyl, CH$_2$CH$_2$SO$_2$C$_2$-C$_3$ alkoxyalkyl or C$_1$-C$_2$ alkyl substituted with C$_3$-cycloalkoxy, cyclopropylmethoxy, C$_3$-C$_4$ haloalkynyloxy, C$_2$-C$_3$ aminoalkoxy, C$_1$-C$_2$ carbamoyloxy. OP(O)(OC$_1$-C$_2$ alkyl)$_2$, OSi(CH$_3$)$_3$, OSi(CH$_3$)$_2$C(CH$_3$)$_3$, C$_3$-cycloalkylthio, cyclopropylmethylthio, C$_2$-C$_3$ alkenylthio, C$_3$-C$_4$ haloalkynylthio, C$_2$-C$_3$ aminoalkylthio, SH, SP(O)(OC$_1$-C$_2$ alkyl)$_2$, C$_3$-cycloalkylsulfinyl, cyclopropylmethylsulfinyl, C$_3$-C$_4$ haloalkynylsulfinyl, C$_2$-C$_3$ aminoalkylsulfinyl, C$_3$-cycloalkylsulfonyl, cyclopropylmethylsulfonyl C$_2$-C$_3$ alkenylsulfonyl, C$_3$-C$_4$ haloalkenylsulfonyl or C$_2$-C$_3$ aminoalkylsulfonyl.

16. Compounds of claim 15 wherein
R$_2$ is OCH$_2$CH$_3$, OCH(CH$_3$)$_2$, C$_3$-haloalkynyloxy, SCH$_2$CH$_3$, SCH(CH$_3$)$_2$, C$_3$-haloalkynylthio, S(O)CH$_3$S, (O)CH$_2$S(O)CH(CH$_3$)$_2$, C$_3$-haloalkynylsulfinyl, SO$_2$CH$_2$CH$_3$, SO$_2$CH(CH$_3$)$_2$, C$_3$-haloalkynylsulfonyl, vinyl, allyl, CH$_2$C(O)N(CH$_3$)$_2$, NHCH$_3$, N(CH$_3$)$_2$, CH$_2$OCH$_3$, CH$_2$OCH$_2$CF$_3$, CH$_2$CH$_2$OC$_2$ haloalkenyl, CH$_2$CH$_2$OCH$_2$C≡CH, CH$_2$CH$_2$OCH$_2$CH$_2$OCH$_3$, CH$_2$OC(O)CH$_3$, CH$_2$OC(O)OCH$_3$, $CH_2OH$, $CH_2OSO_2CH_3$, $CH_2OSO_2CF_3$, $CH_2OSO_2CH_2CF_3$, $CH_2SCH_3$, $CH_2SCH_2CF_3$, $CH_2CH_2SC_2$ haloalkenyl, $CH_2CH_2SCH_2C{\equiv}CH$, $CH_2CH_2SCH_2CH_2OCH_3$, $CH_2S(O)CH_3$, $CH_2S(O)CH_2CF_3$, $CH_2CH_2S(O)CH_2CF_3$, $CH_2CH_2S(O)C_2$ haloalkenyl, $CH_2CH_2S(O)CH_2C{\equiv}CH$, $CH_2CH_2S(O)CH_2CH_2OCH_3$, $CH_2SO_2CH_3$, $CH_2SO_2CH_2CF_3$, $CH_2CH_2SO_2CH_2CF_3$, $CH_2CH_2SO_2C_2$ haloalkenyl, $CH_2CH_2SO_2CH_2C{\equiv}CH$, $CH_2CH_2SO_2CH_2CH_2OCH_3$, or $CH_2$ substituted with cyclopropoxy, cyclopropylmethoxy, $C_3$-haloalkynyloxy, $OCH_2CH_2NH_2$, $OC(O)NH_2$, $OP(O)(OCH_3)_2$, $OSi(CH_3)_3$, $OSi(CH_3)_2C(CH_3)_3$, cyclopropylthio, cyclopropylmethylthio, allylthio, $C_3$-haloalkenylthio, $SCH_2CH_2NH_2$, SH, $SP(O)(OCH_3)_2$, cyclopropylsulfinyl, cyclopropylmethylsulfinyl, $C_3$-haloalkynylsulfinyl, $S(O)CH_2CH_2NH_2$, cyclopropylsulfonyl, cyclopropylmethylsulfonyl, allylsulfonyl, $C_3$-haloalkenylsulfonyl or $SO_2CH_2CH_2NH_2$.

17. Compounds of claim 1 wherein
$R_2$ is $OCF_2H$, $C_2$–$C_6$ haloalkoxy, $C_2$–$C_6$ alkenyloxy, $C_2$–$C_6$ haloalkenyloxy, $C_2$–$C_4$ alkoxyalkoxy, $C_2$–$C_4$ haloalkoxyalkoxy, $C_2$–$C_4$ alkylthioalkoxy, $C_2$–$C_4$ haloalkylthioalkoxy, $C_2$–$C_4$ alkylsulfinylalkoxy, $C_2$–$C_4$ haloalkylsulfinylalkoxy, $C_2$–$C_4$ alkylsulfonylalkoxy, $C_2$–$C_4$ haloalkylsulfonylalkoxy, $SCF_2H$, $C_2$–$C_6$ haloalkylthio, $C_2$–$C_6$ alkenylthio, $C_2$–$C_6$ haloalkenylthio, $C_2$–$C_4$ alkoxyalkylthio, $C_2$–$C_4$ haloalkoxyalkylthio, $C_2$–$C_4$ alkylthioalkylthio, $C_2$–$C_4$ haloalkylthioalkylthio, $C_1$–$C_6$ haloalkylsulfinyl, $C_2$–$C_6$ alkenylsulfinyl, $C_2$–$C_6$ haloalkenylsulfinyl, $C_2$–$C_4$ alkoxyalkylsulfinyl, $C_2$–$C_4$ haloalkoxyalkylsulfinyl, $C_1$–$C_6$ haloalkylsulfonyl, $C_2$–$C_6$ alkenylsulfonyl, $C_2$–$C_6$ haloalkenylsulfonyl, $C_2$–$C_4$ alkoxyalkylsulfonyl or $C_2$–$C_4$ haloalkoxyalkylsulfonyl.

18. Compounds of claim 17 wherein
$R_2$ is $OCF_2H$, $C_2$–$C_3$ haloalkoxy, $C_2$–$C_3$ alkenyloxy, $C_2$–$C_3$ haloalkenyloxy, $C_2$–$C_3$ alkoxyalkoxy, $C_2$–$C_3$ haloalkoxyalkoxy, $C_2$–$C_3$ alkylthioalkoxy, $C_2$–$C_3$ haloalkylthioalkoxy, $C_2$–$C_3$ alkylsulfinylalkoxy, $C_2$–$C_3$ haloalkylsulfinylalkoxy, $C_2$–$C_3$ alkylsulfonylalkoxy, $C_2$–$C_3$ haloalkylsulfonylalkoxy, $SCF_2H$, $C_2$–$C_3$ haloalkylthio, $C_2$–$C_3$ alkenylthio, $C_2$–$C_3$ haloalkenylthio, $C_2$–$C_3$ alkoxyalkylthio $C_2$–$C_3$ haloalkoxyalkylthio, $C_2$–$C_3$ alkylthioalkylthio, $C_2$–$C_3$ haloalkylthioalkylthio, $C_1$–$C_3$ haloalkylsulfinyl, $C_2$–$C_3$ alkenylsulfinyl, $C_2$–$C_3$ haloalkenylsulfinyl, $C_2$–$C_3$ alkoxyalkylsulfinyl, $C_2$–$C_3$ haloalkoxyalkylsulfinyl, $C_1$–$C_3$ haloalkylsulfonyl, $C_2$–$C_3$ alkenylsulfonyl, $C_2$–$C_3$ haloalkenylsulfonyl, $C_2$–$C_3$ alkoxysulfonyl or $C_2$–$C_3$ haloalkoxyalkylsulfonyl.

19. Compounds of claim 18 wherein
$R_2$ is $OCF_2H$, $OCH_2CF_3$, allyloxy, $C_3$-haloalkenyloxy, $OCH_2CH_2OCH_3$, $OCH_2OCH_2CF_3$, $OCH_2CH_2SCH_3$, $OCH_2CH_2SO_2CH_3$, $OCH_2SO_2CH_2CF_2$, $SCF_2H$, $SCH_2CF_3$, allylthio, $C_2$-haloalkenylthio, $SCH_2CH_2OCH_3$, $SCH_2OCH_2CF_3$, $SCH_2CH_2SCH_3$, $SCH_2SCH_2CF_3$, $S(O)CH_2CF_3$, allylsulfinyl, $C_2$-haloalkenylsulfinyl, $S(O)CH_2CH_2OCH_3$, $S(O)CH_2OCH_2CF_3$, $SO_2CH_2CF_3$, allylsulfonyl, $C_2$-haloalkenylsulfonyl, $SO_2CH_2CH_2OCH_3$ or $SO_2CH_2OCH_2CF_3$.

20. Compounds of claim 1 wherein
$R_2$ is $C_3$–$C_6$ alkynyloxy, $C_3$–$C_6$ alkynylthio, $C_3$–$C_6$ alkynylsulfinyl or $C_3$–$C_6$ alkynylsulfonyl.

21. Compounds of claim 20 wherein
$R_2$ is $C_3$–$C_4$ alkynyloxy $C_3$–$C_4$ alkynylthio, $C_3$–$C_4$ alkynylsulfinyl or $C_3$–$C_4$ alkynylsulfonyl.

22. Compounds of claim 21 wherein
$R_2$ is propargyloxy, propargylthio propargylsulfinyl or propargylsulfonyl.

23. Compounds of claim 1 wherein
$R_2$ is $OCF_2H$, $C_2$–$C_6$ haloalkoxy, $C_2$–$C_6$ haloalkenyloxy, $C_2$–$C_4$ alkoxyalkoxy, $C_2$–$C_4$ haloalkoxyalkoxy, $C_2$–$C_4$ alkylthioalkoxy, $C_2$–$C_4$ haloalkylthioalkoxy, $C_2$–$C_4$ alkylsulfinylalkoxy, $C_2$–$C_4$ haloalkylsulfinylalkoxy, $C_2$–$C_4$ alkylsulfonylalkoxy, $C_2$–$C_4$ haloalkylsulfonylalkoxy, $SCF_2H$, $C_2$–$C_6$ haloalkylthio, $C_2$–$C_6$ haloalkenylthio, $C_2$–$C_4$ alkoxyalkylthio, $C_2$–$C_4$ haloalkoxyalkylthio, $C_2$–$C_4$ alkylthioalkylthio, $C_2$–$C_4$ haloalkylthioalkylthio, $C_1$–$C_6$ haloalkylsulfinyl, $C_2$–$C_6$ haloalkenylsulfinyl, $C_2$–$C_4$ alkoxyalkylsulfinyl, $C_2$–$C_4$ haloalkoxyalkylsulfinyl, $C_1$–$C_6$ haloalkylsulfonyl, $C_2$–$C_6$ haloalkenylsulfonyl, $C_2$–$C_4$ alkoxyalkylsulfonyl or $C_2$–$C_4$ haloalkoxyalkylsulfonyl.

24. Compounds of claim 23 wherein
$R_2$ is $OCF_2H$, $C_2$–$C_3$ haloalkoxy, $C_2$–$C_3$ haloalkenyloxy, $C_2$–$C_3$ alkoxyalkoxy, $C_2$–$C_3$ haloalkoxyalkoxy, $C_2$–$C_3$ alkylthioalkoxy, $C_2$–$C_3$ haloalkylthioalkoxy, $C_2$–$C_3$ alkylsulfinylalkoxy, $C_2$–$C_3$ haloalkylsulfinylalkoxy, $C_2$–$C_3$ alkylsulfonylalkoxy $C_2$–$C_3$ haloalkylsulfonylalkoxy, $SCF_2H$, $C_2$–$C_3$ haloalkylthio $C_2$–$C_3$ alkenylthio $C_2$–$C_3$ haloalkenylthio $C_2$–$C_3$ alkoxyalkylthio, $C_2$–$C_3$ haloalkoxyalkylthio, $C_2$–$C_3$ alkylthioalkylthio $C_2$–$C_3$ haloalkylthioalkylthio, $C_1$–$C_3$ haloalkylsulfinyl, $C_2$–$C_3$ haloalkenylsulfinyl $C_2$–$C_3$ alkoxyalkylsulfinyl, $C_2$–$C_4$ haloalkoxyalkylsulfinyl, $C_1$–$C_3$ haloalkylsulfonyl, $C_2$–$C_3$ haloalkenylsulfonyl $C_2$–$C_3$ alkoxyalkylsulfonyl or $C_2$–$C_3$ haloalkoxyalkylsulfonyl.

25. Compounds of claim 24 wherein
$R_2$ is $OCF_2H$, OCH $C_3$-haloalkenyloxy, $OCH_2CH_2OCH_3$, $OCH_2OCH_2CF_3$, $OCH_2CH_2SCH_3$, $OCH_2SCH_2CF_3$, $OCH_2CH_2S(O)CH_3$, $OCH_2S(O)CH_2CF_3$, $OCH_2CH_2SO_2CH_3$, $OCH_2SO_2CH_2CF_2$, $SCF_2H$, $SCH_2CF_3$, $C_2$-haloalkenylthio, $SCH_2CH_2OCH_3$, $SCH_2OCH_2CF_3$, $SCH_2CH_2SCH_3$, $SCH_2SCH_2CF_3$, $S(O)CH_2C_2$-haloalkenylsulfinyl, $S(O)CH_2CH_2OCH_3$, $S(O)CH_2OCH_2CF_3$, $SO_2CH_2CF_3$, $C_2$-haloalkenylsulfonyl, $SO_2CH_2CH_2OCH_3$ or $SO_2CH_2OCH_2CF_3$.

26. Compounds of claim 1 wherein
$R_2$ is $C_2$–$C_6$ haloalkynyl.

27. Compounds of claim 26 wherein
$R_2$ is $C_3$–$C_4$ haloalkynyl.

28. Compounds of claim 27 wherein
$R_2$ is $C_3$-haloalkynyl.

29. Compounds of claim 1 wherein
$R_2$ is $CH_2F$, $CHF_2$, $CH_2Cl$, $CHCl_2$, $CH_2Br$, $CHBr_2$ or $C_2$–$C_6$ alkyl substituted with 1–3 atoms of F, Cl or Br.

30. Compounds of claim 29 wherein
$R_2$ is $CH_2F$, $CHF_2$, $CH_2Cl$, $CHCl_2$, $CH_2Br$, $CHBr_2$ or $C_2$–$C_3$ alkyl substituted with 1–3 atoms of F, Cl or Br.

31. Compounds of claim 30 wherein
$R_2$ is $CH_2F$, $CHF_2$, $CH_2Cl$, $CHCl_2$, $CH_2Br$, $CHBr_2$, $CH_2CH_2Cl$, $CH_2CH_2F$, $CH_2CF_3$, $CF_2CF_2H$ or $CF_2CF_2Cl$.

32. Compounds of claim 1 wherein
$R_2$ is $OCF_2H$, $C_2$-$C_6$ haloalkoxy $C_2$-$C_6$ haloalkenyloxy, $C_3$-$C_6$ alkynyloxy, $C_2$-$C_4$ alkoxyalkoxy, $C_2$-$C_4$ haloalkoxyalkoxy, $C_2$-$C_4$ alkylthioalkoxy, $C_2$-$C_4$ haloalkylthioalkoxy, $C_2$-$C_4$ alkylsulfinylalkoxy, $C_2$-$C_4$ haloalkylsulfinylalkoxy, $C_2$-$C_4$ alkylsulfonylalkoxy, $C_2$-$C_4$ haloalkylsulfonylalkoxy, $SCF_2H$, $C_2$-$C_6$ haloalkylthio, $C_2$-$C_6$ haloalkenylthio, $C_3$-$C_6$ alkynylthio $C_2$-$C_4$ alkoxyalkylthio, $C_2$-$C_4$ haloalkoxyalkylthio $C_2$-$C_4$ alkylthioalkylthio, $C_2$-$C_4$ haloalkylthioalkylthio, $C_1$-$C_6$ haloalkylsulfinyl, $C_2$-$C_6$ haloalkenylsulfinyl, $C_3$-$C_6$ alkynylsulfinyl. $C_2$-$C_4$ alkoxyalkylsulfinyl, $C_2$-$C_4$ haloalkoxyalkylsulfinyl, $C_1$-$C_6$ haloalkylsulfonyl. $C_2$-$C_6$ haloalkenylsulfonyl $C_3$-$C_6$ alkynylsulfonyl, $C_2$-$C_4$ alkoxyalkylsulfonyl or $C_2$-$C_4$ haloalkoxyalkylsulfonyl.

33. Compounds of claim 32 wherein
$R_2$ is $OCF_2H$, $C_2$-$C_3$ haloalkoxy, $C_2$-$C_3$ haloalkenyloxy, $C_3$-$C_4$ alkynyloxy, $C_2$-$C_3$ alkoxyalkoxy, $C_2$-$C_3$ haloalkoxyalkoxy, $C_2$-$C_3$ alkylthioalkoxy, $C_2$-$C_3$ haloalkylthioalkoxy, $C_2$-$C_3$ alkylsulfinylalkoxy, $C_2$-$C_3$ haloalkylsulfinylalkoxy, $C_2$-$C_3$ alkylsulfonylalkoxy, $C_2$-$C_3$ haloalkylsulfonylalkoxy, $SCF_2H$, $C_2$-$C_3$ haloalkylthio, $C_2$-$C_3$ haloalkenylthio, $C_2$-$C_4$ alkynylthio, $C_2$-$C_3$ alkoxyalkylthio, $C_2$-$C_3$ haloalkoxyalkylthio, $C_2$-$C_3$ alkylthioalkylthio, $C_2$-$C_3$ haloalkylthioalkylthio, $C_1$-$C_3$ haloalkylsulfinyl, $C_2$-$C_3$ haloalkenylsulfinyl, $C_3$-$C_4$ alkynylsulfinyl, $C_2$-$C_3$ alkoxyalkylsulfinyl, $C_2$-$C_3$ haloalkoxyalkylsulfinyl, $C_1$-$C_3$ haloalkylsulfonyl, $C_2$-$C_3$ haloalkenylsulfonyl, $C_3$-$C_4$ alkynylsulfonyl, $C_2$-$C_3$ alkoxyalkylsulfonyl or $C_2$-$C_3$ haloalkoxyalkylsulfonyl.

34. Compounds of claim 33 wherein
$R_2$ is $OCF_2H$, $OCH_2CF_3$, $C_3$-haloalkenyloxy, propargyloxy, $OCH_2CH_2OCH_3$, $OCH_2OCH_2CF_3$, $OCH_2CH_2SCH_3$, $OCH_2SCH_2CF_3$, $OCH_2CH_2S(O)CH_3$, $OCH_2S(O)CH_2CF_3$, $OCH_2CH_2SO_2CH_3$, $OCH_2SO_2CH_2CF_3$, $SCF_2H$, $SCH_2CF_3$, $C_2$-haloalkenylthio, propargylthio, $SCH_2CH_2OCH_3$, $SCH_2OCH_2CF_3$, $SCH_2CH_2SCH_3$, $SCH_2SCH_2CF_3$, $S(O)CH_2CF_3$, $C_2$-haloalkenylsulfinyl, propargylsulfinyl, $S(O)CH_2CH_2OCH_3$, $S(O)CH_2OCH_2CF_3$, $SO_2CH_2CF_3$, $C_2$-haloalkenylsulfonyl, propargylsulfonyl, $SO_2CH_2CH_2OCH_3$ or $SO_2CH_2OCH_2CF_3$.

35. Compounds of claim 1 wherein
$R_2$ is $C_2$-$C_6$ haloalkenyl.

36. Compounds of claim 35 wherein
$R_2$ is $C_2$-$C_3$ haloalkenyl.

37. Compounds of claim 36 wherein
$R_2$ is $CF_2$=CFCl or CF=CFCF_3.

38. Compounds of claim 1 wherein
$R_2$ is $C_3$-$C_6$ cycloalkoxy, $C_4$-$C_6$ cycloalkylalkoxy, $C_2$-$C_4$ cyanoalkoxy, $OCH_2C(O)CH_3$, $OCH_2CH_2C(O)CH_3$, $C_2$-$C_4$ aminoalkoxy, $C_3$-$C_6$ cycloalkylthio, $C_4$—$C_6$ cycloalkylalkylthio, $C_2$-$C_4$ cyanoalkylthio, $SCH_2C(O)CH_3$, $SCH_2CH_2C(O)CH_3$, $C_2$-$C_4$ aminoalkylthio, $SC_6H_5$, $SCH_2C_6H_5$, $C_3$-$C_6$ cycloalkylsulfinyl, $C_4$-$C_6$ cycloalkylalkylsulfinyl, $C_2$-$C_4$ cyanoalkylsulfinyl, $S(O)CH_2C(O)CH_3$, $S(O)CH_2CH_2C(O)CH_3$, $C_2$-$C_4$ aminoalkylsulfinyl, $C_3$-$C_6$ cycloalkylsulfonyl, $C_4$-$C_6$ cycloalkylalkylsulfonyl, $C_2$-$C_4$ cyanoalkylsulfonyl, $SO_2CH_2C(O)CH_3$, $SO_2CH_2CH_2C(O)CH_3$, $C_2$-$C_4$ aminoalkylsulfonyl or $OC(O)C_1$-$C_4$ alkyl.

39. Compounds of claim 38 wherein
$R_2$ is $C_3$-$C_4$ cycloalkoxy, $C_4$-$C_5$ cycloalkylalkoxy, $C_2$-$C_3$ cyanoalkoxy, $OCH_2C(O)CH_3$, $OCH_2CH_2C(O)CH_3$, $CH_3$, $C_2$-$C_3$ aminoalkoxy, $C_3$-$C_4$ cycloalkylthio, $C_4$-$C_5$ cycloalkylalkylthio, $C_2$-$C_3$ cyanoalkylthio, $SCH_2C(O)CH_3$, $SCH_2CH_2C(O)CH_3$, $C_2$-$C_3$ aminoalkylthio, $SC_6H_5$, $SCH_2C_6H_5$, $C_3$-$C_4$ cycloalkylsulfinyl, $C_4$-$C_5$ cycloalkylalkylsulfinyl, $C_2$-$C_3$ cyanoalkylsulfinyl, $S(O)CH_2C(O)CH_3$, $S(O)CH_2CH_2C(O)CH_3$, $C_2$-$C_3$ aminoalkylsulfinyl, $C_3$-$C_4$ cycloalkylalkylsulfonyl, $C_4$-$C_5$ cyanoalkylsulfonyl, $C_2$-$C_3$ cyanoalkylsulfonyl, $SO_2CH_2C(O)CH_3$, $SO_2CH_2CH_2C(O)CH_3$, $C_2$-$C_3$ aminoalkylsulfonyl or $OC(O)C_1$-$C_2$ alkyl.

40. Compounds of claim 39 wherein
$R_2$ is cyclopropoxy, cyclopropylmethoxy, $OCHCH_2CN$, $OCH_2C(O)CH_3$, $OCH_2CH_2C(O)CH_3$, $OCH_2CH_2NH_2$, cyclopropylthio, cyclopropylmethylthio, $SCH_2CH_2CN$, $SCH_2C(O)CH_3$, $SCH_2CH_2C(O)CH_3$, $SCH_2CH_2NH_2$, $SC_6H_5$, $SCH_2C_6H_5$, cyclopropylsulfinyl, cyclopropylmethylsulfinyl, $S(O)CH_2CH_2CN$, $S(O)CH_2C(O)CH_3$, $S(O)CH_2CH_2C(O)CH_3$, $S(O)CH_2CH_2NH_2$, cyclopropylsulfonyl, cyclopropylmethylsulfonyl, $SO_2CH_2CH_2CN$, $SO_2CH_2C(O)CH_3$, SO $SO_2CH_2CH_2C(O)CH_3$, $SO_2CH_2CH_2NH_2$ or $OC(O)CH_3$.

41. Compounds of claim 1 wherein
$R_2$ is $CH_2OC_1$-$C_4$ haloalkyl of 1 or 2 halogens, $CH(CH_3)OC_1$-$C_4$ haloalkyl of 1 or 2 halogens, $C(CH_3)_2OC_1$-$C_4$ haloalkyl of 1 or 2 halogens, $CH(CH_2CH_3)OC_1$-$C_4$ haloalkyl of 1 or 2 halogens, $C(CH_3)(CH_2CH_3)OC_1$-$C_4$ haloalkyl of 1 or 2 halogens, $CH(CH_2(CH_2CH_2CH_3)OC_1$-$C_4$ haloalkyl of 1 or 2 halogens, $CH[CH(CH_3)_2]OC_1$-$C_4$ haloalkyl of 1 or 2 halogens, $CH_2OC_2$-$C_4$ haloalkenyl $CH(CH_3)OC_2$-$C_4$ haloalkenyl, $C(CH_3)_2OC_2$-$C_4$ haloalkenyl, $CH(CH_2CH_3)OC_2$-$C_4$ haloalkenyl, $C(CH_3)(CH_3)OC_2$-$C_4$ haloalkenyl, $CH(CH_2CH_2CH_3)OC_2$-$C_4$ haloalkenyl, $CH[CH(CH_3)_2]OC_2$-$C_4$ haloalkenyl, $CH_2OC_3$-$C_4$ alkynyl, $CH(CH_3)OC_3$-$C_4$ alkynyl, $CH(CH_2CH_3)OC_3$-$C_4$ alkynyl, $C(CH_3)(CH_2CH_3)OC_3$-$C_4$ alkynyl, $CH(CH_2CH_2CH_3)OC_3$-$C_4$ alkynyl, $CH[CH(CH_3)_2]OC_3$-$C_4$ alkynyl, $C(CH_3)_2OC_3$-$C_4$ alkynyl, $CH_2OC_2$-$C_4$ alkoxyalkyl, $CH(CH_3)OC_2$-$C_4$ alkoxyalkyl, $C(CH_3)_2OC_2$-$C_4$ alkoxyalkyl, $CH(CH_2CH_3)OC_2$-$C_4$ alkoxyalkyl, $C(CH_3)(CH_2CH_3)OC_2$-$C_4$ alkoxyalkyl, $CH(CH_2CH_2CH_3)OC_2$-$C_4$ alkoxyalkyl, $CH[CH(CH_3)_2]OC_2$-$C_4$ alkoxyalkyl, $CH_2SC_1$-$C_4$ haloalkyl of 1 or 2 halogens, $CH(CH_3)SC_1$-$C_4$ haloalkyl of 1 or 2 halogens, $C(CH_3)_2SC_1$-$C_4$ haloalkyl of 1 or 2 halogens, $CH(CH_2CH_3)SC_1$-$C_4$ haloalkyl of 1 or 2 halogens, $C(CH_3)(CH_2CH_3)SC_1$-$C_4$ haloalkyl of 1 or 2 halogens, $CH(CH_2CH_2CH_3)SC_1$-$C_4$ haloalkyl of 1 or 2 halogens, $CH[CH(CH_3)_2]SC_1$-$C_4$ haloalkyl of 1 or 2 halogens, $CH_2SC_2$-$C_4$ haloalkenyl, $CH(CH_3)SC_2$-$C_4$ haloalkenyl, $C(CH_3)_2SC_2$-$C_4$ haloalkenyl, $CH(CH_2CH_3)SC_2$-$C_4$ haloalkenyl, $C(CH_3)(CH_2CH_3)SC_2$-$C_4$ haloalkenyl, $CH(CH_2CH_2CH_3)SC_2$-$C_4$ haloalkenyl, $CH[CH(CH_3)_2]SC_2$-$C_4$ haloalkenyl, $CH_2SC_3$-$C_4$ alkynyl, $CH(CH_3)SC_3$-$C_4$ alkynyl, C(CH$_3$)$_2$SC$_3$–C$_4$ alkynyl, CH(CH$_2$CH$_3$)SC$_3$–C$_4$ alkynyl, C(CH$_3$)(CH$_2$CH$_3$)SC$_3$–C$_4$ alkynyl, CH(CH$_2$CH$_2$CH$_3$)SC$_3$–C$_4$ alkynyl, CH[CH(CH$_3$)$_2$]SC$_3$–C$_4$ alkynyl, CH$_2$SC$_2$–C$_4$ alkoxyalkyl, CH(CH$_3$)SC$_2$–C$_4$ alkoxyalkyl, C(CH$_3$)$_2$SC$_2$–C$_4$ alkoxyalkyl, CH(CH$_2$CH$_3$)SC$_2$–C$_4$ alkoxyalkyl, C(CH$_3$)(CH$_2$CH$_3$)SC$_2$–C$_4$ alkoxyalkyl, CH[CH(CH$_3$)$_2$]SC$_2$–C$_4$ alkoxyalkyl, CH$_2$S(O)C$_1$–C$_4$ haloalkyl of 1 or 2 halogens, CH(CH$_3$)S(O)C$_1$–C$_4$ haloalkyl of 1 or 2 halogens, C(CH$_3$)$_2$S(O)C$_1$–C$_4$ haloalkyl of 1 or 2 halogens, CH(CH$_2$CH$_3$)S(O)C$_1$–C$_4$ haloalkyl of 1 or 2 halogens, C(CH$_3$)(CH$_2$CH$_3$)S(O)C$_1$–C$_4$ haloalkyl of 1 or 2 halogens CH(CH$_2$CH$_2$CH$_3$)S(O)C$_1$–C$_4$ haloalkyl of 1 or 2 halogens, CH[CH(CH$_3$)$_2$]S(O)C$_1$–C$_4$ haloalkyl of 1 or 2 halogens, CH$_2$S(O)C$_2$–C$_4$ haloalkenyl, CH(CH$_3$)S(O)C$_2$–C$_4$ haloalkenyl, C(CH$_3$)$_2$S(O)C$_2$–C$_4$ haloalkenyl, CH(CH$_2$CH$_3$)S(O)C$_2$–C$_4$ haloalkenyl, C(CH$_3$)(CH$_2$CH$_3$)S(O)C$_2$–C$_4$ haloalkenyl, CH(CH$_2$CH$_2$CH$_3$)S(O)C$_2$–C$_4$ haloalkenyl, CH[CH(CH$_3$)$_2$]S(O)C$_2$–C$_4$ haloalkenyl, CH$_2$S(O)C$_3$–C$_4$ alkynyl, CH(CH$_3$)S(O)C$_3$–C$_4$ alkynyl C(CH$_3$)$_2$S(O)C$_3$–C$_4$ alkynyl. CH(CH$_2$CH$_3$)S(O)C$_3$–C$_4$ alkynyl, C(CH$_3$)(CH$_2$CH$_3$)S(O)C$_3$–C$_4$ alkynyl, CH(CH$_2$CH$_2$CH$_3$)S(O)C$_3$–C$_4$ alkynyl, CH[CH(CH$_3$)$_2$]S(O)C$_3$–C$_4$ alkynyl, CH$_2$S(O)C$_2$–C$_4$ alkoxyalkyl, CH(CH$_3$)S(O)C$_2$–C$_4$ alkoxyalkyl, C(CH$_3$)$_2$S(O)C$_2$–C$_4$ alkoxyalkyl, CH(CH$_2$CH$_3$)S(O)C$_2$–C$_4$ alkoxyalkyl, C(CH$_3$)(CH$_2$CH$_3$)S(O)C$_2$–C$_4$ alkoxyalkyl, CH(CH$_2$CH$_2$CH$_3$)S(O)C$_2$–C$_4$ alkoxyalkyl, CH[CH(CH$_3$)$_2$]S(O)C$_2$–C$_4$ alkoxyalkyl, CH$_2$SO$_2$C$_1$–C$_4$ haloalkyl of 1 or 2 halogens, CH(CH$_3$)SO$_2$C$_1$–C$_4$ haloalkyl of 1 or 2 halogens, C(CH$_3$)$_2$SO$_2$C$_1$–C$_4$ haloalkyl of 1 or 2 halogens, CH(CH$_2$CH$_3$)SO$_2$C$_1$–C$_4$ haloalkyl of 1 or 2 halogens, C(CH$_3$)(CH$_2$CH$_3$)SO$_2$C$_1$–C$_4$ haloalkyl of 1 or 2 halogens, CH(CH$_2$CH$_2$CH$_3$)SO$_2$C$_1$–C$_4$ haloalkyl of 1 or 2 halogens, CH[CH(CH$_3$)$_2$]SO$_2$C$_1$–C$_4$ haloalkyl of 1 or 2 halogens, CH$_2$SO$_2$C$_2$–C$_4$ haloalkenyl, CH(CH$_3$)SO$_2$C$_2$–C$_4$ haloalkenyl, C(CH$_3$)$_2$SO$_2$C$_2$–C$_4$ haloalkenyl, CH(CH$_2$CH$_3$)SOC$_2$–C$_4$ haloalkenyl, C(CH$_3$)(CH$_2$CH$_3$)SO$_2$C$_2$–C$_4$ haloalkenyl, CH(CH$_2$CH$_2$CH$_3$)SO$_2$C$_2$–C$_4$ haloalkenyl, CH[CH(CH$_3$)$_2$]SO$_2$C$_2$–C$_4$ haloalkenyl, CH$_2$SO$_2$C$_3$–C$_4$ alkynyl, CH(CH$_3$)SO$_2$C$_3$–C$_4$ alkynyl, C(CH$_3$)$_2$SO$_2$C$_3$–C$_4$ alkynyl, CH(CH$_2$CH$_3$)SO$_2$C$_3$–C$_4$ alkynyl, C(CH$_3$)(CH$_2$CH$_3$)SO$_2$C$_3$–C$_4$ alkynyl, CH(CH$_2$CH$_2$CH$_3$)SO$_2$C$_3$–C$_4$ alkynyl, CH[CH(CH$_3$)$_2$]SO$_2$C$_3$–C$_4$ alkynyl, CH$_2$SO$_2$C$_2$–C$_4$ alkoxyalkyl, CH(CH$_3$)SO$_2$C$_2$–C$_4$ alkoxyalkyl, C(CH$_3$)$_2$SO$_2$C$_2$–C$_4$ alkoxyalkyl, CH(CH$_2$CH$_3$)SO$_2$C$_2$–C$_4$ alkoxyalkyl, C(CH$_3$)(CH$_2$CH$_3$)SO$_2$C$_2$–C$_4$ alkoxyalkyl, CH(CH$_2$CH$_2$CH$_3$)SO$_2$C$_2$–C$_4$ alkoxyalkyl, CH[CH(CH$_3$)$_2$]SO$_2$C$_2$–C$_4$ alkoxyalkyl, CH$_2$CH$_2$OC$_1$–C$_4$ alkyl, CH$_2$CH$_2$CH$_2$OC$_1$–C$_4$ alkyl, CH$_2$CH$_2$CH$_2$CH$_2$OC$_1$–C$_4$ alkyl, CH(CH$_3$)CH$_2$OC$_1$–C$_4$ alkyl, C(CH$_3$)$_2$CH$_2$OC$_1$–C$_4$ alkyl, CH(CH$_2$CH$_3$)CH$_2$OC$_1$–C$_4$ alkyl, CH$_2$CH(CH$_3$)OC$_1$–C$_4$ alkyl, CH$_2$C(CH$_3$)$_2$OC$_1$–C$_4$ alkyl CH$_2$CH(CH$_2$CH$_3$)OC$_1$–C$_4$ alkyl, CH(CH$_3$)CH(CH$_3$)OC$_1$–C$_4$ alkyl, CH$_2$CH$_2$OC$_1$–C$_4$ haloalkyl, CH$_2$CH$_2$CH$_2$OC$_1$–C$_4$ haloalkyl, CH$_2$CH$_2$CH$_2$CH$_2$OC$_1$–C$_4$ haloalkyl. CH$_2$(CH$_3$)CH$_2$OC$_1$–C$_4$ haloalkyl, C(CH$_3$)$_2$CH$_2$OC$_1$–C$_4$ haloalkyl, CH(CH$_2$CH$_3$)CH$_2$OC$_1$–C$_4$ haloalkyl. CH$_2$CH(CH$_3$)OC$_1$–C$_4$ haloalkyl, CH$_2$C(CH$_3$)$_2$OC$_1$–C$_4$ haloalkyl, CH$_2$CH(CH$_2$CH$_3$)OC$_1$–C$_4$ haloalkyl, CH(CH$_3$)CH(CH$_3$)OC$_1$–C$_4$ haloalkyl, CH$_2$CH$_2$OC$_1$–C$_4$ alkylcarbonyl, CH$_2$CH$_2$CH$_2$OC$_1$–C$_4$ alkylcarbonyl, CH$_2$CH$_2$CH$_2$CH$_2$OC$_1$–C$_4$ alkylcarbonyl, CH(CH$_3$)CH$_2$OC$_1$–C$_4$ alkylcarbonyl, C(CH$_3$)$_2$CH$_2$OC$_1$–C$_4$ alkylcarbonyl, CH(CH$_2$CH$_3$)CH$_2$OC$_1$–C$_4$ alkylcarbonyl, CH$_2$CH(CH$_3$)OC$_1$–C$_4$ alkylcarbonyl, CH$_2$C(CH$_3$)$_2$OC$_1$–C$_4$ alkylcarbonyl, CH$_2$CH(CH$_2$CH$_3$)OC$_1$–C$_4$ alkylcarbonyl, CH(CH$_3$)CH(CH$_3$)OC$_1$–C$_4$ alkylcarbonyl, CH$_2$CH$_2$OC$_1$–C$_4$ haloalkylcarbonyl, CH$_2$CH$_2$CH$_2$OC$_1$–C$_4$ haloalkylcarbonyl, CH$_2$CH$_2$CH$_2$CH$_2$OC$_1$–C$_4$ haloalkylcarbonyl, CH(CH$_3$)CH$_2$OC$_1$–C$_4$ haloalkylcarbonyl, C(CH$_3$)$_2$CH$_2$OC$_1$–C$_4$ haloalkylcarbonyl, CH(CH$_2$CH$_3$)CH$_2$OC$_1$–C$_4$ haloalkylcarbonyl, CH$_2$CH(CH$_3$)OC$_1$–C$_4$ haloalkylcarbonyl, CH$_2$C(CH$_3$)$_2$OC$_1$–C$_4$ haloalkylcarbonyl, CH$_2$CH(CH$_2$CH$_3$)OC$_2$C$_1$–C$_4$ haloalkylcarbonyl, CH(CH$_3$)CH(CH$_3$)OC$_1$–C$_4$ haloalkylcarbonyl, CH$_2$CH$_2$OC$_1$–C$_4$ alkoxycarbonyl, CH$_2$CH$_2$CH$_2$OC$_1$–C$_4$ alkoxycarbonyl, CH$_2$CH$_2$CH$_2$CH$_2$OC$_1$–C$_4$ alkoxycarbonyl, CH(CH$_3$)CH$_2$OC$_1$–C$_4$ alkoxycarbonyl, C(CH$_3$)$_2$CH$_2$OC$_1$–C$_4$ alkoxycarbonyl, CH$_2$(CH$_2$CH$_3$)CH$_2$OC$_1$–C$_4$ alkoxycarbonyl, CH$_2$CH(CH$_3$)OC$_1$–C$_4$ alkoxycarbonyl, CH$_2$C(CH$_3$)$_2$OC$_1$–C$_4$ alkoxycarbonyl, CH$_2$CH(CH$_2$CH$_3$)OC$_1$–C$_4$ alkoxycarbonyl, CH(CH$_3$)CH(CH$_3$)OC$_1$–C$_4$ alkoxycarbonyl, CH$_2$CH$_2$OH, CH$_2$CH$_2$CH$_2$OH, CH$_2$CH$_2$CH$_2$CH$_2$OH, CH(CH$_3$)CH$_2$OH, C(CH$_3$)$_2$CH$_2$OH, CH(CH$_2$CH$_3$)CH$_2$OH, CH$_2$CH(CH$_3$)OH, CH$_2$C(CH$_3$)$_2$OH, CH$_2$CH(CH$_2$CH$_3$)OH, CH(CH$_3$)CH(CH$_3$)OH, CH$_2$CH$_2$OC$_1$–C$_4$ alkylsulfonyl, CH$_2$CH$_2$CH$_2$OC$_1$–C$_4$ alkylsulfonyl, CH$_2$CH$_2$CH$_2$CH$_2$OC$_1$–C$_4$ alkylsulfonyl, CH(CH$_3$)CH$_2$OC$_1$–C$_4$ alkylsulfonyl, C(CH$_3$)$_2$CH$_2$OC$_1$–C$_4$ alkylsulfonyl, CH(CH$_2$CH$_3$)CH$_2$OC$_1$–C$_4$ alkylsulfonyl, CH$_2$CH(CH$_3$)OC$_1$–C$_4$ alkylsulfonyl, CH$_2$C(CH$_3$)$_2$OC$_1$–C$_4$ alkylsulfonyl, CH$_2$CH(CH$_2$CH$_3$)OC$_1$–C$_4$ alkylsulfonyl, CH(CH$_3$)CH(CH$_3$)OC$_1$–C$_4$ alkylsulfonyl, CH$_2$CH$_2$OC$_1$–C$_4$ haloalkylsulfonyl, CH$_2$CH$_2$CH$_2$OC$_1$–C$_4$ haloalkylsulfonyl, CH$_2$CH$_2$CH$_2$CH$_2$OC$_1$–C$_4$ haloalkylsulfonyl, CH(CH$_3$)CH$_2$OC$_1$–C$_4$ haloalkylsulfonyl, C(CH$_3$)$_2$CH$_2$OC$_1$–C$_4$ haloalkylsulfonyl, CH(CH$_2$CH$_3$)CH$_2$OC$_1$–C$_4$ haloalkylsulfonyl, CH$_2$CH(CH$_3$)OC$_1$–C$_4$ haloalkylsulfonyl, CH$_2$C(CH$_3$)$_2$OC$_1$–C$_4$ haloalkylsulfonyl, CH$_2$CH(CH$_2$CH$_3$)OC$_1$–C$_4$ haloalkylsulfonyl, CH(CH$_3$)CH(CH$_3$)OC$_1$–C$_4$ haloalkylsulfonyl, CH$_2$CH$_2$SC$_1$–C$_4$ alkyl, CH$_2$CH$_2$CH$_2$SC$_1$–C$_4$ alkyl, CH$_2$CH$_2$CH$_2$CH$_2$SC$_1$–C$_4$ alkyl, CH(CH$_3$)CH$_2$SC$_1$–C$_4$ alkyl CH(CH$_3$)CH$_2$SC$_1$–C$_4$ alkyl, C(CH$_3$)$_2$CH$_2$SC$_1$–C$_4$ alkyl, CH(CH$_2$CH$_3$)CH$_2$SC$_1$–C$_4$ alkyl, CH$_2$CH(CH$_3$)SC$_1$–C$_4$ alkyl, CH$_2$C(CH$_3$)$_2$SC$_1$–C$_4$ alkyl, CH$_2$CH(CH$_2$CH$_3$)SC$_1$–C$_4$ alkyl, CH(CH$_3$)CH(CH$_3$)SC$_1$–C$_4$ alkyl, CH$_2$CH$_2$SC$_1$–C$_4$ haloalkyl, $CH_2CH_2CH_2SC_1-C_4$ haloalkyl, $CH_2CH_2CH_2CH_2SC_1-C_4$ haloalkyl, $CH(CH_3)CH_2SC_1-C_4$ CH haloalkyl, $C(CH_3)_2CH_2SC_1-C_4$ haloalkyl, $CH(CH_2CH_3)CH_2SC_1-C_4$ haloalkyl, $CH_2CH(CH_3)SC_1-C_4$ haloalkyl, $CH_2C(CH_3)_2SC_1-C_4$ haloalkyl, $CH_2CH(CH_2CH_3)SC_1-C_4$ haloalkyl, $CH(CH_3)CH(CH_3)SC_1-C_4$ haloalkyl, $CH_1CH_2S(O)C_1-C_4$ alkyl, $CH_2CH_2CH_2S(O)C_1-C_4$ alkyl, $CH_2CH_2CH_2CH_2S(O)C_1-C_4$ alkyl, $CH(CH_3)CH_2S(O)C_1-C_4$ alkyl, $C(CH_3)_2CH_2S(O)C_1-C_4$ alkyl, $CH(CH_2CH_3)CH_2S(O)C_1-C_4$ alkyl, $CH_2CH(CH_3)S(OC_1-C_4$ alkyl, $CH_2C(CH_3)_2S(O)C_1-C_4$ alkyl, $CH_2CH(CH_2CH_3)S(O)C_1-C_4$ alkyl, $CH(CH_3)CH(CH_3)S(O)C_1-C_4$ alkyl, $CH_2CH_2SO_2C_1-C_4$ alkyl, $CH_2CH_2CH_2SO_1C_1-C_4$ alkyl, $CH_2CH_2CH_2CH_2SO_2C_1-C_4$ alkyl, $CH(CH_3)CH_2SO_2C_1-C_4$ alkyl, $C(CH_3)_2CH_2SO_2C_1-C_4$ alkyl, $CH(CH_2CH_3)CH_2SO_2C_1 \propto C_4$ alkyl, $CH_2CH(CH_3)SO_2C_1-C_4$ alkyl, $CH_2C(CH_3)_2SO_2C_1-C_4$ alkyl, $CH_2CH(CH_2CH_3)SO_2C_1-C_4$ alkyl or $CH(CH_3)CH(CH_3)SO_2C_1-C_4$ alkyl,

42. Compounds of claim 41 wherein
$R_2$ is $CH_2OC_1-C_2$ haloalkyl of 1 or 2 halogens, $CH_2OC_2-C_3$ haloalkenyl, $CH_2OC_3-C_4$ alkynyl, $CH_2OC_2-C_3$ alkoxyalkyl, $CH_2SC_1-C_2$ haloalkyl, of 1 or 2 halogens, $CH_2SC_2-C_3$ haloalkenyl, $CH_2SC_3-C_4$ alkynyl, $CH_2SC_2-C_3$ alkoxyalkyl, $CH_2S(O)C_1-C_2$ haloalkyl of 1 or 2 halogens, $CH_2S(O)C_2-C_3$ haloalkenyl, $CH_2S(O)C_3-C_4$ alkynyl, $CH_2S(O)C_2-C_3$ alkoxyalkyl, $CH_2SO_2C_1-C_2$ haloalkyl of 1 or 2 halogens, $CH_2SO_2C_2-C_3$ haloalkenyl, $CH_2SO_2C_3-C_4$ alkynyl, $CH_2SO_2C_2-C_3$ alkoxyalkyl, $CH_2CH_2OC_1-C_2$ alkyl, $CH_2CH_2OC_1-C_2$ haloalkyl, $CH_2CH_2OC_1-C_2$ alkylcarbonyl, $CH_2CH_2OC_1-C_2$ haloalkylcarbonyl, $CH_2CH_2OC_1-C_2$ alkoxycarbonyl, $CH_2CH_2OH$, $CH_2CH_2OC_1-C_2$ alkylsulfonyl, $CH_2CH_2OC_1-C_2$ haloalkylsulfonyl, $CH_2CH_2SC_1-C_2$ alkyl, $CH_2CH_2SC_1-C_2$ haloalkyl, $CH_2CH_2S(O)C_1-C_2$ alkyl or $CH_2CH_2SO_2C_1-C_2$ alkyl.

43. Compounds of claim 42 wherein
$R_2$ is $CH_2OCF_2H$, $CH_2OCH_2CH_2F$, $CH_2OC_3$ haloalkenyl, $CH_2OCH_2C\equiv CH$, $CH_2OCH_2CH_2OCH_3$, $CH_2SCF_2H$, $CH_2SCH_2CH_2F$, $CH_2SC_2$ haloalkenyl, $CH_2SCH_2C\equiv CH$, $CH_2SCH_2CH_2OCH_3$, $CH_2S(O)CF_2H$, $CH_2S(O)CH_2CH_2F$, $CH_2S(O)C_2$ haloalkenyl, $CH_2S(O)CH_2C\equiv CH$, $CH_2S(O)CH_2CH_2OCH_3$, $CH_2SO_2CF_2H$, $CH_2SO_2CH_2CH_2F$, $CH_2SO_2C_2$-haloalkenyl, $CH_2SO_2CH_2C\equiv CH$, $CH_2SO_2CH_2CH_2OCH_3$, $CH_2CH_2OCH_3$, $CH_2CH_2OCF_2H$, $CH_2CH_2OCH_2CF_3$, $CH_2CH_2OC(O)CF_3CH$ CH, $CH_2CH_3OC(O)CF_3$, $CH_2CH_2OH$, $CH_2CH_2OSO_2CH_3$, $CH_2CH_2OSO_2CF_3$, $CH_2CH_2OSO_2CF_2CF_3$, $CH_2CH_2SCH_3$, $CH_2CH_2SCF_2H$, $CH_2CH_2SCH_2CF_3$, $CH_2CH_2S(O)CH_3$ or $CH_2CH_2SO_2CH_3$.

* * * * *

UNITED STATES PATENT AND TRADEMARK OFFICE
CERTIFICATE OF CORRECTION

PATENT NO. : 4,981,509

DATED : January 1, 1991

INVENTOR(S) : Craig L. Hillemann

It is certified that error appears in the above-identified patent and that said Letters Patent is hereby corrected as shown below:

Column 6, line 3, change "alkylsulfonylalkoxy" to
--alkylsulfinylalkoxy --.

Column 6, line 14, change "$SCH_2CH_2CH_2C(O)CH_3$" to
-- $SCH_2CH_2C(O)CH_3$ --

Column 6, line 23, change "$C_1-C_4$ haloalkylsulfo-" to -- $C_1-C_8$ haloalkylsulfo- --.

Column 6, line 24, change "$C_1-C_8$ haloalkenylsulfonyl" to
-- $C_2-C_6$ haloalkenylsulfonyl --.

Column 6, line 25, change "$C_2-C_6$ alkynylsulfonyl" to -- $C_3-C_6$ alkynylsulfonyl --.

Column 6, line 26, change "$C_3-C_6$ alkoxyalkylsulfonyl" to
-- $C_2-C_4$ alkoxyalkylsulfonyl --.

Column 6, line 30, change "$C_1-C_4$" to -- $C_2-C_6$ --.

Column 6, line 34, change "$C_1-C_4$ cycloalkoxy" to -- $C_3-C_4$ cycloalkoxy --.

Column 6, line 35, change "$C_1-C_4$ alkenyloxy" to -- $C_2-C_4$ alkenyloxy --.

Column 6, line 36, change "$C_1-C_4$ alkynyloxy" to -- $C_3-C_4$ alkynyloxy--; "$C_1-C_4$ haloalkynyloxy" to -- $C_3-C_4$ haloalkynyloxy --; "$C_1-C_4$ alkox-" to -- $C_2-C_4$ alkox- --.

Column 6, line 38, change "oarbamoyloxy" to -- carbamoyloxy --.

UNITED STATES PATENT AND TRADEMARK OFFICE
CERTIFICATE OF CORRECTION

PATENT NO. : 4,981,509

DATED : January 1, 1991

INVENTOR(S) : Craig L. Hillemann

It is certified that error appears in the above-identified patent and that said Letters Patent is hereby corrected as shown below:

Column 6, line 40, change "$C_1$-$C_4$ haloalkylsulfonyloxy" to -- $C_1$-$C_2$ haloalkylsulfonyloxy --.

Column 6, line 42, change "$C_1$-$C_4$ cycloalkylthio" to -- $C_3$-$C_4$ cycloalkylthio --.

Column 6, line 43, change "$C_1$-$C_4$ alkenylthio" to -- $C_2$-$C_4$ alkinylthio --.

Column 6, line 44, change "$C_1$-$C_4$ alkynylthio" to -- $C_2$-$C_4$ alkynylthio --; "$C_1$-$C_4$ haloalkynylthio" to --$C_3$-$C_4$ haloalkynylthio --.

Column 6, line 45, change "$C_1$-$C_4$ alkoxyalkylthio" to -- $C_2$-$C_4$ alkoxyalkylthio --.

Column 6, line 49, change "$C_1$-$C_4$ haloalkynyl-" to -- $C_3$-$C_4$ haloalkynyl- --.

Column 6, line 53, change "$C_1$-$C_4$ alkenylsulfonyl" to -- $C_2$-$C_4$ alkenylsulfonyl--; "$C_1$-$C_4$ haloalkenylsulfonyl" to -- $C_2$-$C_4$ haloalkenylsulfonyl --.

Column 6, line 58, change "$C_1$-$C_4$ cyano-" to -- $C_2$-$C_4$ cyano- --.

Column 7, line 34, change "$CH_2CHF$, $CF_2CF_3$" to -- $CH_2CH_2F$, $CF_2CF_3$ --.

Column 8, line 16, change "$OCH_2CH_F$," to -- $OCH_2CH_2F$, --. .

Column 9, line 48, change "alxysulfonyl" to -- alkylsulfonyl --.

UNITED STATES PATENT AND TRADEMARK OFFICE
CERTIFICATE OF CORRECTION

PATENT NO. : 4,981,509
DATED : January 1, 1991
INVENTOR(S) : Craig L. Hillemann

It is certified that error appears in the above-indentified patent and that said Letters Patent is hereby corrected as shown below:

Column 10, line 12, change "$CH(CH_2CH(CH_3)CH_2SC_3-C_4$" to -- $CH(CH_2CH_3)CH_2SC_3-C_4$ --.

Column 10, line 13, change "$CH_2C(CH$ alkynyl, $CH(CH$ alkynyl, alkynyl" to -- $CH_2CH(CH_3)SC_3-C_4$ alkynyl, $CH_2C(CH_3)_2SC_3-C_4$ alkynyl --.

Column 10, line 36, change "alkyl" to -- haloalkyl --.
Column 10, line 37, change "alkyl" to -- haloalkyl --.
Column 12, line 14, change "$C_3-C_{haloalkynyloxy}$" to -- $C_3-C_4$ haloalkynyloxy --.
Column 13, line 34, change "haloalkylthio, $C_{12}14C_6$" to -- haloalkylthio, $C_2-C_6$ --.

In the Tables:

Table I, columns 63-64, entry number 14, column heading "X" (4th from left), change ")$CH_3$" to -- $OCH_3$ --.

Table I, columns 99-100, entry number 82, column heading

UNITED STATES PATENT AND TRADEMARK OFFICE
CERTIFICATE OF CORRECTION

PATENT NO. : 4,981,509

DATED : January 1, 1991

INVENTOR(S) : Craig L. Hillemann

It is certified that error appears in the above-identified patent and that said Letters Patent is hereby corrected as shown below:

"m.p.(°C)" (7th from left), change "77-79" to -- 114-116 --.

Table I, columns 101-102, entry number 1, column heading "m.p. (°C)" (7th from left), add -- 77-79 --.

Table I, columns 101-102, entry number 41, column heading "m.p.(°C)" (7th from left), delete "136(d)".

Table I, columns 101-102, entry number 68, column heading "Y" (5th from left), change "$OCH_2CF_N$" to -- $OCH_2CF_3$ --.

Table I, columns 101-102, entry number 68, column heading "Z" (6th from left), add -- N --.

Table I, columns 103-104, entry number 42, column heading "X" (4th from left), add -- $CH_3$ --.

Table I, columns 103-104, entry number 42, column heading "Y" (5th from left), add -- $CH_3$ --.

Table I, columns, 103-104, entry number 42, column heading "Z" (6th from left), add -- N --.

Table I, columns 103-104, entry number 43, column heading "$R_2$" (2nd from left), change "($CH_3$" to -- $(CH_2)_3OCH_3$ --.

Table I, columns 103-104, entry number 43, column heaidng "X" (4th from left), add -- $OCH_3$ --.

Table I, columns 103-104, entry number 43, column heading "Y" (5th from left), add -- $CH_3$ --.

UNITED STATES PATENT AND TRADEMARK OFFICE
CERTIFICATE OF CORRECTION

PATENT NO. : 4,981,509

DATED : January 1, 1991

INVENTOR(S) : Craig L. Hillemann

Page 5 of 11

It is certified that error appears in the above-identified patent and that said Letters Patent is hereby corrected as shown below:

Table I, columns 103-104, entry number 43, column heading "Z" (6th from left), add -- N --.

Table I, columns 111-112, entry number 17, column heading "Y" (5th from left), add -- $OCH_3$ --.

Table I, columns 111-112, entry number 17, column heading "Z" (6th from left), add -- CH --.

Table Ia, columns 165-166, entry number 11, column heading "R" (3rd from left), change "2" to -- H --.

Table Ia, columns 165-166, entry number 11, column heading "X" (4th from left), change "H" to -- $OCH_3$ --.

Table Ia, columns 165-166, entry number 11, column heading "Y" (5th from left), change "$OCH_3$" to -- Cl --.

Table Ia, columns 165-166, entry number 11, column heading "Z" (6th from left), change "Cl" to -- CH --.

Table Ia, columns 165-166, entry number 11, column heading "m.p.(°C)", (7th from left), delete "CH".

Table Ia, columns 165-166, entry number 15, column heading "Y" (5th from left), change "CH" to -- $OCH_3$ --.

Table Ia, columns 165-166, entry number 15, column heading "Z" (6th from left), add -- CH --.

Table Ia, columns 165-166, entry number 16, delete entire line.

UNITED STATES PATENT AND TRADEMARK OFFICE
CERTIFICATE OF CORRECTION

PATENT NO. : 4,981,509

DATED : January 1, 1991

INVENTOR(S) : Craig L. Hillemann

It is certified that error appears in the above-identified patent and that said Letters Patent is hereby corrected as shown below:

Table Ia, columns 165-166, entry number 19, column heading "Y" (5th from left), change "CH" to -- $CH_3$ --.

Table Ia, columns 165-166, entry number 19, column heading "Z" (6th from left), add -- CH --.

Table Ib, columns 171-172, entry number 3, column heading "Y" (4th from left), change "CH" to -- $OCH_3$ --.

Table Ib, columns 171-172, entry number 3, column heading "Z" (5th from left), add -- CH --.

Table I, columns 297-320, change table heading "I" to -- Ih --.

Table I, columns 303-304, entry number 32, column heading "Y" (4th from left), change "$Oc_2H_5$" to -- $OC_2H_5$ --.

Table I, columns 319-320, entry number 34, column heading "R" (2nd from left), change "$OCH_3$" to -- H --.

Table I, columns 319-320, entry number 34, column heading "Y" (4th from left), change "CH" to -- $OCH_3$ --.

Table I, columns 319-320, entry number 34, column heading "Z" (5th from left), add -- CH --.

In the Claims:

Column 362, line 65, change "$C_2C_4$ haloalkylthioalkoxy" to.-- $C_2-C_4$ haloalkylthioalkoxy --.

Column 363, line 11, delete "sulfinyl".

UNITED STATES PATENT AND TRADEMARK OFFICE
CERTIFICATE OF CORRECTION

PATENT NO. : 4,981,509

DATED : January 1, 1991

INVENTOR(S) : Craig L. Hillemann

It is certified that error appears in the above-identified patent and that said Letters Patent is hereby corrected as shown below:

Column 363, line 18, change "$C_4C_6$ cycloalkylalkylsul-" to -- $C_4$-$C_6$ cycloalkylalkylsul- --.

Column 363, line 20, change "$C_2C_6$haloalkenylsulfonyl" to -- $C_2$-$C_6$ haloalkenylsulfonyl --.

Column 363, line 22, change "yalklsulfonyl" to -- yalkylsulfonyl --.

Column 363, line 25, change "$CH_2$" to -- $CHF_2$ --.

Column 363, line 26, change "$C_2$-$C_6$ substituted" to -- $C_2$-$C_6$ alkyl substituted --.

Column 363, line 28, change "$NHC_3$" to -- $NHCH_3$ --.

Column 363, line 35, change "$C_1C_4$ alkoxycar-" to -- $C_1$-$C_4$ alkoxycar- --.

Column 363, line 57, change "$CH_3$, or $OC_2H_5$" to -- $CH_3$, $OCH_3$ or $OC_2H_5$ --.

Column 365, line 2, change "alkyl $C(CH_3)_2OC_1$-$C_4$" to -- alkyl, $C(CH_3)_2OC_1$-$C_4$--.

Column 365, line 3, change "alkyl" to -- alkyl, --.

Column 365, line 6, change "alkyl" to -- alkyl, --.

Column 365, line 16, change "$CH_2CH_2CH_2Ch_2OC_2$-$C_4$" to -- $CH_2CH_2CH_2CH_2OC_2$-$C_4$ --.

Column 365, line 45, change "$CH_2OC$-" to -- $CH_2OC_1$- --.

Column 365, line 65, change "$Ch_2OC_1$-$C_4$" to --$CH_2OC_1$-$C_4$--.

UNITED STATES PATENT AND TRADEMARK OFFICE
CERTIFICATE OF CORRECTION

PATENT NO. : 4,981,509  Page 8 of 11

DATED : January 1, 1991

INVENTOR(S) : Craig L. Hillemann

It is certified that error appears in the above-identified patent and that said Letters Patent is hereby corrected as shown below:

Column 366, line 11, change "CH(CH$_2$CH$_3$))SC$_1$-C$_4$" to -- CH(CH$_2$CH$_3$)SC$_1$-C$_4$ --.

Column 366, line 27, change "CH$_2$CH$_2$CH$_2$Ch$_2$SC$_3$-C$_4$" to -- CH$_2$CH$_2$CH$_2$CH$_2$SC$_3$-C$_4$ --.

Column 366, line 43, change "CH$_2$CH(CH$_2$CH$_3$)SC$_2$-C$_4$" to -- CH$_2$CH(CH$_2$CH$_3$)SC$_2$-C$_4$ --.

Column 366, line 47, change ",-C$_4$ alkyl" to -- , -C$_4$ alkyl, --.

Column 366, line 50, change "alkyl of at least" to -- haloalkyl of at least --.

Column 366, line 51, change "alkyl of at least" to -- haloalkyl of at least --.

Column 366, line 52, change "alkyl of at least" to -- haloalkyl of at least --.

Column 366, line 53, change "alkyl of at least" to -- haloalkyl of at least --.

Column 366, line 54, change "alkyl of at least" to -- haloalkyl of at least --.

Column 366, line 55, change "alkyl of" to -- haloalkyl of --.

Column 366, line 57, change "alkyl of at least" to -- haloalkyl of at least --.

Column 368, line 38, change "CH$_2$CH$_S$C$_2$-C$_3$" should read --CH$_2$CH$_2$SC$_2$-3--.

UNITED STATES PATENT AND TRADEMARK OFFICE
CERTIFICATE OF CORRECTION

PATENT NO. : 4,981,509

DATED : January 1, 1991

INVENTOR(S) : Craig L. Hillemann

It is certified that error appears in the above-identified patent and that said Letters Patent is hereby corrected as shown below:

Column 368, line 62, change "S(O)CH$_3$S, (O)CH$_2$S(O)CH(CH$_3$)$_2$" to
-- S(O)CH$_3$, S(O)CH$_2$CH$_3$S(O)CH(CH$_3$)$_2$ --.

Column 369, line 60, change "OCH$_2$CH$_2$SCH$_3$, OCH$_2$CH$_2$SO$_2$CH$_3$" to --
OCH$_2$CH$_2$SCH$_3$, OCH$_2$SCH$_2$CF$_3$, OCH$_2$CH$_2$S(O)CH$_3$, OCH$_2$S(O)CH$_2$CF$_3$,
OCH$_2$CH$_2$SO$_2$CH$_3$ --.

Coulumn 369, line 61, change "$_2$SO$_2$CH$_2$CF$_2$" to -- $_2$SO$_2$CH$_2$CF$_3$ --.

Column 370, line 41, change "OCH C$_3$-haloalkenyloxy" to --
OCH$_2$C$_3$-haloalkenyloxy --.

Column 370, line 45, change "$_2$SO$_2$CH$_2$CF$_2$" to -- $_2$SO$_2$CH$_2$CF$_3$ --.

Column 370, line 47, change "S(O)CH$_2$C$_2$" to -- S(O)CH$_2$CF$_3$ --.

Column 370, line 48, change "haloalkenylsulfinyl" to -- C$_2$-haloalkenylsulfinyl --.

Column 371, line 9, change "alkynylthio" to
-- alkynylthio, --.

Column 371, line 10, change "haloalkoxyalkylthio" to --
haloalkoxyalkylthio, --.

Column 371, line 13, change "alkynylsulfinyl" to --
alkynylsulfinyl, --.

Column 371, line 15, change "haloalkenylsulfonyl" to --
haloalkenylsulfonyl, --.

Column 372, line 4, change "C(O)CH$_3$,CH$_3$," to -- C(O)CH$_3$, --.

Column 372, line 18, change "OCHCH$_2$CN" to -- OCH$_2$CH$_2$CN --.

UNITED STATES PATENT AND TRADEMARK OFFICE
CERTIFICATE OF CORRECTION

PATENT NO. : 4,981,509
DATED : January 1, 1991
INVENTOR(S) : Craig L. Hillemann

It is certified that error appears in the above-identified patent and that said Letters Patent is hereby corrected as shown below:

Column 372, line 27, change "$SO_2CH_2C(O)CH_3,SO$" to -- $SO_2CH_2C(O)CH_3$, --.

Column 372, line 36, change "$CH(CH_2(CH_2CH_2CH_3)OC_1-C_4$" to -- $CH(CH_2CH_2CH_3)OC_1-C_4$ --.

Column 372, line 41, change "$C(CH_3)(CH_3)OC_2-C_4$" -- $C(CH_3)(CH_2CH_3)OC_2-C_4$ --.

Coumn 373, line 64, change "$CH(CH_2CH_3)CH_2 OC_1-C_4$" to -- $CH(CH_2CH_3)CH_2OC_1-C_4$ --.

Column 375, line 10, change "$CH_1CH_2S(O)C_1-C_4$" to -- $CH_2CH_2S(O)C_1-C_4$ --.

Column 375, line 19, change "$CH_2CH_2CH_2SO_1C_1-C_4$" to -- $CH_2CH_2CH_2SO_2C_1-C_4$ --.

Column 375, line 23, change "$CH(CH_2CH_3)CH_2SO_2C_1-C_4$" to -- $CH(CH_2CH_3)CH_2SO_2C_1-C_4$ --.

Column 375, line 27, change "alkyl," to -- alkyl. --.

Column 376, line 21, change "$CH_2S(O)C_2$ haloalkenyl" to -- $CH_2S(O)C_2$-haloalkenyl --.

Column 376, line 26, change "$CH_2CH_2OC(O)CF_3CHCH$" to -- $CH_2CH_2OC(O)CH_3$ --.

Column 376, line 27, change "$CH_2CH_3OC(O)CF_3$," to -- $CH_2CH_2OC(O)CF_3$, --.

UNITED STATES PATENT AND TRADEMARK OFFICE
CERTIFICATE OF CORRECTION

PATENT NO. : 4,981,509

DATED : January 1, 1991

INVENTOR(S) : Craig L. Hillemann

It is certified that error appears in the above-indentified patent and that said Letters Patent is hereby corrected as shown below:

Column 376, line 29, change "$CH_2CH_2OSO_2CF_2CF_3$" to -- $CH_2CH_2OSO_2CH_2CF_3$ --

Signed and Sealed this

Tenth Day of May, 1994

*Attest:*

BRUCE LEHMAN

*Attesting Officer*  *Commissioner of Patents and Trademarks*